United States Patent
Lindström et al.

(10) Patent No.: US 11,584,763 B2
(45) Date of Patent: *Feb. 21, 2023

(54) CHROMENOPYRIDINE DERIVATIVES AS PHOSPHATIDYLINOSITOL PHOSPHATE KINASE INHIBITORS

(71) Applicant: HIBERCELL, INC., New York, NY (US)

(72) Inventors: Johan Lindström, Holo (SE); Lars Boukharta Persson, Uppsala (SE); Jenny Viklund, Hagersten (SE); Rickard Forsblom, Tullinge (SE); Tobias Ginman, Tullinge (SE); Edward A. Kesicki, New York, NY (US); Eugene R. Hickey, Danbury, CT (US); Markus K. Dahlgren, Shelton, CT (US); Aleksey I. Gerasyuto, Flemington, NJ (US)

(73) Assignee: HiberCell, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/956,981

(22) PCT Filed: Dec. 21, 2018

(86) PCT No.: PCT/US2018/067261
§ 371 (c)(1),
(2) Date: Jun. 22, 2020

(87) PCT Pub. No.: WO2019/126730
PCT Pub. Date: Jun. 27, 2019

(65) Prior Publication Data
US 2021/0253600 A1    Aug. 19, 2021

Related U.S. Application Data

(60) Provisional application No. 62/609,578, filed on Dec. 22, 2017.

(51) Int. Cl.
| | |
|---|---|
| C07D 519/00 | (2006.01) |
| C07D 491/052 | (2006.01) |
| C07D 401/04 | (2006.01) |
| A61K 9/00 | (2006.01) |

(52) U.S. Cl.
CPC ......... C07D 519/00 (2013.01); C07D 401/04 (2013.01); C07D 491/052 (2013.01); A61K 9/0019 (2013.01); A61K 9/0053 (2013.01)

(58) Field of Classification Search
CPC ............... C07D 519/00; C07D 401/04; C07D 491/052; A61K 9/0019; A61K 9/0053
See application file for complete search history.

(56) References Cited

U.S. PATENT DOCUMENTS

| | | | |
|---|---|---|---|
| 4,111,942 A | 9/1978 | Lee et al. | |
| 5,262,564 A | 11/1993 | Kun et al. | |
| 2009/0039765 A1 | 2/2009 | Uetani et al. | |
| 2013/0165436 A1 | 6/2013 | Caravatti et al. | |
| 2016/0285010 A1 | 9/2016 | Yoon et al. | |
| 2017/0253605 A1* | 9/2017 | Yu ..................... A61K 31/4162 |
| 2020/0331913 A1 | 10/2020 | Lindstrom et al. | |
| 2020/0392156 A1 | 12/2020 | Kesicki | |
| 2020/0392162 A1 | 12/2020 | Kesicki | |
| 2021/0253600 A1 | 8/2021 | Lindstrom et al. | |
| 2021/0317136 A1 | 10/2021 | Lindstrom et al. | |

FOREIGN PATENT DOCUMENTS

| | | |
|---|---|---|
| CN | 101801383 A | 8/2010 |
| KR | 2015/0009297 A | 1/2015 |
| KR | 2016/0050361 A | 5/2016 |
| WO | WO-1997/019087 A1 | 5/1997 |
| WO | WO-1998/027060 A1 | 6/1998 |
| WO | WO-2008/028168 A1 | 3/2008 |
| WO | WO-2009/035575 A1 | 3/2009 |
| WO | WO-2009/097014 A2 | 8/2009 |
| WO | WO-2009/108912 A1 | 9/2009 |
| WO | WO-2009/155527 A2 | 12/2009 |
| WO | WO-2010/077680 A2 | 7/2010 |
| WO | WO-2010/121225 A2 | 10/2010 |
| WO | WO-2011/053861 A1 | 5/2011 |

(Continued)

OTHER PUBLICATIONS

Haddach et al. "Synthesis and SAR of inhibitors of protein kinase CK2: Novel tricyclic quinoline analogs" Bioorganic & Medicinal Chemistry Letters 22 (2012) pp. 45-48.

Hinchliffe et al. "The type II PIPkins (PtdIns5P 4-kinases): enzymes in search of a function?" Introduction: the PtdInsP kinase (PIPkin) family, Mar. 5, 1999, pp. 657-661.

Liu et al. "Structural Determinants of CX-4945 Derivatives as Protein Kinase CK2 Inhibitors: A Computational Study" *Int. J. Mol. Sci.* 2011, 12, pp. 7004-7021.

Pierre et al. "7-(4H-1,2,4-Triazol-3-yl)benzo[c][2,6]naphthyridines: A novel class of Pim kinase inhibitors with potent cell antiproliferative activity" Bioorganic & Medicinal Chemistry Letters 21 (2011) pp. 6687-6692.

(Continued)

*Primary Examiner* — Jean P Cornet
(74) *Attorney, Agent, or Firm* — Goodwin Procter LLP

(57) ABSTRACT

The invention relates to inhibitors of PI5P4K inhibitors useful in the treatment of cancers, neurodegenerative diseases, inflammatory disorders, and metabolic diseases, having the Formula:

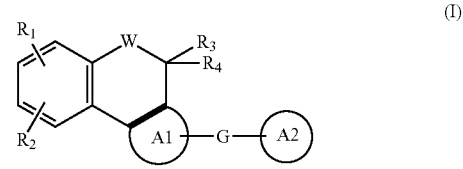

(I)

where A1, A2, G, R1, R2, R3, R4, and W are described herein.

16 Claims, No Drawings

(56) References Cited

FOREIGN PATENT DOCUMENTS

| WO | WO-2012/012264 A1 | 1/2012 |
|----|-------------------|--------|
| WO | WO-2012/054493 A1 | 4/2012 |
| WO | WO-2012/110860 A1 | 8/2012 |
| WO | WO-2012/112245 A1 | 8/2012 |
| WO | WO-2013/055780 A1 | 4/2013 |
| WO | WO-2013/109739 A1 | 7/2013 |
| WO | WO-2013/180376 A1 | 12/2013 |
| WO | WO-2014/119636 A1 | 8/2014 |
| WO | WO-2015/147247 A1 | 10/2015 |
| WO | WO2015/196759 * | 12/2015 |
| WO | WO-2015196759 A1 | 12/2015 |
| WO | WO-2016/129694 A1 | 8/2016 |
| WO | WO-2016/210291 A1 | 12/2016 |
| WO | WO-2016/210296 A1 | 12/2016 |
| WO | WO-2017/095100 A1 | 6/2017 |
| WO | WO-2018/106192 A1 | 6/2018 |
| WO | WO-2019/126730 A1 | 6/2019 |

OTHER PUBLICATIONS

Pierre et al. "Discovery and SAR of 5-(3-Chlorophenylamino)benzo[c][2,6]naphthyridine-8-carboxylic Acid (CX-4945), the First Clinical Stage Inhibitor of Protein Kinase CK2 for the Treatment of Cancer" J. Med. Chem. 2011, 54, pp. 635-654.

Pierre et al. "Novel potent pyrimido[4,5-c]quinoline inhibitors of protein kinase CK2: SAR and preliminary assessment of their analgesic and anti-viral properties" Bioorganic & Medicinal Chemistry Letters 21 (2011) pp. 1687-1691.

Pourbasheer et al. "QSAR study of CK2 inhibitors by GA-MLR and GA-SVM methods" Arabian Journal of Chemistry (2019) 12, pp. 2141-2149.

Shahin et al. "Identification of novel inhibitors for Pim-1 kinase using pharmacophore modeling based on a novel method for selecting pharmacophore generation subsets" J Comput Aided Mol Des (2016) 30: pp. 39-68.

Swellmeen et al. "Structure based drug design of Pim-1 kinase followed by pharmacophore guided synthesis of quinolone-based inhibitors" Bioorganic & Medicinal Chemistry 25 (2017) pp. 4855-4875.

Wang et al. "Exploring the prominent performance of CX-4945 derivatives as protein kinase CK2 inhibitors by a combined computational study" *Mol. BioSyst.*, 2014, 10, pp. 1196-1210.

Zhou et al. "Exploring the crucial structural elements required for tricyclic quinoline analogs as protein kinase CK2 inhibitors by a combined computational analysis" Med Chem Res (2013) 22: pp. 4410-4422.

Zhou et al. "Structural Basis for Low-Affinity Binding of Non-R2 Carboxylate-Substituted Tricyclic Quinoline Analogs to CK2α: Comparative Molecular Dynamics Simulation Studies" Chem Biol Drug Des 2015; 85: pp. 189-200.

International Search Report and Written Opinion dated Mar. 14, 2019 for International Application No. PCT/US2018/067261.

U.S. Appl. No. 16/904,064 US 2020/0392162, Chromenopyrimidine Derivatives as Phosphatidylinsitol Phosphate Kinase Inhibitors, filed Jun. 17, 2020.

Shim et al. "Deletion of the gene Pip4k2c, a novel phosphatidylinositol kinase, results in hyperactivation of the immune system" vol. 113, May 6, 2016, pp. 7596-7601.

Sumita et al. "The lipid kinase PI5P4β is an intracellular GTP sensor for metabolism and tumorigensis" *Mol Cell*. Jan. 21, 2016; 61(2): pp. 187-198 (29 pages).

* cited by examiner

CHROMENOPYRIDINE DERIVATIVES AS PHOSPHATIDYLINOSITOL PHOSPHATE KINASE INHIBITORS

CROSS-REFERENCE TO RELATED APPLICATIONS

This application is a U.S. National Phase Application, filed under 35 U.S.C. 371, of International Application No. PCT/US2018/067261, filed on Dec. 21, 2018, which claims the benefit and priority to U.S. Provisional Application No. 62/609,578, filed Dec. 22, 2017, the entire contents of each of which are incorporated herein by reference in their entirety.

FIELD OF INVENTION

The present invention is directed to inhibitors of phosphatidylinositol-5-phosphate-4-kinase (PI5P4K) useful in the treatment of diseases or disorders associated with PI5P4K enzymes. In particular, the invention is concerned with compounds and compositions inhibiting PI5P4K, methods of treating diseases or disorders associated with PI5P4K, and methods of synthesis of these compounds.

BACKGROUND OF THE INVENTION

A minor but ubiquitous component of cells, phosphoinositol lipids are pivotal players in many intracellular signal transduction pathways. Phosphoinositol lipids are formed when phosphatidylinositol (PtdIns) is converted, by the catalytic action of lipid kinases, to polyphosphoinositides. As a prototypic example, the membrane associated phospholipid, phosphatidylinositol-4,5-bisphosphate (PtdIns(4,5)P2), is formed by two successive phosphorylations of PtdIns by the phosphotidylinositolphosphate kinases (PIP kinases).

PtdIns(4,5)P2 is a substrate for phospholipase C (PLC) and is converted into the second messengers inositol-1,4,5-trisphosphate and diacylglycerol (DAG). Phosphoinositides are involved in regulating a broad spectrum of activities from cytoskeletal assembly and motility to vesicle trafficking and exocytosis to transduction of intracellular signals including stimulating the release of intracellular calcium stores (Hinchliffe et al., Biochem. Soc. Trans., 1999, 27, 657-661).

PIP kinases comprise a unique and promiscuous family of enzymes that catalyze the production of polyphosphorylated inositol lipids from monophosphorylated phosphoinositides. Isolation and purification of several different PIP kinase enzymes able to catalyze phosphorylation of phosphatidylinositol 4-phosphate and produce PtdIns(4,5)P2 led to the further categorization of these enzymes, dubbed the phosphatidylinositol 4-phosphate 5-kinases (PIP5Ks), into two types having different activities. The PIP kinases have no homology to other lipid or protein kinases at the primary sequence level, and are distinguished from each other by their lack of immuno-crossreactivity and by the fact that type I PIP5Ks are stimulated in vitro by phosphatidic acid, whereas the type II PIP5Ks are not. Furthermore, the recent discovery that the type II PTP5Ks are able to phosphorylate multiple lipid substrates in vitro suggests that this family of kinases is potentially able to generate several distinct, often subcellularly compartmentalized, phosphoinositol products for regulation of a variety of physiologically important processes (Hinchliffe et al., Biochem. Soc. Trans., 1999, 27, 657-661).

One particular species of PI, phosphatidylinositol 5-phosphate (PI5P), has been implicated in the regulation of the tumor suppressor ING2 and the oncogene AKT. The phosphatidylinositol 5-phosphate 4-kinase (PI5P4K) family (α, β, γ isoforms) catalyzes the conversion of PI5P to PI4, 5 P2. These enzymes therefore represent one means by which cells can regulate endogenous PI5P levels. Mice deficient for PI5P4Kβ (PI5P4Kβ−/−) have been shown to exhibit enhanced insulin sensitivity and activation of AKT in skeletal muscle.

The pharmacological modulation of PIP5KII-beta activity and/or expression is therefore believed to be an appropriate point of therapeutic intervention in pathological conditions in which cell differentiation, proliferation, and/or motility are compromised, such as cancer or inflammation, and in metabolic disorders.

Currently, there are no known therapeutic agents which effectively inhibit the synthesis of PIP5KII-beta. Inhibition of PI5P4K with small molecule inhibitors, therefore, has the potential to be a treatment for cancers and other disorders. For this reason, there remains a considerable need for novel and potent small molecule inhibitors and agents capable of effectively inhibiting PIP5KII-beta function.

SUMMARY OF THE INVENTION

A first aspect of the invention relates to compounds of Formula (I):

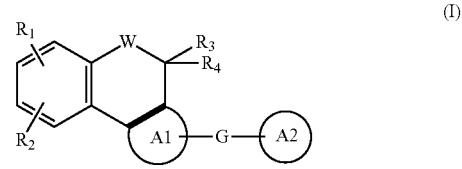

and pharmaceutically acceptable salts, prodrugs, solvates, hydrates, isomers, and tautomers, thereof, wherein:

Ring A1 is 5- to 6-membered heteroaryl;

Ring A2 is heteroaryl optionally substituted with one or more $R_8$;

W is —O—, —NH—, —N($C_{1-6}$ alkyl)-, —N($C_{3-8}$ cycloalkyl)-, —N(aryl)-, or —N(heteroaryl)-;

G is a bond, —O—, —NH—, or —N($C_{1-6}$ alkyl)-;

$R_1$ is —N($R_5$)C(O)$R_6$, —C(O)N($R_5$)($R_6$), —S(O)$_2$N($R_5$)($R_6$), —N($R_5$)S(O)$_2R_6$, or heteroaryl wherein the heteroaryl is optionally substituted with one or more $R_7$;

$R_2$ is —H, halogen, —OH, —NH$_2$, —NO$_2$, —CN, —COOH, —C(O)NH$_2$, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl;

$R_3$ and $R_4$ are each independently —H, halogen, $C_{1-6}$ alkyl, $C_{1-6}$ alkoxy, or $C_{3-6}$ cycloalkyl, wherein the alkyl, alkoxy, or cycloalkyl is optionally substituted with one or more halogen, —OH, and —NH$_2$; or $R_3$ and $R_4$ when taken together with the atom to which they are attached form a $C_{3-8}$ cycloalkyl or heterocyclyl;

$R_5$ and $R_6$ are independently, at each occurrence, —H, $C_{1-6}$ alkyl, $C_{2-6}$ alkenyl, or $C_{2-6}$ alkynyl, wherein the alkyl, alkenyl, or alkynyl is optionally substituted with one or more $R_7$; or $R_5$ and $R_6$ when taken together with the atom to which they are each attached form a heterocycle optionally substituted with one or more $R_7$;

$R_7$ is independently —H, halogen, —OH, —NH$_2$, —NO$_2$, —CN, $C_{1-6}$ alkyl, $C_{1-6}$ alkoxy, $C_{3-8}$ cycloalkyl, heterocyclyl, aryl, or heteroaryl;

$R_8$ is independently —N(R$_9$)C(O)R$_{10}$, —N(R$_9$)C(O)OR$_{10}$, —N(R$_9$)C(O)N(R$_9$)(R$_{10}$), —N(R$_9$)C(O)N(R$_9$)(R$_{11}$), —N(R$_9$)S(O)$_2$R$_{10}$, —N(R$_9$)S(O)$_2$N(R$_9$)(R$_{10}$), —S(O)$_2$R$_{10}$—N(R$_9$)(R$_{10}$), —OR$_{10}$, —CF$_3$, —CHF$_2$, —R$_{10}$, —N(R$_9$)C(O)R$_{11}$, —N(R$_9$)(R$_{11}$) or halogen; or two $R_8$ with the atoms they are attached form a $C_{4-8}$ cycloalkyl or heterocyclyl, wherein the heterocyclyl or cycloalkyl is optionally substituted with one or more $R_{12}$;

each $R_9$ or $R_{10}$ is independently, at each occurrence, —H, $C_{1-6}$ alkyl, $C_{3-8}$ cycloalkyl, or heterocyclyl, wherein the alkyl, cycloalkyl, or heterocyclyl is optionally substituted with one or more $R_{13}$; or $R_9$ and $R_{10}$ when taken together with the atom to which they are each attached form a heterocycle ring optionally substituted with one or more $R_{14}$ each $R_{11}$ is aryl, $C_{3-8}$ cycloalkyl, heterocyclyl, or heteroaryl, wherein the aryl or heteroaryl group is optionally substituted with one or more $R_{18}$ and the cycloalkyl or heterocyclyl is optionally substituted with one or more $R_{19}$;

each $R_{12}$ is independently $C_{1-6}$ alkyl, $C_{3-6}$ cycloalkyl, —OR$_{20}$, —C(O)R$_{20}$, —C(O)OR$_{20}$, —S(O)$_2$R$_{20}$, or oxo; or two $R_{12}$ taken together can form a $C_{3-8}$ cycloalkyl or heterocyclyl, wherein the cycloalkyl or heterocyclyl are optionally substituted with one or more $R_{14}$;

$R_{13}$ is —H, halogen, —CN, oxo, $C_{1-6}$ alkyl, —OR$_{20}$, —C(O)$_2$R$_{20}$, $C_{3-8}$ cycloalkyl, heterocyclyl, heteroaryl, aryl, or —C(O)N(R$_{22}$)(R$_{22}$), wherein the alkyl, aryl, or heteroaryl, is optionally substituted with one or more $R_{15}$;

$R_{14}$ is independently —C(O)OR$_{20}$; —C(O)R$_{20}$, —OR$_{20}$, oxo, $C_{1-6}$ alkyl, heterocycle, $C_{3-8}$ cycloalkyl, or aryl, wherein the alkyl, heterocycle, cycloalkyl, or aryl is optionally substituted with one or more $R_{16}$; or two $R_{14}$ taken together can form a $C_{3-6}$ cycloalkyl or heterocyclyl;

$R_{15}$ is —H, $C_{1-6}$ alkyl, $C_{1-6}$ alkoxy, heteroaryl, aryl, —N(R$_{22}$)(R$_{22}$), —N(R$_{22}$)C(O)OR$_{22}$, or —N(R$_{22}$)C(O)—U—N(R$_{22}$)—Z;

U is —(CH$_2$)$_p$—, —(CH$_2$)$_p$—Ar—, —CH═CH(CH$_2$)$_p$—, or heterocyclyl;

Z is —R$_{22}$ or —C(O)—U—N(R$_{22}$)(R$_{22}$);

$R_{16}$ is $C_{3-8}$ cycloalkyl, heterocyclyl, heteroaryl, or aryl, wherein the heterocyclyl, cycloalkyl, heteroaryl or aryl is optionally substituted with one or more $R_{17}$;

$R_{17}$ is independently —OR$_{22}$, —N(R$_{22}$)(R$_{22}$), or —N(R$_{22}$)C(O)—V—N(R$_{22}$)-E;

V is —(CH$_2$)$_n$—, —(CH$_2$)$_n$—Ar—, or —CH═CH(CH$_2$)$_n$—;

E is —R$_{22}$ or —C(O)—V—N(R$_{22}$)(R$_{22}$);

Ar is aryl;

$R_{18}$ is halogen, $C_{1-6}$ alkyl, $C_{3-6}$ cycloalkyl, —OR$_{20}$, —N(R$_{20}$)(R$_{21}$), —C(O)R$_{20}$, oxo, —N(R$_{22}$)C(O)OR$_{22}$, —N(R$_{22}$)C(O)-Q-N(R$_{22}$)—F, or —N(R$_{22}$)-Q-N(R$_{22}$)—F;

Q is —CH═CH(CH$_2$)$_m$—, —(CH$_2$)$_m$—, —(CH$_2$O)$_m$—, —(CH$_2$)$_m$—Ar—, or —(CH$_2$CH$_2$O)$_o$—(CH$_2$)$_m$—;

F is —H, $C_{1-6}$ alkyl, aryl, heteroaryl, —C(O)-Q-R$_{22}$, or —C(O)-Q-N(R$_{22}$)(R$_{22}$), wherein the alkyl, aryl, or heteroaryl is optionally substituted with one or more $R_{22}$; or two $R_{18}$ when on adjacent atoms may be taken together with the atoms to which they are each attached to form a $C_{3-8}$ cycloalkyl or heterocyclic group optionally substituted with —OR$_{21}$ or oxo;

$R_{19}$ is independently —H, halogen, —OH, —NH$_2$, oxo, —C(O)R$_{20}$, —OR$_{22}$, $C_{3-6}$ cycloalkyl, or $C_{1-6}$ alkyl; or two $R_{19}$ when on adjacent atoms may be taken together with the atoms to which they are each attached to form an aryl or heteroaryl group optionally substituted with one or more $R_{22}$;

$R_{20}$ is —H, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl;

$R_{21}$ is —H, $C_{1-6}$ alkyl, or —C(O)R$_{22}$;

each $R_{22}$ is independently —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl;

each p is independently 1-4;

each n is independently 1-4;

each m is independently 1-4; and o is 1-3.

Another aspect of the invention relates to a method of treating a disease or disorder associated with modulation of PI5P4K. The method comprises administering to a patient in need of a treatment for diseases or disorders associated with modulation of PI5P4K an effective amount of a compound of Formula (I), or a pharmaceutically acceptable salt, hydrate, solvate, prodrug, stereoisomer, or tautomer thereof.

Another aspect of the invention is directed to a method of inhibiting PI5P4K. The method involves administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting PI5P4K.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting PI5P4K.

The present invention further provides methods of treating a disease or disorder associated with modulation of PI5P4K including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of PI5P4K that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention further provides compounds and compositions with an improved efficacy and safety profile relative to known PI5P4K inhibitors. The present disclosure also provides agents with novel mechanisms of action toward PI5P4K enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present invention provides the medical community with a novel pharmacological strategy for the treatment of diseases and disorders associated with PI5P4K enzymes.

DETAILED DESCRIPTION OF THE INVENTION

The present invention relates to compounds and compositions that are capable of inhibiting the activity PI5P4K. The invention features methods of treating, preventing or ameliorating a disease or disorder in which PI5P4K plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of PI5P4K dependent diseases and disorders by inhibiting the activity of PI5P4K enzymes. Inhibition of PI5P4K provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the invention, the compounds of Formula (I) are described:

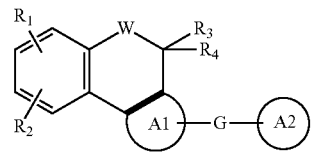

(I)

and pharmaceutically acceptable salts, hydrates, solvates, prodrugs, stereoisomers, and tautomers thereof, wherein A1, A2, G, R1, R2, R3, R4, and W are described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$)haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$.

The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, or B, the remaining ring atoms being C. Heteroaryl as herein defined also means a bicyclic heteroaromatic group wherein the heteroatom is selected from N, O, S, P, or B. Heteroaryl as herein defined also means a tricyclic heteroaromatic group containing one or more ring heteroatoms selected from N, O, S, P, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1,2-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated ring, e.g., a 5-membered heteroaromatic ring containing 1-3 heteroatoms selected from N, S, or O, or a 6-membered heteroaromatic ring containing 1-3 nitrogens, wherein the saturated or partially unsaturated ring includes 0-4 heteroatoms selected from N, O, S, P, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Cycloalkylalkyl" means monocyclic saturated carbon rings containing 3-24 carbon atoms further substituted with ($C_1$-$C_6$) alkyl groups. In general cycloalkylalkyl groups herein described display the following formula

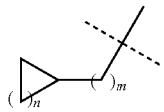

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

"Heterocyclyl" or "heterocycloalkyl" monocyclic rings containing carbon and heteroatoms taken from containing one or more ring heteroatoms selected from N, O, S, P, or B and wherein there is not delocalized 7 electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "amino" as used herein means a substituent containing at least one nitrogen atom. Specifically, —$NH_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or —$NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N($CH_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting PI5P4K, which are useful for the treatment of diseases and disorders associated with modulation of a PI5P4K enzyme. The invention further relates to compounds, or pharmaceutically acceptable salts, hydrates, solvates, prodrugs, stereoisomers, or tautomers thereof, which are useful for inhibiting PI5P4K.

In one embodiment, the compounds of Formula (I) have the structure of Formula (Ia):

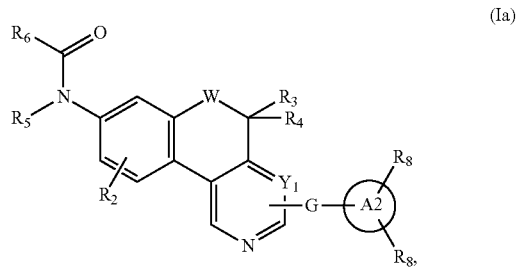

wherein $Y_1$ is CH or N.

In another embodiment, the compounds of Formula (I) have the structure of Formula (Ib):

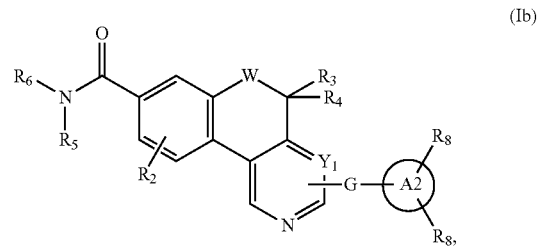

wherein $Y_1$ is CH or N.

In another embodiment, the compounds of Formula (I) have the structure of Formula (Ic):

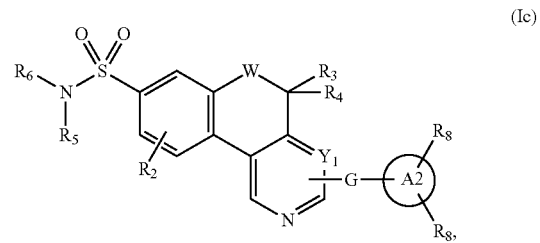

wherein $Y_1$ is CH or N.

In another embodiment, the compounds of Formula (I) have the structure of Formula (Id):

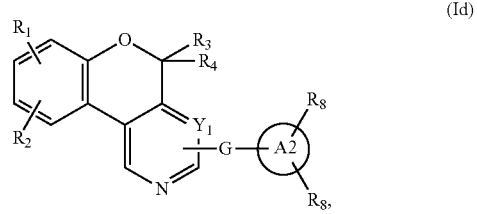

wherein $Y_1$ is CH or N.

In another embodiment, the compounds of Formula (I) have the structure of Formula (Ie):

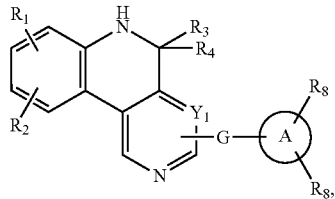

(Ie)

wherein $Y_1$ is CH or N.

In another embodiment, the compounds of Formula (I) have the structure of Formula (If):

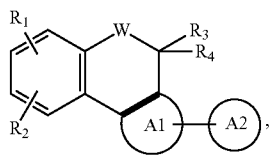

(If)

wherein $Y_1$ is CH or N.

In another embodiment, the compounds of Formula (I) have the structure of Formula (Ig):

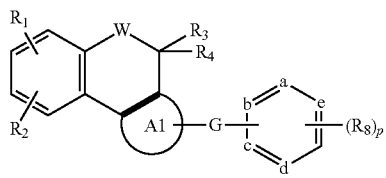

(Ig)

wherein $Y_1$ is CH or N.

In another embodiment, the compounds of Formula (I) have the structure of Formula (Ih):

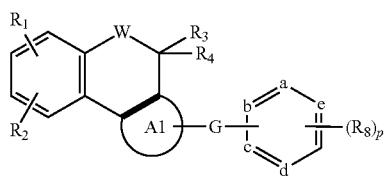

(Ih)

wherein:

a, b, c, and d, are each independently C or N, wherein at least one of a, b, c, and d is N, and no more than two of a, b, c, and d, are N;

$X_3$ and $Y_3$ are each independently —O—, —CH$_2$—, or —N(R$_8$)—;

ρ is 1, 2, or 3.

In another embodiment, the compounds of Formula (I) have the structure of Formula (Ii):

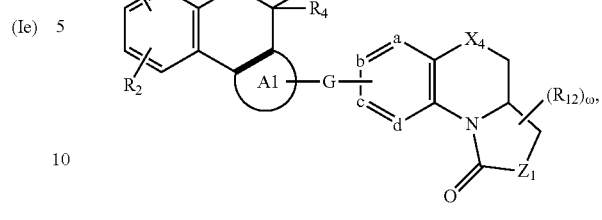

(Ii)

wherein:

a, b, c, and d, are each independently C or N, wherein at least one of a, b, c, and d is N; and no more than two of a, b, c, d, and e, are N;

$X_4$ and $Z_1$ are each independently —O—, —N(R$_{12}$)—, or —C(R$_{12}$)(R$_{12}$)—; and ω is 1, 2, or 3.

In another embodiment, the compounds of Formula (I) have the structure of Formula (Ij):

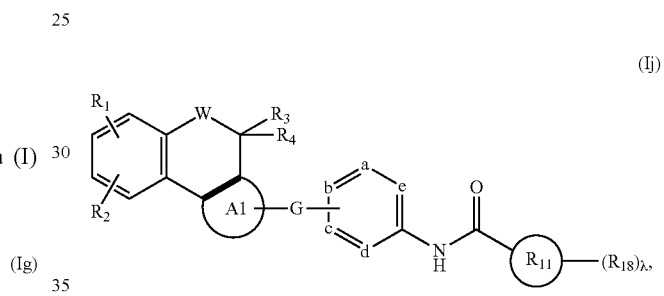

(Ij)

wherein:

a, b, c, d, and e, are each independently C or N, wherein at least one of a, b, c, d, and e is N, and no more than two of a, b, c, d, and e, are N; and λ is 1, 2, or 3.

In another embodiment, the compounds of Formula (I) have the structure of Formula (Ik):

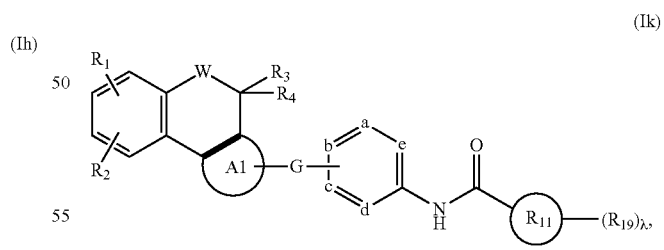

(Ik)

wherein:

a, b, c, d, and e, are each independently C or N, wherein at least one of a, b, c, d, and e is N, and no more than two of a, b, c, d, and e, are N; and λ is 1, 2, or 3.

In another embodiment, the compounds of Formula (I) have the structure of Formula (Il):

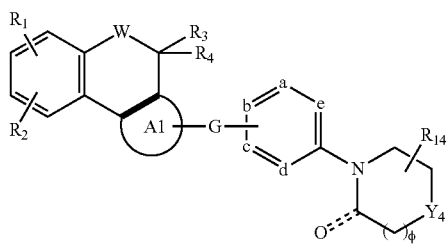

(II)

wherein:
a, b, c, d, and e, are each independently C or N, wherein at least one of a, b, c, d, and e is N, and no more than two of a, b, c, d, and e, are N;
$Y_4$ is —O—, —N($R_{14}$)—, or —C($R_{14}$)($R_{14}$)—; and
Φ is 0, 1, or 2.

In another embodiment, the compounds of Formula (I) have the structure of Formula (Im):

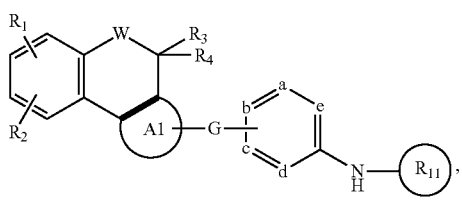

(Im)

wherein:
a, b, c, d, and e, are each independently C or N, wherein at least one of a, b, c, d, and e is N, and no more than two of a, b, c, d, and e, are N.

In another embodiment, the compounds of Formula (I) have the structure of Formula (In):

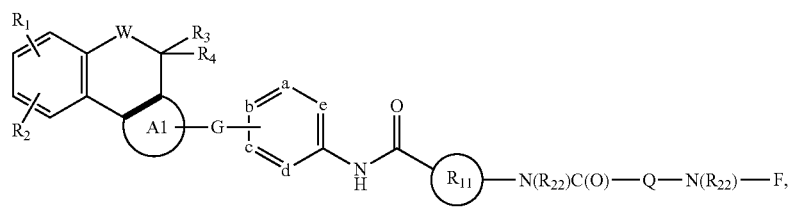

(In)

wherein:
a, b, c, d, and e, are each independently C or N, wherein at least one of a, b, c, d, and e is N, and no more than two of a, b, c, d, and e, are N.

In another embodiment, the compounds of Formula (I) have the structure of Formula (Io):

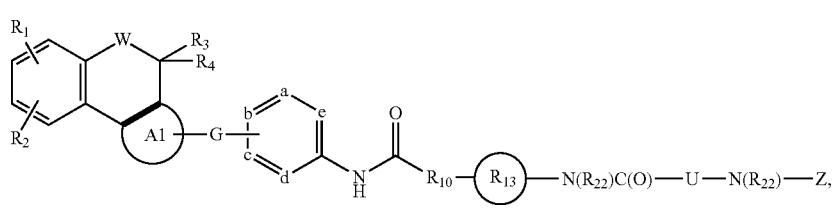

(Io)

wherein:
a, b, c, d, and e, are each independently C or N, wherein at least one of a, b, c, d, and e is N, and no more than two of a, b, c, d, and e, are N.

In another embodiment, the compounds of Formula (I) have the structure of Formula (Ip):

(Ip)

wherein:

a, b, c, d, and e, are each independently C or N, wherein at least one of a, b, c, d, and e is N, and no more than two of a, b, c, d, and e, are N.

In some embodiments of the compounds of Formula I, $R_1$ is —$N(R_5)C(O)R_6$, —$C(O)N(R_5)(R_6)$, —$S(O)_2N(R_5)(R_6)$, —$N(R_5)S(O)_2R_6$, or heteroaryl, wherein heteroaryl is optionally substituted with one or more $R_7$. In another embodiment, $R_1$ is —$N(R_5)C(O)R_6$, —$C(O)N(R_5)(R_6)$, —$S(O)_2N(R_5)(R_6)$, —$N(R_5)S(O)_2R_6$, or heteroaryl. In another embodiment, $R_1$ is —$N(R_5)C(O)R_6$, —$C(O)N(R_5)(R_6)$, —$S(O)_2N(R_5)(R_6)$, or —$N(R_5)S(O)_2R_6$. In another embodiment, $R_1$ is —$N(R_5)C(O)R_6$, —$C(O)N(R_5)(R_6)$, or —$S(O)_2N(R_5)(R_6)$. In another embodiment, $R_1$ is —$N(R_5)C(O)R_6$ or —$C(O)N(R_5)(R_6)$. In another embodiment, $R_1$ is —$N(R_5)C(O)R_6$. In another embodiment, $R_1$ is —$C(O)N(R_5)(R_6)$. In another embodiment, $R_1$ is —$S(O)_2N(R_5)(R_6)$. In another embodiment, $R_1$ is —$N(R_5)S(O)_2R_6$. In another embodiment, $R_1$ is heteroaryl. In another embodiment, $R_1$ is heteroaryl optionally substituted with one or more $R_7$.

In some embodiments of the compounds of Formula I, W is —O—, —NH—, —$N(C_{1-6}$ alkyl)-, —$N(C_{3-8}$ cycloalkyl)-, —N(aryl)-, or —N(heteroaryl)-. In another embodiment, W is —O—, —NH—, —$N(C_{1-6}$ alkyl)-, —$N(C_{3-8}$ cycloalkyl)-, or —N(aryl)-. In another embodiment, W is —O—, —NH—, —$N(C_{1-6}$ alkyl)-, or —$N(C_{3-8}$ cycloalkyl)-. In another embodiment, W is —O—, —NH—, or —$N(C_{1-6}$ alkyl)-. In another embodiment, W is —O— or —NH—. In another embodiment, W is —O—. In another embodiment, W is —NH—. In another embodiment, W is —O—. In another embodiment, W is —$N(C_{1-6}$ alkyl)-. In another embodiment, W is —$N(C_{3-8}$ cycloalkyl)-. In another embodiment, W is —N(aryl)-. In another embodiment, W is —N(heteroaryl)-.

In some embodiments of the compounds of Formula I, $R_2$ is H, halogen, —OH, —$NH_2$, —$NO_2$, —CN, —COOH, —$C(O)NH_2$, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl. In another embodiment, $R_2$ is H, halogen, —OH, —$NH_2$, —$NO_2$, —CN, —COOH, —$C(O)NH_2$, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, or aryl. In another embodiment, $R_2$ is H, halogen, —OH, —$NH_2$, —$NO_2$, —CN, —COOH, —$C(O)NH_2$, $C_{1-6}$ alkyl, $C_{1-6}$ alkoxy, $C_{2-6}$ alkenyl, $C_{2-6}$ alkynyl, $C_{3-8}$ cycloalkyl, or heterocyclyl. In another embodiment, $R_2$ is H, halogen, —OH, —$NH_2$, —$NO_2$, —CN, —COOH, —$C(O)NH_2$, $C_{1-6}$ alkyl, $C_{1-6}$ alkoxy, $C_{2-6}$ alkenyl, $C_{2-6}$ alkynyl, or $C_{3-8}$ cycloalkyl. In another embodiment, $R_2$ is H, halogen, —OH, —$NH_2$, —$NO_2$, —CN, —COOH, —$C(O)NH_2$, $C_{1-6}$ alkyl, $C_{1-6}$ alkoxy, $C_{2-6}$ alkenyl, or $C_{2-6}$ alkynyl. In another embodiment, $R_2$ is H, halogen, —OH, —$NH_2$, —$NO_2$, —CN, —COOH, —$C(O)NH_2$, $C_{1-6}$ alkyl, $C_{1-6}$ alkoxy, or $C_{2-6}$ alkenyl. In another embodiment, $R_2$ is H, halogen, —OH, —$NH_2$, —$NO_2$, —CN, —COOH, —$C(O)NH_2$, $C_{1-6}$ alkyl, or $C_{1-6}$ alkoxy. In another embodiment, $R_2$ is H, halogen, —OH, —$NH_2$, —$NO_2$, —CN, —COOH, —$C(O)NH_2$, or $C_{1-6}$ alkyl. In another embodiment, $R_2$ is H, halogen, —OH, —$NH_2$, —$NO_2$, —CN, —COOH, or $C(O)NH_2$. In another embodiment, $R_2$ is H, halogen, —OH, —$NH_2$, —$NO_2$, —CN, or —COOH. In another embodiment, $R_2$ is H, halogen, —OH, —$NH_2$, —$NO_2$, or —CN. In another embodiment, $R_2$ is H, halogen, —OH, —$NH_2$, or —$NO_2$. In another embodiment, $R_2$ is H, halogen, —OH, or —$NH_2$. In another embodiment, $R_2$ is H, halogen, or —OH. In another embodiment, $R_2$ is H or halogen. In another embodiment, $R_2$ is H. In another embodiment, $R_2$ is —OH. In another embodiment, $R_2$ is —$NH_2$. In another embodiment, $R_2$ is halogen. In another embodiment, $R_2$ is —$NO_2$. In another embodiment, $R_2$ is —CN. In another embodiment, $R_2$ is —COOH. In another embodiment, $R_2$ is —$C(O)NH_2$. In another embodiment, $R_2$ is $C_{1-6}$ alkyl. In another embodiment, $R_2$ is $C_{1-6}$ alkoxy. In another embodiment, $R_2$ is $C_{2-6}$ alkenyl. In another embodiment, $R_2$ is $C_{2-6}$ alkynyl. In another embodiment, $R_2$ is $C_{3-8}$ cycloalkyl. In another embodiment, $R_2$ is heterocyclyl. In another embodiment, $R_2$ is aryl. In another embodiment, $R_2$ is heteroaryl.

In some embodiments of the compounds of Formula I, $R_3$ is —H, halogen, $C_{1-6}$ alkyl, $C_{1-6}$ alkoxy, or $C_{3-6}$ cycloalkyl. In another embodiment, $R_3$ is —H, halogen, or $C_{1-6}$ alkyl. In another embodiment, $R_3$ is —H or halogen. In another embodiment, $R_3$ is —H. In another embodiment, $R_3$ is halogen. In another embodiment, $R_3$ is $C_{1-6}$ alkyl. In another embodiment, $R_3$ is $C_{1-6}$ alkoxy. In another embodiment, $R_3$ is $C_{3-6}$ cycloalkyl. In another embodiment, $R_3$ is $C_{1-6}$ alkyl optionally substituted with one or more halogen, —OH, and —$NH_2$. In another embodiment, $R_3$ is $C_{3-6}$ cycloalkyl optionally substituted with one or more halogen, —OH, and —$NH_2$. In another embodiment, $R_3$ is $C_{1-6}$ alkoxy optionally substituted with one or more halogen, —OH, and —$NH_2$.

In some embodiments of the compounds of Formula I, $R_4$ is —H, halogen, $C_{1-6}$ alkyl, $C_{1-6}$ alkoxy, or $C_{3-6}$ cycloalkyl. In another embodiment, $R_4$ is —H, halogen, or $C_{1-6}$ alkyl. In another embodiment, $R_4$ is —H or halogen. In another embodiment, $R_4$ is —H. In another embodiment, $R_4$ is halogen. In another embodiment, $R_4$ is $C_{1-6}$ alkyl. In another embodiment, $R_4$ is $C_{1-6}$ alkoxy. In another embodiment, $R_4$ is $C_{3-6}$ cycloalkyl. In another embodiment, $R_4$ is $C_{1-6}$ alkyl optionally substituted with one or more halogen, —OH, and —$NH_2$. In another embodiment, $R_4$ is $C_{3-6}$ cycloalkyl optionally substituted with one or more halogen, —OH, and —$NH_2$. In another embodiment, $R_4$ is $C_{1-6}$ alkoxy optionally substituted with one or more halogen, —OH, and —$NH_2$.

In other embodiments of the compounds of Formula I, $R_3$ and $R_4$ when taken together with the atom to which they are attached form a $C_{3-6}$ cycloalkyl or heterocyclyl. In another embodiment, $R_3$ and $R_4$ when taken together with the atom to which they are attached form a $C_{3-8}$ cycloalkyl. In another embodiment, $R_3$ and $R_4$ when taken together with the atom to which they are attached form a heterocyclyl.

In some embodiments, Ring A2 is heteroaryl. In yet another embodiment, Ring A2 is heteroaryl optionally substituted with one or more $R_5$. In yet other embodiments, Ring A1 is a 5- or 6-membered heteroaryl. In other embodiments, Ring A1 is a 5-membered heteroaryl. In other embodiments, Ring A1 is a 6-membered heteroaryl.

In some embodiments of the compounds of Formula I, $R_5$ is, at each occurrence, —H, $C_{1-6}$ alkyl, $C_{2-6}$ alkenyl, or $C_{2-6}$ alkynyl. In another embodiment, $R_5$ is, —H, $C_{1-6}$ alkyl, or $C_{2-6}$ alkenyl. In another embodiment, $R_5$ is —H or $C_{1-6}$ alkyl. In another embodiment, $R_5$ is —H. In another embodiment, $R_5$ is $C_{1-6}$ alkyl. In another embodiment, $R_5$ is $C_{2-6}$ alkenyl. In another embodiment, $R_5$ is $C_{2-6}$ alkynyl. In another embodiment, $R_5$ is $C_{1-6}$ alkyl optionally substituted with one or more $R_7$. In another embodiment, $R_5$ is $C_{2-6}$ alkenyl optionally substituted with one or more $R_7$. In another embodiment, $R_5$ is $C_{2-6}$ alkynyl optionally substituted with one or more $R_7$.

In some embodiments of the compounds of Formula I, $R_6$ is, at each occurrence, —H, $C_{1-6}$ alkyl, $C_{2-6}$ alkenyl, or $C_{2-6}$ alkynyl. In another embodiment, $R_6$ is, —H, $C_{1-6}$ alkyl, or $C_{2-6}$ alkenyl. In another embodiment, $R_6$ is —H or $C_{1-6}$ alkyl. In another embodiment, $R_6$ is —H. In another embodiment, $R_6$ is $C_{1-6}$ alkyl. In another embodiment, $R_6$ is $C_{2-6}$ alkenyl. In another embodiment, $R_6$ is $C_{2-6}$ alkynyl. In another embodiment, $R_6$ is $C_{1-6}$ alkyl optionally substituted with one or more $R_7$. In another embodiment, $R_6$ is $C_{2-6}$ alkenyl optionally substituted with one or more $R_7$. In another embodiment, $R_6$ is $C_{2-6}$ alkynyl optionally substituted with one or more $R_7$.

In other embodiments of the compounds of Formula I, $R_5$ and $R_6$ when taken together with the atom to which they are each attached form a heterocycle. In other embodiments of the compounds of Formula I, $R_5$ and $R_6$ when taken together with the atom to which they are each attached form a heterocycle optionally substituted with one or more $R_7$.

In other embodiments of the compounds of Formula I, $R_7$ is H, halogen, —OH, —NH$_2$, —NO$_2$, —CN, $C_{1-6}$ alkyl, $C_{1-6}$ alkoxy, $C_{3-8}$ cycloalkyl, heterocyclyl, aryl, or heteroaryl. In some embodiments, $R_7$ is H. In some embodiments, $R_7$ is halogen. In some embodiments, $R_7$ is —OH. In some embodiments, $R_7$ is —NH$_2$. In some embodiments, $R_7$ is —NO$_2$. In some embodiments, $R_7$ is —CN. In some embodiments, $R_7$ is $C_{1-6}$ alkyl. In some embodiments, $R_7$ is $C_{1-6}$ alkoxy. In some embodiments, $R_7$ is $C_{3-8}$ cycloalkyl. In some embodiments, $R_7$ is heterocyclyl. In some embodiments, $R_7$ is $C_{3-8}$ cycloalkyl. In some embodiments, $R_7$ aryl. In some embodiments, $R_7$ is heteroaryl.

In other embodiments of the compounds of Formula I, $R_5$ is -N($R_9$)C(O)$R_{10}$, —N($R_9$)C(O)O$R_{10}$, —N($R_9$)C(O)N($R_9$)($R_{10}$), —N($R_9$)C(O)N($R_9$)($R_{11}$), —N($R_9$)S(O)$_2$$R_{10}$, —N($R_9$)S(O)$_2$N($R_9$)($R_{10}$), —S(O)$_2$$R_{10}$, —N($R_9$)($R_{10}$), —O$R_{10}$, —CF$_3$, —CHF$_2$, —$R_{10}$, —N($R_9$)C(O)$R_{11}$, —N($R_9$)($R_{11}$) or halogen. In another embodiment, $R_5$ is-N($R_9$)C(O)$R_{10}$. In another embodiment, $R_5$ is —N($R_9$)C(O)O$R_{10}$. In another embodiment, $R_5$ is-N($R_9$)C(O)N($R_9$)($R_{10}$). In another embodiment, $R_5$ is —N($R_9$)C(O)N($R_9$)($R_{11}$). In another embodiment, $R_5$ is —N($R_9$)S(O)$_2$$R_{10}$. In another embodiment, $R_5$ is —N($R_9$)S(O)$_2$N($R_9$)($R_{10}$). In another embodiment, $R_5$ is —S(O)$_2$$R_{10}$. In another embodiment, $R_5$ is —N($R_9$)($R_{10}$). In another embodiment, $R_5$ is —O$R_{10}$. In another embodiment, $R_5$ is —CF$_3$. In another embodiment, $R_5$ is —CHF$_2$. In another embodiment, $R_5$ is —$R_{10}$. In another embodiment, $R_5$ is —N($R_9$)C(O)$R_{11}$. In another embodiment, $R_5$ is —N($R_9$)($R_{11}$). In another embodiment, $R_5$ is halogen.

In other embodiments of the compounds of Formula I, two $R_8$ with the atoms they are attached form a $C_{4-8}$ cycloalkyl or heterocyclyl. In some embodiments, two $R_8$ with the atoms they are attached form a $C_{4-8}$ cycloalkyl. In some embodiments, two $R_8$ with the atoms they are attached form a heterocyclyl. In some embodiments, two $R_8$ with the atoms they are attached form a $C_{4-8}$ cycloalkyl optionally substituted with one or more $R_{12}$. In some embodiments, two $R_8$ with the atoms they are attached form a heterocyclyl optionally substituted with one or more $R_{12}$.

In some embodiments of the compounds of Formula I, $R_9$ is —H, $C_{1-6}$ alkyl, $C_{3-8}$ cycloalkyl, or heterocyclyl. In another embodiment, $R_9$ is —H. In another embodiment, $R_9$ is $C_{1-6}$ alkyl. In another embodiment, $R_9$ is $C_{3-8}$ cycloalkyl. In another embodiment, $R_9$ is heterocyclyl. In another embodiment, $R_9$ is $C_{1-6}$ alkyl optionally substituted with one or more $R_{13}$. In another embodiment, $R_9$ is $C_{3-8}$ cycloalkyl optionally substituted with one or more $R_{13}$. In another embodiment, $R_9$ is heterocyclyl optionally substituted with one or more $R_{13}$.

In some embodiments of the compounds of Formula I, $R_{10}$ is —H, $C_{1-6}$ alkyl, $C_{3-8}$ cycloalkyl, or heterocyclyl. In another embodiment, $R_{10}$ is —H. In another embodiment, $R_{10}$ is $C_{1-6}$ alkyl. In another embodiment, $R_{10}$ is $C_{3-8}$ cycloalkyl. In another embodiment, $R_{10}$ is heterocyclyl. In another embodiment, $R_{10}$ is $C_{1-6}$ alkyl optionally substituted with one or more $R_{13}$. In another embodiment, $R_{10}$ is $C_{3-8}$ cycloalkyl optionally substituted with one or more $R_{13}$. In another embodiment, $R_{10}$ is heterocyclyl optionally substituted with one or more $R_{13}$.

In other embodiments of the compounds of Formula I, $R_9$ and $R_{10}$ when taken together with the atom to which they are each attached form a heterocycle ring. In another embodiment, $R_9$ and $R_{10}$ when taken together with the atom to which they are each attached form a heterocycle ring optionally substituted with one or more $R_{14}$.

In other embodiments of the compounds of Formula I, $R_1$ is aryl, $C_{3-8}$ cycloalkyl, heterocyclyl, or heteroaryl. In another embodiment, $R_1$ is aryl. In another embodiment, $R_1$ is heteroaryl. In another embodiment, $R_1$ is $C_{3-8}$ cycloalkyl. In another embodiment, $R_1$ is heterocyclyl. In another embodiment, $R_1$ is aryl optionally substituted with one or more $R_{18}$. In another embodiment, $R_1$ is heteroaryl optionally substituted with one or more $R_{18}$. In another embodiment, $R_1$ is $C_{3-8}$ cycloalkyl optionally substituted with one or more $R_{19}$. In another embodiment, $R_1$ is heterocyclyl optionally substituted with one or more $R_{19}$.

In other embodiments of the compounds of Formula I, each $R_{12}$ is $C_{1-6}$ alkyl, $C_{3-6}$ cycloalkyl, —O$R_{20}$, —C(O)$R_{20}$, —C(O)O$R_{20}$, —S(O)$_2$$R_{20}$, or oxo. In another embodiment, $R_{12}$ is $C_{1-6}$ alkyl. In another embodiment, $R_{12}$ is $C_{3-6}$ cycloalkyl. In another embodiment, $R_{12}$ is —O$R_{20}$. In another embodiment, $R_{12}$ is —C(O)$R_{20}$. In another embodiment, $R_{12}$ is —C(O)O$R_{20}$. In another embodiment, $R_{12}$ is —S(O)$_2$$R_{20}$. In another embodiment, $R_{12}$ is oxo. In other embodiments of the compounds of Formula I, two $R_{12}$ on the same carbon are taken together to form a $C_{3-6}$ cycloalkyl.

In some embodiments of the compounds of Formula I, $R_{13}$ is H, halogen, —CN, $C_{1-6}$ alkyl, —O$R_{20}$, —C(O)$_2$$R_{20}$, $C_{3-8}$ cycloalkyl, heterocyclyl, heteroaryl, aryl, or —C(O)N($R_{22}$)($R_{22}$). In another embodiment, $R_{13}$ is H. In another embodiment, $R_{13}$ is halogen. In another embodiment, $R_{13}$ is —CN. In another embodiment, $R_{13}$ is —O$R_{20}$. In another embodiment, $R_{13}$ is —C(O)$_2$$R_{20}$. In another embodiment, $R_{13}$ is —C(O)N($R_{22}$)($R_{22}$). In another embodiment, $R_{13}$ is aryl. In another embodiment, $R_{13}$ is heterocyclyl. In another embodiment, $R_{13}$ is $C_{1-6}$ alkyl. In another embodiment, $R_{13}$ is $C_{3-8}$ cycloalkyl. In another embodiment, $R_{13}$ is aryl optionally substituted with one or more $R_{15}$. In another embodiment, $R_{13}$ is heterocyclyl optionally substituted with one or more $R_{15}$. In another embodiment, $R_{13}$ is $C_{1-6}$ alkyl optionally substituted with one or more $R_{15}$. In another embodiment, $R_{13}$ is $C_{3-8}$ cycloalkyl optionally substituted with one or more $R_{15}$.

In some embodiments of the compounds of Formula I, $R_{14}$ is independently —C(O)O$R_{20}$, —C(O)$R_{20}$, oxo, $C_{1-6}$ alkyl, heterocycle, $C_{3-6}$ cycloalkyl, or aryl. In another embodiment, $R_{14}$ is-C(O)O$R_{20}$. In another embodiment, $R_{14}$ is oxo. In another embodiment, $R_{14}$ is $C_{1-6}$ alkyl. In another embodiment, $R_{14}$ is heterocycle. In another embodiment, $R_{14}$ is $C_{3-6}$ cycloalkyl. In another embodiment, $R_{14}$ is $C_{3-6}$ aryl. In another embodiment, $R_{14}$ is $C_{1-6}$ alkyl optionally substituted with one or more $R_{16}$. In another embodiment, $R_{14}$ is heterocycle optionally substituted with one or more $R_{16}$. In another embodiment, $R_{14}$ is $C_{3-6}$ cycloalkyl optionally substituted with one or more $R_{16}$. In another embodiment, $R_{14}$ is $C_{3-6}$ aryl optionally substituted with one or more $R_{16}$.

In some embodiments of the compounds of Formula I, $R_{15}$ is H, $C_{1-6}$ alkyl, $C_{1-6}$ alkoxy, heteroaryl, aryl, —N($R_{22}$)($R_{22}$), —N($R_{22}$)C(O)O$R_{22}$, or —N($R_{22}$)C(O)—U—N($R_{22}$)—Z. In one embodiment, $R_{15}$ is H. In one embodiment, $R_{15}$ is $C_{1-6}$ alkyl. In one embodiment, $R_{15}$ is $C_{1-6}$ alkoxy. In one embodiment, $R_{15}$ is heteroaryl. In one embodiment, $R_{15}$ is aryl. In one embodiment, $R_{15}$ is —$N(R_{22})(R_{22})$. In one embodiment, $R_{15}$ is —$N(R_{22})C(O)OR_{22}$. In one embodiment, $R_{15}$ is —$N(R_{22})C(O)$—U—$N(R_{22})$—Z.

In other embodiments of the compounds of Formula I, U is —$(CH_2)_p$—, —$(CH_2)_p$—Ar—, —CH=CH$(CH_2)_p$—, or heterocyclyl. In another embodiment, U is —$(CH_2)_p$—. In another embodiment, U is —$(CH_2)_p$—Ar—. In another embodiment, U is —CH=CH$(CH_2)_p$—. In another embodiment, U is heterocyclyl.

In some embodiments of the compounds of Formula I, Z is —$R_{22}$ or —C(O)—U—$N(R_{22})(R_{22})$. In other embodiments, Z is —$R_{22}$. In other embodiments, Z is —C(O)—U—$N(R_{22})(R_{22})$.

In some embodiments of the compounds of Formula I, $R_{16}$ is $C_{3-8}$ cycloalkyl, heterocyclyl, heteroaryl, or aryl. In another embodiment, $R_{16}$ is $C_{3-8}$ cycloalkyl. In another embodiment, $R_{16}$ is heterocyclyl. In another embodiment, $R_{16}$ is heteroaryl. In another embodiment, $R_{16}$ is aryl optionally substituted with one or more $R_{17}$. In another embodiment, $R_{16}$ is $C_{3-8}$ cycloalkyl optionally substituted with one or more $R_{17}$. In another embodiment, $R_{16}$ is heterocyclyl optionally substituted with one or more $R_{17}$. In another embodiment, $R_{16}$ is heteroaryl optionally substituted with one or more $R_{17}$. In another embodiment, $R_{16}$ is aryl optionally substituted with one or more $R_{17}$.

In some embodiments of the compounds of Formula I, $R_{17}$ is independently —$OR_{22}$, —$N(R_{22})(R_{22})$, or —$N(R_{22})$C(O)—V—$N(R_{22})$-E. In one embodiment, $R_{17}$ is —$OR_{22}$. In one embodiment, $R_{17}$ is-$N(R_{22})(R_{22})$. In one embodiment, $R_{17}$ is —$N(R_{22})C(O)$—V—$N(R_{22})$-E.

In other embodiments of the compounds of Formula I, V is —$(CH_2)_n$—, —$(CH_2)_n$—Ar—, or —CH=CH$(CH_2)_n$—. In one embodiment, $R_{17}$ is —$(CH_2)_n$—. In one embodiment, $R_{17}$ is —$(CH_2)_n$—Ar—. In one embodiment, $R_{17}$ is —CH=CH$(CH_2)_n$—. In one embodiment, Ar is aryl.

In some embodiments of the compounds of Formula I, E is —$R_{22}$ or —C(O)—V—$N(R_{22})(R_{22})$. In one embodiment, E is —$R_{22}$. In one embodiment, E is —C(O)—V—$N(R_{22})(R_{22})$.

In some embodiments of the compounds of Formula I, $R_1$ is halogen, $C_{1-6}$ alkyl, $C_{3-6}$ cycloalkyl, —$OR_{20}$, —$N(R_{20})(R_{21})$, —C(O)$R_{20}$, oxo, —$N(R_{22})C(O)OR_{22}$, —$N(R_{22})C(O)$-Q-$N(R_{22})$—F, or —$N(R_{22})$-Q-$N(R_{22})$—F. In another embodiment, $R_{18}$ halogen. In another embodiment, $R_{18}$ is $C_{1-6}$ alkyl. In another embodiment, $R_{18}$ is $C_{3-6}$ cycloalkyl. In another embodiment, R is —$OR_{20}$. In another embodiment, $R_{18}$ is —$N(R_{20})(R_{21})$. In another embodiment, $R_{18}$ is —C(O)$R_{20}$. In another embodiment, $R_{18}$ is oxo. In another embodiment, $R_{18}$ is —$N(R_{22})C(O)OR_{22}$. In another embodiment, $R_{18}$ is —$N(R_{22})C(O)$-Q-$N(R_{22})$—F. In another embodiment, $R_{18}$ is —$N(R_{22})$-Q-$N(R_{22})$—F.

In some embodiments of the compounds of Formula I, two $R_{18}$ when on adjacent atoms may be taken together with the atoms to which they are each attached to form a heterocyclic group. In another embodiment, two $R_{18}$ when on adjacent atoms may be taken together with the atoms to which they are each attached to form a heterocyclic group optionally substituted with —$OR_{21}$ or oxo.

In other embodiments of the compounds of Formula I, Q is —CH=CH$(CH_2)_m$—, —$(CH_2)_m$—, —$(CH_2O)_m$—, —$(CH_2)_m$Ar—, or —$(CH_2CH_2O)_o$—$(CH_2)_m$—. In another embodiment, Q is —CH=CH$(CH_2)_m$—. In another embodiment, Q is —$(CH_2)_m$—. In another embodiment, Q is —$(CH_2CH_2O)_o$—$CH_2CH_2$—. In another embodiment, Q is —$(CH_2O)_m$. In another embodiment, Q is —$(CH_2)_m$—Ar—. Yet in another embodiment, Q is —$(CH_2CH_2O)_o$—$(CH_2)_m$.

In other embodiments of the compounds of Formula I, F is H, $C_{1-6}$ alkyl, aryl, heteroaryl, —C(O)-Q-$R_{22}$, or —C(O)-Q-$N(R_{22})(R_{22})$. In another embodiment, F is H. In another embodiment, F is $C_{1-6}$ alkyl. In another embodiment, F is —C(O)-Q-$N(R_{22})(R_{22})$. In another embodiment, F is aryl. In another embodiment, F is heteroaryl. In another embodiment, F is —C(O)-Q-$R_{22}$.

In other embodiments of the compounds of Formula I, F is H, $C_{1-6}$ alkyl, aryl, heteroaryl, wherein the alkyl, aryl, or heteroaryl is optionally substituted with one or more $R_{22}$. In another embodiment, F is H. In another embodiment, F is $C_{1-6}$ alkyl, wherein the alkyl is optionally substituted with one or more $R_{22}$. In another embodiment, F is —C(O)-Q-$N(R_{22})(R_{22})$. In another embodiment, F is aryl, wherein the aryl is optionally substituted with one or more $R_{22}$. In another embodiment, F is heteroaryl, wherein the heteroaryl is optionally substituted with one or more $R_{22}$. In another embodiment, F is —C(O)-Q-$R_{22}$.

In some embodiments of the compounds of Formula I, $R_{19}$ is —H, halogen, —OH, —$NH_2$, oxo, —C(O)$R_{20}$, —$OR_{22}$, $C_{3-6}$ cycloalkyl, or $C_{1-6}$ alkyl. In one embodiment, $R_{19}$ is —H. In one embodiment, $R_{19}$ is halogen. In one embodiment, $R_1$ is —OH. In one embodiment, $R_{19}$ is —$NH_2$. In one embodiment, $R_{19}$ is oxo. In one embodiment, $R_1$ is —C(O)$R_{20}$. In one embodiment, $R_{19}$ is —$OR_{22}$. In one embodiment, $R_{19}$ is $C_{3-6}$ cycloalkyl. In one embodiment, $R_{19}$ is $C_{1-6}$ alkyl.

In some embodiments of the compounds of Formula I, two $R_1$ when on adjacent atoms may be taken together with the atoms to which they are each attached to form an aryl group. In one embodiment, two $R_1$ when on adjacent atoms may be taken together with the atoms to which they are each attached to form an aryl group optionally substituted with one or more $R_{22}$.

In some embodiments of the compounds of Formula I, $R_{20}$ is —H, $C_{1-6}$ alkyl, $C_{2-6}$ alkenyl, $C_{2-6}$ alkynyl, $C_{3-8}$ cycloalkyl, heterocyclyl, aryl, or heteroaryl. In another embodiment, $R_{20}$ is —H. In another embodiment, $R_{20}$ is $C_{1-6}$ alkyl. In another embodiment, $R_{20}$ is $C_{2-6}$ alkenyl. In another embodiment, $R_{20}$ is $C_{2-6}$ alkynyl. In another embodiment, $R_{20}$ is $C_{3-8}$ cycloalkyl. In another embodiment, $R_{20}$ is heterocyclyl. In another embodiment, $R_{20}$ is aryl. In another embodiment, $R_{20}$ is heteroaryl. In another embodiment, $R_{20}$ is $C_{1-6}$ alkyl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{20}$ is $C_{2-6}$ alkenyl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{20}$ is $C_{2-6}$ alkynyl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{20}$ is $C_{3-8}$ cycloalkyl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{20}$ is heterocyclyl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{20}$ is aryl. In another embodiment, $R_{20}$ is heteroaryl optionally substituted with one or more H, halogen, —CN, —OH, $C_{1-6}$ alkyl, $C_{1-6}$ alkoxy, $C_{3-8}$ cycloalkyl, heterocyclyl, heteroaryl, or aryl.

In other embodiments of the compounds of Formula I, $R_{21}$ is —H, $C_{1-6}$ alkyl, or —C(O)$R_{22}$. In one embodiment, $R_{21}$ is —H. In one embodiment, $R_{21}$ is $C_{1-6}$ alkyl. In one embodiment, $R_{21}$ is —C(O)$R_{22}$.

In other embodiment of the compounds of Formula I, $R_{22}$ is —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl. In another embodiment, $R_{22}$ is —H. In another embodiment, $R_{22}$ is $C_{1-6}$ alkyl. In another embodiment, $R_{22}$ is $C_{1-6}$ alkoxy. In another embodiment, $R_{22}$ is $C_{2-6}$ alkenyl. In another embodiment, $R_{22}$ is $C_{2-6}$ alkynyl. In another embodiment, $R_{22}$ is $C_{3-8}$ cycloalkyl. In another embodiment, $R_{22}$ is heterocyclyl. In another embodiment, $R_{22}$ is aryl. In another embodiment, $R_{22}$ is heteroaryl.

In one embodiment, p is 1, 2, 3, or 4. In another embodiment p is 1, 2, or 3. In another embodiment p is 1 or 2. In another embodiment p is 1. In another embodiment p is 2. In another embodiment p is 3. In another embodiment p is 4.

In one embodiment, n is 1, 2, 3, or 4. In another embodiment n is 1, 2, or 3. In another embodiment n is 1 or 2. In another embodiment n is 1. In another embodiment n is 2. In another embodiment n is 3. In another embodiment n is 4.

In one embodiment, m is 1, 2, 3, or 4. In another embodiment m is 1, 2, or 3. In another embodiment m is 1 or 2. In another embodiment m is 1. In another embodiment m is 2. In another embodiment m is 3. In another embodiment m is 4.

In one embodiment, o is 1, 2, or 3. In another embodiment o is 1 or 2. In another embodiment o is 1. In another embodiment o is 2. In another embodiment o is 3.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —NH—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —NH—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{1-6}$ alkyl)-, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{1-6}$ alkyl)-, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{3-8}$ cycloalkyl)-, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{3-8}$ cycloalkyl)-, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(aryl)-, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N(aryl)-, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)S(O)$_2$$R_6$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is —N($R_5$)S(O)$_2$$R_6$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is heteroaryl, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is heteroaryl wherein heteroaryl is optionally substituted with one or more $R_7$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$.

In some embodiments of the compounds of Formula I, $R_1$ is heteroaryl, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is heteroaryl wherein heteroaryl is optionally substituted with one or more $R_7$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —NH—, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —NH—, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{1-6}$ alkyl)-, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{1-6}$ alkyl)-, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{3-8}$ cycloalkyl)-, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N($C_{3-8}$ cycloalkyl)-, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(aryl)-, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N(aryl)-, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is a bond, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is a bond, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —O—, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —O—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is —O—, Ring A1 is a 6-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —O—, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —O—, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —O—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —N($C_{1-6}$ alkyl)-, Ring A1 is a 5-membered heteroaryl, Ring A2 is heteroaryl optionally substituted with one or more $R_5$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —N($C_{1-6}$ alkyl)-, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —N(heteroaryl)-, $R_2$ is H, $R_3$ is $C_{1-6}$ alkyl, $R_4$ is —H, G is —N($C_{1-6}$ alkyl)-, Ring A1 is a 6-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —N($C_{1-6}$ alkyl)-, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —N($C_{1-6}$ alkyl)-, Ring A1 is a 5-membered heteroaryl, Ring A2 is heteroaryl optionally substituted with one or more $R_8$.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —N($C_{1-6}$ alkyl)-, Ring A1 is a 6-membered heteroaryl, Ring A2 is heteroaryl optionally substituted with one or more $R_8$.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{11}$, $R_{11}$ is aryl or heteroaryl optionally substituted with one or more $R_{15}$, $R_{15}$ is —N($R_{22}$)C(O)-Q-N($R_{22}$)—F, or —N($R_{22}$)-Q-N($R_{22}$)—F.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{11}$, $R_{11}$ is aryl or heteroaryl optionally substituted with one or more $R_{15}$, $R_{15}$ is —N($R_{22}$)C(O)-Q-N($R_{22}$)—F, or —N($R_{22}$)-Q-N($R_{22}$)—F.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_5$, $R_5$ is —N($R_9$)C(O)$R_{11}$, Rn is aryl or heteroaryl optionally substituted with one or more $R_{15}$, $R_{15}$ is —N($R_{22}$)C(O)-Q-N($R_{22}$)—F, or —N($R_{22}$)-Q-N($R_{22}$)—F.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_1$, $R_1$ is aryl or heteroaryl optionally substituted with one or more $R_{18}$, $R_{18}$ is —N($R_{22}$)C(O)-Q-N($R_{22}$)—F, or —N($R_{22}$)-Q-N($R_{22}$)—F.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_1$, $R_1$ is aryl or heteroaryl optionally substituted with one or more $R_{18}$, $R_{18}$ is —N($R_{22}$)C(O)-Q-N($R_{22}$)—F, or —N($R_{22}$)-Q-N($R_{22}$)—F.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{11}$, R is aryl or heteroaryl optionally substituted with one or more $R_{18}$, $R_{18}$ is —N($R_{22}$)C(O)-Q-N($R_{22}$)—F, or —N($R_{22}$)-Q-N($R_{22}$)—F.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_{10}$ is $C_{1-6}$ alkyl, $C_{3-8}$ cycloalkyl, or heterocyclyl optionally substituted with one or more $R_{13}$, $R_{13}$ is alkyl optionally substituted with one or more $R_{15}$, $R_{15}$ is N($R_{22}$)C(O)—U—N($R_{22}$)—Z.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_{14}$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —N($R_5$)C(O)$R_6$, W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_{14}$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_{14}$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —C(O)N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_{14}$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 5-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_{14}$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —S(O)$_2$N($R_5$)($R_6$), W is —O—, $R_2$ is H, $R_3$ is $C_{1-6}$ alkyl, $R_4$ is —H, G is —NH—, Ring A1 is a 6-membered heteroaryl, Ring A2 is heteroaryl optionally substituted with one or more $R_8$, $R_8$ is —N($R_9$)C(O)$R_{10}$, $R_9$ and $R_{10}$ are taken together with the atom to which they are each attached form a heterocycle ring optionally substituted with one or more $R_4$, $R_{14}$ is $C_{1-6}$ alkyl, heterocycle, $C_{3-6}$ cycloalkyl, or aryl optionally substituted with one or more $R_{16}$, $R_{16}$ is $C_{3-8}$ cycloalkyl, heterocyclyl, heteroaryl, or aryl optionally substituted with one or more $R_{17}$, $R_{17}$ is —N($R_{22}$)C(O)—V—N($R_{22}$)-E.

In some embodiments of the compounds of Formula I, $R_1$ is —N($R_5$)C(O)$R_6$, W is —O—, $R_2$ is H, $R_3$ and $R_4$ are taken together with the atom to which they are attached form a $C_{3-8}$ cycloalkyl or heterocyclyl, G is —NH—, Ring A1 is a 6-membered heteroaryl, Ring A2 is heteroaryl optionally substituted with one or more $R_5$.

In some embodiments of the compounds of Formula I, $R_1$ is —N($R_5$)C(O)$R_6$, W is —NH—, $R_2$ is H, $R_3$ and $R_4$ when taken together with the atom to which they are attached form a $C_{3-8}$ cycloalkyl or heterocyclyl, G is —NH—, Ring A1 is a 5-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ and $R_4$ when taken together with the atom to which they are attached form a $C_{3-8}$ cycloalkyl or heterocyclyl, G is —NH—, Ring A1 is a 5-membered heteroaryl, Ring A2 is heteroaryl optionally substituted with one or more $R_5$.

In some embodiments of the compounds of Formula I, $R_1$ is —C(O)N($R_5$)($R_6$), W is —O—, $R_2$ is H, $R_3$ and $R_4$ when taken together with the atom to which they are attached form a $C_{3-8}$ cycloalkyl or heterocyclyl, G is —NH—, Ring A1 is a 6-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ and $R_4$ when taken together with the atom to which they are attached form a $C_{3-8}$ cycloalkyl or heterocyclyl, G is —NH—, Ring A1 is a 5-membered heteroaryl, Ring A2 is heteroaryl optionally substituted with one or more $R_5$.

In some embodiments of the compounds of Formula I, $R_1$ is —S(O)$_2$N($R_5$)($R_6$), W is —O—, $R_2$ is H, $R_3$ and $R_4$ when taken together with the atom to which they are attached form a $C_{3-8}$ cycloalkyl or heterocyclyl, G is —NH—, Ring A1 is a 6-membered heteroaryl, Ring A2 is heteroaryl optionally substituted with one or more $R_5$.

Non-limiting illustrative compounds of the present disclosure include:

N,N,5-trimethyl-3-((5-(2-oxopyrrolidin-1-yl)pyridin-3-yl)amino)-5H-chromeno[4,3-c]pyridine-8-carboxamide;

N,N,5-trimethyl-3-(pyridin-3-ylamino)-5H-chromeno[4,3-c]pyridine-8-carboxamide;

1-(3-((1-acetyl-2,3-dihydro-1H-pyrido[2,3-b][1,4]oxazin-7-yl)amino)-5-methyl-5H-chromeno[4,3-c]pyridin-8-yl)pyrrolidin-2-one;

5-cyclopropyl-N,N-dimethyl-3-((5-(2-oxopyrrolidin-1-yl)pyridin-3-yl)amino)-5H-chromeno[4,3-c]pyridine-8-carboxamide;

1-(3-((5-(difluoromethoxy)pyridin-3-yl)amino)-5-methyl-5H-chromeno[4,3-c]pyridin-8-yl)pyrrolidin-2-one;

N,N,5-trimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide;

(6aS)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

5-cyclopropyl-N,N-dimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide;

1-(5-((5-methyl-8-(2-oxopyrrolidin-1-yl)-5H-chromeno[4,3-c]pyridin-3-yl)amino)pyridin-3-yl)cyclopropane-1-carbonitrile;

5-cyclopropyl-N,N-dimethyl-3-(pyridin-3-ylamino)-5H-chromeno[4,3-c]pyridine-8-carboxamide;

1-(5-methyl-3-(pyridin-3-ylamino)-5H-chromeno[4,3-c]pyridin-8-yl)pyrrolidin-2-one;

1-methyl-3-(5-((5-methyl-8-(2-oxopyrrolidin-1-yl)-5H-chromeno[4,3-c]pyridin-3-yl)amino)pyridin-3-yl)imidazolidin-2-one;

N,N,5,6-tetramethyl-3-(pyridin-3-ylamino)-5,6-dihydrobenzo[c][2,6]naphthyridine-8-carboxamide;

N-methyl-N-(5-((5-methyl-8-(2-oxopyrrolidin-1-yl)-5H-chromeno[4,3-c]pyridin-3-yl)amino)pyridin-3-yl)methanesulfonamide;

1-(5-methyl-3-((1-(methylsulfonyl)-2,3-dihydro-TH-pyrido[2,3-b][1,4]oxazin-7-yl)amino)-5H-chromeno[4,3-c]pyridin-8-yl)pyrrolidin-2-one;

1-(3-((5-fluoropyridin-3-yl)amino)-5-methyl-5H-chromeno[4,3-c]pyridin-8-yl)pyrrolidin-2-one;

1-(3-((1-(cyclopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one;

(S)-2-(((R)-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(S)-2-(((S)-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

1-(5-methyl-3-((5-(2-oxopyrrolidin-1-yl)pyridin-3-yl)amino)-5H-chromeno[4,3-c]pyridin-8-yl)pyrrolidin-2-one;

1-(5-methyl-3-(pyrido[2,3-b]pyrazin-7-ylamino)-5H-chromeno[4,3-c]pyridin-8-yl)pyrrolidin-2-one;

1-(3-((1,5-naphthyridin-3-yl)amino)-5-methyl-5H-chromeno[4,3-c]pyridin-8-yl)pyrrolidin-2-one;
1-(5-methyl-3-(pyrimidin-5-ylamino)-5H-chromeno[4,3-c]pyridin-8-yl)pyrrolidin-2-one;
N-cyclopropyl-N-(5-((5-methyl-8-(2-oxopyrrolidin-1-yl)-5H-chromeno[4,3-c]pyridin-3-yl)amino)pyridin-3-yl)methanesulfonamide;
1-(5-methyl-3-((1-(methylsulfonyl)-1H-pyrrolo[3,2-b]pyridin-6-yl)amino)-5H-chromeno[4,3-c]pyridin-8-yl)pyrrolidin-2-one;
1-(5-methyl-3-((1-pivaloyl-2,3-dihydro-1H-pyrido[2,3-b][1,4]oxazin-7-yl)amino)-5H-chromeno[4,3-c]pyridin-8-yl)pyrrolidin-2-one;
1-(5-((5-methyl-8-(2-oxopyrrolidin-1-yl)-5H-chromeno[4,3-c]pyridin-3-yl)amino)pyridin-3-yl)imidazolidin-2-one;
1-(3-((2,3-dihydro-[1,4]dioxino[2,3-b]pyridin-7-yl)amino)-5-methyl-5H-chromeno[4,3-c]pyridin-8-yl)pyrrolidin-2-one;
1-(5-methyl-3-(thiazolo[5,4-b]pyridin-6-ylamino)-5H-chromeno[4,3-c]pyridin-8-yl)pyrrolidin-2-one;
1-(3-((1-(cyclopropanecarbonyl)-2,3-dihydro-1H-pyrido[2,3-b][1,4]oxazin-7-yl)amino)-5-methyl-5H-chromeno[4,3-c]pyridin-8-yl)pyrrolidin-2-one;
3-((1-(cyclopropylsulfonyl)-2,3-dihydro-TH-pyrido[2,3-b][1,4]oxazin-7-yl)amino)-N,N,5-trimethyl-5H-chromeno[4,3-c]pyridine-8-carboxamide;
N,N,5-trimethyl-3-((1-pivaloyl-2,3-dihydro-1H-pyrido[2,3-b][1,4]oxazin-7-yl)amino)-5H-chromeno[4,3-c]pyridine-8-carboxamide;
3-((1-(cyclopropanecarbonyl)-2,3-dihydro-TH-pyrido[2,3-b][1,4]oxazin-7-yl)amino)-N,N,5-trimethyl-5H-chromeno[4,3-c]pyridine-8-carboxamide;
3-((1-acetyl-2,3-dihydro-1H-pyrido[2,3-b][1,4]oxazin-7-yl)amino)-N,N,5-trimethyl-5H-chromeno[4,3-c]pyridine-8-carboxamide;
N,N,5-trimethyl-3-((1-(methylsulfonyl)-2,3-dihydro-1H-pyrido[2,3-b][1,4]oxazin-7-yl)amino)-5H-chromeno[4,3-c]pyridine-8-carboxamide;
1-(5-methyl-3-((5-(trifluoromethyl)pyridin-3-yl)amino)-5H-chromeno[4,3-c]pyridin-8-yl)pyrrolidin-2-one;
N-(2-methoxy-5-((5-methyl-8-(2-oxopyrrolidin-1-yl)-5H-chromeno[4,3-c]pyridin-3-yl)amino)pyridin-3-yl)acetamide;
N-(2-methoxy-5-((5-methyl-8-(2-oxopyrrolidin-1-yl)-5H-chromeno[4,3-c]pyridin-3-yl)amino)pyridin-3-yl)methanesulfonamide;
1-(3-((1-isobutyryl-2,3-dihydro-1H-pyrido[2,3-b][1,4]oxazin-7-yl)amino)-5-methyl-5H-chromeno[4,3-c]pyridin-8-yl)pyrrolidin-2-one;
(S)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
N-(2-methoxy-5-((5-methyl-8-(2-oxopyrrolidin-1-yl)-5H-chromeno[4,3-c]pyridin-3-yl)amino)pyridin-3-yl)-N-methylmethanesulfonamide;
1-(5-((5-methyl-8-(2-oxopyrrolidin-1-yl)-5H-chromeno[4,3-c]pyridin-3-yl)amino)pyridin-3-yl)-3-(thiazol-4-ylmethyl)imidazolidin-2-one;
methyl 7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate;
1-(5-methyl-3-((5-(methylsulfonyl)pyridin-3-yl)amino)-5H-chromeno[4,3-c]pyridin-8-yl)pyrrolidin-2-one;
1-(3-((1-(2-hydroxyacetyl)-2,3-dihydro-1H-pyrido[2,3-b][1,4]oxazin-7-yl)amino)-5-methyl-5H-chromeno[4,3-c]pyridin-8-yl)pyrrolidin-2-one;
methyl 7-((8-(dimethylcarbamoyl)-5-methyl-5H-chromeno[4,3-c]pyridin-3-yl)amino)-2,3-dihydro-1H-pyrido[2,3-b][1,4]oxazine-1-carboxylate;
N-(2-methoxy-5-((5-methyl-8-(2-oxopyrrolidin-1-yl)-5H-chromeno[4,3-c]pyridin-3-yl)amino)pyridin-3-yl)-N-methylacetamide;
1-(5,6-dimethyl-3-(pyridin-3-ylamino)-5,6-dihydrobenzo[c][2,6]naphthyridin-8-yl)pyrrolidin-2-one;
1-(9-fluoro-5-methyl-3-(pyridin-3-ylamino)-5H-chromeno[4,3-c]pyridin-8-yl)pyrrolidin-2-one;
(6aS)-2-((5,6-dimethyl-8-(2-oxopyrrolidin-1-yl)-5,6-dihydrobenzo[c][2,6]naphthyridin-3-yl)amino)-6,6a,7,8-tetrahydro-9H-pyrido[2,3-b]pyrrolo[1,2-d][1,4]oxazin-9-one;
methyl 7-((8-(2-oxopyrrolidin-1-yl)-5H-chromeno[4,3-c]pyridin-3-yl)amino)-2,3-dihydro-1H-pyrido[2,3-b][1,4]oxazine-1-carboxylate;
(S)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(5-methyl-3-((5-morpholinopyridin-3-yl)amino)-5H-chromeno[4,3-c]pyridin-8-yl)pyrrolidin-2-one;
1-(3-((1-(2-hydroxy-2-methylpropanoyl)-2,3-dihydro-1H-pyrido[2,3-b][1,4]oxazin-7-yl)amino)-5-methyl-5H-chromeno[4,3-c]pyridin-8-yl)pyrrolidin-2-one;
1-(3-((1-(cyclopropanecarbonyl)-2,3-dihydro-1H-pyrido[2,3-b][1,4]oxazin-7-yl)amino)-5H-chromeno[4,3-c]pyridin-8-yl)pyrrolidin-2-one;
1-(3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one;
(S)-2-((8-(2-oxopyrrolidin-1-yl)spiro[chromeno[4,3-c]pyridine-5,3'-oxetan]-3-yl)amino)-6,6a,7,8-tetrahydro-9H-pyrido[2,3-b]pyrrolo[1,2-d][1,4]oxazin-9-one;
(S)-2-((8-(2-oxopyrrolidin-1-yl)spiro[chromeno[4,3-c]pyridine-5,1'-cyclobutan]-3-yl)amino)-6,6a,7,8-tetrahydro-9H-pyrido[2,3-b]pyrrolo[1,2-d][1,4]oxazin-9-one;
7-((5-methyl-8-(2-oxopyrrolidin-1-yl)-5H-chromeno[4,3-c]pyridin-3-yl)amino)-1H-pyrido[2,3-b][1,4]oxazin-2(3H)-one;
1-(3-((2,3-dihydro-1H-pyrido[2,3-b][1,4]oxazin-7-yl)amino)-5-methyl-5H-chromeno[4,3-c]pyridin-8-yl)pyrrolidin-2-one;
1-(5-methyl-3-((5-methylpyridin-3-yl)amino)-5H-chromeno[4,3-c]pyridin-8-yl)pyrrolidin-2-one;
(6aS)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(3-((2,3-dihydro-[1,4]dioxino[2,3-b]pyridin-7-yl)amino)-5,6-dimethyl-5,6-dihydrobenzo[c][2,6]naphthyridin-8-yl)pyrrolidin-2-one;
1-(3-((1-(cyclopropylsulfonyl)-2,3-dihydro-1H-pyrido[2,3-b][1,4]oxazin-7-yl)amino)-5H-chromeno[4,3-c]pyridin-8-yl)pyrrolidin-2-one;
1-(3-((1-(isopropylsulfonyl)-2,3-dihydro-1H-pyrido[2,3-b][1,4]oxazin-7-yl)amino)-5H-chromeno[4,3-c]pyridin-8-yl)pyrrolidin-2-one;
4-(5-((5-methyl-8-(2-oxopyrrolidin-1-yl)-5H-chromeno[4,3-c]pyridin-3-yl)amino)pyridin-3-yl)morpholin-3-one;
1-(3-((1-(1-hydroxycyclopropane-1-carbonyl)-2,3-dihydro-1H-pyrido[2,3-b][1,4]oxazin-7-yl)amino)-5-methyl-5H-chromeno[4,3-c]pyridin-8-yl)pyrrolidin-2-one;
1-(3-((1-(2-hydroxypropanoyl)-2,3-dihydro-1H-pyrido[2,3-b][1,4]oxazin-7-yl)amino)-5-methyl-5H-chromeno[4,3-c]pyridin-8-yl)pyrrolidin-2-one;
1-(3-((1-(isopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one;

(S)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

N-(5-((5-methyl-8-(2-oxopyrrolidin-1-yl)-5H-chromeno[4,3-c]pyridin-3-yl)amino)pyridin-3-yl)acetamide;

1-benzyl-3-(5-((5-methyl-8-(2-oxopyrrolidin-1-yl)-5H-chromeno[4,3-c]pyridin-3-yl)amino)pyridin-3-yl)urea;

3-amino-N-(5-((5-methyl-8-(2-oxopyrrolidin-1-yl)-5H-chromeno[4,3-c]pyridin-3-yl)amino)pyridin-3-yl)benzamide;

1-(5-methyl-3-(pyridazin-4-ylamino)-5H-chromeno[4,3-c]pyridin-8-yl)pyrrolidin-2-one;

1-(5-methyl-3-(pyridazin-3-ylamino)-5H-chromeno[4,3-c]pyridin-8-yl)pyrrolidin-2-one;

1-(5-((9-fluoro-5,5-dimethyl-8-(2-oxopyrrolidin-1-yl)-5H-chromeno[4,3-c]pyridin-3-yl)amino)pyridin-3-yl)imidazolidin-2-one;

1-methyl-3-(5-((5-methyl-8-(2-oxopyrrolidin-1-yl)-5H-chromeno[4,3-c]pyridin-3-yl)amino)pyridin-3-yl)urea;

N-(5-((5-methyl-8-(2-oxopyrrolidin-1-yl)-5H-chromeno[4,3-c]pyridin-3-yl)amino)pyridin-3-yl)-3-phenylpropanamide;

N-(5-((5-methyl-8-(2-oxopyrrolidin-1-yl)-5H-chromeno[4,3-c]pyridin-3-yl)amino)pyridin-3-yl)-2-phenylacetamide;

(1S,2S)—N-(5-((5-methyl-8-(2-oxopyrrolidin-1-yl)-5H-chromeno[4,3-c]pyridin-3-yl)amino)pyridin-3-yl)-2-phenylcyclopropane-1-carboxamide;

N-(5-((5-methyl-8-(2-oxopyrrolidin-1-yl)-5H-chromeno[4,3-c]pyridin-3-yl)amino)pyridin-3-yl)picolinamide;

N-(5-((5-methyl-8-(2-oxopyrrolidin-1-yl)-5H-chromeno[4,3-c]pyridin-3-yl)amino)pyridin-3-yl)nicotinamide;

N-(5-((5-methyl-8-(2-oxopyrrolidin-1-yl)-5H-chromeno[4,3-c]pyridin-3-yl)amino)pyridin-3-yl)isonicotinamide;

4-fluoro-N-(5-((5-methyl-8-(2-oxopyrrolidin-1-yl)-5H-chromeno[4,3-c]pyridin-3-yl)amino)pyridin-3-yl)benzamide;

3-fluoro-N-(5-((5-methyl-8-(2-oxopyrrolidin-1-yl)-5H-chromeno[4,3-c]pyridin-3-yl)amino)pyridin-3-yl)benzamide;

3-methoxy-N-(5-((5-methyl-8-(2-oxopyrrolidin-1-yl)-5H-chromeno[4,3-c]pyridin-3-yl)amino)pyridin-3-yl)benzamide;

4-methoxy-N-(5-((5-methyl-8-(2-oxopyrrolidin-1-yl)-5H-chromeno[4,3-c]pyridin-3-yl)amino)pyridin-3-yl)benzamide;

1-(5-methyl-3-((5-(pyridin-2-ylamino)pyridin-3-yl)amino)-5H-chromeno[4,3-c]pyridin-8-yl)pyrrolidin-2-one;

1-(5-methyl-3-((5-(pyridazin-3-ylamino)pyridin-3-yl)amino)-5H-chromeno[4,3-c]pyridin-8-yl)pyrrolidin-2-one;

N-(5-((5-methyl-8-(2-oxopyrrolidin-1-yl)-5H-chromeno[4,3-c]pyridin-3-yl)amino)pyridin-3-yl)-3-phenylbutanamide;

2-methyl-N-(5-((5-methyl-8-(2-oxopyrrolidin-1-yl)-5H-chromeno[4,3-c]pyridin-3-yl)amino)pyridin-3-yl)-3-phenylpropanamide;

N-(5-((5-methyl-8-(2-oxopyrrolidin-1-yl)-5H-chromeno[4,3-c]pyridin-3-yl)amino)pyridin-3-yl)tetrahydrofuran-2-carboxamide;

N-(5-((5-methyl-8-(2-oxopyrrolidin-1-yl)-5H-chromeno[4,3-c]pyridin-3-yl)amino)pyridin-3-yl)benzo[d][1,3]dioxole-5-carboxamide;

N-(5-((5-methyl-8-(2-oxopyrrolidin-1-yl)-5H-chromeno[4,3-c]pyridin-3-yl)amino)pyridin-3-yl)benzo[d][1,3]dioxole-4-carboxamide;

1-(5-methyl-3-((5-(methylsulfonyl)quinolin-3-yl)amino)-5H-chromeno[4,3-c]pyridin-8-yl)pyrrolidin-2-one;

methyl 7-((9-fluoro-5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate;

N-(5-((5-methyl-8-(2-oxopyrrolidin-1-yl)-5H-chromeno[4,3-c]pyridin-3-yl)amino)pyridin-3-yl)-2-oxopyrrolidine-3-carboxamide;

N-(5-((5-methyl-8-(2-oxopyrrolidin-1-yl)-5H-chromeno[4,3-c]pyridin-3-yl)amino)pyridin-3-yl)-2,3-dihydro-1H-indene-2-carboxamide;

N-(5-((5-methyl-8-(2-oxopyrrolidin-1-yl)-5H-chromeno[4,3-c]pyridin-3-yl)amino)pyridin-3-yl)pyrazolo[1,5-a]pyridine-2-carboxamide;

N-(5-((5-methyl-8-(2-oxopyrrolidin-1-yl)-5H-chromeno[4,3-c]pyridin-3-yl)amino)pyridin-3-yl)-2,3-dihydrobenzofuran-2-carboxamide;

methyl (5-((5-methyl-8-(2-oxopyrrolidin-1-yl)-5H-chromeno[4,3-c]pyridin-3-yl)amino)pyridin-3-yl)carbamate;

4-((5-((5-methyl-8-(2-oxopyrrolidin-1-yl)-5H-chromeno[4,3-c]pyridin-3-yl)amino)pyridin-3-yl)amino)-4-oxobutanoic acid;

N-(5-((5-methyl-8-(2-oxopyrrolidin-1-yl)-5H-chromeno[4,3-c]pyridin-3-yl)amino)pyridin-3-yl)-1H-indole-6-carboxamide;

N-(5-((5-methyl-8-(2-oxopyrrolidin-1-yl)-5H-chromeno[4,3-c]pyridin-3-yl)amino)pyridin-3-yl)-1H-indole-4-carboxamide;

N-(5-((5-methyl-8-(2-oxopyrrolidin-1-yl)-5H-chromeno[4,3-c]pyridin-3-yl)amino)pyridin-3-yl)-1H-benzo[d]imidazole-7-carboxamide;

N-(5-((5-methyl-8-(2-oxopyrrolidin-1-yl)-5H-chromeno[4,3-c]pyridin-3-yl)amino)pyridin-3-yl)imidazo[1,2-a]pyridine-2-carboxamide;

N-(5-((5-methyl-8-(2-oxopyrrolidin-1-yl)-5H-chromeno[4,3-c]pyridin-3-yl)amino)pyridin-3-yl)-1H-indole-2-carboxamide;

2-(imidazo[1,2-a]pyridin-3-yl)-N-(5-((5-methyl-8-(2-oxopyrrolidin-1-yl)-5H-chromeno[4,3-c]pyridin-3-yl)amino)pyridin-3-yl)acetamide;

1-(5-((9-fluoro-5-methyl-8-(2-oxopyrrolidin-1-yl)-5H-chromeno[4,3-c]pyridin-3-yl)amino)pyridin-3-yl)imidazolidin-2-one;

4-formamido-3-hydroxy-N-(5-((5-methyl-8-(2-oxopyrrolidin-1-yl)-5H-chromeno[4,3-c]pyridin-3-yl)amino)pyridin-3-yl)benzamide;

N-(5-((5-methyl-8-(2-oxopyrrolidin-1-yl)-5H-chromeno[4,3-c]pyridin-3-yl)amino)pyridin-3-yl)pyridazine-4-carboxamide;

6-amino-N-(5-((5-methyl-8-(2-oxopyrrolidin-1-yl)-5H-chromeno[4,3-c]pyridin-3-yl)amino)pyridin-3-yl)pyrazine-2-carboxamide;

2-hydroxy-N-(5-((5-methyl-8-(2-oxopyrrolidin-1-yl)-5H-chromeno[4,3-c]pyridin-3-yl)amino)pyridin-3-yl)-3-phenylpropanamide;

N-(5-((5-methyl-8-(2-oxopyrrolidin-1-yl)-5H-chromeno[4,3-c]pyridin-3-yl)amino)pyridin-3-yl)imidazo[1,2-a]pyridine-3-carboxamide;

N-(5-((5-methyl-8-(2-oxopyrrolidin-1-yl)-5H-chromeno[4,3-c]pyridin-3-yl)amino)pyridin-3-yl)pyrazolo[1,5-a]pyridine-3-carboxamide;

1-(3-((2,3-dihydro-[1,4]dioxino[2,3-b]pyridin-7-yl)amino)-5,5-dimethyl-5H-chromeno[4,3-c]pyridin-8-yl)pyrrolidin-2-one;

1-(3-((2,3-dihydro-[1,4]dioxino[2,3-b]pyridin-7-yl)amino)-9-fluoro-5-methyl-5H-chromeno[4,3-c]pyridin-8-yl)pyrrolidin-2-one;

1-(3-((2,3-dihydro-[1,4]dioxino[2,3-b]pyridin-7-yl)amino)-9-fluoro-5,5-dimethyl-5H-chromeno[4,3-c]pyridin-8-yl)pyrrolidin-2-one;

2-hydroxy-N-(5-((5-methyl-8-(2-oxopyrrolidin-1-yl)-5H-chromeno[4,3-c]pyridin-3-yl)amino)pyridin-3-yl)acetamide;

N-(5-((5-methyl-8-(2-oxopyrrolidin-1-yl)-5H-chromeno[4,3-c]pyridin-3-yl)amino)pyridin-3-yl)benzo[d]oxazole-6-carboxamide;

1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-5-carboxamide;

N-(5-((5-methyl-8-(2-oxopyrrolidin-1-yl)-5H-chromeno[4,3-c]pyridin-3-yl)amino)pyridazin-3-yl)acetamide;

N-(5-((5-methyl-8-(2-oxopyrrolidin-1-yl)-5H-chromeno[4,3-c]pyridin-3-yl)amino)pyridin-3-yl)imidazo[1,2-a]pyridine-7-carboxamide;

1-(3-((2,3-dihydro-[1,4]dioxino[2,3-b]pyridin-7-yl)amino)-5H-chromeno[4,3-c]pyridin-8-yl)pyrrolidin-2-one;

1-(5-((5-methyl-8-(2-oxopyrrolidin-1-yl)-5H-chromeno[4,3-c]pyridin-3-yl)amino)pyridin-3-yl)-3-(pyridin-2-yl)urea;

1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-6-carboxamide;

N-(5-((5-methyl-8-(2-oxopyrrolidin-1-yl)-5H-chromeno[4,3-c]pyridin-3-yl)amino)pyridin-3-yl)imidazo[1,2-a]pyridine-5-carboxamide;

1-(3-((2,3-dihydro-[1,4]dioxino[2,3-b]pyridin-7-yl)amino)-9-fluoro-5H-chromeno[4,3-c]pyridin-8-yl)pyrrolidin-2-one;

1-(5-methyl-4-(pyridin-4-yl)-5H-chromeno[4,3-c]pyridin-8-yl)pyrrolidin-2-one;

1-(3-((5-(4-(3-methoxypropanoyl)piperazin-1-yl)pyridin-3-yl)amino)-5H-chromeno[4,3-c]pyridin-8-yl)pyrrolidin-2-one;

1-(3-((5-(4-(3-methoxypropanoyl)piperazin-1-yl)pyridin-3-yl)amino)-5-methyl-5H-chromeno[4,3-c]pyridin-8-yl)pyrrolidin-2-one;

1-(3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one;

(E)-4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)but-2-enamide;

2-amino-N-(5-((5-methyl-8-(2-oxopyrrolidin-1-yl)-5H-chromeno[4,3-c]pyridin-3-yl)amino)pyridin-3-yl)isonicotinamide;

1-(9-fluoro-3-((5-(4-(3-methoxypropanoyl)piperazin-1-yl)pyridin-3-yl)amino)-5H-chromeno[4,3-c]pyridin-8-yl)pyrrolidin-2-one;

1-(9-fluoro-3-((5-(4-(3-methoxypropanoyl)piperazin-1-yl)pyridin-3-yl)amino)-5-methyl-5H-chromeno[4,3-c]pyridin-8-yl)pyrrolidin-2-one;

1-(9-fluoro-3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one;

1-(5-((8-(2-oxopyrrolidin-1-yl)-5H-chromeno[4,3-c]pyridin-3-yl)amino)pyridin-3-yl)imidazolidin-2-one;

(E)-4-(4-(dimethylamino)but-2-enamido)-N-(5-((5-methyl-8-(2-oxopyrrolidin-1-yl)-5H-chromeno[4,3-c]pyridin-3-yl)amino)pyridin-3-yl)benzamide;

(6aS)-8,8-dimethyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(6aS)-2-((9-fluoro-5-methyl-8-(2-oxopyrrolidin-1-yl)-5H-chromeno[4,3-c]pyridin-3-yl)amino)-8,8-dimethyl-6,6a,7,8-tetrahydro-9H-pyrido[2,3-b]pyrrolo[1,2-d][1,4]oxazin-9-one;

1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-4-carboxamide;

(6aR)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(6aS)-2-((9-fluoro-5-methyl-8-(2-oxopyrrolidin-1-yl)-5H-chromeno[4,3-c]pyridin-3-yl)amino)-8-methyl-6,6a,7,8-tetrahydro-9H-pyrido[2,3-b]pyrrolo[1,2-d][1,4]oxazin-9-one;

(6aR)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(R)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(R)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(R)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(6aS)-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)butanamide;

(E)-4-(dimethylamino)-N-(2-((3-(3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide;

(6a'S)-2'-((5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one;

(S)-2'-((5-(3-fluoro-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one;

(6a'S)-2'-((9-fluoro-5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one;

(E)-N-(5-((5,5-dimethyl-8-(2-oxopyrrolidin-1-yl)-5H-chromeno[4,3-c]pyridin-3-yl)amino)pyridin-3-yl)-4-(4-(dimethylamino)but-2-enamido)benzamide;

(E)-N-(3-(3-((5-((5,5-dimethyl-8-(2-oxopyrrolidin-1-yl)-5H-chromeno[4,3-c]pyridin-3-yl)amino)pyridin-3-yl)amino)-3-oxopropyl)phenyl)-4-(dimethylamino)but-2-enamide;

(E)-4-(4-(dimethylamino)but-2-enamido)-N-(5-((8-(2-oxopyrrolidin-1-yl)-5H-chromeno[4,3-c]pyridin-3-yl)amino)pyridin-3-yl)benzamide;

1-(5-((9-fluoro-8-(2-oxopyrrolidin-1-yl)-5H-chromeno[4,3-c]pyridin-3-yl)amino)pyridin-3-yl)imidazolidin-2-one;

1-(5-((5,5-dimethyl-8-(2-oxopyrrolidin-1-yl)-5H-chromeno[4,3-c]pyridin-3-yl)amino)pyridin-3-yl)imidazolidin-2-one;

(6aS)-2-((9-fluoro-5-methyl-8-(2-oxopyrrolidin-1-yl)-5H-chromeno[4,3-c]pyridin-3-yl)amino)-8-hydroxy-6,6a,7,8-tetrahydro-9H-pyrido[2,3-b]pyrrolo[1,2-d][1,4]oxazin-9-one;

(E)-4-(dimethylamino)-N-(2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide;
1-(4-(pyridin-4-yl)-5H-chromeno[4,3-c]pyridin-8-yl)pyrrolidin-2-one;
1-(5-methyl-4-(pyridin-4-ylamino)-5H-chromeno[4,3-c]pyridin-8-yl)pyrrolidin-2-one;
(S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;
(S)-2-((5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;
(3aR)-8-((5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one;
N-(5-((9-fluoro-5,5-dimethyl-8-(2-oxopyrrolidin-1-yl)-5H-chromeno[4,3-c]pyridin-3-yl)amino)-2-methoxypyridin-3-yl)acetamide;
N-(5-((5,5-dimethyl-8-(2-oxopyrrolidin-1-yl)-5H-chromeno[4,3-c]pyridin-3-yl)amino)-2-methoxypyridin-3-yl)acetamide;
1-(5-methyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one;
(6aS,8R)-2-((9-fluoro-5-methyl-8-(2-oxopyrrolidin-1-yl)-5H-chromeno[4,3-c]pyridin-3-yl)amino)-8-hydroxy-8-methyl-6,6a,7,8-tetrahydro-9H-pyrido[2,3-b]pyrrolo[1,2-d][1,4]oxazin-9-one;
(6aS,8R)-8-hydroxy-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(5,5-dimethyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one;
N-(5-((5-methyl-8-(2-oxopyrrolidin-1-yl)-5H-chromeno[4,3-c]pyridin-3-yl)amino)pyridin-3-yl)-1H-benzo[d]imidazole-4-carboxamide;
(3aR)-8-((9-fluoro-5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one;
4-(4-(dimethylamino)butanamido)-N-(5-((5-methyl-8-(2-oxopyrrolidin-1-yl)-5H-chromeno[4,3-c]pyridin-3-yl)amino)pyridin-3-yl)benzamide;
1-(5-methyl-3-(((S)-2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one;
(S)-1-(5,5-dimethyl-3-((2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one;
(6aS)-8-hydroxy-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(5-methyl-3-(oxazolo[4,5-b]pyridin-6-ylamino)-5H-chromeno[4,3-c]pyridin-8-yl)pyrrolidin-2-one;
1-(5,5-dimethyl-3-((1-methyl-2,3-dihydro-1H-pyrido[2,3-b][1,4]oxazin-7-yl)amino)-5H-chromeno[3,4-d]pyrimidin-8-yl)pyrrolidin-2-one;
(S)-2-((5,5-dimethyl-8-(4-methylisoxazol-3-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(S)-2-((5,5-dimethyl-8-(4-methyl-4H-1,2,4-triazol-3-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;
(S)-2-((5,5-dimethyl-8-(4-methyl-4H-1,2,4-triazol-3-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
N-(5-((5,5-dimethyl-8-(2-oxopyrrolidin-1-yl)-5H-chromeno[4,3-c]pyridin-3-yl)amino)pyridin-3-yl)-4-(2-(2-(2-(2-((2-(2,6-dioxopiperidin-3-yl)-1,3-dioxoisoindolin-4-yl)amino)ethoxy)ethoxy)ethoxy)acetamido)benzamide; and
N-(5-((5,5-dimethyl-8-(2-oxopyrrolidin-1-yl)-5H-chromeno[4,3-c]pyridin-3-yl)amino)pyridin-3-yl)-4-(4-(2-((2-(2,6-dioxopiperidin-3-yl)-1,3-dioxoisoindolin-4-yl)oxy)acetamido)butanamido)benzamide.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of PI5P4K. In one embodiment, the compounds of the present invention are inhibitors of PI5P4K.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Scheme 1 which comprise different sequences of assembling intermediates or compounds (II). Starting materials are either commercially available or made by known procedures in the reported literature or as illustrated below.

A compound of formula (I) may be obtained (Scheme 1) by starting from, for example, a compound of formula (II), wherein LG represents a leaving group including but not limited to, halogen (e.g., chlorine, bromine or iodine), or an alkyl-, aryl- or haloalkyl-sulfonate (such as triflate), and reacting said compound (II) with a compound of formula A2-G, wherein A2-G is defined below and represents a cyclic amine either as free base or a salt (such as HCl, TFA or acetic acid), optionally under the influence of a transition metal catalyst as described in for example *Metal-Catalyzed Cross-Coupling Reactions, 2nd Completely Revised and Enlarged Edition* by A. de Meijere and F. Diederich, Wiley VCH, 2004.

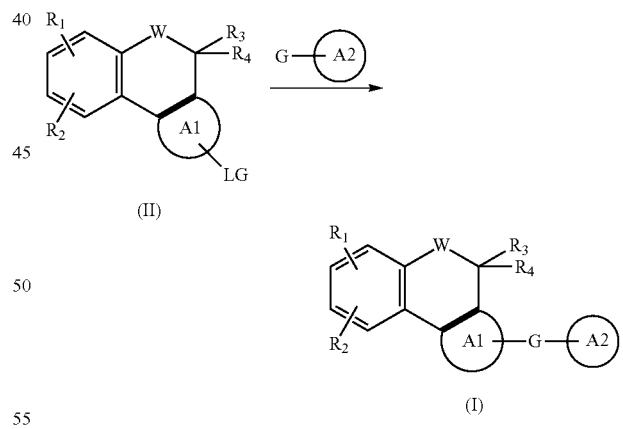

Scheme 1

The reaction may be carried out by coupling of a compound of formula (II), with an appropriate amine of formula A. The reaction may also be carried out using a suitable metal catalyst including, but not limited to, a palladium catalyst, e.g., di-tert-butylphosphinoferrocene palladium (II) dichloride, tetrakis(triphenylphosphine)palladium (0), palladium (II) diphenylphosphinoferrocene dichloride, palladium (II) acetate or bis(dibenzylideneacetone) palladium (0). Optionally a suitable ligand for example triphenylphosphine, tri-tert-butylphosphine or 2-(dicyclohexylphosphino) biphenyl or 2-dicyclohexylphosphino-2',4',6'-triisopropylbiphenyl is employed. Suitable base, including an (e.g., triethyl amine), an alkali metal or alkaline earth metal carbonate or hydroxide, or phosphate base, (e.g., potassium carbonate, sodium carbonate, cesium carbonate, sodium hydroxide, or potassium phosphate), may be used in the reaction. Said reaction may be performed at a temperature range between +20° C. and +160° C., in suitable solvents, including, but not limited to, toluene, tetrahydrofuran, 2-methyl-tetrahydrofuran, 1,4-dioxane, 1,2-dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (I) is obtained.

Compounds of formula (II) and A are commercially available compounds, or are known in the literature, or they are prepared by standard processes known in the art. A compound of formula (I), (II) or A may be separated into its enantiomers by standard processes known in the art by for example chromatography on a chiral stationary phase.

Methods of Using the Disclosed Compounds

Another aspect of the invention relates to a method of treating a disease or disorder associated with modulation of PI5P4K. The method comprises administering to a patient in need of a treatment for diseases or disorders associated with modulation of PI5P4K an effective amount the compositions and compounds of Formula (I).

In another aspect, the present invention is directed to a method of inhibiting PI5P4K. The method involves administering to a patient in need thereof an effective amount of a compound of Formula (I).

Another aspect of the present invention relates to a method of treating, preventing, inhibiting or eliminating a disease or disorder in a patient associated with the inhibition of PI5P4K, the method comprising administering to a patient in need thereof an effective amount of a compound of Formula (I). In one embodiment, the disease may be, but not limited to, cancer or cell proliferative disorder, a metabolic disorder, neurodegenerative disease, and an inflammatory disease.

The present invention also relates to the use of an inhibitor of PI5P4K for the preparation of a medicament used in the treatment, prevention, inhibition or elimination of a disease or condition mediated by PI5P4K, wherein the medicament comprises a compound of Formula (I).

In another aspect, the present invention relates to a method for the manufacture of a medicament for treating, preventing, inhibiting, or eliminating a disease or condition mediated by PI5P4K, wherein the medicament comprises a compound of Formula (I).

Another aspect of the present invention relates to a compound of Formula (I) for use in the manufacture of a medicament for treating a disease associated with inhibiting PI5P4K.

In another aspect, the present invention relates to the use of a compound of Formula (I) in the treatment of a disease associated with inhibiting PI5P4K.

Another aspect of the invention relates to a method of treating cancer. The method comprises administering to a patient in need thereof an effective amount of a compound of Formula (I).

In another aspect of the invention, the method relates to treating a cell proliferative disease. The method comprises administering to a patient in need thereof an effective amount of a compound of Formula (I).

In yet another aspect, the present invention relates to a method of treating a neurodegenerative disease. The method comprises administering to a patient in need thereof an effective amount of a compound of Formula (I).

In another aspect, the present invention relates to a method of treating an inflammatory disease or condition. The method comprises administering to a patient in need thereof an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of PI5P4K for the preparation of a medicament used in treatment, prevention, inhibition or elimination of a disease or disorder associated with cancer or cell proliferative disorder, a metabolic disorder, neurodegenerative disease, and an inflammatory disease.

In another embodiment, the present invention relates to a compound of Formula (I) or a pharmaceutical composition comprising a compound of the present invention and a pharmaceutically acceptable carrier used for the treatment of cancers or cell proliferatives disorders including, but not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In another embodiment, the present invention relates to a compound of Formula (I) or a pharmaceutical composition comprising a compound of the present invention and a pharmaceutically acceptable carrier used for the treatment of neurodegenerative diseases including, but not limited to, brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infaction including embolic occlusion and thrombotic occlusion as well as intracranial hemorrhage of any type, intracranial and intravertebral lesions, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

In another embodiment, the present invention relates to a compound of Formula (I) or a pharmaceutical composition comprising a compound of the present invention and a pharmaceutically acceptable carrier used for the treatment of inflammatory disease. In some embodiments, the inflammatory disease is associated with a metabolic disorder. In some embodiments the treated inflammation is associated with, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In yet another embodiment, the present invention relates to a compound of Formula (I) or a pharmaceutical composition comprising a compound of the present invention and a pharmaceutically acceptable carrier used for the treatment of a metabolic disease including, but not limited, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In another embodiment, the present invention relates to a compound of Formula (I) or a pharmaceutical composition comprising a compound of the present invention and a pharmaceutically acceptable carrier used for the treatment of inflammatory disease associated with inflammatory disease. In some embodiments the treated inflammation is associated with, but not limited to, ileitis, ulcerative colitis, Barrett's syndrome, or Crohn's disease.

In some embodiments, the patient is selected for treatment based on gene amplification and/or elevated tumor expression of PI5P4K. In other embodiments, the patient is selected for treatment based on gene amplification and/or elevated tumor expression of PI5P4Kα gene, PI5P4Kβ gene, or PI5P4Kγ gene. In other embodiments, the patient is selected for the treatment based on tumor expression of p53 mutations.

In some embodiments, administration of a compound of Formula (I) or a pharmaceutical composition comprising a compound of the present invention and a pharmaceutically acceptable carrier induces a change in the cell cycle or cell viability.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of PI5P4K including, cancer or cell proliferative disorder, a metabolic disorder, neurodegenerative disease, and an inflammatory disease, comprising administering to a patient suffering from at least one of said diseases or disorder a compound of Formula (I).

One therapeutic use of the compounds or compositions of the present invention which inhibit PI5P4K is to provide treatment to patients or subjects suffering from c cancer or cell proliferative disorder, a metabolic disorder, neurodegenerative disease, and an inflammatory disease.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios.

Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: the residual solvent signal of DMSO-d6 δ 2.5, CDCl3 δ 7.26 or Methanol-d4 δ 3.31. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% $NH_3$ or aqueous 0.1% acetic acid or aqueous 0.1% formic acid) and B (acetonitrile or methanol). Mass spectrometer (MS) analyses were performed in positive ion mode using electrospray ionization (ES+).

Preparative chromatography was run on a Gilson-PREP GX271 or GX281 with Trilution 1c as software on a reverse phase column. A linear gradient was applied using for example mobile phase A (aqueous 0.1% NH3 or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Abbreviations used in the following examples and elsewhere herein are:

atm atmosphere
br broad
Amphos (4-(N,N-Dimethylamino)phenyl)di-tert-butyl phosphine
anh. anhydrous
aq. aqueous
BINAP (±)-2,2'-Bis(diphenylphosphino)-1,1'-binaphthalene
BrettPhos 2-(dicyclohexylphosphino)3,6-dimethoxy-2',4',6'-triisopropyl-1,1'-biphenyl
BrettPhos Pd G3 [(2-Di-cyclohexylphosphino-3,6-dimethoxy-2',4',6'-triisopropyl-1,1'-biphenyl)-2-(2'-amino-1,1'-biphenyl)]palladium(II) methanesulfonate
BuLi butyl lithium
DCM dichloromethane
DIAD diisopropyl azodiformate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine
DMF N,N-dimethyl formamide
DMSO dimethyl sulfoxide
EDCI.HCl 1-(3-Dimethylaminopropyl)-3-ethylcarbodiimide Hydrochloride
EtOAc ethyl acetate
EtOH ethanol
h hour(s)
HBTU 3-[Bis(dimethylamino)methyliumyl]-3H-benzotriazol-1-oxide hexafluorophosphate
HPLC high pressure (or performance) liquid chromatography
KOtBu potassium tert-butoxide
LCMS liquid chromatography mass spectrometry
LHMDS Lithium bis(trimethylsilyl)amide
MeCN acetonitrile
2-MeTHF 2-methyl tetrahydrofuran
MeOH methanol
n-BuLi butyl lithium
NaOtBu sodium tert-butoxide
PEPPSI-iPr [1,3-Bis(2,6-Diisopropylphenyl)imidazol-2-ylidene](3-chloropyridyl)palladium(II) dichloride
PdCl$_2$(Amphos) Bis(di-tert-butyl(4-dimethylaminophenyl)phosphine)dichloropalladium(II)
Pd$_2$(dba)$_3$ Tris(dibenzylideneacetone)dipalladium(O)
Pd(OAc)$_2$ palladium(II) acetate
PdCl$_2$(dppf) [1,1'-Bis(diphenylphosphino)ferrocene]dichloropalladium(II)
quant. Quantitative
rac racemic mixture
rt room temperature
Rt retention time
sat. saturated
TBAB tetrabutylammonium bromide
TFA trifluoroacetic acid
THF tetrahydrofuran
XantPhos 4,5-Bis(diphenylphosphino)-9,9-dimethylxanthene
XPhos 2-Dicyclohexylphosphino-2',4',6'-triisopropylbiphenyl
ESI electrospray ionization
HATU [bis(dimethylamino)methylene]-1H-1,2,3-triazolo[4,5-b]pyridinium 3-oxide hexafluorophosphate
m multiplet
MeMgCl methylmagnesium chloride
MHz megahertz
min minutes
MS molecular sieves
MsCl methanesulfonyl chloride
MW microwave
NMR nuclear magnetic resonance
ppm parts per million
TLC thin layer chromatography Example 1: Intermediate 1—Methyl 4-(6-chloro-4-formyl-3-pyridyl)-3-fluoro-benzoate

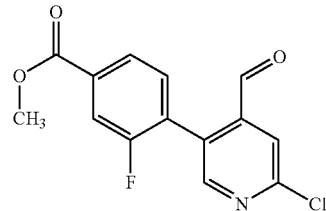 [SMILES: COC(=O)c1ccc(-c2cnc(Cl)cc2C=O)c(F)c1]

(2-Fluoro-4-methoxycarbonyl-phenyl)boronic acid (220 mg, 1.11 mmol), 5-bromo-2-chloro-pyridine-4-carbaldehyde (230 mg, 1.04 mmol), PdCl$_2$(PPh$_3$)$_2$ (37 mg, 0.05 mmol) and K$_2$CO$_3$ (360 mg, 2.61 mmol) were taken up in MeCN (5 ml) and water (1 ml) and the resulting mixture was stirred at 70° C. for 1 h. When cooled to rt the mixture was concentrated and the resulting residue was diluted with water (3 ml) and extracted with EtOAc (2×5 ml). The combined organics were purified on a silica gel column eluted with 0-50% EtOAc in heptane to give the product as a gum (210 mg, 69%). MS ES+ m/z 294 [M+H]$^+$.

Example 2: Intermediate 2—Methyl 4-[6-chloro-4-(1-hydroxyethyl)-3-pyridyl]-3-fluoro-benzoate

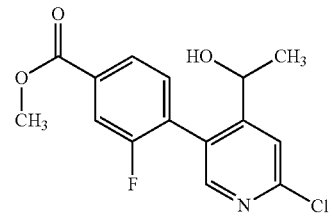 [SMILES: COC(=O)c1ccc(-c2cnc(Cl)cc2C(C)O)c(F)c1]

3M MeMgCl in THF (286 μl, 0.86) was added dropwise to a solution of methyl 4-(6-chloro-4-formyl-3-pyridyl)-3-fluoro-benzoate (210 mg, 0.72 mmol) in THF (5 ml) at 0° C. under a nitrogen atmosphere and the resulting mixture was stirred at 0° C. for 1 h. Sat. aq. NH$_4$Cl (2 ml) was added followed by water (2 ml) and EtOAc (5 ml). The organic layer was separated and the aqueous layer extracted with EtOAc (2×5 ml). The combined organics were washed with brine, dried over Na$_2$SO$_4$, filtered and concentrated to give the product as a gum (205 mg, 93%). MS ES+ m/z 310 [M+H]$^+$.

Example 3: Intermediate 3—3-Chloro-N,N,5-trimethyl-5H-chromeno[4,3-c]pyridine-8-carboxamide

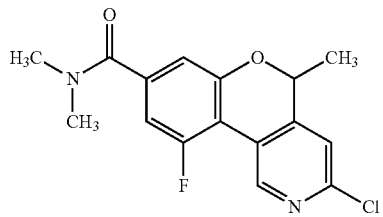 [SMILES: CC1Oc2cc(C(=O)N(C)C)cc(F)c2-c2cnc(Cl)cc21]

NaH (60% in mineral oil, 51 mg, 1.32 mmol) was added to a solution of methyl 4-[6-chloro-4-(1-hydroxyethyl)-3-pyridyl]-3-fluoro-benzoate (205 mg, 0.66 mmol) in THF (5 ml) at 0° C. under a nitrogen atmosphere. The mixture was stirred at 0° C. for 30 min and then at rt overnight. More NaH (60% in mineral oil, 51 mg, 1.32 mmol) was added and the mixture was stirred at 40° C. for 3.5 h, followed by 50° C. for 4 h. The resulting mixture was cooled to rt. Water (3 ml) and EtOAc (4 ml) were added to the mixture. The aqueous layer was separated and the organic layer extracted with 1M aq. NaOH (1 ml). The aqueous layers were combined and pH adjusted to ~3 using 2M aq. HCl. The formed precipitate was collected, washed with water and dried to give the product as a solid (3-chloro-5-methyl-5H-chromeno[4,3-c]pyridine-8-carboxylic acid). The solid was taken up in SOCl$_2$ (2 ml, 27.4 mmol). A drop of DMF was added to the resulting solution and the resulting mixture was stirred at 70° C. for 1 h. When cooled to rt the mixture was concentrated and the resulting residue was taken up in DCM (5 ml) and added slowly to 40% aq. dimethylamine (3 ml, 23.9 mmol) at rt. The resulting mixture was stirred at rt for 1 h and the organic layer separated. The aqueous layer was extracted with DCM (2×3 ml) and the combined organics were washed with sat. aq. NaHCO$_3$, dried over Na$_2$SO$_4$, filtered, concentrated and purified on a silica gel column eluted with 0-100% EtOAc in heptane to give the product as an oil (75 mg, 38%). MS ES+ m/z 303 [M+H]$^+$.

Example 4: Intermediate 4—1-(5-Amino-3-pyridyl)pyrrolidin-2-one

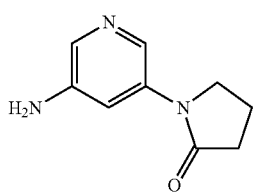 [SMILES: Nc1cncc(N2CCCC2=O)c1]

5-Bromopyridin-3-amine (10 g, 57.8 mmol), pyrrolidin-2-one (9 ml, 63.2 mmol), K$_2$CO$_3$ (15 g, 115.6 mmol), CuI (1.1 g, 5.78 mmol) and DMEDA (1.3 ml, 8.42 mmol) were taken up in 1,4-dioxane (100 ml) and the resulting mixture was refluxed overnight. After cooling to rt, EtOAc was added and the mixture filtered through celite. The filtrate was concentrated and purified on a silica gel column to give the product as a solid (6 g, 59%). MS ES+ m/z 178 [M+H]$^+$.

Example 5: Intermediate 5—(5S)-5-[(3-bromo-5-nitro-2-pyridyl)oxymethyl]pyrrolidin-2-one

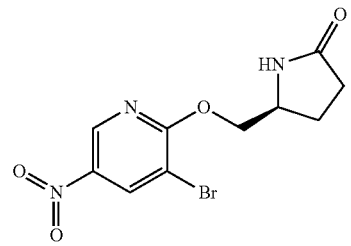 [SMILES: O=C1CC[C@@H](COc2ncc([N+](=O)[O-])cc2Br)N1]

3-Bromo-2-chloro-5-nitro-pyridine (1 g, 4.21 mmol), (5S)-5-(hydroxymethyl)pyrrolidin-2-one (500 mg, 4.34 mmol) and K$_2$CO$_3$ (700 mg, 5.06 mmol) were taken up in MeCN (10 ml) and the resulting mixture was stirred at 70° C. overnight. More (5S)-5-(hydroxymethyl)pyrrolidin-2-one (130 mg, 1.13 mmol) and K$_2$CO$_3$ (300 mg, 2.17 mmol) were added and stirring continued at 70° C. for 5 h. After cooling to rt, the mixture was diluted with water (10 ml) and EtOAc (10 ml) and the organic layer separated. The remaining aqueous layer was further extracted with EtOAc (2×10 ml) and the combined organics were washed with brine, dried over Na$_2$SO$_4$, filtered and concentrated to give the product as a solid (1.13 g, 85%). MS ES+ m/z 316 [M+H]$^+$.

Example 6: Intermediate 6—(6S)-12-nitro-8-oxa-2,10-diazatricyclo[7.4.0.02,6]trideca-1(9),10,12-trien-3-one

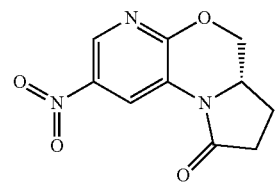 [SMILES: O=C1CC[C@H]2COc3ncc([N+](=O)[O-])cc3N12]

(5S)-5-[(3-bromo-5-nitro-2-pyridyl)oxymethyl]pyrrolidin-2-one (1.13 g, 3.57 mmol), CuI (75 mg, 0.39 mmol), N,N'-dimethylethylenediamine (85 μl, 0.8 mmol) and K$_2$CO$_3$ (0.99 g, 7.15 mmol) were taken up in EtOAc (20 ml) and the resulting mixture was stirred at 70° C. for 2 h. More CuI (75 mg, 0.39 mmol) and N,N'-dimethylethylenediamine (85 μl, 0.8 mmol) were added and the mixture was refluxed for 2 h. Cs$_2$CO$_3$ (2 g, 6.14 mmol) and 1,4-dioxane (20 ml) were added and stirring continued at 100° C. overnight. When cooled to rt the mixture was filtered through celite and rinsed with EtOAc (2×5 ml). The filtrate was washed with half-saturated brine (20 ml), dried over Na$_2$SO$_4$, filtered and concentrated to give the product as a solid (720 mg, 86%). MS ES+ m/z 236 [M+H]$^+$.

Example 7: Intermediate 7—(6S)-12-amino-8-oxa-2,10-diazatricyclo[7.4.0.02,6]trideca-1(9),10,12-trien-3-one

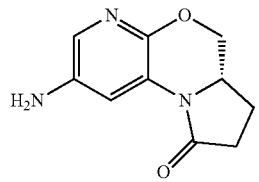

(6S)-12-nitro-8-oxa-2,10-diazatricyclo[7.4.0.02,6]trideca-1(9),10,12-trien-3-one (357 mg, 1.52 mmol), Fe (509 mg, 9.11 mmol) and ammonium chloride (244 mg, 4.55 mmol) were taken up in EtOH/H$_2$O (4:1, 12.5 ml) and the resulting mixture was refluxed for 1.5 h. After cooling to rt the mixture was filtered through celite, rinsed with MeOH and the filtrate was concentrated. The resulting residue was suspended in water and pH was adjusted to about ~7 by careful addition of a sat. aq. NaHCO$_3$. The mixture was extracted with EtOAc and the combined organics were dried over Na$_2$SO$_4$, filtered and concentrated to give the product as a solid (212 mg, 68%). MS ES+ m/z 206 [M+H]$^+$.

Example 8: Intermediate 8—Methyl 4-[6-chloro-4-[cyclopropyl(hydroxy)methyl]-3-pyridyl]-3-fluoro-benzoate

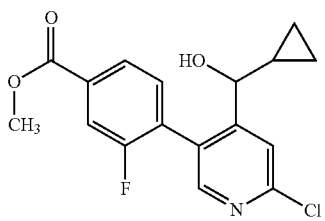 [SMILES: COC(=O)c1ccc(-c2cnc(Cl)cc2C(O)C2CC2)c(F)c1]

The title compound was prepared as described in Intermediate 2, replacing MeMgCl for bromo(cyclopropyl)magnesium, to give the product as a solid (1.2 g, 99%). MS ES+ m/z 336 [M+H]$^+$.

Example 9: Intermediate 9—3-Chloro-5-cyclopropyl-5H-chromeno[4,3-c]pyridine-8-carboxylic acid

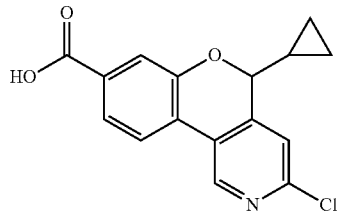 [SMILES: O=C(O)c1ccc2c(c1)OC(C1CC1)c1cc(Cl)ncc1-2]

NaH (60% in mineral oil, 429 mg, 10.7 mmol) was added to a solution of methyl 4-[6-chloro-4-[cyclopropyl(hydroxy)methyl]-3-pyridyl]-3-fluoro-benzoate (1.2 g, 3.57 mmol) in THF (15 ml) at 0° C. under a nitrogen atmosphere. The mixture was stirred at 50° C. for 4 h. When cooled to rt, water (10 ml) and EtOAc (20 ml) were added, the aqueous layer was separated and the organic layer extracted with 1M aq. NaOH (10 ml). The aqueous layers were combined and pH adjusted to about ~3 using 2M aq. HCl. The formed precipitate was collected, washed with water and dried to give the product as a solid (900 mg, 84%). MS ES+ m/z 302 [M+H]$^+$.

Example 10: Intermediate 10—3-Chloro-5-cyclopropyl-N,N-dimethyl-5H-chromeno[4,3-c]pyridine-8-carboxamide

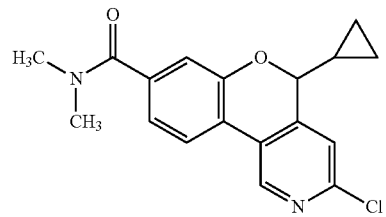 [SMILES: CN(C)C(=O)c1ccc2c(c1)OC(C1CC1)c1cc(Cl)ncc1-2]

3-Chloro-5-cyclopropyl-5H-chromeno[4,3-c]pyridine-8-carboxylic acid (900 mg, 2.66 mmol), N-methylmethanamine HCl (326 mg, 3.99 mmol), HBTU (1.11 g, 2.93 mmol) and TEA (1.11 ml, 7.98 mmol) were dissolved in DMF and the mixture was stirred at rt overnight. Water and EtOAc were added, the organic layer separated and the aqueous layer extracted with EtOAc. The combined organics were concentrated and purified on silica gel column, eluted with 50% EtOAc in heptane, to give the product as a solid (600 mg, 69%). MS ES+ m/z 329 [M+H]$^+$.

Example 11: Intermediate 11—4-(6-Chloro-4-formyl-3-pyridyl)-3-fluoro-N,N-dimethyl-benzamide

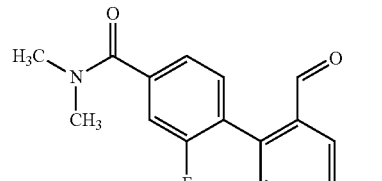

The title compound was prepared as described in Intermediate 1, replacing (2-Fluoro-4-methoxycarbonyl-phenyl) boronic acid for [4-(dimethylcarbamoyl)-2-fluoro-phenyl] boronic acid, to give the product as a gum (1.2 g, quant). MS ES+ m/z 307 [M+H]$^+$.

Example 12: Intermediate 12—4-[6-Chloro-4-(1-hydroxyethyl)-3-pyridyl]-3-fluoro-N,N-dimethyl-benzamide

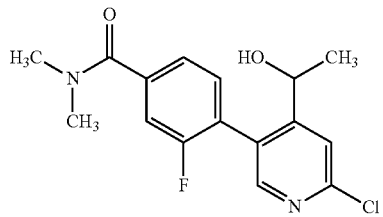 [SMILES: CC(O)c1cc(Cl)ncc1-c1ccc(C(=O)N(C)C)cc1F]

The title compound was prepared as described in Intermediate 2, starting from 4-(6-chloro-4-formyl-3-pyridyl)-3-fluoro-N,N-dimethyl-benzamide, to give the product as a gum (1.19 g, 94%). MS ES+ m/z 323 [M+H]+.

Example 13: Intermediate 13—4-(4-Acetyl-6-chloro-3-pyridyl)-3-fluoro-N,N-dimethyl-benzamide

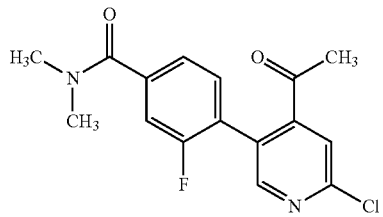 [SMILES: CC(=O)c1cc(Cl)ncc1-c1ccc(C(=O)N(C)C)cc1F]

Dess-Martin periodinane (2 g, 4.72 mmol) was added to a solution of 4-[6-chloro-4-(1-hydroxyethyl)-3-pyridyl]-3-fluoro-N,N-dimethyl-benzamide (1.10 g, 3.41 mmol) in DCM (15 ml) at rt and the resulting mixture was stirred at rt for 1 h. Sat. aq. Na$_2$S$_2$O$_3$ (10 ml) and sat. aq. NaHCO$_3$ (20 ml) were added, the mixture was stirred at rt for 30 min and then filtered. The filter cake was washed with DCM (2×3 ml) and discarded. The organic layer was separated and the aqueous layer extracted with DCM (2×10 ml). The combined organics were washed with sat. aq. NaHCO$_3$ (15 ml), dried over Na$_2$SO$_4$, filtered, concentrated and purified on a silica gel column eluted with 0-100% EtOAc in heptane to give the product as a solid (828 mg, 76%). MS ES+ m/z 321 [M+H]+.

Example 14: Intermediate 14—3-Chloro-N,N,5,6-tetramethyl-5H-benzo[c][2,6]naphthyridine-8-carboxamide

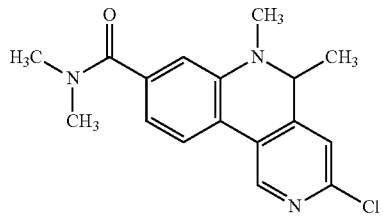 [SMILES: CC1c2cc(Cl)ncc2-c2ccc(C(=O)N(C)C)cc2N1C]

4-(4-Acetyl-6-chloro-3-pyridyl)-3-fluoro-N,N-dimethyl-benzamide (300 mg, 0.94 mmol) was taken up in 2-methyltetrahydrofuran (5 ml) and titanium(IV) isopropoxide (560 µl, 1.87 mmol) was added. After 15 min at rt 40% MeNH$_2$ in MeOH (600 µl, 5.34 mmol) was added and the resulting mixture was stirred at rt over weekend. MeOH (3 ml) was added and the mixture cooled to 0° C. NaBH$_4$ (177 mg, 4.68 mmol) was added portion-wise and after 10 min the cooling bath was removed and the mixture stirred at rt for 3 h. Water (10 ml), sat. aq. NH$_4$Cl (5 ml) and EtOAc (5 ml) were added and the mixture stirred at rt for 30 min. The organic layer was separated and the aqueous layer extracted with EtOAc (3×5 ml). The combined organics were washed with brine, dried over Na$_2$SO$_4$, filtered, concentrated and purified on a silica gel column eluted with 0-100% EtOAc in heptane to give the product as a gum (130 mg, 44%). MS ES+ m/z 316 [M+H]+.

Example 15: Intermediate 15—[2-Fluoro-4-(2-oxopyrrolidin-1-yl)phenyl]boronic acid

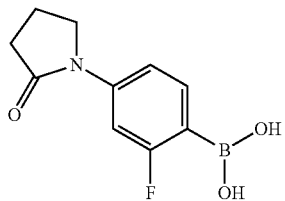 [SMILES: O=C1CCCN1c1ccc(B(O)O)c(F)c1]

n-BuLi (2.5M in hexanes, 5.20 ml, 13 mmol) was added dropwise over 10 min to a solution of 1-(4-bromo-3-fluoro-phenyl)pyrrolidin-2-one (3 g, 11.6 mmol) and triisopropyl borate (3.5 ml, 15.2 mmol) in THF (20 ml) at −78° C. and the resulting mixture was stirred for 3 h. More n-BuLi (2.5M in hexanes, 5.20 ml, 13 mmol) was added dropwise over 5 min and the resulting mixture was stirred for 1.5 h. Water (10 ml) was added and the mixture allowed to reach rt. Diethy-lether (20 ml) was added and the aqueous layer separated. The organic layer was extracted with 1M aq. NaOH (10 ml) and the aqueous layers were combined. The pH was adjusted to about ~1 using conc. HCl and the mixture was extracted with EtOAc (3×10 ml). The combined organics were dried over Na$_2$SO$_4$, filtered and concentrated to give the product as a solid (1.45 g, 43%), which was used in the next step. MS ES+ m/z 224 [M+H]+.

Example 16: Intermediate 16—2-Chloro-5-[2-fluoro-4-(2-oxopyrrolidin-1-yl)phenyl]pyridine-4-carbaldehyde

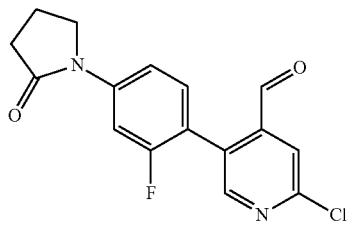 [SMILES: O=Cc1cc(Cl)ncc1-c1ccc(N2CCCC2=O)cc1F]

The title compound was prepared as described in Intermediate 1, replacing (2-fluoro-4-methoxycarbonyl-phenyl) boronic acid for [2-fluoro-4-(2-oxopyrrolidin-1-yl)phenyl] boronic acid, to give the product as a gum (475 mg, 25%). MS ES+ m/z 319 [M+H]+.

Example 17: Intermediate 17—1-[4-[6-Chloro-4-(1-hydroxyethyl)-3-pyridyl]-3-fluoro-phenyl]pyrrolidin-2-one

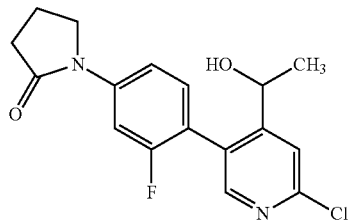 [SMILES: CC(O)c1cc(Cl)ncc1-c1ccc(N2CCCC2=O)cc1F]

The title compound was prepared as described in Intermediate 2, starting from 2-chloro-5-[2-fluoro-4-(2-oxopyrrolidin-1-yl)phenyl]pyridine-4-carbaldehyde, to give the product as a gum (460 mg, 92%). MS ES+ m/z 335 [M+H]$^+$.

Example 18: Intermediate 18—1-(3-Chloro-5-methyl-5H-chromeno[4,3-c]pyridin-8-yl)pyrrolidin-2-one

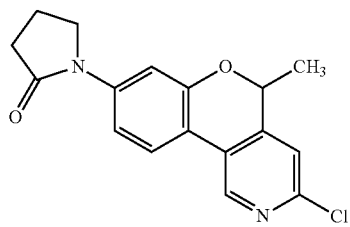 [SMILES: CC1Oc2cc(N3CCCC3=O)ccc2-c2cnc(Cl)cc21]

The title compound was prepared as described in Intermediate 9, starting from 1-[4-[6-chloro-4-(1-hydroxyethyl)-3-pyridyl]-3-fluoro-phenyl]pyrrolidin-2-one, stirring the mixture at rt for 2 h and purification on a silica gel column eluted with 0-80% EtOAc in heptane, to give the product as a solid (300 mg, 71%). MS ES+ m/z 315 [M+H]$^+$.

Example 19: Intermediate 19—1-(5-Amino-3-pyridyl)cyclopropanecarbonitrile

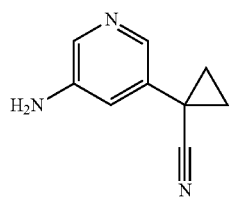 [SMILES: N#CC1(c2cncc(N)c2)CC1]

rac-BINAP (73 mg, 0.12 mmol) and Pd$_2$(dba)$_3$ (53 mg, 0.06 mmol) were taken up in 1,4-dioxane (2 ml) and stirred at 50° C. for 15 min. NaOtBu (224 mg, 2.33 mmol), diphenylmethanimine (235 µl, 1.40 mmol) and 1-(5-bromo-3-pyridyl)cyclopropanecarbonitrile (260 mg, 1.17 mmol) were added together with 1,4-dioxane (3 ml) and the resulting mixture was stirred at 100° C. for 1.5 h. When cooled to rt EtOH (5 ml) was followed by hydroxylamine HCl (162 mg, 2.33 mmol) and sodium acetate (287 mg, 3.50 mmol) and the resulting mixture was stirred at rt overnight. The mixture was heated at 70° C. for 1 h. More Hydroxylamine chloride (162 mg, 2.33 mmol) and sodium acetate (287 mg, 3.50 mmol) were added and stirring continued at 70° C. for 2 h. When cooled to rt the mixture was concentrated and the resulting residue was taken up in half-saturated NaHCO$_3$ (10 ml) and EtOAc (10 ml). The organic layer was separated and the aqueous layer extracted with EtOAc (2×10 ml). The combined organics were washed with brine, dried over Na$_2$SO$_4$, filtered, concentrated and purified on a silica gel column eluted with 0-50% (10% MeOH in EtOAc with NH$_3$) in heptane to give the product as an oil (110 mg, 59%). MS ES+ m/z 160 [M+H]$^+$.

Example 20: Intermediate 20—1-(7-Bromo-2,3-dihydropyrido[2,3-b][1,4]oxazin-1-yl)ethanone

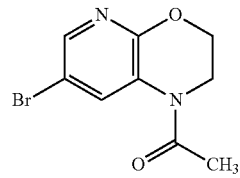

7-Bromo-2,3-dihydro-1H-pyrido[2,3-b][1,4]oxazine (1 g, 4.65 mmol) and Et$_3$N (971 µl, 6.98 mmol) were taken up in 2-MeTHF (5 ml) and cooled to 0° C. Acetyl chloride (398 µl, 5.58 mmol) was added and the resulting mixture was stirred at rt for 1 h. DCM (10 ml) was added followed by acetyl chloride (398 µl, 5.58 mmol) and the mixture was stirred at rt for 1 h. EtOAc (20 ml) and water (10 ml) were added and the organic layer separated. To the aqueous layer was added 2M aq. NaOH (5 ml) and EtOAc (10 ml) and the organic layer separated. The combined organics were washed with sat. aq. NaHCO$_3$, brine, dried over Na$_2$SO$_4$, filtered and concentrated. Recrystallization from 2-propanol gave the product as a white solid (875 mg, 73%). MS ES+ m/z 257 [M+H]$^+$.

Example 21: Intermediate 21—tert-Butyl N-(1-acetyl-2,3-dihydropyrido[2,3-b][1,4]oxazin-7-yl)carbamate

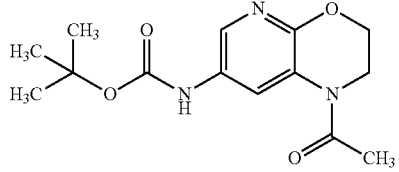 [SMILES: CC(=O)N1CCOc2ncc(NC(=O)OC(C)(C)C)cc21]

The title compound was prepared as described in Example 31, replacing pyridine-3-amine for tert-butyl carbamate and 3-chloro-N,N,5-trimethyl-5H-chromeno[4,3-c]pyridine-8-carboxamide for 1-(7-bromo-2,3-dihydropyrido[2,3-b][1,4]oxazin-1-yl)ethanone, to give the product as a solid (157 mg, 28%). MS ES+ m/z 294 [M+H]$^+$.

Example 22: Intermediate 22—1-(7-Amino-2,3-dihydropyrido[2,3-b][1,4]oxazin-1-yl)ethenone

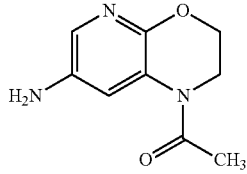

tert-Butyl N-(1-acetyl-2,3-dihydropyrido[2,3-b][1,4]oxazin-7-yl)carbamate (157 mg, 0.54 mmol) was dissolved in DCM (3 mL). TFA (0.41 ml, 5.35 mmol) was added and the reaction was stirred at room temperature for 2 h. The mixture was concentrated and the resulting residue was dissolved in EtOAc and washed with sat. aq. Na$_2$CO$_3$ and brine. The organic layer was dried over MgSO$_4$, filtered and concentrated to give the product as a solid (106 mg, quant.). MS ES+ m/z 194 [M+H]$^+$.

Example 23: Intermediate 23—1-[4-(4-Acetyl-6-chloro-3-pyridyl)-3-fluoro-phenyl]pyrrolidin-2-one

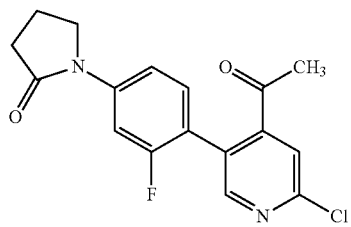 [SMILES: CC(=O)c1cc(Cl)ncc1-c1ccc(N2CCCC2=O)cc1F]

The title compound was prepared as described in Intermediate 13, replacing 4-[6-chloro-4-(1-hydroxyethyl)-3-pyridyl]-3-fluoro-N,N-dimethyl-benzamide for 1-[4-[6-chloro-4-(1-hydroxyethyl)-3-pyridyl]-3-fluoro-phenyl]pyrrolidin-2-one, to give the product as a solid (250 mg, 84%). MS ES+ m/z 333 [M+H]$^+$.

Example 24: Intermediate 24—1-[4-[6-Chloro-4-[1-(methylamino)ethyl]-3-pyridyl]-3-fluoro-phenyl]pyrrolidin-2-one

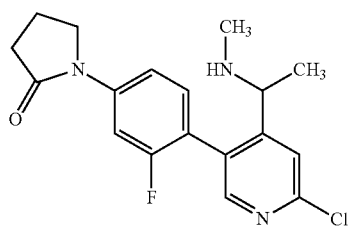 [SMILES: CNC(C)c1cc(Cl)ncc1-c1ccc(N2CCCC2=O)cc1F]

1-[4-(4-Acetyl-6-chloro-3-pyridyl)-3-fluoro-phenyl]pyrrolidin-2-one (250 mg, 0.75 mmol) was taken up in 2-MeTHF (5 ml) and titanium(IV) isopropoxide (500 µl, 1.68 mmol) was added. After 15 min at rt MeNH$_2$ in THF (2M, 2.25 ml, 4.51 mmol) was added and the resulting mixture was stirred at rt overnight. MeOH (3 ml) was added and the mixture cooled to 0° C. NaBH$_4$ (142 mg, 3.76 mmol) was added portion wise and after 10 min the cooling bath was removed and the mixture stirred at rt for 3 h. Water, sat. aq. NH$_4$C and EtOAc were added and the mixture stirred at rt for 30 min. The organic layer was separated and the aqueous layer extracted with EtOAc. The combined organics were washed with brine, dried over Na$_2$SO$_4$, filtered and concentrated to give the product as a solid (242 mg, 93%). MS ES+m/z 348 [M+H]$^+$.

Example 25: Intermediate 25—1-(3-Chloro-5,6-dimethyl-5H-benzo[c][2,6]naphthyridin-8-yl)pyrrolidin-2-one

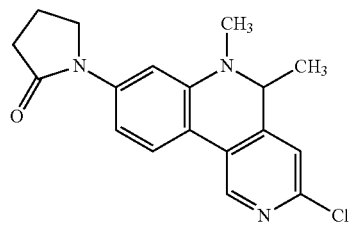 [SMILES: CC1c2cc(Cl)ncc2-c2ccc(N3CCCC3=O)cc2N1C]

The title compound was prepared as described in Intermediate 9, except starting from 1-[4-[6-chloro-4-[1-(methylamino)ethyl]-3-pyridyl]-3-fluoro-phenyl]pyrrolidin-2-one, quenching with MeOH and concentrating the mixture, to give the crude product as a solid (245 mg, quant.). MS ES+ m/z 328 [M+H]$^+$.

Example 26: Intermediate 26—1-(4-Bromo-2,5-difluoro-phenyl)pyrrolidin-2-one

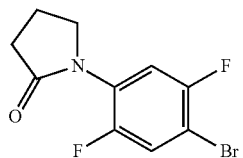 [SMILES: O=C1CCCN1c1cc(F)c(Br)cc1F]

1-Bromo-2,5-difluoro-4-iodo-benzene (5 g, 15.7 mmol), CuI (450 mg, 2.36 mmol) and CsF (5.4 g, 35.5 mmol) were taken up in EtOAc (30 ml) and the resulting mixture was degassed with nitrogen for 10 min. Pyrrolidin-2-one (1.31 ml, 17.2 mmol) and N,N'-dimethylethylenediamine (0.5 ml, 4.7 mmol) were added and the resulting mixture was stirred at 50° C. for 4 h. More CuI (450 mg, 2.36 mmol) and N,N'-dimethylethylenediamine (0.5 ml, 4.7 mmol) were added and stirring continued overnight. More CuI (450 mg, 2.36 mmol), N,N'-dimethylethylenediamine (0.5 ml, 4.7 mmol), CsF (2 g, 13.17 mmol), pyrrolidin-2-one (0.75 ml, 9.85 mmol) and EtOAc (15 ml) were added and stirring continued at 80° C. overnight. When cooled to rt the mixture was filtered, the filter cake washed with EtOAc (2×10 ml) and the filtrate washed with 0.5M aq. HCl (60 ml), 5% NH$_4$OH (50 ml), brine, dried over Na$_2$SO$_4$, filtered, concentrated and purified on a silica gel column eluted with 0-75% EtOAc in heptane to give the product as a solid (2.13 g, 49%). MS ES+ m/z 276 [M+H]$^+$.

Example 27: Intermediate 27—1-[2,5-Difluoro-4-(4,4,5,5-tetramethyl-1,3,2-dioxaborolan-2-yl)phenyl]pyrrolidin-2-one

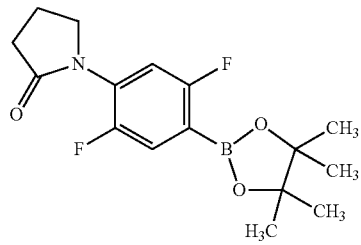 [SMILES: CC1(C)OB(c2cc(F)c(N3CCCC3=O)cc2F)OC1(C)C]

1-(4-Bromo-2,5-difluoro-phenyl)pyrrolidin-2-one (2.10 g, 7.61 mmol), 4,4,5,5-tetramethyl-2-(4,4,5,5-tetramethyl-1,3,2-dioxaborolan-2-yl)-1,3,2-dioxaborolane (2.50 g, 9.84 mmol) and KOAc (2.24 g, 22.8 mmol) were taken up in toluene (10 ml) and degassed with nitrogen for 5 min. Pd(dppf)Cl$_2$ (500 mg, 0.68 mmol) was added and the resulting mixture was stirred at 100° C. overnight. When cooled to rt EtOAc (10 ml) and water (10 ml) were added to the mixture and the mixture filtered through celite. The organic layer was separated and the aqueous layer extracted with EtOAc (2×10 ml). The combined organics were washed with brine, stirred with Na$_2$SO$_4$ and active charcoal, filtered through a plug of silica and concentrated to give the product as a solid, which was used without further purification (2.9 g). MS ES+ m/z 324 [M+H]$^+$.

Example 28: Intermediate 28—2-Chloro-5-[2,5-difluoro-4-(2-oxopyrrolidin-1-yl)phenyl]pyridine-4-carbaldehyde

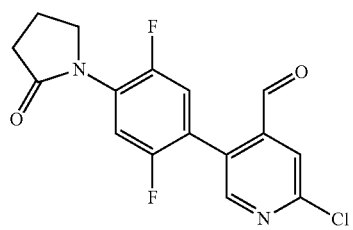 [SMILES: O=Cc1cc(Cl)ncc1-c1cc(F)c(N2CCCC2=O)cc1F]

The title compound was prepared as described in Intermediate 1, replacing (2-Fluoro-4-methoxycarbonyl-phenyl) boronic acid for 1-[2,5-difluoro-4-(4,4,5,5-tetramethyl-1,3,2-dioxaborolan-2-yl)phenyl]pyrrolidin-2-one, using 1,4-dioxane instead of MeCN and stirring the mixture at 90° C. for 1 h, to give the product as a solid (1.37 g, 64%). MS ES+ m/z 337 [M+H]$^+$.

Example 29: Intermediate 29—1-[4-[6-Chloro-4-(1-hydroxyethyl)-3-pyridyl]-2,5-difluoro-phenyl]pyrrolidin-2-one

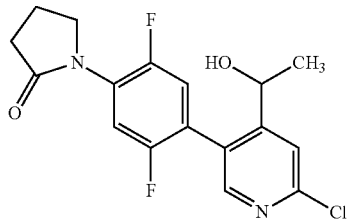 [SMILES: CC(O)c1cc(Cl)ncc1-c1cc(F)c(N2CCCC2=O)cc1F]

The title compound was prepared as described in Intermediate 2, starting from 2-chloro-5-[2,5-difluoro-4-(2-oxopyrrolidin-1-yl)phenyl]pyridine-4-carbaldehyde, to give the product as a gum (1.19 g, 94%). MS ES+ m/z 353 [M+H]$^+$.

Example 30: Intermediate 30—1-(3-Chloro-9-fluoro-5-methyl-5H-chromeno[4,3-c]pyridin-8-yl)pyrrolidin-2-one

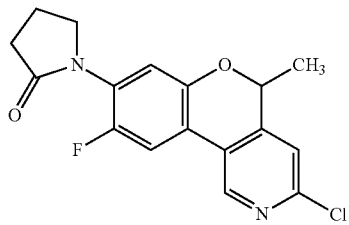 [SMILES: CC1Oc2cc(N3CCCC3=O)c(F)cc2-c2cnc(Cl)cc21]

The title compound was prepared as described in Intermediate 9, starting from 1-[4-[6-chloro-4-(1-hydroxyethyl)-3-pyridyl]-2,5-difluoro-phenyl]pyrrolidin-2-one, stirring the mixture at rt for 2 h and purification on a silica gel column eluted with 0-80% EtOAc in heptane, to give the product as a solid (685 mg, 54%). MS ES+ m/z 333 [M+H]$^+$.

Example 31: N,N,5-trimethyl-3-(pyridin-3-ylamino)-5H-chromeno[4,3-c]pyridine-8-carboxamide

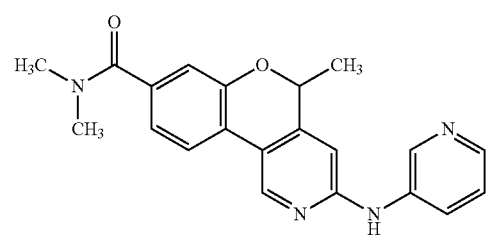 [SMILES: CC1Oc2cc(C(=O)N(C)C)ccc2-c2cnc(Nc3cccnc3)cc21]

XantPhos (14 mg, 0.03 mmol) and Pd$_2$(dba)$_3$ (11 mg, 0.01 mmol) were taken up in 1,4-dioxane (2 ml) and stirred at 50° C. for 20 min. A solution of 3-chloro-N,N,5-trimethyl-5H-chromeno[4,3-c]pyridine-8-carboxamide (75 mg, 0.25 mmol) in 1,4-dioxane (2 ml) was added followed by pyridin-3-amine (30 mg, 0.32 mmol) and NaOtBu (64 mg, 0.66 mmol) and the resulting mixture was stirred at 100° C. for 2 h. After cooling at rt, the mixture was diluted with EtOAc (3 ml) and filtered. The filtrate was concentrated and the resulting residue was dissolved in MeOH, filtered and purified by preparative HPLC to give the product as a solid. $^1$H NMR (500 MHz, DMSO-d$_6$) δ ppm 1.55 (d, J=6.62 Hz, 3H), 2.96 (br s, 6H), 5.29-5.36 (m, 1H), 6.75 (s, 1H), 6.96 (d, J=1.58 Hz, 1H), 7.07 (dd, J=7.88, 1.58 Hz, 1H), 7.29-7.36 (m, 1H), 7.93 (d, J=8.20 Hz, 1H), 8.13 (dd, J=4.73, 1.26 Hz, 1H), 8.22 (ddd, J=8.35, 2.68, 1.58 Hz, 1H), 8.73 (s, 1H), 8.83 (s, 1H), 9.50 (s, 1H). MS ES+ m/z 361 [M+H]$^+$.

Example 32: N,N,5-trimethyl-3-((5-(2-oxopyrrolidin-1-yl)pyridin-3-yl)amino)-5H-chromeno[4,3-c]pyridine-8-carboxamide

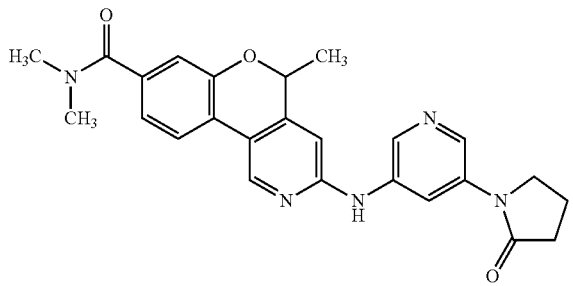 [SMILES: CC1Oc2cc(C(=O)N(C)C)ccc2-c2cnc(Nc3cncc(N4CCCC4=O)c3)cc21]

The title compound was prepared as described in accordance with the accordance with the procedures of Example 31, replacing pyridine-3-amine for 1-(5-amino-3-pyridyl)pyrrolidin-2-one and stirring at 100° C. overnight, to give the product as a solid (6 mg, 4%). $^1$H NMR (500 MHz, CHLOROFORM-d) δ ppm 1.63 (d, J=6.62 Hz, 3H), 2.21-2.30 (m, 2H), 2.63-2.69 (m, 2H), 3.04-3.09 (m, 3H), 3.14 (br s, 3H), 3.96 (t, J=7.09 Hz, 2H), 5.20 (q, J=6.73 Hz, 1H), 6.83 (s, 1H), 7.05 (s, 1H), 7.12 (d, J=7.83 Hz, 1H), 7.73 (d, J=7.88 Hz, 1H), 7.77-7.92 (m, 1H), 8.41 (br s, 1H), 8.54-8.61 (m, 2H), 8.73 (s, 1H). MS ES+ m/z 444 [M+H]$^+$.

Example 33: N,N,5-trimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide

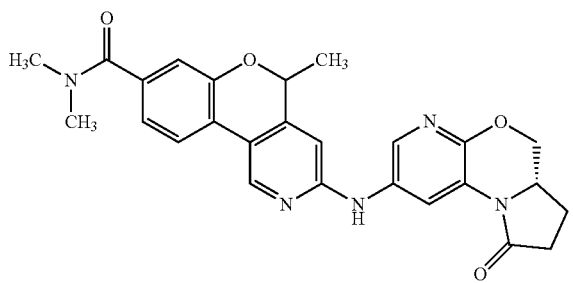 [SMILES: CC1Oc2cc(C(=O)N(C)C)ccc2-c2cnc(Nc3cnc4c(c3)N3C(=O)CC[C@H]3CO4)cc21]

The title compound was prepared as described in accordance with the procedures of Example 31, replacing pyridine-3-amine for (6S)-12-amino-8-oxa-2,10-diazatricyclo[7.4.0.0^{2,6}]trideca-1(9),10,12-trien-3-one and stirring at 100° C. overnight, to give the product as a solid (6 mg, 3%). $^1$H NMR (500 MHz, METHANOL-d$_4$) δ ppm 1.60 (dd, 3H), 1.75-1.84 (m, 1H), 2.32-2.40 (m, 1H), 2.52 (ddd, 1H), 2.71-2.80 (m, 1H), 3.07 (s, 3H), 3.12 (s, 3H), 3.92-4.00 (m, 1H), 4.11-4.18 (m, 1H), 4.65 (dd, 1H), 5.20 (q, 1H), 6.65 (s, 1H), 7.01 (d, 1H), 7.10 (dd, 1H), 7.86 (d, 1H), 8.29 (d, 1H), 8.58 (s, 1H), 9.12 (dd, 1H). MS ES+ m/z 472 [M+H]$^+$.

Example 34: 5-cyclopropyl-N,N-dimethyl-3-(pyridin-3-ylamino)-5H-chromeno[4,3-c]pyridine-8-carboxamide

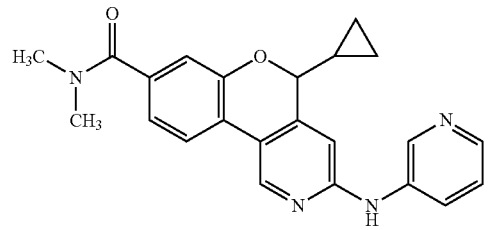 [SMILES: CN(C)C(=O)c1ccc2c(c1)OC(C1CC1)c1cc(Nc3cccnc3)ncc1-2]

The title compound was prepared as described in accordance with the procedures of Example 31, replacing 3-chloro-N,N,5-trimethyl-5H-chromeno[4,3-c]pyridine-8-carboxamide for 3-chloro-5-cyclopropyl-N,N-dimethyl-5H-chromeno[4,3-c]pyridine-8-carboxamide and stirring at 100° C. overnight, to give the product as a solid (15 mg, 6%). $^1$H NMR (500 MHz, METHANOL-d$_4$) δ ppm 0.50-0.62 (m, 2H), 0.66-0.77 (m, 2H), 1.26-1.33 (m, 1H), 3.05 (s, 3H), 3.10 (s, 3H), 4.33 (d, J=8.83 Hz, 1H), 6.89 (s, 1H), 7.02 (s, 1H), 7.09 (d, J=7.69 Hz, 1H), 7.24-7.40 (m, 1H), 7.86 (d, J=7.88 Hz, 1H), 8.09 (dd, J=4.73, 1.58 Hz, 1H), 8.27 (ddd, J=8.43, 2.60, 1.26 Hz, 1H), 8.63 (s, 1H), 8.83 (d, J=2.21 Hz, 1H). MS ES+ m/z 387 [M+H]$^+$.

Example 35: 5-cyclopropyl-N,N-dimethyl-3-((5-(2-oxopyrrolidin-1-yl)pyridin-3-yl)amino)-5H-chromeno[4,3-c]pyridine-8-carboxamide

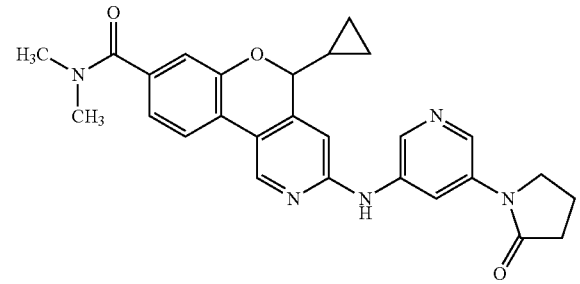 [SMILES: CN(C)C(=O)c1ccc2c(c1)OC(C1CC1)c1cc(Nc3cncc(N4CCCC4=O)c3)ncc1-2]

The title compound was prepared as described in accordance with the procedures of Example 31, replacing pyridine-3-amine for 1-(5-amino-3-pyridyl)pyrrolidin-2-one and 3-chloro-N,N,5-trimethyl-5H-chromeno[4,3-c]pyridine-8-carboxamide for 3-Chloro-5-cyclopropyl-N,N-dimethyl-5H-chromeno[4,3-c]pyridine-8-carboxamide, and stirring at 100° C. overnight, to give the product as a solid (35 mg, 20%). $^1$H NMR (500 MHz, DMSO-d$_6$) δ ppm 0.50-0.60 (m, 2H), 0.63-0.76 (m, 2H), 1.23-1.32 (m, 1H), 2.08-2.17 (m, 2H), 2.53-2.56 (m, 2H), 2.94-3.03 (m, 6H), 3.85-3.92 (m, 2H), 4.46-4.52 (m, 1H), 6.94-6.97 (m, 1H), 6.99 (d, J=1.58 Hz, 1H), 7.07 (dd, J=7.88, 1.58 Hz, 1H), 7.96 (d, J=7.88 Hz, 1H), 8.39 (d, J=2.21 Hz, 1H), 8.59 (t, J=2.21 Hz, 1H), 8.75-8.76 (m, 1H), 8.77-8.79 (m, 1H), 9.61 (s, 1H). MS ES+ m/z 470 [M+H]$^+$.

Example 36: 5-cyclopropyl-N,N-dimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide

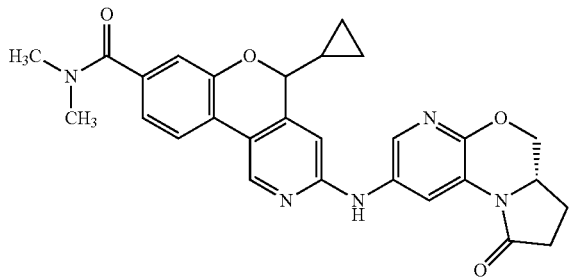 [SMILES: CN(C)C(=O)c1ccc2c(c1)OC(C1CC1)c1cc(Nc3cnc4c(c3)N3C(=O)CC[C@H]3CO4)ncc1-2]

The title compound was prepared as described in in accordance with the procedures of Example 31, replacing pyridine-3-amine for (6S)-12-amino-8-oxa-2,10-diazatricyclo[7.4.0.02,6]trideca-1(9),10,12-trien-3-one and 3-chloro-N,N,5-trimethyl-5H-chromeno[4,3-c]pyridine-8-carboxamide for 3-chloro-5-cyclopropyl-N,N-dimethyl-5H-chromeno[4,3-c]pyridine-8-carboxamide, and stirring at 100° C. overnight, to give the product as a solid (6 mg, 4%). $^1$H NMR (500 MHz, DMSO-$d_6$) δ ppm 0.55 (td, J=7.96, 4.89 Hz, 2H), 0.62-0.71 (m, 2H), 1.22-1.29 (m, 1H), 1.67-1.75 (m, 1H), 2.20-2.26 (m, 1H), 2.39 (br d, J=1.58 Hz, 1H), 2.65-2.74 (m, 1H), 2.97 (br s, 6H), 3.91 (t, J=10.56 Hz, 1H), 4.05-4.11 (m, 1H), 4.45 (dd, J=9.14, 2.21 Hz, 1H), 4.59 (dd, J=10.88, 2.99 Hz, 1H), 6.87 (s, 1H), 6.98 (d, J=1.58 Hz, 1H), 7.06 (dd, J=7.88, 1.89 Hz, 1H), 7.93 (d, J=8.20 Hz, 1H), 8.44 (s, 1H), 8.68 (s, 1H), 8.97 (dd, J=2.52, 1.58 Hz, 1H), 9.40 (s, 1H). MS ES+ m/z 498 [M+H]$^+$.

Example 37: N,N,5,6-tetramethyl-3-(pyridin-3-ylamino)-5,6-dihydrobenzo[c][2,6]naphthyridine-8-carboxamide

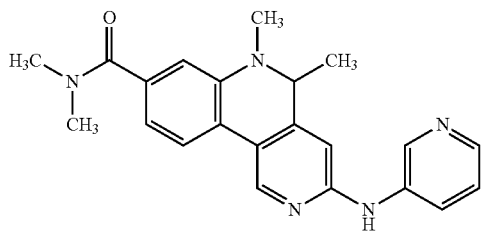 [SMILES: CC1c2cc(Nc3cccnc3)ncc2-c2ccc(C(=O)N(C)C)cc2N1C]

Pd$_2$(dba)$_3$ (18 mg, 0.02 mmol) and BrettPhos (21 mg, 0.04 mmol) were taken up in 1,4-dioxane (1 ml) and stirred at 50° C. for 15 min. A solution of 3-chloro-N,N,5,6-tetramethyl-5H-benzo[c][2,6]naphthyridine-8-carboxamide (125 mg, 0.4 mmol) in 1,4-dioxane (3 ml), pyridin-3-amine (56 mg, 0.59 mmol) and Cs$_2$CO$_3$ (358 mg, 1.10 mmol) were added and the resulting mixture was stirred at 100° C. overnight. After cooling to rt, EtOAc (5 ml) and half-saturated brine (5 ml) were added to the mixture and the organic layer separated. The remaining aqueous layer was further extracted with EtOAc (5 ml). The combined organics where washed with brine, dried over Na$_2$SO$_4$, filtered, concentrated and purified by preparative HPLC to give the product as a solid (48 mg, 33%). $^1$H NMR (500 MHz, DMSO-$d_6$) δ ppm 1.07 (d, J=6.62 Hz, 3H), 2.92 (s, 3H), 2.97 (br s, 6H), 4.51 (q, J=6.52 Hz, 1H), 6.65 (d, J=1.58 Hz, 1H), 6.67 (s, 1H), 6.78 (dd, J=7.57, 1.58 Hz, 1H), 7.28-7.31 (m, 1H), 7.82 (d, J=7.88 Hz, 1H), 8.10 (dd, J=4.57, 1.42 Hz, 1H), 8.21 (ddd, J=8.35, 2.68, 1.58 Hz, 1H), 8.70 (s, 1H), 8.80-8.82 (m, 1H), 9.36 (s, 1H). MS ES+ m/z 374 [M+H]$^+$.

Example 38: 1-(5-methyl-3-(pyridin-3-ylamino)-5H-chromeno[4,3-c]pyridin-8-yl)pyrrolidin-2-one

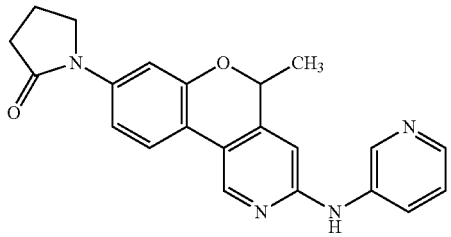 [SMILES: CC1Oc2cc(N3CCCC3=O)ccc2-c2cnc(Nc3cccnc3)cc21]

The title compound was prepared as described in accordance with the procedures of Example 31, replacing 3-chloro-N,N,5-trimethyl-5H-chromeno[4,3-c]pyridine-8-carboxamide for 1-(3-chloro-5-methyl-5H-chromeno[4,3-c]pyridin-8-yl)pyrrolidin-2-one, to give the product as a solid (12 mg, 10%). $^1$H NMR (500 MHz, DMSO-$d_6$) δ ppm 1.54 (d, J=6.62 Hz, 3H), 2.03-2.10 (m, 2H), 2.49-2.51 (m, 2H, obscured by DMSO), 3.81-3.90 (m, 2H), 5.25-5.31 (m, 1H), 6.75 (s, 1H), 7.28-7.34 (m, 2H), 7.41 (d, J=2.21 Hz, 1H), 7.88 (d, J=8.51 Hz, 1H), 8.12 (dd, J=4.73, 1.58 Hz, 1H), 8.23 (ddd, J=8.43, 2.60, 1.58 Hz, 1H), 8.67 (s, 1H), 8.83 (d, J=2.21 Hz, 1H), 9.46 (s, 1H). MS ES+ m/z 373 [M+H]$^+$.

Example 39: 1-(5-((5-methyl-8-(2-oxopyrrolidin-1-yl)-5H-chromeno[4,3-c]pyridin-3-yl)amino)pyridin-3-yl)cyclopropane-1-carbonitrile

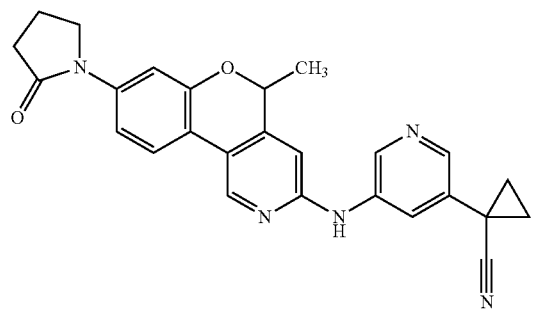 [SMILES: CC1Oc2cc(N3CCCC3=O)ccc2-c2cnc(Nc3cncc(C4(C#N)CC4)c3)cc21]

The title compound was prepared as described in accordance with the procedures of Example 31, replacing pyridine-3-amine for 1-(5-amino-3-pyridyl)cyclopropanecarbonitrile and 3-chloro-N,N,5-trimethyl-5H-chromeno[4,3-c]pyridine-8-carboxamide for 1-(3-chloro-5-methyl-5H-chromeno[4,3-c]pyridin-8-yl)pyrrolidin-2-one, to give the product as a solid (15 mg, 7%). $^1$H NMR (500 MHz, DMSO-$d_6$) δ ppm 1.54 (d, J=6.62 Hz, 3H), 1.69-1.77 (m, 2H), 1.89-1.97 (m, 2H), 2.02-2.10 (m, 2H), 2.52-2.64 (m, 2H), 3.81-3.91 (m, 2H), 5.34 (q, J=6.62 Hz, 1H), 6.85 (s, 1H), 7.34 (dd, J=8.83, 2.21 Hz, 1H), 7.41 (d, J=2.21 Hz, 1H), 7.93 (d, J=8.83 Hz, 1H), 8.22 (d, J=1.89 Hz, 1H), 8.50

(t, J=1.89 Hz, 1H), 8.77 (s, 1H), 9.18-9.27 (m, 1H), 10.30 (br s, 1H). MS ES+ m/z 438 [M+H]⁺.

Example 40: (6aS)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

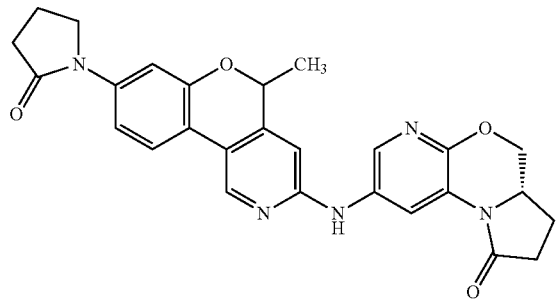 [SMILES: CC1Oc2cc(N3CCCC3=O)ccc2-c2cnc(Nc3cnc4c(c3)N3C(=O)CC[C@H]3CO4)cc21]

The title compound was prepared as described in accordance with the procedures of Example 37, replacing pyridine-3-amine for (6S)-12-amino-8-oxa-2,10-diazatricyclo[7.4.0.02,6]trideca-1(9),10,12-trien-3-one and 3-chloro-N,N,5-trimethyl-5H-chromeno[4,3-c]pyridine-8-carboxamide for 1-(3-chloro-5-methyl-5H-chromeno[4,3-c]pyridin-8-yl)pyrrolidin-2-one, and stirring at 100° C. for 40 min, to give the product as a solid (113 mg, 39%). ¹H NMR (500 MHz, DMSO-$d_6$) δ ppm 1.53 (dd, J=6.62, 1.58 Hz, 3H), 1.64-1.78 (m, 1H), 2.02-2.11 (m, 2H), 2.17-2.28 (m, 1H), 2.37-2.50 (m, 2H), 2.64-2.72 (m, 1H), 3.80-3.93 (m, 3H), 4.08 (tdd, J=9.62, 9.62, 6.94, 3.15 Hz, 1H), 4.59 (dd, J=10.88, 2.99 Hz, 1H), 5.25 (q, J=6.52 Hz, 1H), 6.66-6.68 (m, 1H), 7.24-7.39 (m, 1H), 7.40 (d, J=2.21 Hz, 1H), 7.87 (d, J=8.83 Hz, 1H), 8.39 (dd, J=2.52, 1.26 Hz, 1H), 8.60 (s, 1H), 8.97 (dd, J=4.10, 2.52 Hz, 1H), 9.29 (d, J=2.84 Hz, 1H). MS ES+ m/z 484 [M+H]⁺.

Example 41: 1-(3-((5-(difluoromethoxy)pyridin-3-yl)amino)-5-methyl-5H-chromeno[4,3-c]pyridin-8-yl)pyrrolidin-2-one

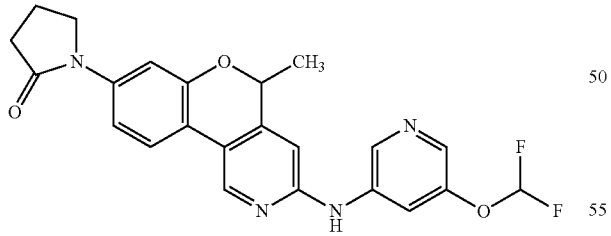

The title compound was prepared as described in accordance with the procedures of Example 31, replacing pyridine-3-amine for 5-(difluoromethoxy)pyridin-3-amine and 3-chloro-N,N,5-trimethyl-5H-chromeno[4,3-c]pyridine-8-carboxamide for 1-(3-chloro-5-methyl-5H-chromeno[4,3-c]pyridin-8-yl)pyrrolidin-2-one, to give the product as a solid (18 mg, 13%). ¹H NMR (500 MHz, DMSO-$d_6$) δ ppm 1.54 (d, J=6.62 Hz, 3H), 2.02-2.09 (m, 2H), 2.48-2.50 (m, 2H, obscured by DMSO), 3.82-3.87 (m, 2H), 5.29 (q, J=6.73 Hz, 1H), 6.77 (s, 1H), 7.30 (t, J=73.50 Hz, 1H), 7.32 (dd, J=8.51, 2.21 Hz, 1H), 7.41 (d, J=2.21 Hz, 1H), 7.90 (d, J=8.51 Hz, 1H), 8.00 (d, J=2.52 Hz, 1H), 8.32 (t, J=2.36 Hz, 1H), 8.62 (d, J=2.21 Hz, 1H), 8.72 (s, 1H), 9.72 (s, 1H). MS ES+ m/z 439 [M+H]⁺.

Example 42: 1-(3-((1-acetyl-2,3-dihydro-1H-pyrido[2,3-b][1,4]oxazin-7-yl)amino)-5-methyl-5H-chromeno[4,3-c]pyridin-8-yl)pyrrolidin-2-one

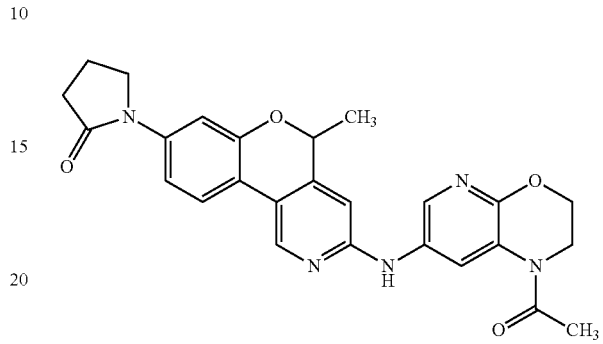

The title compound was prepared as described in accordance with the procedure of Example 37, replacing pyridine-3-amine for 1-(7-amino-2,3-dihydropyrido[2,3-b][1,4]oxazin-1-yl)ethenone and 3-chloro-N,N,5-trimethyl-5H-chromeno[4,3-c]pyridine-8-carboxamide for 1-(3-chloro-5-methyl-5H-chromeno[4,3-c]pyridin-8-yl)pyrrolidin-2-one, and stirring at 100° C. for 40 min, to give the product as a solid (42 mg, 46%). ¹H NMR (500 MHz, DMSO-$d_6$) δ ppm 1.53 (d, J=6.62 Hz, 3H), 2.00-2.13 (m, 2H), 2.31 (s, 3H), 2.48-2.50 (m, 2H, obscured by DMSO), 3.76-3.94 (m, 4H), 4.32-4.40 (m, 2H), 5.25 (q, J=6.62 Hz, 1H), 6.66 (s, 1H), 7.31 (dd, J=8.51, 2.21 Hz, 1H), 7.39 (m, 1H), 7.86 (d, J=8.83 Hz, 1H), 8.27 (br s, 1H), 8.60 (s, 1H), 9.21 (s, 1H). MS ES+ m/z 472 [M+H]⁺.

Example 43: 1-(5,6-dimethyl-3-(pyridin-3-ylamino)-5,6-dihydrobenzo[c][2,6]naphthyridin-8-yl)pyrrolidin-2-one

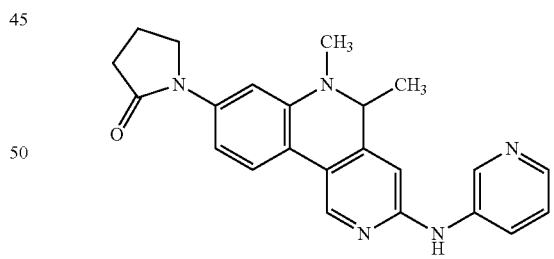

Pyridin-3-amine (121 mg, 1.29 mmol), 1-(3-chloro-5,6-dimethyl-5H-benzo[c][2,6]naphthyridin-8-yl)pyrrolidin-2-one (169 mg, 0.52 mmol) and Cs₂CO₃ (336 mg, 1.03 mmol) were taken up in DMF (2 ml) and the mixture was degassed with nitrogen for 5 min. BrettPhos Pd G3 (23 mg, 0.03 mmol) and BrettPhos (14 mg, 0.03 mmol) were added and the mixture was stirred at 120° C. overnight. After cooling to rt, the mixture was filtered through celite and concentrated. The residue was dissolved in EtOAc, washed with water, brine, concentrated and purified by preparative HPLC to give the product as a solid (7 mg, 3%). ¹H NMR (500 MHz, CHLOROFORM-d) δ ppm 1.17 (d, J=6.62 Hz, 2H), 1.27-1.27 (m, 1H), 2.19 (t, J=7.57 Hz, 2H), 2.65 (t, J=8.04 Hz, 2H), 3.01 (s, 3H), 3.93 (t, J=7.09 Hz, 2H), 4.33 (d, J=6.62 Hz, 1H), 6.54-6.57 (m, 1H), 6.58 (s, 1H), 6.89 (dd, J=8.20, 2.21 Hz, 1H), 7.33 (d, J=2.21 Hz, 1H), 7.69 (d, J=8.51 Hz, 1H), 7.90-7.97 (m, 1H), 8.30 (dd, J=4.73, 1.26 Hz, 1H), 8.61 (s, 1H), 8.62 (s, 1H). MS ES+ m/z 386 [M+H]$^+$.

Example 44: (6aS)-2-((5,6-dimethyl-8-(2-oxopyrrolidin-1-yl)-5,6-dihydrobenzo[c][2,6]naphthyridin-3-yl)amino)-6,6a,7,8-tetrahydro-9H-pyrido[2,3-b]pyrrolo[1,2-d][1,4]oxazin-9-one

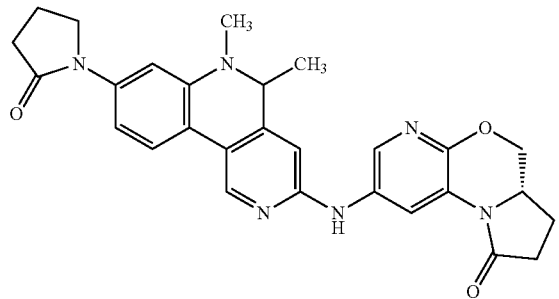 [SMILES: CC1c2cc(Nc3cnc4c(c3)N3C(=O)CC[C@H]3CO4)ncc2-c2ccc(N3CCCC3=O)cc2N1C]

The title compound was prepared as described in accordance with the procedure of Example 43, replacing pyridine-3-amine for (6S)-12-amino-8-oxa-2,10-diazatricyclo[7.4.0.02,6]trideca-1(9),10,12-trien-3-one to give the product as a solid (23 mg, 14%). $^1$H NMR (500 MHz, DMSO-d$_6$) δ ppm 1.06 (dd, J=6.62, 2.84 Hz, 3H), 1.63-1.77 (m, 1H), 2.02-2.23 (m, 2H), 2.19-2.28 (m, 1H), 2.39 (br d, J=16.39 Hz, 1H), 2.62-2.73 (m, 1H), 2.90 (s, 3H), 3.82-4.01 (m, 3H), 4.02-4.12 (m, 1H), 4.45 (br d, J=6.62 Hz, 1H), 4.58 (dd, J=10.72, 3.15 Hz, 1H), 6.58 (s, 1H), 6.98 (dd, J=8.51, 1.89 Hz, 1H), 7.13 (d, J=1.89 Hz, 1H), 7.76 (d, J=8.51 Hz, 1H), 8.36 (dd, J=9.14, 2.52 Hz, 1H), 8.57 (s, 1H), 8.95 (dd, J=6.94, 2.52 Hz, 1H), 9.12 (s, 1H), 2H obscured by DMSO. MS ES+ m/z 497 [M+H]$^+$.

Example 45: 1-(3-((2,3-dihydro-[1,4]dioxino[2,3-b]pyridin-7-yl)amino)-5,6-dimethyl-5,6-dihydrobenzo[c][2,6]naphthyridin-8-yl)pyrrolidin-2-one

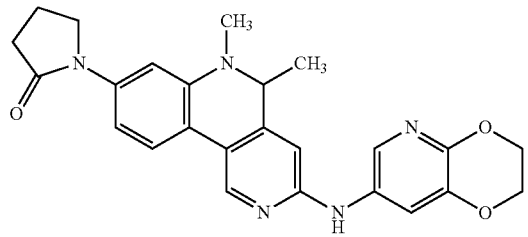 [SMILES: CC1c2cc(Nc3cnc4c(c3)OCCO4)ncc2-c2ccc(N3CCCC3=O)cc2N1C]

The title compound was prepared as described in in accordance with the procedure of Example 43, replacing pyridine-3-amine for 2,3-dihydro-[1,4]dioxino[2,3-b]pyridin-7-amine to give the product as a solid (22 mg, 13%). $^1$H NMR (500 MHz, DMSO-d$_6$) δ ppm 1.05 (d, J=6.62 Hz, 3H), 2.04-2.10 (m, 2H), 2.90 (s, 3H), 3.87 (t, J=7.41 Hz, 2H), 4.25 (dt, J=3.78, 2.21 Hz, 2H), 4.35 (dt, J=3.78, 2.21 Hz, 2H), 4.46 (d, J=6.62 Hz, 1H), 6.56 (s, 1H), 6.98 (dd, J=8.35, 2.05 Hz, 1H), 7.13 (d, J=2.21 Hz, 1H), 7.75 (d, J=8.51 Hz, 1H), 7.82 (d, J=2.52 Hz, 1H), 7.92 (d, J=2.52 Hz, 1H), 8.60 (s, 1H), 9.02-9.08 (m, 1H) 2H obscured by DMSO. MS ES+ m/z 444 [M+H]$^+$.

Example 46: 1-(9-fluoro-5-methyl-3-(pyridin-3-ylamino)-5H-chromeno[4,3-c]pyridin-8-yl)pyrrolidin-2-one

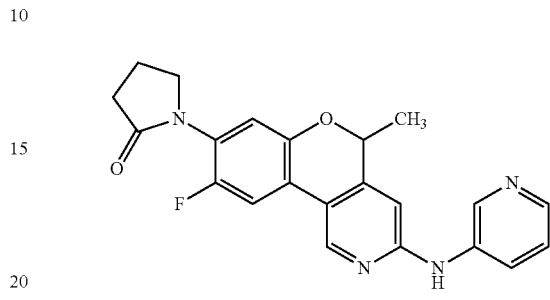

The title compound was prepared as described in accordance with the procedures of Example 31, replacing 3-chloro-N,N,5-trimethyl-5H-chromeno[4,3-c]pyridine-8-carboxamide for 1-(3-chloro-9-fluoro-5-methyl-5H-chromeno[4,3-c]pyridin-8-yl)pyrrolidin-2-one and NaOtBu for Cs$_2$CO$_3$, to give the product as a solid (12 mg, 10%). $^1$H NMR (500 MHz, DMSO-d$_6$) δ ppm 1.54 (d, J=6.62 Hz, 3H), 2.07-2.15 (m, 2H), 2.43 (t, J=8.04 Hz, 2H), 3.74-3.80 (m, 2H), 5.26-5.35 (m, 1H), 6.74 (s, 1H), 7.06 (d, J=6.62 Hz, 1H), 7.28-7.33 (m, 1H), 7.86 (d, J=11.66 Hz, 1H), 8.13 (dd, J=4.57, 1.42 Hz, 1H), 8.21 (ddd, J=8.35, 2.68, 1.26 Hz, 1H), 8.71 (s, 1H), 8.82 (d, J=2.21 Hz, 1H), 9.50 (s, 1H). MS ES+ m/z 391 [M+H]$^+$.

Example 47: (6aS)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

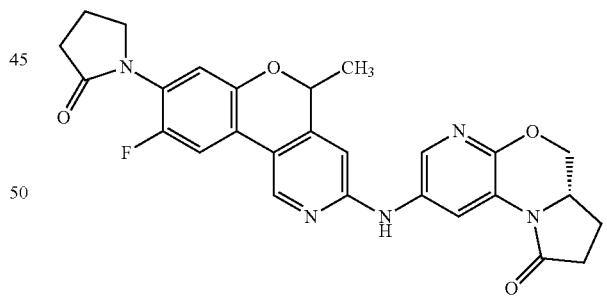

The title compound was prepared as described in accordance with the procedures of Example 43, replacing pyridine-3-amine for (6S)-12-amino-8-oxa-2,10-diazatricyclo[7.4.0.02,6]trideca-1(9),10,12-trien-3-one and 1-(3-chloro-5,6-dimethyl-5H-benzo[c][2,6]naphthyridin-8-yl)pyrrolidin-2-one for 1-[9-fluoro-5-methyl-3-(3-pyridylamino)-5H-chromeno[4,3-c]pyridin-8-yl]pyrrolidin-2-one, and stirring for 1 h, to give the product as a solid (193 mg, 45%). H NMR (500 MHz, DMSO-d$_6$) δ ppm 1.53 (dd, J=6.46, 1.42 Hz, 3H), 1.69-1.74 (m, 1H), 2.08-2.15 (m, 2H), 2.20-2.26 (m, 1H), 2.39-2.45 (m, 3H), 2.66-2.70 (m, 1H), 3.75-3.80 (m, 2H), 3.93 (d, J=10.72 Hz, 1H), 4.05-4.11 (m, 1H), 4.59 (dd, J=10.72, 3.15 Hz, 1H), 5.26 (q, J=6.83 Hz, 1H), 6.68 (s, 1H), 7.05 (d, J=6.94 Hz, 1H), 7.86 (s, 1H), 8.39 (dd, J=2.52, 1.26 Hz, 1H), 8.65 (s, 1H), 8.97 (dd, J=3.94, 2.68 Hz, 1H), 9.38 (d, J=2.52 Hz, 1H). MS ES+ m/z 502 [M+H]+.

Example 48: N-methyl-N-(5-((5-methyl-8-(2-oxopyrrolidin-1-yl)-5H-chromeno[4,3-c]pyridin-3-yl)amino)pyridin-3-yl)methanesulfonamide

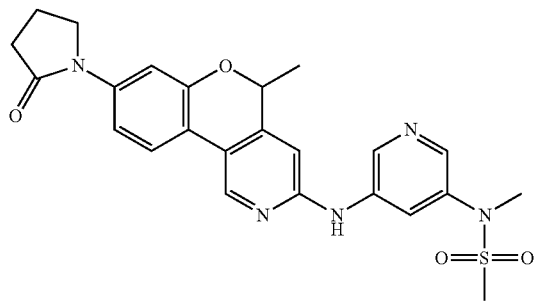 [SMILES: CC1Oc2cc(N3CCCC3=O)ccc2-c2cnc(Nc3cncc(N(C)S(C)(=O)=O)c3)cc21]

Step 1: Preparation of 1-(4-bromo-3-fluorophenyl)pyrrolidin-2-one

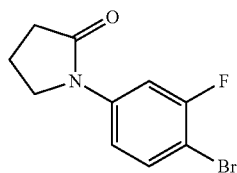

1-Bromo-2-fluoro-4-iodobenzene (40.0 g, 133 mmol), CsF (50.5 g, 332 mmol) and CuI (7.60 g, 39.8 mmol) were taken up in EtOAc (300 mL) and the resulting mixture was degassed with nitrogen for 10 min. Pyrrolidin-2-one (13.6 g, 159 mmol) and N,N'-dimethylethylenediamine (5.3 mL, 80 mmol) were added and the resulting mixture was stirred at 50° C. for 18 h. A purple solution was formed gradually. LCMS (Rt=0.655 min; MS Calcd: 257.0. MS Found: 257.8 [M+H]+). When cooled to 20° C., the mixture was filtered, the filter cake washed with EtOAc (100 ml), and the filtrate combined with the next time reaction, washed with HCl (0.5 M, 100 mL), 5% NH3.H2O (100 mL), dried over Na2SO4, filtered and concentrated to give 1-(4-bromo-3-fluorophenyl)pyrrolidin-2-one (33.6 g, yield: 95%) as a pale yellow solid.

1H NMR (400 MHz, CDCl3) δ 2.10-2.24 (2H, m), 2.61 (2H, t, J=8.0 Hz), 3.82 (2H, t, J=7.2 Hz), 7.24-7.27 (1H, m), 7.48 (1H, dd, J=8.0, 8.0 Hz), 7.65 (1H, dd, J=8.0, 2.4 Hz).

Step 2: Preparation of 1-(3-fluoro-4-(4,4,5,5-tetramethyl-1,3,2-dioxaborolan-2-yl)phenyl)pyrrolidin-2-one

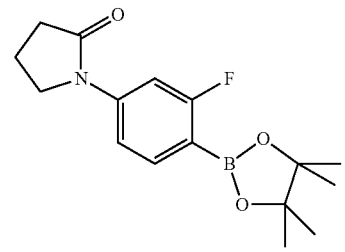 [SMILES: CC1(C)OB(c2ccc(N3CCCC3=O)cc2F)OC1(C)C]

A mixture of 1-(4-bromo-3-fluorophenyl)pyrrolidin-2-one (12.0 g, 46.5 mmol), B2Pin2 (17.7 g, 69.7 mmol) and Pd(dppf)Cl2 (3.40 g, 4.65 mmol) in toluene (200 mL) was stirred at 100° C. for 40 h under N2 atmosphere. A red solution turned to black gradually. LCMS (Rt=0.689 min; MS Calcd: 305.2. MS Found: 306.1 [M+H]+). The reaction mixture was cooled to 20° C. and filtered through silica gel and washed with MTBE (800 mL). The solvent was evaporated under reduced pressure to give 1-(3-fluoro-4-(4,4,5,5-tetramethyl-1,3,2-dioxaborolan-2-yl)phenyl)pyrrolidin-2-one (20.0 g, crude) as a black brown gum.

Step 3: Preparation of 2-chloro-5-(2-fluoro-4-(2-oxopyrrolidin-1-yl)phenyl)isonicotinaldehyde

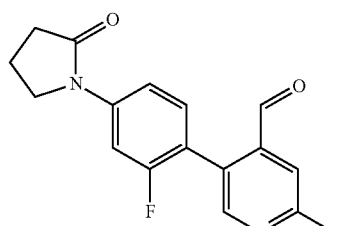

1-(3-Fluoro-4-(4,4,5,5-tetramethyl-1,3,2-dioxaborolan-2-yl)phenyl)pyrrolidin-2-one (7.84 g, 35.6 mmol), 5-bromo-2-chloroisonicotinaldehyde (16.0 g, 37.3 mmol), Pd(PPh3)4 (1.64 g, 1.42 mmol) and K2CO3 (14.8 g, 106 mmol) were taken up in MeCN (160 mL) and H2O (40 mL) and the resulting mixture was stirred at 70° C. for 2 h. A black solution was formed. LCMS (Rt=0.649 min; MS Calcd: 319.1. MS Found: 341.8 [M+Na]+). When cooled to 20° C. the mixture was diluted with half-saturated brine (50 mL) and EtOAc (50 ml). The organic layer was separated and the aqueous layer extracted with EtOAc (50 mL×2). The combined organics were dried over Na2SO4, filtered through a plug of silica and concentrated to give 2-chloro-5-(2-fluoro-4-(2-oxopyrrolidin-1-yl)phenyl)isonicotinaldehyde (13.8 g, crude) as a black brown gum.

Step 4: Preparation of 1-(4-(6-chloro-4-(1-hydroxy-ethyl)pyridin-3-yl)-3-fluorophenyl)pyrrolidin-2-one

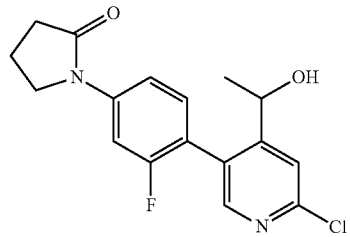 [SMILES: CC(O)c1cc(Cl)ncc1-c1ccc(N2CCCC2=O)cc1F]

MeMgBr (3 M in Et₂O, 30 mL) was added slowly to a solution of 2-chloro-5-(2-fluoro-4-(2-oxopyrrolidin-1-yl)phenyl)isonicotinaldehyde (11.3 g, 35.4 mmol) in THF (200 mL) at 0° C. under N₂ atmosphere to give a suspension. The resulting mixture was stirred at 0° C. for 2 h. LCMS (Rt=0.617 min; MS Calcd: 334.1. MS Found: 334.9 [M+H]⁺). Sat. aq.NH₄Cl (80 mL) was added followed by EtOAc (80 mL). The organic layer was separated and the aqueous layer extracted with EtOAc (100 mL×2). The combined organics were dried over Na₂SO₄, filtered and concentrated to give 1-(4-(6-chloro-4-(1-hydroxyethyl)pyridin-3-yl)-3-fluorophenyl)pyrrolidin-2-one (12.5 g, crude) as a black brown gum.

Step 5: Preparation of 1-(3-chloro-5-methyl-5H-chromeno[4,3-c]pyridin-8-yl)pyrrolidin-2-one

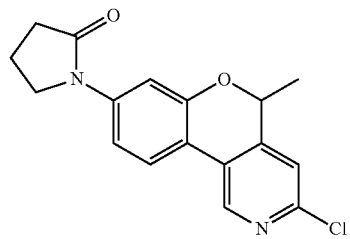 [SMILES: CC1Oc2cc(N3CCCC3=O)ccc2-c2cnc(Cl)cc21]

NaH (2.82 g, 70.5 mmol, 60% in mineral oil) was added to a solution of 1-(4-(6-chloro-4-(1-hydroxyethyl)pyridin-3-yl)-3-fluorophenyl)pyrrolidin-2-one (11.8 g, 35.3 mmol) in THF (150 mL) at 20° C. and the resulting mixture was stirred at 20° C. for 2 h. A black solution was formed. LCMS (Rt=0.654 min; MS Calcd: 314.1. MS Found: 314.9 [M+H]⁺). Sat. aq. NH₄Cl (80 mL) was added and the mixture extracted with EtOAc (80 mL×3). The combined organic layer was dried over Na₂SO₄, filtered, concentrated. The residue was purified by Combi Flash (60% EtOAc in pentane) to give 1-(3-chloro-5-methyl-5H-chromeno[4,3-c]pyridin-8-yl)pyrrolidin-2-one (1.22 g, 3.88 mmol, yield: 11% for four steps) as a yellow solid.

¹H NMR (400 MHz, CDCl₃) δ 1.62 (3H, d, J=6.8 Hz), 2.10-2.24 (2H, m), 2.63 (2H, t, J=8.0 Hz), 3.87 (2H, t, J=8.0 Hz), 5.19 (1H, q, J=6.8 Hz), 7.10 (1H, s), 7.32 (1H, d, J=2.0 Hz), 7.41 (1H, dd, J=8.4, 2.0 Hz), 7.72 (1H, d, J=8.8 Hz), 8.64 (1H, s).

Step 6: Preparation of tert-butyl (5-methyl-8-(2-oxopyrrolidin-1-yl)-5H-chromeno[4,3-c]pyridin-3-yl)carbamate

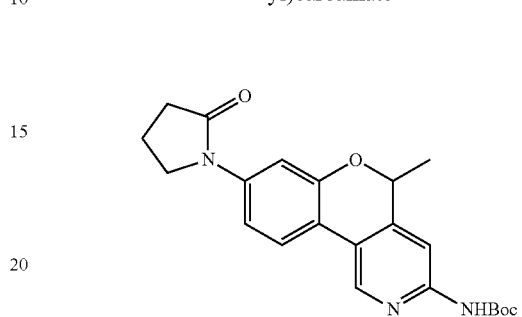

A mixture of Pd₂(dba)₃ (44 mg, 0.047 mmol) and Xantphos (55 mg, 0.095 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (300 mg, 0.953 mmol), BocNH₂ (167 mg, 1.43 mmol) in 1,4-dioxane (10 mL) and Cs₂CO₃ (776 mg, 2.38 mmol) were added, and the resulting mixture was stirred at 100° C. for 16 h. A black brown mixture was formed. LCMS (Rt=0.688 min; MS Calcd: 395.2. MS Found: 396.0 [M+H]⁺). The reaction mixture was diluted with DCM (20 mL), filtered and concentrated to give tert-butyl (5-methyl-8-(2-oxopyrrolidin-1-yl)-5H-chromeno[4,3-c]pyridin-3-yl)carbamate (500 mg, crude) as a black brown gum.

Step 7: Preparation of 1-(3-amino-5-methyl-5H-chromeno[4,3-c]pyridin-8-yl)pyrrolidin-2-one

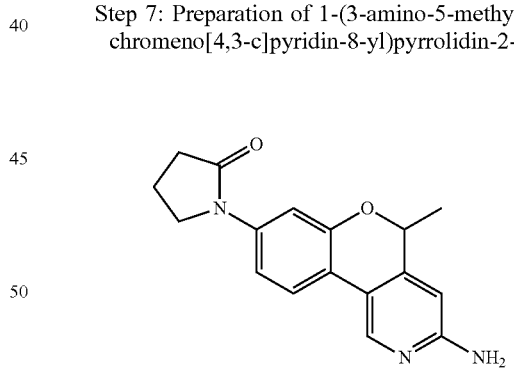

To a stirred solution of tert-butyl (5-methyl-8-(2-oxopyrrolidin-1-yl)-5H-chromeno[4,3-c]pyridin-3-yl)carbamate (370 mg, 0.935 mmol) in DCM (6 mL) was added HCl/EtOAc (4 M, 61 mL) at 20° C. The yellow solution turned to suspension, the reaction mixture was stirred for 1 hour. TLC indicated the starting material was consumed completely, and one new spot with larger polarity was detected. The mixture was concentrated. The residue was purified by Combi Flash (1% Et₃N in EtOAc) to give 1-(3-amino-5-methyl-5H-chromeno[4,3-c]pyridin-8-yl)pyrrolidin-2-one (200 mg, yield: 55% for two steps) as a yellow solid.

Step 8: Preparation of N-(5-bromopyridin-3-yl)methanesulfonamide

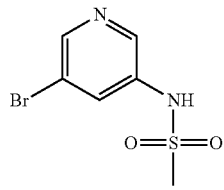

A solution of 5-bromopyridin-3-amine (500 mg, 2.89 mmol) and pyridine (4.3 mL, 54 mmol) was stirred in DCM (20 mL), then MsCl (331 mg, 2.89 mmol) was added into the above solution at 0° C., which was stirred at 20° C. for 16 h. A yellow solution was formed. TLC showed the starting material was consumed completely. The solution was diluted with $H_2O$ (30 mL) and was extracted with DCM (15 mL×3). The organic layer was washed with brine (15 mL), dried over $Na_2SO_4$ to give N-(5-bromopyridin-3-yl)methanesulfonamide (700 mg, yield: 96%) as a yellow solid.

Step 9: Preparation of N-(5-bromopyridin-3-yl)-N-methylmethanesulfonamide

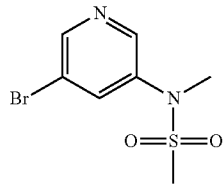

A solution of N-(5-bromopyridin-3-yl)methanesulfonamide (700 mg, 2.79 mmol) in DMF (8 mL) was treated with $K_2CO_3$ (771 mg, 5.58 mmol) and $CH_3I$ (594 mg, 4.18 mmol) at 20° C. for 18 h. A black brown solution was formed. TLC showed the starting material was consumed completely. The reaction was concentrated under reduced pressure. The residue was purified by Combi Flash (40% EtOAc in pentane) to give N-(5-bromopyridin-3-yl)-N-methylmethanesulfonamide (563 mg, yield: 76%) as a red solid. $^1$H NMR (400 MHz, CDCl$_3$) δ 2.91 (3H, s), 3.37 (3H, s), 7.92 (1H, t, J=2.0 Hz), 8.57 (1H, d, J=2.0 Hz), 8.59 (1H, d, J=2.0 Hz).

Step 10: Preparation of tert-butyl (5-(N-methylmethylsulfonamido)pyridin-3-yl)carbamate

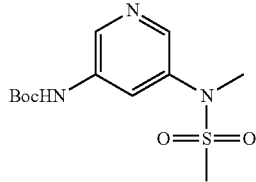

A mixture of Pd$_2$(dba)$_3$ (86 mg, 0.094 mmol) and XantPhos (109 mg, 0.189 mmol) in 1,4-dioxane (1 mL) was stirred at 50° C. for 10 min. N-(5-bromopyridin-3-yl)-N-methylmethanesulfonamide (500 mg, 1.89 mmol), BocNH$_2$ (331 mg, 2.83 mmol) in dioxane (15 mL) and Cs$_2$CO$_3$ (1.54 g, 4.71 mmol) were added and the resulting mixture was stirred at 100° C. for 16 h. A black brown mixture was formed. TLC indicated the starting material was consumed completely. The reaction mixture was diluted with DCM (10 mL), filtered and concentrated. The residue was purified by Combi Flash (60% EtOAc in pentane) to give tert-butyl (5-(N-methylmethylsulfonamido)pyridin-3-yl)carbamate (275 mg, yield: 48%) as a brown solid.

$^1$H NMR (400 MHz, CDCl$_3$) δ 1.53 (9H, s), 2.91 (3H, s), 3.36 (3H, s), 6.73 (1H, brs), 8.08 (1H, s), 8.33 (1H, d, J=2.4 Hz), 8.36 (1H, d, J=2.4 Hz).

Step 11: Preparation of N-(5-aminopyridin-3-yl)-N-methylmethanesulfonamide

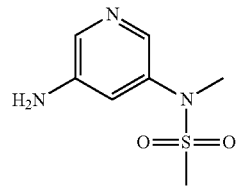

To a stirred solution of tert-butyl (5-(N-methylmethylsulfonamido)pyridin-3-yl)carbamate (275 mg, 0.912 mmol) in DCM (5 mL) was added HCl/EtOAc (4 M, 8 mL) at 20° C. The yellow solution turned to suspension, the reaction mixture was stirred for 1 hour. TLC indicated the starting material was consumed completely, and one new spot with larger polarity was detected. The mixture was concentrated to give N-(5-aminopyridin-3-yl)-N-methylmethanesulfonamide (215 mg, yield: 99%) as a yellow solid.

$^1$H NMR (400 MHz, DMSO-d$_6$) δ 3.13 (3H, s), 3.29 (3H, s), 7.60 (1H, t, J=2.4 Hz), 7.92 (1H, d, J=2.0 Hz), 8.09 (1H, d, J=2.0 Hz).

Step 12: Preparation of N-methyl-N-(5-((5-methyl-8-(2-oxopyrrolidin-1-yl)-5H-chromeno[4,3-c]pyridin-3-yl)amino)pyridin-3-yl)methanesulfonamide

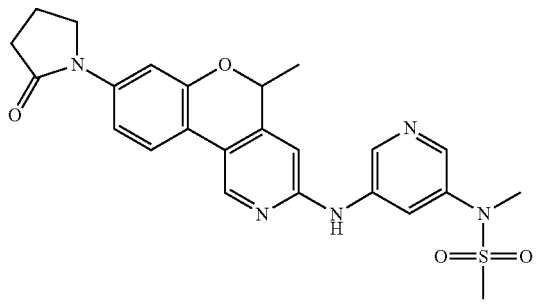 [SMILES: CC1Oc2cc(N3CCCC3=O)ccc2-c2cnc(Nc3cncc(N(C)S(C)(=O)=O)c3)cc21]

A mixture of Pd$_2$(dba)$_3$ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), N-(5-aminopyridin-3-yl)-N-methylmethanesulfonamide (45 mg, 0.19 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.595 min; MS Calcd: 479.2. MS Found: 480.0

[M+H]⁺). The reaction mixture was diluted with DCM (10 mL), filtered and concentrated. The residue was purified by prep-HPLC (0.05% NH₃.H₂O as an additive) and lyophilized to give N-methyl-N-(5-((5-methyl-8-(2-oxopyrrolidin-1-yl)-5H-chromeno[4,3-c]pyridin-3-yl)amino)pyridin-3-yl)methanesulfonamide (22.8 mg, yield: 30%) as a white solid.

LC-MS (Shimadzu LCMS 2010, mobile phase: C) 10 mM NH₄HCO₃ in Water; D) MECN. Gradient: 1% D increase to 5% D within 0.6 min; 5% DB increase to 100% D within 3.4 min; then back to 1% D within 0.3 min. Flow rate 0.8 mL/min) purity is 100%, Rt=2.640 min; MS Calcd.: 479.2, MS Found: 480.3 [M+H]⁺.

¹H NMR (400 MHz, DMSO-d₆) δ 1.53 (3H, d, J=6.0 Hz), 2.02-2.09 (2H, m), 2.64 (2H, overlap with DMSO), 3.04 (3H, s), 3.29 (3H, s), 3.84 (2H, t, J=6.8 Hz), 5.28 (1H, q, J=6.4 Hz), 6.75 (1H, s), 7.32 (1H, dd, J=8.4, 2.0 Hz), 7.40 (1H, s), 7.89 (1H, d, J=8.4 Hz), 8.19 (1H, s), 8.29 (1H, s), 8.70 (1H, s), 8.75 (1H, s), 9.61 (1H, brs).

Example 49: 1-(5-methyl-3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one

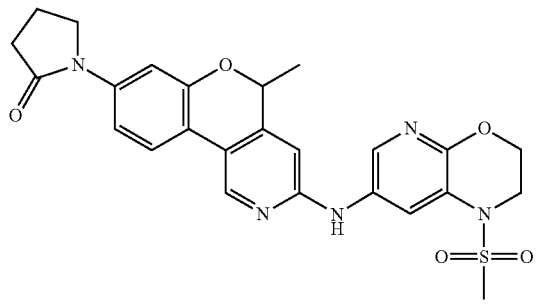 [SMILES: CC1Oc2cc(N3CCCC3=O)ccc2-c2cnc(Nc3cnc4c(c3)N(S(C)(=O)=O)CCO4)cc21]

Step 1: Preparation of 7-bromo-1-(methylsulfonyl)-2,3-dihydro-1H-pyrido[2,3-b][1,4]oxazine

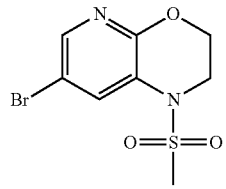

To a solution of 7-bromo-2,3-dihydro-H-pyrido[2,3-b][1,4]oxazine (300 mg, 1.40 mmol) in DCM (5 mL) was added pyridine (221 mg, 2.80 mmol) and MsCl (321 mg, 2.80 mmol) at 15° C., the mixture was stirred at 15° C. for 16 h. A red solution was formed. Crude LCMS showed the purity of the product (Rt=0.757 min; MS Calcd: 292.0. MS Found: 292.7 [M+H]⁺). The mixture was added sat.NH₃.H₂O (10 mL), extracted with DCM (10 mL×3), and dried over Na₂SO₄, the residue was purified by Combi Flash (DCM) to give 7-bromo-1-(methylsulfonyl)-2,3-dihydro-1H-pyrido[2,3-b][1,4]oxazine (350 mg, yield: 85%) as a white solid.

¹H NMR (400 MHz, CDCl₃) δ 1.55 (3H, s), 3.90 (2H, t, J=4.4 Hz), 4.45 (2H, t, J=4.4 Hz), 8.08 (1H, d, J=2.0 Hz), 8.19 (1H, d, J=2.0 Hz).

Step 2: Preparation of tert-butyl (1-(methylsulfonyl)-2,3-dihydro-1H-pyrido[2,3-b][1,4]oxazin-7-yl) carbamate

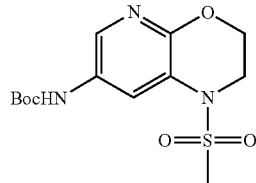 [SMILES: CC(C)(C)OC(=O)Nc1cnc2c(c1)N(S(C)(=O)=O)CCO2]

A mixture of Pd₂(dba)₃ (55 mg, 0.060 mmol) and XantPhos (69 mg, 0.12 mmol) in 1,4-dioxane (1 mL) was stirred at 50° C. for 10 min. 7-Bromo-1-(methylsulfonyl)-2,3-dihydro-1H-pyrido[2,3-b][1,4]oxazine (350 mg, 1.19 mmol), BocNH₂ (210 mg, 1.79 mmol) in dioxane (10 mL) and Cs₂CO₃ (973 mg, 2.98 mmol) were added, and the resulting mixture was stirred at 100° C. for 16 h. A black brown mixture was formed. LCMS (Rt=0.596 min; MS Calcd: 329.1. MS Found: 330.1 [M+H]⁺). The reaction mixture was diluted with DCM (20 mL), filtered and concentrated. The residue was purified by Combi Flash (60% EtOAc in pentane) to give tert-butyl (1-(methylsulfonyl)-2,3-dihydro-1H-pyrido[2,3-b][1,4]oxazin-7-yl)carbamate (270 mg, yield: 69%) as a yellow gum.

¹H NMR (400 MHz, CDCl₃) δ 1.51 (9H, s), 3.02 (3H, s), 3.88 (2H, t, J=8.4 Hz), 4.41 (2H, t, J=8.0 Hz), 6.42 (1H, brs), 8.01 (1H, s), 8.16 (1H, s).

Step 3: Preparation of 1-(methylsulfonyl)-2,3-dihydro-H-pyrido[2,3-b][1,4]oxazin-7-amine

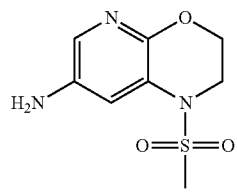

To a stirred solution of tert-butyl (1-(methylsulfonyl)-2,3-dihydro-1H-pyrido[2,3-b][1,4]oxazin-7-yl)carbamate (270 mg, 0.820 mmol) in DCM (4 mL) was added HCl/EtOAc (4 M, 10 mL) at 20° C. The red solution turned to suspension, then the reaction mixture was stirred for 1 h. TLC indicated the starting material was consumed completely, and one major new spot with larger polarity was detected. The mixture was concentrated to give 1-(methylsulfonyl)-2,3-dihydro-1H-pyrido[2,3-b][1,4]oxazin-7-amine (240 mg, yield: 97%) as an off-white solid.

¹H NMR (400 MHz, DMSO-d₆) δ 3.25 (3H, s), 3.84 (2H, t, J=4.4 Hz), 4.32 (2H, brs), 4.43 (2H, t, J=4.4 Hz), 7.96 (1H, d, J=2.0 Hz), 8.03 (1H, d, J=2.0 Hz).

Step 4: Preparation of 1-(5-methyl-3-((1-(methyl-sulfonyl)-2,3-dihydro-1H-pyrido[2,3-b][1,4]oxazin-7-yl)amino)-5H-chromeno[4,3-c]pyridin-8-yl)pyrrolidin-2-one Example 50: 1-(3-((5-fluoropyridin-3-yl)amino)-5-methyl-5H-chromeno[4,3-c]pyridin-8-yl)pyrrolidin-2-one

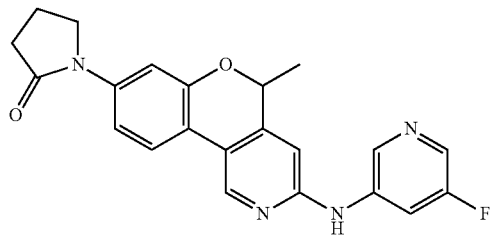 [SMILES: CC1Oc2cc(N3CCCC3=O)ccc2-c2cnc(Nc3cncc(F)c3)cc21]

Step 1: Preparation of tert-butyl (5-fluoropyridin-3-yl)carbamate

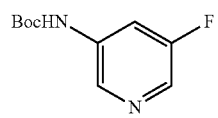 [SMILES: CC(C)(C)OC(=O)Nc1cncc(F)c1]

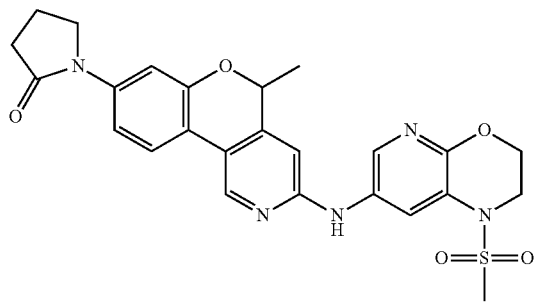

A mixture of Pd$_2$(dba)$_3$ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), 1-(methylsulfonyl)-2,3-dihydro-1H-pyrido[2,3-b][1,4]oxazin-7-amine (84 mg, 0.28 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.587 min; MS Calcd: 507.2. MS Found: 508.3 [M+H]$^+$). The reaction mixture was diluted with DCM (10 mL), filtered and concentrated. The residue was purified by prep-HPLC (normal phase, Hexane-IPA (50-100% B)) and lyophilized to give impure product (25 mg) as a yellow solid, then purified by prep-HPLC (0.05% NH$_3$.H$_2$O as an additive) and lyophilized to give 1-(5-methyl-3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one (18.1 mg, yield: 22%) as a white solid.

LC-MS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 96.38%, Rt=2.190 min; MS Calcd.: 507.2, MS Found: 508.1 [M+H]$^+$.

$^1$H NMR (400 MHz, D$_2$O+CDCl$_3$) δ 1.58 (3H, d, J=6.8 Hz), 2.12-2.21 (2H, m), 2.63 (2H, t, J=8.0 Hz), 3.06 (3H, s), 3.84 (2H, t, J=6.0 Hz), 3.91 (2H, t, J=4.8 Hz), 4.45 (2H, t, J=4.4 Hz), 5.13 (1H, q, J=6.4 Hz), 6.52 (1H, s), 7.28 (1H, overlap with CDCl$_3$), 7.37 (1H, dd, J=8.0, 2.0 Hz), 7.66 (1H, d, J=7.6 Hz), 8.07 (1H, d, J=2.0 Hz), 8.27 (1H, d, J=2.0 Hz), 8.50 (1H, s).

A mixture of Pd$_2$(dba)$_3$ (78 mg, 0.085 mmol) and Xantphos (99 mg, 0.17 mmol) in 1,4-dioxane (1 mL) was stirred at 50° C. for 10 min. 3-Bromo-5-fluoropyridine (300 mg, 1.70 mmol), BocNH$_2$ (300 mg, 2.56 mmol) in dioxane (10 mL) and Cs$_2$CO$_3$ (1.39 g, 4.26 mmol) were added and the resulting mixture was stirred at 100° C. for 16 h. A black brown mixture was formed. LCMS (Rt=0.619 min; MS Calcd: 212.1. MS Found: 213.0 [M+H]$^+$). The reaction mixture was diluted with DCM (10 mL), filtered and concentrated. The residue was purified by Combi Flash (17% EtOAc in pentane) to give tert-butyl (5-fluoropyridin-3-yl)carbamate (360 mg, yield: 99%) as a yellow solid.

$^1$H NMR (400 MHz, CDCl$_3$) δ 1.53 (9H, s), 6.65 (1H, brs), 7.85 (1H, d, J=9.2 Hz), 8.14 (1H, d, J=2.0 Hz), 8.15-8.16 (1H, m).

Step 2: Preparation of 5-fluoropyridin-3-amine

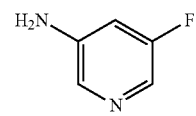

To a stirred solution of tert-butyl (5-fluoropyridin-3-yl)carbamate (350 mg, 1.65 mmol) in DCM (4 mL) was added HCl/EtOAc (4 M, 15 mL) at 20° C. The yellow solution turned to suspension. Then the reaction mixture was stirred for 1 hour. TLC indicated the starting material was consumed completely, and one new spot with larger polarity was detected. The mixture was concentrated to give 5-fluoropyridin-3-amine (245 mg, yield: 100%) as a yellow solid.

$^1$H NMR (400 MHz, DMSO-d$_6$) δ 7.27 (2H, t, J=11.2 Hz), 7.33 (1H, dt, J=10.8, 2.0 Hz), 7.93 (1H, d, J=2.0 Hz), 8.07-8.11 (1H, m).

Step 3: Preparation of 1-(3-((5-fluoropyridin-3-yl)amino)-5-methyl-5H-chromeno[4,3-c]pyridin-8-yl)pyrrolidin-2-one

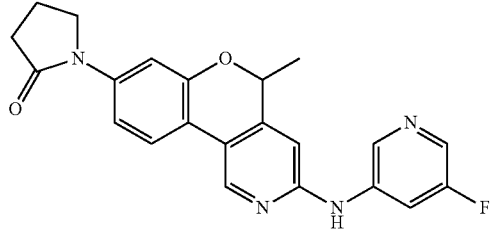 [SMILES: CC1Oc2cc(N3CCCC3=O)ccc2-c2cnc(Nc3cncc(F)c3)cc21]

A mixture of Pd$_2$(dba)$_3$ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), 5-fluoropyridin-3-amine (28 mg, 0.19 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.639 min; MS Calcd: 390.2. MS Found: 391.1 [M+H]$^+$). The reaction mixture was diluted with DCM (10 mL), filtered and concentrated. The residue was purified by prep-HPLC (0.05% NH$_3$.H$_2$O as an additive) and lyophilized to give impure product (20 mg) as an off-white solid. The impure product was purified by prep-HPLC (0.05% NH$_3$.H$_2$O as an additive) and lyophilized to give 1-(3-((5-fluoropyridin-3-yl)amino)-5-methyl-5H-chromeno[4,3-c]pyridin-8-yl)pyrrolidin-2-one (7.3 mg, yield: 12%) as a white solid.

LC-MS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.62%, Rt=3.234 min; MS Calcd.: 390.2, MS Found: 391.2 [M+H]$^+$.

$^1$H NMR (400 MHz, DMSO-d$_6$) δ 1.52 (3H, d, J=6.4 Hz), 2.00-2.06 (2H, m), 2.48 (2H, overlap with DMSO), 3.82 (2H, t, J=7.2 Hz), 5.27 (1H, q, J=6.8 Hz), 6.78 (1H, s), 7.30 (1H, dd, J=8.4, 2.4 Hz), 7.39 (1H, d, J=2.0 Hz), 7.87 (1H, d, J=8.4 Hz), 8.04 (1H, d, J=2.8 Hz), 8.39 (1H, dt, J=12.4, 2.0 Hz), 8.53 (1H, t, J=2.0 Hz), 8.70 (1H, s), 9.92 (1H, brs).

Example 51: N-cyclopropyl-N-(5-((5-methyl-8-(2-oxopyrrolidin-1-yl)-5H-chromeno[4,3-c]pyridin-3-yl)amino)pyridin-3-yl)methanesulfonamide

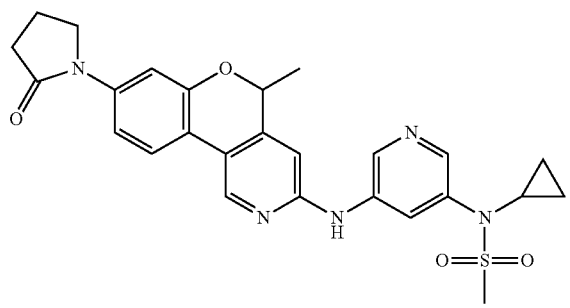 [SMILES: CC1Oc2cc(N3CCCC3=O)ccc2-c2cnc(Nc3cncc(N(C4CC4)S(C)(=O)=O)c3)cc21]

Step 1: Preparation of 5-bromo-N-cyclopropylpyridin-3-amine

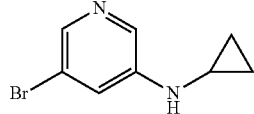 [SMILES: Brc1cncc(NC2CC2)c1]

To a mixture of 3,5-dibromopyridine (2.01 g, 8.48 mmol), cyclopropanamine (969 mg, 17.0 mmol), Cu (54 mg, 0.85 mmol) in H$_2$O (3 mL) were added and the resulting mixture was stirred at 100° C. for 42 h. A black brown mixture was formed. LCMS (Rt=0.453 min; MS Calcd: 214.0. MS Found: 214.8 [M+H]$^+$). The reaction mixture was diluted with DCM (20 mL), and was extracted with DCM (10 mL×3), dried over Na$_2$SO$_4$ and concentrated. The residue was purified by Combi Flash (45% EtOAc in pentane) to give 5-bromo-N-cyclopropylpyridin-3-amine (220 mg, yield: 12%) as a yellow solid.

Step 2: Preparation of N-(5-bromopyridin-3-yl)-N-cyclopropylmethanesulfonamide

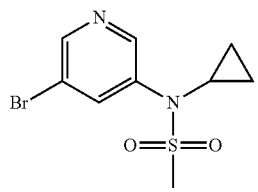

A solution of 5-bromo-N-cyclopropylpyridin-3-amine (220 mg, 1.03 mmol) and pyridine (2 mL) was stirred in DCM (5 mL), then MsCl (142 mg, 1.24 mmol) was added into the above solution at 0° C., which was stirred at 20° C. for 16 h. A red solution was formed. LCMS (Rt=0.591 min; MS Calcd: 292.0. MS Found: 292.7 [M+H]$^+$). The solution was diluted with H$_2$O (20 mL) and was extracted with DCM (10 mL×3). The organic layer was dried over Na$_2$SO$_4$, and concentrated. The residue was purified by Combi Flash (50% EtOAc in pentane) to give N-(5-bromopyridin-3-yl)-N-cyclopropylmethanesulfonamide (160 mg, yield: 53%) as a yellow solid.

$^1$H NMR (400 MHz, CDCl$_3$) δ 0.77-0.82 (2H, m), 0.94-1.02 (2H, m), 2.92-2.97 (1H, m), 2.98 (3H, s), 7.87 (1H, t, J=2.0 Hz), 8.52-8.61 (2H, m).

Step 3: Preparation of tert-butyl (5-(N-cyclopropylmethylsulfonamido)pyridin-3-yl)carbamate

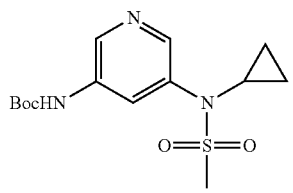 [SMILES: CC(C)(C)OC(=O)Nc1cncc(N(C2CC2)S(C)(=O)=O)c1]

A mixture of Pd$_2$(dba)$_3$ (25 mg, 0.027 mmol) and XantPhos (32 mg, 0.055 mmol) in 1,4-dioxane (1 mL) was stirred at 50° C. for 10 min. N-(5-bromopyridin-3-yl)-N-cyclopropylmethanesulfonamide (160 mg, 0.550 mmol), BocNH$_2$ (97 mg, 0.824 mmol) in dioxane (6 mL) and Cs$_2$CO$_3$ (448 mg, 1.37 mmol) were added, and the resulting mixture was stirred at 100° C. for 16 h. A black brown mixture was formed. LCMS (Rt=0.586 min; MS Calcd: 327.1. MS Found: 327.9 [M+H]$^+$). The reaction mixture was diluted with DCM (15 mL), filtered and concentrated. The residue was purified by Combi Flash (90% EtOAc in pentane) to give tert-butyl (5-(N-cyclopropylmethylsulfonamido)pyridin-3-yl)carbamate (179 mg, yield: 99%) as a yellow solid.

Step 4: Preparation of N-(5-aminopyridin-3-yl)-N-cyclopropylmethanesulfonamide

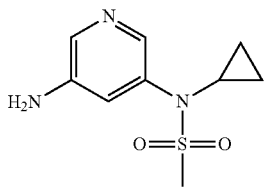

To a stirred solution of tert-butyl (5-(N-cyclopropylmethylsulfonamido)pyridin-3-yl)carbamate (179 mg, 0.547 mmol) in DCM (3 mL) was added HCl/EtOAc (4 M, 7 mL) at 20° C. The yellow solution turned to suspension, the reaction mixture was stirred for 1 hour. TLC indicated the starting material was consumed completely, and one new spot with larger polarity was detected. The mixture was concentrated to give N-(5-aminopyridin-3-yl)-N-cyclopropylmethanesulfonamide (124 mg, yield: 100%) as a yellow solid.

$^1$H NMR (400 MHz, DMSO-d$_6$) δ 0.64-0.72 (2H, m), 0.85-0.93 (2H, m), 3.19 (3H, s), 3.20-3.24 (1H, m), 7.56 (1H, t, J=2.0 Hz), 7.92 (1H, d, J=2.0 Hz), 8.07 (1H, d, J=2.0 Hz).

Step 5: Preparation of N-cyclopropyl-N-(5-((5-methyl-8-(2-oxopyrrolidin-1-yl)-5H-chromeno[4,3-c]pyridin-3-yl)amino)pyridin-3-yl)methanesulfonamide

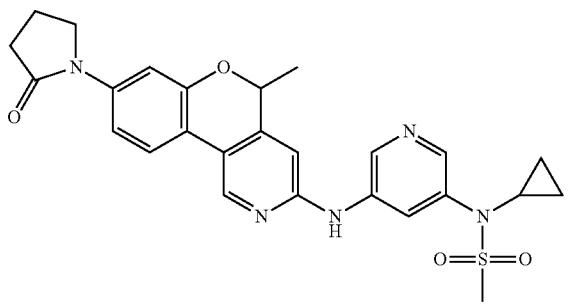 [SMILES: CC1Oc2cc(N3CCCC3=O)ccc2-c2cnc(Nc3cncc(N(C4CC4)S(C)(=O)=O)c3)cc21]

A mixture of Pd$_2$(dba)$_3$ (7 mg, 0.008 mmol) and BrettPhos (8 mg, 0.002 mmol) in 1,4-dioxane (1 mL) was stirred at 50° C. for 10 min. 1-(3-Chloro-5-methyl-H-chromeno[4,3-c]pyridin-8-yl)pyrrolidin-2-one (50 mg, 0.16 mmol), N-(5-aminopyridin-3-yl)-N-cyclopropylmethanesulfonamide (50 mg, 0.19 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.616 min; MS Calcd: 505.2. MS Found: 506.1 [M+H]$^+$). The reaction mixture was diluted with DCM (10 mL), filtered and concentrated. The residue was purified by prep-HPLC (0.05% NH$_3$.H$_2$O as an additive) and lyophilized to give N-cyclopropyl-N-(5-((5-methyl-8-(2-oxopyrrolidin-1-yl)-5H-chromeno[4,3-c]pyridin-3-yl)amino)pyridin-3-yl)methanesulfonamide (10.2 mg, yield: 13%) as a white solid.

LC-MS (Shimadzu LCMS 2010, mobile phase: C) 10 mM NH$_4$HCO$_3$ in Water; D) MECN. Gradient: 1% D increase to 5% D within 0.6 min; 5% DB increase to 100% D within 3.4 min; then back to 1% D within 0.3 min. Flow rate 0.8 mL/min) purity is 100%, Rt=2.766 min; MS Calcd.: 505.2, MS Found: 506.3 [M+H]$^+$.

$^1$H NMR (400 MHz, CDCl$_3$) δ 0.81-0.86 (2H, m), 0.94-0.99 (2H, m), 1.61 (3H, d, J=6.8 Hz), 2.14-2.21 (2H, m), 2.63 (2H, t, J=8.4 Hz), 2.95-3.00 (1H, m), 3.01 (3H, s), 3.87 (2H, t, J=7.2 Hz), 5.15 (1H, q, J=6.4 Hz), 6.65 (1H, s), 6.70 (1H, brs), 7.27 (1H, s), 7.40 (1H, dd, J=8.4, 2.0 Hz), 7.68 (1H, d, J=8.4 Hz), 8.08 (1H, d, J=2.0 Hz), 8.26 (1H, d, J=2.0 Hz), 8.52 (1H, d, J=2.4 Hz), 8.56 (1H, s).

Example 52: 1-(3-((1-(cyclopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one

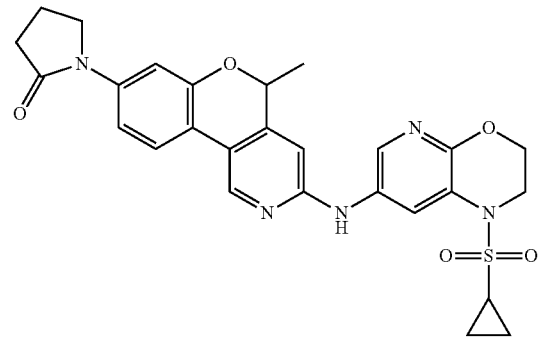 [SMILES: CC1Oc2cc(N3CCCC3=O)ccc2-c2cnc(Nc3cnc4c(c3)N(S(=O)(=O)C3CC3)CCO4)cc21]

Step 1: Preparation of 7-bromo-1-(cyclopropylsulfonyl)-2,3-dihydro-1H-pyrido[2,3-b][1,4]oxazine

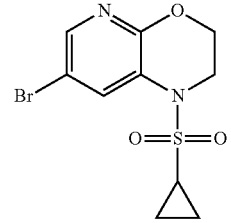 [SMILES: O=S(=O)(C1CC1)N1CCOc2ncc(Br)cc21]

To a solution of 7-bromo-2,3-dihydro-1H-pyrido[2,3-b][1,4]oxazine (300 mg, 1.40 mmol) in pyridine (10 mL) was added cyclopropanesulfonyl chloride (787 mg, 5.60 mmol) under nitrogen. The resulting mixture was stirred for 40 h at 20° C. The orange solution was formed. LCMS showed the starting material was not consumed. Additional cyclopropanesulfonyl chloride (787 mg, 5.60 mmol) was added, and stirred for 60 h at 50° C. The solution turned to black. LCMS showed the starting material was consumed nearly, and the purity of desired product (Rt=0.625 min; MS Calcd: 320.0. MS Found: 320.8 [M+H]⁺). Pyridine was removed under reduced pressure. The residue was purified by Combi Flash (50% EtOAc in pentane) to give 7-bromo-1-(cyclopropylsulfonyl)-2,3-dihydro-1H-pyrido[2,3-b][1,4]oxazine (343 mg, yield: 77%) as a yellow solid.

¹H NMR (400 MHz, CDCl₃) δ 1.00-1.13 (2H, m), 1.21-1.31 (2H, m), 2.40-2.52 (1H, m), 3.87 (2H, t, J=4.4 Hz), 4.48 (2H, t, J=4.8 Hz), 8.07 (1H, d, J=2.0 Hz), 8.22 (1H, d, J=2.4 Hz).

Step 2: Preparation of tert-butyl (1-(cyclopropylsulfonyl)-2,3-dihydro-1H-pyrido[2,3-b][1,4]oxazin-7-yl)carbamate

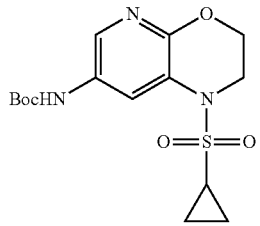

A mixture of Pd₂(dba)₃ (49 mg, 0.053 mmol) and XantPhos (62 mg, 0.11 mmol) in 1,4-dioxane (1 mL) was stirred at 50° C. for 10 min. 7-Bromo-1-(cyclopropylsulfonyl)-2,3-dihydro-1H-pyrido[2,3-b][1,4]oxazine (340 mg, 1.07 mmol), BocNH₂ (187 mg, 1.60 mmol) in dioxane (12 mL) and Cs₂CO₃ (868 mg, 2.66 mmol) were added and the resulting mixture was stirred at 100° C. for 16 h. A black brown mixture was formed. LCMS (Rt=0.639 min; MS Calcd: 355.1. MS Found: 356.1 [M+H]⁺). The reaction mixture was diluted with DCM (10 mL), filtered and concentrated. The residue was purified by Combi Flash (55% EtOAc in pentane) to give tert-butyl (1-(cyclopropylsulfonyl)-2,3-dihydro-1H-pyrido[2,3-b][1,4]oxazin-7-yl)carbamate (375 mg, yield: 99%) as a yellow solid.

¹H NMR (400 MHz, CDCl₃) δ 1.00-1.09 (2H, m), 1.25-1.30 (2H, m), 1.51 (9H, s), 2.44-2.54 (1H, m), 3.87 (2H, t, J=4.4 Hz), 4.45 (2H, t, J=4.4 Hz), 6.57 (1H, brs), 8.03 (1H, d, J=2.0 Hz), 8.18 (1H, d, J=2.4 Hz).

Step 3: Preparation of 1-(cyclopropylsulfonyl)-2,3-dihydro-1H-pyrido[2,3-b][1,4]oxazin-7-amine

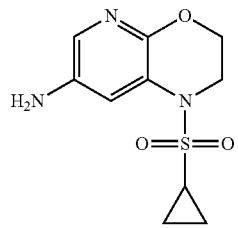 [SMILES: Nc1cnc2c(c1)N(S(=O)(=O)C1CC1)CCO2]

To a stirred solution of tert-butyl (1-(cyclopropylsulfonyl)-2,3-dihydro-1H-pyrido[2,3-b][1,4]oxazin-7-yl)carbamate (375 mg, 1.06 mmol) in DCM (6 mL) was added HCl/EtOAc (4 M, 8 mL) at 20° C. The yellow solution turned to suspension. Then the reaction mixture was stirred for 1 hour. TLC indicated the starting material was consumed completely, and one new spot with larger polarity was detected. The mixture was concentrated to afford 1-(cyclopropylsulfonyl)-2,3-dihydro-TH-pyrido[2,3-b][1,4]oxazin-7-amine (305 mg, yield: 99%) as a yellow solid.

¹H NMR (400 MHz, DMSO-d₆) δ 0.94-1.12 (4H, m), 2.89-3.02 (1H, m), 3.82-3.94 (2H, m), 4.42-4.52 (2H, m), 8.04 (1H, s), 8.07 (1H, s).

Step 4: Preparation of 1-(3-((1-(cyclopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one

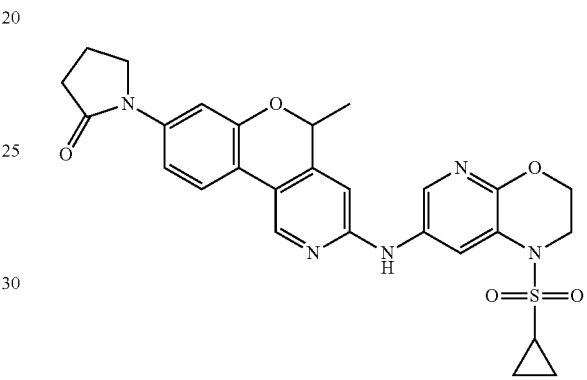

A mixture of Pd₂(dba)₃ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), 1-(cyclopropylsulfonyl)-2,3-dihydro-1H-pyrido[2,3-b][1,4]oxazin-7-amine (56 mg, 0.19 mmol) in dioxane (3 mL) and Cs₂CO₃ (155 mg, 0.476 mmol) were added and the resulting mixture was stirred at 100° C. for 16 h. A black brown mixture was formed. LCMS (Rt=0.604 min; MS Calcd: 533.2. MS Found: 534.1 [M+H]⁺). The reaction mixture was diluted with DCM (10 mL), filtered and concentrated. The residue was purified by prep-HPLC (0.05% NH₃.H₂O as an additive) and lyophilized to give 1-(3-((1-(cyclopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one (19.4 mg, yield: 23%) as a white solid.

LC-MS (Shimadzu LCMS 2010, mobile phase: C) 10 mM NH₄HCO₃ in Water; D) MECN. Gradient: 1% D increase to 5% D within 0.6 min; 5% DB increase to 100% D within 3.4 min; then back to 1% D within 0.3 min. Flow rate 0.8 mL/min) purity is 99.54%, Rt=2.786 min; MS Calcd.: 533.2, MS Found: 534.3 [M+H]⁺.

¹H NMR (400 MHz, DMSO-d₆) δ 1.02-1.08 (4H, m), 1.51 (3H, d, J=6.8 Hz), 2.00-2.09 (2H, m), 2.49 (2H, overlap with DMSO), 2.85-2.93 (1H, m), 3.80-3.86 (4H, m), 4.39 (2H, t, J=4.4 Hz), 5.23 (1H, q, J=6.4 Hz), 6.64 (1H, s), 7.30 (1H, dd, J=8.8, 2.0 Hz), 7.38 (1H, d, J=2.0 Hz), 7.86 (1H, d, J=8.8 Hz), 8.33 (1H, d, J=2.4 Hz), 8.38 (1H, d, J=2.4 Hz), 8.59 (1H, s), 9.30 (1H, brs).

Example 53: 1-methyl-3-(5-((5-methyl-8-(2-oxopyrrolidin-1-yl)-5H-chromeno[4,3-c]pyridin-3-yl)amino)pyridin-3-yl)imidazolidin-2-one

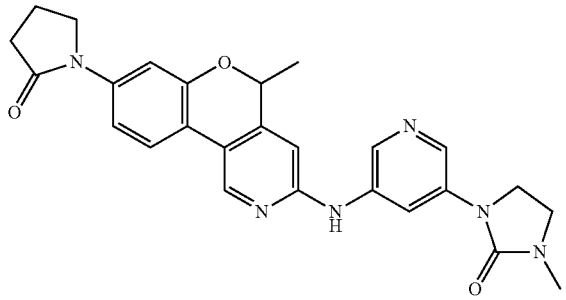 [SMILES: CC1Oc2cc(N3CCCC3=O)ccc2-c2cnc(Nc3cncc(N4CCN(C)C4=O)c3)cc21]

Step 1: Preparation of 1-(5-bromopyridin-3-yl)-3-methylimidazolidin-2-one

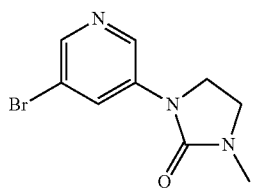

To a solution of 1-(5-bromopyridin-3-yl)imidazolidin-2-one (500 mg, 2.07 mmol) in THF (10 mL) was added NaH (99 mg, 2.5 mmol, 60% in mineral oil) portion-wise at 0° C., the reaction was warmed to 15° C. and stirred for 0.5 hour. MeI (382 mg, 2.69 mmol) was added and the mixture was stirred at 15° C. for another 16 h. A red suspension was formed. Crude LCMS showed the purity of the product (Rt=0.681 min; MS Calcd: 255.0. MS Found: 255.8 [M+H]$^+$). The reaction was diluted with H$_2$O (10 mL), extracted with EtOAc (10 mL×3), dried over Na$_2$SO$_4$ and concentrated to give a crude product which was purified by Combi Flash (60% EtOAc in pentane) to give 1-(5-bromopyridin-3-yl)-3-methylimidazolidin-2-one (310 mg, yield: 58%) as a light yellow solid.

$^1$H NMR (400 MHz, CDCl$_3$) δ 2.92 (3H, s), 3.53-3.57 (2H, m), 3.81-3.85 (2H, m), 8.33 (1H, d, J=2.0 Hz), 8.43 (1H, t, J=2.0 Hz), 8.52 (1H, d, J=2.0 Hz).

Step 2: Preparation of tert-butyl (5-(3-methyl-2-oxoimidazolidin-1-yl)pyridin-3-yl)carbamate

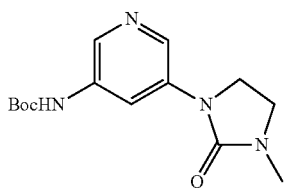 [SMILES: CN1CCN(c2cncc(NC(=O)OC(C)(C)C)c2)C1=O]

A mixture of Pd$_2$(dba)$_3$ (55 mg, 0.060 mmol) and XantPhos (70 mg, 0.12 mmol) in 1,4-dioxane (1 mL) was stirred at 50° C. for 10 min. 1-(5-Bromopyridin-3-yl)-3-methylimidazolidin-2-one (310 mg, 1.21 mmol), BocNH$_2$ (212 mg, 1.82 mmol) in dioxane (10 mL) and Cs$_2$CO$_3$ (986 mg, 3.03 mmol) were added and the resulting mixture was stirred at 100° C. for 16 h. A black brown mixture was formed. LCMS (Rt=0.530 min; MS Calcd: 292.2; MS Found: 293.1 [M+H]$^+$). The reaction mixture was diluted with DCM (20 mL), filtered and concentrated. The residue was purified by Combi Flash (EtOAc) to give tert-butyl (5-(3-methyl-2-oxoimidazolidin-1-yl)pyridin-3-yl)carbamate (300 mg, yield: 85%) as a white solid.

$^1$H NMR (400 MHz, CDCl$_3$) δ 1.52 (9H, s), 2.91 (3H, s), 3.51 (2H, t, J=8.4 Hz), 3.84 (2H, t, J=8.4 Hz), 6.60 (1H, brs), 8.26 (1H, s), 8.28 (1H, s), 8.45 (1H, s).

Step 3: Preparation of 1-(5-aminopyridin-3-yl)-3-methylimidazolidin-2-one

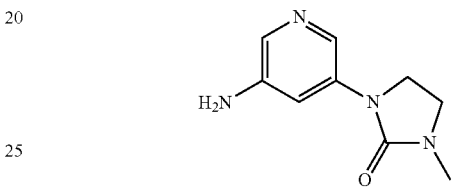

To a stirred solution of tert-butyl (5-(3-methyl-2-oxoimidazolidin-1-yl)pyridin-3-yl)carbamate (300 mg, 1.03 mmol) in DCM (4 mL) was added HCl/EtOAc (4 M, 10 mL) at 20° C. The yellow solution turned to suspension, the reaction mixture was stirred for 1 hour. TLC indicated the starting material was consumed completely, and one new spot with larger polarity was detected. The mixture was concentrated to give 1-(5-aminopyridin-3-yl)-3-methylimidazolidin-2-one (234 mg, yield: 100%) as an off-white solid.

$^1$H NMR (400 MHz, DMSO-d$_6$) δ 2.79 (3H, s), 3.51 (2H, t, J=8.4 Hz), 3.80 (2H, t, J=8.8 Hz), 6.53 (2H, brs), 7.62 (1H, s), 7.66 (1H, s), 8.34 (1H, s).

Step 4: Preparation of 1-methyl-3-(5-((5-methyl-8-(2-oxopyrrolidin-1-yl)-5H-chromeno[4,3-c]pyridin-3-yl)amino)pyridin-3-yl)imidazolidin-2-one

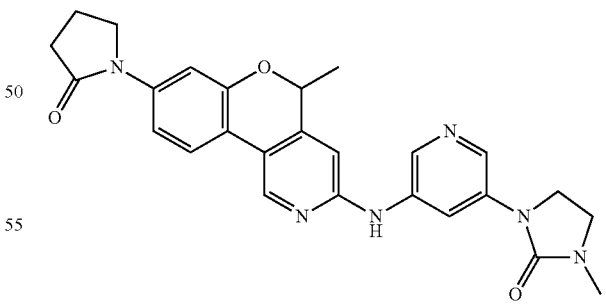

A mixture of Pd$_2$(dba)$_3$ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), 1-(5-aminopyridin-3-yl)-3-methylimidazolidin-2-one (72 mg, 0.32 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.591 min; MS Calcd: 470.2. MS Found: 471.3 [M+H]$^+$). The reaction mixture was diluted with DCM (10 mL), filtered and concentrated. The residue was purified by prep-HPLC (0.05% NH$_3$.H$_2$O as an additive) and lyophilized to give 1-methyl-3-(5-((5-methyl-8-(2-oxopyrrolidin-1-yl)-5H-chromeno[4,3-c]pyridin-3-yl)amino)pyridin-3-yl)imidazolidin-2-one (24.3 mg, yield: 33%) as an off-white solid.

LC-MS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.53%, Rt=2.854 min; MS Calcd.: 470.2, MS Found: 471.2 [M+H]$^+$.

$^1$H NMR (400 MHz, DMSO-d$_6$) δ 1.53 (3H, d, J=6.4 Hz), 2.02-2.09 (2H, m), 2.55 (2H, overlap with DMSO), 2.79 (3H, s), 3.49 (2H, t, J=6.0 Hz), 3.78-3.87 (4H, m), 5.26 (1H, q, J=6.8 Hz), 6.75 (1H, s), 7.31 (1H, dd, J=8.8, 2.0 Hz), 7.39 (1H, d, J=2.0 Hz), 7.89 (1H, d, J=8.8 Hz), 8.29 (1H, d, J=2.4 Hz), 8.47 (1H, t, J=2.4 Hz), 8.59 (1H, d, J=2.4 Hz), 8.66 (1H, s), 9.46 (1H, brs).

Example 54: 1-(5-methyl-3-((5-(2-oxopyrrolidin-1-yl)pyridin-3-yl)amino)-5H-chromeno[4,3-c]pyridin-8-yl)pyrrolidin-2-one

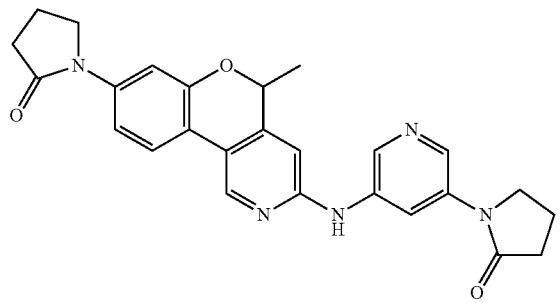 [SMILES: CC1Oc2cc(N3CCCC3=O)ccc2-c2cnc(Nc3cncc(N4CCCC4=O)c3)cc21]

Step 1: Preparation of 1-(5-bromopyridin-3-yl)pyrrolidin-2-one

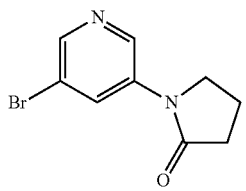

A mixture of 3,5-dibromopyridine (2.00 g, 8.44 mmol), pyrrolidin-2-one (861 mg, 10.1 mmol), K$_2$CO$_3$ (4.08 g, 29.5 mmol), CuI (80 mg, 0.42 mmol), TMEA (49 mg, 0.42 mmol) in dioxane (30 mL) was stirred at 110° C. for 20 h. A blue solution was formed gradually. Then added pyrrolidin-2-one (862 mg, 10.1 mmol), TMEA (49 mg, 0.42 mmol), CuI (80 mg, 0.42 mmol) and stirred at 110° C. for 20 h. The previous mixture was added pyrrolidin-2-one (862 mg, 10.1 mmol), CuI (80 mg, 0.42 mmol), TMEA (49 mg, 0.42 mmol) and stirred at 110° C. for 20 hour still. The addition procedure was repeated three times. LCMS (Rt=0.542 min; MS Calcd: 242.0. MS Found: 243.1 [M+H]$^+$). The reaction mixture was diluted with EtOAc (30 mL), filtered and concentrated. The residue was purified by Combi Flash (48% EtOAc in pentane) to give impure product (2.00 g) as red liquid, then the impure product was diluted with EtOAc (50 mL), washed with NaOH (5% in water, 15 mL×3). The organic layer was dried over anhydrous sodium sulfate, and concentrated in vacuum to give 1-(5-bromopyridin-3-yl)pyrrolidin-2-one (400 mg, yield: 20%) as a yellow solid.

$^1$H NMR (400 MHz, CDCl$_3$) δ 2.20-2.26 (2H, m), 2.64 (2H, t, J=7.6 Hz), 3.88 (2H, t, J=6.8 Hz), 8.44 (1H, d, J=2.0 Hz), 8.49 (1H, t, J=2.0 Hz), 8.64 (1H, d, J=2.0 Hz).

Step 2: Preparation of tert-butyl (5-(2-oxopyrrolidin-1-yl)pyridin-3-yl)carbamate

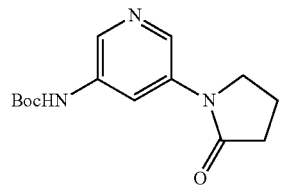 [SMILES: CC(C)(C)OC(=O)Nc1cncc(N2CCCC2=O)c1]

A mixture of Pd$_2$(dba)$_3$ (57 mg, 0.062 mmol) and XantPhos (72 mg, 0.12 mmol) in 1,4-dioxane (1 mL) was stirred at 50° C. for 10 min. 1-(5-Bromopyridin-3-yl)pyrrolidin-2-one (300 mg, 1.24 mmol), BocNH$_2$ (218 mg, 1.87 mmol) in dioxane (12 mL) and Cs$_2$CO$_3$ (1.01 g, 3.11 mmol) were added and the resulting mixture was stirred at 100° C. for 16 h. A black brown mixture was formed. LCMS (Rt=0.530 min; MS Calcd: 277.1. MS Found: 277.9 [M+H]$^+$). The reaction mixture was diluted with DCM (20 mL), filtered and concentrated. The residue was purified by Combi Flash (80% EtOAc in pentane) to give tert-butyl (5-(2-oxopyrrolidin-1-yl)pyridin-3-yl)carbamate (231 mg, yield: 67%) as a white solid.

$^1$H NMR (400 MHz, CDCl$_3$) δ 1.52 (9H, s), 2.16-2.26 (2H, m), 2.62 (2H, t, J=8.0 Hz), 3.90 (2H, t, J=7.2 Hz), 6.59 (1H, brs), 8.36 (2H, s), 8.51 (1H, s).

Step 3: Preparation of 1-(5-aminopyridin-3-yl)pyrrolidin-2-one

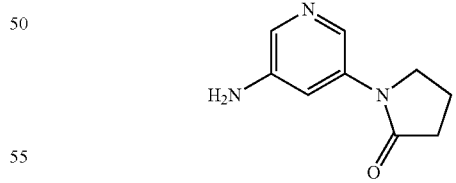

To a stirred solution of tert-butyl (5-(2-oxopyrrolidin-1-yl)pyridin-3-yl)carbamate (230 mg, 0.829 mmol) in DCM (6 mL) was added HCl/EtOAc (4 M, 8 mL) at 20° C. The red solution turned to suspension, the reaction mixture was stirred for 1 hour. TLC indicated the starting material was consumed completely, and one new spot with larger polarity was detected. The mixture was concentrated to give 1-(5-aminopyridin-3-yl)pyrrolidin-2-one (146 mg, yield: 99%) as a black brown solid. Used in the next step without further purification.

¹H NMR (400 MHz, DMSO-d₆) δ 2.06-2.13 (2H, m), 2.54 (2H, t, J=7.2 Hz), 3.82 (2H, t, J=6.4 Hz), 7.81 (1H, s), 7.88 (1H, s), 8.38 (1H, s).

Step 4: Preparation of 1-(5-methyl-3-((5-(2-oxopyrrolidin-1-yl)pyridin-3-yl)amino)-5H-chromeno[4,3-c]pyridin-8-yl)pyrrolidin-2-one

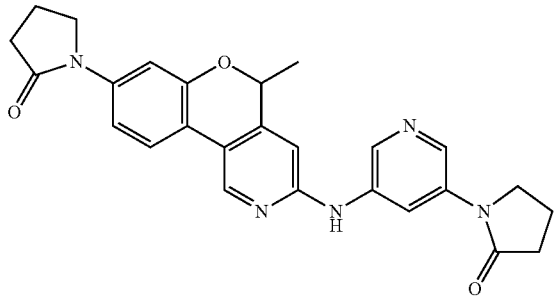 [SMILES: CC1Oc2cc(N3CCCC3=O)ccc2-c2cnc(Nc3cncc(N4CCCC4=O)c3)cc21]

A mixture of Pd₂(dba)₃ (7 mg, 0.008 mmol) and BrettPhos (8 mg, 0.002 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (50 mg, 0.16 mmol), 1-(5-aminopyridin-3-yl)pyrrolidin-2-one (50 mg, 0.16 mmol) in dioxane (3 mL) and Cs₂CO₃ (155 mg, 0.476 mmol) were added and the resulting mixture was stirred at 100° C. for 16 h. A black brown mixture was formed. LCMS (Rt=0.586 min; MS Calcd: 455.2. MS Found: 456.0 [M+H]⁺). The reaction mixture was diluted with DCM (10 mL), filtered and concentrated. The residue was purified by prep-HPLC (0.05% NH₃.H₂O as an additive) and lyophilized to give 1-(5-methyl-3-((5-(2-oxopyrrolidin-1-yl)pyridin-3-yl)amino)-5H-chromeno[4,3-c]pyridin-8-yl)pyrrolidin-2-one (12.3 mg, yield: 17%) as an off-white solid.

LC-MS (Shimadzu LCMS 2010, mobile phase: C) 10 mM NH₄HCO₃ in Water; D) MECN. Gradient: 1% D increase to 5% D within 0.6 min; 5% DB increase to 100% D within 3.4 min; then back to 1% D within 0.3 min. Flow rate 0.8 mL/min) purity is 100%, Rt=2.573 min; MS Calcd.: 455.2, MS Found: 456.3 [M+H]⁺.

¹H NMR (400 MHz, DMSO-d₆) δ 1.53 (3H, d, J=6.4 Hz), 2.01-2.16 (4H, m), 2.50 (4H, overlap with DMSO), 3.81-3.90 (4H, m), 5.27 (1H, q, J=7.2 Hz), 6.76 (1H, s), 7.31 (1H, dd, J=8.8, 1.6 Hz), 7.40 (1H, s), 7.88 (1H, d, J=8.8 Hz), 8.35 (1H, s), 8.58 (1H, t, J=2.4 Hz), 8.67 (1H, s), 8.71 (1H, d, J=2.0 Hz), 9.46 (1H, brs).

Example 55: 1-(5-((5-methyl-8-(2-oxopyrrolidin-1-yl)-5H-chromeno[4,3-c]pyridin-3-yl)amino)pyridin-3-yl)imidazolidin-2-one

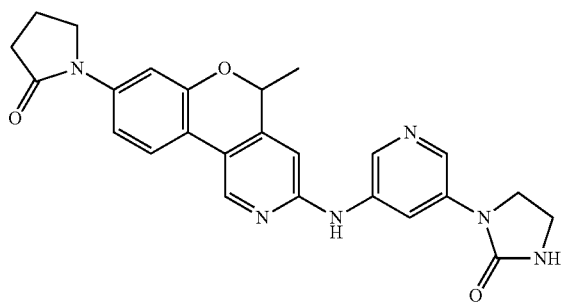 [SMILES: CC1Oc2cc(N3CCCC3=O)ccc2-c2cnc(Nc3cncc(N4CCNC4=O)c3)cc21]

A mixture of Pd₂(dba)₃ (16 mg, 0.017 mmol) and BrettPhos (18 mg, 0.034 mmol) was stirred at 50° C. for 10 min. 1-(3-Amino-5-methyl-5H-chromeno[4,3-c]pyridin-8-yl)pyrrolidin-2-one (100 mg, 0.338 mmol), 1-(5-bromopyridin-3-yl)imidazolidin-2-one (245 mg, 1.02 mmol) in dioxane (5 mL) and Cs₂CO₃ (441 mg, 1.35 mmol) were added and the resulting mixture was stirred at 100° C. for 18 h. A black brown mixture was formed. In a separate vial, a mixture of Pd₂(dba)₃ (16 mg, 0.017 mmol) and BrettPhos (18 mg, 0.034 mmol) was stirred at 50° C. for 15 min and added to the previous reaction mixture together with additional Cs₂CO₃ (441 mg, 1.35 mmol). The resulting reaction mixture was stirred at 100° C. for 18 h. LCMS (Rt=0.583 min; MS Calcd: 456.2. MS Found: 457.1 [M+H]⁺). The reaction mixture was diluted with DCM (15 mL), filtered and concentrated. The residue was purified by Combi Flash (10% DCM in EtOAc), then the impure product (70 mg) was purified by prep-HPLC (0.05% NH₃.H₂O as an additive) and lyophilized to give 1-(5-((5-methyl-8-(2-oxopyrrolidin-1-yl)-5H-chromeno[4,3-c]pyridin-3-yl)amino)pyridin-3-yl)imidazolidin-2-one (8.0 mg, yield: 5%) as a white solid.

LC-MS (Shimadzu LCMS 2010, mobile phase: C) 10 mM NH₄HCO₃ in Water; D) MECN. Gradient: 1% D increase to 5% D within 0.6 min; 5% DB increase to 100% D within 3.4 min; then back to 1% D within 0.3 min. Flow rate 0.8 mL/min) purity is 95.39%, Rt=2.454 min; MS Calcd.: 456.2, MS Found: 457.3 [M+H]⁺.

¹H NMR (400 MHz, DMSO-d₆) δ 1.53 (3H, d, J=6.8 Hz), 2.02-2.10 (2H, m), 2.54 (2H, overlap with DMSO), 3.46 (2H, t, J=8.0 Hz), 3.81-3.93 (4H, m), 5.27 (1H, q, J=6.0 Hz), 6.76 (1H, s), 7.12 (1H, brs), 7.32 (1H, dd, J=8.4, 2.0 Hz), 7.40 (1H, d, J=2.0 Hz), 7.89 (1H, d, J=8.8 Hz), 8.27 (1H, d, J=2.0 Hz), 8.42 (1H, t, J=2.0 Hz), 8.64 (1H, d, J=2.0 Hz), 8.66 (1H, s), 9.43 (1H, brs).

Example 56: 1-(5-((5-methyl-8-(2-oxopyrrolidin-1-yl)-5H-chromeno[4,3-c]pyridin-3-yl)amino)pyridin-3-yl)-3-(thiazol-4-ylmethyl)imidazolidin-2-one

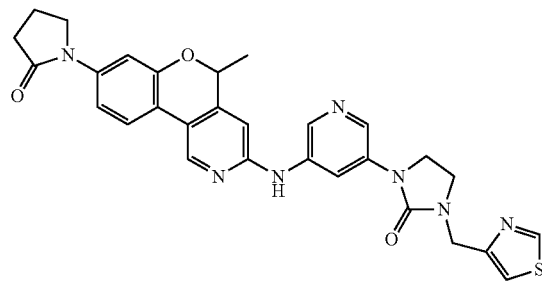 [SMILES: CC1Oc2cc(N3CCCC3=O)ccc2-c2cnc(Nc3cncc(N4CCN(Cc5cscn5)C4=O)c3)cc21]

Step 1: Preparation of 1-(5-bromopyridin-3-yl)-3-(thiazol-4-ylmethyl)imidazolidin-2-one

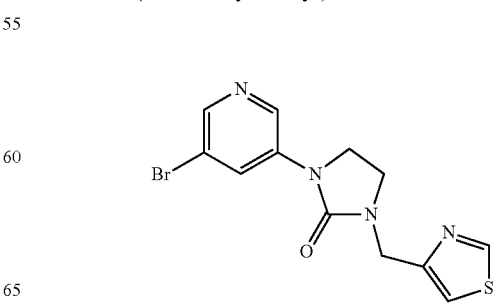

To a solution of 1-(5-bromopyridin-3-yl)imidazolidin-2-one (100 mg, 0.413 mmol) in DMF (2 mL) was added NaH (66 mg, 1.6 mmol, 60% in mineral oil) and then the mixture was stirred at 25° C. for 30 min. To the mixture was added 4-(chloromethyl)thiazole hydrogen chloride (105 mg, 0.619 mmol) at 0° C. and the mixture was stirred at 25° C. for 3 h. A gray suspension was formed. LCMS showed 1-(5-bromopyridin-3-yl)imidazolidin-2-one was consumed completely and desired product (Rt=0.560 min; MS Calcd: 338.0. MS Found: 338.7 [M+H]$^+$) was detected. The mixture was combined with another batch and the combined mixture was poured into sat. aq.NH$_4$Cl (50 mL), extracted with EtOAc (50 mL×3). The combined organic layer was washed with brine (50 mL×6), dried over Na$_2$SO$_4$ and concentrated to dryness. The residue was purified by Combi Flash (eluenting with EtOAc) to give 1-(5-bromopyridin-3-yl)-3-(thiazol-4-ylmethyl)imidazolidin-2-one (288 mg, yield: 93%) as a yellow gum.

$^1$H NMR (400 MHz, CDCl$_3$) δ 3.60-3.70 (2H, m), 3.80-3.89 (m, 2H), 4.67 (2H, s), 7.32 (1H, d, J=2.0 Hz), 8.34 (1H, d, J=2.0 Hz), 8.47 (1H, t, J=2.0 Hz), 8.52 (1H, d, J=2.0 Hz), 8.81 (1H, s).

Step 2: Preparation of 1-(5-((5-methyl-8-(2-oxopyrrolidin-1-yl)-5H-chromeno[4,3-c]pyridin-3-yl)amino)pyridin-3-yl)-3-(thiazol-4-ylmethyl)imidazolidin-2-one

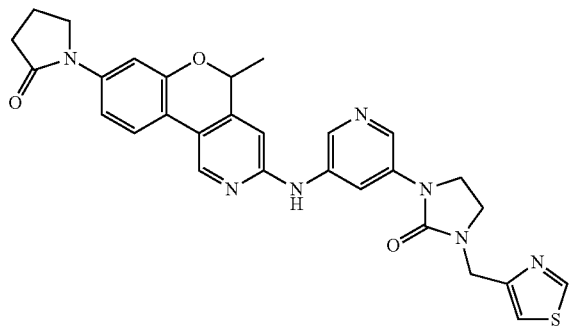 [SMILES: CC1Oc2cc(N3CCCC3=O)ccc2-c2cnc(Nc3cncc(N4CCN(Cc5cscn5)C4=O)c3)cc21]

A mixture of Pd$_2$(dba)$_3$ (16 mg, 0.017 mmol) and BrettPhos (18 mg, 0.034 mmol) was stirred at 50° C. for 10 min. 1-(3-amino-5-methyl-5H-chromeno[4,3-c]pyridin-8-yl)pyrrolidin-2-one (50 mg, 0.17 mmol), 1-(5-bromopyridin-3-yl)-3-(thiazol-4-ylmethyl)imidazolidin-2-one (69 mg, 0.20 mmol) in dioxane (4 mL) and Cs$_2$CO$_3$ (165 mg, 0.508 mmol) were added and the resulting mixture was stirred at 100° C. for 16 h. A black brown mixture was formed. LCMS (Rt=0.603 min; MS Calcd: 553.2. MS Found: 554.1 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(5-((5-methyl-8-(2-oxopyrrolidin-1-yl)-5H-chromeno[4,3-c]pyridin-3-yl)amino)pyridin-3-yl)-3-(thiazol-4-ylmethyl)imidazolidin-2-one (39.6 mg, yield: 42%) as a white solid.

LC-MS (Shimadzu LCMS 2010, mobile phase: C) 10 mM NH$_4$HCO$_3$ in Water; D) MECN. Gradient: 1% D increase to 5% D within 0.6 min; 5% DB increase to 100% D within 3.4 min; then back to 1% D within 0.3 min. Flow rate 0.8 mL/min) purity is 100%, Rt=2.610 min; MS Calcd.: 553.2, MS Found: 554.3 [M+H]$^+$.

$^1$H NMR (400 MHz, DMSO-d$_6$) δ 1.53 (3H, d, J=6.4 Hz), 2.01-2.10 (2H, m), 2.52 (2H, overlap with DMSO), 3.51 (2H, t, J=7.6 Hz), 3.80-3.90 (4H, m), 4.56 (2H, s), 5.26 (1H, q, J=6.4 Hz), 6.75 (1H, s), 7.31 (1H, dd, J=8.8, 2.0 Hz), 7.39 (1H, d, J=2.0 Hz), 7.63 (1H, d, J=2.0 Hz), 7.88 (1H, d, J=8.4 Hz), 8.31 (1H, d, J=1.6 Hz), 8.49 (1H, t, J=2.0 Hz), 8.59 (1H, d, J=2.0 Hz), 8.66 (1H, s), 9.10 (1H, d, J=1.6 Hz), 9.45 (1H, brs).

Example 57: 1-(5-methyl-3-((1-(methylsulfonyl)-1H-pyrrolo[3,2-b]pyridin-6-yl)amino)-5H-chromeno[4,3-c]pyridin-8-yl)pyrrolidin-2-one

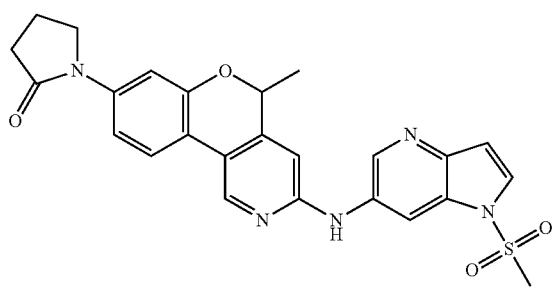 [SMILES: CC1Oc2cc(N3CCCC3=O)ccc2-c2cnc(Nc3cnc4ccn(S(C)(=O)=O)c4c3)cc21]

Step 1: Preparation of 6-bromo-1-(methylsulfonyl)-1H-pyrrolo[3,2-b]pyridine

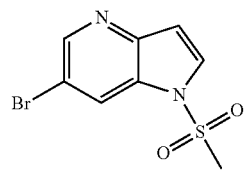

A solution of 6-bromo-1H-pyrrolo[3,2-b]pyridine (700 mg, 3.55 mmol) and pyridine (5.3 mL, 66 mmol) was stirred in DCM (10 mL), then MsCl (488 mg, 4.26 mmol) was added into the above solution at 0° C., which was stirred at 20° C. for 16 h. A yellow solution was formed. LCMS is 98% (Rt=0.609 min; MS Calcd: 273.9. MS Found: 274.8 [M+H]$^+$). The solution was diluted with H$_2$O (20 mL) and was extracted with DCM (20 mL×3). The organic layer was washed with brine (15 mL), dried over Na$_2$SO$_4$, and concentrated. The residue was purified by Combi Flash (50% EtOAc in pentane) to give impure product (700 mg) as a white solid. Then the product was washed with PE:EtOAc=3:1 (5 mL×3), the filtrate was concentrated to give 6-bromo-1-(methylsulfonyl)-1H-pyrrolo[3,2-b]pyridine (200 mg, yield: 20%) as a white solid.

$^1$H NMR (400 MHz, CDCl$_3$) δ 3.81 (3H, s), 6.92 (1H, d, J=3.6 Hz), 7.67 (1H, d, J=3.6 Hz), 8.38 (1H, d, J=2.0 Hz), 8.67 (1H, d, J=1.6 Hz).

Step 2: Preparation of 1-(5-methyl-3-((1-(methylsulfonyl)-1H-pyrrolo[3,2-b]pyridin-6-yl)amino)-5H-chromeno[4,3-c]pyridin-8-yl)pyrrolidin-2-one

Example 58: 1-(3-((1-(1-hydroxycyclopropane-1-carbonyl)-2,3-dihydro-1H-pyrido[2,3-b][1,4]oxazin-7-yl)amino)-5-methyl-5H-chromeno[4,3-c]pyridin-8-yl)pyrrolidin-2-one

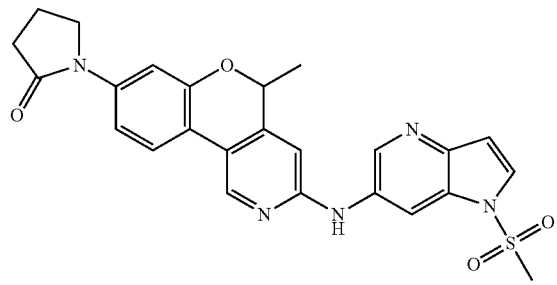 [SMILES: CC1Oc2cc(N3CCCC3=O)ccc2-c2cnc(Nc3cnc4ccn(S(C)(=O)=O)c4c3)cc21]

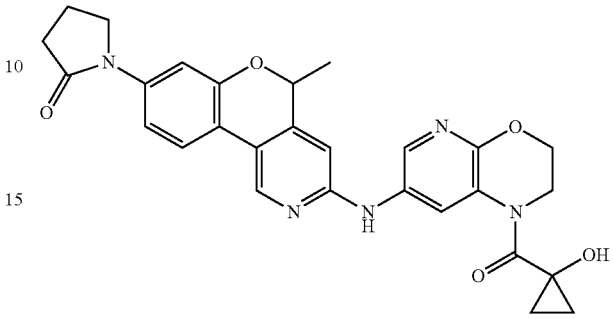

Step 1: Preparation of 1-acetoxycyclopropane-1-carboxylic acid

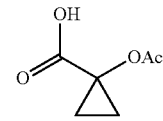

A mixture of Pd$_2$(dba)$_3$ (5 mg, 0.005 mmol) and BrettPhos (5 mg, 0.01 mmol) in 1,4-dioxane (1 mL) was stirred at 50° C. for 10 min. 1-(3-Amino-5-methyl-5H-chromeno[4,3-c]pyridin-8-yl)pyrrolidin-2-one (30 mg, 0.10 mmol), 6-bromo-1-(methylsulfonyl)-1H-pyrrolo[3,2-b]pyridine (28 mg, 0.10 mmol) in dioxane (3 mL) and Cs$_2$CO$_3$ (99 mg, 0.30 mmol) were added and the resulting mixture was stirred at 100° C. for 18 h. A black brown mixture was formed. LCMS showed the most of starting material was not consumed. In a separate vial, a mixture of Pd$_2$(dba)$_3$ (5 mg, 0.005 mmol) and BrettPhos (5 mg, 0.01 mmol) in 1,4-dioxane (1 mL) was stirred at 50° C. for 15 min and added to the previous reaction mixture together with additional Cs$_2$CO$_3$ (99 mg, 0.30 mmol), 6-bromo-1-(methylsulfonyl)-1H-pyrrolo[3,2-b]pyridine (80 mg, 0.29 mmol). The resulting reaction mixture was stirred at 100° C. for 18 h. LCMS (Rt=0.603 min; MS Calcd: 489.2. MS Found: 490.0 [M+H]$^+$). The reaction mixture was diluted with DCM (10 mL), filtered and concentrated. The residue was purified by Combi Flash (10% MeOH in EtOAc), then the impure product (50 mg) was purified by prep-HPLC (0.05% NH$_3$.H$_2$O as an additive) and lyophilized to give 1-(5-methyl-3-((1-(methylsulfonyl)-1H-pyrrolo[3,2-b]pyridin-6-yl)amino)-5H-chromeno[4,3-c]pyridin-8-yl)pyrrolidin-2-one (8.4 mg, yield: 17%) as a white solid.

LC-MS (Shimadzu LCMS 2010, mobile phase: C) 10 mM NH$_4$HCO$_3$ in Water; D) MeCN. Gradient: 1% D increase to 5% D within 0.6 min; 5% DB increase to 100% D within 3.4 min; then back to 1% D within 0.3 min. Flow rate 0.8 mL/min) purity is 96.44%, Rt=2.776 min; MS Calcd.: 489.2, MS Found: 490.2 [M+H]$^+$.

$^1$H NMR (400 MHz, DMSO-d$_6$) δ 1.55 (3H, d, J=6.4 Hz), 2.02-2.09 (2H, m), 2.57 (2H, overlap with DMSO), 3.47 (3H, s), 3.85 (2H, t, J=8.0 Hz), 5.29 (1H, q, J=6.4 Hz), 6.78 (1H, s), 6.89 (1H, d, J=4.0 Hz), 7.32 (1H, dd, J=8.8, 2.0 Hz), 7.41 (1H, d, J=2.4 Hz), 7.73 (1H, d, J=4.0 Hz), 7.94 (1H, d, J=8.8 Hz), 8.69 (1H, s), 8.79 (1H, d, J=2.4 Hz), 8.83 (1H, d, J=2.0 Hz), 9.66 (1H, brs).

1-Hydroxycyclopropane-1-carboxylic acid (600 mg, 5.88 mmol) was slowly added acetyl chloride (923 mg, 11.8 mmol) at 0° C. Then the reaction mixture was warmed to 20° C., stirred at 20° C. for 18 h under N$_2$ atmosphere. A brown solution was formed gradually. Acetyl chloride was removed under reduced pressure to give 1-acetoxycyclopropane-1-carboxylic acid (840 mg, yield: 99%) as a black brown solid.

$^1$H NMR (400 MHz, DMSO-d$_6$) δ 1.10-1.20 (2H, m), 1.30-1.40 (2H, m), 2.01 (3H, s), 13.11 (1H, brs).

Step 2: Preparation of 1-(7-bromo-2,3-dihydro-1H-pyrido[2,3-b][1,4]oxazine-1-carbonyl)cyclopropyl acetate

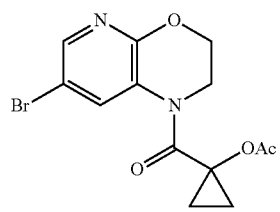

In a separate vial, to a solution of 1-acetoxycyclopropane-1-carboxylic acid (804 mg, 5.58 mmol) in DCM (5 mL) was added oxalyl chloride (885 mg, 6.98 mmol). The yellow solution was stirred at 20° C. for 0.5 hour. The mixture was concentrated to give crude 1-(chlorocarbonyl)cyclopropyl acetate as a yellow oil.

To a solution of 7-bromo-2,3-dihydro-1H-pyrido[2,3-b][1,4]oxazine (300 mg, 1.40 mmol) in DCM (5 mL) was added Et$_3$N (706 mg, 6.98 mmol). The reaction mixture was cooled to 0° C. and then dropwise added 1-(chlorocarbonyl)

cyclopropyl acetate in DCM (5 mL). The reaction mixture was then warmed to 20° C., stirred at 20° C. for 16 h under N₂ atmosphere. A red solution was formed. LCMS (Rt=0.588 min, MS Calcd.: 340.0. MS Found: 340.8 [M+H]⁺). TLC showed the starting material was consumed completely. The reaction mixture was concentrated. The residue was purified by Combi Flash (78% DCM in PE (1% Et₃N as an additive)) to give 1-(7-bromo-2,3-dihydro-1H-pyrido[2,3-b][1,4]oxazine-1-carbonyl)cyclopropyl acetate (475 mg, yield: 99% for two steps) as a red gum.

Step 3: Preparation of 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carbonyl)cyclopropyl acetate

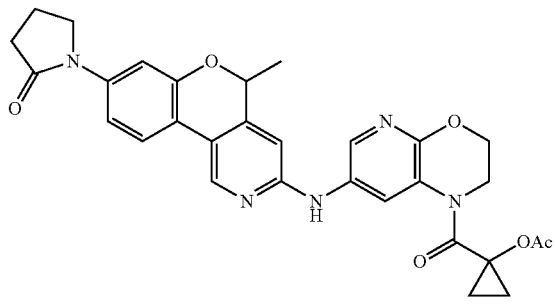 [SMILES: CC(=O)OC1(C(=O)N2CCOc3ncc(Nc4cc5c(cn4)-c4ccc(N6CCCC6=O)cc4OC5C)cc32)CC1]

A mixture of Pd₂(dba)₃ (34 mg, 0.037 mmol) and Brett-Phos (40 mg, 0.074 mmol) in 1,4-dioxane (1 mL) was stirred at 50° C. for 10 min. Compound 7 (110 mg, 0.372 mmol), 1-(3-amino-5-methyl-5H-chromeno[4,3-c]pyridin-8-yl)pyrrolidin-2-one 2 (190 mg, 0.558 mmol) in 1,4-dioxane (7 mL) and Cs₂CO₃ (364 mg, 1.12 mmol) were added. The resulting mixture was stirred at 100° C. for 6 h. A black brown mixture was formed. LCMS (Rt=0.597 min; MS Calcd: 555.2. MS Found: 556.1 [M+H]⁺). The reaction mixture was diluted with DCM (10 mL), filtered and concentrated. The residue was purified by prep-HPLC (normal phase, PE-EtOH) and concentrated to give 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carbonyl)cyclopropyl acetate (50 mg, yield: 24%) as a yellow solid.

Step 4: Preparation of 1-(3-((1-(1-hydroxycyclopropane-1-carbonyl)-2,3-dihydro-1H-pyrido[2,3-b][1,4]oxazin-7-yl)amino)-5-methyl-5H-chromeno[4,3-c]pyridin-8-yl)pyrrolidin-2-one

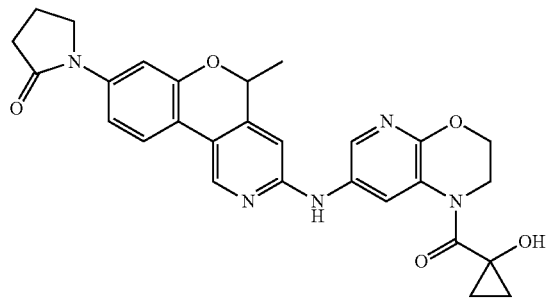 [SMILES: CC1Oc2cc(N3CCCC3=O)ccc2-c2cnc(Nc3cnc4c(c3)N(C(=O)C3(O)CC3)CCO4)cc21]

To a solution of 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carbonyl)cyclopropyl acetate (50 mg, 0.090 mmol) in 1,4-dioxane (3 mL) was added MeOH (1.1 mL, 27 mmol). Then the yellow solution was added K₂CO₃ (37 mg, 0.27 mmol), stirred at 20° C. for 4 h. LCMS (Rt=0.563 min; MS Calcd: 513.2. MS Found: 514.1 [M+H]⁺). The reaction mixture was filtered and concentrated. The residue was purified by prep-HPLC (0.05% NH₃.H₂O as an additive) and lyophilized to give 1-(3-((1-(1-hydroxycyclopropane-1-carbonyl)-2,3-dihydro-1H-pyrido[2,3-b][1,4]oxazin-7-yl)amino)-5-methyl-5H-chromeno[4,3-c]pyridin-8-yl)pyrrolidin-2-one (7.0 mg, yield: 15%) as a white solid.

¹H NMR (400 MHz, DMSO-d₆) δ 0.85-0.95 (2H, m), 1.10-1.20 (2H, m), 1.52 (3H, d, J=6.4 Hz), 2.01-2.09 (2H, m), 2.55 (2H, overlap with DMSO), 3.84 (2H, t, J=7.2 Hz), 4.14 (2H, t, J=4.0 Hz), 4.39 (2H, t, J=4.0 Hz), 5.23 (1H, q, J=6.4 Hz), 6.62 (1H, brs), 6.66 (1H, s), 7.30 (1H, dd, J=8.8, 2.0 Hz), 7.38 (1H, d, J=2.0 Hz), 7.86 (1H, d, J=8.8 Hz), 8.24 (1H, d, J=2.4 Hz), 8.59 (1H, s), 8.61 (1H, d, J=2.4 Hz), 9.21 (1H, brs).

Example 59: 1-(3-((1-(2-hydroxy-2-methylpropanoyl)-2,3-dihydro-1H-pyrido[2,3-b][1,4]oxazin-7-yl)amino)-5-methyl-5H-chromeno[4,3-c]pyridin-8-yl)pyrrolidin-2-one

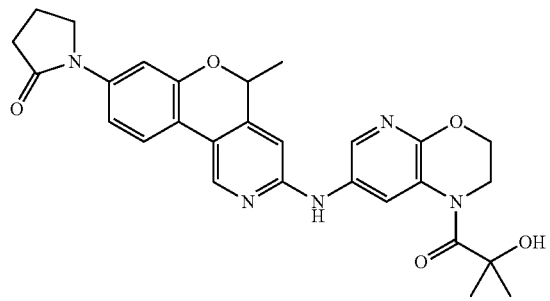 [SMILES: CC1Oc2cc(N3CCCC3=O)ccc2-c2cnc(Nc3cnc4c(c3)N(C(=O)C(C)(C)O)CCO4)cc21]

Step 1: Preparation of 2-acetoxy-2-methylpropanoic acid

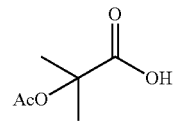

2-Hydroxy-2-methylpropanoic acid (4.00 g, 38.4 mmol) was slowly added acetyl chloride (5.5 mL, 76.9 mmol) at 20° C. Then the reaction mixture was stirred at 20° C. for 12 h under N₂ atmosphere. A colorless solution was formed gradually. Acetyl chloride was removed under reduced pressure to afford 2-acetoxy-2-methylpropanoic acid (8 g, crude) as colorless oil.

¹H NMR (400 MHz, CDCl₃) δ 1.57 (6H, s), 2.06 (3H, s), 11.91 (1H, brs).

Step 2: Preparation of 1-(7-bromo-2,3-dihydro-1H-pyrido[2,3-b][1,4]oxazin-1-yl)-2-methyl-1-oxopropan-2-ylacetate

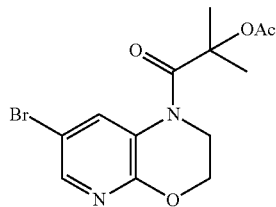 [SMILES: CC(=O)OC(C)(C)C(=O)N1CCOc2ncc(Br)cc21]

To a solution of 2-acetoxy-2-methylpropanoic acid (1.09 g, 7.44 mmol) in DCM (6 mL), DMF (68 mg, 0.93 mmol) was added oxalyl chloride (0.814 mL, 9.30 mmol). The reaction mixture was stirred at 10° C. for 0.5 hour. A light yellow solution was formed. The mixture was concentrated to give crude 1-chloro-2-methyl-1-oxopropan-2-yl acetate as a yellow oil. To a solution of 7-bromo-2,3-dihydro-1H-pyrido[2,3-b][1,4]oxazine (100 mg, 0.465 mmol) in DCM (6 mL) was added Et$_3$N (1.29 mL, 9.30 mmol). The reaction mixture was cooled to 0° C. and then dropwise added to the crude product 1-chloro-2-methyl-1-oxopropan-2-yl acetate in DCM (4 mL). The reaction mixture was then warmed to 10° C., stirred at 10° C. for 12 h under N$_2$ atmosphere. The colorless solution turned to an orange solution gradually. LCMS (Rt=0.614 min; MS Calcd: 342.0. MS Found: 342.9 [M+H]$^+$). The reaction mixture was concentrated. The residue was purified by Combi Flash (1% Et$_3$N in DCM) to afford 1-(7-bromo-2,3-dihydro-1H-pyrido[2,3-b][1,4]oxazin-1-yl)-2-methyl-1-oxopropan-2-yl acetate (320 mg, yield: 50% over three steps) as yellow oil.

Step 3: Preparation of 2-methyl-1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-yl acetate

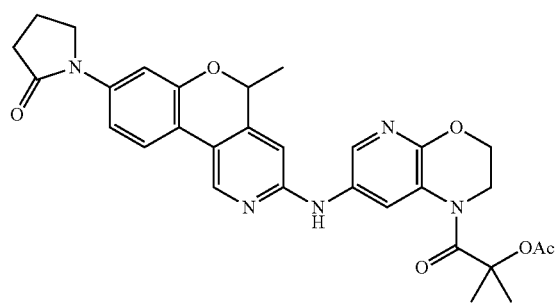 [SMILES: CC(=O)OC(C)(C)C(=O)N1CCOc2ncc(Nc3cc4c(cn3)-c3ccc(N5CCCC5=O)cc3OC4C)cc21]

A mixture of Pd$_2$(dba)$_3$ (37 mg, 0.041 mmol) and BrettPhos (44 mg, 0.081 mmol) in 1,4-dioxane (1 mL) was stirred at 50° C. for 10 min. 1-(3-amino-5-methyl-5H-chromeno[4,3-c]pyridin-8-yl)pyrrolidin-2-one (120 mg, 0.406 mmol), 1-(7-bromo-2,3-dihydro-1H-pyrido[2,3-b][1,4]oxazin-1-yl)-2-methyl-1-oxopropan-2-yl acetate (160 mg, 0.467 mmol) in 1,4-dioxane (7 mL) and Cs$_2$CO$_3$ (397 mg, 1.22 mmol) were added and the resulting mixture was stirred at 100° C. for 6 h. A black brown mixture was formed. LCMS (Rt=0.615 min; MS Calcd: 557.2. MS Found: 558.0 [M+H]$^+$). The reaction mixture was diluted with DCM (20 mL), filtered and concentrated. The residue was purified by prep-HPLC (normal phase, Hexane-EtOH) and concentrated to give 2-methyl-1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-yl acetate (90 mg, yield: 40%) as a yellow solid.

Step 4: Preparation of 1-(3-((1-(2-hydroxy-2-methylpropanoyl)-2,3-dihydro-1H-pyrido[2,3-b][1,4]oxazin-7-yl)amino)-5-methyl-5H-chromeno[4,3-c]pyridin-8-yl)pyrrolidin-2-one

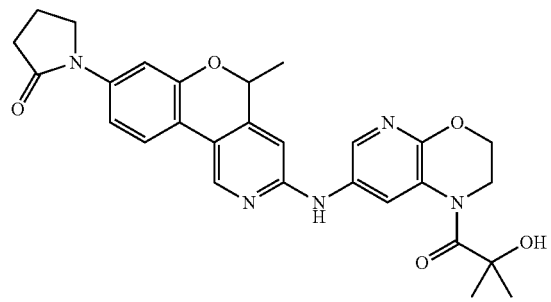 [SMILES: CC1Oc2cc(N3CCCC3=O)ccc2-c2cnc(Nc3cnc4c(c3)N(C(=O)C(C)(C)O)CCO4)cc21]

To a solution of 2-methyl-1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-yl acetate (90 mg, 0.16 mmol) in dioxane (4 mL) was added MeOH (1.3 mL, 32 mmol). Then the yellow solution was added K$_2$CO$_3$ (67 mg, 0.48 mmol), stirred at 20° C. for 4 h. LCMS (Rt=0.695 min; MS Calcd: 515.2. MS Found: 516.1 [M+H]$^+$). The reaction mixture was filtered and concentrated. The residue was purified by prep-HPLC (0.05% NH$_3$.H$_2$O as an additive) and lyophilized to give 1-(3-((1-(2-hydroxy-2-methylpropanoyl)-2,3-dihydro-1H-pyrido[2,3-b][1,4]oxazin-7-yl)amino)-5-methyl-5H-chromeno[4,3-c]pyridin-8-yl)pyrrolidin-2-one (20.6 mg, yield: 25%) as a white solid.

$^1$H NMR (400 MHz, DMSO-d$_6$) δ 1.42 (6H, s), 1.51 (3H, d, J=6.4 Hz), 2.00-2.09 (2H, m), 2.53 (2H, overlap with DMSO), 3.83 (2H, t, J=7.6 Hz), 4.30-4.40 (4H, m), 5.23 (1H, q, J=6.4 Hz), 5.85 (1H, brs), 6.64 (1H, s), 7.29 (1H, dd, J=8.8, 2.0 Hz), 7.38 (1H, d, J=2.0 Hz), 7.85 (1H, d, J=8.8 Hz), 8.33 (1H, d, J=2.4 Hz), 8.44 (1H, d, J=2.4 Hz), 8.58 (1H, s), 9.18 (1H, brs).

Example 60: 1-(3-((1-(2-hydroxypropanoyl)-2,3-dihydro-1H-pyrido[2,3-b][1,4]oxazin-7-yl)amino)-5-methyl-5H-chromeno[4,3-c]pyridin-8-yl)pyrrolidin-2-one

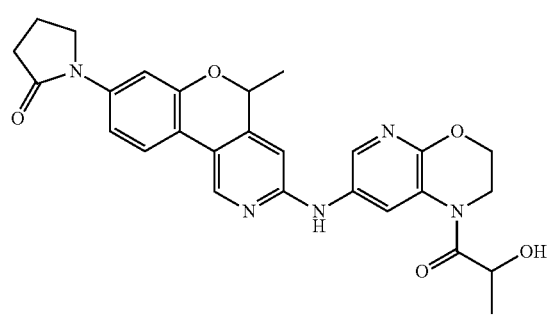 [SMILES: CC(O)C(=O)N1CCOc2ncc(Nc3cc4c(cn3)-c3ccc(N5CCCC5=O)cc3OC4C)cc21]

Step 1: Preparation of 2-acetoxypropanoic acid

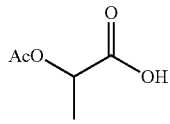

2-hydroxypropanoic acid (4.00 g, 44.4 mmol) was slowly added acetyl chloride (6.34 mL, 88.8 mmol) at 20° C. Then the reaction mixture was stirred at 20° C. for 12 h under $N_2$ atmosphere. A colorless solution was formed gradually. Acetyl chloride was removed under reduced pressure to afford 2-acetoxypropanoic acid (7 g, crude) as colorless oil.

$^1$H NMR (400 MHz, CDCl$_3$) δ 1.53 (3H, d, J=7.2 Hz), 2.10 (3H, s), 5.10 (1H, q, J=7.2 Hz), 10.41 (1H, brs).

Step 2: Preparation of 1-(7-bromo-2,3-dihydro-1H-pyrido[2,3-b][1,4]oxazin-1-yl)-1-oxopropan-2-ylacetate

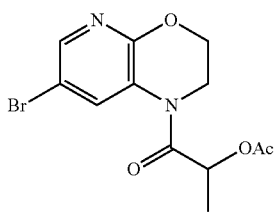 [SMILES: CC(=O)OC(C)C(=O)N1CCOc2ncc(Br)cc21]

To a solution of 2-acetoxypropanoic acid (983 mg, 7.44 mmol) in DCM (6 mL), DMF (68 mg, 0.93 mmol) was added oxalyl chloride (0.814 mL, 9.30 mmol). The reaction mixture was stirred at 10° C. for 0.5 hour. A light yellow solution was formed. The mixture was concentrated to give 1-chloro-1-oxopropan-2-yl acetate as a yellow oil. To a solution of 7-bromo-2,3-dihydro-1H-pyrido[2,3-b][1,4]oxazine (400 mg, 1.86 mmol) in DCM (10 mL) was added Et$_3$N (1.29 mL, 9.30 mmol). The reaction mixture was cooled to 0° C. and then dropwise added the crude product 1-chloro-1-oxopropan-2-yl acetate in DCM (4 mL). The reaction mixture was then warmed to 10° C., stirred at 10° C. for 12 h under N$_2$ atmosphere. The colorless solution turned to orange gradually. LCMS (Rt=0.583 min; MS Calcd: 330.0; MS Found: 330.8 [M+H]$^+$). The reaction mixture was concentrated. The residue was purified by Combi Flash (1% Et$_3$N in DCM) to afford 1-(7-bromo-2,3-dihydro-1H-pyrido[2,3-b][1,4]oxazin-1-yl)-1-oxopropan-2-yl acetate (500 mg, yield: 82% over three steps) as yellow oil.

Step 3: Preparation of 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-ylacetate

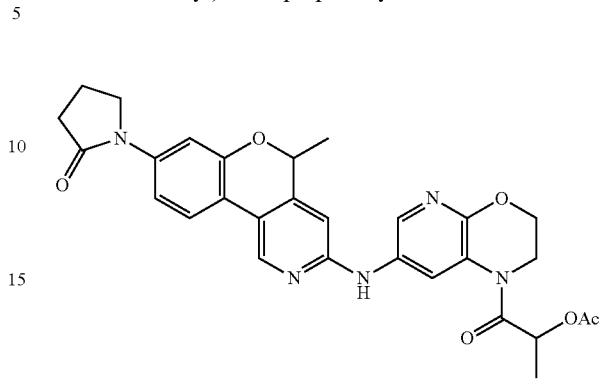

A mixture of Pd$_2$(dba)$_3$ (37 mg, 0.040 mmol) and BrettPhos (43 mg, 0.81 mmol) in 1,4-dioxane (1 mL) was stirred at 50° C. for 10 min. 1-(3-amino-5-methyl-5H-chromeno[4,3-c]pyridin-8-yl)pyrrolidin-2-one (120 mg, 0.406 mmol), 1-(7-bromo-2,3-dihydro-1H-pyrido[2,3-b][1,4]oxazin-1-yl)-1-oxopropan-2-yl acetate (160 mg, 0.487 mmol) in 1,4-dioxane (7 mL) and Cs$_2$CO$_3$ (397 mg, 1.22 mmol) were added and the resulting mixture was stirred at 100° C. for 6 h. A black brown mixture was formed. LCMS (Rt=0.595 min; MS Calcd: 543.2; MS Found: 544.0 [M+H]$^+$). The reaction mixture was diluted with DCM (20 mL), filtered and concentrated. The residue was purified by prep-HPLC (normal phase, Hexane-EtOH) and concentrated to give 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-yl acetate (140 mg, yield: 63%) as a yellow solid.

Step 4: Preparation of 1-(3-((1-(2-hydroxypropanoyl)-2,3-dihydro-1H-pyrido[2,3-b][1,4]oxazin-7-yl)amino)-5-methyl-5H-chromeno[4,3-c]pyridin-8-yl)pyrrolidin-2-one

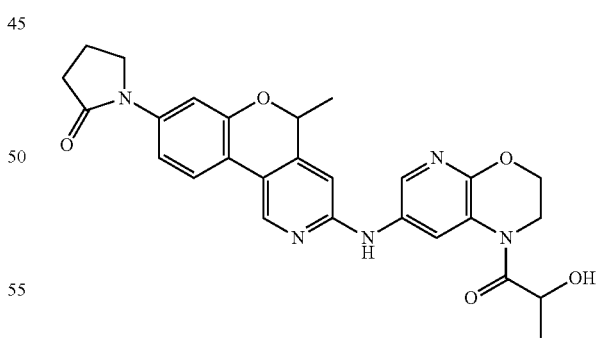

To a solution of 1-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-1-oxopropan-2-yl acetate (140 mg, 0.257 mmol) in dioxane (6 mL) was added MeOH (2.1 mL, 51 mmol). Then the yellow solution was added K$_2$CO$_3$ (107 mg, 0.772 mmol), stirred at 20° C. for 3 h. LCMS (Rt=0.562 min; MS Calcd: 501.2. MS Found: 502.0 [M+H]$^+$). The reaction mixture was filtered and concentrated. The residue was purified by prep-HPLC (0.05%

NH$_3$·H$_2$O as an additive) and lyophilized to give 1-(3-((1-(2-hydroxypropanoyl)-2,3-dihydro-H-pyrido[2,3-b][1,4]oxazin-7-yl)amino)-5-methyl-5H-chromeno[4,3-c]pyridin-8-yl)pyrrolidin-2-one (31.6 mg, yield: 24%) as a white solid.

$^1$H NMR (400 MHz, DMSO-d$_6$) δ 1.29 (3H, d, J=6.4 Hz), 1.51 (3H, d, J=6.4 Hz), 2.00-2.09 (2H, m), 2.53 (2H, overlap with DMSO), 3.83 (2H, t, J=7.6 Hz), 3.87-4.08 (2H, m), 4.30-4.40 (2H, m), 4.62-4.68 (1H, m), 5.23 (1H, q, J=6.4 Hz), 5.44 (1H, d, J=7.2 Hz), 6.65 (1H, s), 7.29 (1H, dd, J=8.8, 2.4 Hz), 7.38 (1H, d, J=2.4 Hz), 7.85 (1H, d, J=8.8 Hz), 8.28 (1H, d, J=2.0 Hz), 8.58 (1H, s), 8.67 (1H, brs), 9.22 (1H, s).

Example 61: 1-(3-((1-(2-hydroxyacetyl)-2,3-dihydro-1H-pyrido[2,3-b][1,4]oxazin-7-yl)amino)-5-methyl-5H-chromeno[4,3-c]pyridin-8-yl)pyrrolidin-2-one

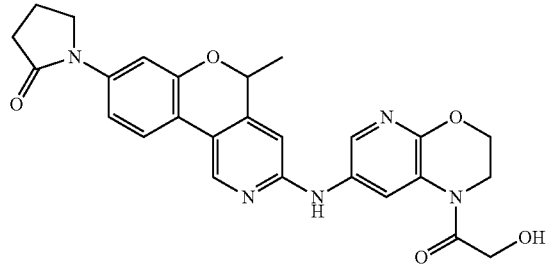 [SMILES: CC1Oc2cc(N3CCCC3=O)ccc2-c2cnc(Nc3cnc4c(c3)N(C(=O)CO)CCO4)cc21]

Step 1: Preparation of 2-(7-bromo-2,3-dihydro-1H-pyrido[2,3-b][1,4]oxazin-1-yl)-2-oxoethyl acetate

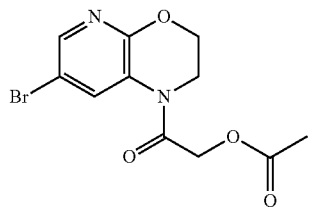 [SMILES: CC(=O)OCC(=O)N1CCOc2ncc(Br)cc21]

To a solution of 7-bromo-2,3-dihydro-H-pyrido[2,3-b][1,4]oxazine (537 mg, 2.50 mmol) in DCM (12 mL) was added pyridine (1.01 mL, 12.5 mmol). The reaction mixture was cooled to 0° C. and then dropwise added 2-chloro-2-oxoethyl acetate in DCM (6 mL). The reaction mixture was then warmed to 20° C., stirred at 20° C. for 12 h under N$_2$ atmosphere. The colorless solution turned to yellow gradually. LCMS (Rt=0.560 min; MS Calcd: 313.9; MS Found: 314.8 [M+H]$^+$). The reaction mixture was concentrated. The residue was purified by Combi Flash (1% Et$_3$N in DCM) to afford 2-(7-bromo-2,3-dihydro-1H-pyrido[2,3-b][1,4]oxazin-1-yl)-2-oxoethyl acetate (630 mg, yield: 80%) as a yellow solid.

$^1$H NMR (400 MHz, CDCl$_3$) 2.21 (3H, s), 3.86 (2H, t, J=4.4 Hz), 4.67 (2H, t, J=4.8 Hz), 4.85 (2H, s), 8.08 (1H, d, J=2.4 Hz), 8.55 (1H, brs).

Step 2: Preparation of 2-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-2-oxoethylacetate

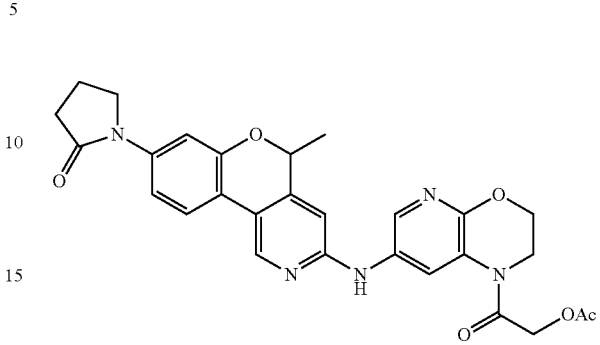

A mixture of Pd$_2$(dba)$_3$ (28 mg, 0.030 mmol) and BrettPhos (33 mg, 0.060 mmol) in 1,4-dioxane (1 mL) was stirred at 50° C. for 10 min. 1-(3-amino-5-methyl-5H-chromeno[4,3-c]pyridin-8-yl)pyrrolidin-2-one (90 mg, 0.30 mmol), 2-(7-bromo-2,3-dihydro-1H-pyrido[2,3-b][1,4]oxazin-1-yl)-2-oxoethyl acetate (100 mg, 0.317 mmol) in dioxane (6 mL) and Cs$_2$CO$_3$ (298 mg, 0.914 mmol) were added and the resulting mixture was stirred at 100° C. for 16 h. A black brown mixture was formed. LCMS (Rt=0.555 min; MS Calcd: 529.2. MS Found: 530.1 [M+H]$^+$). The reaction mixture was diluted with DCM (10 mL), filtered and concentrated. The residue was purified by prep-HPLC (normal phase, Hexane-EtOH) and lyophilized to give 2-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-2-oxoethyl acetate (30 mg, yield: 19%) as a red solid.

Step 3: Preparation of 1-(3-((1-(2-hydroxyacetyl)-2,3-dihydro-1H-pyrido[2,3-b][1,4]oxazin-7-yl)amino)-5-methyl-5H-chromeno[4,3-c]pyridin-8-yl)pyrrolidin-2-one

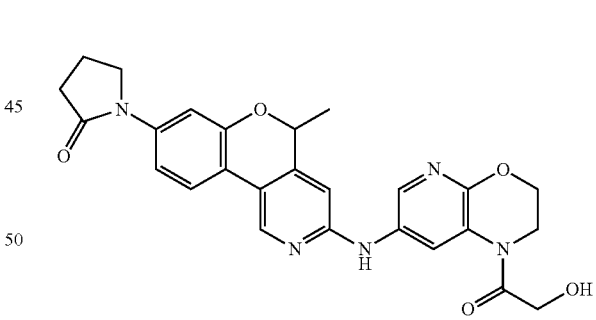

To a solution of 2-(7-((5-methyl-8-(2-oxopyrrolidin-1-yl)-5H-chromeno[4,3-c]pyridin-3-yl)amino)-2,3-dihydro-1H-pyrido[2,3-b][1,4]oxazin-1-yl)-2-oxoethyl acetate (30 mg, 0.056 mmol) in dioxane (2 mL) was added MeOH (363 mg, 11.3 mmol). Then the yellow solution was added K$_2$CO$_3$ (23 mg, 0.17 mmol), stirred at 20° C. for 3 h. LCMS (Rt=0.552 min; MS Calcd: 487.2. MS Found: 488.0 [M+H]$^+$). The reaction mixture was filtered and concentrated. The residue was purified by prep-HPLC (0.05% NH$_3$·H$_2$O as an additive) and lyophilized to give 1-(3-((1-(2-hydroxyacetyl)-2,3-dihydro-1H-pyrido[2,3-b][1,4]oxazin-7-yl)amino)-5-methyl-5H-chromeno[4,3-c]pyridin-8-yl)pyrrolidin-2-one (12.5 mg, yield: 45%) as a white solid.

$^1$H NMR (400 MHz, DMSO-d$_6$) δ 1.52 (3H, d, J=6.4 Hz), 2.01-2.09 (2H, m), 2.55 (2H, overlap with DMSO), 3.80-3.86 (4H, m), 4.30-4.35 (4H, m), 5.08 (1H, t, J=6.0 Hz), 5.23 (1H, q, J=6.0 Hz), 6.66 (1H, s), 7.30 (1H, dd, J=8.4, 2.0 Hz), 7.38 (1H, d, J=1.6 Hz), 7.85 (1H, d, J=8.4 Hz), 8.27 (1H, d, J=2.4 Hz), 8.59 (1H, s), 8.80 (1H, brs), 9.24 (1H, s).

Example 62: 1-(3-((2,3-dihydro-[1,4]dioxino[2,3-b]pyridin-7-yl)amino)-5-methyl-5H-chromeno[4,3-c]pyridin-8-yl)pyrrolidin-2-one

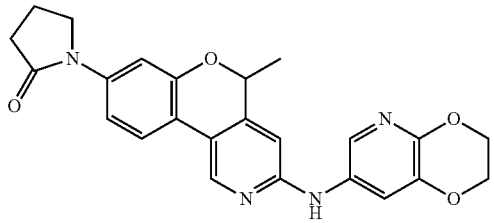 [SMILES: CC1Oc2cc(N3CCCC3=O)ccc2-c2cnc(Nc3cnc4c(c3)OCCO4)cc21]

Step 1: Preparation of tert-butyl (2,3-dihydro-[1,4]dioxino[2,3-b]pyridin-7-yl)carbamate

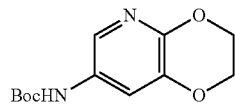

A mixture of 7-bromo-2,3-dihydro-[1,4]dioxino[2,3-b]pyridine (500 mg, 2.31 mmol), BocNH$_2$ (325 mg, 2.78 mmol), Pd$_2$(dba)$_3$ (106 mg, 0.116 mmol), XantPhos (201 mg, 0.347 mmol) and Cs$_2$CO$_3$ (1.13 g, 3.47 mmol) in anhydrous dioxane (5 mL) was degassed and purged with N$_2$ for 3 times. Then the resulting reaction mixture was heated at 100° C. for 16 h under N$_2$ atmosphere. LCMS (Rt=0.752 min; MS Calcd: 252.1. MS Found: 252.9 [M+H]$^+$). To the reaction mixture was added water (25 mL), then extracted with EtOAc (25 mL×3). The combined organic layer was washed brine (25 mL), dried over anhydrous Na$_2$SO$_4$ and concentrated. The residue was purified by Combi Flash (20% to 50% DCM in EtOAc) to give tert-butyl (2,3-dihydro-[1,4]dioxino[2,3-b]pyridin-7-yl)carbamate (400 mg, yield: 69%) as a yellow solid.

$^1$H NMR (400 MHz, CDCl$_3$) δ 1.51 (9H, s), 4.21-4.24 (2H, m), 4.37-4.40 (2H, m), 6.44 (1H, brs), 7.55 (1H, s), 7.64 (1H, d, J=2.4 Hz).

Step 2: Preparation of 2,3-dihydro-[1,4]dioxino[2,3-b]pyridin-7-amine

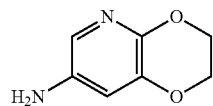

To a solution of tert-butyl (2,3-dihydro-[1,4]dioxino[2,3-b]pyridin-7-yl)carbamate (400 mg, 1.59 mmol) in EtOAc (5 mL) was added 4N HCl gas in EtOAc (20 mL) at 10-15° C. Then the reaction mixture was stirred at 10-15° C. for 2 h.

The reaction mixture turned into cloudy from clear solution. LCMS indicated the starting material was consumed up. The reaction mixture was concentrated to give 2,3-dihydro-[1,4]dioxino[2,3-b]pyridin-7-amine (290 mg, yield: 97%, HCl salt) as a yellow solid.

$^1$H NMR (400 MHz, DMSO-d$_6$) δ 4.29-4.32 (2H, m), 4.43-4.45 (2H, m), 7.37 (1H, d, J=2.4 Hz), 7.80 (1H, d, J=2.4 Hz).

Step 3: Preparation of 1-(3-((2,3-dihydro-[1,4]dioxino[2,3-b]pyridin-7-yl)amino)-5-methyl-5H-chromeno[4,3-c]pyridin-8-yl)pyrrolidin-2-one

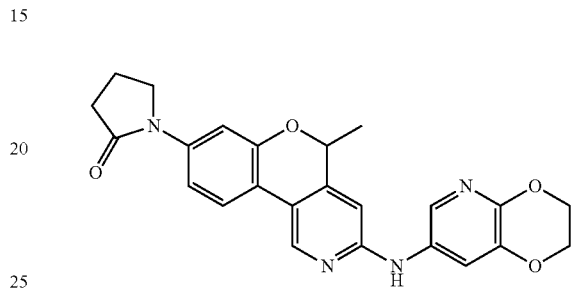

A mixture of 1-(3-chloro-5-methyl-5H-chromeno[4,3-c]pyridin-8-yl)pyrrolidin-2-one (80 mg, 0.25 mmol), 2,3-dihydro-[1,4]dioxino[2,3-b]pyridin-7-amine (72 mg, 0.38 mmol, HCl salt), Pd$_2$(dba)$_3$ (12 mg, 0.013 mmol), BrettPhos (14 mg, 0.025 mmol) and Cs$_2$CO$_3$ (248 mg, 0.762 mmol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS (Rt=0.693 min; MS Calcd: 430.2. MS Found: 431.0 [M+H]$^+$). To the reaction mixture was added water (25 mL), then extracted with EtOAc/THF (25 mL×2, 1/1). The combined organic layer was washed with brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give 1-(3-((2,3-dihydro-[1,4]dioxino[2,3-b]pyridin-7-yl)amino)-5-methyl-5H-chromeno[4,3-c]pyridin-8-yl)pyrrolidin-2-one (40.4 mg, yield: 37%) as a yellow solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. purity is 99.74%, Rt=1.254 min; MS Calcd.: 430.2, MS Found: 431.0 [M+H]$^+$.

$^1$H NMR (400 MHz, DMSO-d$_6$) δ 1.52 (3H, d, J=6.4 Hz), 2.01-2.10 (2H, m), 2.52-2.54 (2H, m), 3.75-3.86 (2H, m), 4.20-4.30 (2H, m), 4.35-4.40 (2H, m), 5.26 (1H, q, J=6.4 Hz), 6.67 (1H, s), 7.31 (1H, dd, J=8.5, 2.3 Hz), 7.40 (1H, d, J=2.0 Hz), 7.82 (1H, d, J=2.5 Hz), 7.86 (1H, d, J=8.8 Hz), 7.94 (1H, d, J=2.5 Hz), 8.61 (1H, s), 9.34 (1H, brs).

Example 63: 1-(5-methyl-3-(pyrido[2,3-b]pyrazin-7-ylamino)-5H-chromeno[4,3-c]pyridin-8-yl)pyrrolidin-2-one

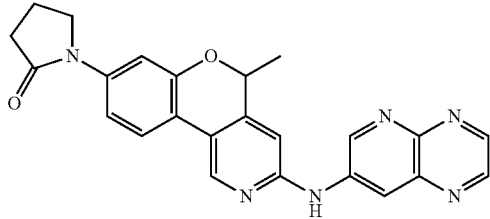 [SMILES: CC1Oc2cc(N3CCCC3=O)ccc2-c2cnc(Nc3cnc4nccnc4c3)cc21]

Step 1: Preparation of tert-butyl pyrido[2,3-b]pyrazin-7-ylcarbamate

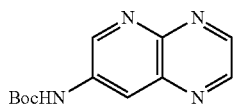

A mixture of 7-bromopyrido[2,3-b]pyrazine (500 mg, 2.38 mmol), BocNH$_2$ (335 mg, 2.86 mmol), Pd$_2$(dba)$_3$ (109 mg, 0.119 mmol), XantPhos (207 mg, 0.357 mmol) and Cs$_2$CO$_3$ (1.16 g, 3.57 mmol) in anhydrous dioxane (10 mL) was degassed and purged with N$_2$ for 3 times. Then the resulting reaction mixture was heated at 110° C. for 16 h. A black suspension was formed. To the reaction mixture was added water (25 mL) and EtOAc (25 mL), then filtered through a pad of celite and the solid was washed with EtOAc (20 mL×3). The filtrate was separated and the aqueous layer was extracted with EtOAc (25 mL×2). The combined organic layer was washed with brine (25 mL), dried over anhydrous Na$_2$SO$_4$ and concentrated. The residue was purified by Combi Flash (35% to 70% EtOAc in pentane) to give tert-butyl pyrido[2,3-b]pyrazin-7-ylcarbamate (150 mg, yield: 26%) as a yellow solid.

$^1$H NMR (400 MHz, DMSO-d$_6$) δ 1.54 (9H, s), 8.61 (1H, s), 8.95-9.00 (2H, m), 9.13 (1H, d, J=2.8 Hz), 10.29 (1H, brs).

Step 2: Preparation of pyrido[2,3-b]pyrazin-7-amine

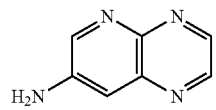

To a solution of tert-butyl pyrido[2,3-b]pyrazin-7-ylcarbamate (150 mg, 0.609 mmol) in EtOAc (2 mL) was added 4 N HCl in EtOAc (10 mL) from 10-15° C. Then the reaction mixture was stirred at 10-15° C. for 1 hour. The reaction mixture turned into brown cloudy from yellow solution. Crude LCMS (Rt=0.382 min; MS Calcd: 146.1; MS Found: 147.0 [M+H]$^+$). The reaction mixture was concentrated to give pyrido[2,3-b]pyrazin-7-amine (100 mg, yield: 90%, HCl salt) as a brown solid.

$^1$H NMR (400 MHz, DMSO-d$_6$) δ 7.40 (1H, d, J=2.8 Hz), 8.72 (1H, s), 8.78 (1H, d, J=2.4 Hz), 8.83 (1H, s).

Step 3: Preparation of 1-(5-methyl-3-(pyrido[2,3-b]pyrazin-7-ylamino)-5H-chromeno[4,3-c]pyridin-8-yl)pyrrolidin-2-one

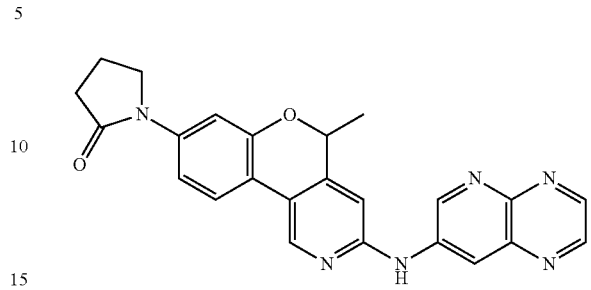

A mixture of 1-(3-chloro-5-methyl-5H-chromeno[4,3-c]pyridin-8-yl)pyrrolidin-2-one (80 mg, 0.25 mmol), pyrido[2,3-b]pyrazin-7-amine (70 mg, 0.38 mmol, HCl salt), Pd$_2$(dba)$_3$ (12 mg, 0.013 mmol), BrettPhos (14 mg, 0.025 mmol) and Cs$_2$CO$_3$ (248 mg, 0.762 mmol) in anhydrous dioxane (2 mL) was degassed and purged with N$_2$ for 3 times. Then the reaction mixture was heated at 100° C. for 16 h under N$_2$ atmosphere. Crude LCMS (Rt=0.382 min; MS Calcd: 424.2. MS Found: 425.0 [M+H]$^+$). The mixture was filtered through a pad of celite and the solid was washed with MeOH (5 mL×3). The filtrate was concentrated and the residue was purified by prep-HPLC (0.225% FA as an additive). Most of the MeCN was removed under reduced pressure and the remaining part was lyophilized to give 1-(5-methyl-3-(pyrido[2,3-b]pyrazin-7-ylamino)-5H-chromeno[4,3-c]pyridin-8-yl)pyrrolidin-2-one (3.8 mg, yield: 3.5%) as a red solid.

LC-MS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=2.558 min; MS Calcd.: 424.2, MS Found: 425.3 [M+H]$^+$.

$^1$H NMR (400 MHz, DMSO-d$_6$) δ 1.58 (3H, d, J=6.4 Hz), 2.05-2.10 (2H, m), 2.55-2.60 (2H, m), 3.80-3.90 (2H, m), 5.35 (1H, q, J=6.4 Hz), 6.92 (1H, s), 7.35 (1H, d J=8.4 Hz), 7.43 (1H, s), 7.95 (1H, d, J=8.8 Hz), 8.60-8.90 (2H, m), 8.93 (1H, s), 9.15-9.25 (2H, m), 10.27 (1H, brs).

Example 64: 1-(3-((1,5-naphthyridin-3-yl)amino)-5-methyl-5H-chromeno[4,3-c]pyridin-8-yl)pyrrolidin-2-one

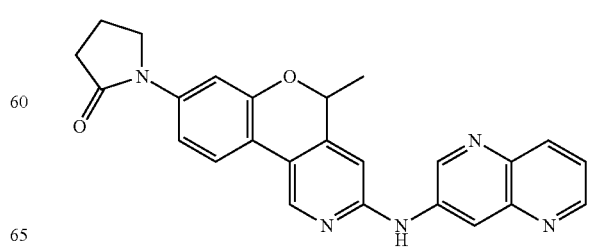

Step 1: Preparation of tert-butyl (1,5-naphthyridin-3-yl)carbamate

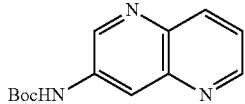 [SMILES: CC(C)(C)OC(=O)Nc1cnc2cccnc2c1]

A mixture of 3-bromo-1,5-naphthyridine (300 mg, 1.44 mmol), BocNH$_2$ (202 mg, 1.72 mmol), Pd$_2$(dba)$_3$ (66 mg, 0.072 mmol), XantPhos (125 mg, 0.215 mmol) and Cs$_2$CO$_3$ (701 mg, 2.15 mmol) in anhydrous dioxane (8 mL) was degassed and purged with N$_2$ for 3 times. Then the resulting reaction mixture was heated at 110° C. for 16 h. The reaction mixture turned into yellow suspension from red. The reaction mixture was cooled to room temperature, then diluted with water (25 mL) and extracted with EtOAc (25 mL×3). The combined organic layer was filtered and the filtrate was washed with brine (25 mL), dried over anhydrous Na$_2$SO$_4$ and concentrated. The residue was purified by Combi Flash (25% to 60% EtOAc in pentane to give tert-butyl (1,5-naphthyridin-3-yl)carbamate (253 mg, yield: 72%) as a yellow solid.

$^1$H NMR (400 MHz, CDCl$_3$) δ 1.57 (9H, s), 7.03 (1H, brs), 7.53 (1H, dd, J=8.0, 4.0 Hz), 8.33 (1H, d, J=8.4 Hz), 8.50 (1H, s), 8.90-9.00 (2H, m).

Step 2: Preparation of 1,5-naphthyridin-3-amine

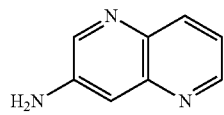

To a solution of tert-butyl (1,5-naphthyridin-3-yl)carbamate (253 mg, 1.03 mmol) in EtOAc (5 mL) was added 4 N HCl in EtOAc (10 mL) at 10-15° C. Then the reaction mixture was stirred at 10-15° C. for 2 h. The reaction mixture turned into cloudy from clear solution. The mixture was concentrated to give 1,5-naphthyridin-3-amine (160 mg, yield: 85% yield, HCl salt) as a yellow solid.

$^1$H NMR (400 MHz, DMSO-d$_6$) δ 7.44 (1H, d, J=2.4 Hz), 7.70 (1H, dd, J=8.4, 6.0 Hz), 8.75-8.85 (2H, m), 8.90 (1H, d, J=4.8 Hz).

Step 3: Preparation of 1-(3-((1,5-naphthyridin-3-yl)amino)-5-methyl-5H-chromeno[4,3-c]pyridin-8-yl)pyrrolidin-2-one

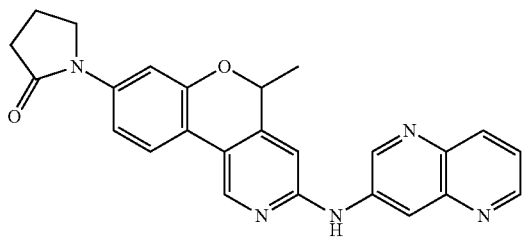 [SMILES: CC1Oc2cc(N3CCCC3=O)ccc2-c2cnc(Nc3cnc4cccnc4c3)cc21]

A mixture of 1-(3-chloro-5-methyl-5H-chromeno[4,3-c]pyridin-8-yl)pyrrolidin-2-one (80 mg, 0.25 mmol), 1,5-naphthyridin-3-amine (55 mg, 0.30 mmol, HCl salt), Pd$_2$(dba)$_3$ (12 mg, 0.013 mmol), BrettPhos (14 mg, 0.025 mmol) and Cs$_2$CO$_3$ (248 mg, 0.762 mmol) in anhydrous dioxane (2 mL) was degassed and purged with N$_2$ for 3 times. Then the resulting reaction mixture was stirred at 100° C. for 16 h. The reaction mixture turned into yellow suspension from black. Crude LCMS (Rt=0.733 min; MS Calcd: 423.2. MS Found: 424.1 [M+H]$^+$). The reaction mixture was filtered and the solid was washed with MeOH (5 mL×3). The filtrate was concentrated and the residue was purified by prep-HPLC (0.225% FA as an additive). Most of the MeCN was removed under reduced pressure and the remaining part was lyophilized to give 1-(3-((1,5-naphthyridin-3-yl)amino)-5-methyl-5H-chromeno[4,3-c]pyridin-8-yl)pyrrolidin-2-one (6.6 mg, yield: 5.5%) as a red solid.

LC-MS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=2.371 min; MS Calcd.: 423.2, MS Found: 424.3 [M+H]$^+$.

$^1$H NMR (400 MHz, DMSO-d$_6$) δ 1.58 (3H, d, J=6.4 Hz), 2.00-2.15 (2H, m), 2.55-2.60 (2H, m), 3.80-3.95 (2H, m), 5.35 (1H, q, J=6.4 Hz), 6.90 (1H, s), 7.36 (1H, dd J=8.4, 2.0 Hz), 7.44 (1H, d, J=2.4 Hz), 7.61 (1H, dd, J=8.4, 4.4 Hz), 7.96 (1H, d, J=8.8 Hz), 8.38 (1H, d, J=8.3 Hz), 8.83 (1H, s), 8.92 (1H, d, J=2.8 Hz), 9.04 (1H, d, J=2.8 Hz), 9.13 (1H, d, J=2.3 Hz), 10.12 (1H, brs).

Example 65: 1-(5-methyl-3-(thiazolo[5,4-b]pyridin-6-ylamino)-5H-chromeno[4,3-c]pyridin-8-yl)pyrrolidin-2-one

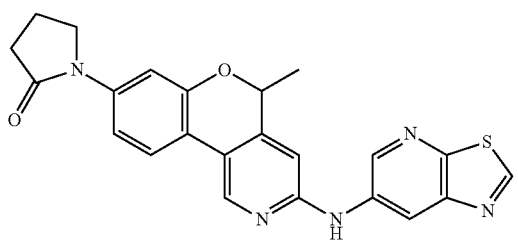 [SMILES: CC1Oc2cc(N3CCCC3=O)ccc2-c2cnc(Nc3cnc4scnc4c3)cc21]

A mixture of 1-(3-amino-5-methyl-5H-chromeno[4,3-c]pyridin-8-yl)pyrrolidin-2-one (100 mg, 0.339 mmol), 6-bromothiazolo[5,4-b]pyridine (109 mg, 0.508 mmol), Pd$_2$(dba)$_3$ (31 mg, 0.034 mmol), BrettPhos (36 mg, 0.068 mmol) and Cs$_2$CO$_3$ (221 mg, 0.677 mmol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS (Rt=0.750 min; MS Calcd: 429.1; MS Found: 430.0 [M+H]$^+$). To the reaction mixture was added water (25 mL), then extracted with EtOAc/THF (25 mL×3, 1/1). The combined organic layer was washed with brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give the product, which was further triturated with MeCN (3 mL), then filtered and washed with MeCN (0.5 mL×2) and lyophilized to give 1-(5-methyl-3-(thiazolo[5,4-b]pyridin-6-ylamino)-5H-chromeno[4,3-c]pyridin-8-yl)pyrrolidin-2-one (14.2 mg, yield: 10%) as a yellow solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. purity is 99.80%, Rt=1.400 min; MS Calcd.: 429.1, MS Found: 430.0 [M+H]$^+$.

$^1$H NMR (400 MHz, DMSO-d$_6$) δ 1.56 (3H, d, J=6.4 Hz), 2.01-2.10 (2H, m), 2.52-2.54 (2H, m), 3.80-3.90 (2H, m), 5.31 (1H, q, J=6.4 Hz), 6.79 (1H, s), 7.33 (1H, dd, J=8.7, 2.1 Hz), 7.42 (1H, d, J=2.0 Hz), 7.91 (1H, d, J=8.8 Hz), 8.76 (1H, s), 8.79 (1H, d, J=2.5 Hz), 9.14 (1H, d, J=2.5 Hz), 9.50 (1H, s), 9.78 (1H, brs).

Example 66: N-(5-((9-fluoro-5,5-dimethyl-8-(2-oxopyrrolidin-1-yl)-5H-chromeno[4,3-c]pyridin-3-yl)amino)-2-methoxypyridin-3-yl)acetamide

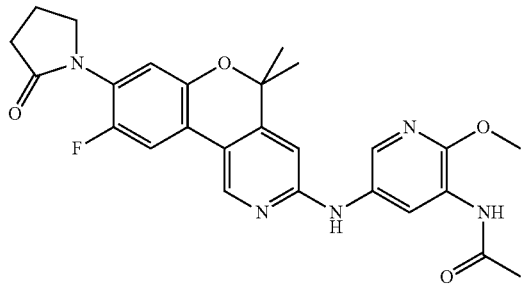 [SMILES: COc1ncc(Nc2cc3c(cn2)-c2cc(F)c(N4CCCC4=O)cc2OC3(C)C)cc1NC(C)=O]

A mixture of Pd$_2$(dba)$_3$ (18 mg, 0.019 mmol) and Brettphos (21 mg, 0.038 mmol) in 1,4-dioxane (1 mL) was stirred at 50° C. for 10 min. 1-(3-amino-9-fluoro-5,5-dimethyl-5H-chromeno[4,3-c]pyridin-8-yl)pyrrolidin-2-one (80 mg, 0.24 mmol), N-(5-bromo-2-methoxypyridin-3-yl)acetamide (59 mg, 0.24 mmol) in dioxane (4 mL) and Cs$_2$CO$_3$ (199 mg, 0.611 mmol) were added and the resulting mixture was stirred at 100° C. for 15 hours. A black brown mixture was formed. LCMS showed that the purity of the desired product is 60% (Rt=0.610 min; MS Calcd: 491.2. MS Found: 492.1 [M+H]$^+$). The reaction mixture was diluted with DCM (10 mL), filtered and concentrated. The residue was purified by prep-HPLC (0.05% NH$_3$.H$_2$O as an additive) and lyophilized to give N-(5-((9-fluoro-5,5-dimethyl-8-(2-oxopyrrolidin-1-yl)-5H-chromeno[4,3-c]pyridin-3-yl)amino)-2-methoxypyridin-3-yl)acetamide (70.3 mg, yield: 59%) as a light yellow solid.

$^1$H NMR (400 MHz, DMSO-d$_6$) δ 1.55 (6H, s), 2.06-2.13 (5H, m), 2.43 (2H, t, J=7.6 Hz), 3.77 (2H, t, J=7.2 Hz), 3.91 (3H, s), 6.73 (1H, s), 7.02 (1H, d, J=6.8 Hz), 7.86 (1H, d, J=12.0 Hz), 8.31 (1H, d, J=2.4 Hz), 8.58 (1H, d, J=2.0 Hz), 8.66 (1H, s), 9.26 (1H, brs), 9.36 (1H, brs).

Example 67: N,N,5-trimethyl-3-((1-pivaloyl-2,3-dihydro-1H-pyrido[2,3-b][1,4]oxazin-7-yl)amino)-5H-chromeno[4,3-c]pyridine-8-carboxamide

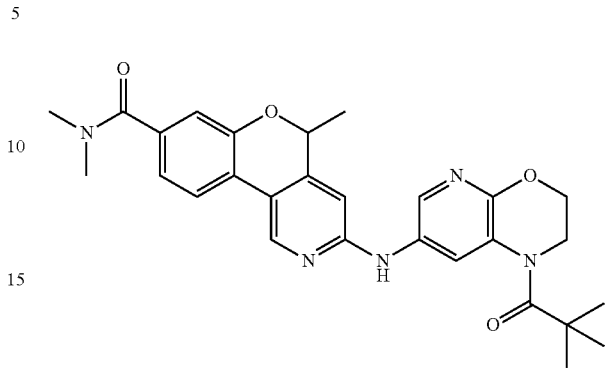

Step 1: Preparation of 4-bromo-3-fluoro-N,N-dimethylbenzamide

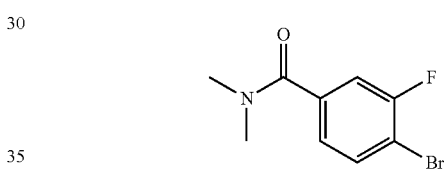

To a suspension of 4-bromo-3-fluorobenzoic acid (20.0 g, 91.3 mmol) in SOCl$_2$ (100 mL) was added DMF (0.5 mL) at 10-15° C. Then the reaction mixture was heated at 80° C. for 2 h. The mixture turned into yellow solution from suspension. The reaction mixture was concentrated and the residue was diluted with anhydrous toluene (50 mL) and concentrated in turn for 3 times to remove most of SOCl$_2$. Then the residue was dissolved in anhydrous DCM (50 mL) and added dropwise to a mixture of dimethylamine HCl salt (14.9 g, 183 mmol) and Et$_3$N (37.0 g, 365 mmol) in anhydrous DCM (150 mL) at 0° C. After the completion of the addition, the reaction mixture was stirred at 10-15° C. for 2 h. A lot of precipitate was formed after stirring. To the reaction mixture was added water (100 mL), then extracted with DCM (100 mL×3). The combined organic layer was washed with 1N aqueous HCl (100 mL), 1N aqueous NaOH (100 mL), brine (100 mL), dried over anhydrous Na$_2$SO$_4$ and concentrated to give 4-bromo-3-fluoro-N,N-dimethylbenzamide (22.3 g, yield: 99%) as a yellow solid.

$^1$H NMR (400 MHz, CDCl$_3$) δ 2.99 (3H, s), 3.10 (3H, s), 7.10 (1H, dd, J=8.2, 1.3 Hz), 7.20 (1H, dd, J=8.6, 1.9 Hz), 7.60 (1H, dd, J=8.2, 6.9 Hz).

Step 2: Preparation of 3-fluoro-N,N-dimethyl-4-(4,4,5,5-tetramethyl-1,3,2-dioxaborolan-2-yl)benzamide

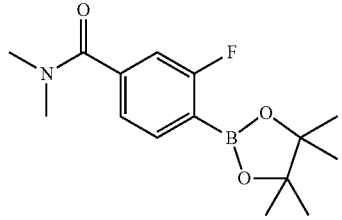

A mixture of 4-bromo-3-fluoro-N,N-dimethylbenzamide (5.00 g, 20.3 mmol), B$_2$Pin$_2$ (7.74 g, 30.5 mmol), Pd(dppf)Cl$_2$ (1.49 g, 2.03 mmol) and KOAc (5.98 g, 61.0 mmol) in anhydrous dioxane (50 mL) was degassed and purged with N$_2$ for 3 times. Then the reaction mixture was heated at 90° C. for 16 h. The reaction mixture turned into black from red suspension. To the reaction mixture was added water (200 mL) and EtOAc (200 mL), then filtered through a pad of celite. The filtrate was separated and aqueous layer was extracted with EtOAc (100 mL×2). The combined organic layer was washed with brine (100 mL), dried over anhydrous Na$_2$SO$_4$ and concentrated. The residue was purified by Combi Flash (30% to 75% EtOAc in pentane) to give 3-fluoro-N,N-dimethyl-4-(4,4,5,5-tetramethyl-1,3,2-dioxaborolan-2-yl)benzamide (5.50 g, yield: 92%) as a yellow solid.

$^1$H NMR (400 MHz, CDCl$_3$) δ 1.35 (12H, s), 2.93 (3H, s), 3.08 (3H, s), 7.09 (1H, dd, J=9.3, 1.3 Hz), 7.16 (1H, dd, J=7.5, 1.3 Hz), 7.76 (1H, dd, J=7.5, 6.0 Hz).

Step 3: Preparation of 1-(5-bromo-2-chloropyridin-4-yl)ethan-1-ol

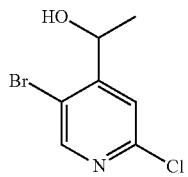

To a solution of 5-bromo-2-chloroisonicotinaldehyde (5.00 g, 22.7 mmol) in anhydrous THF (100 mL) was added MeMgBr (15.1 mL, 45.4 mmol, 3 M in Et$_{2}$O) dropwise at 0° C. After the completion of addition, the reaction mixture was stirred at 10-15° C. for 2 h. The reaction mixture turned into brown solution from yellow. The reaction mixture was quenched with saturated aqueous NH$_4$Cl (200 mL) and extracted with EtOAc (200 mL×2). The combined organic layer was washed with brine (100 mL), dried over anhydrous Na$_2$SO$_4$ and concentrated to give 1-(5-bromo-2-chloropyridin-4-yl)ethan-1-ol (5.30 g, yield: 99%) as a yellow solid.

$^1$H NMR (400 MHz, CDCl$_3$) δ 1.47 (3H, d, J=6.8 Hz), 2.90 (1H, d, J=3.6 Hz), 5.05-5.15 (1H, m), 7.59 (1H, s), 8.35 (1H, s).

Step 4: Preparation of 4-(6-chloro-4-(1-hydroxyethyl)pyridin-3-yl)-3-fluoro-N,N-dimethylbenzamide

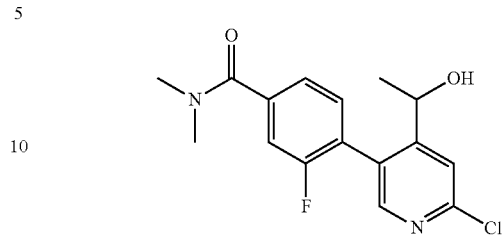

A mixture of 1-(5-bromo-2-chloropyridin-4-yl)ethan-1-ol (2.00 g, 8.46 mmol), 3-fluoro-N,N-dimethyl-4-(4,4,5,5-tetramethyl-1,3,2-dioxaborolan-2-yl)benzamide (2.73 g, 9.30 mmol), Pd(dppf)Cl$_2$ (619 mg, 0.846 mmol) and Na$_2$CO$_3$ (2.69 g, 25.37 mmol) in dioxane (50 mL) and H$_2$O (10 mL) was degassed and purged with N$_2$ for 3 times. Then the resulting reaction mixture was heated at 90° C. for 16 h. The reaction mixture turned into black from red. LCMS (Rt=0.726 min; MS Calcd: 322.1. MS Found: 322.8 [M+H]$^+$). To the reaction mixture was added water (100 mL), then extracted with EtOAc (100 mL×3). The combined organic layer was washed with brine (100 mL), dried over anhydrous Na$_2$SO$_4$ and concentrated. The residue was purified by Combi Flash (50% to 100% EtOAc in pentane) to give 4-(6-chloro-4-(1-hydroxyethyl)pyridin-3-yl)-3-fluoro-N,N-dimethylbenzamide (1.44 g, yield: 53%) as yellow gum.

Step 5: Preparation of 3-chloro-N,N,5-trimethyl-5H-chromeno[4,3-c]pyridine-8-carboxamide

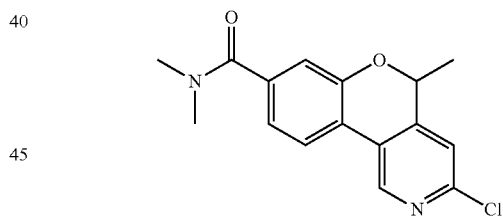

To a solution of 4-(6-chloro-4-(1-hydroxyethyl)pyridin-3-yl)-3-fluoro-N,N-dimethylbenzamide (1.44 g, 4.46 mmol) in anhydrous THF (60 mL) was added NaH (357 mg, 8.92 mmol, 60% dispersion in mineral oil) at 10-15° C. Then the reaction mixture was stirred at 25° C. for 3 h. The reaction mixture was turned into brown suspension from gray. Crude LCMS (Rt=0.792 min; MS Calcd: 302.1. MS Found: 302.8 [M+H]$^+$). The reaction mixture was quenched with saturated aqueous NH$_4$Cl (50 mL), then extracted with EtOAc (100 mL×2). The combined organic layer was washed with brine (50 mL), dried over anhydrous Na$_2$SO$_4$ and concentrated. The residue was purified by Combi Flash (50% to 100% EtOAc in pentane) to give 3-chloro-N,N,5-trimethyl-5H-chromeno[4,3-c]pyridine-8-carboxamide (1.00 g, yield: 74%) as a white solid.

$^1$H NMR (400 MHz, CDCl$_3$) δ 1.64 (3H, d, J=6.8 Hz), 3.02 (3H, s), 3.12 (3H, s), 5.22 (1H, q, J=6.8 Hz), 7.07 (1H, s), 7.10-7.15 (2H, m), 7.79 (1H, d, J=8.0 Hz), 8.72 (1H, s).

Step 6: Preparation of tert-butyl (8-(dimethylcarbamoyl)-5-methyl-5H-chromeno[4,3-c]pyridin-3-yl)carbamate

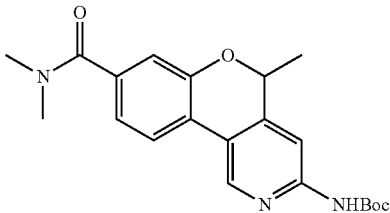 [SMILES: CC1Oc2cc(C(=O)N(C)C)ccc2-c2cnc(NC(=O)OC(C)(C)C)cc21]

A mixture of 3-chloro-N,N,5-trimethyl-5H-chromeno[4,3-c]pyridine-8-carboxamide (800 mg, 2.64 mmol), BocNH$_2$ (464 mg, 3.96 mmol), Pd$_2$(dba)$_3$ (121 mg, 0.132 mmol), XantPhos (153 mg, 0.264 mmol) and Cs$_2$CO$_3$ (1.72 g, 5.28 mmol) in anhydrous dioxane (25 mL) was degassed and purged with N$_2$ for 3 times. Then the resulting reaction mixture was heated at 100° C. for 16 h. The reaction mixture turned into yellow suspension from red. Crude LCMS (Rt=0.817 min; MS Calcd: 383.1. MS Found: 383.9 [M+H]$^+$). The reaction mixture was diluted with water (50 mL) and then extracted with EtOAc (50 mL×3). The combined organic layer was washed with brine (50 mL), dried over anhydrous Na$_2$SO$_4$ and concentrated to give tert-butyl (8-(dimethylcarbamoyl)-5-methyl-5H-chromeno[4,3-c]pyridin-3-yl)carbamate (1.14 g, crude) as brown gum, which was directly used for the next step without further purification.

Step 7: Preparation of 3-amino-N,N,5-trimethyl-5H-chromeno[4,3-c]pyridine-8-carboxamide

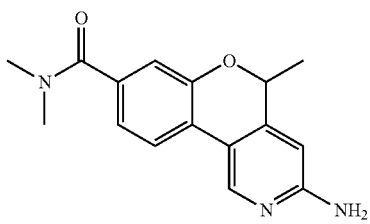 [SMILES: CC1Oc2cc(C(=O)N(C)C)ccc2-c2cnc(N)cc21]

To a solution of tert-butyl (8-(dimethylcarbamoyl)-5-methyl-5H-chromeno[4,3-c]pyridin-3-yl)carbamate (1.14 g, crude) in anhydrous DCM (10 mL) was added TFA (10 mL) at 10-15° C. Then the reaction mixture was stirred at 10-15° C. for 2 h. The reaction mixture turned into yellow solution from brown. Crude LCMS (Rt=0.627 min; MS Calcd: 283.1; MS Found: 283.9 [M+H]$^+$). The reaction mixture was concentrated and the residue was basified with 1N aqueous NaOH to pH=10, then extracted with DCM (50 mL×3). The combined organic layer was washed with brine (25 mL), dried over anhydrous Na$_2$SO$_4$ and concentrated. The residue was purified by Combi Flash (0 to 10% MeOH in EtOAc) to give 3-amino-N,N,5-trimethyl-5H-chromeno[4,3-c]pyridine-8-carboxamide (550 mg, yield: 65% for 2 steps) as a yellow solid.

$^1$H NMR (400 MHz, CDCl$_3$) δ 1.56 (3H, d, J=6.8 Hz), 3.02 (3H, s), 3.10 (3H, s), 4.66 (2H, brs), 5.10 (1H, q, J=6.8 Hz), 6.29 (1H, s), 7.01 (1H, s), 7.07 (1H, dd, J=8.0, 1.6 Hz), 7.68 (1H, d, J=8.0 Hz), 8.44 (1H, s).

Step 8: Preparation of N,N,5-trimethyl-3-((1-pivaloyl-2,3-dihydro-1H-pyrido[2,3-b][1,4]oxazin-7-yl)amino)-5H-chromeno[4,3-c]pyridine-8-carboxamide

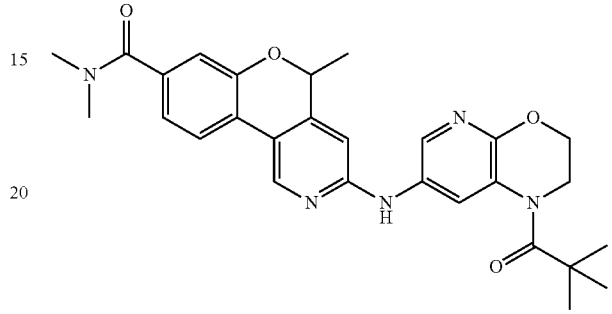

A mixture of 3-amino-N,N,5-trimethyl-5H-chromeno[4,3-c]pyridine-8-carboxamide (80 mg, 0.28 mmol), 1-(7-bromo-2,3-dihydro-1H-pyrido[2,3-b][1,4]oxazin-1-yl)-2,2-dimethylpropan-1-one (127 mg, 0.424 mmol), Pd$_2$(dba)$_3$ (26 mg, 0.028 mmol), BrettPhos (30 mg, 0.056 mmol) and Cs$_2$CO$_3$ (184 mg, 0.565 mol) in anhydrous dioxane (3 mL) was degassed and purged with N$_2$ for 3 times. Then the resulting reaction mixture was heated at 100° C. for 16 hr under N$_2$ atmosphere. The reaction mixture turned into yellow suspension from red. Crude LCMS (Rt=0.734 min; MS Calcd: 501.2. MS Found: 502.1 [M+H]$^+$). The reaction mixture was diluted with DCM (20 mL) then filtered through a pad of celite. The filtrate was concentrated and the residue purified by prep-HPLC (0.05% NH$_3$.H$_2$O as an additive). Most of MeCN was removed under reduced pressure and the remaining part was lyophilized to give N,N,5-trimethyl-3-((1-pivaloyl-2,3-dihydro-1H-pyrido[2,3-b][1,4]oxazin-7-yl)amino)-5H-chromeno[4,3-c]pyridine-8-carboxamide (46.4 mg, yield: 33%) as a yellow solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. the purity is 95.98%, Rt=1.340 min; MS Calcd.: 501.2, MS Found: 502.1 [M+H]$^+$.

$^1$H NMR (400 MHz, DMSO-d$_6$) δ 1.33 (9H, s), 1.54 (3H, d, J=6.4 Hz), 3.37 (6H, s), 3.95-4.05 (2H, m), 4.30-4.40 (2H, m), 5.27 (1H, q, J=6.4 Hz), 6.67 (1H, s), 6.95 (1H, s), 7.06 (1H, d, J=7.6 Hz), 7.92 (1H, dd, J=8.0, 1.2 Hz), 8.30 (1H, d, J=2.4 Hz), 8.37 (1H, s), 8.67 (1H, s), 9.27 (1H, brs).

Example 68: 3-((1-(cyclopropanecarbonyl)-2,3-di-hydro-1H-pyrido[2,3-b][1,4]oxazin-7-yl)amino)-N,N,5-trimethyl-5H-chromeno[4,3-c]pyridine-8-carboxamide

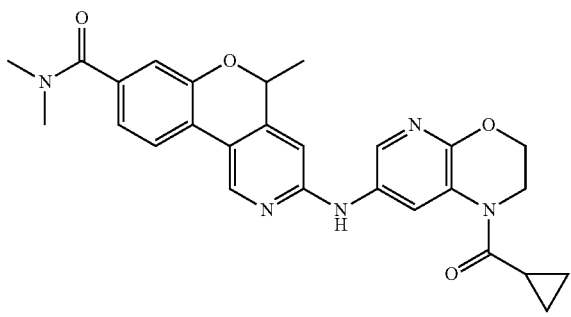 [SMILES: CC1Oc2cc(C(=O)N(C)C)ccc2-c2cnc(Nc3cnc4c(c3)N(C(=O)C3CC3)CCO4)cc21]

A mixture of 3-amino-N,N,5-trimethyl-5H-chromeno[4,3-c]pyridine-8-carboxamide (80 mg, 0.28 mmol), (7-bromo-2,3-dihydro-1H-pyrido[2,3-b][1,4]oxazin-1-yl)(cyclopropyl)methanone (120 mg, 0.424 mmol), Pd$_2$(dba)$_3$ (26 mg, 0.028 mmol), BrettPhos (30 mg, 0.056 mmol) and Cs$_2$CO$_3$ (184 mg, 0.565 mol) in anhydrous dioxane (3 mL) was degassed and purged with N$_2$ for 3 times. Then the resulting reaction mixture was heated at 100° C. for 16 hr under N$_2$ atmosphere. The reaction mixture turned into yellow suspension from red. Crude LCMS (Rt=0.712 min; MS Calcd: 485.2. MS Found: 486.1 [M+H]$^+$). The reaction mixture was diluted with DCM (20 mL) then filtered through a pad of celite. The filtrate was concentrated and the residue purified by prep-HPLC (0.05% NH$_3$.H$_2$O as an additive). The desired fraction was concentrated and the residue was triturated with MeCN (3 mL), then washed with MeCN (0.5 mL×2) and then lyophilized to give 3-((1-(cyclopropanecarbonyl)-2,3-dihydro-1H-pyrido[2,3-b][1,4]oxazin-7-yl)amino)-N,N,5-trimethyl-5H-chromeno[4,3-c]pyridine-8-carboxamide (22.9 mg, yield: 17%) as a white solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. purity is 99.74%, Rt=1.254 min; MS Calcd.: 430.2, MS Found: 431.0 [M+H]$^+$.

$^1$H NMR (400 MHz, DMSO-d$_6$) δ 0.90-1.00 (4H, m), 1.53 (3H, d, J=6.4 Hz), 2.15-2.30 (1H, m), 2.96 (6H, s), 3.95-4.00 (2H, m), 4.35-4.40 (2H, m), 5.29 (1H, q, J=6.4 Hz), 6.67 (1H, s), 6.95 (1H, d, J=1.6 Hz), 7.06 (1H, dd, J=8.0, 1.6 Hz), 7.94 (1H, d, J=8.0 Hz), 8.20 (1H, s), 8.60-8.65 (2H, m), 9.37 (1H, brs).

Example 69: methyl 7-((8-(dimethylcarbamoyl)-5-methyl-5H-chromeno[4,3-c]pyridin-3-yl)amino)-2,3-dihydro-1H-pyrido[2,3-b][1,4]oxazine-1-carboxylate

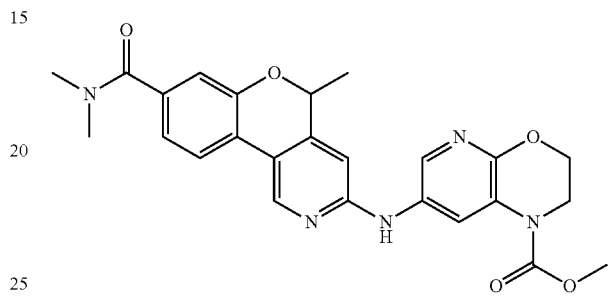

A mixture of 3-amino-N,N,5-trimethyl-5H-chromeno[4,3-c]pyridine-8-carboxamide (80 mg, 0.28 mmol), methyl 7-bromo-2,3-dihydro-1H-pyrido[2,3-b][1,4]oxazine-1-carboxylate (116 mg, 0.424 mmol), Pd$_2$(dba)$_3$ (26 mg, 0.028 mmol), BrettPhos (30 mg, 0.056 mmol) and Cs$_2$CO$_3$ (184 mg, 0.565 mol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS (Rt=0.777 min; MS Calcd: 475.2. MS Found: 476.0 [M+H]$^+$). The reaction mixture was diluted with dioxane (5 mL) then filtered through a pad of celite and the solid was washed with dioxane (10 mL×3). The filtrate was concentrated and the residue purified by prep-HPLC (0.05% NH$_3$.H$_2$O as an additive). Most of MeCN was removed under reduced pressure and the remaining part was lyophilized to give methyl 7-((8-(dimethylcarbamoyl)-5-methyl-5H-chromeno[4,3-c]pyridin-3-yl)amino)-2,3-dihydro-1H-pyrido[2,3-b][1,4]oxazine-1-carboxylate (30.2 mg, yield: 22%) as a yellow solid.

LC-MS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 96.46%, Rt=2.490 min; MS Calcd.: 475.2, MS Found: 476.3 [M+H]$^+$.

$^1$H NMR (400 MHz, DMSO-d$_6$) δ 1.54 (3H, d, J=6.8 Hz), 2.96 (6H, s), 3.79 (3H, s), 3.85-3.90 (2H, m), 4.30-4.35 (2H, m), 5.31 (1H, q, J=6.4 Hz), 6.68 (1H, s), 6.95 (1H, d, J=1.6 Hz), 7.06 (1H, dd, J=8.0, 1.2 Hz), 7.93 (1H, d, J=8.0 Hz), 8.28 (1H, d, J=2.8 Hz), 8.65-8.70 (2H, m), 9.33 (1H, brs).

Example 70: 3-((1-acetyl-2,3-dihydro-1H-pyrido[2,3-b][1,4]oxazin-7-yl)amino)-N,N,5-trimethyl-5H-chromeno[4,3-c]pyridine-8-carboxamide

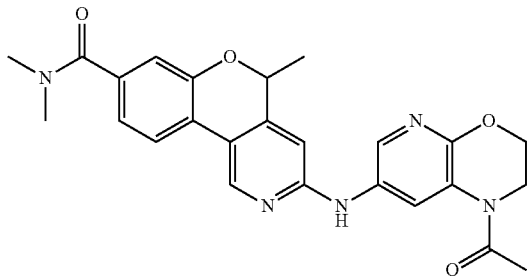 [SMILES: CC(=O)N1CCOc2ncc(Nc3cc4c(cn3)-c3ccc(C(=O)N(C)C)cc3OC4C)cc21]

Step 1: Preparation of 1-(7-bromo-2,3-dihydro-H-pyrido[2,3-b][1,4]oxazin-1-yl)ethan-1-one

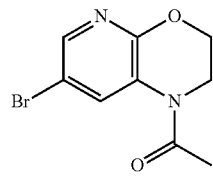

To a solution of 7-bromo-2,3-dihydro-1H-pyrido[2,3-b][1,4]oxazine (260 mg, 1.21 mmol) and DMAP (30 mg, 0.24 mmol) in anhydrous pyridine (5 mL) was added acetyl chloride (380 mg, 4.84 mmol) dropwise at 10-15° C. Then the reaction mixture was stirred at 10-15° C. for 2 h. The reaction mixture turned into brown solution from yellow. Crude LCMS (Rt=0.683 min; MS Calcd: 256.0. MS Found: 256.9 [M+H]$^+$). To the reaction mixture was added water (50 mL), then extracted with DCM (50 mL×2). The combined organic layer was washed with brine (50 mL), dried over anhydrous Na$_2$SO$_4$ and concentrated. The residue was purified by Combi Flash (5% to 10% DCM in EtOAc, 1% TEA as additive) to give 1-(7-bromo-2,3-dihydro-1H-pyrido[2,3-b][1,4]oxazin-1-yl)ethan-1-one (240 mg, yield: 77%) as yellow gum.

$^1$H NMR (400 MHz, CDCl$_3$) δ 2.35 (3H, s), 3.90-4.00 (2H, m), 4.45-4.50 (2H, m), 8.11 (1H, s), 8.69 (1H, s).

Step 2: Preparation of 3-((1-acetyl-2,3-dihydro-1H-pyrido[2,3-b][1,4]oxazin-7-yl)amino)-N,N,5-trimethyl-5H-chromeno[4,3-c]pyridine-8-carboxamide

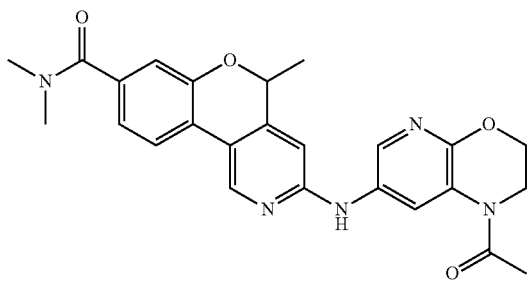 [SMILES: CC(=O)N1CCOc2ncc(Nc3cc4c(cn3)-c3ccc(C(=O)N(C)C)cc3OC4C)cc21]

A mixture of 3-amino-N,N,5-trimethyl-5H-chromeno[4,3-c]pyridine-8-carboxamide (80 mg, 0.28 mmol), 1-(7-bromo-2,3-dihydro-1H-pyrido[2,3-b][1,4]oxazin-1-yl)ethan-1-one (109 mg, 0.424 mmol), Pd$_2$(dba)$_3$ (26 mg, 0.028 mmol), BrettPhos (30 mg, 0.056 mmol) and Cs$_2$CO$_3$ (184 mg, 0.565 mol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS (Rt=0.679 min; MS Calcd: 459.2. MS Found: 460.1 [M+H]$^+$). The reaction mixture was diluted with DCM (20 mL) then filtered through a pad of celite. The filtrate was concentrated and the residue purified by prep-HPLC (0.05% NH$_3$.H$_2$O as an additive). Most of MeCN was removed under reduced pressure and the remaining part was lyophilized to give 3-((1-acetyl-2,3-dihydro-1H-pyrido[2,3-b][1,4]oxazin-7-yl)amino)-N,N,5-trimethyl-5H-chromeno[4,3-c]pyridine-8-carboxamide (51.8 mg, yield: 40%) as a yellow solid.

LC-MS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 98.12%, Rt=2.167 min; MS Calcd.: 459.2, MS Found: 460.4 [M+H]$^+$.

$^1$H NMR (400 MHz, DMSO-d$_6$) δ 1.53 (3H, d, J=6.8 Hz), 2.28 (3H, s), 2.96 (6H, s), 3.85-3.90 (2H, m), 4.30-4.40 (2H, m), 5.31 (1H, q, J=6.8 Hz), 6.67 (1H, s), 6.95 (1H, s), 7.06 (1H, dd, J=8.0, 1.6 Hz), 7.92 (1H, d, J=8.0 Hz), 8.29 (1H, s), 8.67 (1H, s), 8.80 (1H, s), 9.32 (1H, brs).

Example 71: N,N,5-trimethyl-3-((1-(methylsulfonyl)-2,3-dihydro-1H-pyrido[2,3-b][1,4]oxazin-7-yl)amino)-5H-chromeno[4,3-c]pyridine-8-carboxamide

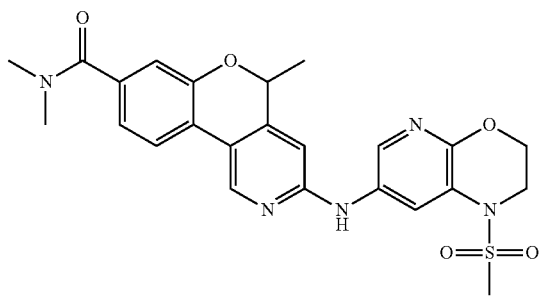 [SMILES: CC1Oc2cc(C(=O)N(C)C)ccc2-c2cnc(Nc3cnc4c(c3)N(S(C)(=O)=O)CCO4)cc21]

A mixture of 3-amino-N,N,5-trimethyl-5H-chromeno[4,3-c]pyridine-8-carboxamide (80 mg, 0.28 mmol), 7-bromo-1-(methylsulfonyl)-2,3-dihydro-1H-pyrido[2,3-b][1,4]oxazine (124 mg, 0.424 mmol), Pd$_2$(dba)$_3$ (26 mg, 0.028 mmol), BrettPhos (30 mg, 0.056 mmol) and Cs$_2$CO$_3$ (184 mg, 0.565 mol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS (Rt=0.713 min; MS Calcd: 495.2. MS Found: 496.1 [M+H]$^+$). To the reaction mixture was added water (25 mL), then extracted with EtOAc (25 mL×2). The combined organic layer was washed with brine (25 mL), dried over anhydrous Na$_2$SO$_4$ and concentrated. The residue was purified by prep-HPLC (0.225% formic acid as an additive). Most of MeCN was removed under reduced pressure and the remaining part was lyophilized to give N,N,5-trimethyl-3-((1-(methylsulfonyl)-2,3-dihydro-1H-pyrido[2,3-b][1,4]oxazin-7-yl)amino)-5H-chromeno[4,3-c]pyridine-8-carboxamide (24.1 mg, yield: 17%) as a white solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. the purity is 95.71%, Rt=1.245 min; MS Calcd.: 495.2, MS Found: 496.0 [M+H]$^+$.

$^1$H NMR (400 MHz, DMSO-d$_6$) δ 1.54 (3H, d, J=6.4 Hz), 2.96 (6H, s), 3.22 (3H, s), 3.80-3.85 (2H, m), 4.35-4.40 (2H, m), 5.29 (1H, q, J=6.4 Hz), 6.68 (1H, s), 6.96 (1H, d, J=1.6 Hz), 7.06 (1H, dd, J=8.0, 1.6 Hz), 7.93 (1H, d, J=8.0 Hz), 8.30-8.40 (2H, m), 8.68 (1H, s), 9.40 (1H, brs).

Example 72: 3-((1-(cyclopropylsulfonyl)-2,3-dihydro-1H-pyrido[2,3-b][1,4]oxazin-7-yl)amino)-N,N,5-trimethyl-5H-chromeno[4,3-c]pyridine-8-carboxamide

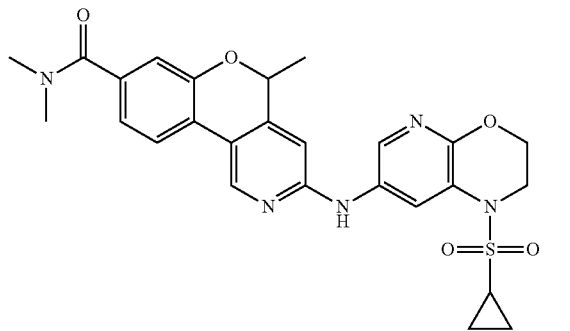 [SMILES: CC1Oc2cc(C(=O)N(C)C)ccc2-c2cnc(Nc3cnc4c(c3)N(S(=O)(=O)C3CC3)CCO4)cc21]

A mixture of 3-chloro-N,N,5-trimethyl-5H-chromeno[4,3-c]pyridine-8-carboxamide (80 mg, 0.26 mmol), 1-(cyclopropylsulfonyl)-2,3-dihydro-1H-pyrido[2,3-b][1,4]oxazin-7-amine (116 mg, 0.396 mmol, HCl salt), Pd$_2$(dba)$_3$ (12 mg, 0.013 mmol), BrettPhos (14 mg, 0.026 mmol) and Cs$_2$CO$_3$ (258 mg, 0.793 mmol) in anhydrous dioxane (3 mL) was degassed and purged with N$_2$ for 3 times. The resulting reaction mixture was heated at 100° C. for 16 hour under N$_2$ atmosphere. The reaction mixture turned into yellow suspension from red. Then Pd$_2$(dba)$_3$ (24 mg, 0.026 mmol), BrettPhos (28 mg, 0.052 mmol) and Cs$_2$CO$_3$ (172 mg, 0.529 mmol) were added to the reaction mixture under N$_2$ atmosphere and the resulting reaction mixture was stirred at 100° C. for 48 h. Crude LCMS (Rt=0.719 min; MS Calcd: 521.2, MS Found: 522.0 [M+H]$^+$). To the reaction mixture was added water (25 mL) and extracted with EtOAc/THF (25 mL×2, 1/1). The combined organic layer was washed with brine (25 mL), dried over anhydrous Na$_2$SO$_4$ and concentrated. The residue was purified by prep-HPLC (0.05% NH$_3$.H$_2$O as an additive). Most of MeCN was removed under reduced pressure and the remaining part was lyophilized to give 3-((1-(cyclopropylsulfonyl)-2,3-dihydro-1H-pyrido[2,3-b][1,4]oxazin-7-yl)amino)-N,N,5-trimethyl-5H-chromeno[4,3-c]pyridine-8-carboxamide (18.9 mg, yield: 14%) as a yellow solid.

LCMS was taken on a quadrupole Mass Spectrometer on Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven Tem.: 50° C., Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min. purity is 96.25%, Rt=1.307 min; MS Calcd.: 521.2, MS Found: 522.0 [M+H]$^+$.

$^1$H NMR (400 MHz, DMSO-d$_6$) δ 0.90-1.10 (4H, m), 1.54 (3H, d, J=5.6 Hz), 2.85-3.05 (7H, m), 3.80-3.90 (2H, m), 4.35-4.45 (2H, m), 5.25-5.35 (1H, m), 6.68 (1H, s), 6.96 (1H, s), 7.06 (1H, d, J=7.6 Hz), 7.94 (1H, d, J=7.6 Hz), 8.35-8.40 (2H, m), 8.67 (1H, s), 9.41 (1H, brs).

Example 73: (S)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

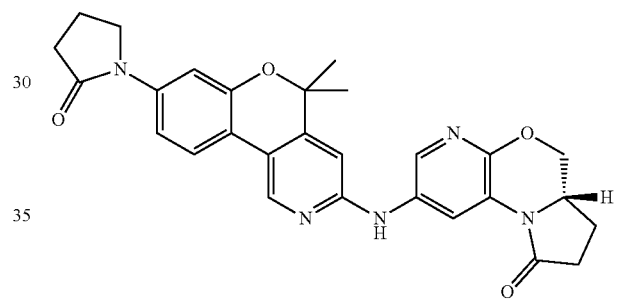

Step 1: Preparation of methyl 5-bromo-2-chloroisonicotinate

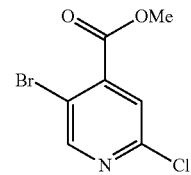 [SMILES: COC(=O)c1cc(Cl)ncc1Br]

To a suspension of 5-bromo-2-chloroisonicotinic acid (5.00 g, 21.2 mmol) in MeOH (50 mL) was added dropwise SOCl$_2$ (8.20 g, 69.0 mmol, 5 mL) at 0° C. The reaction was warmed to about 20° C. and then refluxed (70° C.) for 3 hrs. A slight yellow cloudy was formed. TLC (PE/EtOAc=1:1, by UV) showed 5-bromo-2-chloroisonicotinic acid (Rf~0) was consumed completely and a new spot (Rf~0.5) was formed. After cooling to 20° C., the solvent was concentrated in vacuum. The residue was diluted with EtOAc (200 mL), washed with saturated aqueous NaHCO$_3$ (100 mL×2), brine (100 mL), dried over anhydrous sodium sulfate and filtered. The filtrate was concentrated in vacuum to afford methyl 5-bromo-2-chloroisonicotinate (5.00 g, yield: 94%) as yellow liquid.

¹H NMR (400 MHz, DMSO-d₆) δ 3.92 (s, 3H), 7.90 (s, 1H), 8.79 (s, 1H).

Step 2: Preparation of 1-(4-bromo-3-fluorophenyl)pyrrolidin-2-one

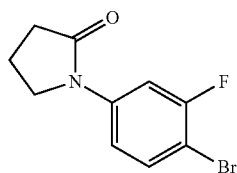 [SMILES: O=C1CCCN1c1ccc(Br)c(F)c1]

1-Bromo-2-fluoro-4-iodobenzene (90.0 g, 299 mmol), CsF (114 g, 748 mmol) and CuI (17.1 g, 89.7 mmol) were taken up in EtOAc (1000 mL) and the resulting mixture was degassed with nitrogen for 10 min. Pyrrolidin-2-one (32.6 g, 383 mmol) and ethane-1,2-diamine (10.8 g, 179 mmol) were added and the resulting mixture was stirred at 50° C. for 18 hrs. A blue suspension was formed. TLC (PE/EtOAc=2:1, by UV) showed 1-bromo-2-fluoro-4-iodobenzene (Rf~0.9) was consumed completely and a main new spot (Rf~0.3) was formed. The suspension was cooling to about 20° C. and then worked up with batch of pyrrolidin-2-one. The combined mixture was filtered and the cake was washed with EtOAc (300 mL×2). The combined filtrate was washed with 0.5 M aq. HCl (1000 mL), 5% NH₄₀H (1000 mL), dried over Na₂SO₄, filtered and concentrated to dryness. The residue was triturated with MTBE/PE (1:1, 200 mL) for 30 min and filtered. The solid was washed with MTBE/PE (1:1, 50 mL) and dried in vacuum to give 1-(4-bromo-3-fluorophenyl)pyrrolidin-2-one (66.0 g, yield: 43%) as an off-white solid.

¹H NMR (400 MHz, CDCl₃) δ 2.14-2.23 (2H, m), 2.63 (2H, t, J=8.0 Hz), 3.83 (2H, t, J=7.2 Hz), 7.25-7.29 (1H, m), 7.47-7.53 (1H, m), 7.65 (1H, dd, J=11.2, 2.8 Hz)

Step 3: Preparation of 1-(3-fluoro-4-(4,4,5,5-tetramethyl-1,3,2-dioxaborolan-2-yl)phenyl)pyrrolidin-2-one

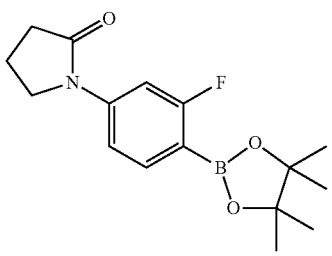 [SMILES: CC1(C)OB(c2ccc(N3CCCC3=O)cc2F)OC1(C)C]

To a mixture of 1-(4-bromo-3-fluorophenyl)pyrrolidin-2-one (10.0 g, 38.8 mmol), B₂Pin₂ (14.8 g, 58.1 mmol) and KOAc (11.4 g, 116 mmol) in toluene (200 mL) was added Pd(dppf)Cl₂ (2.84 g, 3.87 mmol) under N₂ and then the mixture was stirred at 100° C. for 40 hrs under N₂ atmosphere. The red solution turned to black. LCMS showed about 11% of 1-(4-bromo-3-fluorophenyl)pyrrolidin-2-one (Rt=0.650 min; MS Calcd: 257.0. MS Found: 257.9 [M+H]⁺) was remained and desired product (50% purity; Rt=0.698 min; MS Calcd: 305.2; MS Found: 305.7 [M+H]⁺) was detected. The mixture was stirred at 100° C. for another 16 hrs. LCMS showed about 3.99% of 1-(4-bromo-3-fluorophenyl)pyrrolidin-2-one (Rt=0.654 min; MS Calcd: 257.0. MS Found: 257.8 [M+H]⁺) was remained and desired product (47% purity; Rt=0.702 min; MS Calcd: 305.2. MS Found: 305.9 [M+H]⁺) was detected. The mixture was stirred at 100° C. for another 16 hrs. LCMS showed 1-(4-bromo-3-fluorophenyl)pyrrolidin-2-one was consumed completely and desired product (48% purity; Rt=0.772 min; MS Calcd: 305.2. MS Found: 223.9 [M-2,3-dimethylbutane]+) was detected. The reaction mixture was cooled to 20° C. and filtered through silica gel and washed with MTBE (800 mL). The solvent was evaporated under reduced pressure to afford the product 1-(3-fluoro-4-(4,4,5,5-tetramethyl-1,3,2-dioxaborolan-2-yl)phenyl)pyrrolidin-2-one (12.0 g, crude) as a black brown solid.

Step 4: Preparation of methyl 2-chloro-5-(2-fluoro-4-(2-oxopyrrolidin-1-yl)phenyl)isonicotinate

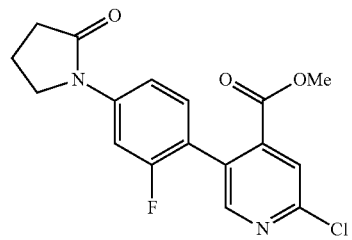 [SMILES: COC(=O)c1cc(Cl)ncc1-c1ccc(N2CCCC2=O)cc1F]

To a suspension of methyl 5-bromo-2-chloroisonicotinate (1.00 g, 3.99 mmol), 1-(3-fluoro-4-(4,4,5,5-tetramethyl-1,3,2-dioxaborolan-2-yl)phenyl)pyrrolidin-2-one (1.58 g, 5.19 mmol, crude) and Pd(dppf)Cl₂ (292 mg, 0.399 mmol) in dioxane (20 mL) was added K₃PO₄ (2.54 g, 12.0 mmol) under N₂ atmosphere and then the resulting mixture was stirred at about 80° C. for 16 hrs. A black solution was formed. LCMS showed methyl 5-bromo-2-chloroisonicotinate was consumed completely and desired MS (Rt=0.818 min; MS Calcd: 348.1. MS Found: 348.9 [M+H]⁺) was detected. TLC (PE/EtOAc=1:1, by UV) showed methyl 5-bromo-2-chloroisonicotinate (Rf~0.8) was consumed completely and a new spot (Rf~0.4) was formed. The mixture was poured into water (50 mL) and extracted with EtOAc (50 mL×4). The combined organic layer was washed with brine (100 mL), dried over Na₂SO₄ and concentrated to dryness. The residue was purified by combi flash (EtOAc in pentane from 0% to 50%) to give methyl 2-chloro-5-(2-fluoro-4-(2-oxopyrrolidin-1-yl)phenyl)isonicotinate (560 mg, yield: 40%) as an off-white solid.

¹H NMR (400 MHz, CDCl₃) δ 2.23 (2H, tt, J=8.0, 6.8 Hz), 2.68 (2H, t, J=8.0 Hz), 3.82 (3H, s), 3.92 (2H, t, J=6.8 Hz), 7.33 (1H, t, J=8.4 Hz), 7.49 (1H, dd, J=8.4, 2.0 Hz), 7.72 (1H, dd, J=12.8, 2.0 Hz), 7.83 (1H, s), 8.44 (1H, s).

Step 5: Preparation of 1-(4-(6-chloro-4-(2-hydroxypropan-2-yl)pyridin-3-yl)-3-fluorophenyl)pyrrolidin-2-one

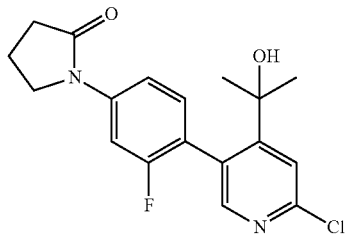 [SMILES: CC(C)(O)c1cc(Cl)ncc1-c1ccc(N2CCCC2=O)cc1F]

To a solution of methyl 2-chloro-5-(2-fluoro-4-(2-oxopyrrolidin-1-yl)phenyl)isonicotinate (550 mg, 1.58 mmol) in THF (10 mL) at −78° C. was added MeMgBr (3 M in THF, 1.16 mL). After the addition, the reaction mixture was allowed to warm to 20° C. and stirred at 20° C. for 1 hr. LCMS (ES7139-20-p1a) showed about 22% methyl 2-chloro-5-(2-fluoro-4-(2-oxopyrrolidin-1-yl)phenyl)isonicotinate (Rt=0.676 min, min; MS Calcd: 348.1; MS Found: 348.8 [M+H]⁺) was remained and desired product (43% purity; Rt=0.627 min; MS Calcd: 348.1. MS Found: 348.8 [M+H]⁺) was detected. TLC (PE/EtOAc=1:1, by UV) showed about 10% of methyl 2-chloro-5-(2-fluoro-4-(2-oxopyrrolidin-1-yl)phenyl)isonicotinate (Rf~0.4) was remained and a new spot (Rf~0.3) was formed. The mixture was poured into sat.aq.NH₄Cl (20 mL) and extracted with EtOAc (20 mL×3). The combined organic layer was washed with brine (40 mL), dried over Na₂SO₄ and concentrated to dryness. The residue was purified by combi flash (EtOAc in pentane from 10% to 50%) to give 1-(4-(6-chloro-4-(2-hydroxypropan-2-yl)pyridin-3-yl)-3-fluorophenyl)pyrrolidin-2-one (150 mg, yield: 27%) as a yellow solid.

¹H NMR (400 MHz, CDCl₃) δ 1.44 (3H, s), 1.47 (3H, s), 1.71 (1H, s), 2.15-2.35 (2H, m), 2.69 (2H, t, J=8.0 Hz), 3.92 (2H, t, J=7.2 Hz), 7.22 (1H, J=8.4 Hz), 7.47 (1H, dd, J=8.4 Hz, 2.0 Hz), 7.66 (1H, dd, J=11.6 Hz, 2.0 Hz), 7.70 (1H, s), 8.07 (1H, s).

Step 6: Preparation of 1-(3-chloro-5,5-dimethyl-5H-chromeno[4,3-c]pyridin-8-yl)pyrrolidin-2-one

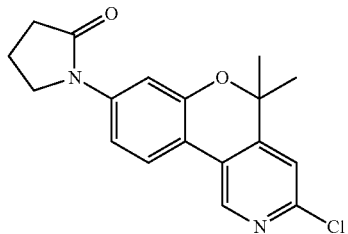 [SMILES: CC1(C)Oc2cc(N3CCCC3=O)ccc2-c2cnc(Cl)cc21]

To a solution of 1-(4-(6-chloro-4-(2-hydroxypropan-2-yl)pyridin-3-yl)-3-fluorophenyl)pyrrolidin-2-one (100 mg, 0.287 mmol) in THF (3 mL) was added NaH (24 mg, 0.59 mmol, 60% in mineral oil) at about 25° C. and then the mixture was stirred at 25° C. for 2 h. A yellow suspension was formed. TLC (PE/EtOAc=1:1, by UV) showed 1-(4-(6-chloro-4-(2-hydroxypropan-2-yl)pyridin-3-yl)-3-fluorophenyl)pyrrolidin-2-one was consumed completely and a new spot was formed. Sat.aq.NH₄Cl (10 mL) was added and the mixture extracted with EtOAc (10 mL×3). The combined organics were washed with brine (20 mL), dried over Na₂SO₄, filtered, concentrated to dryness. The residue was purified on a silica gel column eluted with 0-100% EtOAc in pentane to give 1-(3-chloro-5,5-dimethyl-5H-chromeno[4,3-c]pyridin-8-yl)pyrrolidin-2-one (110 mg, yield: 78%) as a light yellow solid.

¹H NMR (400 MHz, CDCl₃) δ 1.64 (6H, s), 2.15-2.30 (2H, m), 2.66 (2H, t, J=8.0 Hz), 3.90 (2H, t, J=7.2 Hz), 7.17 (1H, s), 7.32 (1H, d, J=2.4 Hz), 7.46 (1H, dd, J=8.4 Hz, 2.0 Hz), 7.75 (1H, d, J=8.8 Hz), 8.70 (1H, s).

Step 7: Preparation of (S)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

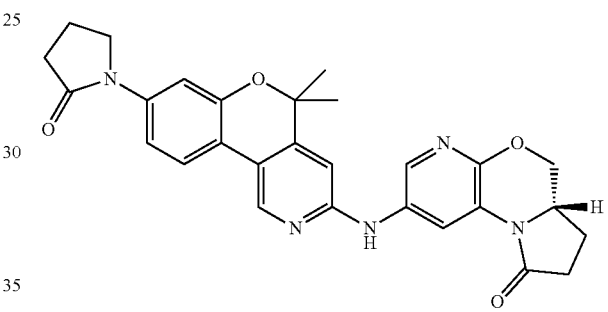

To a suspension of 1-(3-chloro-5,5-dimethyl-5H-chromeno[4,3-c]pyridin-8-yl)pyrrolidin-2-one (50 mg, 0.15 mmol), (S)-2-amino-6,6a,7,8-tetrahydro-9H-pyrido[2,3-b]pyrrolo[1,2-d][1,4]oxazin-9-one (47 mg, 0.23 mmol) and Cs₂CO₃ (149 mg, 0.456 mmol) in dioxane (1 mL) was added Pd₂(dba)₃ (14 mg, 0.015 mmol), BrettPhos (16 mg, 0.030 mmol) under N₂ and then the mixture was stirred at 100° C. for 16 hrs. A brown suspension was formed. LCMS showed 1-(3-chloro-5,5-dimethyl-5H-chromeno[4,3-c]pyridin-8-yl)pyrrolidin-2-one was consumed completely and 62% of desired product (Rt=0.585 min, MS Calcd: 497.2. MS Found: 498.1 [M+H]⁺) was detected. The mixture was diluted with DCM/MeOH (10:1, 10 mL) and filtered. The cake was washed with DCM/MeOH (10:1, 5 mL). The filtrate was concentrated to dryness. The residue was purified by prep-HPLC (0.225% FA as an additive) to give (S)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (42 mg, yield: 54%; 0.514 FA salt) as an off-white solid.

¹H NMR (400 MHz, DMSO-d₆) δ 1.55 (6H, d, J=2.4 Hz), 1.64-1.75 (1H, m), 2.00-2.10 (2H, m), 2.17-2.27 (1H, m), 2.33-2.35 (2H, m), 2.59-2.65 (1H, m), 2.67-2.73 (1H, m), 3.81-3.94 (3H, m), 4.03-4.11 (1H, m), 4.58 (1H, dd, J=10.8 Hz, 3.2 Hz), 6.74 (1H, s), 7.29 (1H, dd, J=8.4 Hz, 2.0 Hz), 7.39 (1H, d, J=2.0 Hz), 7.88 (1H, d, J=8.8 Hz), 8.16 (0.5H, s), 8.38 (1H, d, J=2.4 Hz), 8.62 (1H, s), 8.97 (1H, d, J=2.4 Hz), 9.29 (1H, s).

Example 74: 1-(3-((1-(cyclopropylsulfonyl)-2,3-dihydro-1H-pyrido[2,3-b][1,4]oxazin-7-yl)amino)-5H-chromeno[4,3-c]pyridin-8-yl)pyrrolidin-2-one

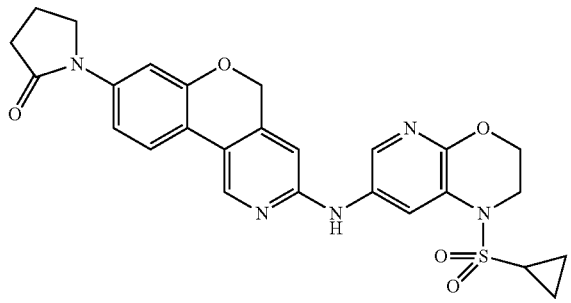 [SMILES: O=C1CCCN1c1ccc2c(c1)OCc1cc(Nc3cnc4c(c3)N(S(=O)(=O)C3CC3)CCO4)ncc1-2]

Step 1: Preparation of (5-bromo-2-chloropyridin-4-yl)methanol

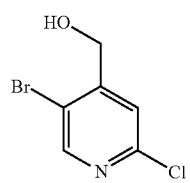

To a solution of methyl methyl 5-bromo-2-chloroisonicotinate (13.0 g, 51.9 mmol) in THF (100 mL) was added NaBH₄ (7.85 g, 208 mmol) and LiCl (8.80 g, 208 mmol) at 0° C. The reaction was warmed to about 25° C. and stirred for 64 hrs. A white suspension was formed. TLC (PE/EtOAc=1:1, by UV) showed methyl 5-bromo-2-chloroisonicotinate was consumed completely and a new spot was formed. The mixture was poured into water (300 mL) and extracted with EtOAc (200 mL×3). The combined organic layer was washed with brine (300 mL×2), dried over Na₂SO₄ and concentrated to dryness to give (5-bromo-2-chloropyridin-4-yl)methanol (10.7 g, 92% yield) as a white solid.

¹H NMR (400 MHz, CDCl₃) δ 2.07 (1H, brs), 4.77 (2H, d, J=4.8 Hz), 7.60 (1H, s), 8.44 (1H, s).

Step 2: Preparation of 1-(4-(6-chloro-4-(hydroxymethyl)pyridin-3-yl)-3-fluorophenyl)pyrrolidin-2-one

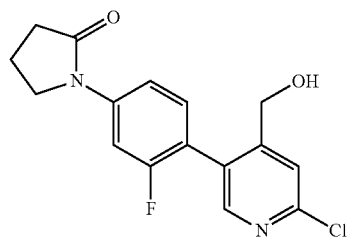 [SMILES: O=C1CCCN1c1ccc(-c2cnc(Cl)cc2CO)c(F)c1]

A mixture of (5-bromo-2-chloropyridin-4-yl)methanol (9.70 g, 43.6 mmol) and 1-(3-fluoro-4-(4,4,5,5-tetramethyl-1,3,2-dioxaborolan-2-yl)phenyl)pyrrolidin-2-one (19.14 g, 45.8 mmol), Pd(dppf)Cl₂·CH₂Cl₂ (3.56 g, 4.36 mmol) and Na₂CO₃ (13.9 g, 131 mmol) in dioxane (150 mL)/H₂O (30 mL) was degassed and purged with N₂ for 3 times. Then the resulting reaction mixture was heated at 90° C. for 16 hrs. A black suspension was formed. TLC (EtOAc/PE=1:1, by UV) showed (5-bromo-2-chloropyridin-4-yl)methanol was consumed completely and one major new spot with larger polarity was detected. The mixture was combined with last batch and the combined mixture was poured into water (300 mL) and extracted with EtOAc (300 mL×3). The organic layer was washed with brine (100 mL), dried over Na₂SO₄ and concentrated to dryness. The residue was purified by Combi Flash (eluenting with EtOAc in pentane from 0% to 100%) to give 1-(4-(6-chloro-4-(hydroxymethyl)pyridin-3-yl)-3-fluorophenyl)pyrrolidin-2-one (4.5 g, 29%) as a gray solid.

¹H NMR (400 MHz, CDCl₃) δ 1.87 (1H, t, J=6.0 Hz), 2.17-2.28 (2H, m), 2.63-2.70 (2H, m), 3.85-3.95 (2H, m), 4.60 (2H, d, J=6.0 Hz), 7.23 (1H, t, J=8.4 Hz), 7.41-7.48 (1H, m), 7.66-7.74 (2H, m) 8.21 (1H, s)

Step 3: Preparation of 1-(3-chloro-5H-chromeno[4,3-c]pyridin-8-yl)pyrrolidin-2-one

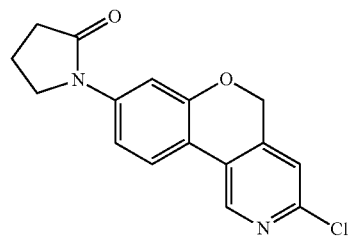 [SMILES: O=C1CCCN1c1ccc2c(c1)OCc1cc(Cl)ncc1-2]

To a solution of 1-(4-(6-chloro-4-(hydroxymethyl)pyridin-3-yl)-3-fluorophenyl)pyrrolidin-2-one (4.50 g, 14.0 mmol) in THF (100 mL) was added NaH (1.68 g, 42.1 mmol, 60% in mineral oil) at about 25° C. and then the mixture was stirred at 25° C. for 2 hrs. A yellow suspension was formed. TLC (PE/EtOAc=1:1, by UV) showed 1-(4-(6-chloro-4-(hydroxymethyl)pyridin-3-yl)-3-fluorophenyl)pyrrolidin-2-one was consumed completely and a new spot was formed. Sat. aq. NH₄Cl (200 mL) was added and the mixture was extracted with EtOAc (200 mL×3). The combined organics were washed with brine (300 mL), dried over Na₂SO₄, filtered, concentrated to dryness. The residue was purified on a silica gel column eluted with 0-10% MeOH in DCM to give 1-(3-chloro-5H-chromeno[4,3-c]pyridin-8-yl)pyrrolidin-2-one (2.3 g, 55% yield) as a gray solid.

¹H NMR (400 MHz, CDCl₃) δ 2.15-2.26 (2H, m), 2.21 (2H, t, J=8.0 Hz), 3.90 (2H, t, J=7.2 Hz), 5.11 (2H, s), 7.15 (1H, s), 7.35-7.39 (1H, m), 7.45 (1H, dd, J=8.8, 2.4 Hz), 7.75 (1H, d, J=8.4 Hz), 8.68 (s, 1H).

127

Step 4: Preparation of 1-(3-((1-(cyclopropylsulfonyl)-2,3-dihydro-1H-pyrido[2,3-b][1,4]oxazin-7-yl)amino)-5H-chromeno[4,3-c]pyridin-8-yl)pyrrolidin-2-one

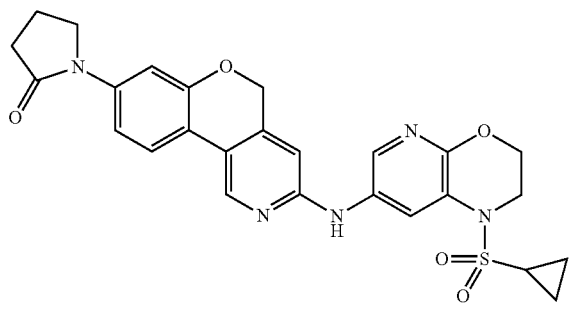 [SMILES: O=C1CCCN1c1ccc2c(c1)OCc1cc(Nc3cnc4c(c3)N(S(=O)(=O)C3CC3)CCO4)ncc1-2]

To a suspension of 1-(3-chloro-5H-chromeno[4,3-c]pyridin-8-yl)pyrrolidin-2-one (80 mg, 0.28 mmol), 1-(cyclopropylsulfonyl)-2,3-dihydro-1H-pyrido[2,3-b][1,4]oxazin-7-amine (109 mg, 0.341 mmol) and $Cs_2CO_3$ (278 mg, 0.853 mmol) in dioxane (5 mL) was added $Pd_2(dba)_3$ (26 mg, 28 µmol) and BrettPhos (31 mg, 57 µmol) under $N_2$. Then the mixture was stirred at 100° C. for 16 hrs. A brown suspension was formed. LCMS showed 1-(3-chloro-5H-chromeno[4,3-c]pyridin-8-yl)pyrrolidin-2-one was consumed completely and desired product (36% purity; Rt=0.727 min; MS Calcd: 519.2. MS Found: 519.9 [M+H]$^+$) was detected. TLC (DCM/MeOH=10:1, by UV) showed 1-(3-chloro-5H-chromeno[4,3-c]pyridin-8-yl)pyrrolidin-2-one was consumed completely and a new spot was formed. The mixture was diluted with DCM/MeOH (10:1, 30 mL) and filtered. The cake was washed with DCM/MeOH (10:1, 10 mL). The filtrate was concentrated to dryness. The residue was purified by Combi Flash (MeOH in DCM from 0% to 10%) to give crude product, which was triturated with MeCN (7 mL) at 25° C. for 2 hrs. The mixture was filtered and the cake was washed with MeCN (2 mL). The solid was triturated with DMSO/$H_2O$ (2 mL/5 mL) at 20° C. for 1 h and filtered. The cake was washed with MeCN (2 mL) and dried in reduced pressure to give 1-(3-((1-(cyclopropylsulfonyl)-2,3-dihydro-1H-pyrido[2,3-b][1,4]oxazin-7-yl)amino)-5H-chromeno[4,3-c]pyridin-8-yl)pyrrolidin-2-one (45.8 mg, 30% yield) as a yellow solid.

$^1$H NMR (400 MHz, DMSO-$d_6$) δ 1.03-1.12 (4H, m), 2.02-2.15 (2H, m), 2.55 (2H, overlap with DMSO), 2.87-2.95 (1H, m), 3.81-3.88 (4H, m), 4.41 (2H, t, J=4.4 Hz), 5.09 (2H, s), 6.85 (1H, s), 7.30-7.40 (2H, m), 7.87 (1H, d, J=8.4 Hz), 8.37 (1H, d, J=2.0 Hz), 8.41 (1H, d, J=2.0 Hz), 8.59 (1H, s), 9.31 (1H, brs).

128

Example 75: (S)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

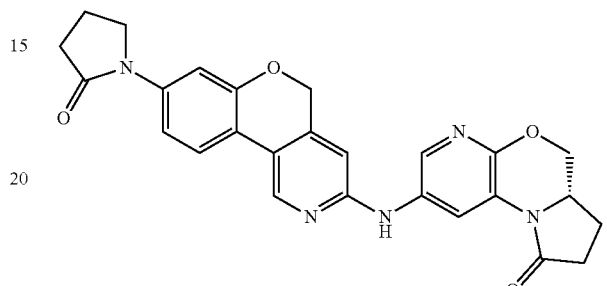

To a suspension of 1-(3-chloro-5H-chromeno[4,3-c]pyridin-8-yl)pyrrolidin-2-one (80 mg, 0.27 mmol), (S)-2-amino-6,6a,7,8-tetrahydro-9H-pyrido[2,3-b]pyrrolo[1,2-d][1,4]oxazin-9-one (66 mg, 0.32 mmol) and $Cs_2CO_3$ (260 mg, 0.796 mmol) in dioxane (5 mL) was added $Pd_2(dba)_3$ (24 mg, 0.027 mmol), BrettPhos (29 mg, 0.053 mmol) under $N_2$. Then the mixture was stirred at 100° C. for 16 hrs. A brown suspension was formed. LCMS showed 1-(3-chloro-5H-chromeno[4,3-c]pyridin-8-yl)pyrrolidin-2-one was consumed completely and desired product (Rt=0.676 min; MS Calcd: 469.2. MS Found: 470.0 [M+H]$^+$) was detected. The mixture was diluted with DCM/MeOH (10:1, 10 mL) and filtered. The cake was washed with DCM/MeOH (10:1, 5 mL). The filtrate was concentrated to dryness. The residue was triturated with DMSO/MECN/MeOH (1:1:1, 5 mL) and filtered. The cake was washed with MECN (2 mL) and the solid was triturated with MECN (2 mL) for 16 hrs at 25° C. The mixture was filtered and the cake was washed with MECN (1 mL) and dried in reduced pressure to give (S)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (31 mg, 24% yield) as an off-white solid.

$^1$H NMR (400 MHz, DMSO-$d_6$) δ 1.65-1.75 (1H, m), 2.00-2.11 (2H, m), 2.17-2.28 (1H, m), 2.35-2.48 (2H, m), 2.55 (2H, overlap with DMSO), 2.62-2.67 (1H, m), 3.80-3.94 (3H, m), 4.03-4.13 (1H, m), 4.58 (1H, dd, J=10.8 Hz, 3.2 Hz), 5.09 (2H, s), 6.65 (1H, s), 7.33 (1H, dd, J=8.8 Hz, 2.4 Hz), 7.37 (1H, d, J=2.4 Hz), 7.86 (1H, d, J=8.4 Hz), 8.41 (1H, d, J=2.8 Hz), 8.59 (1H, s), 8.96 (1H, d, J=2.4 Hz), 9.29 (1H, brs).

Example 76: 1-(3-((1-(cyclopropanecarbonyl)-2,3-dihydro-1H-pyrido[2,3-b][1,4]oxazin-7-yl)amino)-5H-chromeno[4,3-c]pyridin-8-yl)pyrrolidin-2-one

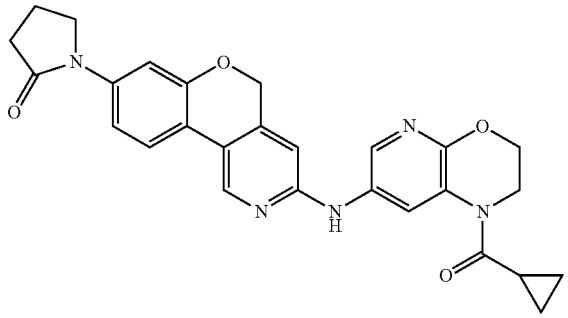 [SMILES: O=C1CCCN1c1ccc2c(c1)OCc1cc(Nc3cnc4c(c3)N(C(=O)C3CC3)CCO4)ncc1-2]

To a suspension of 1-(3-amino-5H-chromeno[4,3-c]pyridin-8-yl)pyrrolidin-2-one (80 mg, 0.28 mmol), (7-bromo-2,3-dihydro-1H-pyrido[2,3-b][1,4]oxazin-1-yl)(cyclopropyl)methanone (97 mg, 0.34 mmol) and $Cs_2CO_3$ (278 mg, 0.853 mmol) in dioxane (5 mL) was added $Pd_2(dba)_3$ (26 mg, 0.028 mmol), BrettPhos (31 mg, 0.057 mmol) under $N_2$. Then the mixture was stirred at 100° C. for 16 hrs. A brown suspension was formed. LCMS showed -(3-amino-5H-chromeno[4,3-c]pyridin-8-yl)pyrrolidin-2-one was consumed completely and desired product (Rt=0.707 min; MS Calcd: 469.2. MS Found: 484.0 [M+H]$^+$) was detected. The mixture was diluted with DCM/MeOH (10:1, 10 mL) and filtered. The cake was washed with DCM/MeOH (10:1, 5 mL). The filtrate was concentrated to dryness. The residue was triturated with DMSO/MECN (1:1, 5 mL) and filtered. The cake was washed with MECN (2 mL) and the solid was triturated with MECN (2 mL) for 16 h at 25° C. The mixture was filtered and the cake was washed with MECN (1 mL). The cake was triturated with MECN (3 mL) at 25° C. for 16 hrs. The mixture was filtered and the cake was washed with MECN (1 mL). The cake was lyophilized for 18 hrs to give 1-(3-((1-(cyclopropanecarbonyl)-2,3-dihydro-1H-pyrido[2,3-b][1,4]oxazin-7-yl)amino)-5H-chromeno[4,3-c]pyridin-8-yl)pyrrolidin-2-one (31.6 mg, 23% yield) as a yellow solid.

$^1$H NMR (400 MHz, DMSO-d$_6$) δ 0.90-1.04 (4H, m), 2.01-2.11 (2H, m), 2.17-2.26 (1H, m), 2.55 (2H, overlap with DMSO), 3.84 (2H, t, J=7.2 Hz), 3.94-4.03 (2H, m), 4.37 (2H, t, J=4.0 Hz), 5.08 (2H, s), 6.64 (1H, s), 7.30-7.40 (2H, m), 7.86 (1H, d, J=8.4 Hz), 8.20 (1H, s), 8.56 (1H, s), 8.62 (1H, d, J=2.0 Hz), 9.27 (1H, s).

Example 77: methyl 7-((8-(2-oxopyrrolidin-1-yl)-5H-chromeno[4,3-c]pyridin-3-yl)amino)-2,3-dihydro-1H-pyrido[2,3-b][1,4]oxazine-1-carboxylate

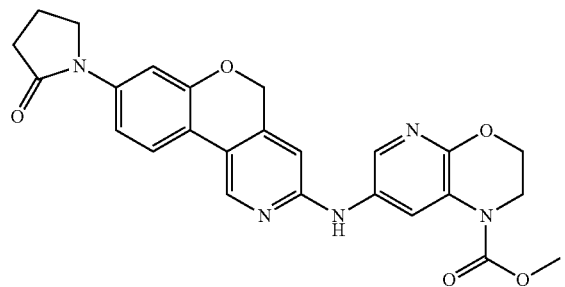 [SMILES: COC(=O)N1CCOc2ncc(Nc3cc4c(cn3)-c3ccc(N5CCCC5=O)cc3OC4)cc21]

To a suspension of 1-(3-amino-5H-chromeno[4,3-c]pyridin-8-yl)pyrrolidin-2-one (80 mg, 0.28 mmol), methyl 7-bromo-2,3-dihydro-1H-pyrido[2,3-b][1,4]oxazine-1-carboxylate (93 mg, 0.34 mmol) and $Cs_2CO_3$ (278 mg, 0.853 mmol) in dioxane (5 mL) was added $Pd_2(dba)_3$ (26 mg, 0.028 mmol), BrettPhos (31 mg, 0.057 mmol) under $N_2$. Then the mixture was stirred at 100° C. for 16 hrs. A brown suspension was formed. LCMS showed 1-(3-amino-5H-chromeno[4,3-c]pyridin-8-yl)pyrrolidin-2-one was consumed completely and desired product (Rt=0.696 min; MS Calcd: 473.2. MS Found: 474.0 [M+H]$^+$) was detected. The mixture was diluted with DCM/MeOH (10:1, 10 mL) and filtered. The cake was washed with DCM/MeOH (10:1, 5 mL). The filtrate was concentrated to dryness. The residue was triturated with DMSO/MECN (1:1, 5 mL) and filtered. The cake was washed with MECN (2 mL) and the solid was triturated with MECN (2 mL) for 16 h at 25° C. The mixture was filtered and the cake was washed with MECN (1 mL) and dried in reduced pressure to give methyl 7-((8-(2-oxopyrrolidin-1-yl)-5H-chromeno[4,3-c]pyridin-3-yl)amino)-2,3-dihydro-1H-pyrido[2,3-b][1,4]oxazine-1-carboxylate (32.6 mg, 24% yield) as a yellow solid.

$^1$H NMR (400 MHz, DMSO-d$_6$) δ 2.01-2.11 (2H, m), 2.55 (2H, overlap with DMSO), 3.79 (3H, s), 3.81-3.89 (4H, m), 4.32 (2H, t, J=4.4 Hz), 5.09 (2H, s), 6.65 (1H, s), 7.33 (1H, dd, J=8.8 Hz, 2.4 Hz), 7.37 (1H, d, J=2.4 Hz), 7.86 (1H, d, J=8.8 Hz), 8.26 (1H, d, J=2.4 Hz), 8.60 (1H, s), 8.64-8.69 (1H, m), 9.22 (1H, brs).

Example 78: 1-(3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one

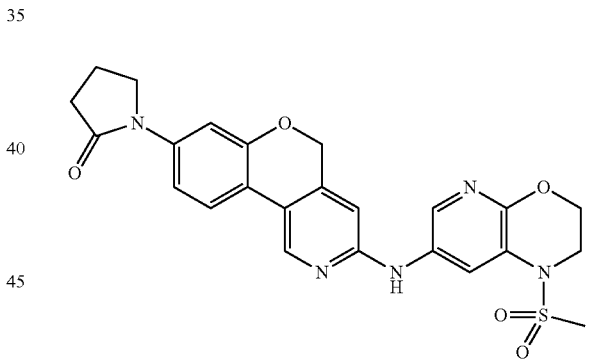

To a suspension of 1-(3-amino-5H-chromeno[4,3-c]pyridin-8-yl)pyrrolidin-2-one (80 mg, 0.28 mmol), 7-bromo-1-(methylsulfonyl)-2,3-dihydro-1H-pyrido[2,3-b][1,4]oxazine (100 mg, 0.341 mmol) and $Cs_2CO_3$ (278 mg, 0.853 mmol) in dioxane (5 mL) was added $Pd_2(dba)_3$ (26 mg, 0.028 mmol), BrettPhos (31 mg, 0.057 mmol) under $N_2$. Then the mixture was stirred at 100° C. for 16 hrs. A brown suspension was formed. LCMS showed 1-(3-amino-5H-chromeno[4,3-c]pyridin-8-yl)pyrrolidin-2-one was consumed completely and desired product (Rt=0.693 min; MS Calcd: 493.1. MS Found: 494.0 [M+H]$^+$) was detected. The mixture was diluted with DCM/MeOH (10:1, 10 mL) and filtered. The cake was washed with DCM/MeOH (10:1, 5 mL). The filtrate was concentrated to dryness. The residue purified by prep-HPLC (column: DuraShell 150*25 mm*5 um; mobile phase: [water (0.05% ammonia hydroxide v/v)-MECN]; B %: 30%-50%,10 min) and lyophilized to give 1-(3-((1-(methylsulfonyl)-2,3-dihydro-1H-pyrido[2,3-b][1, 4]oxazin-7-yl)amino)-5H-chromeno[4,3-c]pyridin-8-yl)pyrrolidin-2-one (46.6 mg, 32% yield) as a yellow solid.

$^1$H NMR (400 MHz, DMSO-$d_6$) δ 2.00-2.10 (2H, m), 2.55 (2H, overlap with DMSO), 3.22 (3H, s), 3.81-3.89 (4H, m), 4.34-4.39 (2H, m), 5.09 (2H, s), 6.65 (1H, s), 7.33 (1H, dd, J=8.4 Hz, 2.0 Hz), 7.37 (1H, d, J=2.0 Hz), 7.86 (1H, d, J=8.8 Hz), 8.36 (2H, s), 8.59 (1H, s), 9.29 (1H, brs).

Example 79: 1-(3-((1-(isopropylsulfonyl)-2,3-dihydro-1H-pyrido[2,3-b][1,4]oxazin-7-yl)amino)-5H-chromeno[4,3-c]pyridin-8-yl)pyrrolidin-2-one

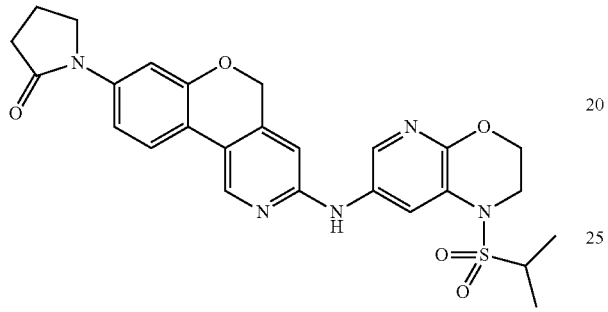

To a suspension of 1-(3-amino-5H-chromeno[4,3-c]pyridin-8-yl)pyrrolidin-2-one (80 mg, 0.28 mmol), 7-bromo-1-(isopropylsulfonyl)-2,3-dihydro-1H-pyrido[2,3-b][1,4]oxazine (109 mg, 0.341 mmol) and Cs$_2$CO$_3$ (278 mg, 0.853 mmol) in dioxane (5 mL) was added Pd$_2$(dba)$_3$ (26 mg, 0.028 mmol), BrettPhos (31 mg, 0.057 mmol) under N$_2$. Then the mixture was stirred at 100° C. for 16 hrs. A brown suspension was formed. LCMS showed 1-(3-amino-5H-chromeno[4,3-c]pyridin-8-yl)pyrrolidin-2-one was consumed completely and desired product (Rt=0.731 min; MS Calcd: 521.2. MS Found: 521.9 [M+H]$^+$) was detected. TLC (DCM/MeOH=10:1, by UV) showed 1-(3-amino-5H-chromeno[4,3-c]pyridin-8-yl)pyrrolidin-2-one was consumed completely and a new spot was formed. The mixture was diluted with DCM/MeOH (10:1, 10 mL) and filtered. The cake was washed with DCM/MeOH (10:1, 5 mL). The filtrate was concentrated to dryness. The residue was purified by Combi Flash (MeOH in DCM from 0% to 10%) to give crude product, which was purified by prep-HPLC (column: DuraShell 150*25 mm*5 um; mobile phase: [water (0.05% ammonia hydroxide v/v)-MECN]; B %: 25%-45%, 10 min) and lyophilized to give 1-(3-((1-(isopropylsulfonyl)-2,3-dihydro-1H-pyrido[2,3-b][1,4]oxazin-7-yl)amino)-5H-chromeno[4,3-c]pyridin-8-yl)pyrrolidin-2-one (41 mg, 28% yield) as a yellow solid.

$^1$H NMR (400 MHz, DMSO-$d_6$) δ 1.35 (6H, d, J=6.8 Hz), 2.00-2.13 (2H, m), 2.55 (2H, overlap with DMSO), 3.72-3.80 (1H, m), 3.80-3.89 (4H, m), 4.35 (2H, t, J=4.0 Hz), 5.09 (2H, s), 6.65 (1H, s), 7.33 (1H, dd, J=8.4 Hz, 2.0 Hz), 7.37 (1H, d, J=2.0 Hz), 7.87 (1H, d, J=8.8 Hz), 8.30 (2H, dd, J=10.8 Hz, 2.4 Hz), 8.57 (1H, s), 9.29 (1H, brs).

Example 80: 1-(5-methyl-3-(pyrimidin-5-ylamino)-5H-chromeno[4,3-c]pyridin-8-yl)pyrrolidin-2-one

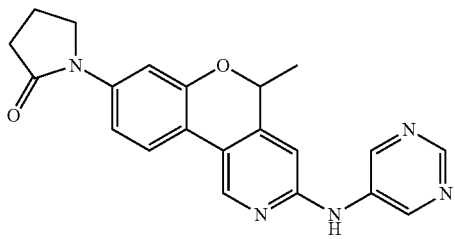 [SMILES: CC1Oc2cc(N3CCCC3=O)ccc2-c2cnc(Nc3cncnc3)cc21]

Step 1: Preparation of 5-bromo-2-chloroisonicotinaldehyde

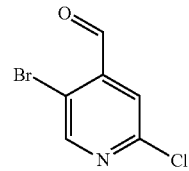

To a solution of LDA (2 M in THF, 296 mL) in THF (500 mL) was added a solution of 5-bromo-2-chloropyridine (95.0 g, 493 mmol) in THF (200 mL) dropwise at −75° C. over a period of 2.5 h under N$_2$. The reaction mixture was stirred at −75° C. for 1 hour. DMF (49 mL, 641 mmol) was then added over a period of 1 hour and the reaction mixture was stirred for 1.5 h. A black solution was formed. TLC showed the starting material was consumed completely. The reaction was quenched by the addition of acetic acid (50 wt % in THF, 100 mL) at −75° C. followed by warming to between −40 and −30° C. over 2 h. The reaction was added H$_2$O (300 mL) slowly and then extracted with EtOAc (500 mL×3). The combined organic phase was dried over anhydrous Na$_2$SO$_4$, filtered and concentrated. The residue was purified by Combi Flash (5% EtOAc in pentane) to give impure product (50 g) as a yellow solid. The solid was washed with PE (50 mL×3) to give 5-bromo-2-chloroisonicotinaldehyde (30.0 g, yield: 28%) as an off-white solid.

$^1$H NMR (400 MHz, DMSO-$d_6$) δ 7.81 (1H, s), 8.85 (1H, s), 10.10 (1H, s).

Step 2: Preparation of 1-(4-bromo-3-fluorophenyl)pyrrolidin-2-one

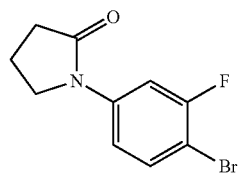 [SMILES: O=C1CCCN1c1ccc(Br)c(F)c1]

1-Bromo-2-fluoro-4-iodobenzene (90.0 g, 299 mmol), CsF (114 g, 748 mmol) and CuI (17.1 g, 89.7 mmol) were taken up in EtOAc (1000 mL) and the resulting mixture was degassed with nitrogen for 10 min. Pyrrolidin-2-one (32.6 g, 383 mmol) and ethane-1,2-diamine (10.8 g, 179 mmol) were added and the resulting mixture was stirred at 50° C. for 18 h. A blue suspension was formed. TLC showed 1-bromo-2-fluoro-4-iodobenzene was consumed completely. The suspension was cooling to about 20° C. and then worked up with last batch reaction. The combined mixture was filtered and the cake was washed with EtOAc (300 mL×2). The combined filtrate was washed with 0.5 M aq. HCl (1000 mL), 5% NH$_{40}$H (1000 mL), dried over Na$_2$SO$_4$, filtered and concentrated to dryness. The residue was triturated with MTBE/PE (1:1, 200 mL) for 30 min and filtered. The solid was washed with MTBE/PE (50 mL) and dried in vacuum to give 1-(4-bromo-3-fluorophenyl)pyrrolidin-2-one (66.0 g, yield: 43%) as an off-white solid.

$^1$H NMR (400 MHz, CDCl$_3$) δ 2.14-2.23 (2H, m), 2.63 (2H, t, J=8.0 Hz), 3.83 (2H, t, J=7.2 Hz), 7.25-7.29 (1H, m), 7.47-7.53 (1H, m), 7.65 (1H, dd, J=11.2 Hz, 2.8 Hz)

Step 3: Preparation of 1-(3-fluoro-4-(4,4,5,5-tetramethyl-1,3,2-dioxaborolan-2-yl)phenyl)pyrrolidin-2-one

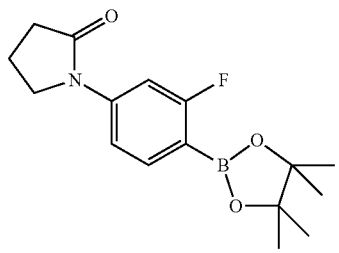 [SMILES: CC1(C)OB(c2ccc(N3CCCC3=O)cc2F)OC1(C)C]

A mixture of 1-(4-bromo-3-fluorophenyl)pyrrolidin-2-one (56.0 g, 217 mmol), B$_2$Pin$_2$ (66.1 g, 260 mmol), KOAc (63.9 g, 650 mmol) and Pd(dppf)Cl$_2$ (7.94 g, 10.8 mmol) in toluene (800 mL) was stirred at 100° C. for 55 h under N$_2$ atmosphere. The red solution turned to black gradually. LCMS (Rt=0.690 min; MS Calcd: 305.2. MS Found: 305.9 [M+H]$^+$). The reaction mixture was cooled to 20° C. and filtered through silica gel and washed with MTBE (1.5 L). The solvent was evaporated under reduced pressure to give 1-(3-fluoro-4-(4,4,5,5-tetramethyl-1,3,2-dioxaborolan-2-yl)phenyl)pyrrolidin-2-one (75.0 g, crude) as a black brown gum.

Step 4: Preparation of 2-chloro-5-(2-fluoro-4-(2-oxopyrrolidin-1-yl)phenyl)isonicotinaldehyde

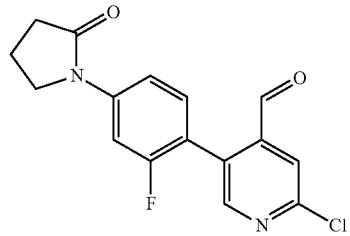 [SMILES: O=Cc1cc(Cl)ncc1-c1ccc(N2CCCC2=O)cc1F]

5-Bromo-2-chloroisonicotinaldehyde (20.0 g, 90.7 mmol), 1-(3-fluoro-4-(4,4,5,5-tetramethyl-1,3,2-dioxaborolan-2-yl)phenyl)pyrrolidin-2-one (33.4 g, crude), Pd(PPh$_3$)$_4$ (3.15 g, 2.72 mmol) and K$_2$CO$_3$ (37.6 g, 272 mmol) were taken up in MeCN (400 mL) and H$_2$O (100 mL) and the resulting mixture was stirred at 70° C. for 2 h. A black solution was formed. LCMS (Rt=0.649 min; MS Calcd: 318.1. MS Found: 318.8 [M+H]$^+$). When cooled to 20° C. the mixture was diluted with half-saturated brine (120 mL) and EtOAc (150 mL). The organic layer was separated, and the aqueous layer was extracted with EtOAc (150 mL×2). The combined organics were dried over Na$_2$SO$_4$, filtered through a plug of silica and concentrated. The residue was combined with last batch, purified by Combi Flash (50% DCM in PE) to give 2-chloro-5-(2-fluoro-4-(2-oxopyrrolidin-1-yl)phenyl)isonicotinaldehyde (47.0 g, crude) as a yellow solid.

Step 5: Preparation of 1-(4-(6-chloro-4-(1-hydroxyethyl)pyridin-3-yl)-3-fluorophenyl)pyrrolidin-2-one

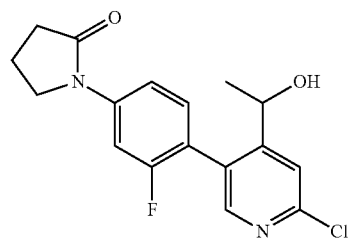 [SMILES: CC(O)c1cc(Cl)ncc1-c1ccc(N2CCCC2=O)cc1F]

MeMgBr (3 M in Et$_2$O, 47 mL) was added slowly to a solution of 2-chloro-5-(2-fluoro-4-(2-oxopyrrolidin-1-yl)phenyl)isonicotinaldehyde (30.0 g, crude) in THF (500 mL) at 0° C. under a nitrogen atmosphere to give a black suspension. The resulting mixture was stirred at 0° C. for 2 h. LCMS (Rt=0.608 min; MS Calcd: 334.1. MS Found: 334.9 [M+H]$^+$). Sat. aq.NH$_4$Cl (200 mL) was added followed by EtOAc (200 mL). The organic layer was separated and the aqueous layer was extracted with EtOAc (180 mL×2). The combined organics were dried over Na$_2$SO$_4$, filtered and concentrated to give 1-(4-(6-chloro-4-(1-hydroxyethyl)pyridin-3-yl)-3-fluorophenyl)pyrrolidin-2-one (31.0 g, crude) as a black brown gum.

Step 6: Preparation of 1-(3-chloro-5-methyl-5H-chromeno[4,3-c]pyridin-8-yl)pyrrolidin-2-one

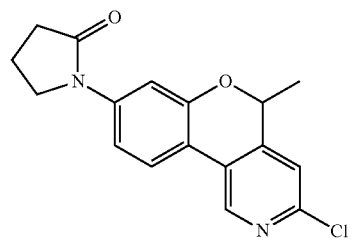 [SMILES: CC1Oc2cc(N3CCCC3=O)ccc2-c2cnc(Cl)cc21]

NaH (4.78 g, 119 mmol, 60% in mineral oil) was added to a solution of 1-(4-(6-chloro-4-(1-hydroxyethyl)pyridin-3-yl)-3-fluorophenyl)pyrrolidin-2-one (20.0 g, crude) in THF (300 mL) at 20° C. and the resulting mixture was stirred at 20° C. for 16 h. A black solution was formed. LCMS (Rt=0.665 min; MS Calcd: 314.1. MS Found: 314.9 [M+H]$^+$). Sat. aq.NH$_4$Cl (80 mL) was added and the mixture extracted with EtOAc (100 mL×3). The combined organic Step 7: Preparation of 1-(5-methyl-3-(pyrimidin-5-ylamino)-5H-chromeno[4,3-c]pyridin-8-yl)pyrrolidin-2-one

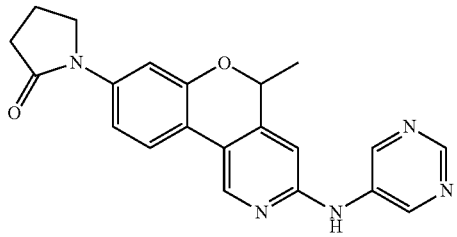 [SMILES: CC1Oc2cc(N3CCCC3=O)ccc2-c2cnc(Nc3cncnc3)cc21]

A mixture of Pd$_2$(dba)$_3$ (7 mg, 0.01 mmol) and BrettPhos (9 mg, 0.02 mmol) in 1,4-dioxane (1 mL) was stirred at 50° C. for 10 min. 1-(3-chloro-5-methyl-5H-chromeno[4,3-c]pyridin-8-yl)pyrrolidin-2-one (50 mg, 0.16 mmol), pyrimidin-5-amine (18 mg, 0.19 mmol) in dioxane (3 mL) and Cs$_2$CO$_3$ (155 mg, 0.476 mmol) were added and the resulting mixture was stirred at 100° C. for 16 h. A black brown mixture was formed. LCMS (Rt=0.605 min; MS Calcd: 373.2. MS Found: 373.9 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(5-methyl-3-(pyrimidin-5-ylamino)-5H-chromeno[4,3-c]pyridin-8-yl)pyrrolidin-2-one (13.8 mg, yield: 23%) as a white solid.

$^1$H NMR (400 MHz, DMSO-d$_6$) δ 1.55 (3H, d, J=6.8 Hz), 2.02-2.09 (2H, m), 2.53 (2H, overlap with DMSO), 3.85 (2H, t, J=7.6 Hz), 5.31 (1H, q, J=6.8 Hz), 6.77 (1H, s), 7.33 (1H, dd, J=8.8, 2.4 Hz), 7.42 (1H, d, J=2.0 Hz), 7.91 (1H, d, J=8.4 Hz), 8.72 (1H, s), 8.73 (1H, s), 9.16 (2H, s), 9.64 (1H, brs).

Example 81: 1-(5-methyl-3-((5-(trifluoromethyl)pyridin-3-yl)amino)-5H-chromeno[4,3-c]pyridin-8-yl)pyrrolidin-2-one

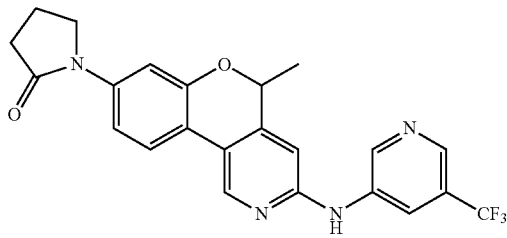 [SMILES: CC1Oc2cc(N3CCCC3=O)ccc2-c2cnc(Nc3cncc(C(F)(F)F)c3)cc21]

A mixture of Pd$_2$(dba)$_3$ (11 mg, 0.012 mmol) and BrettPhos (13 mg, 0.025 mmol) in 1,4-dioxane (1 mL) was stirred at 50° C. for 10 min. 1-(3-chloro-5-methyl-5H-chromeno[4,3-c]pyridin-8-yl)pyrrolidin-2-one (80 mg, 0.25 mmol), 5-(trifluoromethyl)pyridin-3-amine (49 mg, 0.30 mmol) in dioxane (5 mL) and Cs$_2$CO$_3$ (248 mg, 0.762 mmol) were added and the resulting mixture was stirred at 100° C. for 16 h. A black brown mixture was formed. LCMS (Rt=0.702 min; MS Calcd: 440.2. MS Found: 440.9 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(5-methyl-3-((5-(trifluoromethyl)pyridin-3-yl)amino)-5H-chromeno[4,3-c]pyridin-8-yl)pyrrolidin-2-one (25.0 mg, yield: 22%) as a white solid.

$^1$H NMR (400 MHz, DMSO-d$_6$) δ 1.53 (3H, d, J=6.8 Hz), 2.00-2.09 (2H, m), 2.52 (2H, overlap with DMSO), 3.83 (2H, t, J=7.6 Hz), 5.29 (1H, q, J=6.8 Hz), 6.77 (1H, s), 7.30 (1H, dd, J=8.4, 2.0 Hz), 7.39 (1H, d, J=2.0 Hz), 7.91 (1H, d, J=8.4 Hz), 8.42 (1H, s), 8.74 (1H, s), 9.79 (1H, t, J=2.0 Hz), 8.94 (1H, d, J=2.4 Hz), 9.85 (1H, brs).

Example 82: 1-(3-((1-(cyclopropanecarbonyl)-2,3-dihydro-1H-pyrido[2,3-b][1,4]oxazin-7-yl)amino)-5-methyl-5H-chromeno[4,3-c]pyridin-8-yl)pyrrolidin-2-one

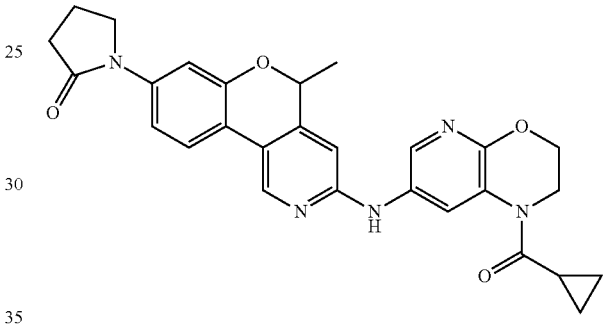

Step 1: Preparation of tert-butyl (5-methyl-8-(2-oxopyrrolidin-1-yl)-5H-chromeno[4,3-c]pyridin-3-yl)carbamate

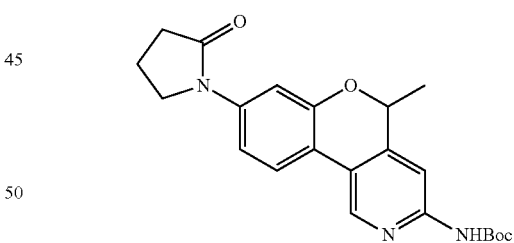

A mixture of Pd$_2$(dba)$_3$ (581 mg, 0.635 mmol) and XantPhos (735 mg, 1.27 mmol) in 1,4-dioxane (1 mL) was stirred at 50° C. for 10 min. 1-(3-Chloro-5-methyl-5H-chromeno[4,3-c]pyridin-8-yl)pyrrolidin-2-one (4.00 g, 12.7 mmol), BocNH$_2$ (1.94 g, 16.5 mmol) in dioxane (80 mL) and Cs$_2$CO$_3$ (10.3 g, 31.7 mmol) were added and the resulting mixture was stirred at 100° C. for 16 h. A black brown mixture was formed. LCMS (Rt=0.680 min; MS Calcd: 395.2. MS Found: 396.1 [M+H]$^+$). The reaction mixture was diluted with DCM (30 mL), filtered and concentrated to give tert-butyl (5-methyl-8-(2-oxopyrrolidin-1-yl)-5H-chromeno[4,3-c]pyridin-3-yl)carbamate (6.00 g, crude) as a black brown gum. Used in the next step without further purification.

Step 2: Preparation of 1-(3-amino-5-methyl-5H-chromeno[4,3-c]pyridin-8-yl)pyrrolidin-2-one

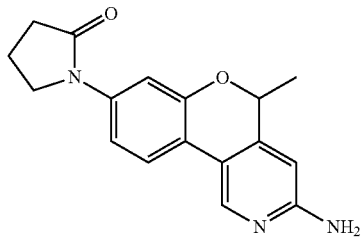 [SMILES: CC1Oc2cc(N3CCCC3=O)ccc2-c2cnc(N)cc21]

To a stirred solution of tert-butyl (5-methyl-8-(2-oxopyrrolidin-1-yl)-5H-chromeno[4,3-c]pyridin-3-yl)carbamate (5.01 g, crude) in DCM (40 mL) was added HCl/EtOAc (4 M, 300 mL) at 20° C. The yellow solution turned to suspension, the reaction mixture was stirred for 20 h. LCMS (Rt=0.522 min; MS Calcd: 295.1. MS Found: 295.8 [M+H]$^+$). The mixture was concentrated. The residue was purified by Combi Flash (1% Et$_3$N in EtOAc) to give 1-(3-amino-5-methyl-5H-chromeno[4,3-c]pyridin-8-yl)pyrrolidin-2-one (2.62 g, yield: 70% for two steps) as a yellow solid.

Step 3: Preparation of (7-bromo-2,3-dihydro-1H-pyrido[2,3-b][1,4]oxazin-1-yl)(cyclopropyl)methanone

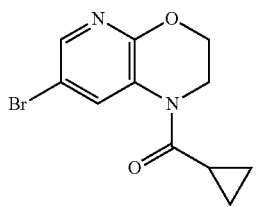 [SMILES: O=C(C1CC1)N1CCOc2ncc(Br)cc21]

In a separate vial, to a solution of cyclopropanecarboxylic acid (240 mg, 2.79 mmol) in DCM (2 mL), DMF (25 mg, 0.35 mmol) was added oxalyl chloride (0.3 mL, 3.5 mmol). The reaction mixture was stirred at 20° C. for 0.5 hour. A light yellow solution was formed. The mixture was concentrated to give crude cyclopropanecarbonyl chloride as a yellow oil.

To a solution of 7-bromo-2,3-dihydro-1H-pyrido[2,3-b][1,4]oxazine in DCM (6 mL) was added Et$_3$N (0.5 mL, 3.5 mmol). The reaction mixture was cooled to 0° C. and then added the resulting crude cyclopropanecarbonyl chloride in DCM (2 mL) dropwise. The reaction mixture was then warmed to 20° C., stirred at 20° C. for 2 h under N$_2$ atmosphere. The colorless solution turned to yellow gradually. LCMS (Rt=0.601 min; MS Calcd: 282.0; MS Found: 282.6 [M+H]$^+$). The reaction mixture was concentrated together with the last batch. The residue was purified by Combi Flash (1% Et$_3$N in DCM) to afford (7-bromo-2,3-dihydro-1H-pyrido[2,3-b][1,4]oxazin-1-yl)(cyclopropyl)methanone (240 mg, yield: 92%) as a yellow gum.

$^1$H NMR (400 MHz, CDCl$_3$) δ 0.95-1.01 (2H, m), 1.17-1.23 (2H, m), 1.89-1.20 (1H, m), 4.02 (2H, t, J=4.8 Hz), 4.46 (2H, t, J=4.8 Hz), 8.06 (1H, d, J=2.4 Hz), 8.20 (1H, brs).

Step 4: Preparation of 1-(3-((1-(cyclopropanecarbonyl)-2,3-dihydro-1H-pyrido[2,3-b][1,4]oxazin-7-yl)amino)-5-methyl-5H-chromeno[4,3-c]pyridin-8-yl)pyrrolidin-2-one

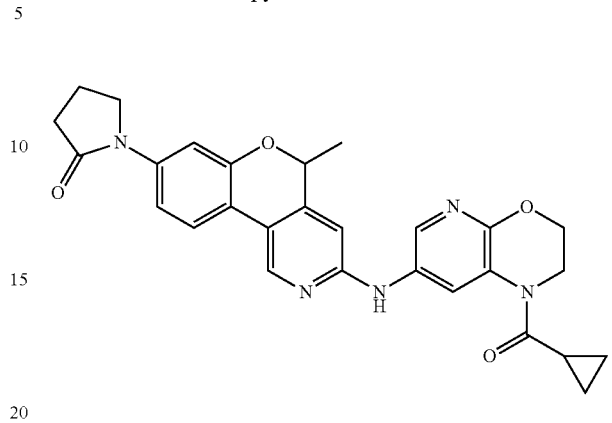

A mixture of Pd$_2$(dba)$_3$ (16 mg, 0.017 mmol) and Brett-Phos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), (7-bromo-2,3-dihydro-1H-pyrido[2,3-b][1,4]oxazin-1-yl)(cyclopropyl)methanone (58 mg, 0.20 mmol) in dioxane (3 mL) and Cs$_2$CO$_3$ (165 mg, 0.508 mmol) were added and the resulting mixture was stirred at 100° C. for 16 h. A black brown mixture was formed. LCMS (Rt=0.598 min; MS Calcd: 497.2; MS Found: 498.0 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(3-((1-(cyclopropanecarbonyl)-2,3-dihydro-1H-pyrido[2,3-b][1,4]oxazin-7-yl)amino)-5-methyl-5H-chromeno[4,3-c]pyridin-8-yl)pyrrolidin-2-one (20.2 mg, yield: 24%) as an off-white solid.

$^1$H NMR (400 MHz, DMSO-d$_6$) δ 0.92-0.99 (4H, m), 1.52 (3H, d, J=6.4 Hz), 2.03-2.09 (2H, m), 2.20-2.33 (1H, m), 2.54 (2H, overlap with DMSO), 3.84 (2H, t, J=6.8 Hz), 3.96-4.00 (2H, m), 4.37 (2H, t, J=4.4 Hz), 5.24 (1H, q, J=6.4 Hz), 6.65 (1H, s), 7.30 (1H, dd, J=8.4, 2.4 Hz), 7.39 (1H, d, J=2.4 Hz), 7.87 (1H, d, J=8.8 Hz), 8.20 (1H, s), 8.57 (1H, s), 8.62 (1H, d, J=2.4 Hz), 9.28 (1H, brs).

Example 83: methyl 7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate

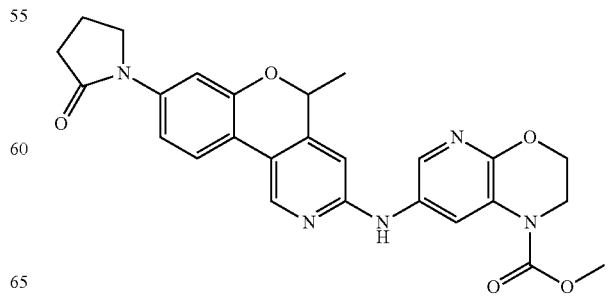

Step 1: Preparation of methyl 7-bromo-2,3-dihydro-1H-pyrido[2,3-b][1,4]oxazine-1-carboxylate

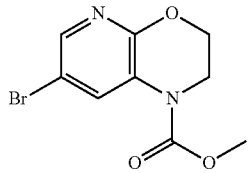

To a solution of 7-bromo-2,3-dihydro-1H-pyrido[2,3-b][1,4]oxazine (1.00 g, 4.65 mmol) in pyridine (15 mL) was added methyl carbonochloridate (659 mg, 6.98 mmol) under nitrogen at 20° C. The resulting mixture was stirred for 16 h. An orange solution was formed. LCMS showed 7-bromo-2,3-dihydro-1H-pyrido[2,3-b][1,4]oxazine was not consumed. Then dropwise added methyl carbonochloridate (659 mg, 6.98 mmol) and DMAP (113 mg, 0.930 mmol). The resulting mixture was stirred for 40 h at 20° C. LCMS showed 7-bromo-2,3-dihydro-1H-pyrido[2,3-b][1,4]oxazine was not consumed still. The resulting mixture was stirred at 50° C. for 20 h. LCMS (Rt=0.602 min; MS Calcd: 274.0. MS Found: 274.8 [M+H]$^+$). The reaction mixture was concentrated. The residue was purified by Combi Flash (45% DCM in PE (1% Et$_3$N as an additive)) to give methyl 7-bromo-2,3-dihydro-1H-pyrido[2,3-b][1,4]oxazine-1-carboxylate (785 mg, yield: 62%) as an off-white solid.

$^1$H NMR (400 MHz, CDCl$_3$) δ 3.86 (3H, s), 3.93 (2H, t, J=5.6 Hz), 4.38 (2H, t, J=4.8 Hz), 7.98 (1H, d, J=2.4 Hz), 8.56 (1H, brs).

Step 2: Preparation of methyl 7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate

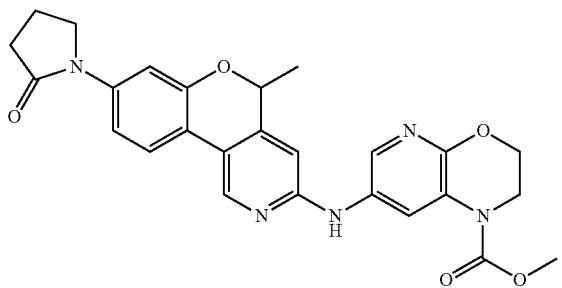 [SMILES: COC(=O)N1CCOc2ncc(Nc3cc4c(cn3)-c3ccc(N5CCCC5=O)cc3OC4C)cc21]

A mixture of Pd$_2$(dba)$_3$ (16 mg, 0.017 mmol) and BrettPhos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), methyl 7-bromo-2,3-dihydro-1H-pyrido[2,3-b][1,4]oxazine-1-carboxylate (46 mg, 0.17 mmol) in dioxane (3 mL) and Cs$_2$CO$_3$ (165 mg, 0.508 mmol) were added and the resulting mixture was stirred at 100° C. for 6 h. A black brown mixture was formed. LCMS (Rt=0.583 min; MS Calcd: 487.2; MS Found: 487.9 [M+H]$^+$). The reaction mixture was diluted with DCM (10 mL), filtered and concentrated. The residue was purified by prep-HPLC (0.05% NH$_3$.H$_2$O as an additive) and lyophilized to give methyl 7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate (12.1 mg, yield: 15%) as a white solid.

$^1$H NMR (400 MHz, DMSO-d$_6$) δ 1.52 (3H, d, J=6.4 Hz), 2.02-2.09 (2H, m), 2.52 (2H, overlap with DMSO), 3.78 (3H, s), 3.81-3.88 (4H, m), 4.31 (2H, t, J=4.0 Hz), 5.24 (1H, q, J=6.4 Hz), 6.66 (1H, s), 7.30 (1H, dd, J=8.4, 2.0 Hz), 7.38 (1H, d, J=2.4 Hz), 7.86 (1H, d, J=8.4 Hz), 8.25 (1H, d, J=2.4 Hz), 8.60 (1H, s), 8.67 (1H, brs), 9.23 (1H, brs).

Example 84: 1-(3-((1-isobutyryl-2,3-dihydro-1H-pyrido[2,3-b][1,4]oxazin-7-yl)amino)-5-methyl-5H-chromeno[4,3-c]pyridin-8-yl)pyrrolidin-2-one

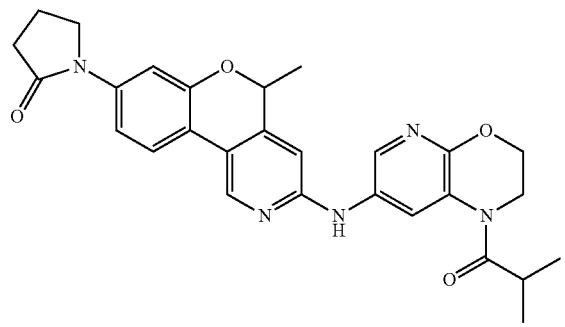 [SMILES: CC(C)C(=O)N1CCOc2ncc(Nc3cc4c(cn3)-c3ccc(N5CCCC5=O)cc3OC4C)cc21]

Step 1: Preparation of 1-(7-bromo-2,3-dihydro-1H-pyrido[2,3-b][1,4]oxazin-1-yl)-2-methylpropan-1-one

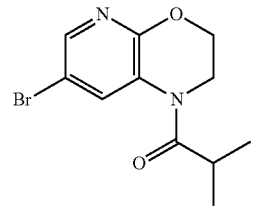

To a solution of 7-bromo-2,3-dihydro-1H-pyrido[2,3-b][1,4]oxazine (600 mg, 2.79 mmol) in DCM (5 mL) was added pyridine (1.1 mL). The reaction mixture was cooled to 0° C. and then added isobutyryl chloride (595 mg, 5.58 mmol) in DCM (2 mL) dropwise. The reaction mixture was then warmed to 10° C., stirred at 10° C. for 12 h under N$_2$ atmosphere. The colorless solution turned to an orange solution gradually. LCMS (Rt=0.603 min; MS Calcd: 286.0. MS Found: 286.7 [M+H]$^+$). The residue was purified by Combi Flash (1% Et$_3$N in DCM) to give 1-(7-bromo-2,3-dihydro-1H-pyrido[2,3-b][1,4]oxazin-1-yl)-2-methylpropan-1-one (700 mg, yield: 88%) as a white solid.

$^1$H NMR (400 MHz, CDCl$_3$) 1.21 (6H, d, J=6.8 Hz), 2.94-2.97 (1H, m), 3.93 (2H, t, J=4.4 Hz), 4.44 (2H, t, J=4.8 Hz), 8.05 (1H, d, J=2.0 Hz), 8.44 (1H, brs).

141

Step 2: Preparation of 1-(3-((1-isobutyryl-2,3-di-hydro-1H-pyrido[2,3-b][1,4]oxazin-7-yl)amino)-5-methyl-5H-chromeno[4,3-c]pyridin-8-yl)pyrrolidin-2-one

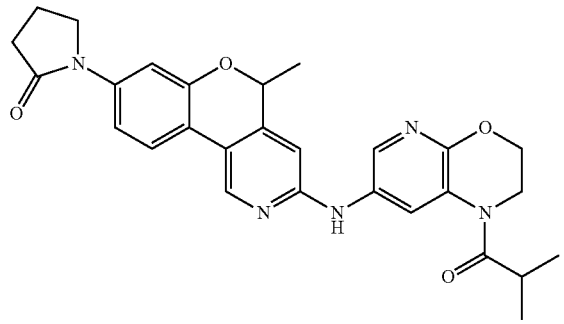 [SMILES: CC(C)C(=O)N1CCOc2ncc(Nc3cc4c(cn3)-c3ccc(N5CCCC5=O)cc3OC4C)cc21]

A mixture of Pd$_2$(dba)$_3$ (16 mg, 0.017 mmol) and Brett-Phos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), 1-(7-bromo-2,3-dihydro-1H-pyrido[2,3-b][1,4]oxazin-1-yl)-2-methylpropan-1-one (58 mg, 0.20 mmol) in dioxane (4 mL) and Cs$_2$CO$_3$ (165 mg, 0.508 mmol) were added and the resulting mixture was stirred at 100° C. for 16 h. A black brown mixture was formed. LCMS (Rt=0.604 min; MS Calcd: 499.2; MS Found: 500.2 [M+H]$^+$). The reaction mixture was diluted with DCM (10 mL), filtered and concentrated. The residue was purified by prep-HPLC (0.225% FA as an additive) and lyophilized to give 1-(3-((1-isobutyryl-2,3-dihydro-1H-pyrido[2,3-b][1,4]oxazin-7-yl)amino)-5-methyl-5H-chromeno[4,3-c]pyridin-8-yl)pyrrolidin-2-one (31.9 mg, yield: 38%) as a yellow solid.

$^1$H NMR (400 MHz, DMSO-d$_6$) δ 1.13 (6H, d, J=6.4 Hz), 1.52 (3H, d, J=6.4 Hz), 2.01-2.09 (2H, m), 2.57 (2H, overlap with DMSO), 3.10-3.30 (1H, m), 3.84 (2H, t, J=7.2 Hz), 3.92 (2H, t, J=4.4 Hz), 4.35 (2H, t, J=4.4 Hz), 5.24 (1H, q, J=6.0 Hz), 6.65 (1H, s), 7.30 (1H, dd, J=8.8, 2.0 Hz), 7.38 (1H, d, J=2.0 Hz), 7.86 (1H, d, J=8.0 Hz), 8.26 (1H, s), 8.57 (2H, s), 9.24 (1H, brs).

Example 85: 1-(3-((1-(isopropylsulfonyl)-2,3-di-hydro-1H-pyrido[2,3-b][1,4]oxazin-7-yl)amino)-5-methyl-5H-chromeno[4,3-c]pyridin-8-yl)pyrrolidin-2-one

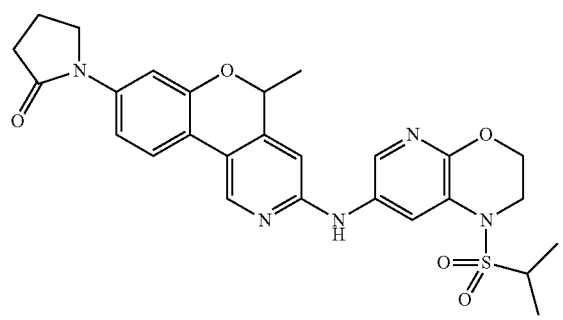 [SMILES: CC1Oc2cc(N3CCCC3=O)ccc2-c2cnc(Nc3cnc4c(c3)N(S(=O)(=O)C(C)C)CCO4)cc21]

142

Step 1: Preparation of 7-bromo-1-(isopropylsulfonyl)-2,3-dihydro-1H-pyrido[2,3-b][1,4]oxazine

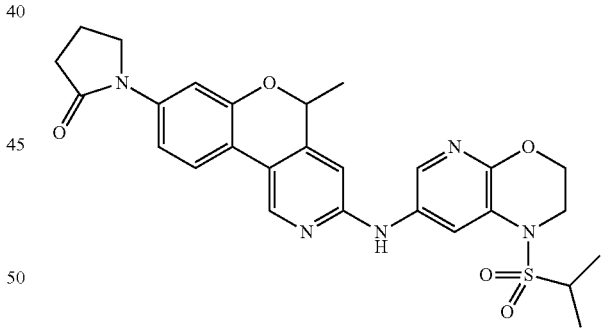

To a solution of 7-bromo-2,3-dihydro-1H-pyrido[2,3-b][1,4]oxazine (1.00 g, 4.65 mmol) in DMF (5 mL) was added NaH (558 mg, 14.0 mmol, 60% in mineral oil) at 0° C. The reaction mixture was heated to 50° C. for 1 hour, and then cooled to 0° C. The reaction mixture was dropwise added propane-2-sulfonyl chloride (1.33 g, 9.30 mmol). The reaction mixture was warmed to 20° C., stirred at 20° C. for 16 h under N$_2$ atmosphere. A black mixture was formed. The reaction mixture was diluted with EtOAc (80 mL). The organic layers were washed with H$_2$O (25 mL×3), dried over Na$_2$SO$_4$, filtered and concentrated. The residue was combined with last batch, purified by Combi Flash (30% EtOAc in pentane (1% Et$_3$N as an additive)) to give 7-bromo-1-(isopropylsulfonyl)-2,3-dihydro-1H-pyrido[2,3-b][1,4]oxazine (610 mg, yield: 34%) as a yellow gum.

$^1$H NMR (400 MHz, CDCl$_3$) δ 1.44 (6H, d, J=7.2 Hz), 3.37-3.48 (1H, m), 3.84 (2H, t, J=4.4 Hz), 4.44 (2H, t, J=4.4 Hz), 7.99 (1H, d, J=2.0 Hz), 8.02 (1H, d, J=2.4 Hz).

Step 2: Preparation of 1-(3-((1-(isopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one A mixture of Pd$_2$(dba)$_3$ (16 mg, 0.017 mmol) and Brett-Phos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), 7-bromo-1-(isopropylsulfonyl)-2,3-dihydro-1H-pyrido[2,3-b][1,4]oxazine (65 mg, 0.20 mmol) in dioxane (4 mL) and Cs$_2$CO$_3$ (165 mg, 0.508 mmol) were added and the resulting mixture was stirred at 100° C. for 16 h. A black brown mixture was formed. LCMS (Rt=0.614 min; MS Calcd: 535.2; MS Found: 536.1 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(3-((1-(isopropylsulfonyl)-2,3-dihydro-1H-pyrido[2,3-b][1,4]oxazin-7-yl)amino)-

5-methyl-5H-chromeno[4,3-c]pyridin-8-yl)pyrrolidin-2-one (42.8 mg, yield: 47%) as an off-white solid.

$^1$H NMR (400 MHz, DMSO-$d_6$) δ 1.34 (6H, d, J=6.8 Hz), 1.52 (3H, d, J=6.4 Hz), 2.01-2.08 (2H, m), 2.56 (2H, overlap with DMSO), 3.71-3.78 (1H, m), 3.80-3.85 (4H, m), 4.34 (2H, t, J=4.4 Hz), 5.23 (1H, q, J=6.4 Hz), 6.65 (1H, s), 7.30 (1H, dd, J=8.8, 2.0 Hz), 7.38 (1H, d, J=2.0 Hz), 7.86 (1H, d, J=8.4 Hz), 8.26 (1H, d, J=2.0 Hz), 8.29 (1H, d, J=2.0 Hz), 8.58 (1H, s), 9.28 (1H, brs).

Example 86: 1-(5-methyl-3-((1-pivaloyl-2,3-dihydro-1H-pyrido[2,3-b][1,4]oxazin-7-yl)amino)-5H-chromeno[4,3-c]pyridin-8-yl)pyrrolidin-2-one

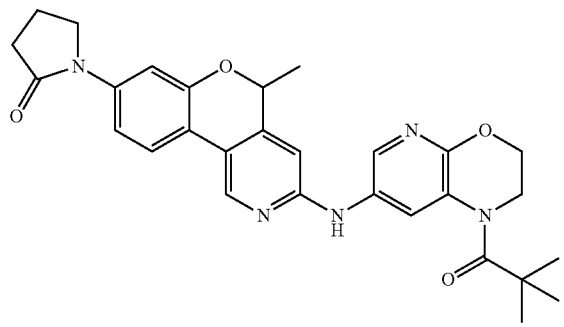 [SMILES: CC1Oc2cc(N3CCCC3=O)ccc2-c2cnc(Nc3cnc4c(c3)N(C(=O)C(C)(C)C)CCO4)cc21]

Step 1: Preparation of 1-(7-bromo-2,3-dihydro-1H-pyrido[2,3-b][1,4]oxazin-1-yl)-2,2-dimethylpropan-1-one

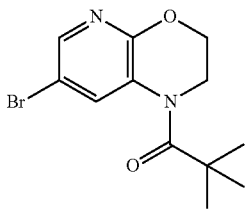 [SMILES: CC(C)(C)C(=O)N1CCOc2ncc(Br)cc21]

To a solution of 7-bromo-2,3-dihydro-1H-pyrido[2,3-b][1,4]oxazine (500 mg, 2.33 mmol) in pyridine (15 mL) was added pivaloyl chloride (700 mg, 5.81 mmol) under nitrogen at 20° C. The resulting mixture was stirred at 50° C. for 16 h. An orange solution was formed. LCMS (Rt=0.653 min; MS Calcd: 300.0. MS Found: 300.7 [M+H]$^+$). The reaction mixture was concentrated. The residue was combined with last batch, purified by Combi Flash (50% DCM in PE (1% Et$_3$N as an additive)) to give 1-(7-bromo-2,3-dihydro-H-pyrido[2,3-b][1,4]oxazin-1-yl)-2,2-dimethylpropan-1-one (680 mg, yield: 89%) as a yellow solid.

Step 2: Preparation of 1-(5-methyl-3-((1-pivaloyl-2,3-dihydro-1H-pyrido[2,3-b][1,4]oxazin-7-yl)amino)-5H-chromeno[4,3-c]pyridin-8-yl)pyrrolidin-2-one

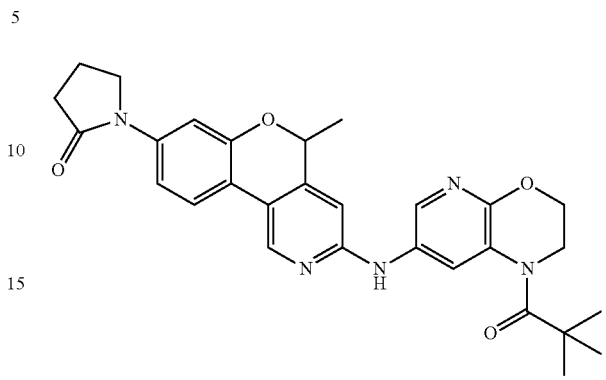

A mixture of Pd$_2$(dba)$_3$ (16 mg, 0.017 mmol) and BrettPhos (18 mg, 0.034 mmol) in 1,4-dioxane (1 mL) was stirred at 50° C. for 10 min. 1-(3-amino-5-methyl-5H-chromeno[4,3-c]pyridin-8-yl)pyrrolidin-2-one (50 mg, 0.17 mmol), 1-(7-bromo-2,3-dihydro-1H-pyrido[2,3-b][1,4]oxazin-1-yl)-2,2-dimethylpropan-1-one (49 mg, 0.16 mmol) in dioxane (4 mL) and Cs$_2$CO$_3$ (165 mg, 0.508 mmol) were added and the resulting mixture was stirred at 100° C. for 18 h. A black brown mixture was formed. A mixture of Pd$_2$(dba)$_3$ (16 mg, 0.017 mmol) and BrettPhos (18 mg, 0.034 mmol) in 1,4-dioxane (1 mL) was stirred at 50° C. for 15 min and added to the previous reaction mixture together with additional Cs$_2$CO$_3$ (165 mg, 0.508 mmol). The resulting reaction mixture was stirred at 100° C. for 18 h. LCMS (Rt=0.605 min; MS Calcd: 513.2. MS Found: 514.0 [M+H]$^+$). The reaction mixture was diluted with DCM (10 mL), filtered and concentrated. The residue was purified by prep-HPLC (0.225% FA as an additive) and lyophilized to give 1-(5-methyl-3-((1-pivaloyl-2,3-dihydro-1H-pyrido[2,3-b][1,4]oxazin-7-yl)amino)-5H-chromeno[4,3-c]pyridin-8-yl)pyrrolidin-2-one (16.0 mg, yield: 19%) as a yellow solid.

$^1$H NMR (400 MHz, DMSO-$d_6$) δ 1.32 (9H, s), 1.52 (3H, d, J=6.4 Hz), 2.02-2.09 (2H, m), 2.53 (2H, overlap with DMSO), 3.83 (2H, t, J=7.6 Hz), 4.02 (2H, t, J=4.0 Hz), 4.35 (2H, t, J=4.4 Hz), 5.23 (1H, q, J=6.4 Hz), 6.64 (1H, s), 7.29 (1H, dd, J=8.4, 2.4 Hz), 7.38 (1H, d, J=2.0 Hz), 7.85 (1H, d, J=8.8 Hz), 8.28 (1H, d, J=2.4 Hz), 8.34 (1H, d, J=2.4 Hz), 8.59 (1H, s), 9.17 (1H, brs).

Example 87: N-(2-methoxy-5-((5-methyl-8-(2-oxopyrrolidin-1-yl)-5H-chromeno[4,3-c]pyridin-3-yl)amino)pyridin-3-yl)acetamide

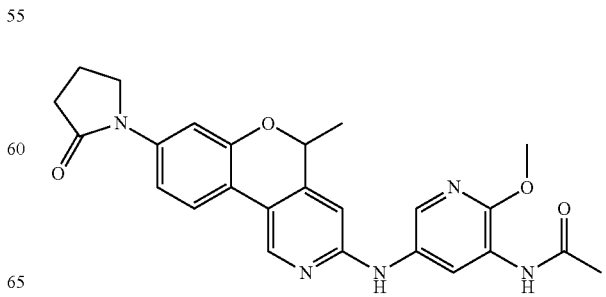

145

Step 1: Preparation of N-(5-bromo-2-methoxypyridin-3-yl)acetamide

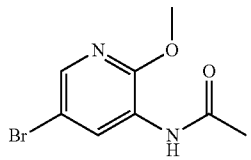

To a solution of 5-bromo-2-methoxypyridin-3-amine (1.00 g, 4.90 mmol) in pyridine (15 mL) was added acetic anhydride (528 mg, 5.18 mmol) dropwise at 0° C. And the resulting mixture was stirred at 20° C. for 12 h. A yellow solution was formed. LCMS (Rt=0.813 min; MS Calcd: 243.9. MS Found: 246.7 [M+H]+). The reaction mixture was concentrated under reduced pressure. The crude product was purified by combi flash (10% EtOAc in pentane (1% Et₃N as an additive)) to give N-(5-bromo-2-methoxypyridin-3-yl) acetamide (1.05 g, yield: 87%) as a white solid.

¹H NMR (400 MHz, CDCl₃) δ 2.23 (3H, s), 4.00 (3H, s), 7.60 (1H, brs), 7.89 (1H, d, J=2.0 Hz), 8.78 (1H, d, J=2.0 Hz).

Step 2: Preparation of N-(2-methoxy-5-((5-methyl-8-(2-oxopyrrolidin-1-yl)-5H-chromeno[4,3-c]pyridin-3-yl)amino)pyridin-3-yl)acetamide

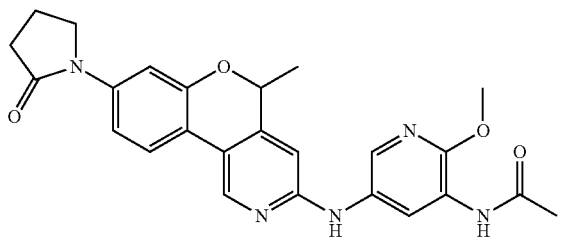 [SMILES: COc1ncc(Nc2cc3c(cn2)-c2ccc(N4CCCC4=O)cc2OC3C)cc1NC(C)=O]

A mixture of Pd₂(dba)₃ (25 mg, 0.027 mmol) and Brett-Phos (29 mg, 0.054 mmol) in 1,4-dioxane (1 mL) was stirred at 50° C. for 10 min. 1-(3-Amino-5-methyl-5H-chromeno[4,3-c]pyridin-8-yl)pyrrolidin-2-one (80 mg, 0.27 mmol), N-(5-bromo-2-methoxypyridin-3-yl)acetamide (79 mg, 0.32 mmol) in dioxane (5 mL) and Cs₂CO₃ (265 mg, 0.813 mmol) were added and the resulting mixture was stirred at 100° C. for 16 h. A black brown mixture was formed. LCMS (Rt=0.586 min; MS Calcd: 459.2. MS Found: 460.0 [M+H]+). The reaction mixture was diluted with DCM (10 mL), filtered and concentrated. The residue was purified by prep-HPLC (0.05% NH₃.H₂O as an additive) and lyophilized to give N-(2-methoxy-5-((5-methyl-8-(2-oxopyrrolidin-1-yl)-5H-chromeno[4,3-c]pyridin-3-yl)amino)pyridin-3-yl)acetamide (50.2 mg, yield: 40%) as an off-white solid.

¹H NMR (400 MHz, DMSO-d₆) δ 1.52 (3H, d, J=6.4 Hz), 2.02-2.09 (2H, m), 2.12 (3H, s), 2.52 (2H, overlap with DMSO), 3.84 (2H, t, J=8.0 Hz), 3.91 (3H, s), 5.23 (1H, q, J=6.4 Hz), 6.66 (1H, s), 7.30 (1H, dd, J=8.8, 2.0 Hz), 7.38 (1H, d, J=2.0 Hz), 7.85 (1H, d, J=8.8 Hz), 8.32 (1H, d, J=2.4 Hz), 8.56-8.59 (2H, m), 9.16 (1H, brs), 9.35 (1H, brs).

146

Example 88: N-(2-methoxy-5-((5-methyl-8-(2-oxopyrrolidin-1-yl)-5H-chromeno[4,3-c]pyridin-3-yl)amino)pyridin-3-yl)methanesulfonamide

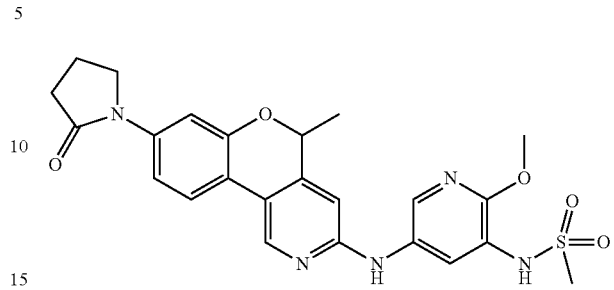

Step 1: Preparation of N-(5-bromo-2-methoxypyridin-3-yl)methanesulfonamide

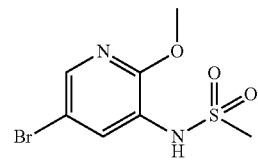

A solution of 5-bromo-2-methoxypyridin-3-amine (1.00 g, 4.93 mmol) and pyridine (7.4 mL, 91 mmol) was stirred in DCM (25 mL), then MsCl (564 mg, 4.93 mmol) was added into the above solution at 0° C., which was stirred at 20° C. for 16 h. A brown solution was formed. LCMS (Rt=0.582 min; MS Calcd: 280.0. MS Found: 280.7 [M+H]+). The solution was diluted with H₂O (20 mL) and was extracted with DCM (15 mL×3). The organic layer was washed with brine (15 mL), dried over Na₂SO₄. The residue was purified by Combi Flash (20% EtOAc in pentane) to give N-(5-bromo-2-methoxypyridin-3-yl)methanesulfonamide (1.06 g, yield: 77%) as an off-white solid.

¹H NMR (400 MHz, CDCl₃) δ 3.04 (3H, s), 3.99 (3H, s), 6.74 (1H, brs), 7.89 (1H, d, J=2.0 Hz), 7.97 (1H, d, J=2.0 Hz).

Step 2: Preparation of N-(2-methoxy-5-((5-methyl-8-(2-oxopyrrolidin-1-yl)-5H-chromeno[4,3-c]pyridin-3-yl)amino)pyridin-3-yl)methanesulfonamide

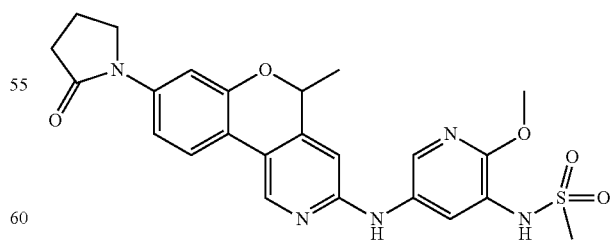

A mixture of Pd₂(dba)₃ (25 mg, 0.027 mmol) and Brett-Phos (29 mg, 0.054 mmol) in 1,4-dioxane (1 mL) was stirred at 50° C. for 10 min. 1-(3-amino-5-methyl-5H-chromeno[4,3-c]pyridin-8-yl)pyrrolidin-2-one (80 mg, 0.27 mmol), N-(5-bromo-2-methoxypyridin-3-yl)methanesulfonamide (91 mg, 0.32 mol) in dioxane (5 mL) and Cs₂CO₃ (265 mg, 0.813 mmol) were added and the resulting mixture was stirred at 100° C. for 16 h. A black brown mixture was formed. LCMS (Rt=0.590 min; MS Calcd: 495.2. MS Found: 496.0 [M+H]⁺). The reaction mixture was diluted with DCM (10 mL), filtered and concentrated. The residue was purified by prep-HPLC (0.05% NH₃.H₂O as an additive) and lyophilized to give N-(2-methoxy-5-((5-methyl-8-(2-oxopyrrolidin-1-yl)-5H-chromeno[4,3-c]pyridin-3-yl)amino)pyridin-3-yl)methanesulfonamide (22.0 mg, yield: 16%) as an off-white solid.

¹H NMR (400 MHz, DMSO-d₆) δ 1.52 (3H, d, J=6.8 Hz), 2.02-2.09 (2H, m), 2.51 (2H, overlap with DMSO), 3.03 (3H, s), 3.83 (2H, t, J=8.0 Hz), 3.88 (3H, s), 5.24 (1H, q, J=6.8 Hz), 6.64 (1H, s), 7.30 (1H, dd, J=8.4, 2.0 Hz), 7.38 (1H, d, J=2.0 Hz), 7.86 (1H, d, J=8.8 Hz), 7.98 (1H, d, J=2.4 Hz), 8.33 (1H, d, J=2.8 Hz), 8.50 (1H, s), 9.05 (1H, brs), 9.22 (1H, brs).

Example 89: N-(2-methoxy-5-((5-methyl-8-(2-oxopyrrolidin-1-yl)-5H-chromeno[4,3-c]pyridin-3-yl)amino)pyridin-3-yl)-N-methylacetamide

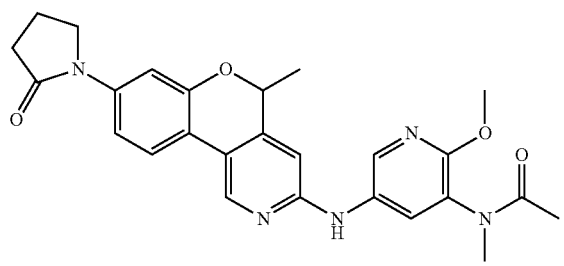 [SMILES: COc1ncc(Nc2cc3c(cn2)-c2ccc(N4CCCC4=O)cc2OC3C)cc1N(C)C(C)=O]

A mixture of Pd₂(dba)₃ (16 mg, 0.017 mmol) and Brett-Phos (18 mg, 0.034 mmol) in dioxane (3 mL) was stirred at 50° C. for 15 minutes under N₂. Then Cs₂CO₃ (165 mg, 0.51 mmol), 1-(3-amino-5-methyl-5H-chromeno[4,3-c]pyridin-8-yl)pyrrolidin-2-one (50 mg, 0.17 mmol) and N-(5-bromo-2-methoxypyridin-3-yl)-N-methylacetamide (44 mg, 0.17 mmol) was added. The resulting mixture was stirred at 100° C. for 12 h under N₂. A black suspension was formed. LCMS the purity of the desired product (Rt=716 min; MS Calcd: 473.5. MS Found: 474.1 [M+H]⁺). The reaction mixture was filtered and then concentrated. The crude product was purified by prep-HPLC (normal Phase, Hexane-EtOH) and lyophilized to give N-(2-methoxy-5-((5-methyl-8-(2-oxopyrrolidin-1-yl)-5H-chromeno[4,3-c]pyridin-3-yl)amino)pyridin-3-yl)-N-methylacetamide (12.0 mg, yield: 15%) as a white solid.

¹H NMR (400 MHz, DMSO-d₆) δ 1.51 (3H, d, J=6.8 Hz), 1.74 (3H, s), 2.03-2.09 (2H, m), 2.52 (2H, overlap with DMSO), 3.05 (3H, s), 3.83 (2H, t, J=7.2 Hz), 3.89 (3H, s), 5.25 (1H, q, J=6.4 Hz), 6.65 (1H, s), 7.30 (1H, dd, J=2.0, 8.0 Hz), 7.39 (1H, d, J=2.0 Hz), 7.85 (1H, d, J=8.0 Hz), 8.18 (1H, d, J=2.0 Hz), 8.39 (1H, s), 8.63 (1H, s), 9.30 (1H, brs).

Example 90: N-(2-methoxy-5-((5-methyl-8-(2-oxopyrrolidin-1-yl)-5H-chromeno[4,3-c]pyridin-3-yl)amino)pyridin-3-yl)-N-methylmethanesulfonamide

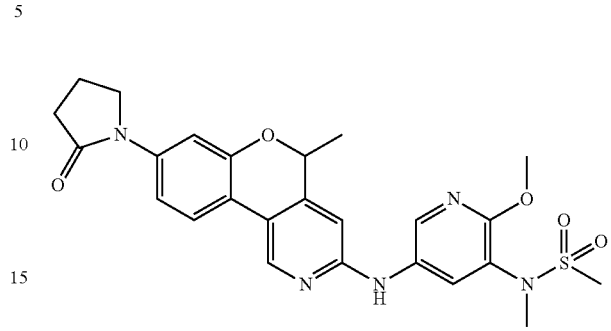

A mixture of Pd₂(dba)₃ (16 mg, 0.017 mmol) and Brett-Phos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), N-(5-bromo-2-methoxypyridin-3-yl)-N-methylmethanesulfonamide (60 mg, 0.20 mmol) in dioxane (4 mL) and Cs₂CO₃ (165 mg, 0.508 mmol) were added and the resulting mixture was stirred at 100° C. for 16 h. A black brown mixture was formed. LCMS (Rt=0.603 min; MS Calcd: 509.2; MS Found: 510.0 [M+H]⁺). The reaction mixture was diluted with DCM (10 mL), filtered and concentrated. The residue was purified by prep-HPLC (0.05% NH₃.H₂O as an additive) and lyophilized to impure product (50 mg), then purified by prep-HPLC (normal phase, Hexane-EtOH) and lyophilized to give N-(2-methoxy-5-((5-methyl-8-(2-oxopyrrolidin-1-yl)-5H-chromeno[4,3-c]pyridin-3-yl)amino)pyridin-3-yl)-N-methylmethanesulfonamide (25.6 mg, yield: 30%) as a white solid.

¹H NMR (400 MHz, DMSO-d₆) δ 1.52 (3H, d, J=6.0 Hz), 2.01-2.09 (2H, m), 2.55 (2H, overlap with DMSO), 3.05 (3H, s), 3.17 (3H, s), 3.84 (2H, t, J=8.0 Hz), 3.91 (3H, s), 5.25 (1H, q, J=6.4 Hz), 6.65 (1H, s), 7.30 (1H, dd, J=8.4, 2.4 Hz), 7.39 (1H, d, J=2.0 Hz), 7.86 (1H, d, J=8.8 Hz), 8.13 (1H, d, J=2.4 Hz), 8.43 (1H, d, J=2.4 Hz), 8.64 (1H, s), 9.29 (1H, brs).

Example 91: 1-(5-methyl-3-((5-(methylsulfonyl)pyridin-3-yl)amino)-5H-chromeno[4,3-c]pyridin-8-yl)pyrrolidin-2-one

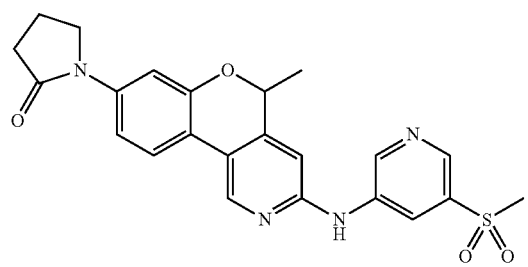 [SMILES: CC1Oc2cc(N3CCCC3=O)ccc2-c2cnc(Nc3cncc(S(C)(=O)=O)c3)cc21]

A mixture of Pd₂(dba)₃ (16 mg, 0.017 mmol) and Brett-Phos (18 mg, 0.034 mmol) in 1,4-dioxane (1 mL) was stirred at 50° C. for 10 min. 1-(3-Amino-5-methyl-5H-chromeno[4,3-c]pyridin-8-yl)pyrrolidin-2-one (50 mg, 0.17 mmol), 3-bromo-5-(methylsulfonyl)pyridine (48 mg, 0.20 mmol) in dioxane (3 mL) and Cs₂CO₃ (165 mg, 0.508 mmol) were added and the resulting mixture was stirred at 100° C. for 16 h. A black brown mixture was formed. LCMS (Rt=0.615 min; MS Calcd: 450.1. MS Found: 451.0 [M+H]⁺). The reaction mixture was diluted with DCM (10 mL), filtered and concentrated. The residue was purified by prep-HPLC (0.05% $NH_3.H_2O$ as an additive) and lyophilized to give 1-(5-methyl-3-((5-(methylsulfonyl)pyridin-3-yl)amino)-5H-chromeno[4,3-c]pyridin-8-yl)pyrrolidin-2-one (9.0 mg, yield: 12%) as a white solid.

¹H NMR (400 MHz, DMSO-$d_6$) δ 1.55 (3H, d, J=6.4 Hz), 2.02-2.09 (2H, m), 2.53 (2H, overlap with DMSO), 3.32 (3H, s), 3.85 (2H, t, J=8.0 Hz), 5.32 (1H, q, J=6.4 Hz), 6.80 (1H, s), 7.33 (1H, dd, J=8.8, 2.4 Hz), 7.42 (1H, d, J=2.4 Hz), 7.94 (1H, d, J=8.8 Hz), 8.58 (1H, d, J=2.0 Hz), 8.77 (1H, s), 8.88 (1H, t, J=2.0 Hz), 9.03 (1H, d, J=2.4 Hz), 9.95 (1H, brs).

Example 92: 1-(5-methyl-3-((5-(methylsulfonyl) quinolin-3-yl)amino)-5H-chromeno[4,3-c]pyridin-8-yl)pyrrolidin-2-one

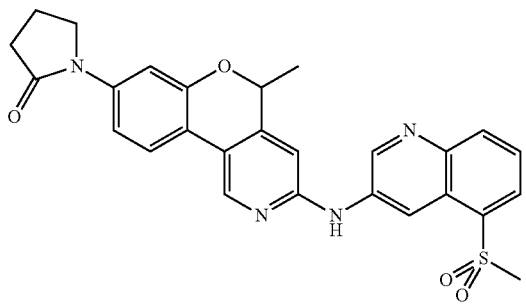 [SMILES: CC1Oc2cc(N3CCCC3=O)ccc2-c2cnc(Nc3cnc4cccc(S(C)(=O)=O)c4c3)cc21]

Step 1: Preparation of 5-(methylthio)quinoline

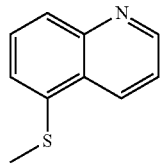

To a mixture of 5-bromoquinoline (2.00 g, 9.61 mmol) in DMSO (10 mL) was added CuI (1.83 g, 9.61 mmol) and DABCO (2.16 g, 19.2 mmol). The mixture was degassed and purged with $N_2$ for 3 times, and stirred at 130° C. for 36 h. A brown suspension was formed. The reaction was repeated to increase the amount of crude brown suspension. The crude mixtures from were combined and filtered. The filtrate was diluted with $H_2O$ (60 mL), extracted with EtOAc (50 mL×3). The combined layer was washed with brine (30 mL), dried over $Na_2SO_4$ and concentrated. The residue was purified by Combi Flash (EtOAc in pentane form 0 to 20%) to give 5-(methylthio)quinoline (900 mg, yield: 9%) as yellow oil.

Step 2: Preparation of 5-(methylsulfonyl)quinoline

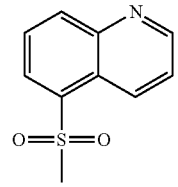

To a mixture of 5-(methylthio)quinoline (900 mg, 1.68 mmol) in MeOH (10 mL) was added mCPBA (905 mg, 4.20 mmol, 80% purity) at 0° C. The mixture was stirred at 0° C. for 2 h to give a colorless solution. TLC (PE/EtOAc=1/1) showed that starting material was consumed and a more polar spot (Rf=0.20) was formed. The mixture was added sat. $Na_2S_2O_3$ (10 mL), extracted with EtOAc (50 mL×3). The combined layer was washed with brine (50 mL), dried over $Na_2SO_4$ and concentrated, the residue was purified by Combi Flash (EtOAc in pentane from 0 to 50%) to give 5-(methylsulfonyl)quinolone (300 mg, yield: 48%) as a white solid.

¹H NMR (400 MHz, CDCl₃) δ 3.21 (3H, s), 7.65 (1H, dd, J=8.8, 4.0 Hz), 7.88 (1H, dd, J=8.4, 7.2 Hz), 8.41 (1H, dd, J=7.6, 1.6 Hz), 8.45 (1H, d, J=9.2 Hz), 8.78 (1H, dd, J=4.4, 1.6 Hz), 9.14 (1H, d, J=8.8 Hz).

Step 3: Preparation of 3-iodo-5-(methylsulfonyl)quinoline

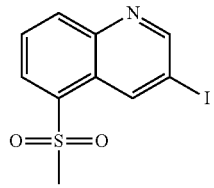

To a solution of 5-(methylsulfonyl)quinolone (300 mg, 1.45 mmol) in MeCN (5 mL) was added 12 (440 mg, 1.74 mmol) and TBHP (1.49 g, 11.6 mmol, 70% purity in $H_2O$). The mixture was stirred at 80° C. for 24 h to give a brown solution. The mixture was added TBHP (298 mg, 2.32 mmol, 70% in $H_2O$) and stirred for another 24 h. The reaction mixture was added sat.$Na_2S_2O_3$ (40 mL), extracted with EtOAc (40 mL×3). The combined organic layer was washed with brine (20 mL), dried over $Na_2SO_4$ and concentrated. The residue was purified by Combi Flash (EtOAc in pentane from 0 to 50%) to give 3-iodo-5-(methylsulfonyl) quinoline (180 mg, yield: 30%) as a white solid.

¹H NMR (400 MHz, CDCl₃) δ 3.20 (3H, s), 7.88 (1H, dd, J=8.8, 7.6 Hz), 8.41-8.36 (2H, m), 9.19 (1H, d, J=2.0 Hz), 9.50 (1H, d, J=1.2 Hz).

Step 4: Preparation of 1-(5-methyl-3-((5-(methyl-sulfonyl)quinolin-3-yl)amino)-5H-chromeno[4,3-c]pyridin-8-yl)pyrrolidin-2-one

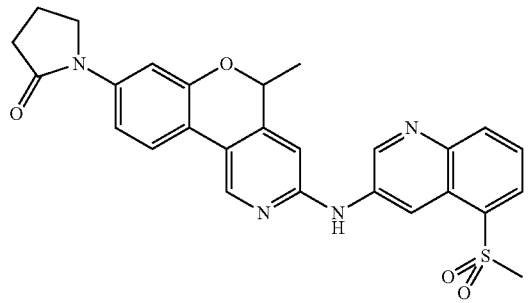 [SMILES: CC1Oc2cc(N3CCCC3=O)ccc2-c2cnc(Nc3cnc4cccc(S(C)(=O)=O)c4c3)cc21]

To a suspension of 1-(3-amino-5-methyl-5H-chromeno[4,3-c]pyridin-8-yl)pyrrolidin-2-one (100 mg, 0.338 mmol) and 3-iodo-5-(methylsulfonyl)quinoline (124 mg, 0.372 mmol) in dioxane (2 mL) was added Pd$_2$(dba)$_3$ (31 mg, 0.033 mmol) BrettPhos (36 mg, 0.067 mmol) and Cs$_2$CO$_3$ (331 mg, 1.02 mmol), purged and degassed with N$_2$ for 3 times. The mixture was stirred at 100° C. for 16 h. A brown suspension was formed. LCMS showed that starting material was consumed and the purity of desired product (Rt=0.779 min; MS Calcd: 500.6. MS Found: 501.3 [M+H]$^+$). The mixture was diluted with H$_2$O (20 mL), extracted with DCM (20 mL×3). The combined layer was washed with brine (20 mL), dried over Na$_2$SO$_4$ and concentrated. The residue was purified by Combi Flash (MeOH in DCM from 0 to 5%) to give an orange solid. It was triturated with MeCN (5 mL×3), filtered and put in vacuum to give 1-(5-methyl-3-((5-(methylsulfonyl)quinolin-3-yl)amino)-5H-chromeno[4,3-c]pyridin-8-yl)pyrrolidin-2-one (82 mg, yield: 48%) as a yellow solid.

$^1$H NMR (400 MHz, DMSO-d$_6$) δ 1.58 (3H, d, J=6.4 Hz), 2.05-2.09 (2H, m), 2.51-2.53 (2H, m, overlapped with DMSO), 3.44 (3H, s), 3.86 (2H, t, J=7.6 Hz), 5.34 (1H, q, J=6.4 Hz), 6.90 (1H, s), 7.36 (1H, dd, J=8.8, 2.4 Hz), 7.43 (1H, d, J=2.4 Hz), 7.73 (1H, dd, J=8.0, 7.6 Hz), 7.96 (1H, d, J=8.4 Hz), 8.22 (1H, dd, J=3.6, 1.2 Hz), 8.26 (1H, d, J=8.8 Hz), 8.76 (1H, s), 9.22 (1H, d, J=2.4 Hz), 9.52 (1H, d, J=2.8 Hz), 10.10 (1H, s)

Example 93: 7-((5-methyl-8-(2-oxopyrrolidin-1-yl)-5H-chromeno[4,3-c]pyridin-3-yl)amino)-1H-pyrido[2,3-b][1,4]oxazin-2(3H)-one

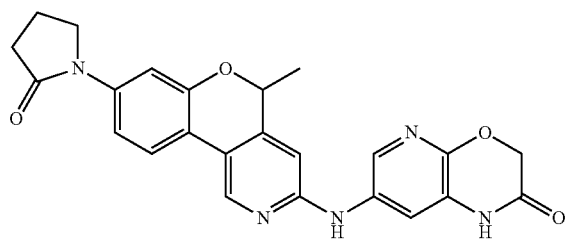 [SMILES: CC1Oc2cc(N3CCCC3=O)ccc2-c2cnc(Nc3cnc4c(c3)NC(=O)CO4)cc21]

Step 1: Preparation of 7-((5-methyl-8-(2-oxopyrrolidin-1-yl)-5H-chromeno[4,3-c]pyridin-3-yl)amino)-1-((2-(trimethylsilyl)ethoxy)methyl)-1H-pyrido[2,3-b][1,4]oxazin-2(3H)-one

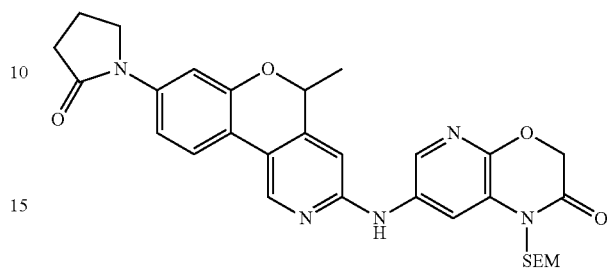

A mixture of Pd$_2$(dba)$_3$ (25 mg, 0.027 mmol) and BrettPhos (29 mg, 0.054 mmol) in 1,4-dioxane (1 mL) was stirred at 50° C. for 10 min. 1-(3-amino-5-methyl-5H-chromeno[4,3-c]pyridin-8-yl)pyrrolidin-2-one (80 mg, 0.27 mmol), 7-bromo-1-((2-(trimethylsilyl)ethoxy)methyl)-1H-pyrido[2,3-b][1,4]oxazin-2(3H)-one (117 mg, 0.325 mmol) in dioxane (7 mL) and Cs$_2$CO$_3$ (176 mg, 0.542 mmol) were added and the resulting mixture was stirred at 100° C. for 16 h. A black brown mixture was formed. LCMS (Rt=0.718 min; MS Calcd: 573.2. MS Found: 574.1 [M+H]$^+$). The reaction mixture was diluted with dioxane (10 mL), filtered and concentrated. The residue was purified by Combi Flash (EtOAc) to give 7-((5-methyl-8-(2-oxopyrrolidin-1-yl)-5H-chromeno[4,3-c]pyridin-3-yl)amino)-1-((2-(trimethylsilyl)ethoxy)methyl)-1H-pyrido[2,3-b][1,4]oxazin-2(3H)-one (145 mg, yield: 93%) as a light yellow solid.

Step 2: Preparation of 7-((5-methyl-8-(2-oxopyrrolidin-1-yl)-5H-chromeno[4,3-c]pyridin-3-yl)amino)-1H-pyrido[2,3-b][1,4]oxazin-2(3H)-one

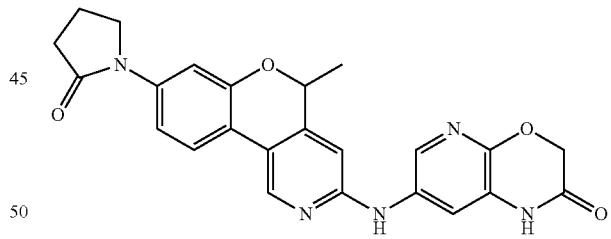

To a solution of 7-((5-methyl-8-(2-oxopyrrolidin-1-yl)-5H-chromeno[4,3-c]pyridin-3-yl)amino)-1-((2-(trimethylsilyl)ethoxy)methyl)-1H-pyrido[2,3-b][1,4]oxazin-2(3H)-one (145 mg, 0.253 mmol) in DCM (5 mL) was added TFA (3.9 mL, 53 mmol) at 10° C., and it was stirred at 10° C. for 1 hour. Then the mixture was concentrated under reduced pressure and the residue was diluted with MeOH (5 mL) and then ethylenediamine (576 mg, 5.05 mmol) was added at 10° C. The residue was stirred at 10° C. for 16 h. The yellow solution turned to white suspension gradually. Crude LCMS showed that the purity of product was 92% (Rt=0.553 min, MS Calcd.: 443.2. MS Found: 443.9 [M+H]$^+$). The mixture was concentrated under reduced pressure. The residue was purified by prep-HPLC (0.225% FA as an additive) and lyophilized to give 7-((5-methyl-8-(2-oxopyrrolidin-1-yl)-

5H-chromeno[4,3-c]pyridin-3-yl)amino)-1H-pyrido[2,3-b][1,4]oxazin-2(3H)-one (11.5 mg, yield: 10%) as a red solid.

¹H NMR (400 MHz, DMSO-d₆) δ 1.52 (3H, d, J=6.4 Hz), 2.02-2.09 (2H, m), 2.53 (2H, overlap with DMSO), 3.83 (2H, t, J=8.0 Hz), 4.70 (2H, s), 5.24 (1H, q, J=6.4 Hz), 6.66 (1H, s), 7.31 (1H, dd, J=8.8, 2.4 Hz), 7.38 (1H, d, J=2.0 Hz), 7.77 (1H, d, J=2.4 Hz), 7.86 (1H, d, J=8.4 Hz), 8.06 (1H, d, J=2.0 Hz), 8.59 (1H, s), 9.32 (1H, brs), 10.86 (1H, brs).

Example 94: 1-(3-((2,3-dihydro-1H-pyrido[2,3-b][1,4]oxazin-7-yl)amino)-5-methyl-5H-chromeno[4,3-c]pyridin-8-yl)pyrrolidin-2-one

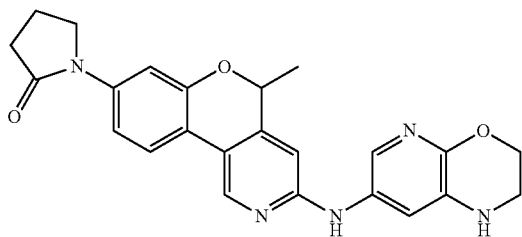 [SMILES: CC1Oc2cc(N3CCCC3=O)ccc2-c2cnc(Nc3cnc4c(c3)NCCO4)cc21]

A mixture of Pd₂(dba)₃ (28 mg, 0.030 mmol) and Brett-Phos (33 mg, 0.061 mmol) in 1,4-dioxane (1 mL) was stirred at 50° C. for 10 min. 1-(3-Amino-5-methyl-5H-chromeno[4,3-c]pyridin-8-yl)pyrrolidin-2-one (90 mg, 0.30 mmol), 2-(7-bromo-2,3-dihydro-1H-pyrido[2,3-b][1,4]oxazin-1-yl)-2-oxoethyl acetate (100 mg, 0.317 mmol) in dioxane (5 mL) and Cs₂CO₃ (298 mg, 0.914 mmol) were added and the resulting mixture was stirred at 100° C. for 16 h. A black brown mixture was formed. TLC indicated the most of starting material was consumed. The reaction mixture was diluted with DCM (10 mL), filtered and concentrated. The residue was purified by Combi Flash (1% Et₃N in EtOAc), then the impure product (50 mg) was purified by prep-HPLC (0.05% NH₃.H₂O as an additive) and lyophilized to give 1-(3-((2,3-dihydro-1H-pyrido[2,3-b][1,4]oxazin-7-yl)amino)-5-methyl-5H-chromeno[4,3-c]pyridin-8-yl)pyrrolidin-2-one (5.9 mg, yield: 5%) as an off-white solid.

¹H NMR (400 MHz, DMSO-d₆) δ 1.50 (3H, d, J=5.6 Hz), 2.00-2.09 (2H, m), 2.58 (2H, overlap with DMSO), 3.25-3.29 (2H, m), 3.83 (2H, t, J=6.0 Hz), 4.17-4.24 (2H, m), 5.21 (1H, q, J=6.0 Hz), 6.09 (1H, s), 6.61 (1H, s), 7.30 (1H, d, J=7.6 Hz), 7.36 (2H, d, J=4.8 Hz), 7.59 (1H, s), 7.83 (1H, d, J=8.4 Hz), 8.55 (1H, brs), 8.94 (1H, brs).

Example 95: 4-(5-((5-methyl-8-(2-oxopyrrolidin-1-yl)-5H-chromeno[4,3-c]pyridin-3-yl)amino)pyridin-3-yl)morpholin-3-one

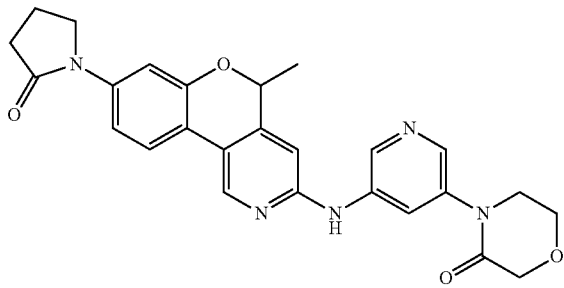 [SMILES: CC1Oc2cc(N3CCCC3=O)ccc2-c2cnc(Nc3cncc(N4CCOCC4=O)c3)cc21]

Step 1: Preparation of 4-(5-bromopyridin-3-yl)morpholin-3-one

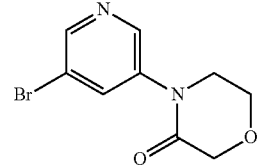 [SMILES: O=C1COCCN1c1cncc(Br)c1]

A solution of Pd₂(dba)₃ (322 mg, 0.352 mmol) and XantPhos (204 mg, 0.352 mmol) in dioxane (10 mL) was stirred at 50° C. for 5 min under N₂. Then 3,5-dibromopyridine (1.00 g, 4.20 mmol), morpholin-3-one (356 mg, 0.352 mmol) and Cs₂CO₃ (2.30 g, 7.00 mmol) was added to the solution. The resulting mixture was stirred at 100° C. for 12 h under N₂. A black brown solid was formed. TLC (EtOAc/PE=2:1) showed starting material was consumed completely and the new point was formed at Rf=0.28. The reaction mixture was filtered and the filtrate was concentrated. Amounts of crude product were increased using the same procedure. The combined amounts of crude were then purified by combi flash (with 6% EtOAc in pentane) to give 4-(5-bromopyridin-3-yl)morpholin-3-one (510 mg, yield: 51%) as a yellow solid.

¹H NMR (400 MHz, CDCl₃) δ 3.81 (2H, t, J=5.2 Hz), 4.05 (2H, t, J=5.2 Hz), 4.36 (2H, s), 7.97 (1H, d, J=2.0 Hz), 8.57 (2H, dd, J=4.0, 2.0 Hz).

Step 2: Preparation of 4-(5-((5-methyl-8-(2-oxopyrrolidin-1-yl)-5H-chromeno[4,3-c]pyridin-3-yl)amino)pyridin-3-yl)morpholin-3-one

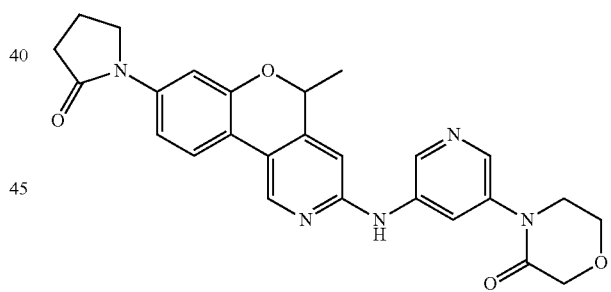

A mixture of Pd₂(dba)₃ (22 mg, 0.024 mmol) and Brett-Phos (25 mg, 0.047 mmol) in dioxane (3 mL) was stirred at 50° C. for 5 min under N₂. Then Cs₂CO₃ (232 mg, 0.711 mmol), 1-(3-amino-5-methyl-5H-chromeno[4,3-c]pyridin-8-yl)pyrrolidin-2-one (70 mg, 0.24 mmol) and 4-(5-bromopyridin-3-yl)morpholin-3-one (79 mg, 0.30 mmol) was added to the mixture. The resulting mixture was stirred at 100° C. for 18 h under N₂. A black suspension was formed. LCMS showed starting material was consumed completely and the purity of the desired product (Rt=0.567 min; MS Calcd: 471.2. MS Found: 472.2 [M+H]⁺). The reaction mixture was filtered and the filtrate was concentrated. The crude product was purified by prep-HPLC (0.05% NH₃.H₂O as an additive) and lyophilized to give 4-(5-((5-methyl-8-(2-oxopyrrolidin-1-yl)-5H-chromeno[4,3-c]pyridin-3-yl)amino)pyridin-3-yl)morpholin-3-one (27 mg, yield: 24%) as a yellow solid.

$^1$H NMR (400 MHz, DMSO-d$_6$) δ 1.53 (3H, d, J=2.4 Hz), 2.01-2.08 (2H, m), 2.50 (2H, overlap with DMSO), 3.78 (2H, t, J=5.2 Hz), 3.83 (2H, t, J=7.6 Hz), 4.01 (2H, t, J=5.2 Hz), 4.52 (2H, s), 5.27 (1H, q, J=6.6 Hz), 6.75 (1H, s), 7.31 (1H, dd, J=8.4, 2.0 Hz), 7.39 (1H, d, J=2.0 Hz), 7.88 (1H, d, J=8.8 Hz), 8.17 (1H, d, J=2.0 Hz), 8.35 (1H, t, J=2.0 Hz), 8.68 (2H, m), 9.58 (1H, brs).

Example 96: 1-(5-methyl-3-((5-morpholinopyridin-3-yl)amino)-5H-chromeno[4,3-c]pyridin-8-yl)pyrrolidin-2-one

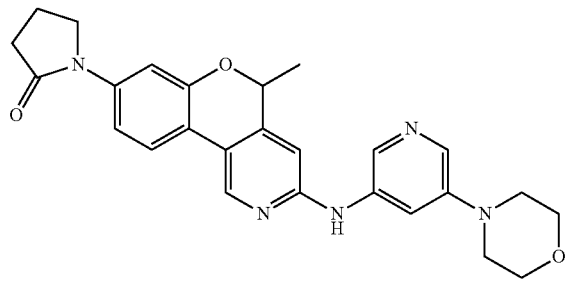 [SMILES: CC1Oc2cc(N3CCCC3=O)ccc2-c2cnc(Nc3cncc(N4CCOCC4)c3)cc21]

Step 1: Preparation of 4-(5-bromopyridin-3-yl)morpholine

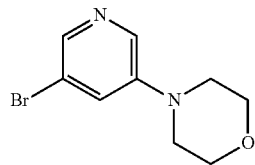

To a solution of 3,5-dibromopyridine (1.10 g, 4.60 mmol) in dioxane (2 mL) was added morpholine (200 mg, 2.30 mmol), Cs$_2$CO$_3$ (1.10 g, 3.20 mmol), XantPhos (39 mg, 0.068 mmol) and Pd$_2$(dba)$_3$ (62 mg, 0.068 mmol). The resulting mixture was degassed and purged with N$_2$ for three times and then stirred at 90° C. for 5 h under N$_2$. A yellow suspension was formed. TLC-Plate 1 (EtOAc/PE=1:1) showed starting material was consumed and new spots were formed at Rf=0.22 and 0.82. LCMS showed the starting material was consumed nearly and the purity of the desired product (Rt=0.439 min; MS Calcd: 242.0. MS Found: 244.7 [M+H]$^+$). H$_2$O (15 mL) and DCM (20 mL) was added to the reaction mixture and then separated. The combined organic layer was washed with brine (10 mL) dried over anhydrous Na$_2$SO$_4$ and concentrated. The crude product was purified by combi flash (50% EtOAc in pentane) and concentrated to give 4-(5-bromopyridin-3-yl)morpholine (300 mg, yield: 38%) as a light yellow solid.

$^1$H NMR (400 MHz, CDCl$_3$) δ 3.21 (4H, t, J=5.2 Hz), 3.87 (4H, t, J=4.8 Hz), 7.30 (1H, t, J=2.0 Hz), 8.16 (1H, d, J=2.0 Hz), 8.21 (1H, d, J=2.4 Hz).

Step 2: Preparation of 1-(5-methyl-3-((5-morpholinopyridin-3-yl)amino)-5H-chromeno[4,3-c]pyridin-8-yl)pyrrolidin-2-one

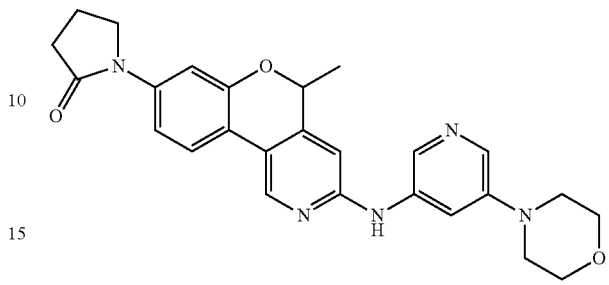

To a mixture of Pd$_2$(dba)$_3$ (15 mg, 0.017 mmol) in dioxane (1 mL) was added BrettPhos (18 mg, 0.034 mmol). The resulting mixture was degassed and purged with N$_2$ and then stirred at 50° C. for 10 min. The reaction mixture was cooled to 20° C. and 1-(3-amino-5-methyl-5H-chromeno[4,3-c]pyridin-8-yl)pyrrolidin-2-one (50 mg, 0.17 mmol), 4-(5-bromopyridin-3-yl)morpholine (54 mg, 0.22 mmol) and Cs$_2$CO$_3$ (165 mg, 0.500 mmol) were added and then stirring at 100° C. for 18 h under N$_2$. A black suspension was formed. LCMS showed the starting material was consumed completely and the purity of the desired product (Rt=0.701 min; MS Calcd: 457.1. MS Found: 458.2 [M+H]$^+$). The reaction mixture was filtered and the filtrate was concentrated. The crude product was purified by prep-HPLC (0.05% NH$_3$.H$_2$O as an additive) and lyophilized to give 1-(5-methyl-3-((5-morpholinopyridin-3-yl)amino)-5H-chromeno[4,3-c]pyridin-8-yl)pyrrolidin-2-one (27.7 mg, yield: 35%) as an off-white solid.

$^1$H NMR (400 MHz, DMSO-d$_6$) δ 1.52 (3H, d, J=6.8 Hz), 2.01-2.09 (2H, m), 2.50 (2H, overlap with DMSO), 3.15 (4H, t, J=4.8 Hz), 3.77 (4H, t, J=4.8 Hz), 3.83 (2H, t, J=7.6 Hz), 5.26 (1H, q, J=6.4 Hz), 6.72 (1H, s), 7.30 (1H, dd, J=8.4, 2.4 Hz), 7.38 (1H, d, J=2.4 Hz), 7.87 (3H, dd, J=8.8 Hz, 2.0 Hz), 8.28 (1H, d, J=2.0 Hz), 8.66 (1H, s), 9.32 (1H, brs).

Example 97: 1-(5-methyl-3-((5-methylpyridin-3-yl)amino)-5H-chromeno[4,3-c]pyridin-8-yl)pyrrolidin-2-one

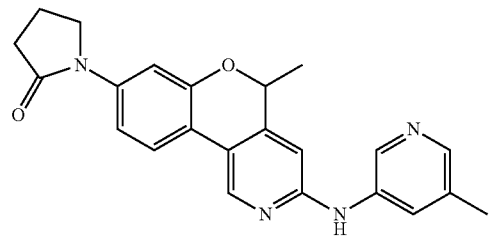 [SMILES: Cc1cncc(Nc2cc3c(cn2)-c2ccc(N4CCCC4=O)cc2OC3C)c1]

A mixture of Pd$_2$(dba)$_3$ (15 mg, 0.017 mmol) and BrettPhos (18 mg, 0.034 μmol) in dioxane (2 mL) was degassed and purged with N$_2$ for three times. The resulting mixture was stirred 50° C. for 30 min. 1-(3-Chloro-5-methyl-5H-chromeno[4,3-c]pyridin-8-yl)pyrrolidin-2-one (53 mg, 0.17 mmol), 5-methylpyridin-3-amine (24 mg, 0.22 mmol) were added. And then the resulting mixture was stirred at 100° C.

for 16 h under N$_2$. A black suspension was formed. LCMS showed starting material was consumed completely and the purity of the desired product (Rt=0.698 min; MS Calcd: 386.1. MS Found: 387.0 [M+H]$^+$). The reaction mixture was filtered and the filtrate was concentrated. The crude product was purified by prep-HPLC (0.05% NH$_3$.H$_2$O as an additive) and lyophilized to give 1-(5-methyl-3-((5-methylpyridin-3-yl)amino)-5H-chromeno[4,3-c]pyridin-8-yl)pyrrolidin-2-one (14.3 mg, yield: 22%) as a white solid.

$^1$H NMR (400 MHz, DMSO-d$_6$) δ 1.53 (3H, d, J=6.8 Hz), 2.02-2.09 (2H, m), 2.28 (3H, s) 2.52 (2H, overlap with DMS), 3.84 (2H, t, J=7.6 Hz), 5.27 (1H, q, J=6.5 Hz), 6.72 (1H, s), 7.31 (1H, dd, J=8.4, 2.4 Hz), 7.40 (1H, d, J=2.0 Hz), 7.87 (1H, d, J=8.8 Hz), 7.95 (1H, d, J=2.0 Hz), 8.08 (1H, d, J=2.0 Hz), 8.60 (1H, d, J=2.0 Hz), 8.68 (1H, s), 9.36 (1H, brs).

Example 98: methyl (5-((5-methyl-8-(2-oxopyrrolidin-1-yl)-5H-chromeno[4,3-c]pyridin-3-yl)amino)pyridin-3-yl)carbamate

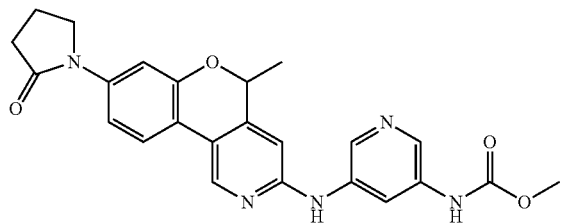 [SMILES: COC(=O)Nc1cncc(Nc2cc3c(cn2)-c2ccc(N4CCCC4=O)cc2OC3C)c1]

Step 1: Preparation of methyl (5-bromopyridin-3-yl)carbamate

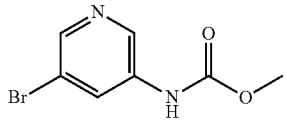

To a solution of 5-bromopyridin-3-amine (1.00 g, 5.78 mmol) and pyridine (1.4 mL) in DCM (10 mL) was added methyl chloroformate (1.36 g, 14.4 mmol). The resulting mixture was stirred at 24° C. for 2 h. A yellow solution was formed. LCMS (Rt=0.658 min; MS Calcd: 230.0. MS Found: 230.7 [M+H]$^+$). The reaction mixture was diluted with 10% aqueous CuSO$_4$ (60 mL), then separated and the aqueous layer was extracted with DCM (20 mL×3). The combined organic layer was concentrated and the crude product was triturated with MTBE (13 mL) to give methyl (5-bromopyridin-3-yl)carbamate (900 mg, yield: 67%) as a gray solid.

$^1$H NMR (400 MHz, CDCl$_3$) δ 3.81 (3H, s), 6.93 (1H, s), 8.26 (1H, s), 8.40-8.75 (2H, m)

Step 2: Preparation of methyl (5-((5-methyl-8-(2-oxopyrrolidin-1-yl)-5H-chromeno[4,3-c]pyridin-3-yl)amino)pyridin-3-yl)carbamate

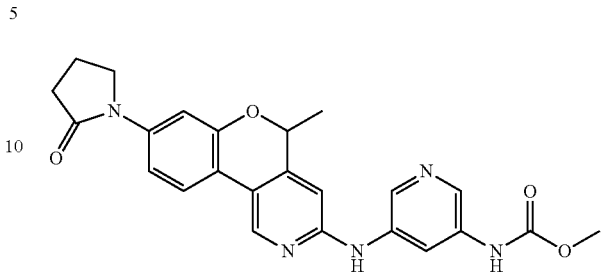

To a suspension of 1-(3-amino-5-methyl-5H-chromeno[4,3-c]pyridin-8-yl)pyrrolidin-2-one (70 mg, 0.24 mmol), methyl (5-bromopyridin-3-yl)carbamate (66 mg, 0.28 mmol), BrettPhos (25 mg, 0.047 mmol) and Cs$_2$CO$_3$ (232 mg, 0.711 mmol) in anhydrous dioxane (3 mL) was added Pd$_2$(dba)$_3$ (22 mg, 0.024 mmol) under N$_2$ atmosphere. The resulting mixture was stirred at 90° C. for 12 h under N$_2$ atmosphere. A black brown suspension was formed. LCMS (Rt=0.589 min; MS Calcd: 445.1. MS Found: 446.0 [M+H]$^+$). The reaction mixture was concentrated and the crude product was purified by prep-HPLC (0.225% FA as an additive) and lyophilized to give methyl (5-((5-methyl-8-(2-oxopyrrolidin-1-yl)-5H-chromeno[4,3-c]pyridin-3-yl)amino)pyridin-3-yl)carbamate (35.5 mg, yield: 32%) as a yellow solid.

$^1$H NMR (400 MHz, DMSO-d$_6$) δ 1.54 (3H, d, J=6.8 Hz), 2.02-2.09 (2H, m), 2.5-2.53 (2H, overlapped with DMSO), 3.72 (3H, s), 3.84 (2H, t, J=7.9 Hz), 5.29 (1H, q, J=6.6 Hz), 6.77 (1H, s), 7.33 (1H, dd, J=8.7, 2.1 Hz), 7.40 (1H, d, J=2.0 Hz), 7.91 (1H, d, J=8.8 Hz), 8.27 (1H, s), 8.42 (1H, s), 8.68 (1H, s), 8.78 (1H, s), 9.74 (1H, brs), 10.09 (1H, brs).

Example 99: 1-methyl-3-(5-((5-methyl-8-(2-oxopyrrolidin-1-yl)-5H-chromeno[4,3-c]pyridin-3-yl)amino)pyridin-3-yl)urea

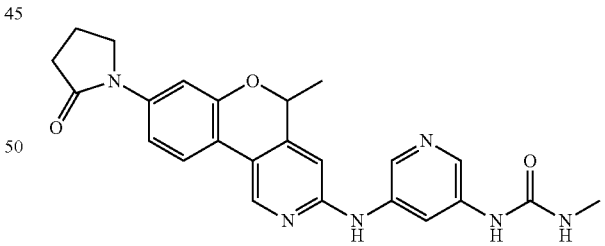

To a mixture of 1-(3-amino-5-methyl-5H-chromeno[4,3-c]pyridin-8-yl)pyrrolidin-2-one (70 mg, 0.24 mmol), 1-(5-bromopyridin-3-yl)-3-methylurea (65 mg, 0.28 mmol), Cs$_2$CO$_3$ (232 mg, 0.711 mmol) in dioxane (3 mL) was added Pd$_2$(dba)$_3$ (22 mg, 0.024 mmol) and BrettPhos (25 mg, 0.047 mmol) under N$_2$ atmosphere. The resulting mixture was stirred at 100° C. for 12 h under N$_2$ atmosphere. A red solution was formed. LCMS (Rt=0.682 min; MS Calcd: 444.1. MS Found: 445.1 [M+H]$^+$). The reaction mixture was filtered and the filtrated was concentrated. The residue was purified by prep-HPLC (0.225% FA as an additive) and lyophilized to give 1-methyl-3-(5-((5-methyl-8-(2-oxopyrrolidin-1-yl)-5H-chromeno[4,3-c]pyridin-3-yl)amino)pyridin-3-yl)urea (8.7 mg, yield: 8%) as a yellow solid.

¹H NMR (400 MHz, DMSO-d$_6$) δ 1.55 (3H, d, J=6.5 Hz), 2.03-2.10 (2H, m), 2.52-2.53 (2H, overlapped with DMSO), 2.69 (3H, d, J=4.5 Hz), 3.85 (2H, t, J=7.9 Hz), 5.31 (1H, q, J=6.7 Hz), 6.48 (1H, d, J=4.8 Hz), 6.81 (1H, s), 7.35 (1H, dd, J=8.5, 2.3 Hz), 7.41 (1H, d, J=2.0 Hz), 7.92 (1H, d, J=8.8 Hz), 8.42 (1H, t, J=2.0 Hz), 8.46 (1H, d, J=1.8 Hz), 8.71 (1H, s), 8.87 (1H, d, J=1.8 Hz), 9.38 (1H, brs), 10.00 (1H, brs).

Example 100: N-(5-((5-methyl-8-(2-oxopyrrolidin-1-yl)-5H-chromeno[4,3-c]pyridin-3-yl)amino)pyridin-3-yl)acetamide

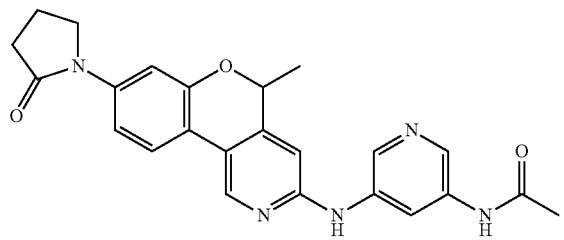 [SMILES: CC(=O)Nc1cncc(Nc2cc3c(cn2)-c2ccc(N4CCCC4=O)cc2OC3C)c1]

Step 1: Preparation of N-(5-bromopyridin-3-yl)acetamide

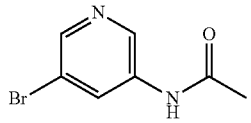

To a solution of 5-bromopyridin-3-amine (1.00 g, 5.78 mmol) in pyridine (10 mL) was added acetic anhydride (708 mg, 6.94 mmol) at N$_2$ atmosphere. The resulting mixture was stirred at 25° C. for 12 h. A yellow solution was formed. LCMS (Rt=0.422 min; MS Calcd: 214.0. MS Found: 214.7 [M+H]$^+$). The reaction mixture was concentrated under reduced pressure. Water (20 mL) was added to the resulting mixture and then extracted with EtOAc (20 mL×3). The combined organic layer was washed with saturated aqueous NaHCO$_3$ (50 mL×3), brine (20 mL), dried over anhydrous Na$_2$SO$_4$ and concentrated to give N-(5-bromopyridin-3-yl)acetamide (1.21 g, yield: 97%) as a yellow solid.

¹HNMR (400 MHz, CDCl$_3$) δ 2.21 (3H, s), 7.78 (1H, brs), 8.37-8.41 (1H, m), 8.42-8.47 (2H, m)

Step 2: Preparation of N-(5-((5-methyl-8-(2-oxopyrrolidin-1-yl)-5H-chromeno[4,3-c]pyridin-3-yl)amino)pyridin-3-yl)acetamide

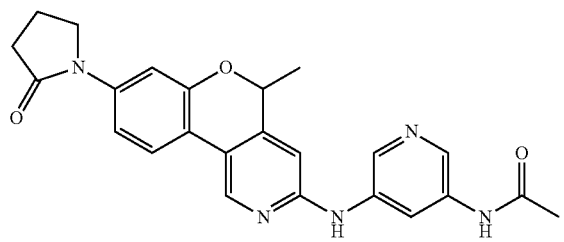 [SMILES: CC(=O)Nc1cncc(Nc2cc3c(cn2)-c2ccc(N4CCCC4=O)cc2OC3C)c1]

A mixture of BrettPhos (25 mg, 0.047 mmol) and Pd$_2$(dba)$_3$ (22 mg, 0.024 mmol) in anhydrous dioxane (1 mL) was stirred at 50° C. for 5 min under N$_2$ atmosphere. Then 1-(3-amino-5-methyl-5H-chromeno[4,3-c]pyridin-8-yl)pyrrolidin-2-one (70 mg, 0.24 mmol), N-(5-bromopyridin-3-yl)acetamide (61 mg, 0.28 mmol) and Cs$_2$CO$_3$ (232 mg, 0.711 mmol) were added under N$_2$ atmosphere and the resulting mixture was stirred at 100° C. for 12 h under N$_2$ atmosphere. A black suspension was formed. LCMS (Rt=0.721 min; MS Calcd: 429.1; MS Found: 430.0 [M+H]$^+$). The reaction mixture was filtered and the filtrate was concentrated. The crude product was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)acetamide (31.2 mg, yield: 31%) as a yellow solid.

¹H NMR (400 MHz, DMSO-d$_6$) δ 1.55 (3H, d, J=6.3 Hz), 2.04-2.12 (2H, m), 2.13 (3H, s), 2.52-2.53 (2H, overlapped with DMSO), 3.84 (2H, t, J=7.5 Hz), 5.31 (1H, q, J=6.8 Hz), 6.80 (1H, s), 7.35 (1H, d, J=8.7 Hz), 7.40 (1H, d, J=2.0 Hz), 7.91 (1H, d, J=8.5 Hz), 8.50 (1H, d, J=1.8 Hz), 8.57 (1H, s), 8.70 (1H, s), 8.92 (1H, s), 9.94 (1H, brs), 10.51 (1H, brs).

Example 101: 2-hydroxy-N-(5-((5-methyl-8-(2-oxopyrrolidin-1-yl)-5H-chromeno[4,3-c]pyridin-3-yl)amino)pyridin-3-yl)acetamide

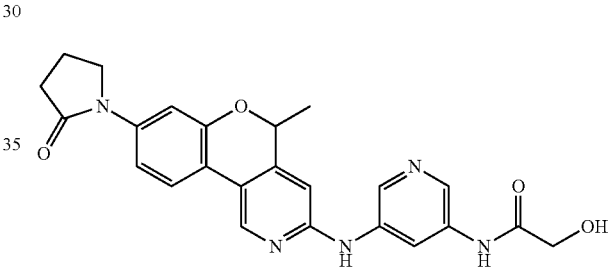

Step 1: Preparation of 2-acetoxyacetic acid

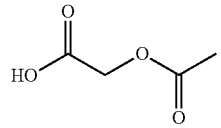

To a solution of 2-hydroxyacetic acid (500 mg, 6.57 mmol) in pyridine (2 mL) was added acetic anhydride (691 mg, 6.77 mmol) at 0° C. The resulting mixture was stirred at 25° C. for 12 h. A yellow solution was formed. The reaction mixture was concentrated and the residue was diluted with saturated aqueous NaHCO$_3$ (10 mL) and EtOAc (20 mL) then separated. The aqueous layer was acidified with 1N aqueous HCl to adjust pH=6 and extracted with EtOAc (30 mL×2), DCM (20 mL×2). The combined organic concentrated to give 2-acetoxyacetic acid (100 mg, crude) as a white solid, which was directly used for next step without purification.

¹H NMR (400 MHz, DMSO-d$_6$) δ 1.98 (3H, s), 4.09 (2H, s)

Step 2: Preparation of tert-butyl (5-((5-methyl-8-(2-oxopyrrolidin-1-yl)-5H-chromeno[4,3-c]pyridin-3-yl)amino)pyridin-3-yl)carbamate

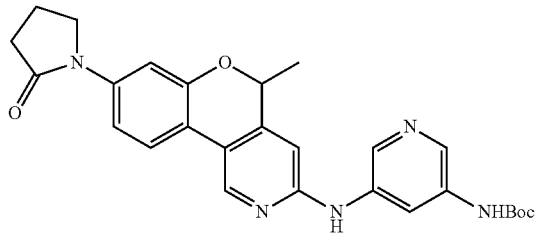 [SMILES: CC1Oc2cc(N3CCCC3=O)ccc2-c2cnc(Nc3cncc(NC(=O)OC(C)(C)C)c3)cc21]

To a mixture of 1-(3-amino-5-methyl-5H-chromeno[4,3-c]pyridin-8-yl)pyrrolidin-2-one (1.60 g, 5.42 mmol), tert-butyl (5-bromopyridin-3-yl)carbamate (1.78 g, 6.50 mmol), Cs$_2$CO$_3$ (5.30 g, 16.3 mmol) and BrettPhos (582 mg, 1.08 mmol) in anhydrous dioxane (40 mL) was added Pd$_2$(dba)$_3$ (496 mg, 0.542 mmol) under N$_2$ atmosphere. Then the resulting mixture was stirred at 90° C. for 16 h under N$_2$ atmosphere. A red suspension was formed. LCMS (Rt=0.753 min; MS Calcd: 487.2. MS Found: 488.3 [M+H]$^+$). The reaction mixture was diluted with water (30 mL), THF (20 mL) and EtOAc (50 mL) and separated. The aqueous layer was extracted with THF/EtOAc (30 mL×3, 1/2). The combined organic layer was washed with brine (50 mL), dried over anhydrous Na$_2$SO$_4$ and concentrated. The residue was purified by Combi Flash (3% MeOH in DCM) to give tert-butyl (5-((5-methyl-8-(2-oxopyrrolidin-1-yl)-5H-chromeno[4,3-c]pyridin-3-yl)amino)pyridin-3-yl)carbamate (1.90 g, yield: 68%) as a red solid.

$^1$H NMR (400 MHz, CDCl$_3$) δ 1.52 (9H, s), 1.58 (3H, d, J=6.8 Hz), 2.11-2.20 (2H, m), 2.62 (2H, t, J=8.2 Hz), 3.85 (2H, t, J=7.8 Hz), 5.12 (1H, q, J=6.5 Hz), 6.65 (1H, s), 6.85 (1H, s), 7.08 (1H, s), 7.25 (1H, d, J=2.1 Hz) 7.33 (1H, dd, J=8.7, 2.1 Hz), 7.64 (1H, d, J=8.5 Hz), 8.13 (1H, d, J=2.3 Hz), 8.30-8.32 (2H, m), 8.51 (1H, brs).

Step 3: Preparation of 1-(3-((5-aminopyridin-3-yl)amino)-5-methyl-5H-chromeno[4,3-c]pyridin-8-yl)pyrrolidin-2-one

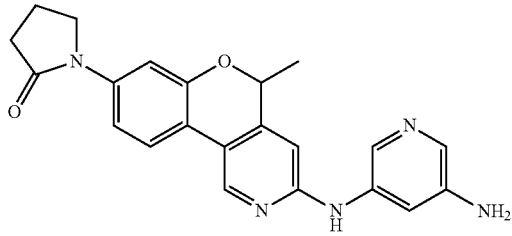 [SMILES: CC1Oc2cc(N3CCCC3=O)ccc2-c2cnc(Nc3cncc(N)c3)cc21]

To a suspension of tert-butyl (5-((5-methyl-8-(2-oxopyrrolidin-1-yl)-5H-chromeno[4,3-c]pyridin-3-yl)amino)pyridin-3-yl)carbamate (1.90 g, 3.90 mmol) in EtOAc (4 mL) was added HCl/EtOAc (40 mL, 4 M in EtOAc). The resulting mixture was stirred at 20° C. for 12 h. A yellow suspension was formed. LCMS (Rt=0.571 min; MS Calcd: 387.1; MS Found: 388.1[M+H]$^+$). The reaction mixture was concentrated to give 1-(3-((5-aminopyridin-3-yl)amino)-5-methyl-5H-chromeno[4,3-c]pyridin-8-yl)pyrrolidin-2-one (2.70 g, crude, HCl salt) as a yellow solid, which was used for the next step directly.

$^1$H NMR (400 MHz, DMSO-d$_6$) δ 1.53 (3H, d, J=6.8 Hz), 1.99-2.10 (2H, m), 2.51-2.53 (2H, overlapped with DMSO), 3.84 (2H, t, J=7.8 Hz), 5.30 (1H, q, J=6.7 Hz), 6.94 (1H, s), 7.33 (1H, dd, J=8.5, 2.2 Hz), 7.40 (1H, d, J=2.3 Hz), 7.61 (1H, s), 7.79 (1H, t, J=2.1 Hz), 7.90 (1H, t, J=8.5 Hz), 8.65 (1H, s), 8.71 (1H, s), 10.47 (1H, brs), 10.95 (1H, brs), 11.90 (1H, brs).

Step 4: Preparation of 2-((5-((5-methyl-8-(2-oxopyrrolidin-1-yl)-5H-chromeno[4,3-c]pyridin-3-yl)amino)pyridin-3-yl)amino)-2-oxoethylacetate

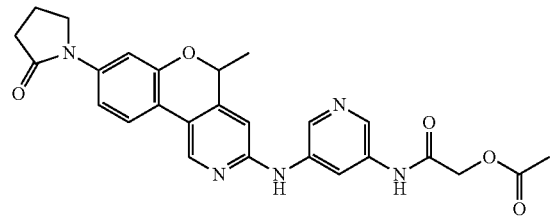 [SMILES: CC(=O)OCC(=O)Nc1cncc(Nc2cc3c(cn2)-c2ccc(N4CCCC4=O)cc2OC3C)c1]

A mixture of 1-(3-((5-aminopyridin-3-yl)amino)-5-methyl-5H-chromeno[4,3-c]pyridin-8-yl)pyrrolidin-2-one (60 mg, 0.14 mmol), 2-acetoxyacetic acid (33 mg, 0.28 mmol) and EDCI.HCl (54 mg, 0.28 mmol) in pyridine (3 mL) was stirred at 50° C. for 2 h. A yellow solution was formed. LCMS (Rt=0.692 min; MS Calcd: 487.2. MS Found: 488.3 [M+H]$^+$). The reaction mixture was diluted with water (5 mL) and EtOAc (10 mL) then separated. The aqueous layer was extracted with EtOAc (10 mL×4). The combined organic layer was dried over anhydrous Na$_2$SO$_4$ and concentrated under reduced pressure to give 2-((5-((5-methyl-8-(2-oxopyrrolidin-1-yl)-5H-chromeno[4,3-c]pyridin-3-yl)amino)pyridin-3-yl)amino)-2-oxoethyl acetate (82 mg, crude) as yellow gum, which was directly used for next step without purification.

Step 5: Preparation of 2-hydroxy-N-(5-((5-methyl-8-(2-oxopyrrolidin-1-yl)-5H-chromeno[4,3-c]pyridin-3-yl)amino)pyridin-3-yl)acetamide

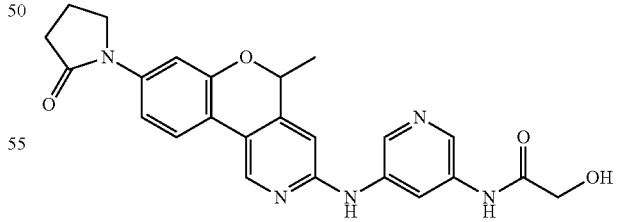

To a solution of 2-((5-((5-methyl-8-(2-oxopyrrolidin-1-yl)-5H-chromeno[4,3-c]pyridin-3-yl)amino)-2-oxoethyl acetate (82 mg, 0.17 mmol) in THF/MeOH (6 mL, 2/1) was added 1N aqueous NaOH (2 mL) at 25° C. The resulting mixture was stirred at 25° C. for 2 h. A yellow solution was formed. LCMS (Rt=0.561 min; MS Calcd: 445.1. MS Found: 446.1 [M+H]$^+$). The reaction mixture was diluted with EtOAc (10 mL) and H$_2$O (5 mL)

then separated. The aqueous layer was extracted with EtOAc (20 mL×3). The combined organic layer was washed with brine (15 mL), dried over anhydrous $Na_2SO_4$ and concentrated. The residue was purified by prep-HPLC (0.225% FA as an additive) and lyophilized, then triturated with MeCN (0.5 mL) to give 2-hydroxy-N-(5-((5-methyl-8-(2-oxopyrrolidin-1-yl)-5H-chromeno[4,3-c]pyridin-3-yl)amino)pyridin-3-yl)acetamide (9.9 mg, yield: 13% for 3 steps) as a yellow solid.

$^1$H NMR (400 MHz, DMSO-$d_6$) δ 1.55 (3H, d, J=6.5 Hz), 1.99-2.10 (2H, m), 2.50-2.52 (2H, m, overlapped with DMSO), 3.85 (2H, t, J=8.0 Hz), 4.07 (2H, s), 5.31 (1H, q, J=6.7 Hz), 6.80 (1H, s), 7.34 (1H, dd, J=8.5, 2.3 Hz), 7.41 (1H, d, J=2.3 Hz), 7.91 (1H, d, J=8.5 Hz), 8.52 (1H, s), 8.67-8.71 (2H, m), 8.85 (1H, s), 9.77 (1H, brs), 10.14 (1H, brs).

Example 102: 1-(5-((5-methyl-8-(2-oxopyrrolidin-1-yl)-5H-chromeno[4,3-c]pyridin-3-yl)amino)pyridin-3-yl)-3-(pyridin-2-yl)urea

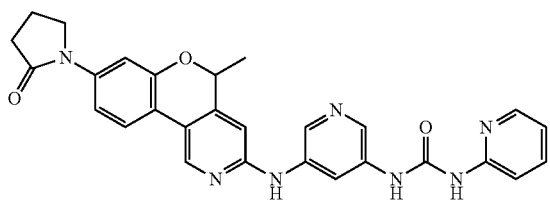 [SMILES: CC1Oc2cc(N3CCCC3=O)ccc2-c2cnc(Nc3cncc(NC(=O)Nc4ccccn4)c3)cc21]

Step 1: Preparation of 1-(5-bromopyridin-3-yl)-3-(pyridin-2-yl)urea

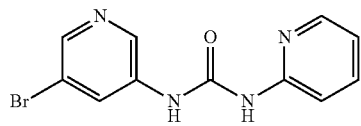 [SMILES: O=C(Nc1cncc(Br)c1)Nc1ccccn1]

A solution of pyridine (0.7 mL) and triphosgene (2.57 g, 8.66 mmol) in DCM (6 mL) was stirred at 0° C. for 20 minutes. A solution of 5-bromopyridin-3-amine (300 mg, 1.73 mmol) in DCM (6 mL) was added dropwise at 0° C. The resulting mixture was stirred at 25° C. for 1 hour. Then pyridin-2-amine (136 mg, 1.45 mmol) was added at 0° C. The resulting mixture was stirred at 25° C. for 12 h. A light red suspension was formed. LCMS showed the purity of desired product (Rt=0.682 min; MS Calcd: 292.0. MS Found: 293.1 [M+H]$^+$). The reaction mixture was diluted with DCM (20 mL), $H_2O$ (10 mL) and separated. The aqueous layer was extracted with DCM (15 mL×2) and EtOAc/THF (15 mL×2, 2/1). The combined organic layer was dried over anhydrous $Na_2SO_4$ and concentrated. The residue was purified by Combi Flash (3% MeOH in DCM) to give 1-(5-bromopyridin-3-yl)-3-(pyridin-2-yl)urea (100 mg, yield: 20%) as a white solid.

$^1$H NMR (400 MHz, DMSO-$d_6$) δ 7.05 (1H, t, J=6.4 Hz), 7.45 (1H, d, J=8.0 Hz), 7.78 (1H, t, J=7.9 Hz), 8.31-8.39 (3H, m), 8.63 (1H, s), 9.70 (1H, brs), 10.98 (1H, brs).

Step 2: Preparation of 1-(5-((5-methyl-8-(2-oxopyrrolidin-1-yl)-5H-chromeno[4,3-c]pyridin-3-yl)amino)pyridin-3-yl)-3-(pyridin-2-yl)urea

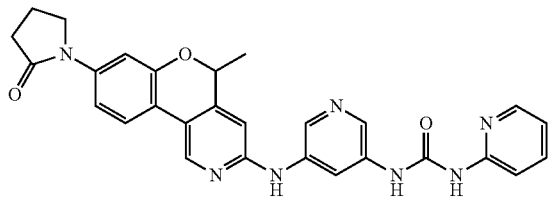 [SMILES: CC1Oc2cc(N3CCCC3=O)ccc2-c2cnc(Nc3cncc(NC(=O)Nc4ccccn4)c3)cc21]

To a suspension of 1-(3-amino-5-methyl-5H-chromeno[4,3-c]pyridin-8-yl)pyrrolidin-2-one (60 mg, 0.20 mmol), 1-(5-bromopyridin-3-yl)-3-(pyridin-2-yl)urea (70 mg, 0.24 mol), BrettPhos (22 mg, 0.041 mmol) and $Cs_2CO_3$ (199 mg, 0.609 mmol) in anhydrous dioxane (10 mL) was added $Pd_2(dba)_3$ (18 mg, 0.020 mmol) under $N_2$ atmosphere. The resulting mixture was stirred at 90° C. for 12 h under $N_2$ atmosphere. A black brown suspension was formed. LCMS (Rt=0.743 min; MS Calcd: 507.2. MS Found: 508.4 [M+H]$^+$). The reaction mixture was filtered and the filtrate was concentrated. The residue was purified by prep-HPLC (0.225% FA as an additive) twice and lyophilized to give 1-(5-((5-methyl-8-(2-oxopyrrolidin-1-yl)-5H-chromeno[4,3-c]pyridin-3-yl)amino)pyridin-3-yl)-3-(pyridin-2-yl)urea (4.4 mg, yield: 4%) as a white solid.

$^1$H NMR (400 MHz, DMSO-$d_6$) δ 1.55 (3H, d, J=6.5 Hz), 2.03-2.10 (2H, m), 2.51-2.53 (2H, overlapped with DMSO), 3.85 (2H, t, J=7.8 Hz), 5.29 (1H, q, J=6.8 Hz), 6.77 (1H, s), 7.03-7.06 (1H, m), 7.33 (1H, dd, J=8.5, 2.1 Hz), 7.41 (1H, d, J=2.2 Hz), 7.54 (1H, d, J=8.3 Hz), 7.58-7.80 (1H, m), 7.91 (1H, d, J=8.7 Hz), 8.26 (1H, d, J=2.2 Hz), 8.32 (1H, d, J=4.3 Hz), 8.45 (1H, t, J=2.1 Hz), 8.63 (1H, d, J=2.2 Hz), 8.69 (1H, s), 9.20 (1H, brs), 9.52 (1H, brs), 10.57 (1H, brs).

Example 103: 1-benzyl-3-(5-((5-methyl-8-(2-oxopyrrolidin-1-yl)-5H-chromeno[4,3-c]pyridin-3-yl)amino)pyridin-3-yl)urea

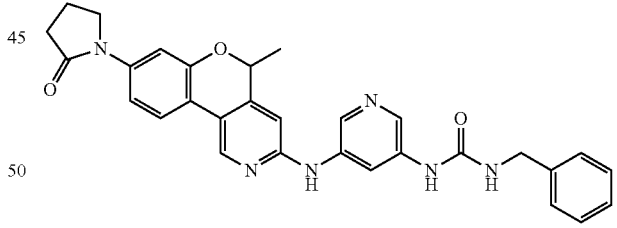

Step 1: Preparation of 1-benzyl-3-(5-bromopyridin-3-yl)urea

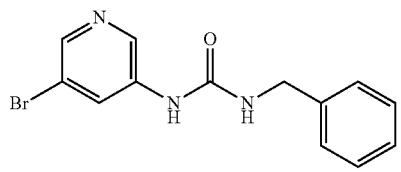 [SMILES: O=C(NCc1ccccc1)Nc1cncc(Br)c1]

To a mixture of 5-bromopyridin-3-amine (1.00 g, 5.80 mmol) and Et₃N (1.6 mL) in DCM (10 mL) was added (isocyanatomethyl)benzene (924 mg, 6.94 mmol) at 0° C. The resulting mixture was stirred at 25° C. for 12 h. A white suspension was formed. LCMS (Rt=0.601 min; MS Calcd: 305.0. MS Found: 305.9 [M+H]⁺). The reaction mixture was concentrated and the crude product was purified by Combi Flash (5% MeOH in DCM) then triturated with DCM/PE (5 mL, 1/3) to give a mixture of 1-benzyl-3-(5-bromopyridin-3-yl)urea and side product 3-((3-benzylureido)methyl)benzene-1-ylium, which was used for next step without purification.

Step 2: Preparation of 1-benzyl-3-(5-((5-methyl-8-(2-oxopyrrolidin-1-yl)-5H-chromeno[4,3-c]pyridin-3-yl)amino)pyridin-3-yl)urea

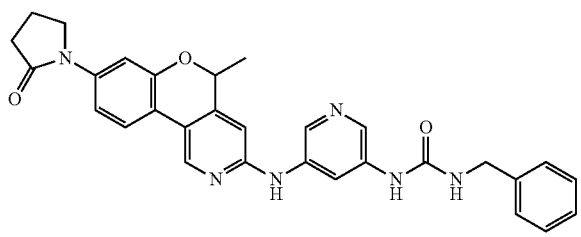 [SMILES: CC1Oc2cc(N3CCCC3=O)ccc2-c2cnc(Nc3cncc(NC(=O)NCc4ccccc4)c3)cc21]

A mixture of 1-(3-amino-5-methyl-5H-chromeno[4,3-c]pyridin-8-yl)pyrrolidin-2-one (70 mg, 0.24 mmol), 1-benzyl-3-(5-bromopyridin-3-yl)urea (116 mg, crude), Cs₂CO₃ (232 mg, 0.711 mmol), BrettPhos (25 mg, 0.047 mmol) and Pd₂(dba)₃ (22 mg, 0.024 mol) in anhydrous dioxane (0.5 mL) were stirred at 100° C. for 12 h under N₂ atmosphere. A white suspension was formed. LCMS (Rt=0.745 min; MS Calcd: 520.2. MS Found: 521.1 [M+H]⁺). The reaction mixture was filtered and the filtrate was concentrated. The crude product was purified by prep-HPLC (0.225% FA as an additive) and lyophilized to give 1-benzyl-3-(5-((5-methyl-8-(2-oxopyrrolidin-1-yl)-5H-chromeno[4,3-c]pyridin-3-yl)amino)pyridin-3-yl)urea (12.9 mg, yield: 9%) as a white solid.

¹H NMR (400 MHz, DMSO-d₆) δ 1.53 (3H, d, J=6.6 Hz), 2.01-2.09 (2H, m), 2.51-2.53 (2H, overlapped with DMSO), 3.85 (2H, t, J=8.0 Hz), 4.32 (2H, d, J=5.9 Hz), 5.27 (1H, q, J=6.4 Hz), 6.79 (1H, s), 6.81 (1H, t, J=5.9 Hz), 7.23-7.29 (1H, m), 7.30-7.36 (4H, m), 7.39 (1H, d, J=2.2 Hz), 7.88 (1H, d, J=8.7 Hz), 8.13 (1H, s), 8.23 (1H, s), 8.34 (1H, s), 8.58 (1H, s), 8.90 (1H, s), 9.52 (1H, brs), 10.57 (1H, brs).

Example 104: N-(5-((5-methyl-8-(2-oxopyrrolidin-1-yl)-5H-chromeno[4,3-c]pyridin-3-yl)amino)pyridin-3-yl)-2-oxopyrrolidine-3-carboxamide

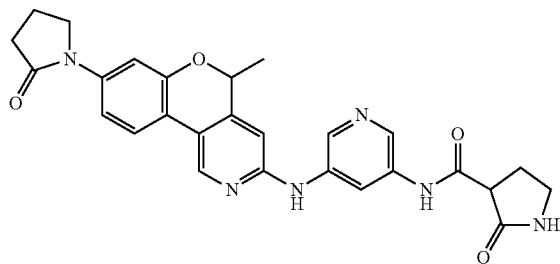 [SMILES: CC1Oc2cc(N3CCCC3=O)ccc2-c2cnc(Nc3cncc(NC(=O)C4CCNC4=O)c3)cc21]

A solution of 1-(3-((5-aminopyridin-3-yl)amino)-5-methyl-5H-chromeno[4,3-c]pyridin-8-yl)pyrrolidin-2-one (60 mg, 0.14 mmol), 2-oxopyrrolidine-3-carboxylic acid (27 mg, 0.21 mmol) and EDCI.HCl (40 mg, 0.21 mmol) in pyridine (4 mL) was stirred at 50° C. for 2 h under N₂ atmosphere. A brown solution was formed. LCMS (Rt=0.675 min; MS Calcd: 498.2. MS Found: 499.3 [M+H]⁺). The reaction mixture was diluted with saturated aqueous NaHCO₃ (5 mL) and DCM (15 mL) then separated. The aqueous layer was extracted with DCM (15 mL×3). The combined organic layer was concentrated and the residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)-2-oxopyrrolidine-3-carboxamide (36.3 mg, yield: 49%) as a yellow solid.

¹H NMR (400 MHz, DMSO-d₆) δ 1.54 (3H, d, J=6.5 Hz), 2.01-2.09 (2H, m), 2.25-2.28 (1H, m), 2.35-2.41 (1H, m), 2.51-2.53 (2H, overlap with DMSO), 3.20-3.36 (3H, m), 3.83 (2H, t, J=8.0 Hz), 5.27 (1H, q, J=6.6 Hz), 6.75 (1H, s), 7.31 (1H, dd, J=8.7, 1.9 Hz), 7.39 (1H, d, J=2.3 Hz), 7.89 (1H, d, J=8.5 Hz), 7.97 (1H, s), 8.39 (1H, s), 8.58 (1H, t, J=2.0 Hz), 8.63 (1H, s), 8.67 (1H, brs), 9.57 (1H, brs), 10.41 (1H, brs).

Example 105: 4-((5-((5-methyl-8-(2-oxopyrrolidin-1-yl)-5H-chromeno[4,3-c]pyridin-3-yl)amino)pyridin-3-yl)amino)-4-oxobutanoic acid

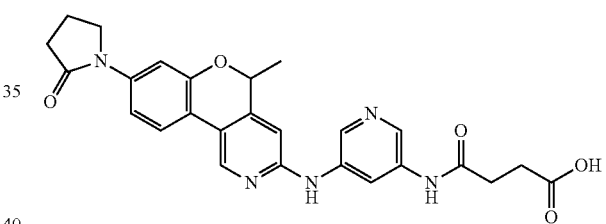

Step 1: Preparation of tert-butyl 4-((5-bromopyridin-3-yl)amino)-4-oxobutanoate

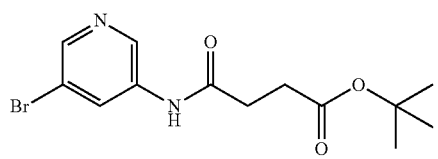 [SMILES: CC(C)(C)OC(=O)CCC(=O)Nc1cncc(Br)c1]

A mixture of 5-bromopyridin-3-amine (300 mg, 1.73 mmol), mono-tert-butyl succinic acid (301 mg, 1.73 mmol) and EDCI.HCl (365 mg, 1.90 mmol) in pyridine (5 mL) was heated at 50° C. for 1 hour. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was triturated with pentane/EtOAC (3 mL, 3/1) to give tert-butyl 4-((5-bromopyridin-3-yl)amino)-4-oxobutanoate (470 mg, yield: 82%) as a yellow solid.

¹H NMR (400 MHz DMSO-d₆) δ 1.39 (9H, s), 2.52-2.55 (2H, m), 2.57-2.62 (2H, m), 8.30-8.40 (2H, m), 8.62-8.65 (1H, m), 10.41 (1H, brs)

Step 2: Preparation of 4-((5-((5-methyl-8-(2-oxopyrrolidin-1-yl)-5H-chromeno[4,3-c]pyridin-3-yl)amino)pyridin-3-yl)amino)-4-oxobutanoic acid

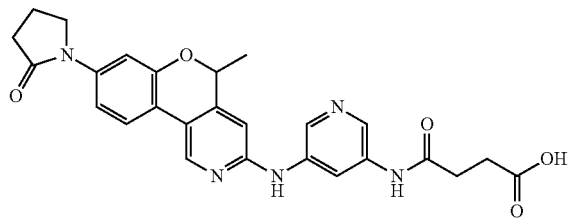 [SMILES: CC1Oc2cc(N3CCCC3=O)ccc2-c2cnc(Nc3cncc(NC(=O)CCC(=O)O)c3)cc21]

A mixture of 1-(3-amino-5-methyl-5H-chromeno[4,3-c]pyridin-8-yl)pyrrolidin-2-one (60 mg, 0.18 mmol, HCl salt), tert-butyl 4-((5-bromopyridin-3-yl)amino)-4-oxobutanoate (60 mg, 0.18 mmol), Pd₂(dba)₃ (17 mg, 0.018 mmol), BrettPhos (19 mg, 0.036 mmol), Cs₂CO₃ (118 mg, 0.362 mmol) in anhydrous dioxane (3 mL) was degassed and purged with N₂ for 3 times. Then the resulting reaction mixture was heated at 90° C. for 20 h under N₂ atmosphere. The reaction mixture turned into yellow suspension from red suspension. LCMS (Rt=0.564 min; MS Calcd: 487.2. MS Found: 488.1 [M+H]⁺). The reaction mixture was diluted with water (10 mL), adjusted pH=6 by 0.1 N aqueous HCl solution, and extracted with EtOAc (20 mL×3). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 4-((5-((5-methyl-8-(2-oxopyrrolidin-1-yl)-5H-chromeno[4,3-c]pyridin-3-yl)amino)pyridin-3-yl)amino)-4-oxobutanoic acid (26.7 mg, yield: 30%) as a yellow solid.

¹H NMR (400 MHz DMSO-d₆) δ 1.54 (3H, d, J=6.5 Hz), 2.02-2.09 (2H, m), 2.52-2.54 (2H, m, overlapped with the peak of DMSO), 2.56 (2H, t, J=6.0 Hz), 2.60-2.65 (2H, m), 3.79-3.88 (2H, m), 5.27 (1H, q, J=6.4 Hz), 6.76 (1H, s), 7.32 (1H, dd, J=8.7, 2.1 Hz), 7.40 (1H, d, J=2.0 Hz), 7.89 (1H, d, J=8.8 Hz), 8.38 (1H, s), 8.52-8.55 (1H, m), 8.65-8.70 (2H, m), 9.60 (1H, brs), 10.28 (1H, brs).

Example 106: 3-amino-N-(5-((5-methyl-8-(2-oxopyrrolidin-1-yl)-5H-chromeno[4,3-c]pyridin-3-yl)amino)pyridin-3-yl)benzamide

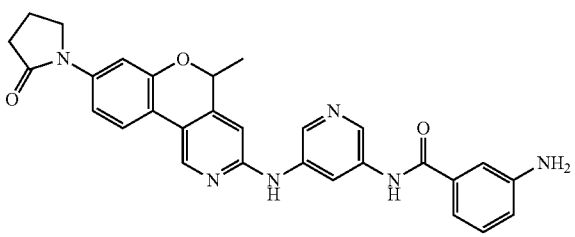 [SMILES: CC1Oc2cc(N3CCCC3=O)ccc2-c2cnc(Nc3cncc(NC(=O)c4cccc(N)c4)c3)cc21]

Step 1: Preparation of tert-butyl (3-((5-((5-methyl-8-(2-oxopyrrolidin-1-yl)-5H-chromeno[4,3-c]pyridin-3-yl)amino)pyridin-3-yl)carbamoyl)phenyl)carbamate

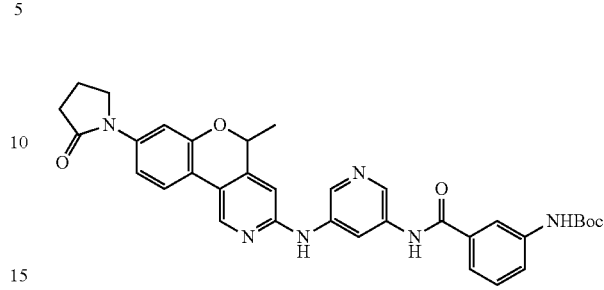

A mixture of 1-(3-amino-5-methyl-5H-chromeno[4,3-c]pyridin-8-yl)pyrrolidin-2-one (60 mg, 0.20 mmol), tert-butyl (3-((5-bromopyridin-3-yl)carbamoyl)phenyl)carbamate (88 mg, 0.22 mmol), Pd₂(dba)₃ (19 mg, 0.020 mmol), BrettPhos (22 mg, 0.041 mmol), Cs₂CO₃ (132 mg, 0.406 mmol) in t-Amyl alcohol (3 mL) was degassed and purged with N₂ for 3 times. Then the resulting reaction mixture was heated at 90° C. for 16 h under N₂ atmosphere. The reaction mixture turned into gray suspension from white suspension. LCMS (Rt=0.788 min; MS Calcd: 606.3. MS Found: 607.1 [M+H]⁺). The reaction mixture was diluted with water (20 mL) and extracted with EtOAc/THF (25 mL×2, 1/1). The combined organic layer was washed with water (30 mL×2), brine (30 mL×2), dried over anhydrous Na₂SO₄, filtered and concentrated to give tert-butyl (3-((5-((5-methyl-8-(2-oxopyrrolidin-1-yl)-5H-chromeno[4,3-c]pyridin-3-yl)amino)pyridin-3-yl)carbamoyl)phenyl)carbamate (110 mg, crude) as a yellow solid. It was used for next step without further purification.

Step 2: Preparation of 3-amino-N-(5-((5-methyl-8-(2-oxopyrrolidin-1-yl)-5H-chromeno[4,3-c]pyridin-3-yl)amino)pyridin-3-yl)benzamide

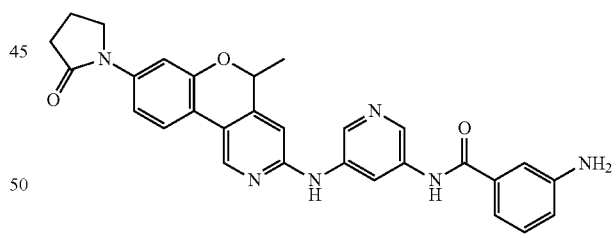

To a stirred solution of tert-butyl (3-((5-((5-methyl-8-(2-oxopyrrolidin-1-yl)-5H-chromeno[4,3-c]pyridin-3-yl)amino)pyridin-3-yl)carbamoyl)phenyl)carbamate (80 mg, crude) in DCM (2 mL) was added TFA (2 mL) dropwise at 25° C. The reaction mixture was stirred at 25° C. for 3 h. A yellow solution was formed. LCMS (Rt=0.690 min; MS Calcd: 506.2; MS Found: 507.1 [M+H]⁺). The mixture was concentrated and the residue was basified with saturated Na₂CO₃ aqueous solution (10 mL) to pH=10 and extracted with EtOAc/THF (20 mL×3, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 3-amino-N-(5-((5-methyl- 8-(2-oxopyrrolidin-1-yl)-5H-chromeno[4,3-c]pyridin-3-yl) amino)pyridin-3-yl)benzamide (25.9 mg, yield: 25% for two steps) as a yellow solid.

$^1$H NMR (400 MHz DMSO-d$_6$) δ 1.55 (3H, d, J=6.8 Hz), 2.02-2.10 (2H, m), 2.52-2.54 (2H, m, overlapped with the peak of DMSO), 3.82-3.88 (2H, m), 5.29 (1H, q, J=6.4 Hz), 6.77-6.81 (2H, m), 7.10-7.15 (2H, m), 7.18 (1H, t, J=8.0 Hz), 7.33 (1H, dd, J=8.5, 2.3 Hz), 7.41 (1H, d, J=2.3 Hz), 7.89 (1H, d, J=8.8 Hz), 8.49 (1H, s), 8.65-8.68 (1H, m), 8.69 (1H, s), 8.70-8.75 (1H, m), 9.55 (1H, brs), 10.31 (1H, brs). Note: two protons of aniline were not observed.

Example 107: N-(5-((5-methyl-8-(2-oxopyrrolidin-1-yl)-5H-chromeno[4,3-c]pyridin-3-yl)amino)pyridin-3-yl)-2-phenylacetamide

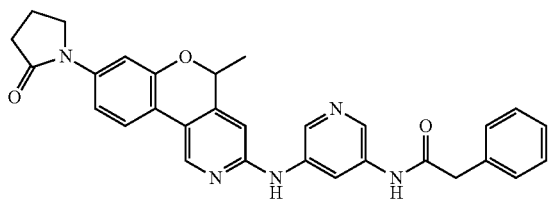 [SMILES: CC1Oc2cc(N3CCCC3=O)ccc2-c2cnc(Nc3cncc(NC(=O)Cc4ccccc4)c3)cc21]

Step 1: Preparation N-(5-aminopyridin-3-yl)-2-phenylacetamide

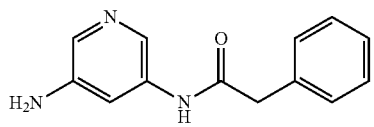 [SMILES: Nc1cncc(NC(=O)Cc2ccccc2)c1]

A mixture of 2-phenylacetic acid (374 mg, 2.75 mmol), pyridine-3,5-diamine (300 mg, 2.75 mmol) and EDCI.HCl (580 mg, 3.02 mmol) in pyridine (5 mL) was heated at 50° C. for 2 h. A black solution was formed. LCMS (Rt=0.405 min; MS Calcd: 227.1. MS Found: 227.9 [M+H]$^+$). The mixture was concentrated and the residue was poured into water (20 mL) and stirred for 2 minutes. The aqueous layer was extracted with ethyl acetate (20 mL×3). The combined organic layer was washed with water (30 mL×2) and brine (30 mL), dried over anhydrous Na$_2$SO$_4$, filtered and concentrated. The residue was purified by Combi Flash (50% to 100% EtOAc in pentane) to give N-(5-aminopyridin-3-yl)-2-phenylacetamide (450 mg, yield: 61%) as a light yellow solid.

Step 2: Preparation of N-(5-((5-methyl-8-(2-oxopyrrolidin-1-yl)-5H-chromeno[4,3-c]pyridin-3-yl) amino)pyridin-3-yl)-2-phenylacetamide

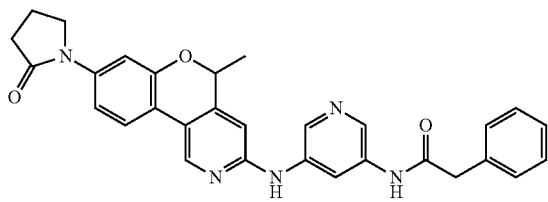 [SMILES: CC1Oc2cc(N3CCCC3=O)ccc2-c2cnc(Nc3cncc(NC(=O)Cc4ccccc4)c3)cc21]

A mixture of 1-(3-chloro-5-methyl-5H-chromeno[4,3-c] pyridin-8-yl)pyrrolidin-2-one (60 mg, 0.19 mmol), N-(5-aminopyridin-3-yl)-2-phenylacetamide (61 mg, 0.23 mmol), Pd$_2$(dba)$_3$ (18 mg, 0.019 mmol), BrettPhos (21 mg, 0.038 mmol), Cs$_2$CO$_3$ (124 mg, 0.381 mmol) in anhydrous dioxane (3 mL) was degassed and purged with N$_2$ for 3 times. Then the resulting reaction mixture was heated at 90° C. for 16 h under N$_2$ atmosphere. The reaction mixture turned into gray suspension from red suspension. LCMS (Rt=0.800 min; MS Calcd: 505.2. MS Found: 506.1 [M+H]$^+$). The mixture was diluted with water (20 mL) and extracted with EtOAc (20 mL×2). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl) amino)pyridin-3-yl)-2-phenylacetamide (7.4 mg, yield: 8%) as a yellow solid.

$^1$H NMR (400 MHz DMSO-d$_6$) δ 1.51-1.56 (3H, m), 2.02-2.10 (2H, m), 2.62-2.64 (2H, m, overlapped with the peak of DMSO), 3.68-3.72 (2H, m), 3.82-3.88 (2H, m), 5.24-5.32 (1H, m), 6.72-6.77 (1H, m), 7.22-7.41 (7H, m), 7.86-7.92 (1H, m), 8.38 (1H, s), 8.55 (1H, s), 8.60-8.68 (2H, m), 9.55 (1H, brs), 10.42 (1H, brs).

Example 108: N-(5-((5-methyl-8-(2-oxopyrrolidin-1-yl)-5H-chromeno[4,3-c]pyridin-3-yl)amino)pyridin-3-yl)-1H-indole-6-carboxamide

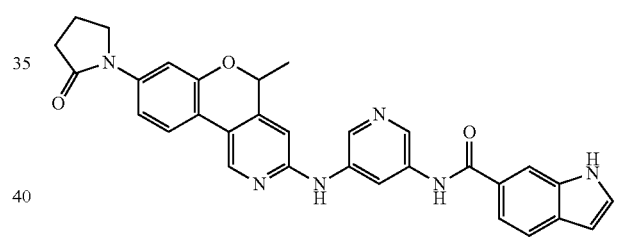

Step 1: Preparation of N-(5-bromopyridin-3-yl)-1H-indole-6-carboxamide

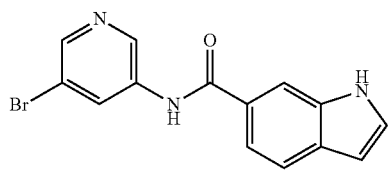 [SMILES: O=C(Nc1cncc(Br)c1)c1ccc2cc[nH]c2c1]

A mixture of 1H-indole-6-carboxylic acid (307 mg, 1.90 mmol), 5-bromopyridin-3-amine (300 mg, 1.73 mmol) and EDCI.HCl (365 mg, 1.90 mmol) in pyridine (5 mL) was heated at 50° C. for 1 hour. An orange solution was formed. LCMS (Rt=0.733 min; MS Calcd: 315.0. MS Found: 315.9 [M+H]$^+$). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was triturated with pentane/EtOAC (3 mL, 3/1) to give N-(5-bromopyridin-3-yl)-1H-indole-6-carboxamide (440 mg, yield: 80%) as a light yellow solid.

¹H NMR (400 MHz DMSO-d₆) δ 6.55 (1H, t, J=2.0 Hz), 7.60 (1H, t, J=2.8 Hz), 7.68 (1H, s), 8.12 (1H, s), 8.43 (1H, d, J=2.0 Hz), 8.49 (1H, s), 8.58 (1H, t, J=2.1 Hz), 8.97 (1H, d, J=2.3 Hz), 10.55 (1H, brs), 11.55 (1H, brs).

Step 2: Preparation of N-(5-((5-methyl-8-(2-oxopyrrolidin-1-yl)-5H-chromeno[4,3-c]pyridin-3-yl)amino)pyridin-3-yl)-1H-indole-6-carboxamide

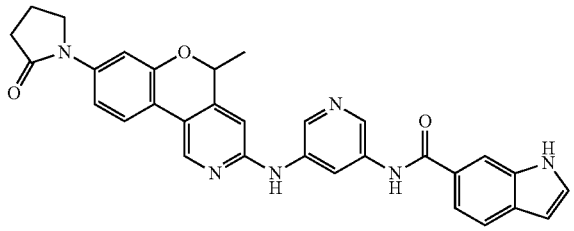 [SMILES: CC1Oc2cc(N3CCCC3=O)ccc2-c2cnc(Nc3cncc(NC(=O)c4ccc5cc[nH]c5c4)c3)cc21]

A mixture of 1-(3-amino-5-methyl-5H-chromeno[4,3-c]pyridin-8-yl)pyrrolidin-2-one (60 mg, 0.020 mmol), N-(5-bromopyridin-3-yl)-1H-indole-6-carboxamide (71 mg, 0.22 mmol), Pd₂(dba)₃ (19 mg, 0.020 mmol), BrettPhos (22 mg, 0.041 mmol), Cs₂CO₃ (132 mg, 0.406 mmol) in dioxane (3 mL) was degassed and purged with N₂ for 3 times. Then the resulting reaction mixture was heated at 90° C. for 14 h under N₂ atmosphere. The reaction mixture turned into yellow suspension from red suspension. LCMS (Rt=0.733 min; MS Calcd: 530.2. MS Found: 531.3 [M+H]⁺). The mixture was diluted with water (20 mL) and extracted with EtOAc/THF (20 mL×3, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)-1H-indole-6-carboxamide (7.37 mg, yield: 6.5%) as a yellow solid.

¹H NMR (400 MHz DMSO-d₆) δ 1.56 (3H, d, J=6.5 Hz), 2.02-2.10 (2H, m), 2.52-2.54 (2H, m, overlapped with the peak of DMSO), 3.82-3.88 (2H, m), 5.30 (1H, q, J=6.5 Hz), 6.54-6.57 (1H, m), 6.80 (1H, s), 7.33 (1H, dd, J=8.8, 2.3 Hz), 7.41 (1H, d, J=2.3 Hz), 7.58 (1H, t, J=2.8 Hz), 7.69 (2H, s), 7.90 (1H, d, J=8.8 Hz), 8.12 (1H, d, J=0.8 Hz), 8.57 (1H, s), 8.70 (1H, s), 8.73-8.77 (2H, m), 9.65 (1H, brs), 10.46 (1H, brs), 11.52 (1H, brs).

Example 109: N-(5-((5-methyl-8-(2-oxopyrrolidin-1-yl)-5H-chromeno[4,3-c]pyridin-3-yl)amino)pyridin-3-yl)benzo[d]oxazole-6-carboxamide

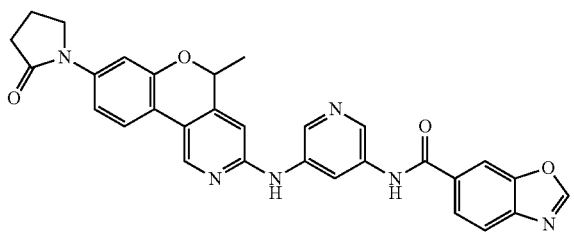 [SMILES: CC1Oc2cc(N3CCCC3=O)ccc2-c2cnc(Nc3cncc(NC(=O)c4ccc5ncoc5c4)c3)cc21]

Step 1: 1ˢᵗ Batch

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), benzo[d]oxazole-6-carboxylic acid (28 mg, 0.17 mmol) and EDCI.HCl (33 mg, 0.17 mmol) in pyridine (2 mL) was heated at 30° C. for 4 h. A yellow solution was formed. LCMS (Rt=0.713 min; MS Calcd: 532.2; MS Found: 533.1 [M+H]⁺). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by prep-HPLC (0.225% FA as an additive) and lyophilized to give side product 4-formamido-3-hydroxy-N-(5-((5-methyl-8-(2-oxopyrrolidin-1-yl)-5H-chromeno[4,3-c]pyridin-3-yl)amino)pyridin-3-yl)benzamide (109A) (15.9 mg, yield: 20%) as a yellow solid.

¹H NMR (400 MHz DMSO-d₆) δ 1.56 (3H, d, J=6.5 Hz), 2.02-2.10 (2H, m), 2.52-2.54 (2H, m, overlapped with the peak of DMSO), 3.84 (2H, t, J=7.4 Hz), 5.29 (1H, q, J=6.5 Hz), 6.81 (1H, s), 7.32 (1H, dd, J=8.5, 2.0 Hz), 7.40 (1H, d, J=2.0 Hz), 7.48-7.53 (2H, m), 7.89 (1H, d, J=8.5 Hz), 8.27 (1H, d, J=8.5 Hz), 8.37 (1H, d, J=1.3 Hz), 8.56-8.62 (1H, m), 8.70 (1H, s), 8.74 (1H, s), 8.84 (1H, s), 9.78 (1H, brs), 9.84 (1H, brs), 10.51 (2H, brs).

Step 2: 2ⁿᵈ Batch

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), benzo[d]oxazole-6-carboxylic acid (28 mg, 0.17 mmol) and EDCI.HCl (33 mg, 0.17 mmol) in pyridine (2 mL) was heated at 30° C. for 4 h. A yellow solution was formed. LCMS (Rt=0.713 min; MS Calcd: 532.2; MS Found: 533.1 [M+H]⁺). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by prep-HPLC (0.05% NH₃.H₂O as an additive) and lyophilized to give N-(5-((5-methyl-8-(2-oxopyrrolidin-1-yl)-5H-chromeno[4,3-c]pyridin-3-yl)amino)pyridin-3-yl)benzo[d]oxazole-6-carboxamide (21.7 mg, yield: 29%) as a gray solid.

¹H NMR (400 MHz DMSO-d₆) δ 1.56 (3H, d, J=6.5 Hz), 2.02-2.10 (2H, m), 2.52-2.54 (2H, m, overlapped with the peak of DMSO), 3.82-3.88 (2H, m), 5.29 (1H, q, J=6.8 Hz), 6.79 (1H, s), 7.33 (1H, dd, J=8.4, 2.1 Hz), 7.41 (1H, d, J=2.3 Hz), 7.90 (1H, d, J=8.8 Hz), 7.98 (1H, d, J=8.3 Hz), 8.08 (1H, dd, J=8.4, 1.6 Hz), 8.45 (1H, s), 8.52 (1H, d, J=2.0 Hz), 8.65-8.73 (3H, m), 8.96 (1H, s), 9.54 (1H, brs), 10.55 (1H, brs).

Example 110: N-(5-((5-methyl-8-(2-oxopyrrolidin-1-yl)-5H-chromeno[4,3-c]pyridin-3-yl)amino)pyridin-3-yl)-3-phenylpropanamide

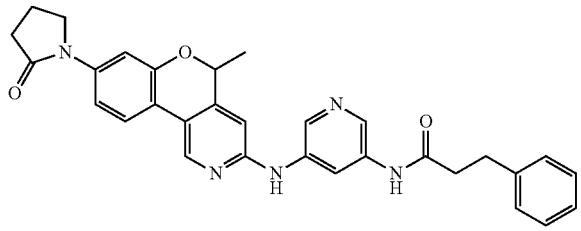 [SMILES: CC1Oc2cc(N3CCCC3=O)ccc2-c2cnc(Nc3cncc(NC(=O)CCc4ccccc4)c3)cc21]

Step 1: Preparation of N-(5-aminopyridin-3-yl)-3-phenylpropanamide

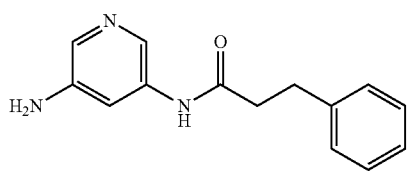 [SMILES: Nc1cncc(NC(=O)CCc2ccccc2)c1]

A mixture of 3-phenylpropanoic acid (413 mg, 2.75 mmol), pyridine-3,5-diamine (300 mg, 2.75 mmol) and EDCI.HCl (580 mg, 3.03 mmol) in pyridine (5 mL) was heated at 50° C. for 2 h. A black solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL×2), dried over anhydrous Na$_2$SO$_4$, filtered and concentrated. The residue was purified by Combi Flash (50% to 100% EtOAc in pentane) to give N-(5-aminopyridin-3-yl)-3-phenylpropanamide (400 mg, yield: 59%) as a light yellow solid.

$^1$H NMR (400 MHz DMSO-d$_6$) 2.63 (2H, t, J=7.7 Hz), 2.91 (2H, t, J=7.7 Hz), 5.34 (2H, brs), 7.15-7.22 (1H, m), 7.23-7.32 (4H, m), 7.38 (1H, t, J=2.3 Hz), 7.63 (1H, d, J=2.5 Hz), 7.86 (1H, d, J=2.0 Hz), 9.83 (1H, brs).

Step 2: Preparation of N-(5-((5-methyl-8-(2-oxopyrrolidin-1-yl)-5H-chromeno[4,3-c]pyridin-3-yl)amino)pyridin-3-yl)-3-phenylpropanamide

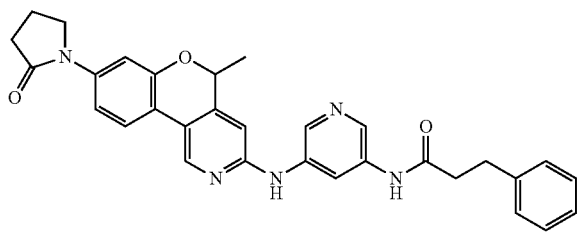 [SMILES: CC1Oc2cc(N3CCCC3=O)ccc2-c2cnc(Nc3cncc(NC(=O)CCc4ccccc4)c3)cc21]

A mixture of 1-(3-chloro-5-methyl-5H-chromeno[4,3-c]pyridin-8-yl)pyrrolidin-2-one (60 mg, 0.19 mmol), N-(5-aminopyridin-3-yl)-3-phenylpropanamide (61 mg, 0.23 mmol), Pd$_2$(dba)$_3$ (18 mg, 0.019 mmol), BrettPhos (21 mg, 0.038 mmol), Cs$_2$CO$_3$ (124 mg, 0.381 mmol) in dioxane (3 mL) was degassed and purged with N$_2$ for 3 times. Then the resulting reaction mixture was heated at 90° C. for 16 h under N$_2$ atmosphere. The reaction mixture turned into gray suspension from red suspension. LCMS (Rt=0.750 min; MS Calcd: 519.2. MS Found: 520.1 [M+H]$^+$). The mixture was diluted with water (20 mL) and extracted with EtOAc (20 mL×2). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)-3-phenylpropanamide (30.2 mg, yield: 30%) as a yellow solid.

$^1$H NMR (400 MHz DMSO-d$_6$) δ 1.55 (3H, d, J=6.5 Hz), 2.02-2.10 (2H, m), 2.52-2.54 (2H, m, overlapped with the peak of DMSO), 2.69 (2H, t, J=7.7 Hz), 2.94 (2H, t, J=7.7 Hz), 3.84 (2H, t, J=7.5 Hz), 5.28 (1H, q, J=6.4 Hz), 6.76 (1H, s), 7.17-7.23 (1H, m), 7.25-7.35 (5H, m), 7.41 (1H, d, J=1.8 Hz), 7.89 (1H, d, J=8.5 Hz), 8.34 (1H, s), 8.48-8.53 (1H, m), 8.63-8.70 (2H, m), 9.53 (1H, brs), 10.15 (1H, brs).

Example 111: (1S,2S)—N-(5-((5-methyl-8-(2-oxopyrrolidin-1-yl)-5H-chromeno[4,3-c]pyridin-3-yl)amino)pyridin-3-yl)-2-phenylcyclopropane-1-carboxamide

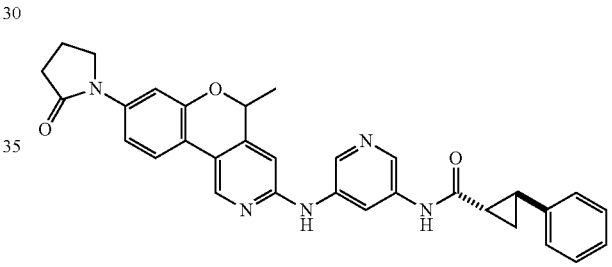

Step 1: Preparation of (1S,2S)—N-(5-aminopyridin-3-yl)-2-phenylcyclopropane-1-carboxamide

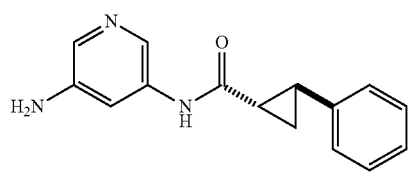 [SMILES: Nc1cncc(NC(=O)[C@H]2C[C@@H]2c2ccccc2)c1]

A mixture of (1S,2S)-2-phenylcyclopropane-1-carboxylic acid (360 mg, 2.22 mmol), pyridine-3,5-diamine (242 mg, 2.22 mmol) and EDCI.HCl (468 mg, 2.44 mmol) in pyridine (5 mL) was heated at 50° C. for 2 h. A black solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by Combi Flash (50% to 100% EtOAc in pentane) to give (1S,2S)—N-(5-aminopyridin-3-yl)-2-phenylcyclopropane-1-carboxamide (390 mg, yield: 64%) as a light yellow solid.

$^1$H NMR (400 MHz DMSO-d$_6$) δ 1.34-1.40 (1H, m), 1.45-1.52 (1H, m), 2.05-2.11 (1H, m), 2.33-2.41 (1H, m), 5.33 (2H, brs), 7.15-7.23 (3H, m), 7.26-7.32 (2H, m), 7.34 (1H, t, J=2.1 Hz), 7.62 (1H, d, J=2.5 Hz), 7.89 (1H, d, J=2.0 Hz), 10.14 (1H, brs).

Step 2: Preparation of (1S,2S)—N-(5-((5-methyl-8-(2-oxopyrrolidin-1-yl)-5H-chromeno[4,3-c]pyridin-3-yl)amino)pyridin-3-yl)-2-phenylcyclopropane-1-carboxamide

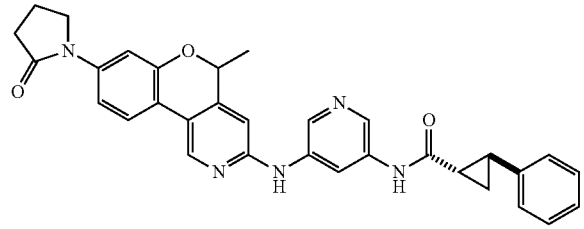 [SMILES: CC1Oc2cc(N3CCCC3=O)ccc2-c2cnc(Nc3cncc(NC(=O)[C@H]4C[C@@H]4c4ccccc4)c3)cc21]

A mixture of 1-(3-chloro-5-methyl-5H-chromeno[4,3-c]pyridin-8-yl)pyrrolidin-2-one (60 mg, 0.19 mmol), (1S, 2S)—N-(5-aminopyridin-3-yl)-2-phenylcyclopropane-1-carboxamide (54 mg, 0.21 mmol), Pd$_2$(dba)$_3$ (18 mg, 0.019 mmol), BrettPhos (21 mg, 0.038 mmol), Cs$_2$CO$_3$ (124 mg, 0.381 mmol) in anhydrous dioxane (3 mL) was degassed and purged with N$_2$ for 3 times. Then the resulting reaction mixture was heated at 90° C. for 16 h under N$_2$ atmosphere. The reaction mixture turned into gray suspension from red suspension. LCMS (Rt=0.659 min; MS Calcd: 531.2. MS Found: 532.0 [M+H]$^+$). The mixture was diluted with water (20 mL) and extracted with EtOAc (20 mL×2). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give (1S, 2S)—N-(5-((5-methyl-8-(2-oxopyrrolidin-1-yl)-5H-chromeno[4,3-c]pyridin-3-yl)amino)pyridin-3-yl)-2-phenylcyclopropane-1-carboxamide (21.3 mg, yield: 21%) as a yellow solid.

$^1$H NMR (400 MHz DMSO-d$_6$) δ 51.39-1.46 (1H, m), 1.52-1.58 (4H, m), 2.02-2.10 (2H, m), 2.11-2.17 (1H, m), 2.40-2.44 (1H, m), 2.52-2.54 (2H, m, overlapped with the peak of DMSO), 3.85 (2H, t, J=7.7 Hz), 5.28 (1H, q, J=6.3 Hz), 6.76 (1H, s), 7.19-7.25 (3H, m), 7.29-7.35 (3H, m), 7.41 (1H, d, J=1.8 Hz), 7.89 (1H, d, J=8.5 Hz), 8.39 (1H, s), 8.54 (1H, s), 8.63-8.68 (2H, m), 9.56 (1H, brs), 10.51 (1H, brs).

Example 112: N-(5-((5-methyl-8-(2-oxopyrrolidin-1-yl)-5H-chromeno[4,3-c]pyridin-3-yl)amino)pyridin-3-yl)picolinamide

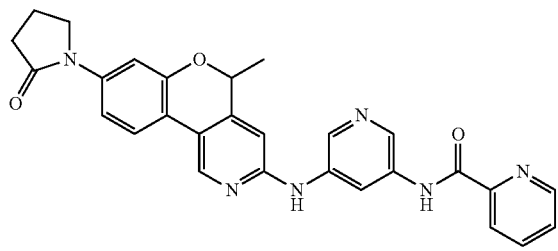 [SMILES: CC1Oc2cc(N3CCCC3=O)ccc2-c2cnc(Nc3cncc(NC(=O)c4ccccn4)c3)cc21]

Step 1: Preparation of N-(5-aminopyridin-3-yl)picolinamide

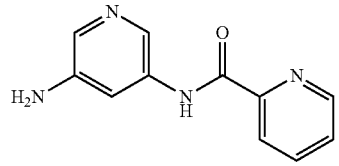 [SMILES: Nc1cncc(NC(=O)c2ccccn2)c1]

A mixture of picolinic acid (338 mg, 2.75 mmol), pyridine-3,5-diamine (300 mg, 2.75 mmol) and EDCI.HCl (580 mg, 3.02 mmol) in pyridine (5 mL) was heated at 50° C. for 2 h. A black solution was formed. LCMS (Rt=0.329 min; MS Calcd: 214.1. MS Found: 214.9 [M+H]$^+$). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL×2), dried over anhydrous Na$_2$SO$_4$, filtered and concentrated. The residue was purified by Combi Flash (50% to 100% EtOAc in pentane) to give N-(5-aminopyridin-3-yl)picolinamide (400 mg, yield: 61%) as alight yellow solid.

$^1$H NMR (400 MHz DMSO-d$_6$) δ 5.39 (2H, brs), 7.64 (1H, t, J=2.3 Hz), 7.67-7.72 (2H, m), 8.08 (1H, td, J=7.7, 1.5 Hz), 8.13-8.17 (2H, m), 8.73-8.76 (1H, m), 10.54 (1H, brs).

Step 2: Preparation of N-(5-((5-methyl-8-(2-oxopyrrolidin-1-yl)-5H-chromeno[4,3-c]pyridin-3-yl)amino)pyridin-3-yl)picolinamide

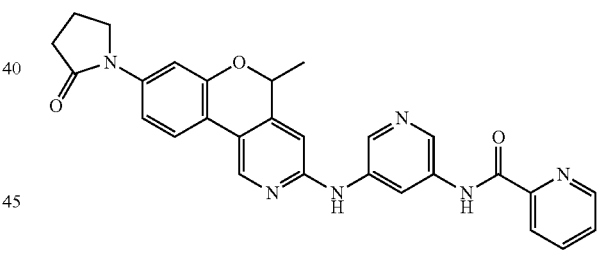

A mixture of 1-(3-chloro-5-methyl-5H-chromeno[4,3-c]pyridin-8-yl)pyrrolidin-2-one (60 mg, 0.19 mmol), N-(5-aminopyridin-3-yl)picolinamide (50 mg, 0.21 mmol), Pd$_2$(dba)$_3$ (18 mg, 0.019 mmol), BrettPhos (21 mg, 0.038 mmol) and Cs$_2$CO$_3$ (124 mg, 0.381 mmol) in anhydrous dioxane (3 mL) was degassed and purged with N$_2$ for 3 times. Then the resulting reaction mixture was heated at 90° C. for 30 h under N$_2$ atmosphere. The reaction mixture turned into gray suspension from red suspension. LCMS (Rt=0.717 min; MS Calcd: 492.2. MS Found: 493.1 [M+H]$^+$). The mixture was diluted with water (10 mL) and filtered and the solid was washed with water (10 mL) and EtOAc (10 mL). The filtrate was concentrated and the residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)picolinamide (7.7 mg, yield: 8%) as a yellow solid.

$^1$H NMR (400 MHz DMSO-d$_6$) δ 1.56 (3H, d, J=6.5 Hz), 2.02-2.10 (2H, m), 2.52-2.54 (2H, m, overlapped with the peak of DMSO), 3.85 (2H, t, J=7.5 Hz), 5.29 (1H, q, J=6.8 Hz), 6.79 (1H, s), 7.33 (1H, dd, J=8.7, 2.1 Hz), 7.41 (1H, d, J=2.3 Hz), 7.72 (1H, dd, J=6.7, 4.9 Hz), 7.90 (1H, d, J=8.8 Hz), 8.11 (1H, td, J=7.7, 1.5 Hz), 8.18-8.21 (1H, m), 8.61 (1H, s), 8.71 (1H, s), 8.74 (1H, s), 8.78 (1H, d, J=4.8 Hz), 8.81-8.85 (1H, m), 9.59 (1H, brs), 10.87 (1H, brs).

Example 113: N-(5-((5-methyl-8-(2-oxopyrrolidin-1-yl)-5H-chromeno[4,3-c]pyridin-3-yl)amino)pyridin-3-yl)nicotinamide

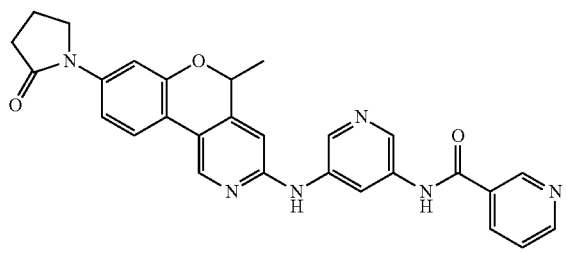 [SMILES: CC1Oc2cc(N3CCCC3=O)ccc2-c2cnc(Nc3cncc(NC(=O)c4cccnc4)c3)cc21]

Step 1: Preparation of N-(5-bromopyridin-3-yl)nicotinamide

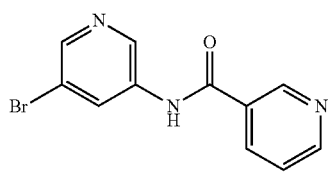 [SMILES: O=C(Nc1cncc(Br)c1)c1cccnc1]

A mixture of nicotinic acid (213 mg, 1.73 mmol), 5-bromopyridin-3-amine (300 mg, 1.73 mmol) and EDCI.HCl (365 mg, 1.91 mmol) in pyridine (3 mL) was heated at 50° C. for 2 h. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous $Na_2SO_4$, filtered and concentrated. The residue was triturated with pentane/EtOAC (3 mL, 3/1) to give N-(5-bromopyridin-3-yl)nicotinamide (400 mg, yield: 82%) as a yellow solid.

$^1$H NMR (400 MHz DMSO-$d_6$) δ 7.60 (1H, dd, J=7.9, 4.9 Hz), 8.31 (1H, dt, J=8.0, 1.9 Hz), 8.46 (1H, d, J=2.0 Hz), 8.51 (1H, t, J=2.1 Hz), 8.80 (1H, dd, J=4.8, 1.5 Hz), 8.90 (1H, d, J=2.3 Hz), 9.13 (1H, d, J=1.8 Hz), 10.81 (1H, brs).

Step 2: Preparation of N-(5-((5-methyl-8-(2-oxopyrrolidin-1-yl)-5H-chromeno[4,3-c]pyridin-3-yl)amino)pyridin-3-yl)nicotinamide

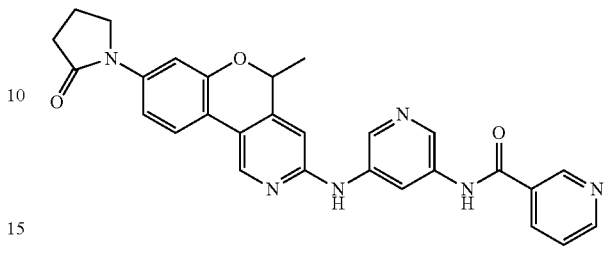

A mixture of 1-(3-amino-5-methyl-5H-chromeno[4,3-c]pyridin-8-yl)pyrrolidin-2-one (60 mg, 0.20 mmol), N-(5-bromopyridin-3-yl)nicotinamide (62 mg, 0.22 mmol), $Pd_2(dba)_3$ (19 mg, 0.020 mmol), BrettPhos (22 mg, 0.041 mmol) and $Cs_2CO_3$ (132 mg, 0.406 mmol) in anhydrous dioxane (3 mL) was degassed and purged with $N_2$ for 3 times. Then the resulting reaction mixture was heated at 90° C. for 16 h under $N_2$ atmosphere. The reaction mixture turned into gray suspension from red suspension. LCMS (Rt=0.682 min; MS Calcd: 492.2; MS Found: 493.1 [M+H]$^+$). The mixture was diluted with water (10 mL) and extracted with EtOAc/THF (20 mL×2, 1/1). The combined organic layer was washed with water (20 mL×2), brine (20 mL×2), dried over anhydrous $Na_2SO_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)nicotinamide (37.4 mg, yield: 36%) as a light yellow solid.

$^1$H NMR (400 MHz DMSO-$d_6$) δ 1.56 (3H, d, J=6.5 Hz), 2.02-2.10 (2H, m), 2.52-2.56 (2H, m, overlapped with the peak of DMSO), 3.82-3.88 (2H, m), 5.29 (1H, q, J=6.3 Hz), 6.79 (1H, s), 7.33 (1H, dd, J=8.8, 2.3 Hz), 7.41 (1H, d, J=2.3 Hz), 7.58-7.64 (1H, m), 7.90 (1H, d, J=9.3 Hz), 8.34 (1H, d, J=7.8 Hz), 8.53 (1H, s), 8.67-8.83 (4H, m), 9.15 (1H, s), 9.62 (1H, brs), 10.69 (1H, brs).

Example 114: N-(5-((5-methyl-8-(2-oxopyrrolidin-1-yl)-5H-chromeno[4,3-c]pyridin-3-yl)amino)pyridin-3-yl)isonicotinamide

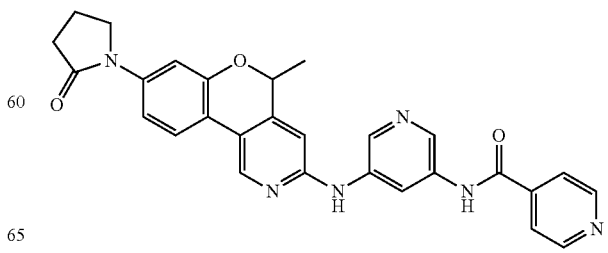

Step 1: Preparation of N-(5-bromopyridin-3-yl)isonicotinamide

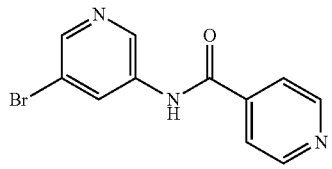 [SMILES: O=C(Nc1cncc(Br)c1)c1ccncc1]

A mixture of isonicotinic acid (213 mg, 1.73 mmol), 5-bromopyridin-3-amine (300 mg, 1.73 mmol) and EDCI.HCl (365 mg, 1.90 mmol) in pyridine (3 mL) was heated at 50° C. for 2 h. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous $Na_2SO_4$, filtered and concentrated. The residue was triturated with pentane/EtOAC (3 mL, 3/1) to give N-(5-bromopyridin-3-yl)isonicotinamide (300 mg, yield: 62%) as a yellow solid.

$^1$H NMR (400 MHz DMSO-$d_6$) δ 7.68-7.90 (2H, m), 8.48-8.53 (2H, m), 8.81-8.85 (2H, m), 8.91 (1H, d, J=2.0 Hz), 10.87 (1H, brs).

Step 2: Preparation of N-(5-((5-methyl-8-(2-oxopyrrolidin-1-yl)-5H-chromeno[4,3-c]pyridin-3-yl)amino)pyridin-3-yl)isonicotinamide

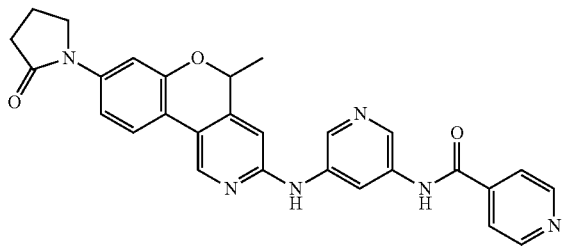 [SMILES: CC1Oc2cc(N3CCCC3=O)ccc2-c2cnc(Nc3cncc(NC(=O)c4ccncc4)c3)cc21]

A mixture of 1-(3-amino-5-methyl-5H-chromeno[4,3-c]pyridin-8-yl)pyrrolidin-2-one (60 mg, 0.20 mmol), N-(5-bromopyridin-3-yl)isonicotinamide (62 mg, 0.22 mmol), $Pd_2(dba)_3$ (19 mg, 0.020 mmol), BrettPhos (22 mg, 0.041 mmol) and $Cs_2CO_3$ (132 mg, 0.406 mmol) in anhydrous dioxane (3 mL) was degassed and purged with $N_2$ for 3 times. Then the resulting reaction mixture was heated at 90° C. for 16 h under $N_2$ atmosphere. The reaction mixture turned into gray suspension from red suspension. LCMS (Rt=0.713 min; MS Calcd: 492.2. MS Found: 493.1 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous $Na_2SO_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)isonicotinamide (15.3 mg, yield: 15%) as a yellow solid.

$^1$H NMR (400 MHz DMSO-$d_6$) δ 1.55 (3H, d, J=6.5 Hz), 2.00-2.10 (2H, m), 2.47-2.49 (2H, m, overlapped with the peak of DMSO), 3.79-3.88 (2H, m), 5.28 (1H, q, J=6.5 Hz), 6.78 (1H, s), 7.31 (1H, dd, J=8.7, 2.1 Hz), 7.40 (1H, d, J=2.3 Hz), 7.86-7.92 (3H, m), 8.52 (1H, s), 8.67 (1H, s), 8.72 (2H, d, J=1.5 Hz), 8.82 (2H, d, J=5.8 Hz), 9.60 (1H, brs), 10.73 (1H, brs).

Example 115: 2-amino-N-(5-((5-methyl-8-(2-oxopyrrolidin-1-yl)-5H-chromeno[4,3-c]pyridin-3-yl)amino)pyridin-3-yl)isonicotinamide

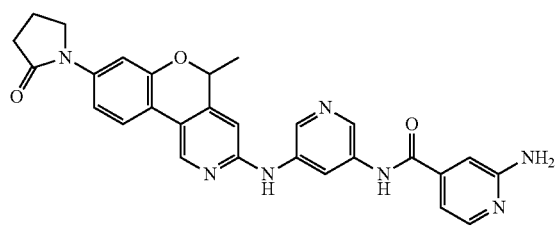 [SMILES: CC1Oc2cc(N3CCCC3=O)ccc2-c2cnc(Nc3cncc(NC(=O)c4ccnc(N)c4)c3)cc21]

Step 1: Preparation of 4-methoxybenzyl 2-(bis(4-methoxybenzyl)amino)isonicotinate

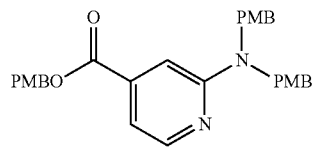

To a solution of ethyl 2-aminoisonicotinate (1.50 g, 9.03 mmol) in anhydrous DMF (20 mL) was added NaH (1.44 g, 36.1 mmol, 60% dispersion in mineral oil) at 0° C. The reaction mixture was stirred at 0° C. for 1 hour. Then PMB-Cl (4-methoxybenzochloride) (5.65 g, 36.1 mmol) was added dropwise to the reaction mixture at 0° C. The resulting reaction mixture was stirred at 25-30° C. for 49 h. The reaction mixture was quenched with saturated aqueous $NH_4Cl$ (50 mL), then extracted with EtOAc (50 mL×3). The combined organic layer was washed with water (50 mL×3), brine (50 mL), dried over anhydrous $Na_2SO_4$ and concentrated. The residue was purified by Combi Flash (10% to 30% EtOAc in pentane) to give 4-methoxybenzyl 2-(bis(4-methoxybenzyl)amino)isonicotinate (160 mg, yield: 3.6%) as a white solid.

Step 2: Preparation of 2-(bis(4-methoxybenzyl)amino)isonicotinic acid

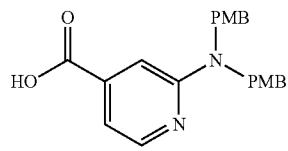

To a solution of 4-methoxybenzyl 2-(bis(4-methoxybenzyl)amino)isonicotinate (160 mg, 0.320 mmol) in THF (4 mL) and MeOH (2 mL) was added 2N aqueous NaOH (4 mL) at 20-25° C. Then the reaction mixture was stirred at 20-25° C. for 2 h. The reaction mixture turned to yellow solution from cloudy. LCMS (Rt=0.763 min; MS Calcd:

378.2. MS Found: 379.0 [M+H]⁺). The reaction mixture was acidified with 2N aqueous HCl to pH=6, then extracted with EtOAc (25 mL×2). The combined organic layer was washed with brine (25 mL), dried over anhydrous Na$_2$SO$_4$ and concentrated. The residue was purified by prep-TLC (DCM/MeOH, 10/1) to give 2-(bis(4-methoxybenzyl)amino)isonicotinic acid (70 mg, yield: 58%) as yellow gum.

$^1$H NMR (400 MHz, CDCl$_3$) δ 3.76 (6H, s), 4.69 (4H, s), 6.81 (4H, d, J=8.4 Hz), 6.90-7.15 (6H, m), 8.26 (1H, s).

Step 3: Preparation of 2-(bis(4-methoxybenzyl)amino)-N-(5-((5-methyl-8-(2-oxopyrrolidin-1-yl)-5H-chromeno[4,3-c]pyridin-3-yl)amino)pyridin-3-yl)isonicotinamide

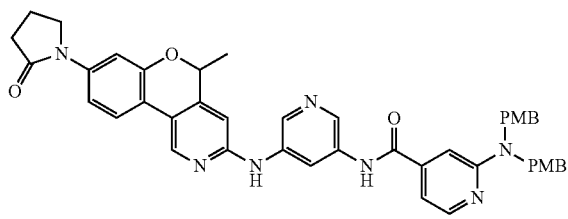

A mixture of 1-(3-((5-aminopyridin-3-yl)amino)-5-methyl-5H-chromeno[4,3-c]pyridin-8-yl)pyrrolidin-2-one (80 mg, 0.17 mmol, HCl salt), 2-(bis(4-methoxybenzyl)amino)isonicotinic acid (70 mg, 0.18 mmol) and EDCI.HCl (33 mg, 0.17 mmol) in pyridine (3 mL) was stirred at 50° C. for 2 h. The reaction mixture turned into yellow solution from colorless. LCMS (Rt=0.855 min; MS Calcd: 747.3. MS Found: 748.4 [M+H]⁺). The reaction mixture was diluted with water (25 mL), then extracted with EtOAc (25 mL×3). The combined organic layer was washed with saturated aqueous NaHCO$_3$ (25 mL), brine (25 mL), dried over anhydrous Na$_2$SO$_4$ and concentrated. The residue was purified by prep-TLC (DCM/MeOH, 10/1) to give 2-(bis(4-methoxybenzyl)amino)-N-(5-((5-methyl-8-(2-oxopyrrolidin-1-yl)-5H-chromeno[4,3-c]pyridin-3-yl)amino)pyridin-3-yl)isonicotinamide (70 mg, yield: 54%) as a yellow solid.

Step 4: Preparation of 2-amino-N-(5-((5-methyl-8-(2-oxopyrrolidin-1-yl)-5H-chromeno[4,3-c]pyridin-3-yl)amino)pyridin-3-yl)isonicotinamide

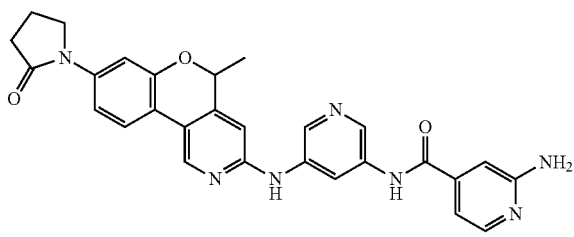 [SMILES: CC1Oc2cc(N3CCCC3=O)ccc2-c2cnc(Nc3cncc(NC(=O)c4ccnc(N)c4)c3)cc21]

A mixture of 2-(bis(4-methoxybenzyl)amino)-N-(5-((5-methyl-8-(2-oxopyrrolidin-1-yl)-5H-chromeno[4,3-c]pyridin-3-yl)amino)pyridin-3-yl)isonicotinamide (70 mg, 0.094 mmol) in TFA (3 mL) was stirred at 50° C. for 2 h. The reaction mixture turned into red solution from yellow. LCMS (Rt=0.688 min; MS Calcd: 507.2. MS Found: 508.3 [M+H]⁺). The reaction mixture was concentrated and the residue was basified with 2N aqueous NaOH to pH=10, then extracted with EtOAc/THF (25 mL×3, 1/1). The combined organic layer was washed with brine (25 mL), dried over anhydrous Na$_2$SO$_4$ and concentrated. The crude product was triturated with MeCN (5 mL), filtered, then washed with MeCN (2 mL×2) and dried under vacuum to give 2-amino-N-(5-((5-methyl-8-(2-oxopyrrolidin-1-yl)-5H-chromeno[4,3-c]pyridin-3-yl)amino)pyridin-3-yl)isonicotinamide (32.4 mg yield: 68%) as a yellow solid.

$^1$H NMR (400 MHz, DMSO-d$_6$) δ 1.55 (3H, d, J=6.6 Hz), 2.02-2.11 (2H, m), 2.53-2.56 (2H, m), 3.85 (2H, t, J=7.8 Hz), 5.29 (1H, q, J=6.5 Hz), 6.24 (2H, brs), 6.78 (1H, s), 6.90 (1H, s), 6.96 (1H, dd, J=5.3, 1.3 Hz), 7.33 (1H, dd, J=8.6, 2.1 Hz), 7.41 (1H, d, J=2.2 Hz), 7.89 (1H, d, J=8.7 Hz), 8.08 (1H, d, J=5.1 Hz), 8.46 (1H, d, J=2.0 Hz), 8.63-8.71 (3H, m), 9.50 (1H, brs), 10.46 (1H, brs).

Example 116: 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-5-carboxamide

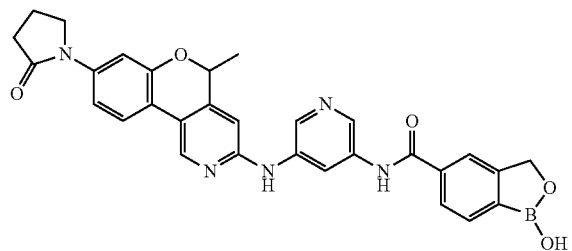

Step 1: Preparation of 3-(acetoxymethyl)-4-bromobenzoic acid

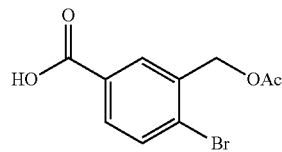 [SMILES: CC(=O)OCc1cc(C(=O)O)ccc1Br]

To a mixture of 4-bromo-3-(hydroxymethyl)benzoic acid (300 mg, 1.30 mmol) in pyridine (10 mL) was added acetic anhydride (132 mg, 1.30 mmol), the reaction mixture was stirred at 25° C. for 2 h to give a yellow solution. LCMS showed the reaction was completed. The mixture was concentrated under reduced pressure to remove pyridine and then diluted with water (10 mL). The pH of the mixture was adjusted to 2 with 2 N aqueous HCl and then extracted with EtOAc (20 mL×2). The combined extracts was washed with brine (25 mL×2), dried over anhydrous Na$_2$SO$_4$, filtered and concentrated under reduced pressure to give 3-(acetoxymethyl)-4-bromobenzoic acid (300 mg, yield: 85%) as a white solid.

$^1$H NMR (400 MHz, DMSO-d$_6$) δ 2.11 (3H, s), 5.17 (2H, s), 7.76-7.85 (2H, m), 8.01 (1H, s), 13.28 (1H, brs).

Step 2: Preparation of 2-bromo-5-((5-((5-methyl-8-(2-oxopyrrolidin-1-yl)-5H-chromeno[4,3-c]pyridin-3-yl)amino)pyridin-3-yl)carbamoyl)benzyl acetate

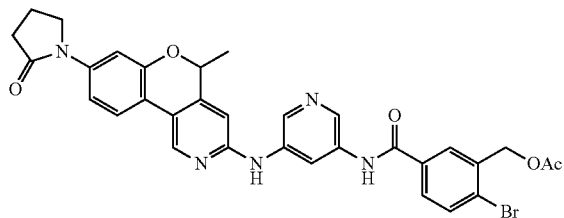 [SMILES: CC(=O)OCc1cc(C(=O)Nc2cncc(Nc3cc4c(cn3)-c3ccc(N5CCCC5=O)cc3OC4C)c2)ccc1Br]

To a mixture of 1-(3-((5-aminopyridin-3-yl)amino)-5-methyl-5H-chromeno[4,3-c]pyridin-8-yl)pyrrolidin-2-one (100 mg, 0.217 mmol, 2HCl salt) and 3-(acetoxymethyl)-4-bromobenzoic acid (119 mg, 0.434 mmol) in pyridine (5 mL) was added EDCI.HCl (83 mg, 0.43 mmol), the reaction mixture was stirred at 50° C. for 2 h to give a yellow solution. LCMS (Rt=0.763 min; MS Calcd: 643.1. MS Found: 644.1 [M+H]$^+$). The mixture was concentrated under reduced pressure and the crude product was washed with MeCN (10 mL×2) to give 2-bromo-5-((5-((5-methyl-8-(2-oxopyrrolidin-1-yl)-5H-chromeno[4,3-c]pyridin-3-yl)amino)pyridin-3-yl)carbamoyl)benzyl acetate (60 mg, yield: 43%) as a yellow solid.

$^1$H NMR (400 MHz, DMSO-d$_6$) δ 1.57 (3H, d, J=6.8 Hz), 2.00-2.12 (2H, m), 2.15 (3H, s), 2.49-2.52 (2H, m), 3.86 (2H, t, J=7.6 Hz), 5.22 (2H, s), 5.34 (1H, q, J=6.4 Hz), 6.90 (1H, s), 7.36 (1H, dd, J=8.4, 2.0 Hz), 7.42 (1H, d, J=2.0 Hz), 7.88-7.99 (3H, m), 8.11 (1H, d, J=2.0 Hz), 8.74-8.79 (2H, m), 8.92 (1H, s), 9.13 (1H, s), 10.31 (1H, brs), 11.14 (1H, brs).

Step 3: Preparation of 5-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate

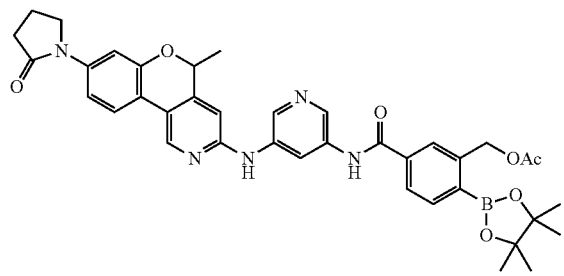 [SMILES: CC(=O)OCc1cc(C(=O)Nc2cncc(Nc3cc4c(cn3)-c3ccc(N5CCCC5=O)cc3OC4C)c2)ccc1B1OC(C)(C)C(C)(C)O1]

The 1$^{st}$ Batch

To a mixture of 2-bromo-5-((5-((5-methyl-8-(2-oxopyrrolidin-1-yl)-5H-chromeno[4,3-c]pyridin-3-yl)amino)pyridin-3-yl)carbamoyl)benzyl acetate (60 mg, 0.093 mmol) in dioxane (8 mL) was added KOAc (27 mg, 0.28 mmol), B$_2$Pin$_2$ (36 mg, 0.14 mmol) and Pd(dppf)Cl$_2$ (7 mg, 0.009 mmol) under N$_2$ atmosphere, then the reaction mixture was stirred at 100° C. under N$_2$ atmosphere for 5 h to give a brown suspension. LCMS (Rt=0.844 min; MS Calcd: 689.3. MS Found: 690.4 [M+H]$^+$). The mixture was diluted with water (15 mL) and then extracted with EtOAc (20 mL×2). The combined extracts was washed with brine (30 mL×2), dried over anhydrous Na$_2$SO$_4$, filtered and concentrated under reduced pressure to give 5-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate (60 mg, crude) as a brown solid.

The 2$^{nd}$ Batch

To a mixture of 2-bromo-5-((5-((5-methyl-8-(2-oxopyrrolidin-1-yl)-5H-chromeno[4,3-c]pyridin-3-yl)amino)pyridin-3-yl)carbamoyl)benzyl acetate (120 mg, 0.187 mmol) in dioxane (10 mL) was added KOAc (55 mg, 0.56 mmol), B$_2$Pin$_2$ (71 mg, 0.28 mmol) and Pd(dppf)Cl$_2$ (14 mg, 0.019 mmol) under N$_2$ atmosphere, then the reaction mixture was stirred at 100° C. under N$_2$ atmosphere for 5 h to give a brown suspension. LCMS (Rt=0.852 min; MS Calcd: 689.3. MS Found: 690.4 [M+H]$^+$). The mixture was diluted with water (10 mL) and then extracted with EtOAc (20 mL×2). The combined extracts was washed with brine (25 mL×2), dried over anhydrous Na$_2$SO$_4$, filtered and concentrated. The residue was combined with the first batch and purified by Combi Flash (DCM/MeOH, 100/1 to 95/5) to give 5-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate (120 mg, average yield: 44%) as a brown solid.

Step 4: Preparation of 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-5-carboxamide

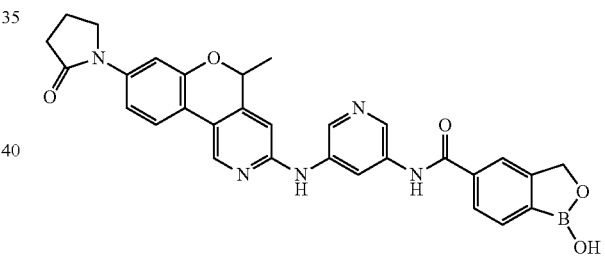

To a mixture of 5-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate (120 mg, 0.174 mmol) in MeOH (8 mL) was added a solution of NaOH (14 mg, 0.35 mmol) in MeOH (2 mL), then the reaction mixture was stirred at 40° C. for 4 h to give a brown solution. LCMS (Rt=0.714 min; MS Calcd: 547.2. MS Found: 548.0 [M+H]$^+$). The mixture was concentrated under reduced pressure. The residue was purified by prep-HPLC (0.05% NH$_3$.H$_2$O as an additive) to give 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-5-carboxamide (12.0 mg, yield: 12%) as a yellow solid.

$^1$H NMR (400 MHz, DMSO-d$_6$) δ 1.55 (3H, d, J=6.4 Hz), 2.00-2.09 (2H, m), 2.49-2.52 (2H, m), 3.84 (2H, t, J=6.8 Hz), 5.10 (2H, s), 5.28 (1H, q, J=6.4 Hz), 6.77 (1H, s), 7.32 (1H, dd, J=8.8, 2.4 Hz), 7.40 (1H, d, J=2.4 Hz), 7.84-7.90 (2H, m), 7.90-7.96 (1H, m), 8.00 (1H, s), 8.49 (1H, d, J=1.6 Hz), 8.64-8.71 (3H, m), 9.39 (1H, brs), 9.50 (1H, brs), 10.50 (1H, brs).

Example 117: 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-6-carboxamide

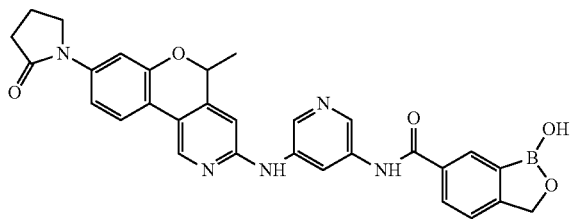 [SMILES: CC1Oc2cc(N3CCCC3=O)ccc2-c2cnc(Nc3cncc(NC(=O)c4ccc5c(c4)B(O)OC5)c3)cc21]

Step 1: Preparation of 3-bromo-4-(hydroxymethyl)benzoic acid

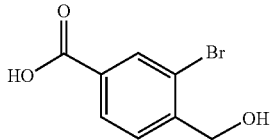 [SMILES: O=C(O)c1ccc(CO)c(Br)c1]

To a mixture of 3-bromo-4-formylbenzoic acid (500 mg, 2.18 mmol) in anhydrous THF (15 mL) was added NaBH$_4$ (83 mg, 2.18 mmol) in portions at 0° C., then warmed to 20° C. and stirred for 3 h to give a black suspension. LCMS showed the reaction was completed. The mixture was quenched with water (10 mL). The pH of the mixture was adjusted to 2 with 1N aqueous HCl, then extracted with EtOAc (20 mL×2), the combined extracts was washed with brine (30 mL×2), dried over anhydrous Na$_2$SO$_4$, filtered and concentrated under reduced pressure to give 3-bromo-4-(hydroxymethyl)benzoic acid (460 mg, yield: 91%) as a white solid.

$^1$H NMR (400 MHz, DMSO-d$_6$) δ 4.56 (2H, d, J=5.2 Hz), 5.63 (1H, brs), 7.67 (1H, d, J=8.0 Hz), 7.97 (1H, dd, J=8.0, 1.6 Hz), 8.04 (1H, d, J=1.6 Hz), 13.19 (1H, brs).

Step 2: Preparation of 4-(acetoxymethyl)-3-bromobenzoic acid

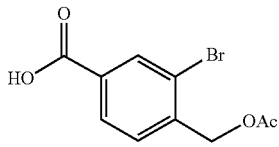

To a mixture of 3-bromo-4-(hydroxymethyl)benzoic acid (460 mg, 1.99 mmol) in pyridine (10 mL) was added acetic anhydride (203 mg, 1.99 mmol), the reaction mixture was stirred at 25° C. for 2 h to give a pale yellow solution. LCMS showed the reaction was completed. The mixture was quenched with water (10 mL) and the pH was adjusted to 1 with 1N aqueous HCl. The mixture was extracted with EtOAc (20 mL×2), the combined extracts was washed with brine (30 mL×2), dried over anhydrous Na$_2$SO$_4$, filtered and concentrated under reduced pressure to give 4-(acetoxymethyl)-3-bromobenzoic acid (500 mg, yield: 92%) as an off-white solid.

$^1$H NMR (400 MHz, DMSO-d$_6$) δ 2.14 (3H, s), 5.17 (2H, s), 7.61 (1H, d, J=8.0 Hz), 7.95 (1H, dd, J=8.0, 1.2 Hz), 8.11 (1H, d, J=1.2 Hz), 13.38 (1H, brs).

Step 3: Preparation of 2-bromo-4-((5-((5-methyl-8-(2-oxopyrrolidin-1-yl)-5H-chromeno[4,3-c]pyridin-3-yl)amino)pyridin-3-yl)carbamoyl)benzylacetate

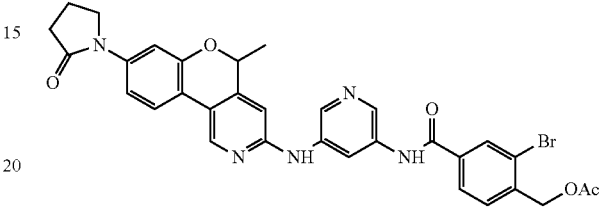

To a mixture of 1-(3-((5-aminopyridin-3-yl)amino)-5-methyl-5H-chromeno[4,3-c]pyridin-8-yl)pyrrolidin-2-one (300 mg, 0.652 mmol, HCl salt) and 4-(acetoxymethyl)-3-bromobenzoic acid (178 mg, 0.652 mmol) in pyridine (10 mL) was added EDCI.HCl (250 mg, 1.30 mmol), the reaction mixture was stirred at 50° C. for 3 h to give a yellow solution. LCMS (Rt=0.759 min; MS Calcd: 643.1. MS Found: 644.1 [M+H]$^+$). The mixture was concentrated under reduced pressure to give a residue. The residue was washed with MeOH (20 mL×2) to give 2-bromo-4-((5-((5-methyl-8-(2-oxopyrrolidin-1-yl)-5H-chromeno[4,3-c]pyridin-3-yl)amino)pyridin-3-yl)carbamoyl)benzyl acetate (280 mg, yield: 67%) as a yellow solid.

$^1$H NMR (400 MHz, DMSO-d$_6$) δ 1.57 (3H, d, J=6.8 Hz), 2.00-2.14 (2H, m), 2.16 (3H, s), 2.50-2.53 (2H, m), 3.86 (2H, t, J=8.0 Hz), 5.22 (2H, s), 5.34 (1H, q, J=6.0 Hz), 6.89 (1H, s), 7.36 (1H, dd, J=8.8, 2.4 Hz), 7.42 (1H, d, J=2.0 Hz), 7.68 (1H, d, J=8.4 Hz), 7.94 (1H, d, J=8.8 Hz), 8.06 (1H, dd, J=8.0, 1.6 Hz), 8.31 (1H, d, J=2.0 Hz), 8.73-8.79 (2H, m), 8.92 (1H, d, J=2.0 Hz), 9.11 (1H, d, J=2.0 Hz), 10.28 (1H, brs), 11.08 (1H, brs).

Step 4: Preparation of 4-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate

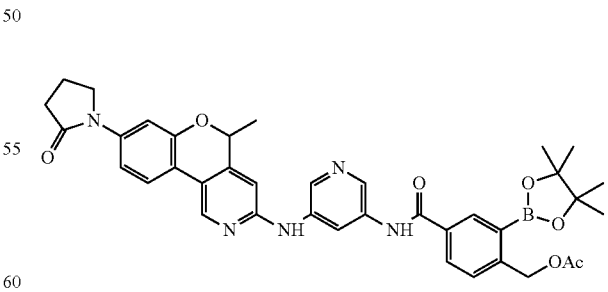

To a mixture of 2-bromo-4-((5-((5-methyl-8-(2-oxopyrrolidin-1-yl)-5H-chromeno[4,3-c]pyridin-3-yl)amino)pyridin-3-yl)carbamoyl)benzyl acetate (200 mg, 0.311 mmol) in dioxane (8 mL) was added KOAc (92 mg, 0.93 mmol), B$_2$Pin$_2$ (119 mg, 0.467 mmol) and Pd(dppf)Cl$_2$ (23 mg, 0.031 mmol) under N$_2$ atmosphere, then the reaction mixture was stirred at 90° C. under N₂ atmosphere for 16 h to give a brown suspension. LCMS (Rt=0.811 min; MS Calcd: 689.3. MS Found: 690.1 [M+H]⁺). The mixture was diluted with water (15 mL) and extracted with EtOAc (20 mL×2). The combined extracts was washed with brine (30 mL×2), dried over anhydrous Na₂SO₄, filtered and concentrated under reduced pressure. The residue was purified by Combi Flash (DCM:MeOH=100/1 to 95/5) to give 4-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate (120 mg, yield: 43%, purity: 77%) as a brown gum.

Step 5: Preparation of 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-6-carboxamide

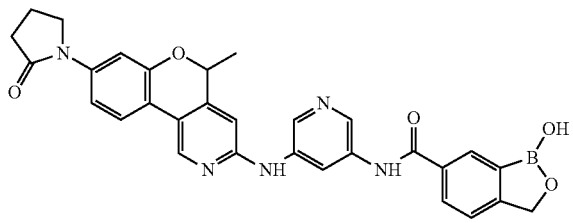 [SMILES: CC1Oc2cc(N3CCCC3=O)ccc2-c2cnc(Nc3cncc(NC(=O)c4ccc5c(c4)B(O)OC5)c3)cc21]

To a mixture of 4-((5-((5-methyl-8-(2-oxopyrrolidin-1-yl)-5H-chromeno[4,3-c]pyridin-3-yl)amino)pyridin-3-yl)carbamoyl)-2-(4,4,5,5-tetramethyl-1,3,2-dioxaborolan-2-yl)benzyl acetate (120 mg, 0.174 mmol) in MeOH (8 mL) was added a solution of NaOH (14 mg, 0.35 mmol) in MeOH (2 mL), then the reaction mixture was stirred at 40° C. for 4 h to give a brown solution. LCMS (Rt=0.717 min; MS Calcd: 547.2. MS Found: 548.1 [M+H]⁺). The mixture was concentrated under reduced pressure. The residue was purified by prep-HPLC (0.05% NH₃.H₂O as an additive) and lyophilized to give 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-6-carboxamide (16.8 mg, yield: 18%) as an off-white solid.

¹H NMR (400 MHz, DMSO-d₆) δ 1.55 (3H, d, J=6.8 Hz), 2.00-2.11 (2H, m), 2.49-2.52 (2H, m), 3.84 (2H, t, J=7.6 Hz), 5.09 (2H, s), 5.27 (1H, q, J=6.0 Hz), 6.77 (1H, s), 7.31 (1H, dd, J=8.8, 2.4 Hz), 7.40 (1H, d, J=2.0 Hz), 7.58 (1H, d, J=7.6 Hz), 7.78 (1H, d, J=8.8 Hz), 8.08 (1H, dd, J=8.0, 1.6 Hz), 8.35 (1H, s), 8.49 (1H, d, J=2.0 Hz), 8.62-8.71 (3H, m), 9.39 (1H, brs), 9.49 (1H, brs), 10.48 (1H, brs).

Example 118: 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-4-carboxamide

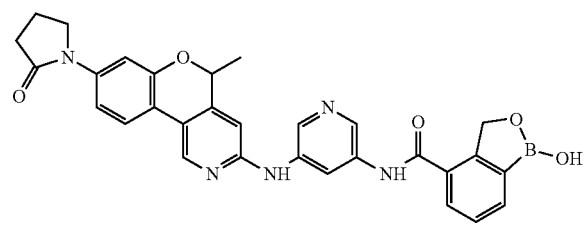 [SMILES: CC1Oc2cc(N3CCCC3=O)ccc2-c2cnc(Nc3cncc(NC(=O)c4cccc5c4COB5O)c3)cc21]

Step 1: Preparation of 3-bromo-2-(hydroxymethyl)-N-(5-((5-methyl-8-(2-oxopyrrolidin-1-yl)-5H-chromeno[4,3-c]pyridin-3-yl)amino)pyridin-3-yl)benzamide

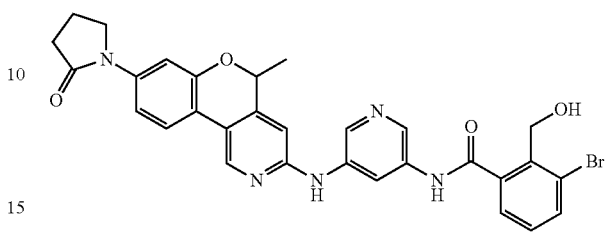

To a mixture of 1-(3-((5-aminopyridin-3-yl)amino)-5-methyl-5H-chromeno[4,3-c]pyridin-8-yl)pyrrolidin-2-one (100 mg, 0.236 mmol, HCl salt) and 4-bromoisobenzofuran-1(3H)-one (75 mg, 0.354 mmol) in toluene (5 mL) was added AlMe₃ (2 M in toluene, 0.47 mL, 0.94 mmol) dropwise at 0° C., then warmed to 25° C. and stirred for 0.5 hour. The reaction mixture was heated at 50° C. and stirred for 4.5 h to give a yellow suspension. LCMS (Rt=0.774 min; MS Calcd: 599.1. MS Found: 600.1 [M+H]⁺). The mixture was quenched with saturated aqueous sodium potassium tartrate (25 mL), followed by EtOAc (15 mL). The white precipitate was filtered and dried under high vacuum to give 3-bromo-2-(hydroxymethyl)-N-(5-((5-methyl-8-(2-oxopyrrolidin-1-yl)-5H-chromeno[4,3-c]pyridin-3-yl)amino)pyridin-3-yl)benzamide (80 mg, yield: 50%) as an off-white solid.

Step 2: Preparation of 2-bromo-6-((5-((5-methyl-8-(2-oxopyrrolidin-1-yl)-5H-chromeno[4,3-c]pyridin-3-yl)amino)pyridin-3-yl)carbamoyl)benzylacetate

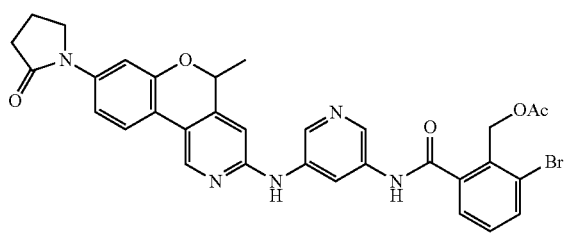 [SMILES: CC(=O)OCc1c(Br)cccc1C(=O)Nc1cncc(Nc2cc3c(cn2)-c2ccc(N4CCCC4=O)cc2OC3C)c1]

To a mixture of 3-bromo-2-(hydroxymethyl)-N-(5-((5-methyl-8-(2-oxopyrrolidin-1-yl)-5H-chromeno[4,3-c]pyridin-3-yl)amino)pyridin-3-yl)benzamide (80 mg, 0.133 mmol) in pyridine (5 mL) was added acetic anhydride (16 mg, 0.16 mmol), the reaction mixture was stirred at 25° C. for 4 h to give a yellow solution. LCMS (Rt=0.796 min; MS Calcd: 643.1; MS Found: 644.2 [M+H]⁺). The mixture was concentrated under reduced pressure to give a residue. The residue was purified by washing with MeOH (10 mL×2) to give 2-bromo-6-((5-((5-methyl-8-(2-oxopyrrolidin-1-yl)-5H-chromeno[4,3-c]pyridin-3-yl)amino)pyridin-3-yl)carbamoyl)benzyl acetate (80 mg, yield: 93%) as an off-white solid.

¹H NMR (400 MHz, DMSO-d₆) δ 1.54 (3H, d, J=6.4 Hz), 1.90 (3H, s), 2.00-2.12 (2H, m), 2.50-2.52 (2H, m), 3.84 (2H, t, J=6.8 Hz), 5.22-5.35 (3H, m), 6.77 (1H, s), 7.33 (1H, dd, J=8.8, 1.6 Hz), 7.40 (1H, s), 7.47 (1H, t, J=7.6 Hz), 7.63

(1H, d, J=7.2 Hz), 7.81-7.92 (2H, m), 8.39 (1H, s), 8.60 (1H, s), 8.65 (1H, s), 8.73 (1H, d, J=2.0 Hz), 9.52 (1H, brs), 10.68 (1H, brs).

Step 3: Preparation of 2-((5-((5-methyl-8-(2-oxopyrrolidin-1-yl)-5H-chromeno[4,3-c]pyridin-3-yl)amino)pyridin-3-yl)carbamoyl)-6-(4,4,5,5-tetramethyl-1,3,2-dioxaborolan-2-yl)benzyl acetate

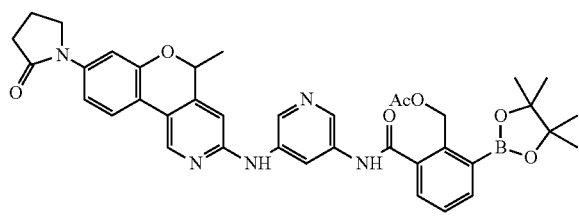 [SMILES: CC(=O)OCc1c(B2OC(C)(C)C(C)(C)O2)cccc1C(=O)Nc1cncc(Nc2cc3c(cn2)-c2ccc(N4CCCC4=O)cc2OC3C)c1]

To a mixture of 2-bromo-6-((5-((5-methyl-8-(2-oxopyrrolidin-1-yl)-5H-chromeno[4,3-c]pyridin-3-yl)amino)pyridin-3-yl)carbamoyl)benzyl acetate (80 mg, 0.12 mmol), B$_2$Pin$_2$ (47 mg, 0.19 mmol), KOAc (49 mg, 0.50 mmol) in dioxane (5 mL) was added Pd(dppf)Cl$_2$ (9 mg, 0.01 mmol) under N$_2$ atmosphere, then the reaction mixture was stirred at 100° C. under N$_2$ atmosphere for 2 h to give a brown suspension. LCMS showed the reaction was completed. The mixture was diluted with water (10 mL) and then extracted with EtOAc (20 mL×2). The combined extracts was washed with brine (25 mL×2), dried over Na$_2$SO$_4$, filtered and concentrated under reduced pressure to give 2-((5-((5-methyl-8-(2-oxopyrrolidin-1-yl)-5H-chromeno[4,3-c]pyridin-3-yl)amino)pyridin-3-yl)carbamoyl)-6-(4,4,5,5-tetramethyl-1,3,2-dioxaborolan-2-yl)benzyl acetate (80 mg, crude) as a brown solid.

Step 4: Preparation of 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-4-carboxamide

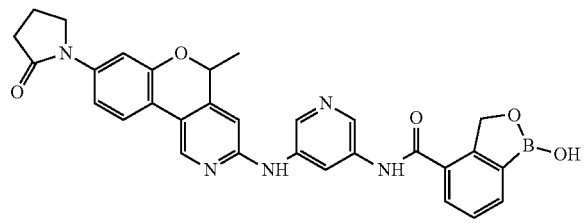 [SMILES: CC1Oc2cc(N3CCCC3=O)ccc2-c2cnc(Nc3cncc(NC(=O)c4cccc5c4COB5O)c3)cc21]

To a mixture of 2-((5-((5-methyl-8-(2-oxopyrrolidin-1-yl)-5H-chromeno[4,3-c]pyridin-3-yl)amino)pyridin-3-yl)carbamoyl)-6-(4,4,5,5-tetramethyl-1,3,2-dioxaborolan-2-yl)benzyl acetate (60 mg, 0.087 mmol) in MeOH (20 mL) was added NaOH (7 mg, 0.2 mmol), the reaction mixture was stirred at 40° C. for 2 h to give a brown solution. LCMS (Rt=0.747 min; MS Calcd: 547.2. MS Found: 548.2 [M+H]$^+$). The mixture was concentrated and the residue was dissolved in MeOH (4 mL). The pH of the mixture was adjusted to 7 with formic acid and standing at 25° C. for 16 h. The brown precipitate was filtered and purified by prep-HPLC (0.225% FA as an additive) purification to give 1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-4-carboxamide (2.26 mg, yield: 4% for 2 steps) as a yellow solid.

$^1$H NMR (400 MHz, DMSO-d$_6$) δ 1.55 (3H, d, J=6.4 Hz), 2.00-2.12 (2H, m), 2.49-2.52 (2H, m), 3.84 (2H, t, J=7.6 Hz), 5.25-5.32 (3H, m), 6.78 (1H, s), 7.32 (1H, dd, J=8.4, 2.0 Hz), 7.40 (1H, d, J=2.0 Hz), 7.58 (1H, t, J=7.2 Hz), 7.88 (1H, d, J=8.8 Hz), 7.97 (1H, d, J=6.8 Hz), 8.11 (1H, d, J=7.6 Hz), 8.48 (1H, s), 8.60-8.71 (2H, m), 8.75 (1H, s), 9.33 (1H, brs), 9.56 (1H, brs), 10.51 (1H, brs).

Example 119: 4-fluoro-N-(5-((5-methyl-8-(2-oxopyrrolidin-1-yl)-5H-chromeno[4,3-c]pyridin-3-yl)amino)pyridin-3-yl)benzamide

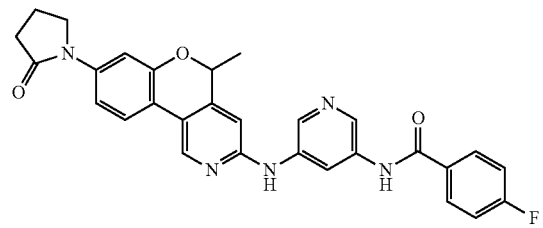 [SMILES: CC1Oc2cc(N3CCCC3=O)ccc2-c2cnc(Nc3cncc(NC(=O)c4ccc(F)cc4)c3)cc21]

Step 1: Preparation of N-(5-bromopyridin-3-yl)-4-fluorobenzamide

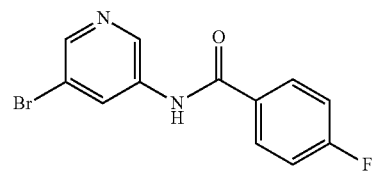 [SMILES: O=C(Nc1cncc(Br)c1)c1ccc(F)cc1]

A mixture of 4-fluorobenzoic acid (267 mg, 1.90 mmol), 5-bromopyridin-3-amine (300 mg, 1.73 mmol) and EDCI.HCl (365 mg, 1.90 mmol) in pyridine (5 mL) was heated at 50° C. for 1 hour. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was triturated with pentane/EtOAC (3 mL, 3/1) to give N-(5-bromopyridin-3-yl)-4-fluorobenzamide (230 mg, yield: 44%) as a light yellow solid.

$^1$H NMR (400 MHz DMSO-d$_6$) δ 7.37-7.45 (2H, m), 8.04-8.09 (2H, m), 8.45 (1H, d, J=2.0 Hz), 8.51 (1H, t, J=2.1 Hz), 8.91 (1H, d, J=2.0 Hz), 10.62 (1H, brs).

Step 2: Preparation of 4-fluoro-N-(5-((5-methyl-8-(2-oxopyrrolidin-1-yl)-5H-chromeno[4,3-c]pyridin-3-yl)amino)pyridin-3-yl)benzamide

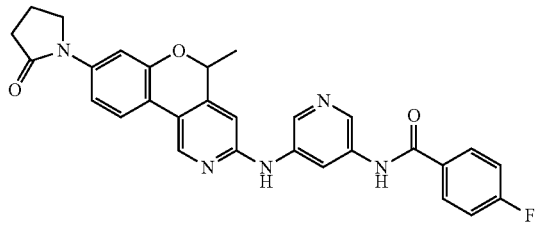 [SMILES: CC1Oc2cc(N3CCCC3=O)ccc2-c2cnc(Nc3cncc(NC(=O)c4ccc(F)cc4)c3)cc21]

A mixture of 1-(3-amino-5-methyl-5H-chromeno[4,3-c]pyridin-8-yl)pyrrolidin-2-one (60 mg, 0.20 mmol), N-(5-bromopyridin-3-yl)-4-fluorobenzamide (66 mg, 0.22 mmol), Pd$_2$(dba)$_3$ (19 mg, 0.020 mmol), BrettPhos (22 mg, 0.041 mmol), Cs$_2$CO$_3$ (132 mg, 0.406 mmol) in dioxane (3 mL) was degassed and purged with N$_2$ for 3 times. Then the resulting reaction mixture was heated at 90° C. for 15 h under N$_2$ atmosphere. The reaction mixture turned into gray suspension from red suspension. LCMS (Rt=0.735 min; MS Calcd: 509.2. MS Found: 510.1 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give 4-fluoro-N-(5-((5-methyl-8-(2-oxopyrrolidin-1-yl)-5H-chromeno[4,3-c]pyridin-3-yl)amino)pyridin-3-yl)benzamide (35.9 mg, yield: 35%) as a yellow solid.

$^1$H NMR (400 MHz DMSO-d$_6$) δ 1.55 (3H, d, J=6.5 Hz), 2.01-2.10 (2H, m), 2.52-2.54 (2H, m, overlapped with the peak of DMSO), 3.84 (2H, t, J=7.4 Hz), 5.28 (1H, q, J=6.4 Hz), 6.78 (1H, s), 7.32 (1H, dd, J=8.7, 2.1 Hz), 7.37-7.43 (3H, m), 7.88 (1H, d, J=8.5 Hz), 8.05 (2H, dd, J=8.8, 5.5 Hz), 8.49 (1H, s), 8.65-8.70 (3H, m), 9.55 (1H, brs), 10.47 (1H, brs).

Example 120: 3-fluoro-N-(5-((5-methyl-8-(2-oxopyrrolidin-1-yl)-5H-chromeno[4,3-c]pyridin-3-yl)amino)pyridin-3-yl)benzamide

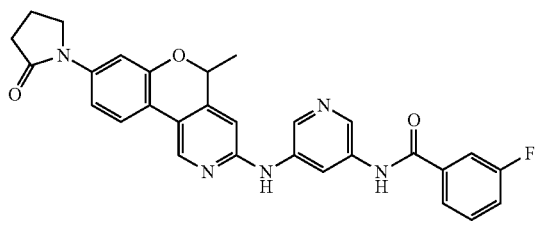 [SMILES: CC1Oc2cc(N3CCCC3=O)ccc2-c2cnc(Nc3cncc(NC(=O)c4cccc(F)c4)c3)cc21]

Step 1: Preparation of N-(5-bromopyridin-3-yl)-3-fluorobenzamide

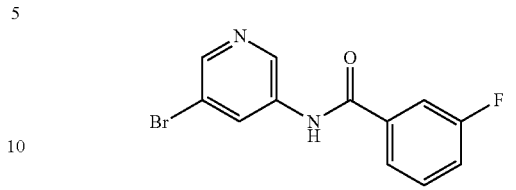

A mixture of 3-fluorobenzoic acid (267 mg, 1.90 mmol), 5-bromopyridin-3-amine (300 mg, 1.73 mmol) and EDCI.HCl (365 mg, 1.90 mmol) in pyridine (5 mL) was heated at 50° C. for 1 hour. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by Combi Flash (30% to 50% EtOAc in pentane) to give N-(5-bromopyridin-3-yl)-3-fluorobenzamide (400 mg, yield: 78%) as a light yellow solid.

$^1$H NMR (400 MHz DMSO-d$_6$) δ 7.50 (1H, td, J=8.3, 2.3 Hz), 7.63 (1H, td, J=8.0, 5.9 Hz), 7.77-7.86 (2H, m), 8.47 (1H, d, J=2.0 Hz), 8.51 (1H, t, J=2.1 Hz), 8.91 (1H, d, J=2.0 Hz), 10.67 (1H, brs).

Step 2: Preparation of 3-fluoro-N-(5-((5-methyl-8-(2-oxopyrrolidin-1-yl)-5H-chromeno[4,3-c]pyridin-3-yl)amino)pyridin-3-yl)benzamide

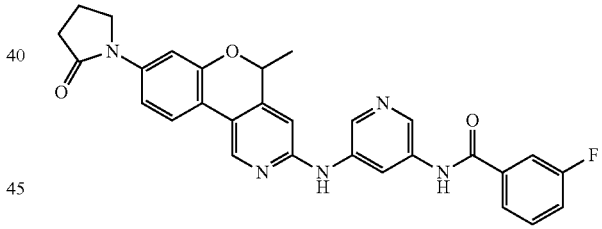

A mixture of 1-(3-amino-5-methyl-5H-chromeno[4,3-c]pyridin-8-yl)pyrrolidin-2-one (60 mg, 0.20 mmol), N-(5-bromopyridin-3-yl)-3-fluorobenzamide (66 mg, 0.22 mmol), Pd$_2$(dba)$_3$ (19 mg, 0.020 mmol), BrettPhos (22 mg, 0.041 mmol), Cs$_2$CO$_3$ (132 mg, 0.406 mmol) in anhydrous dioxane (3 mL) was degassed and purged with N$_2$ for 3 times. Then the resulting reaction mixture was heated at 90° C. for 12 h under N$_2$ atmosphere. The reaction mixture turned into gray suspension from red suspension. LCMS (Rt=0.735 min; MS Calcd: 509.2. MS Found: 510.1 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give 3-fluoro-N-(5-((5-methyl-8-(2-oxopyrrolidin-1-yl)-5H-chromeno[4,3-c]pyridin-3-yl)amino)pyridin-3-yl)benzamide (28.1 mg, yield: 27%) as a yellow solid.

¹H NMR (400 MHz DMSO-d₆) δ 1.55 (3H, d, J=6.5 Hz), 2.01-2.10 (2H, m), 2.52-2.54 (2H, m, overlapped with the peak of DMSO), 3.84 (2H, t, J=7.5 Hz), 5.28 (1H, q, J=6.4 Hz), 6.78 (1H, s), 7.32 (1H, dd, J=8.7, 2.1 Hz), 7.41 (1H, d, J=2.3 Hz), 7.46-7.51 (1H, m), 7.59-7.66 (1H, m), 7.79-7.91 (3H, m), 8.49 (1H, s), 7.65-7.71 (3H, m), 9.53 (1H, brs), 10.50 (1H, brs).

Example 121: 3-methoxy-N-(5-((5-methyl-8-(2-oxopyrrolidin-1-yl)-5H-chromeno[4,3-c]pyridin-3-yl)amino)pyridin-3-yl)benzamide

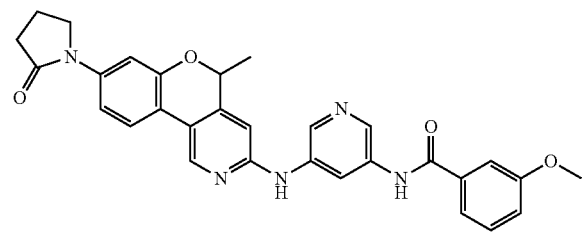 [SMILES: COc1cccc(C(=O)Nc2cncc(Nc3cc4c(cn3)-c3ccc(N5CCCC5=O)cc3OC4C)c2)c1]

Step 1: Preparation of N-(5-bromopyridin-3-yl)-3-methoxybenzamide

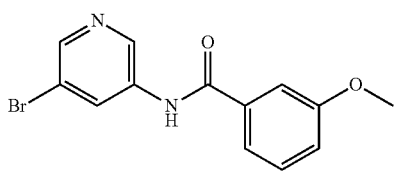 [SMILES: COc1cccc(C(=O)Nc2cncc(Br)c2)c1]

A mixture of 3-methoxybenzoic acid (290 mg, 1.90 mmol), 5-bromopyridin-3-amine (300 mg, 1.73 mmol) and EDCI.HCl (365 mg, 1.90 mmol) in pyridine (5 mL) was heated at 50° C. for 2 h. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by Combi Flash (30% to 50% EtOAc in pentane) to give N-(5-bromopyridin-3-yl)-3-methoxybenzamide (500 mg, yield: 94%) as a light yellow solid.

¹H NMR (400 MHz DMSO-d₆) δ 3.85 (3H, s), 7.20 (1H, d, J=7.8 Hz), 7.44-7.58 (3H, m), 8.44 (1H, s), 8.51 (1H, d, J=2.0 Hz), 8.93 (1H, s), 10.57 (1H, brs).

Step 2: Preparation of 3-methoxy-N-(5-((5-methyl-8-(2-oxopyrrolidin-1-yl)-5H-chromeno[4,3-c]pyridin-3-yl)amino)pyridin-3-yl)benzamide

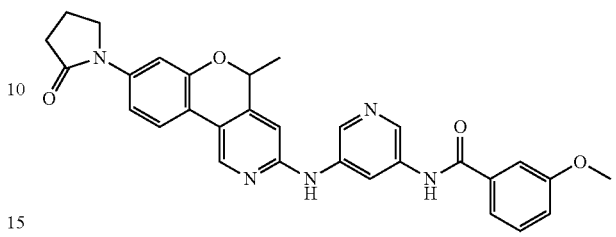

A mixture of 1-(3-amino-5-methyl-5H-chromeno[4,3-c]pyridin-8-yl)pyrrolidin-2-one (60 mg, 0.20 mmol), N-(5-bromopyridin-3-yl)-3-methoxybenzamide (69 mg, 0.22 mmol), Pd₂(dba)₃ (19 mg, 0.020 mmol), BrettPhos (22 mg, 0.041 mmol), Cs₂CO₃ (132 mg, 0.406 mmol) in anhydrous dioxane (3 mL) was degassed and purged with N₂ for 3 times. Then the resulting reaction mixture was heated at 90° C. for 14 h under N₂ atmosphere. The reaction mixture turned into gray suspension from red suspension. LCMS (Rt=0.757 min; MS Calcd: 521.2. MS Found: 522.3 [M+H]⁺). The mixture was diluted with water (20 mL) and extracted with EtOAc/THF (20 mL×2, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 3-methoxy-N-(5-((5-methyl-8-(2-oxopyrrolidin-1-yl)-5H-chromeno[4,3-c]pyridin-3-yl)amino)pyridin-3-yl)benzamide (26.1 mg, yield: 24%) as a yellow solid.

¹H NMR (400 MHz DMSO-d₆) δ 1.55 (3H, d, J=6.5 Hz), 2.01-2.10 (2H, m), 2.52-2.54 (2H, m, overlapped with the peak of DMSO), 3.84 (2H, t, J=7.4 Hz), 3.86 (3H, s), 5.29 (1H, q, J=6.7 Hz), 6.79 (1H, s), 7.20 (1H, dd, J=8.2, 1.9 Hz), 7.32 (1H, dd, J=8.5, 2.3 Hz), 7.41 (1H, d, J=2.0 Hz), 7.49 (1H, t, J=7.9 Hz), 7.52-7.54 (1H, m), 7.58 (1H, d, J=8.0 Hz), 7.89 (1H, d, J=8.8 Hz), 8.55 (1H, d, J=4.3 Hz), 8.69 (1H, s), 8.73 (1H, t, J=2.0 Hz), 8.76-8.79 (1H, m), 9.67 (1H, brs), 10.52 (1H, brs).

Example 122: 4-methoxy-N-(5-((5-methyl-8-(2-oxopyrrolidin-1-yl)-5H-chromeno[4,3-c]pyridin-3-yl)amino)pyridin-3-yl)benzamide

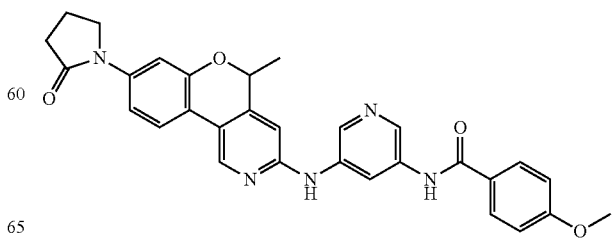

Step 1: Preparation of N-(5-bromopyridin-3-yl)-4-methoxybenzamide

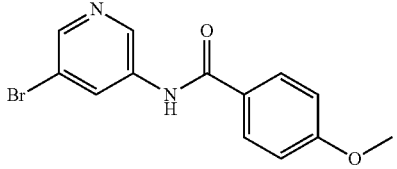 [SMILES: COc1ccc(C(=O)Nc2cncc(Br)c2)cc1]

A mixture of 4-methoxybenzoic acid (290 mg, 1.90 mmol), 5-bromopyridin-3-amine (300 mg, 1.73 mmol) and EDCI.HCl (365 mg, 1.90 mmol) in pyridine (5 mL) was heated at 50° C. for 1 hour. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by Combi Flash (30% to 50% EtOAc in pentane) to give N-(5-bromopyridin-3-yl)-4-methoxybenzamide (400 mg, yield: 74%) as a light yellow solid.

$^1$H NMR (400 MHz DMSO-d$_6$) δ 3.85 (3H, s), 7.09 (2H, d, J=8.8 Hz), 7.98 (2H, d, J=8.8 Hz), 8.42 (1H, d, J=1.8 Hz), 8.51-8.53 (1H, m), 8.92 (1H, d, J=1.8 Hz), 10.44 (1H, brs).

Step 2: Preparation of 4-methoxy-N-(5-((5-methyl-8-(2-oxopyrrolidin-1-yl)-5H-chromeno[4,3-c]pyridin-3-yl)amino)pyridin-3-yl)benzamide

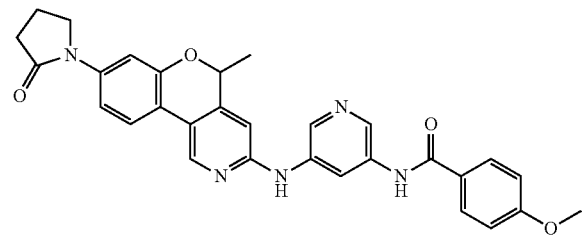 [SMILES: COc1ccc(C(=O)Nc2cncc(Nc3cc4c(cn3)-c3ccc(N5CCCC5=O)cc3OC4C)c2)cc1]

A mixture of 1-(3-amino-5-methyl-5H-chromeno[4,3-c]pyridin-8-yl)pyrrolidin-2-one (60 mg, 0.20 mmol), N-(5-bromopyridin-3-yl)-4-methoxybenzamide (69 mg, 0.22 mmol), Pd$_2$(dba)$_3$ (19 mg, 0.020 mmol), BrettPhos (22 mg, 0.041 mmol), Cs$_2$CO$_3$ (132 mg, 0.406 mmol) in dioxane (3 mL) was degassed and purged with N$_2$ for 3 times. Then the resulting reaction mixture was heated at 90° C. for 15 h under N$_2$ atmosphere. The reaction mixture turned into gray suspension from red suspension. LCMS (Rt=0.735 min; MS Calcd: 521.2. MS Found: 521.9 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give 4-methoxy-N-(5-((5-methyl-8-(2-oxopyrrolidin-1-yl)-5H-chromeno[4,3-c]pyridin-3-yl)amino)pyridin-3-yl)benzamide (27.1 mg, yield: 25%) as a yellow solid.

$^1$H NMR (400 MHz DMSO-d$_6$) δ 1.55 (3H, d, J=6.5 Hz), 2.01-2.10 (2H, m), 2.52-2.54 (2H, m, overlapped with the peak of DMSO), 3.84 (2H, t, J=7.4 Hz), 3.86 (3H, s), 5.29 (1H, q, J=6.7 Hz), 6.80 (1H, s), 7.10 (2H, d, J=8.8 Hz), 7.33 (1H, dd, J=8.5, 2.3 Hz), 7.41 (1H, d, J=2.3 Hz), 7.90 (1H, d, J=8.8 Hz), 8.01 (2H, d, J=8.8 Hz), 8.56 (1H, s), 8.69-8.74 (2H, m), 8.77 (1H, s), 9.68 (1H, brs), 10.41 (1H, brs).

Example 123: N-(5-((5-methyl-8-(2-oxopyrrolidin-1-yl)-5H-chromeno[4,3-c]pyridin-3-yl)amino)pyridin-3-yl)-1H-indole-4-carboxamide

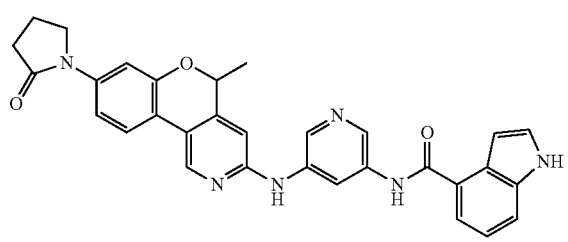 [SMILES: CC1Oc2cc(N3CCCC3=O)ccc2-c2cnc(Nc3cncc(NC(=O)c4cccc5[nH]ccc45)c3)cc21]

Step 1: Preparation of N-(5-bromopyridin-3-yl)-1H-indole-4-carboxamide

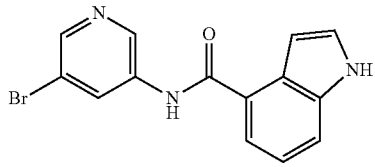 [SMILES: O=C(Nc1cncc(Br)c1)c1cccc2[nH]ccc12]

A mixture of 1H-indole-4-carboxylic acid (307 mg, 1.91 mmol), 5-bromopyridin-3-amine (300 mg, 1.73 mmol) and EDCI.HCl (366 mg, 1.91 mmol) in pyridine (5 mL) was heated at 50° C. for 1 hour. An orange solution was formed. The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was triturated with pentane/EtOAC (3 mL, 3/1) to give N-(5-bromopyridin-3-yl)-1H-indole-4-carboxamide (470 mg, yield: 86%) as a yellow solid.

$^1$H NMR (400 MHz DMSO-d$_6$) δ 6.89 (1H, t, J=2.0 Hz), 7.25 (1H, t, J=7.7 Hz), 7.52 (1H, t, J=2.8 Hz), 7.62 (1H, d, J=6.8 Hz), 7.67 (1H, d, J=8.3 Hz), 8.43 (1H, d, J=2.0 Hz), 8.60 (1H, t, J=2.1 Hz), 8.96 (1H, d, J=2.3 Hz), 10.58 (1H, brs), 11.45 (1H, brs).

Step 2: Preparation of N-(5-((5-methyl-8-(2-oxopyrrolidin-1-yl)-5H-chromeno[4,3-c]pyridin-3-yl)amino)pyridin-3-yl)-1H-indole-4-carboxamide

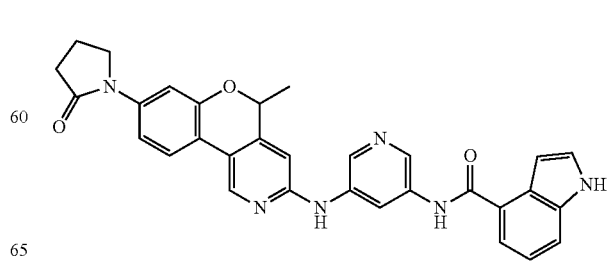

A mixture of 1-(3-amino-5-methyl-5H-chromeno[4,3-c]pyridin-8-yl)pyrrolidin-2-one (60 mg, 0.20 mmol), N-(5-bromopyridin-3-yl)-1H-indole-4-carboxamide (64 mg, 0.20 mmol), Pd₂(dba)₃ (19 mg, 0.020 mmol), BrettPhos (22 mg, 0.041 mmol), Cs₂CO₃ (132 mg, 0.406 mmol) in anhydrous dioxane (3 mL) was degassed and purged with N₂ for 3 times. Then the resulting reaction mixture was heated at 90° C. for 12 h under N₂ atmosphere. The reaction mixture turned into gray suspension from red suspension. LCMS (Rt=0.721 min; MS Calcd: 530.2. MS Found: 531.1 [M+H]⁺). The mixture was diluted with water (20 mL) and extracted with EtOAc/THF (20 mL×2, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)-1H-indole-4-carboxamide (23.6 mg, yield: 22%) as a yellow solid.

¹H NMR (400 MHz DMSO-d₆) δ 1.56 (3H, d, J=6.5 Hz), 2.01-2.10 (2H, m), 2.52-2.54 (2H, m, overlapped with the peak of DMSO), 3.84 (2H, t, J=7.9 Hz), 5.31 (1H, q, J=6.4 Hz), 6.83 (1H, s), 6.89 (1H, t, J=2.0 Hz), 7.26 (1H, t, J=7.8 Hz), 7.33 (1H, dd, J=8.5, 2.3 Hz), 7.41 (1H, d, J=2.3 Hz), 7.52 (1H, t, J=2.8 Hz), 7.66 (2H, dd, J=11.7, 7.4 Hz), 7.90 (1H, d, J=8.8 Hz), 8.64 (1H, s), 8.72 (1H, s), 8.79-8.83 (1H, m), 8.93 (1H, s), 9.85 (1H, brs), 10.62 (1H, brs), 11.45 (1H, brs).

Example 124: N-(5-((5-methyl-8-(2-oxopyrrolidin-1-yl)-5H-chromeno[4,3-c]pyridin-3-yl)amino)pyridin-3-yl)-1H-benzo[d]imidazole-4-carboxamide

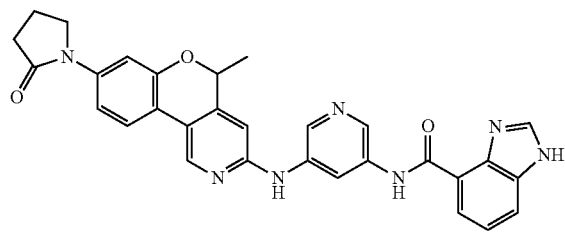 [SMILES: CC1Oc2cc(N3CCCC3=O)ccc2-c2cnc(Nc3cncc(NC(=O)c4cccc5[nH]cnc45)c3)cc21]

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), 1H-benzo[d]imidazole-4-carboxylic acid (57 mg, 0.35 mmol) and EDCI.HCl (30 mg, 0.16 mmol) in pyridine (2 mL) was heated at 30° C. for 12 h. A yellow suspension was formed. LCMS (Rt=0.586 min; MS Calcd: 531.2. MS Found: 532.2 [M+H]⁺). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)-1H-benzo[d]imidazole-4-carboxamide (41.7 mg, yield: 55%) as a yellow solid.

¹H NMR (400 MHz DMSO-d₆) δ 1.56 (3H, d, J=6.5 Hz), 2.01-2.10 (2H, m), 2.52-2.54 (2H, m, overlapped with the peak of DMSO), 3.84 (2H, t, J=7.9 Hz), 5.30 (1H, q, J=6.7 Hz), 6.79 (1H, s), 7.32 (1H, dd, J=8.7, 2.1 Hz), 7.40 (1H, d, J=2.3 Hz), 7.47 (1H, t, J=7.8 Hz), 7.88-7.92 (2H, m), 8.03 (1H, d, J=7.5 Hz), 8.62 (1H, d, J=2.0 Hz), 8.66 (1H, s), 8.72 (1H, s), 8.75 (1H, t, J=2.0 Hz), 8.81 (1H, d, J=2.0 Hz), 9.72 (1H, brs), 12.06 (1H, brs).

Example 125: N-(5-((5-methyl-8-(2-oxopyrrolidin-1-yl)-5H-chromeno[4,3-c]pyridin-3-yl)amino)pyridin-3-yl)pyridazine-4-carboxamide

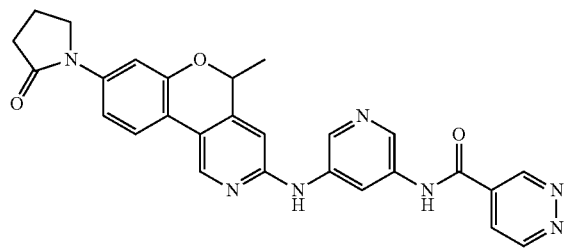 [SMILES: CC1Oc2cc(N3CCCC3=O)ccc2-c2cnc(Nc3cncc(NC(=O)c4ccnnc4)c3)cc21]

Step 1: Preparation of N-(5-bromopyridin-3-yl)pyridazine-4-carboxamide

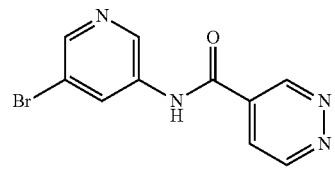 [SMILES: O=C(Nc1cncc(Br)c1)c1ccnnc1]

A mixture of pyridazine-4-carboxylic acid (236 mg, 1.90 mmol), 5-bromopyridin-3-amine (300 mg, 1.73 mmol) and EDCI.HCl (365 mg, 1.90 mmol) in pyridine (5 mL) was heated at 50° C. for 1 hour. A brown solution was formed. The mixture was concentrated and the residue was poured into water (20 mL) and stirred for 2 minutes. The aqueous layer was extracted with EtOAc (20 mL×3). The combined organic layer was washed with water (20 mL×2) and brine (20 mL), dried over anhydrous Na₂SO₄, filtered and concentrated. The residue was triturated with pentane/EtOAC (3 mL, 3/1) to give N-(5-bromopyridin-3-yl)pyridazine-4-carboxamide (400 mg, yield: 74%) as a yellow solid.

¹H NMR (400 MHz DMSO-d₆) δ 8.14 (1H, dd, J=5.4, 2.4 Hz), 8.48-8.53 (2H, m), 8.89 (1H, d, J=2.0 Hz), 9.55 (1H, dd, J=5.4, 1.1 Hz), 9.66 (1H, dd, J=2.3, 1.3 Hz), 11.08 (1H, brs).

Step 2: Preparation of N-(5-((5-methyl-8-(2-oxopyrrolidin-1-yl)-5H-chromeno[4,3-c]pyridin-3-yl)amino)pyridin-3-yl)pyridazine-4-carboxamide

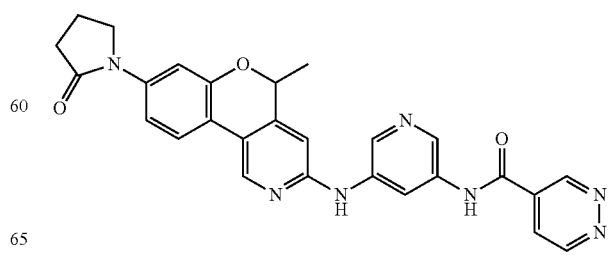

A mixture of 1-(3-amino-5-methyl-5H-chromeno[4,3-c]pyridin-8-yl)pyrrolidin-2-one (60 mg, 0.20 mmol), N-(5-bromopyridin-3-yl)pyridazine-4-carboxamide (113 mg, 0.406 mmol), Pd$_2$(dba)$_3$ (19 mg, 0.020 mmol), BrettPhos (22 mg, 0.041 mmol), Cs$_2$CO$_3$ (132 mg, 0.406 mmol) in anhydrous dioxane (3 mL) was degassed and purged with N$_2$ for 3 times. Then the resulting reaction mixture was heated at 90° C. for 14 h under N$_2$ atmosphere. The reaction mixture turned into gray suspension from red suspension. LCMS (Rt=0.579 min; MS Calcd: 493.2. MS Found: 494.2 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)pyridazine-4-carboxamide (19.4 mg, yield: 19%) as a yellow solid.

$^1$H NMR (400 MHz DMSO-d$_6$) δ 1.55 (3H, d, J=6.8 Hz), 2.01-2.10 (2H, m), 2.52-2.54 (2H, m, overlapped with the peak of DMSO), 3.84 (2H, t, J=7.5 Hz), 5.29 (1H, q, J=6.4 Hz), 6.78 (1H, s), 7.33 (1H, dd, J=8.5, 2.0 Hz), 7.41 (1H, d, J=2.3 Hz), 7.89 (1H, d, J=8.8 Hz), 8.16 (1H, dd, J=5.3, 2.3 Hz), 8.51 (1H, s), 8.66-8.74 (3H, m), 9.53 (1H, d, J=5.3 Hz), 9.61 (1H, s), 9.68 (1H, brs), 10.92 (1H, brs).

Example 126: 6-amino-N-(5-((5-methyl-8-(2-oxopyrrolidin-1-yl)-5H-chromeno[4,3-c]pyridin-3-yl)amino)pyridin-3-yl)pyrazine-2-carboxamide

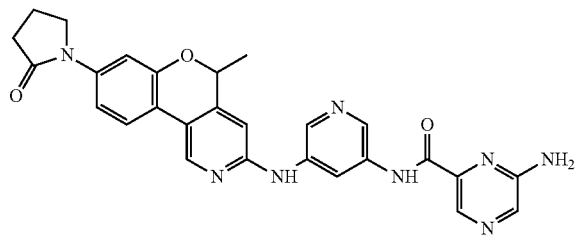 [SMILES: CC1Oc2cc(N3CCCC3=O)ccc2-c2cnc(Nc3cncc(NC(=O)c4cncc(N)n4)c3)cc21]

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), 6-aminopyrazine-2-carboxylic acid (24 mg, 0.17 mmol) and EDCI.HCl (30 mg, 0.16 mmol) in pyridine (2 mL) was heated at 50° C. for 2 h. A black solution was formed. LCMS (Rt=0.687 min; MS Calcd: 508.2; MS Found: 509.1 [M+H]$^+$). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by prep-HPLC (0.225% FA as an additive) and lyophilized to give 6-amino-N-(5-((5-methyl-8-(2-oxopyrrolidin-1-yl)-5H-chromeno[4,3-c]pyridin-3-yl)amino)pyridin-3-yl)pyrazine-2-carboxamide (23.5 mg, yield: 32%) as a yellow solid.

$^1$H NMR (400 MHz DMSO-d$_6$) δ 1.55 (3H, d, J=6.5 Hz), 2.01-2.10 (2H, m), 2.52-2.54 (2H, m, overlapped with the peak of DMSO), 3.84 (2H, t, J=7.7 Hz), 5.30 (1H, q, J=6.4 Hz), 6.80 (1H, s), 6.82 (2H, brs), 7.33 (1H, dd, J=8.7, 2.1 Hz), 7.41 (1H, d, J=2.3 Hz), 7.90 (1H, d, J=8.8 Hz), 8.15 (1H, s), 8.36 (1H, s), 8.55 (1H, s), 8.70 (1H, s), 8.76-8.83 (2H, m), 9.71 (1H, brs), 10.46 (1H, brs).

Example 127: 1-(5-methyl-3-(pyridazin-4-ylamino)-5H-chromeno[4,3-c]pyridin-8-yl)pyrrolidin-2-one

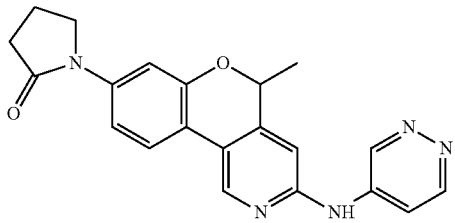 [SMILES: CC1Oc2cc(N3CCCC3=O)ccc2-c2cnc(Nc3ccnnc3)cc21]

A mixture of 1-(3-chloro-5-methyl-5H-chromeno[4,3-c]pyridin-8-yl)pyrrolidin-2-one (80 mg, 0.25 mmol), pyridazin-4-amine (29 mg, 0.31 mmol), Pd$_2$(dba)$_3$ (23 mg, 0.025 mmol), BrettPhos (27 mg, 0.051 mmol), Cs$_2$CO$_3$ (166 mg, 0.508 mmol) in anhydrous dioxane (3 mL) was degassed and purged with N$_2$ for 3 times. Then the resulting reaction mixture was heated at 90° C. for 16 h under N$_2$ atmosphere. The reaction mixture turned into gray suspension from red suspension. LCMS (Rt=0.687 min; MS Calcd: 373.2. MS Found: 374.1 [M+H]$^+$). The mixture was diluted with water (20 mL) and extracted with EtOAc (25 mL×2). The combined organic layer was washed with brine (30 mL×2), dried over anhydrous Na$_2$SO$_4$, filtered and concentrated. The residue was purified by prep-HPLC (0.225% FA as an additive) and lyophilized to give 1-(5-methyl-3-(pyridazin-4-ylamino)-5H-chromeno[4,3-c]pyridin-8-yl)pyrrolidin-2-one (19.6 mg, yield: 21%) as a yellow solid.

$^1$H NMR (400 MHz DMSO-d$_6$) δ 1.55 (3H, d, J=6.5 Hz), 2.01-2.10 (2H, m), 2.52-2.54 (2H, m, overlapped with the peak of DMSO), 3.85 (2H, t, J=7.5 Hz), 5.33 (1H, q, J=6.5 Hz), 6.86 (1H, s), 7.34 (1H, dd, J=8.7, 2.2 Hz), 7.43 (1H, d, J=2.2 Hz), 7.93 (1H, d, J=8.6 Hz), 8.12-8.17 (1H, m), 8.79 (1H, s), 8.87 (1H, d, J=6.1 Hz), 9.29 (1H, d, J=2.2 Hz), 10.07 (1H, brs).

Example 128: 1-(5-methyl-3-(pyridazin-3-ylamino)-5H-chromeno[4,3-c]pyridin-8-yl)pyrrolidin-2-one

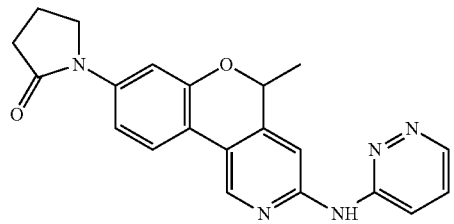 [SMILES: CC1Oc2cc(N3CCCC3=O)ccc2-c2cnc(Nc3cccnn3)cc21]

A mixture of 1-(3-chloro-5-methyl-5H-chromeno[4,3-c]pyridin-8-yl)pyrrolidin-2-one (80 mg, 0.25 mmol), pyridazin-3-amine (29 mg, 0.31 mmol), Pd$_2$(dba)$_3$ (23 mg, 0.025 mmol), BrettPhos (27 mg, 0.051 mmol), Cs$_2$CO$_3$ (166 mg, 0.508 mmol) in anhydrous dioxane (3 mL) was degassed and purged with N$_2$ for 3 times. Then the resulting reaction mixture was heated at 90° C. for 16 h under N$_2$ atmosphere. The reaction mixture turned into gray suspension from red suspension. LCMS (Rt=0.666 min; MS Calcd: 373.2. MS Found: 374.0 [M+H]$^+$). The mixture was diluted with water (20 mL) and extracted with EtOAc (20 mL×2). The combined organic layer was washed with brine (20 mL×2), dried over anhydrous Na$_2$SO$_4$, filtered and concentrated. The residue was purified by prep-HPLC (0.225% FA as an additive) and lyophilized to give 1-(5-methyl-3-(pyridazin-3-ylamino)-5H-chromeno[4,3-c]pyridin-8-yl)pyrrolidin-2-one (31.4 mg, yield: 33%) as a yellow solid.

$^1$H NMR (400 MHz DMSO-d$_6$) δ 1.55 (3H, d, J=6.5 Hz), 2.01-2.10 (2H, m), 2.52-2.54 (2H, m, overlapped with the peak of DMSO), 3.82-3.89 (2H, m), 5.38 (1H, q, J=6.4 Hz), 7.36 (1H, dd, J=8.7, 2.1 Hz), 7.42 (1H, d, J=2.3 Hz), 7.61-7.68 (2H, m), 7.93 (1H, d, J=8.5 Hz), 8.02-8.07 (1H, m), 8.76 (1H, s), 8.82 (1H, d, J=4.3 Hz), 10.51 (1H, brs).

Example 129: N-(5-((5-methyl-8-(2-oxopyrrolidin-1-yl)-5H-chromeno[4,3-c]pyridin-3-yl)amino)pyridazin-3-yl)acetamide

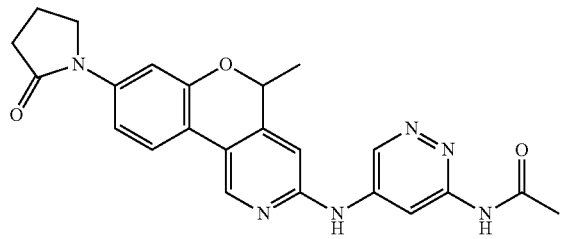 [SMILES: CC(=O)Nc1cc(Nc2cc3c(cn2)-c2ccc(N4CCCC4=O)cc2OC3C)cnn1]

Step 1: Preparation of 5-chloropyridazin-3-amine

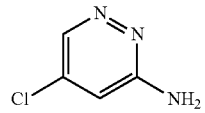

A mixture of 3,5-dichloropyridazine (1.00 g, 6.71 mmol) and liquid NH$_3$ was stirred in a sealed tube for 12 h. A black residue was formed. The residue was purified by Combi Flash (50% to 100% EtOAc in pentane) to give 5-chloropyridazin-3-amine (400 mg, yield: 44%) as a yellow solid.

$^1$H NMR (400 MHz DMSO-d$_6$) δ 6.66 (1H, d, J=2.3 Hz), 6.84 (2H, brs), 8.50 (1H, d, J=2.3 Hz).

Step 2: Preparation of N-(5-chloropyridazin-3-yl)acetamide

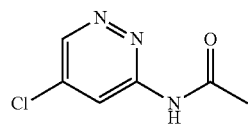

To a solution of 5-chloropyridazin-3-amine (100 mg, 0.772 mmol) and in pyridine (2 mL) was added acetyl chloride (91 mg, 1.2 mmol) dropwise at 30° C. The mixture was stirred at 30° C. for 2 h, and a red solution was formed. The mixture was diluted with water (20 mL) and extracted with EtOAc (20 mL×3). The combined organic layer was washed with water (20 mL×2), brine (20 mL), dried over anhydrous Na$_2$SO$_4$, filtered and concentrated. The residue was purified by Combi Flash (50% to 100% EtOAc in pentane) to give N-(5-chloropyridazin-3-yl)acetamide (30 mg, yield: 23%) as a white solid.

$^1$H NMR (400 MHz DMSO-d$_6$) δ 2.15 (3H, s), 8.07 (1H, d, J=2.3 Hz), 9.13 (1H, d, J=2.0 Hz),

Step 3: Preparation of N-(5-((5-methyl-8-(2-oxopyrrolidin-1-yl)-5H-chromeno[4,3-c]pyridin-3-yl)amino)pyridazin-3-yl)acetamide

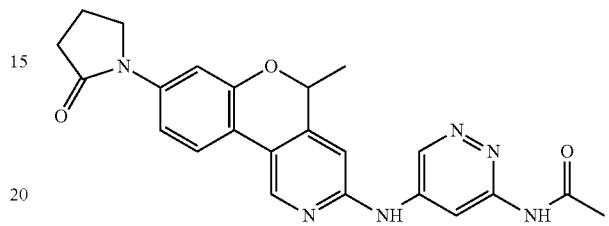

A mixture of 1-(3-amino-5-methyl-5H-chromeno[4,3-c]pyridin-8-yl)pyrrolidin-2-one (40 mg, 0.14 mmol), N-(5-chloropyridazin-3-yl)acetamide (26 mg, 0.15 mmol), Pd$_2$(dba)$_3$ (12 mg, 0.014 mmol), BrettPhos (15 mg, 0.027 mmol), Cs$_2$CO$_3$ (88 mg, 0.27 mmol) in anhydrous dioxane (3 mL) was degassed and purged with N$_2$ for 3 times. Then the resulting reaction mixture was heated at 90° C. for 14 h under N$_2$ atmosphere. The reaction mixture turned into gray suspension from red suspension. LCMS (Rt=0.674 min; MS Calcd: 430.2; MS Found: 431.1 [M+H]$^+$). The mixture was diluted with water (20 mL) and extracted with EtOAc/THF (20 mL×2, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridazin-3-yl)acetamide (14.4 mg, yield: 25%) as a yellow solid.

$^1$H NMR (400 MHz DMSO-d$_6$) δ 1.55 (3H, d, J=6.5 Hz), 2.01-2.09 (2H, m), 2.18 (3H, s), 2.52-2.54 (2H, m, overlapped with the peak of DMSO), 3.85 (2H, t, J=7.9 Hz), 5.38 (1H, q, J=6.4 Hz), 7.37 (1H, dd, J=8.5, 2.0 Hz), 7.42 (1H, d, J=1.8 Hz), 7.46 (1H, s), 7.93 (1H, d, J=8.5 Hz), 8.37 (1H, d, J=2.3 Hz), 8.76-8.81 (2H, m), 10.74-11.07 (2H, m).

Example 130: 1-(5-methyl-3-((5-(pyridin-2-ylamino)pyridin-3-yl)amino)-5H-chromeno[4,3-c]pyridin-8-yl)pyrrolidin-2-one

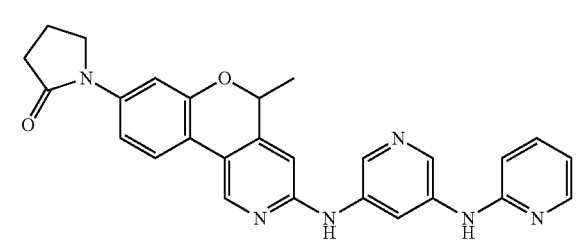 [SMILES: CC1Oc2cc(N3CCCC3=O)ccc2-c2cnc(Nc3cncc(Nc4ccccn4)c3)cc21]

Step 1: Preparation of tert-butyl (5-(pyridin-2-ylamino)pyridin-3-yl)carbamate

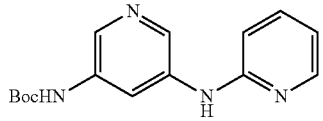 [SMILES: CC(C)(C)OC(=O)Nc1cncc(Nc2ccccn2)c1]

A mixture of tert-butyl (5-bromopyridin-3-yl)carbamate (300 mg, 1.10 mmol), pyridin-2-amine (124 mg, 1.32 mmol), Pd$_2$(dba)$_3$ (101 mg, 0.110 mmol), BrettPhos (118 mg, 0.220 mmol) and Cs$_2$CO$_3$ (716 mg, 2.20 mmol) in anhydrous dioxane (5 mL) was degassed and purged with N$_2$ for 3 times. Then the resulting reaction mixture was stirred at 90° C. for 16 h under N$_2$ atmosphere. The reaction mixture turned into brown suspension from red. LCMS (Rt=0.656 min; MS Calcd: 286.1. MS Found: 287.1 [M+H]$^+$). The reaction mixture was diluted with water (25 mL) and extracted with EtOAc (25 mL×3). The combined organic layer was washed with brine (25 mL), dried over anhydrous Na$_2$SO$_4$ and concentrated. The residue was purified by Combi Flash (40% to 100% EtOAc in pentane) to give tert-butyl (5-(pyridin-2-ylamino)pyridin-3-yl)carbamate (163 mg, yield: 52%) as a yellow solid.

$^1$H NMR (400 MHz, CDCl$_3$) δ 1.53 (9H, s), 6.68 (1H, brs), 6.71 (1H, brs), 6.80 (1H, dd, J=6.8, 5.3 Hz), 6.84 (1H, d, J=8.3 Hz), 7.54 (1H, ddd, J=8.5, 7.1, 2.0 Hz), 8.14 (1H, d, J=2.0 Hz), 8.20-8.26 (2H, m), 8.35 (1H, d, J=2.0 Hz).

Step 2: Preparation of N$^3$-(pyridin-2-yl)pyridine-3,5-diamine

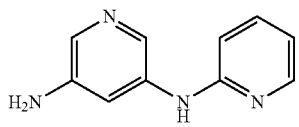 [SMILES: Nc1cncc(Nc2ccccn2)c1]

To a suspension of tert-butyl (5-(pyridin-2-ylamino)pyridin-3-yl)carbamate (163 mg, 0.569 mmol) in EtOAc (5 mL) was added HCl/EtOAc (25 mL, 4N in EtOAc) at 20-25° C. Then the reaction mixture was stirred at 20-25° C. for 2 h. The reaction mixture turned cloudy from yellow solution. The reaction mixture was concentrated and dried under vacuum to give N$^3$-(pyridin-2-yl)pyridine-3,5-diamine (120 mg, yield: 95%, HCl salt) as a yellow solid.

$^1$H NMR (400 MHz, DMSO-d$_6$) δ 6.95 (1H, td, J=6.2, 0.8 Hz), 7.04 (1H, d, J=8.5 Hz), 7.61 (1H, d, J=1.8 Hz), 7.73 (1H, ddd, J=8.5, 7.0, 1.8 Hz), 7.81 (1H, t, J=2.1 Hz), 8.25 (1H, dd, J=5.0, 1.3 Hz), 8.58 (1H, d, J=1.5 Hz), 10.21 (1H, brs).

Step 3: Preparation of 1-(5-methyl-3-((5-(pyridin-2-ylamino)pyridin-3-yl)amino)-5H-chromeno[4,3-c]pyridin-8-yl)pyrrolidin-2-one

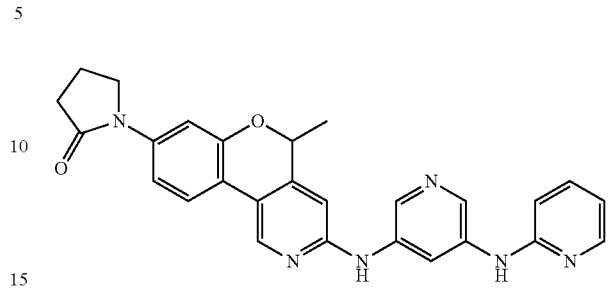

A mixture of 1-(3-chloro-5-methyl-5H-chromeno[4,3-c]pyridin-8-yl)pyrrolidin-2-one (60 mg, 0.19 mmol), N$^3$-(pyridin-2-yl)pyridine-3,5-diamine (64 mg, 0.29 mmol, HCl salt), Pd$_2$(dba)$_3$ (17 mg, 0.019 mmol), BrettPhos (20 mg, 0.038 mmol) and Cs$_2$CO$_3$ (186 mg, 0.572 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.718 min; MS Calcd: 464.2; MS Found: 465.6 [M+H]$^+$). To the reaction mixture was added water (25 mL), then extracted with EtOAc (25 mL×3). The combined organic layer was washed with brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give 1-(5-methyl-3-((5-(pyridin-2-ylamino)pyridin-3-yl)amino)-5H-chromeno[4,3-c]pyridin-8-yl)pyrrolidin-2-one (24.8 mg, yield: 28%, FA salt) as a yellow solid.

$^1$H NMR (400 MHz, DMSO-d$_6$) δ 1.55 (3H, d, J=6.5 Hz), 2.01-2.10 (2H, m), 2.52-2.55 (2H, m), 3.84 (2H, t, J=7.9 Hz), 5.28 (1H, q, J=6.5 Hz), 6.79 (1H, s), 6.84 (1H, td, J=6.1, 0.9 Hz), 6.92 (1H, d, J=8.5 Hz), 7.33 (1H, dd, J=8.7, 2.1 Hz), 7.40 (1H, d, J=2.3 Hz), 7.64 (1H, ddd, J=8.5, 7.0, 2.0 Hz), 7.89 (1H, d, J=8.8 Hz), 8.14 (0.76H, s, FA salt), 8.22 (1H, dd, J=5.0, 1.3 Hz), 8.53 (1H, s), 8.58 (1H, s), 8.64 (1H, t, J=2.1 Hz), 8.67 (1H, s), 9.38 (1H, brs), 9.54 (1H, brs).

Example 131: 1-(5-methyl-3-((5-(pyridazin-3-ylamino)pyridin-3-yl)amino)-5H-chromeno[4,3-c]pyridin-8-yl)pyrrolidin-2-one

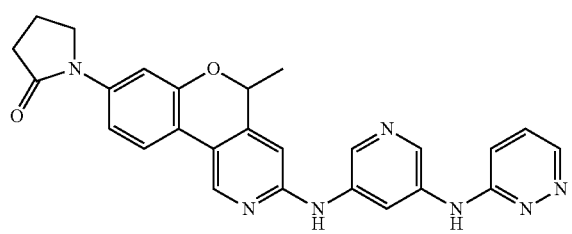 [SMILES: CC1Oc2cc(N3CCCC3=O)ccc2-c2cnc(Nc3cncc(Nc4cccnn4)c3)cc21]

Step 1: Preparation of tert-butyl (5-(pyridazin-3-ylamino)pyridin-3-yl)carbamate

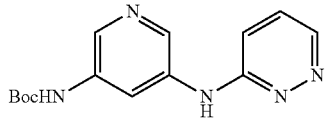 [SMILES: CC(C)(C)OC(=O)Nc1cncc(Nc2cccnn2)c1]

A mixture of tert-butyl (5-bromopyridin-3-yl)carbamate (300 mg, 1.10 mmol), pyridazin-3-amine (125 mg, 1.32 mmol), Pd$_2$(dba)$_3$ (101 mg, 0.110 mmol), BrettPhos (118 mg, 0.220 mmol) and Cs$_2$CO$_3$ (716 mg, 2.20 mmol) in anhydrous dioxane (5 mL) was degassed and purged with N$_2$ for 3 times. Then the resulting reaction mixture was stirred at 90° C. for 16 h under N$_2$ atmosphere. The reaction mixture turned into brown suspension from red. The reaction mixture was diluted with water (25 mL) and EtOAc (25 mL). The solid was filtered and washed with EtOAc (5 mL×4), then dried under vacuum to give tert-butyl (5-(pyridazin-3-ylamino)pyridin-3-yl)carbamate (310 mg, yield: 98%) as a yellow solid.

$^1$H NMR (400 MHz, DMSO-d$_6$) δ 1.50 (9H, s), 7.16 (1H, dd, J=8.9, 1.4 Hz), 7.48 (1H, dd, J=9.0, 4.5 Hz), 8.22 (1H, d, J=2.0 Hz), 8.43 (1H, t, J=2.3 Hz), 8.63 (1H, d, J=2.0 Hz), 8.71 (1H, dd, J=4.5, 1.3 Hz), 9.43 (1H, brs), 9.59 (1H, brs)

Step 2: Preparation of N$^3$-(pyridazin-3-yl)pyridine-3,5-diamine

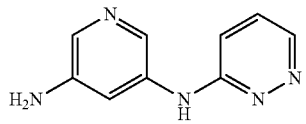 [SMILES: Nc1cncc(Nc2cccnn2)c1]

To a suspension of tert-butyl (5-(pyridazin-3-ylamino)pyridin-3-yl)carbamate (310 mg, 1.08 mmol) in EtOAc (5 mL) was added 4N HCl/EtOAc (25 mL) at 20-25° C. Then the reaction mixture was stirred at 20-25° C. for 2 h. The reaction mixture turned cloudy from solution. The reaction mixture was concentrated and dried under vacuum to give N$^3$-(pyridazin-3-yl)pyridine-3,5-diamine (220 mg, yield: 91%, HCl salt) as a yellow solid.

$^1$H NMR (400 MHz, DMSO-d$_6$) δ 7.76 (1H, d, J=1.8 Hz), 7.82-7.86 (1H, m), 7.90 (1H, t, J=2.0 Hz), 7.91-7.96 (1H, m), 8.57 (1H, d, J=1.5 Hz), 9.02 (1H, dd, J=4.6, 1.1 Hz), 11.34 (1H, brs).

Step 3: Preparation of 1-(5-methyl-3-((5-(pyridazin-3-ylamino)pyridin-3-yl)amino)-5H-chromeno[4,3-c]pyridin-8-yl)pyrrolidin-2-one

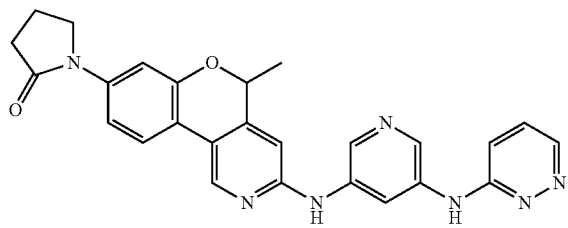 [SMILES: CC1Oc2cc(N3CCCC3=O)ccc2-c2cnc(Nc3cncc(Nc4cccnn4)c3)cc21]

A mixture of 1-(3-chloro-5-methyl-5H-chromeno[4,3-c]pyridin-8-yl)pyrrolidin-2-one (60 mg, 0.19 mmol), N$^3$-(pyridazin-3-yl)pyridine-3,5-diamine (64 mg, 0.29 mmol, HCl salt), Pd$_2$(dba)$_3$ (17 mg, 0.019 mmol), BrettPhos (20 mg, 0.038 mmol) and Cs$_2$CO$_3$ (186 mg, 0.572 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.689 min; MS Calcd: 465.2; MS Found: 466.2 [M+H]$^+$). To the reaction mixture was added water (20 mL) and EtOAc (20 mL). Then the mixture was filtered and the solid was washed with EtOAc (5 mL×2). The crude product was purified by prep-HPLC (0.1% TFA as an additive) Most of the MeCN was removed under reduced pressure and the remaining part was lyophilized to give 1-(5-methyl-3-((5-(pyridazin-3-ylamino)pyridin-3-yl)amino)-5H-chromeno[4,3-c]pyridin-8-yl)pyrrolidin-2-one (3.06 mg, yield: 3.5%, TFA salt) as a yellow solid.

$^1$H NMR (400 MHz, DMSO-d$_6$) δ 1.56 (3H, d, J=6.3 Hz), 2.02-2.11 (2H, m), 2.53-2.55 (2H, m), 3.85 (2H, t, J=7.9 Hz), 5.33 (1H, q, J=6.3 Hz), 6.87 (1H, s), 7.31-7.38 (2H, m), 7.42 (1H, d, J=2.0 Hz), 7.63 (1H, dd, J=8.9, 4.4 Hz), 7.93 (1H, d, J=8.8 Hz), 8.75 (1H, s), 8.83-8.91 (3H, m), 9.02 (1H, brs), 10.23 (2H, brs).

Example 132: N-(5-((5-methyl-8-(2-oxopyrrolidin-1-yl)-5H-chromeno[4,3-c]pyridin-3-yl)amino)pyridin-3-yl)-3-phenylbutanamide

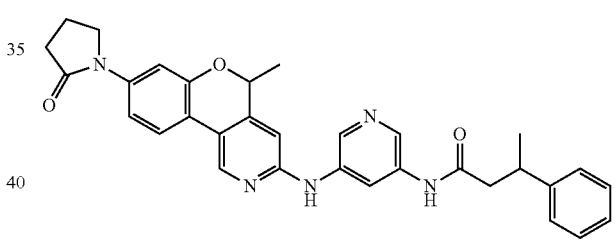

Step 1: Preparation of N-(5-bromopyridin-3-yl)-3-phenylbutanamide

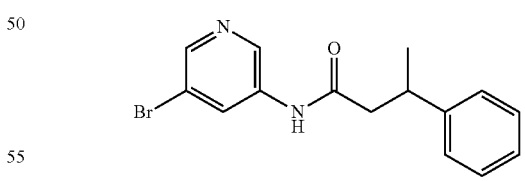

A mixture of 5-bromopyridin-3-amine (300 mg, 1.73 mmol), 3-phenylbutanoic acid (427 mg, 2.60 mmol) and EDCI.HCl (499 mg, 2.60 mmol) in pyridine (4 mL) was stirred at 50° C. for 2 h. The reaction mixture turned into brown solution from yellow. The reaction mixture was concentrated and the residue was diluted with water (25 mL), then extracted with EtOAc (25 mL×3). The combined organic layer was washed with brine (25 mL), dried over anhydrous Na$_2$SO$_4$ and concentrated. The residue was purified by Combi Flash (30% to 50% EtOAc in pentane) to give N-(5-bromopyridin-3-yl)-3-phenylbutanamide (500 mg, yield: 90%) as a yellow solid.

$^1$H NMR (400 MHz, CDCl$_3$) δ 1.38 (3H, d, J=7.0 Hz), 2.64 (2H, d, J=7.5 Hz), 3.30-3.41 (1H, m), 7.21-7.26 (3H, m), 7.29-7.35 (2H, m), 7.37 (1H, brs), 8.15 (1H, d, J=2.3 Hz), 8.29-8.32 (1H, m), 8.33 (1H, d, J=2.0 Hz).

Step 2: Preparation of N-(5-((5-methyl-8-(2-oxopyrrolidin-1-yl)-5H-chromeno[4,3-c]pyridin-3-yl)amino)pyridin-3-yl)-3-phenylbutanamide

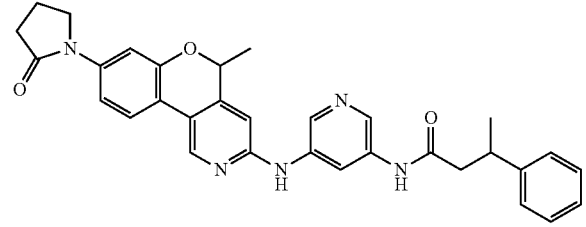 [SMILES: CC(CC(=O)Nc1cncc(Nc2cc3c(cn2)-c2ccc(N4CCCC4=O)cc2OC3C)c1)c1ccccc1]

A mixture of 1-(3-amino-5-methyl-5H-chromeno[4,3-c]pyridin-8-yl)pyrrolidin-2-one (60 mg, 0.20 mmol), N-(5-bromopyridin-3-yl)-3-phenylbutanamide (97 mg, 0.30 mmol), Pd$_2$(dba)$_3$ (19 mg, 0.020 mmol), BrettPhos (22 mg, 0.041 mmol) and Cs$_2$CO$_3$ (199 mg, 0.609 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS showed the purity of desired product (Rt=0.763 min; MS Calcd: 533.2. MS Found: 534.4 [M+H]$^+$). To the reaction mixture was added water (20 mL), then extracted with EtOAc/THF (20 mL×3, 3/1). The combined organic layer was washed with brine (20 mL), dried over anhydrous Na$_2$SO$_4$ and concentrated. The residue was purified by prep-HPLC (0.225% FA as additive) purification. Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)-3-phenylbutanamide (50.7 mg, yield: 47%) as a yellow solid.

$^1$H NMR (400 MHz, DMSO-d$_6$) δ 1.26 (3H, d, J=6.8 Hz), 1.54 (3H, d, J=6.5 Hz), 2.01-2.11 (2H, m), 2.52-2.54 (2H, m), 2.60-2.70 (2H, m), 3.26-3.32 (1H, m), 3.84 (2H, t, J=7.8 Hz), 5.27 (1H, q, J=6.5 Hz), 6.74 (1H, s), 7.16-7.22 (1H, m), 7.27-7.35 (5H, m), 7.40 (1H, d, J=2.0 Hz), 7.89 (1H, d, J=8.5 Hz), 8.28 (1H, s), 8.45 (1H, t, J=2.0 Hz), 8.62 (1H, d, J=2.0 Hz), 8.65 (1H, s), 9.46 (1H, brs), 10.09 (1H, brs).

Example 133: 2-methyl-N-(5-((5-methyl-8-(2-oxopyrrolidin-1-yl)-5H-chromeno[4,3-c]pyridin-3-yl)amino)pyridin-3-yl)-3-phenylpropanamide

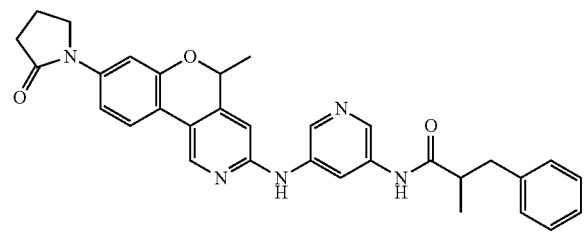 [SMILES: CC(Cc1ccccc1)C(=O)Nc1cncc(Nc2cc3c(cn2)-c2ccc(N4CCCC4=O)cc2OC3C)c1]

Step 1: Preparation of N-(5-bromopyridin-3-yl)-2-methyl-3-phenylpropanamide

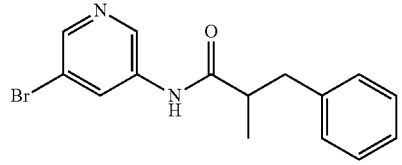 [SMILES: CC(Cc1ccccc1)C(=O)Nc1cncc(Br)c1]

A mixture of 5-bromopyridin-3-amine (300 mg, 1.73 mmol), 2-methyl-3-phenylpropanoic acid (426 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc (25 mL×3). The combined organic layer was washed with brine (25 mL), dried over anhydrous Na$_2$SO$_4$ and concentrated. The crude product was triturated with pentane/EtOAC (10 mL, 3/1) to give N-(5-bromopyridin-3-yl)-2-methyl-3-phenylpropanamide (480 mg, yield: 87%) as an off-white solid.

$^1$H NMR (400 MHz, CDCl$_3$) δ 1.32 (3H, d, J=6.8 Hz), 2.58-2.68 (1H, m), 2.79-2.85 (1H, m), 2.95-3.02 (1H, m), 6.91 (1H, brs), 7.16-7.20 (2H, m), 7.21-7.33 (3H, m), 8.12 (1H, d, J=2.0 Hz), 8.32 (1H, t, J=1.8 Hz), 8.35 (1H, d, J=2.0 Hz).

Step 2: Preparation of 2-methyl-N-(5-((5-methyl-8-(2-oxopyrrolidin-1-yl)-5H-chromeno[4,3-c]pyridin-3-yl)amino)pyridin-3-yl)-3-phenylpropanamide

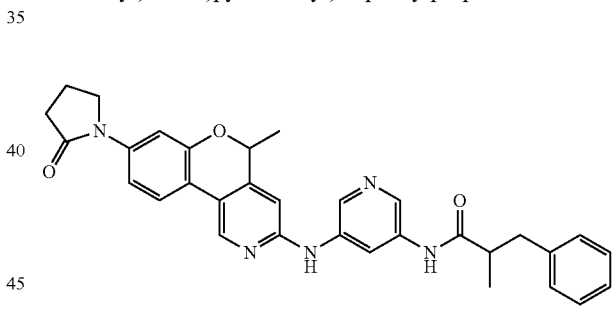

A mixture of 1-(3-amino-5-methyl-5H-chromeno[4,3-c]pyridin-8-yl)pyrrolidin-2-one (60 mg, 0.20 mmol), N-(5-bromopyridin-3-yl)-2-methyl-3-phenylpropanamide (97 mg, 0.30 mmol), Pd$_2$(dba)$_3$ (19 mg, 0.020 mmol), BrettPhos (22 mg, 0.041 mmol) and Cs$_2$CO$_3$ (199 mg, 0.609 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.776 min; MS Calcd: 533.2. MS Found: 534.1 [M+H]$^+$). To the reaction mixture was added water (20 mL), then extracted with EtOAc/THF (20 mL×3, 1/1). The combined organic layer was washed with brine (20 mL), dried over anhydrous Na$_2$SO$_4$ and concentrated. The residue was purified by prep-HPLC (0.225% FA as additive). Most of the MeCN was removed under reduced pressure and the remaining part was lyophilized to give 2-methyl-N-(5-((5-methyl-8-(2-oxopyrrolidin-1-yl)-5H-chromeno[4,3-c]pyridin-3-yl)amino)pyridin-3-yl)-3-phenylpropanamide (39.1 mg, yield: 36%) as a yellow solid.

$^1$H NMR (400 MHz, DMSO-d$_6$) δ 1.12 (3H, d, J=6.8 Hz), 1.55 (3H, d, J=6.5 Hz), 2.01-2.11 (2H, m), 2.52-2.54 (2H, m), 2.64 (1H, dd, J=13.3, 6.8 Hz), 2.79-2.88 (1H, m), 2.99 (1H, dd, J=13.1, 7.5 Hz), 3.85 (2H, t, J=7.8 Hz), 5.28 (1H, q, J=6.5 Hz), 6.75 (1H, s), 7.16-7.21 (1H, m), 7.22-7.31 (4H, m), 7.33 (1H, dd, J=8.7, 2.1 Hz), 7.40 (1H, d, J=2.3 Hz), 7.90 (1H, d, J=8.8 Hz), 8.32 (1H, d, J=2.0 Hz), 8.49 (1H, t, J=2.3 Hz), 8.62 (1H, d, J=2.3 Hz), 8.67 (1H, s), 9.49 (1H, brs), 10.06 (1H, brs).

Example 134: 2-hydroxy-N-(5-((5-methyl-8-(2-oxopyrrolidin-1-yl)-5H-chromeno[4,3-c]pyridin-3-yl)amino)pyridin-3-yl)-3-phenylpropanamide

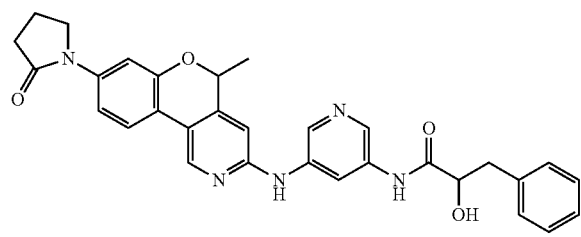 [SMILES: CC1Oc2cc(N3CCCC3=O)ccc2-c2cnc(Nc3cncc(NC(=O)C(O)Cc4ccccc4)c3)cc21]

Step 1: Preparation of 2-acetoxy-3-phenylpropanoic acid

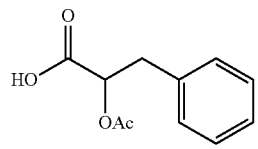 [SMILES: CC(=O)OC(Cc1ccccc1)C(=O)O]

To a solution of 2-hydroxy-3-phenylpropanoic acid (1.20 g, 7.22 mmol) in pyridine (25 mL) was added acetic anhydride (737 mg, 7.22 mmol) at 20-25° C. Then the reaction mixture was stirred at 20-25° C. for 2 h. The reaction mixture turned into brown solution from yellow. The reaction mixture was concentrated and the residue was diluted with EtOAc (100 mL), then washed with 2N aqueous HCl (50 mL×2), brine (50 mL), dried over anhydrous Na$_2$SO$_4$ and concentrated and dried under vacuum to give 2-acetoxy-3-phenylpropanoic acid (1.20 g, yield: 80%) as yellow oil.

$^1$H NMR (400 MHz, CDCl$_3$) δ 2.09 (3H, s), 3.08-3.16 (1H, m), 3.21-3.27 (1H, m), 5.25 (1H, dd, J=9.0, 4.0 Hz), 6.85 (1H, brs), 7.23-7.35 (5H, m).

Step 2: Preparation of 1-((5-((5-methyl-8-(2-oxopyrrolidin-1-yl)-5H-chromeno[4,3-c]pyridin-3-yl)amino)pyridin-3-yl)amino)-1-oxo-3-phenylpropan-2-ylacetate

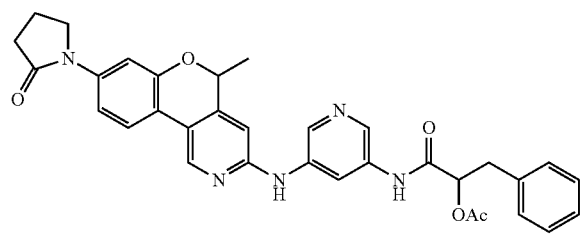 [SMILES: CC(=O)OC(Cc1ccccc1)C(=O)Nc1cncc(Nc2cc3c(cn2)-c2ccc(N4CCCC4=O)cc2OC3C)c1]

A mixture of 1-(3-((5-aminopyridin-3-yl)amino)-5-methyl-5H-chromeno[4,3-c]pyridin-8-yl)pyrrolidin-2-one (100 mg, 0.236 mmol, HCl salt), 2-acetoxy-3-phenylpropanoic acid (74 mg, 0.35 mmol) and EDCI.HCl (68 mg, 0.35 mmol) in pyridine (2 mL) was stirred at 50° C. for 2 h. The reaction mixture turned into brown solution from yellow. The reaction mixture was diluted with water (25 mL), then extracted with EtOAc (25 mL×3). The combined organic layer was washed with saturated aqueous NaHCO$_3$ (25 mL), brine (25 mL), dried over anhydrous Na$_2$SO$_4$ and concentrated to give 1-((5-((5-methyl-8-(2-oxopyrrolidin-1-yl)-5H-chromeno[4,3-c]pyridin-3-yl)amino)pyridin-3-yl)amino)-1-oxo-3-phenylpropan-2-yl acetate (130 mg, yield: 73%) as yellow gum, which was directly used for the next step without further purification.

Step 3: Preparation of 2-hydroxy-N-(5-((5-methyl-8-(2-oxopyrrolidin-1-yl)-5H-chromeno[4,3-c]pyridin-3-yl)amino)pyridin-3-yl)-3-phenylpropanamide

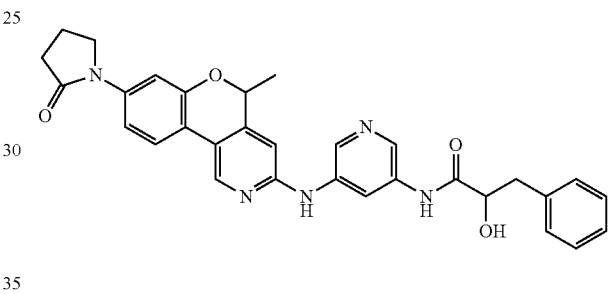

To a solution of 1-((5-((5-methyl-8-(2-oxopyrrolidin-1-yl)-5H-chromeno[4,3-c]pyridin-3-yl)amino)pyridin-3-yl)amino)-1-oxo-3-phenylpropan-2-yl acetate (130 mg, 0.225 mmol) in THF (4 mL) and MeOH (2 mL) was added 2N aqueous NaOH (2 mL) at 20-25° C. Then the resulting reaction mixture was stirred at 20-25° C. for 2 h. The reaction mixture turned into yellow solution from suspension. LCMS (Rt=0.624 min; MS Calcd: 535.2; MS Found: 536.1 [M+H]$^+$). The reaction mixture was concentrated and the residue was diluted with water (25 mL), then extracted with EtOAc/THF (25 mL×3, 1/1). The combined organic layer was washed with brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give 2-hydroxy-N-(5-((5-methyl-8-(2-oxopyrrolidin-1-yl)-5H-chromeno[4,3-c]pyridin-3-yl)amino)pyridin-3-yl)-3-phenylpropanamide (49.6 mg, yield: 41%) as a yellow solid.

$^1$H NMR (400 MHz, DMSO-d$_6$) δ 1.55 (3H, d, J=6.5 Hz), 2.01-2.11 (2H, m), 2.52-2.54 (2H, m), 2.88 (1H, dd, J=13.8, 8.3 Hz), 3.08 (1H, dd, J=13.7, 4.1 Hz), 3.85 (2H, t, J=7.8 Hz), 4.26-4.33 (1H, m), 5.28 (1H, q, J=6.4 Hz), 5.89 (1H, d, J=5.5 Hz), 6.76 (1H, s), 7.18-7.25 (1H, m), 7.27-7.30 (4H, m), 7.33 (1H, dd, J=8.5, 2.3 Hz), 7.41 (1H, d, J=2.0 Hz), 7.89 (1H, d, J=8.8 Hz), 8.38 (1H, d, J=2.0 Hz), 8.57 (1H, t, J=2.1 Hz), 8.65 (1H, d, J=2.3 Hz), 8.67 (1H, s), 9.48 (1H, brs), 9.90 (1H, brs).

Example 135: N-(5-((5-methyl-8-(2-oxopyrrolidin-1-yl)-5H-chromeno[4,3-c]pyridin-3-yl)amino)pyridin-3-yl)tetrahydrofuran-2-carboxamide

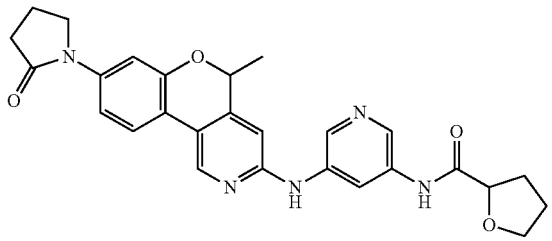 [SMILES: CC1Oc2cc(N3CCCC3=O)ccc2-c2cnc(Nc3cncc(NC(=O)C4CCCO4)c3)cc21]

Step 1: Preparation of N-(5-bromopyridin-3-yl)tetrahydrofuran-2-carboxamide

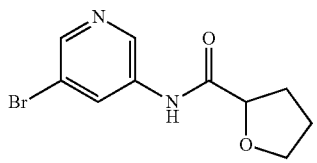 [SMILES: O=C(Nc1cncc(Br)c1)C1CCCO1]

A mixture of 5-bromopyridin-3-amine (300 mg, 1.73 mmol), tetrahydrofuran-2-carboxylic acid (302 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc (25 mL×3). The combined organic layer was washed with brine (25 mL), dried over anhydrous $Na_2SO_4$ and concentrated. The residue was purified by Combi Flash (30% to 50% EtOAc in pentane) to give N-(5-bromopyridin-3-yl)tetrahydrofuran-2-carboxamide (380 mg, yield: 65%) as a yellow solid.

$^1$H NMR (400 MHz, CDCl$_3$) δ 1.88-2.04 (2H, m), 2.12-2.21 (1H, m), 2.34-2.44 (1H, m), 3.93-4.00 (1H, m), 4.02-4.09 (1H, m), 4.48 (1H, dd, J=8.3, 6.0 Hz), 8.42 (1H, d, J=2.0 Hz), 8.49-8.50 (1H, m), 8.51-8.53 (1H, m), 8.57 (1H, brs).

Step 2: Preparation of N-(5-((5-methyl-8-(2-oxopyrrolidin-1-yl)-5H-chromeno[4,3-c]pyridin-3-yl)amino)pyridin-3-yl)tetrahydrofuran-2-carboxamide

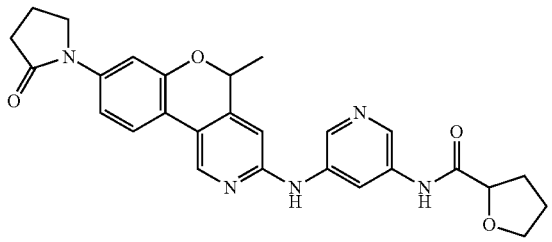 [SMILES: CC1Oc2cc(N3CCCC3=O)ccc2-c2cnc(Nc3cncc(NC(=O)C4CCCO4)c3)cc21]

A mixture of 1-(3-amino-5-methyl-5H-chromeno[4,3-c]pyridin-8-yl)pyrrolidin-2-one (60 mg, 0.20 mmol), N-(5-bromopyridin-3-yl)tetrahydrofuran-2-carboxamide (83 mg, 0.30 mmol), Pd$_2$(dba)$_3$ (19 mg, 0.020 mmol), BrettPhos (22 mg, 0.041 mmol) and Cs$_2$CO$_3$ (199 mg, 0.609 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.724 min; MS Calcd: 485.2. MS Found: 486.2 [M+H]$^+$). To the reaction mixture was added water (20 mL), then extracted with EtOAc/THF (20 mL×3, 3/1). The combined organic layer was washed with brine (20 mL), dried over anhydrous Na$_2$SO$_4$ and concentrated. The residue was purified by prep-HPLC (0.225% FA as an additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)tetrahydrofuran-2-carboxamide (11.7 mg, yield: 12%) as a yellow solid.

$^1$H NMR (400 MHz, DMSO-d$_6$) δ 1.54 (3H, d, J=6.5 Hz), 1.84-1.93 (2H, m), 1.96-2.11 (3H, m), 2.17-2.27 (1H, m), 2.52-2.54 (2H, m), 3.81-3.88 (3H, m), 3.97-4.04 (1H, m), 4.44 (1H, dd, J=8.2, 5.7 Hz), 5.27 (1H, q, J=6.2 Hz), 6.76 (1H, s), 7.32 (1H, dd, J=8.7, 2.1 Hz), 7.40 (1H, d, J=2.0 Hz), 7.89 (1H, d, J=8.5 Hz), 8.40 (1H, s), 8.56-8.59 (1H, m), 8.64-8.66 (1H, m), 8.67 (1H, s), 9.48 (1H, brs), 9.89 (1H, brs).

Example 136: N-(5-((5-methyl-8-(2-oxopyrrolidin-1-yl)-5H-chromeno[4,3-c]pyridin-3-yl)amino)pyridin-3-yl)benzo[d][1,3]dioxole-5-carboxamide

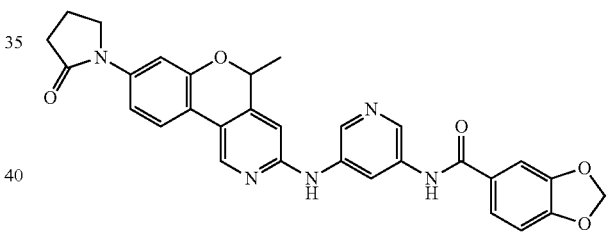

Step 1: Preparation of N-(5-bromopyridin-3-yl)benzo[d][1,3]dioxole-5-carboxamide

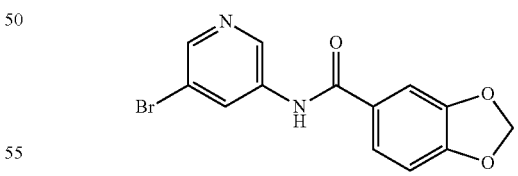

A mixture of 5-bromopyridin-3-amine (300 mg, 1.73 mmol), benzo[d][1,3]dioxole-5-carboxylic acid (431 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc/THF (25 mL×3, 2/1). The combined organic layer was washed with brine (25 mL), dried over anhydrous Na$_2$SO$_4$ and concentrated. The crude product was triturated with pentane/EtOAC (10 mL, 1/1) to give N-(5-bromopyridin-3-yl)benzo[d][1,3]dioxole-5-carboxamide (480 mg, yield: 86%) as a yellow solid.

¹H NMR (400 MHz, CDCl₃) δ 6.08 (2H, s), 6.90 (1H, d, J=8.0 Hz), 7.36 (1H, d, J=1.5 Hz), 7.41 (1H, dd, J=8.2, 1.6 Hz), 7.83 (1H, brs), 8.44 (1H, d, J=2.0 Hz), 8.53-8.58 (2H, m).

Step 2: Preparation of N-(5-((5-methyl-8-(2-oxopyrrolidin-1-yl)-5H-chromeno[4,3-c]pyridin-3-yl)amino)pyridin-3-yl)benzo[d][1,3]dioxole-5-carboxamide

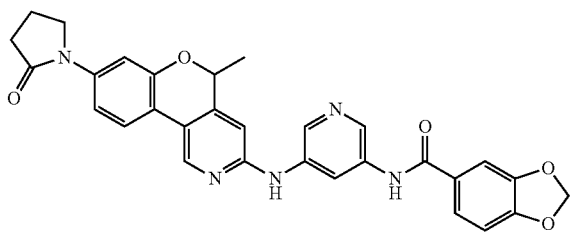

A mixture of 1-(3-amino-5-methyl-5H-chromeno[4,3-c]pyridin-8-yl)pyrrolidin-2-one (60 mg, 0.20 mmol), N-(5-bromopyridin-3-yl)benzo[d][1,3]dioxole-5-carboxamide (98 mg, 0.30 mmol), Pd₂(dba)₃ (19 mg, 0.020 mmol), BrettPhos (22 mg, 0.041 mmol) and Cs₂CO₃ (199 mg, 0.609 mmol) in anhydrous dioxane (3 mL) was degassed and purged with N₂ for 3 times. Then the resulting reaction mixture was stirred at 90° C. for 16 h under N₂ atmosphere. The reaction mixture turned into yellow suspension from red. LCMS (Rt=0.735 min; MS Calcd: 535.2. MS Found: 536.1 [M+H]⁺). To the reaction mixture was added water (20 mL), then extracted with EtOAc/THF (20 mL×3, 3/1). The combined organic layer was washed with brine (20 mL), dried over anhydrous Na₂SO₄ and concentrated. The residue was purified by prep-HPLC (0.225% FA as additive) purification. Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)benzo[d][1,3]dioxole-5-carboxamide (40.0 mg, yield: 37%) as a yellow solid.

¹H NMR (400 MHz, DMSO-d₆) δ 1.55 (3H, d, J=6.5 Hz), 2.01-2.11 (2H, m), 2.52-2.54 (2H, m), 3.84 (2H, t, J=7.7 Hz), 5.29 (1H, q, J=6.6 Hz), 6.16 (2H, s), 6.79 (1H, s), 7.09 (1H, d, J=8.0 Hz), 7.32 (1H, dd, J=8.7, 2.1 Hz), 7.41 (1H, d, J=2.0 Hz), 7.55 (1H, d, J=1.5 Hz), 7.63 (1H, dd, J=8.2, 1.6 Hz), 7.89 (1H, d, J=8.8 Hz), 8.54 (1H, s), 8.68-8.73 (2H, m), 8.77 (1H, s), 9.67 (1H, brs), 10.37 (1H, brs).

Example 137: N-(5-((5-methyl-8-(2-oxopyrrolidin-1-yl)-5H-chromeno[4,3-c]pyridin-3-yl)amino)pyridin-3-yl)benzo[d][1,3]dioxole-4-carboxamide

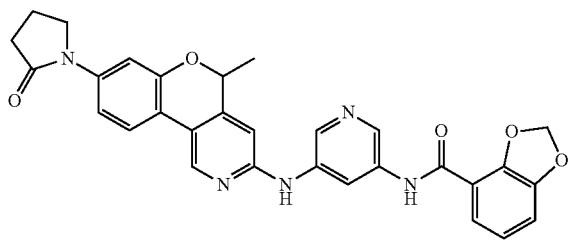 [SMILES: CC1Oc2cc(N3CCCC3=O)ccc2-c2cnc(Nc3cncc(NC(=O)c4cccc5c4OCO5)c3)cc21]

Step 1: Preparation of N-(5-bromopyridin-3-yl)benzo[d][1,3]dioxole-4-carboxamide

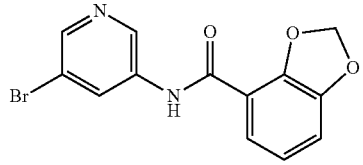 [SMILES: O=C(Nc1cncc(Br)c1)c1cccc2c1OCO2]

A mixture of 5-bromopyridin-3-amine (300 mg, 1.73 mmol), benzo[d][1,3]dioxole-4-carboxylic acid (431 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc (25 mL×3). The combined organic layer was washed with brine (25 mL), dried over anhydrous Na₂SO₄ and concentrated. The crude product was triturated with pentane/EtOAC (10 mL, 1/1) to give N-(5-bromopyridin-3-yl)benzo[d][1,3]dioxole-4-carboxamide (385 mg, yield: 69%) as a yellow solid.

¹H NMR (400 MHz, CDCl₃) δ 6.20 (2H, s), 6.99-7.07 (2H, m), 7.64 (1H, d, J=7.5, 1.8 Hz), 8.44 (1H, d, J=2.0 Hz), 8.57 (1H, d, J=2.3 Hz), 8.60-8.63 (1H, m), 8.83 (1H, brs).

Step 2: Preparation of N-(5-((5-methyl-8-(2-oxopyrrolidin-1-yl)-5H-chromeno[4,3-c]pyridin-3-yl)amino)pyridin-3-yl)benzo[d][1,3]dioxole-4-carboxamide

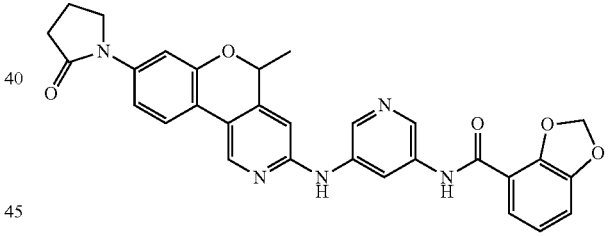

A mixture of 1-(3-amino-5-methyl-5H-chromeno[4,3-c]pyridin-8-yl)pyrrolidin-2-one (60 mg, 0.20 mmol), N-(5-bromopyridin-3-yl)benzo[d][1,3]dioxole-4-carboxamide (98 mg, 0.30 mmol), Pd₂(dba)₃ (19 mg, 0.020 mmol), BrettPhos (22 mg, 0.041 mmol) and Cs₂CO₃ (199 mg, 0.609 mmol) in anhydrous dioxane (3 mL) was degassed and purged with N₂ for 3 times. Then the resulting reaction mixture was stirred at 90° C. for 16 h under N₂ atmosphere. The reaction mixture turned into yellow suspension from red. LCMS (Rt=0.749 min; MS Calcd: 535.2. MS Found: 536.1 [M+H]⁺). To the reaction mixture was added water (20 mL) and EtOAc (20 mL) and the reaction mixture was filtered and the solid was washed with EtOAc (5 mL×2) and dried under vacuum. The crude product was purified by prep-HPLC (0.225% FA as additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)benzo[d][1,3]dioxole-4-carboxamide (23.1 mg, yield: 21%) as a yellow solid.

$^1$H NMR (400 MHz, DMSO-d$_6$) δ 1.55 (3H, d, J=6.5 Hz), 2.01-2.11 (2H, m), 2.52-2.54 (2H, m), 3.85 (2H, t, J=7.8 Hz), 5.30 (1H, q, J=6.5 Hz), 6.18 (2H, s), 6.79 (1H, s), 7.00 (1H, t, J=8.0 Hz), 7.16 (1H, d, J=7.0 Hz), 7.27 (1H, d, J=7.3 Hz), 7.33 (1H, dd, J=8.7, 1.9 Hz), 7.41 (1H, d, J=2.0 Hz), 7.90 (1H, d, J=8.8 Hz), 8.48 (1H, d, J=1.8 Hz), 8.68 (1H, t, J=2.1 Hz), 8.70 (1H, s), 8.81 (1H, d, J=1.5 Hz), 9.70 (1H, brs), 10.22 (1H, brs).

Example 138: N-(5-((5-methyl-8-(2-oxopyrrolidin-1-yl)-5H-chromeno[4,3-c]pyridin-3-yl)amino)pyridin-3-yl)-2,3-dihydro-1H-indene-2-carboxamide

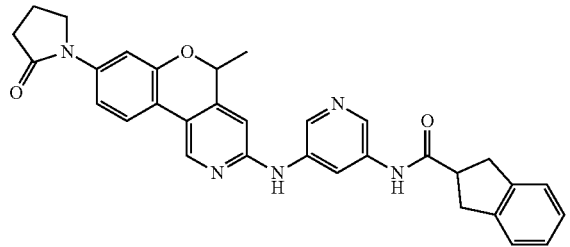 [SMILES: CC1Oc2cc(N3CCCC3=O)ccc2-c2cnc(Nc3cncc(NC(=O)C4Cc5ccccc5C4)c3)cc21]

Step 1: Preparation of N-(5-bromopyridin-3-yl)-2,3-dihydro-1H-indene-2-carboxamide

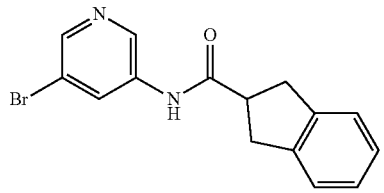

A mixture of 5-bromopyridin-3-amine (300 mg, 1.73 mmol), 2,3-dihydro-1H-indene-2-carboxylic acid (421 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc/THF (25 mL×3, 1/1). The combined organic layer was washed with brine (25 mL), dried over anhydrous Na$_2$SO$_4$ and concentrated. The crude product was triturated with pentane/EtOAC (10 mL, 1/1) to give N-(5-bromopyridin-3-yl)-2,3-dihydro-1H-indene-2-carboxamide (500 mg, yield: 91%) as a yellow solid.

$^1$H NMR (400 MHz, CDCl$_3$) δ 3.23-3.41 (5H, m), 7.18-7.26 (4H, m), 7.39 (1H, brs), 8.41 (1H, d, J=2.0 Hz), 8.43 (1H, d, J=2.3 Hz), 8.48-8.51 (1H, m).

Step 2: Preparation of N-(5-((5-methyl-8-(2-oxopyrrolidin-1-yl)-5H-chromeno[4,3-c]pyridin-3-yl)amino)pyridin-3-yl)-2,3-dihydro-1H-indene-2-carboxamide

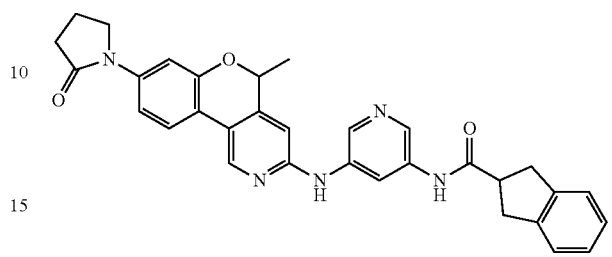

A mixture of 1-(3-amino-5-methyl-5H-chromeno[4,3-c]pyridin-8-yl)pyrrolidin-2-one (60 mg, 0.20 mmol), N-(5-bromopyridin-3-yl)-2,3-dihydro-H-indene-2-carboxamide (97 mg, 0.30 mmol), Pd$_2$(dba)$_3$ (19 mg, 0.020 mmol), BrettPhos (22 mg, 0.041 mmol) and Cs$_2$CO$_3$ (199 mg, 0.609 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.922 min; MS Calcd: 708.3. MS Found: 709.1 [M+H]$^+$). To the reaction mixture was added water (20 mL), then extracted with EtOAc/THF (20 mL×3, 1/1). The combined organic layer was washed with brine (20 mL), dried over anhydrous Na$_2$SO$_4$ and concentrated. The residue was purified by prep-HPLC (0.225% FA as additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)-2,3-dihydro-1H-indene-2-carboxamide (46.0 mg, yield: 43%) as a yellow solid.

$^1$H NMR (400 MHz, DMSO-d$_6$) δ 1.55 (3H, d, J=6.5 Hz), 2.01-2.11 (2H, m), 2.52-2.54 (2H, m), 3.14-3.27 (4H, m), 3.50-3.51 (1H, m), 3.84 (2H, t, J=7.9 Hz), 5.28 (1H, q, J=6.3 Hz), 6.78 (1H, s), 7.13-7.19 (2H, m), 7.22-7.27 (2H, m), 7.33 (1H, dd, J=8.5, 2.0 Hz), 7.40 (1H, d, J=2.3 Hz), 7.90 (1H, d, J=8.8 Hz), 8.46 (1H, s), 8.62 (1H, t, J=2.0 Hz), 8.68 (1H, s), 8.72 (1H, d, J=1.8 Hz), 9.67 (1H, brs), 10.41 (1H, brs).

Example 139: N-(5-((5-methyl-8-(2-oxopyrrolidin-1-yl)-5H-chromeno[4,3-c]pyridin-3-yl)amino)pyridin-3-yl)imidazo[1,2-a]pyridine-2-carboxamide

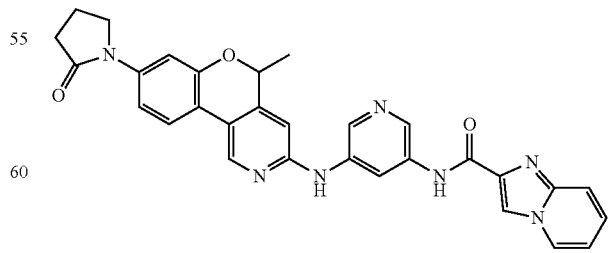

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), imidazo[1,2-a]pyridine-2- carboxylic acid (34 mg, 0.21 mmol) and EDCI.HCl (41 mg, 0.21 mmol) in pyridine (2 mL) was stirred at 50° C. for 2 h. The reaction mixture turned into white suspension from yellow solution. LCMS (Rt=0.750 min; MS Calcd: 531.2. MS Found: 532.1 [M+H]⁺). The reaction mixture was diluted with water (25 mL), and then extracted with EtOAc/THF (25 mL×3, 1/1). The combined organic layer was washed with saturated aqueous NaHCO₃ (25 mL), brine (25 mL), dried over anhydrous Na₂SO₄ and concentrated. The residue was triturated with MeCN (10 mL), then further purified by prep-HPLC (0.225% FA as an additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)imidazo[1,2-a]pyridine-2-carboxamide (29.8 mg, yield: 40%) as a yellow solid.

¹H NMR (400 MHz, DMSO-d₆) δ 1.56 (3H, d, J=6.5 Hz), 2.01-2.11 (2H, m), 2.52-2.54 (2H, m), 3.85 (2H, t, J=7.9 Hz), 5.29 (1H, q, J=6.4 Hz), 6.79 (1H, s), 7.05 (1H, td, J=6.8, 1.1 Hz), 7.33 (1H, dd, J=8.7, 2.1 Hz), 7.39-7.44 (2H, m), 7.69 (1H, dd, J=9.2, 0.9 Hz), 7.90 (1H, d, J=8.8 Hz), 8.58 (1H, s), 8.59 (1H, t, J=2.3 Hz), 8.65 (1H, td, J=6.8, 1.1 Hz), 8.69 (1H, d, J=2.3 Hz), 8.70 (1H, s), 8.78 (1H, t, J=2.3 Hz), 9.52 (1H, brs), 10.51 (1H, brs).

Example 140: N-(5-((5-methyl-8-(2-oxopyrrolidin-1-yl)-5H-chromeno[4,3-c]pyridin-3-yl)amino)pyridin-3-yl)pyrazolo[1,5-a]pyridine-2-carboxamide

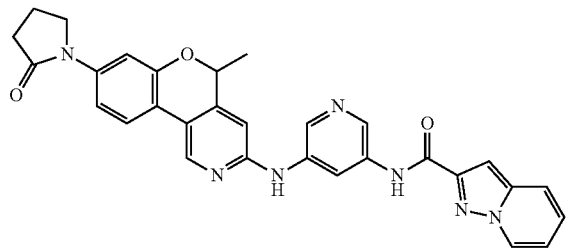 [SMILES: CC1Oc2cc(N3CCCC3=O)ccc2-c2cnc(Nc3cncc(NC(=O)c4cc5ccccn5n4)c3)cc21]

Step 1: Preparation of N-(5-bromopyridin-3-yl)pyrazolo[1,5-a]pyridine-2-carboxamide

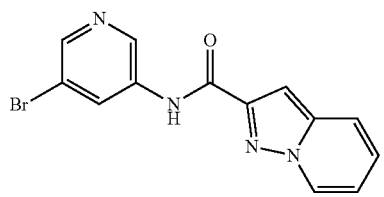 [SMILES: O=C(Nc1cncc(Br)c1)c1cc2ccccn2n1]

A mixture of 5-bromopyridin-3-amine (300 mg, 1.73 mmol), pyrazolo[1,5-a]pyridine-2-carboxylic acid (421 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc/THF (25 mL×3, 3/1). The combined organic layer was washed with brine (25 mL), dried over anhydrous Na₂SO₄ and concentrated. The crude product was triturated with pentane/EtOAC (10 mL, 1/1) to give N-(5-bromopyridin-3-yl)pyrazolo[1,5-a]pyridine-2-carboxamide (498 mg, yield: 91%) as a yellow solid.

¹H NMR (400 MHz, DMSO-d₆) δ 7.12 (1H, td, J=6.9, 1.3 Hz), 7.19 (1H, s), 7.36 (1H, ddd, J=9.0, 6.8, 1.0 Hz), 7.86 (1H, d, J=8.8 Hz), 8.45 (1H, d, J=2.0 Hz), 8.62 (1H, t, J=2.1 Hz), 8.76 (1H, dd, J=7.0, 1.0 Hz), 9.05 (1H, d, J=2.3 Hz), 10.92 (1H, brs).

Step 2: Preparation of N-(5-((5-methyl-8-(2-oxopyrrolidin-1-yl)-5H-chromeno[4,3-c]pyridin-3-yl)amino)pyridin-3-yl)pyrazolo[1,5-a]pyridine-2-carboxamide

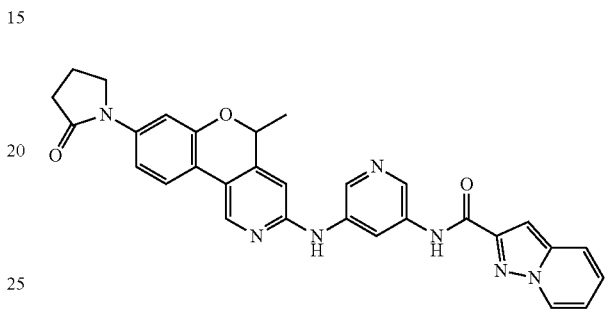

A mixture of 1-(3-amino-5-methyl-5H-chromeno[4,3-c]pyridin-8-yl)pyrrolidin-2-one (60 mg, 0.20 mmol), N-(5-bromopyridin-3-yl)pyrazolo[1,5-a]pyridine-2-carboxamide (97 mg, 0.30 mmol), Pd₂(dba)₃ (19 mg, 0.020 mmol), BrettPhos (22 mg, 0.041 mmol) and Cs₂CO₃ (199 mg, 0.609 mmol) in anhydrous dioxane (3 mL) was degassed and purged with N₂ for 3 times. Then the resulting reaction mixture was stirred at 90° C. for 16 h under N₂ atmosphere. The reaction mixture turned into yellow suspension from red. LCMS indicated 50% of the starting material N-(5-bromopyridin-3-yl)pyrazolo[1,5-a]pyridine-2-carboxamide was remained. To the reaction mixture was added another batch of Pd₂(dba)₃ (19 mg, 0.020 mmol), BrettPhos (22 mg, 0.041 mmol) and Cs₂CO₃ (199 mg, 0.609 mmol). Then the reaction mixture was degassed and purged with N₂ for 3 times. Then the resulting reaction mixture was stirred at 90° C. for another 8 h under N₂ atmosphere. LCMS (Rt=0.726 min; MS Calcd: 531.2; MS Found: 532.1 [M+H]⁺). To the reaction mixture was added water (25 mL), then extracted with EtOAc/THF (25 mL×3, 1/1). The combined organic layer was washed with brine (25 mL), dried over anhydrous Na₂SO₄ and concentrated. The residue was purified by prep-HPLC (0.225% FA as additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)pyrazolo[1,5-a]pyridine-2-carboxamide (12.8 mg, yield: 12%) as a yellow solid.

¹H NMR (400 MHz, DMSO-d₆) δ 1.56 (3H, d, J=6.5 Hz), 2.01-2.11 (2H, m), 2.52-2.54 (2H, m), 3.85 (2H, t, J=7.8 Hz), 5.31 (1H, q, J=6.3 Hz), 6.82 (1H, s), 7.12 (1H, t, J=6.9 Hz), 7.21 (1H, s), 7.31-7.39 (2H, m), 7.41 (1H, d, J=2.3 Hz), 7.86 (1H, d, J=9.0 Hz), 7.91 (1H, d, J=8.5 Hz), 8.65-8.69 (1H, m), 8.72 (1H, s), 8.77 (1H, d, J=7.0 Hz), 8.84-8.91 (2H, m), 9.83 (1H, brs), 10.87 (1H, brs).

Example 141: N-(5-((5-methyl-8-(2-oxopyrrolidin-1-yl)-5H-chromeno[4,3-c]pyridin-3-yl)amino)pyridin-3-yl)-1H-indole-2-carboxamide

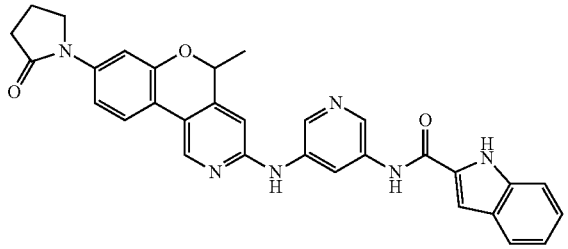 [SMILES: CC1Oc2cc(N3CCCC3=O)ccc2-c2cnc(Nc3cncc(NC(=O)c4cc5ccccc5[nH]4)c3)cc21]

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), 1H-indole-2-carboxylic acid (34 mg, 0.21 mmol) and EDCI.HCl (41 mg, 0.21 mmol) in pyridine (2 mL) was stirred at 50° C. for 2 h. The reaction mixture turned into white suspension from yellow solution. LCMS (Rt=0.780 min; MS Calcd: 530.2. MS Found: 531.1 [M+H]$^+$). The reaction mixture was diluted with water (25 mL), and then extracted with EtOAc (25 mL×3). The combined organic layer was washed with saturated aqueous NaHCO$_3$ (25 mL), brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give N-(5-((5-methyl-8-(2-oxopyrrolidin-1-yl)-5H-chromeno[4,3-c]pyridin-3-yl)amino)pyridin-3-yl)-1H-indole-2-carboxamide (32.8 mg, yield: 44%) as a yellow solid.

$^1$H NMR (400 MHz, DMSO-d$_6$) δ 1.56 (3H, d, J=6.5 Hz), 2.01-2.11 (2H, m), 2.52-2.54 (2H, m), 3.84 (2H, t, J=7.7 Hz), 5.30 (1H, q, J=6.5 Hz), 6.81 (1H, s), 7.07-7.12 (1H, m), 7.26 (1H, t, J=7.5 Hz), 7.33 (1H, dd, J=8.5, 2.3 Hz), 7.41 (1H, d, J=2.0 Hz), 7.47-7.52 (2H, m), 7.71 (1H, d, J=7.8 Hz), 7.89 (1H, d, J=8.5 Hz), 8.61 (1H, s), 8.69 (1H, s), 8.73-8.77 (2H, m), 9.67 (1H, brs), 10.51 (1H, brs), 11.83 (1H, brs).

Example 142: N-(5-((5-methyl-8-(2-oxopyrrolidin-1-yl)-5H-chromeno[4,3-c]pyridin-3-yl)amino)pyridin-3-yl)-2,3-dihydrobenzofuran-2-carboxamide

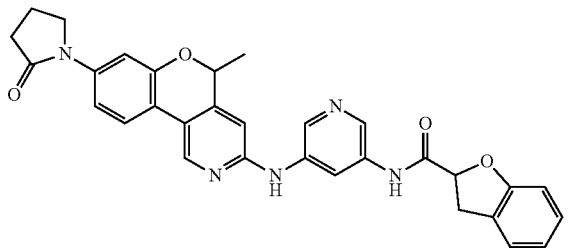 [SMILES: CC1Oc2cc(N3CCCC3=O)ccc2-c2cnc(Nc3cncc(NC(=O)C4Cc5ccccc5O4)c3)cc21]

Step 1: Preparation of N-(5-bromopyridin-3-yl)-2,3-dihydrobenzofuran-2-carboxamide

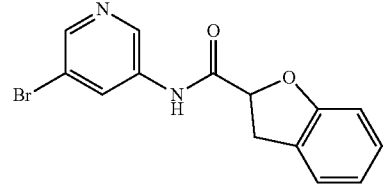 [SMILES: O=C(Nc1cncc(Br)c1)C1Cc2ccccc2O1]

A mixture of 5-bromopyridin-3-amine (300 mg, 1.73 mmol), 2,3-dihydrobenzofuran-2-carboxylic acid (426 mg, 2.60 mmol) and EDCI.HCl (497 mg, 2.60 mmol) in pyridine (4 mL) was stirred at 50° C. for 2 h. The reaction mixture turned into brown solution from yellow. The reaction mixture was concentrated and the residue was diluted with water (25 mL), and then extracted with EtOAc (25 mL×3). The combined organic layer was washed with brine (25 mL), dried over anhydrous Na$_2$SO$_4$ and concentrated. The residue was purified by Combi Flash (20% to 50% EtOAc in pentane) to give N-(5-bromopyridin-3-yl)-2,3-dihydrobenzofuran-2-carboxamide (500 mg, yield: 91%) as yellow gum.

$^1$H NMR (400 MHz, CDCl$_3$) δ 3.49-3.57 (1H, m), 3.64-3.74 (1H, m), 5.28 (1H, dd, J=10.8, 6.5 Hz), 6.94-7.01 (2H, m), 7.18-7.26 (2H, m), 8.39-8.49 (3H, m), 8.54 (1H, d, J=2.3 Hz).

Step 2: Preparation of N-(5-((5-methyl-8-(2-oxopyrrolidin-1-yl)-5H-chromeno[4,3-c]pyridin-3-yl)amino)pyridin-3-yl)-2,3-dihydrobenzofuran-2-carboxamide

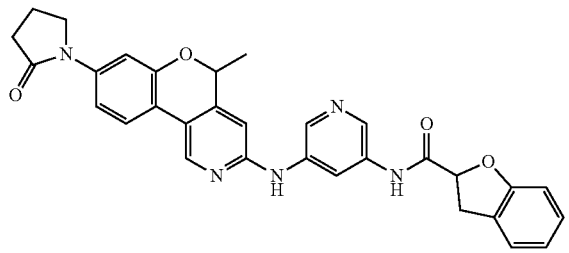 [SMILES: CC1Oc2cc(N3CCCC3=O)ccc2-c2cnc(Nc3cncc(NC(=O)C4Cc5ccccc5O4)c3)cc21]

A mixture of 1-(3-amino-5-methyl-5H-chromeno[4,3-c]pyridin-8-yl)pyrrolidin-2-one (60 mg, 0.20 mmol), N-(5-bromopyridin-3-yl)-2,3-dihydrobenzofuran-2-carboxamide (97 mg, 0.30 mmol) Pd$_2$(dba)$_3$ (19 mg, 0.020 mmol), Brett-Phos (22 mg, 0.041 mmol) and Cs$_2$CO$_3$ (199 mg, 0.609 mmol) in anhydrous dioxane (3 mL) was degassed and purged with N$_2$ for 3 times. Then the resulting reaction mixture was stirred at 90° C. for 16 h under N$_2$ atmosphere. The reaction mixture turned into yellow suspension from red. LCMS (Rt=0.638 min; MS Calcd: 533.2. MS Found: 534.1 [M+H]$^+$). To the reaction mixture was added water (25 mL) and EtOAc (20 mL), then extracted with EtOAc/THF (25 mL×3, 3/1). The combined organic layer was washed with brine (25 mL), dried over anhydrous Na$_2$SO$_4$ and concentrated. The residue was purified by Combi Flash (2% to 10% MeOH in DCM), then triturated with MeCN (10 mL) and dried under vacuum to give N-(5-((5-methyl-8-(2- oxopyrrolidin-1-yl)-5H-chromeno[4,3-c]pyridin-3-yl)amino)pyridin-3-yl)-2,3-dihydrobenzofuran-2-carboxamide (51.7 mg, yield: 48%) as a yellow solid.

¹H NMR (400 MHz, DMSO-d₆) δ 1.54 (3H, d, J=6.6 Hz), 2.01-2.11 (2H, m), 2.52-2.54 (2H, m), 3.40 (1H, dd, J=15.8, 6.8 Hz), 3.52-3.60 (1H, m), 3.84 (2H, t, J=7.8 Hz), 5.27 (1H, q, J=6.5 Hz), 5.37 (1H, dd, J=10.2, 6.7 Hz), 6.75 (1H, s), 6.87-6.94 (2H, m), 7.13-7.19 (1H, m), 7.25-7.28 (1H, m), 7.32 (1H, dd, J=8.6, 2.1 Hz), 7.40 (1H, d, J=2.2 Hz), 7.89 (1H, d, J=8.7 Hz), 8.39 (1H, d, J=1.3 Hz), 8.59-8.63 (2H, m), 8.67 (1H, s), 9.49 (1H, brs), 10.37 (1H, brs).

Example 143: N-(5-((5-methyl-8-(2-oxopyrrolidin-1-yl)-5H-chromeno[4,3-c]pyridin-3-yl)amino)pyridin-3-yl)imidazo[1,2-a]pyridine-3-carboxamide

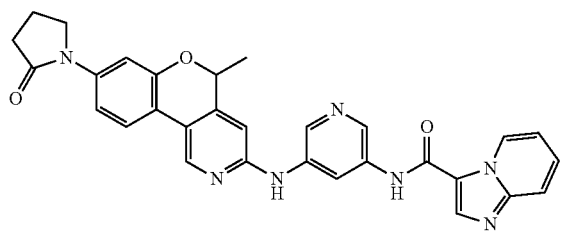 [SMILES: CC1Oc2cc(N3CCCC3=O)ccc2-c2cnc(Nc3cncc(NC(=O)c4cnc5ccccn45)c3)cc21]

A mixture of 1-(3-((5-aminopyridin-3-yl)amino)-5-methyl-5H-chromeno[4,3-c]pyridin-8-yl)pyrrolidin-2-one (60 mg, 0.16 mmol, HCl salt), imidazo[1,2-a]pyridine-3-carboxylic acid (38 mg, 0.23 mmol) and EDCI.HCl (45 mg, 0.23 mmol) in pyridine (2 mL) was heated at 30° C. for 12 h. A yellow suspension was formed. LCMS (Rt=0.689 min; MS Calcd: 531.2. MS Found: 532.1 [M+H]⁺). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)imidazo[1,2-a]pyridine-3-carboxamide (48.6 mg, yield: 59%) as a yellow solid.

¹H NMR (400 MHz DMSO-d₆) δ 1.51-1.54 (3H, m), 2.04-2.16 (2H, m), 2.52-2.54 (2H, m, overlapped with the peak of DMSO), 3.72-4.56 (2H, m), 5.28-5.43 (1H, m), 6.82-7.00 (1H, m), 7.25-7.52 (3H, m), 7.58-7.73 (1H, m), 7.81-8.04 (2H, m), 8.68-9.08 (5H, m), 9.47-9.62 (1H, m), 10.07 (1H, brs), 10.88 (1H, brs).

Example 144: N-(5-((5-methyl-8-(2-oxopyrrolidin-1-yl)-5H-chromeno[4,3-c]pyridin-3-yl)amino)pyridin-3-yl)pyrazolo[1,5-a]pyridine-3-carboxamide

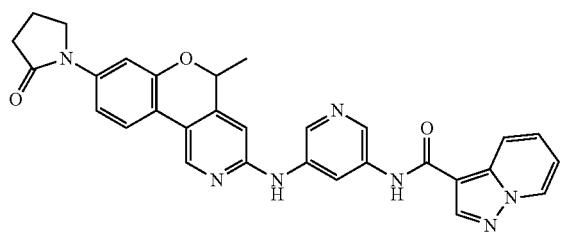 [SMILES: CC1Oc2cc(N3CCCC3=O)ccc2-c2cnc(Nc3cncc(NC(=O)c4cnn5ccccc45)c3)cc21]

A mixture of 1-(3-((5-aminopyridin-3-yl)amino)-5-methyl-5H-chromeno[4,3-c]pyridin-8-yl)pyrrolidin-2-one (60 mg, 0.16 mmol, HCl salt), pyrazolo[1,5-a]pyridine-3-carboxylic acid (38 mg, 0.23 mmol) and EDCI.HCl (45 mg, 0.23 mmol) in pyridine (2 mL) was heated at 30° C. for 12 h. A yellow suspension was formed. LCMS (Rt=0.720 min; MS Calcd: 531.2. MS Found: 532.1 [M+H]⁺). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na₂SO₄, filtered and concentrated. The residue was purified by prep-HPLC (0.225% FA as an additive) and lyophilized to give N-(5-((5-methyl-8-(2-oxopyrrolidin-1-yl)-5H-chromeno[4,3-c]pyridin-3-yl)amino)pyridin-3-yl)pyrazolo[1,5-a]pyridine-3-carboxamide (40.0 mg, yield: 48%) as a yellow solid.

¹H NMR (400 MHz DMSO-d₆) δ 1.56 (3H, d, J=6.5 Hz), 2.02-2.10 (2H, m), 2.52-2.54 (2H, m, overlapped with the peak of DMSO), 3.85 (2H, t, J=7.8 Hz), 5.29 (1H, q, J=6.4 Hz), 6.79 (1H, s), 7.16 (1H, td, J=6.9, 1.3 Hz), 7.32 (1H, dd, J=8.5, 2.3 Hz), 7.41 (1H, d, J=2.3 Hz), 7.57 (1H, t, J=7.8 Hz), 7.90 (1H, d, J=8.5 Hz), 8.30 (1H, d, J=8.8 Hz), 8.52 (1H, s), 8.64-8.72 (3H, m), 8.84-8.89 (2H, m), 9.53 (1H, brs), 10.16 (1H, brs).

Example 145: 2-(imidazo[1,2-a]pyridin-3-yl)-N-(5-((5-methyl-8-(2-oxopyrrolidin-1-yl)-5H-chromeno[4,3-c]pyridin-3-yl)amino)pyridin-3-yl)acetamide

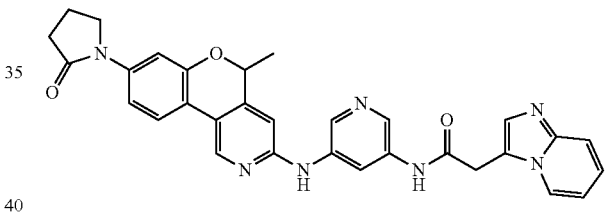

Step 1: Preparation of 2-(imidazo[1,2-a]pyridin-3-yl)acetic acid

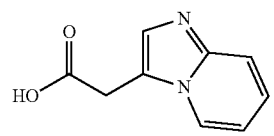

To a solution of pyridin-2-amine (1.00 g, 10.6 mmol) in de-mineralized water (13 mL) was added ethyl (E)-4-oxobut-2-enoate (1.40 g, 10.9 mmol) at 20-25° C. Then the reaction mixture was stirred at 20-25° C. for 1 hour. The reaction mixture turned into red solution from yellow. A solution of KOH (0.8 g) in de-mineralized water (1 mL) was added and the reaction mixture was stirred at 20-25° C. for 1 hour. The pH of the reaction mixture was adjusted to 5-6 with 2N aqueous HCl and the reaction mixture was stirred for further 1 hour at 20-25° C. The resulting product was filtered, washed successively with water (5 mL×2), ethanol (5 mL) and dried under reduced pressure to give 2-(imidazo[1,2-a]pyridin-3-yl)acetic acid (720 mg, yield: 38%) as a yellow solid.

$^1$H NMR (400 MHz, DMSO-d$_6$) δ 4.05 (2H, s), 6.94 (1H, td, J=6.8, 1.1 Hz), 7.25 (1H, ddd, J=9.2, 6.7, 1.0 Hz), 7.49 (1H, s), 7.57 (1H, dt, J=9.0, 1.0 Hz), 8.29-8.33 (1H, m).

Step 2: Preparation of 2-(imidazo[1,2-a]pyridin-3-yl)-N-(5-((5-methyl-8-(2-oxopyrrolidin-1-yl)-5H-chromeno[4,3-c]pyridin-3-yl)amino)pyridin-3-yl)acetamide

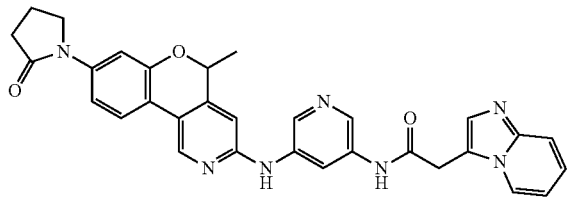 [SMILES: CC1Oc2cc(N3CCCC3=O)ccc2-c2cnc(Nc3cncc(NC(=O)Cc4cnc5ccccn45)c3)cc21]

A mixture of 1-(3-((5-aminopyridin-3-yl)amino)-5-methyl-5H-chromeno[4,3-c]pyridin-8-yl)pyrrolidin-2-one (60 mg, 0.14 mmol, HCl salt), 2-(imidazo[1,2-a]pyridin-3-yl)acetic acid (37 mg, 0.21 mmol) and EDCI.HCl (41 mg, 0.21 mmol) in pyridine (2 mL) was stirred at 50° C. for 2 h. The reaction mixture turned into brown solution from yellow. LCMS (Rt=0.700 min; MS Calcd: 545.2. MS Found: 546.1 [M+H]$^+$). The reaction mixture was diluted with water (25 mL), and then extracted with EtOAc/THF (25 mL×3, 1/1). The combined organic layer was washed with saturated aqueous NaHCO$_3$ (25 mL), brine (25 mL), dried over anhydrous Na$_2$SO$_4$ and concentrated. The residue was purified by prep-HPLC (0.225% FA as an additive). Most of the MeCN was removed under reduced pressure and the remaining part was lyophilized to give 2-(imidazo[1,2-a]pyridin-3-yl)-N-(5-((5-methyl-8-(2-oxopyrrolidin-1-yl)-5H-chromeno[4,3-c]pyridin-3-yl)amino)pyridin-3-yl)acetamide (29.7 mg, yield: 38%) as a yellow solid.

$^1$H NMR (400 MHz, DMSO-d$_6$) δ 1.53 (3H, d, J=6.5 Hz), 2.01-2.11 (2H, m), 2.52-2.54 (2H, m), 3.84 (2H, t, J=7.7 Hz), 4.27 (2H, s), 5.26 (1H, q, J=6.0 Hz), 6.74 (1H, s), 7.23 (1H, t, J=6.8 Hz), 7.32 (1H, dd, J=8.5, 2.0 Hz), 7.39 (1H, d, J=2.0 Hz), 7.56-7.62 (1H, m), 7.78 (1H, d, J=8.8 Hz), 7.82 (1H, s), 7.88 (1H, d, J=8.5 Hz), 8.35 (1H, d, J=1.8 Hz), 8.54-8.56 (1H, m), 8.58 (1H, d, J=2.0 Hz), 8.61-8.66 (2H, m), 9.49 (1H, brs), 10.56 (1H, brs).

Example 146: N-(5-((5-methyl-8-(2-oxopyrrolidin-1-yl)-5H-chromeno[4,3-c]pyridin-3-yl)amino)pyridin-3-yl)imidazo[1,2-a]pyridine-5-carboxamide

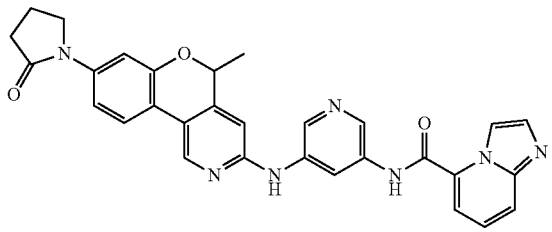 [SMILES: CC1Oc2cc(N3CCCC3=O)ccc2-c2cnc(Nc3cncc(NC(=O)c4cccc5nccn45)c3)cc21]

A mixture of 1-(3-((5-aminopyridin-3-yl)amino)-5-methyl-5H-chromeno[4,3-c]pyridin-8-yl)pyrrolidin-2-one (60 mg, 0.16 mmol, HCl salt), imidazo[1,2-a]pyridine-5-carboxylic acid (38 mg, 0.23 mmol) and EDCI.HCl (45 mg, 0.23 mmol) in pyridine (2 mL) was heated at 30° C. for 48 h. A brown suspension was formed. LCMS (Rt=0.652 min; MS Calcd: 531.2. MS Found: 532.1 [M+H]$^+$). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by prep-TLC (DCM/MeOH, 10/1) then further purified by prep-HPLC (0.05% NH$_3$.H$_2$O as an additive) and lyophilized to give N-(5-((5-methyl-8-(2-oxopyrrolidin-1-yl)-5H-chromeno[4,3-c]pyridin-3-yl)amino)pyridin-3-yl)imidazo[1,2-a]pyridine-5-carboxamide (5.8 mg, yield: 7%) as a yellow solid.

$^1$H NMR (400 MHz DMSO-d$_6$) δ 1.56 (3H, d, J=6.5 Hz), 2.02-2.10 (2H, m), 2.52-2.54 (2H, m, overlapped with the peak of DMSO), 3.85 (2H, t, J=7.8 Hz), 5.29 (1H, q, J=6.5 Hz), 6.79 (1H, s), 7.33 (1H, dd, J=8.5, 2.3 Hz), 7.40-7.47 (2H, m), 7.69 (1H, d, J=7.3 Hz), 7.74 (1H, s), 7.86-7.91 (2H, m), 8.48-8.52 (2H, m), 8.67-8.75 (3H, m), 9.57 (1H, brs), 10.94 (1H, brs).

Example 147: N-(5-((5-methyl-8-(2-oxopyrrolidin-1-yl)-5H-chromeno[4,3-c]pyridin-3-yl)amino)pyridin-3-yl)imidazo[1,2-a]pyridine-7-carboxamide

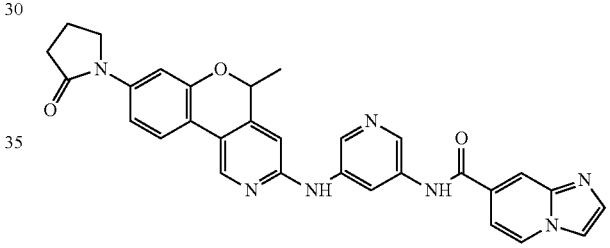

A mixture of 1-(3-((5-aminopyridin-3-yl)amino)-5-methyl-5H-chromeno[4,3-c]pyridin-8-yl)pyrrolidin-2-one (60 mg, 0.16 mmol, HCl salt), imidazo[1,2-a]pyridine-7-carboxylic acid (38 mg, 0.23 mmol) and EDCI.HCl (45 mg, 0.23 mmol) in pyridine (2 mL) was heated at 30° C. for 12 h. A yellow suspension was formed. LCMS (Rt=0.652 min; MS Calcd: 531.2. MS Found: 532.1 [M+H]$^+$). The mixture was concentrated and the residue was poured into water (20 mL) and stirred for 2 minutes. The aqueous layer was extracted with ethyl acetate (20 mL×3). The combined organic layer was washed with water (20 mL×2) and brine (20 mL), dried over anhydrous Na$_2$SO$_4$, filtered and concentrated. The residue was purified by prep-HPLC (0.225% FA as an additive) and further triturated by DMF/DCM (4 mL, 1/1), and then lyophilized to give N-(5-((5-methyl-8-(2-oxopyrrolidin-1-yl)-5H-chromeno[4,3-c]pyridin-3-yl)amino)pyridin-3-yl)imidazo[1,2-a]pyridine-7-carboxamide (20.1 mg, yield: 24%) as a yellow solid.

$^1$H NMR (400 MHz DMSO-d$_6$) δ 1.56 (3H, d, J=6.5 Hz), 2.02-2.10 (2H, m), 2.52-2.54 (2H, m, overlapped with the peak of DMSO), 3.85 (2H, t, J=7.8 Hz), 5.29 (1H, q, J=6.4 Hz), 6.79 (1H, s), 7.32 (1H, dd, J=8.5, 2.3 Hz), 7.41 (1H, d, J=2.0 Hz), 7.44 (1H, dd, J=7.0, 1.5 Hz), 7.79 (1H, s), 7.89 (1H, d, J=8.8 Hz), 8.13 (1H, s), 8.40 (1H, s), 8.54 (1H, d, J=2.0 Hz), 8.67-8.75 (4H, m), 9.52 (1H, brs), 10.56 (1H, brs).

Example 148: (S)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

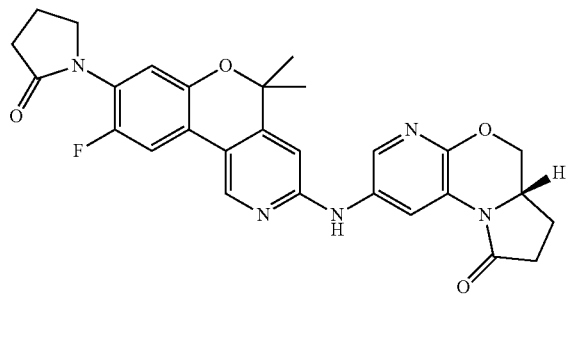 [SMILES: CC1(C)Oc2cc(N3CCCC3=O)c(F)cc2-c2cnc(Nc3cnc4c(c3)N3C(=O)CC[C@H]3CO4)cc21]

Step 1: Preparation of N-(4-bromo-2,5-difluorophenyl)-4-chlorobutanamide

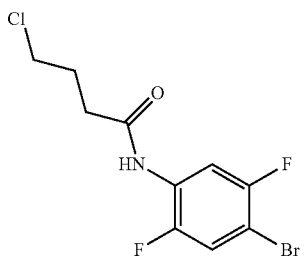 [SMILES: O=C(CCCCl)Nc1cc(F)c(Br)cc1F]

To a solution of 4-bromo-2,5-difluoroaniline (2.85 g, 13.7 mmol) and Et₃N (1.46 g, 14.4 mmol) in THF (40 mL) was added dropwise 4-chlorobutanoyl chloride (2.03 g, 14.4 mmol) at 0° C. under N₂. And the mixture was stirred at 0° C. for 1 hour. The yellow solution turned to suspension. TLC showed the starting material was consumed completely. The reaction suspension was used to next step directly.

Step 2: Preparation of 1-(4-bromo-2,5-difluorophenyl)pyrrolidin-2-one

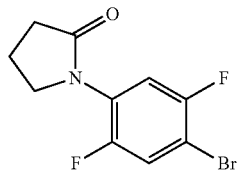 [SMILES: O=C1CCCN1c1cc(F)c(Br)cc1F]

To a solution of N-(4-bromo-2,5-difluorophenyl)-4-chlorobutanamide (4.28 g, 13.7 mmol) in THF (50 mL) was added t-BuOK (3.69 g, 32.8 mmol) at 0° C. and then the mixture was stirred at 20° C. for 16 hours. A red suspension was formed. TLC showed N-(4-bromo-2,5-difluorophenyl)-4-chlorobutanamide was consumed nearly and a new spot was formed. The mixture was poured into sat.aq.NH₄Cl (30 mL) and extracted with EtOAc (30 mL×3). The combined organic layer was washed with brine (20 mL), dried over Na₂SO₄ and concentrated to dryness. The residue was purified by Combi Flash (20% EA in PE) to give 1-(4-bromo-2,5-difluorophenyl)pyrrolidin-2-one (3.04 g, yield: 80%) as a yellow solid.

¹H NMR (400 MHz, CDCl₃) δ 2.16-2.25 (2H, m), 2.56 (2H, t, J=8.0 Hz), 3.84 (2H, t, J=7.2 Hz), 7.30-7.38 (2H, m).

Step 3: Preparation of 1-(2,5-difluoro-4-(4,4,5,5-tetramethyl-1,3,2-dioxaborolan-2-yl)phenyl)pyrrolidin-2-one

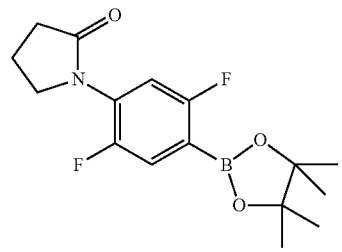 [SMILES: CC1(C)OB(c2cc(F)c(N3CCCC3=O)cc2F)OC1(C)C]

A mixture of 1-(4-bromo-2,5-difluorophenyl)pyrrolidin-2-one (3.04 g, 11.0 mmol), Bispin (3.36 g, 13.2 mmol), KOAc (3.24 g, 33.0 mmol) and Pd(dppf)Cl₂ (403 mg, 0.550 mmol) in toluene (60 mL) was stirred at 100° C. for 16 hours under N₂ atmosphere. The red solution turned to black gradually. LCMS showed the purity of product is 69% (Rt=0.899 min; MS Calcd: 323.2. MS Found: 354.9 [M+CH₃OH]+). TLC indicated the 1-(4-bromo-2,5-difluorophenyl)pyrrolidin-2-one was consumed completely, and one major new spot with lower polarity was detected. The reaction mixture was cooled to 20° C. and filtered through silica gel and washed with MTBE (1 L). The solvent was evaporated under reduced pressure to give 1-(2,5-difluoro-4-(4,4,5,5-tetramethyl-1,3,2-dioxaborolan-2-yl)phenyl)pyrrolidin-2-one (5.00 g, crude) as a yellow gum.

Step 4: Preparation of methyl 2-chloro-5-(2,5-difluoro-4-(2-oxopyrrolidin-1-yl)phenyl)isonicotinate

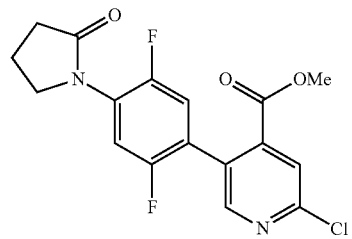 [SMILES: COC(=O)c1cc(Cl)ncc1-c1cc(F)c(N2CCCC2=O)cc1F]

methyl 5-bromo-2-chloroisonicotinate (1.60 g, 6.39 mmol), 1-(2,5-difluoro-4-(4,4,5,5-tetramethyl-1,3,2-dioxaborolan-2-yl)phenyl)pyrrolidin-2-one (3.14 g, 6.71 mmol), K₃PO₄ (4.07 g, 19.2 mmol) and Pd(dppf)Cl₂ (233 mg, 0.319 mmol) were taken up in dioxane (40 mL) and H₂O (10 mL) and the resulting mixture was stirred at 80° C. for 5 hours. A black solution was formed. LCMS showed the purity of the desired product is 45% (Rt=0.655 min; MS Calcd: 366.1. MS Found: 366.8 [M+H]⁺). TLC showed 1-(2,5-difluoro-4-(4,4,5,5-tetramethyl-1,3,2-dioxaborolan-2-yl)phenyl)pyrrolidin-2-one remained. The mixture was concentrated under reduced pressure. The residue was purified by Combi Flash (61% EA in PE) to give methyl 2-chloro-5-(2,5- difluoro-4-(2-oxopyrrolidin-1-yl)phenyl)isonicotinate (1.56 g, yield: 67%) as a yellow solid.

$^1$H NMR (400 MHz, CDCl$_3$) δ 2.18-2.26 (2H, m), 2.59 (2H, t, J=8.0 Hz), 3.83 (3H, s), 3.92 (2H, t, J=6.8 Hz), 7.11 (1H, dd, J=10.8, 6.8 Hz), 7.38 (1H, dd, J=10.8, 6.4 Hz), 7.84 (1H, s), 8.40 (1H, s).

Step 5: Preparation of 1-(4-(6-chloro-4-(2-hydroxy-propan-2-yl)pyridin-3-yl)-2,5-difluorophenyl)pyrrolidin-2-one

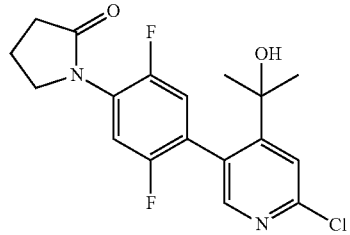 [SMILES: CC(C)(O)c1cc(Cl)ncc1-c1cc(F)c(N2CCCC2=O)cc1F]

MeMgCl (3 M in Et$_2$O, 2.7 mL) was added slowly to a solution of methyl 2-chloro-5-(2,5-difluoro-4-(2-oxopyrrolidin-1-yl)phenyl)isonicotinate (1.00 g, 2.73 mmol) in THF (20 mL) at 0° C. under a nitrogen atmosphere to give a suspension. The resulting mixture was stirred at 0° C. for 2 hours. TLC (Petroleum ether/Ethyl acetate=1:3) showed the starting material was consumed completely. Sat. aq. NH$_4$Cl (20 mL) was added followed by EtOAc (20 mL). The organic layer was separated and the aqueous layer extracted with EtOAc (20 mL×2). The combined organics were dried over Na$_2$SO$_4$, filtered and concentrated. The residue was purified by Combi Flash (65% EA in PE) to give 1-(4-(6-chloro-4-(2-hydroxypropan-2-yl)pyridin-3-yl)-2,5-difluorophenyl)pyrrolidin-2-one (690 mg, crude) as a yellow gum.

Step 6: Preparation of 1-(3-chloro-9-fluoro-5,5-dimethyl-5H-chromeno[4,3-c]pyridin-8-yl)pyrrolidin-2-one

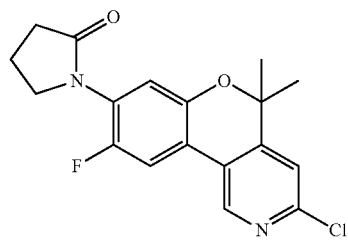 [SMILES: CC1(C)Oc2cc(N3CCCC3=O)c(F)cc2-c2cnc(Cl)cc21]

NaH (150 mg, 3.76 mmol, 60% in mineral oil) was added to a solution of 1-(4-(6-chloro-4-(2-hydroxypropan-2-yl)pyridin-3-yl)-2,5-difluorophenyl)pyrrolidin-2-one (690 mg, 1.88 mmol) in THF (20 mL) at 25° C. and the resulting mixture was stirred at 25° C. for 2 hours. The yellow solution turned to red. TLC indicated one major new spot with lower polarity was detected. LCMS showed the purity of the desired product is 56% (Rt=0.784 min; MS Calcd: 346.1. MS Found: 346.9 [M+H]$^+$). The mixture was added sat. aq. NH$_4$Cl (15 mL), extracted with EtOAc (20 mL×3). The combined organic layer was dried over Na$_2$SO$_4$, filtered, concentrated. The residue was purified by Combi Flash (40% EA in PE) to give 1-(3-chloro-9-fluoro-5,5-dimethyl-5H-chromeno[4,3-c]pyridin-8-yl)pyrrolidin-2-one (220 mg, yield: 33%) as a white solid.

Step 7: Preparation of(S)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

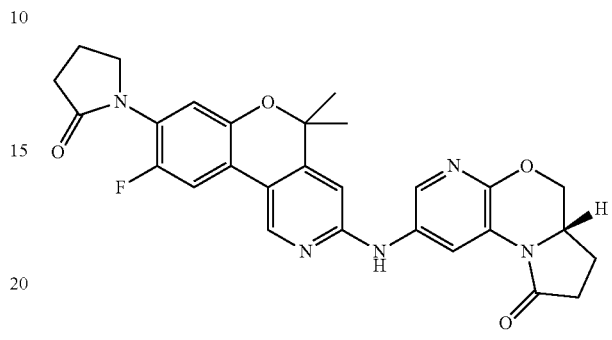

A mixture of Pd$_2$(dba)$_3$ (16 mg, 0.017 mmol) and Brettphos (18 mg, 0.034 mmol) in 1,4-dioxane (1 mL) was stirred at 50° C. for 10 min. 1-(3-chloro-9-fluoro-5,5-dimethyl-5H-chromeno[4,3-c]pyridin-8-yl)pyrrolidin-2-one (60 mg, 0.173 mmol), (S)-2-amino-6,6a,7,8-tetrahydro-9H-pyrido[2,3-b]pyrrolo[1,2-d][1,4]oxazin-9-one (43 mg, 0.21 mmol) in dioxane (6 mL) and Cs$_2$CO$_3$ (169 mg, 0.519 mmol) were added and the resulting mixture was stirred at 100° C. for 16 hours. A black brown mixture was formed. LCMS showed that the purity of the desired product is 57% (Rt=0.700 min; MS Calcd: 515.2. MS Found: 516.1 [M+H]$^+$). The reaction mixture was diluted with DCM (10 mL), filtered and concentrated. The residue was purified by prep-HPLC (0.05% NH$_3$.H$_2$O as an additive) and lyophilized to give (S)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (37.0 mg, yield: 41%) as a white solid.

$^1$H NMR (400 MHz, DMSO-d$_6$) δ 1.54 (6H, s), 1.64-1.75 (1H, m), 2.06-2.13 (2H, m), 2.18-2.26 (1H, m), 2.35-2.45 (3H, m), 2.62-2.72 (1H, m), 3.76 (2H, t, J=7.2 Hz), 3.90 (1H, t, J=10.8 Hz), 4.02-4.12 (1H, m), 4.59 (1H, dd, J=10.8, 3.2 Hz), 6.74 (1H, s), 7.01 (1H, d, J=6.8 Hz), 7.86 (1H, d, J=12.0 Hz), 8.36 (1H, d, J=2.8 Hz), 8.66 (1H, s), 8.95 (1H, d, J=2.8 Hz), 9.37 (1H, brs).

Example 149: 1-(5-((9-fluoro-5,5-dimethyl-8-(2-oxopyrrolidin-1-yl)-5H-chromeno[4,3-c]pyridin-3-yl)amino)pyridin-3-yl)imidazolidin-2-one

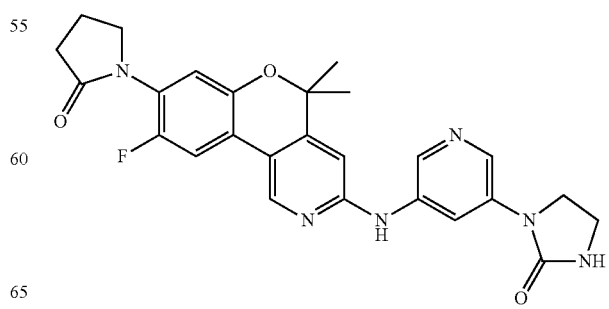

Step 1: Preparation of 1-(3-amino-9-fluoro-5,5-dimethyl-5H-chromeno[4,3-c]pyridin-8-yl)pyrrolidin-2-one

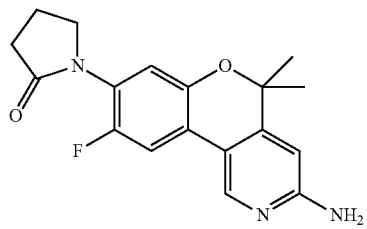 [SMILES: CC1(C)Oc2cc(N3CCCC3=O)c(F)cc2-c2cnc(N)cc21]

A mixture of Pd$_2$(dba)$_3$ (20 mg, 0.022 mmol) and Xantphos (25 mg, 0.043 mmol) in 1,4-dioxane (1 mL) was stirred at 50° C. for 10 min. 1-(3-chloro-9-fluoro-5,5-dimethyl-5H-chromeno[4,3-c]pyridin-8-yl)pyrrolidin-2-one (150 mg, 0.432 mmol), BocNH$_2$ (66 mg, 0.56 mmol) in dioxane (8 mL) and Cs$_2$CO$_3$ (352 mg, 1.08 mmol) were added and the resulting mixture was stirred at 100° C. for 16 hours. A black brown mixture was formed. LCMS showed that the purity of the desired product 1-(3-amino-9-fluoro-5,5-dimethyl-5H-chromeno[4,3-c]pyridin-8-yl)pyrrolidin-2-one is 36% (Rt=0.633 min; MS Calcd: 327.1. MS Found: 328.0 [M+H]$^+$). LCMS showed that the purity of the desired product tert-butyl (9-fluoro-5,5-dimethyl-8-(2-oxopyrrolidin-1-yl)-5H-chromeno[4,3-c]pyridin-3-yl)carbamate is 21% (Rt=0.826 min; MS Calcd: 427.2. MS Found: 450.1 [M+Na]$^+$). TLC showed the starting material was consumed completely. The reaction mixture was diluted with DCM (30 mL), filtered and concentrated. The residue was purified by Combi Flash (60% EA in PE) to give tert-butyl (9-fluoro-5,5-dimethyl-8-(2-oxopyrrolidin-1-yl)-5H-chromeno[4,3-c]pyridin-3-yl)carbamate (37 mg, yield: 20%) as a white solid, purified by Combi Flash (EA) to give 1-(3-amino-9-fluoro-5,5-dimethyl-5H-chromeno[4,3-c]pyridin-8-yl)pyrrolidin-2-one (71 mg, yield: 50%) as a yellow solid.

$^1$H NMR (400 MHz, CDCl$_3$) δ 1.57 (6H, s), 2.16-2.24 (2H, m), 2.57 (2H, t, J=8.0 Hz), 3.82 (2H, t, J=6.8 Hz), 4.60 (2H, brs), 6.34 (1H, s), 6.97 (1H, d, J=6.8 Hz), 7.41 (1H, d, J=11.6 Hz), 8.34 (1H, s).

Step 2: Preparation of 1-(5-((9-fluoro-5,5-dimethyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one

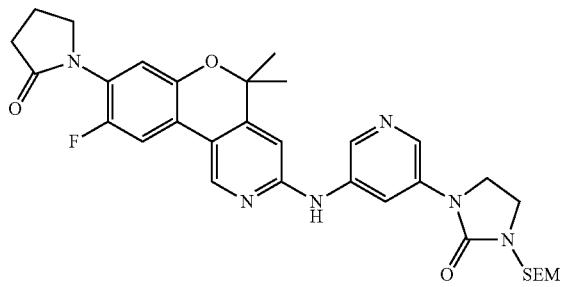 [SMILES: CC1(C)Oc2cc(N3CCCC3=O)c(F)cc2-c2cnc(Nc3cncc(N4CCN(COCC[Si](C)(C)C)C4=O)c3)cc21]

A mixture of Pd$_2$(dba)$_3$ (20 mg, 0.021 mmol) and Brettphos (23 mg, 0.043 mmol) in 1,4-dioxane (1 mL) was stirred at 50° C. for 10 min. 1-(3-amino-9-fluoro-5,5-dimethyl-5H-chromeno[4,3-c]pyridin-8-yl)pyrrolidin-2-one (70 mg, 0.214 mmol), 1-(5-bromopyridin-3-yl)-3-((2-(trimethylsilyl)ethoxy)methyl)imidazolidin-2-one (96 mg, 0.26 mmol) in dioxane (6 mL) and Cs$_2$CO$_3$ (139 mg, 0.428 mmol) were added and the resulting mixture was stirred at 100° C. for 16 hours. A black brown mixture was formed. TLC (Ethyl acetate) showed the starting material was consumed completely. LCMS showed the purity of the desired product is 51% (Rt=0.813 min; MS Calcd: 618.3. MS Found: 619.1 [M+H]$^+$). The reaction mixture was diluted with dioxane (10 mL), filtered and concentrated. The residue was purified by Combi Flash (EtOAc) to give 1-(5-((9-fluoro-5,5-dimethyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (76 mg, yield: 57%) as a yellow solid.

Step 3: Preparation of 1-(5-((9-fluoro-5,5-dimethyl-8-(2-oxopyrrolidin-1-yl)-5H-chromeno[4,3-c]pyridin-3-yl)amino)pyridin-3-yl)imidazolidin-2-one

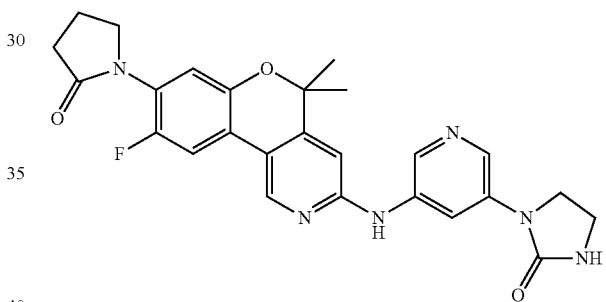

To a solution of 1-(5-((9-fluoro-5,5-dimethyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (76 mg, 0.12 mmol) in DCM (3 mL) was added TFA (1.9 mL, 25 mmol) at 25° C., and it was stirred at 25° C. for 1 hour. Then the mixture was concentrated under reduced pressure and the residue was diluted with MeOH (3 mL), and then EDA (295 mg, 4.91 mmol) was added at 25° C. The residue was stirred at 25° C. for 16 hours. A yellow solution was formed. Crude LCMS showed that the purity of product was 53% (Rt=0.577 min, MS Calcd.: 488.2. MS Found: 489.1 [M+H]$^+$). The mixture was concentrated under reduced pressure. The residue was purified by prep-HPLC (0.05% NH$_3$.H$_2$O as an additive) and lyophilized to give 1-(5-((9-fluoro-5,5-dimethyl-8-(2-oxopyrrolidin-1-yl)-5H-chromeno[4,3-c]pyridin-3-yl)amino)pyridin-3-yl)imidazolidin-2-one (2.79 mg, yield: 5%) as a white solid.

$^1$H NMR (400 MHz, DMSO-d$_6$) δ 1.55 (6H, s), 2.07-2.13 (2H, m), 2.42 (2H, t, J=8.4 Hz), 3.46 (2H, overlap with H$_2$O), 3.77 (2H, t, J=6.8 Hz), 3.89 (2H, t, J=8.8 Hz), 6.83 (1H, s), 7.02 (1H, d, J=6.8 Hz), 7.12 (1H, s), 7.88 (1H, d, J=11.6 Hz), 8.25 (1H, d, J=2.4 Hz), 8.42 (1H, t, J=2.0 Hz), 8.62 (1H, d, J=2.0 Hz), 8.72 (1H, brs), 9.52 (1H, brs).

Example 150: methyl 7-((9-fluoro-5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate

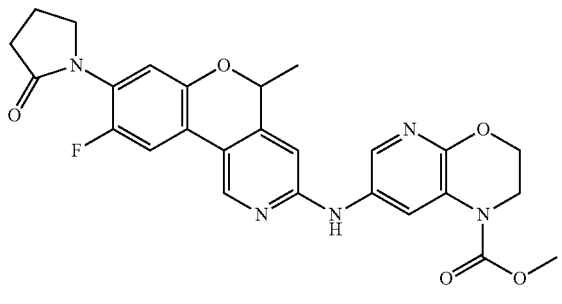 [SMILES: COC(=O)N1CCOc2ncc(Nc3cc4c(cn3)-c3cc(F)c(N5CCCC5=O)cc3OC4C)cc21]

Step 1: Preparation of 1-(5-bromo-2-chloropyridin-4-yl)ethan-1-ol

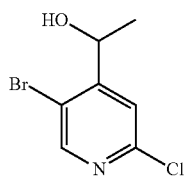

MeMgBr (3 M in Et₂O, 41 mL) was added slowly to a solution of 5-bromo-2-chloroisonicotinaldehyde (15.0 g, 68.0 mmol) in THF (400 mL) at 0° C. under a nitrogen atmosphere. The resulting mixture was stirred at 0° C. for 2 hours. The yellow solution turned to black brown gradually. TLC indicated 5-bromo-2-chloroisonicotinaldehyde was consumed completely, and one new spot with larger polarity was detected. Sat. aq. NH₄Cl (100 mL) was added followed by EtOAc (100 mL). The organic layer was separated and the aqueous layer was extracted with EtOAc (80 mL×2). The combined organics were dried over Na₂SO₄, filtered and concentrated to give 1-(5-bromo-2-chloropyridin-4-yl)ethan-1-ol (15.4 g, yield: 96%) as a yellow solid. Used for the next step without further purification.

$^1$H NMR (400 MHz, DMSO-$d_6$) δ 1.31 (3H, d, J=6.4 Hz), 4.83-4.88 (1H, m), 5.80 (1H, d, J=4.0 Hz), 7.58 (1H, s), 8.52 (1H, s).

Step 2: Preparation of 1-(4-(6-chloro-4-(1-hydroxyethyl)pyridin-3-yl)-2,5-difluorophenyl)pyrrolidin-2-one

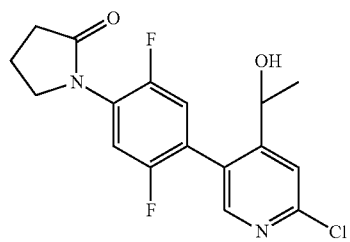 [SMILES: CC(O)c1cc(Cl)ncc1-c1cc(F)c(N2CCCC2=O)cc1F]

1-(5-bromo-2-chloropyridin-4-yl)ethan-1-ol (2.40 g, 10.1 mmol), 1-(2,5-difluoro-4-(4,4,5,5-tetramethyl-1,3,2-dioxaborolan-2-yl)phenyl)pyrrolidin-2-one (3.60 g, 11.1 mmol), K₃PO₄ (6.45 g, 30.4 mmol) and Pd(dppf)Cl₂ (370 mg, 0.506 mmol) were taken up in dioxane (65 mL) and H₂O (15 mL) and the resulting mixture was stirred at 80° C. for 5 hours. A black solution was formed. LCMS showed the purity of the desired product is 25% (Rt=0.746 min; MS Calcd: 352.1. MS Found: 353.1 [M+H]⁺). The mixture was concentrated under reduced pressure. The residue was combined with last batch (es6012-362), purified by Combi Flash (62% EA in PE) to give 1-(4-(6-chloro-4-(1-hydroxyethyl)pyridin-3-yl)-2,5-difluorophenyl)pyrrolidin-2-one (3.33 g, yield: 55% for two steps) as a yellow solid.

Step 3: Preparation of 1-(3-chloro-9-fluoro-5-methyl-5H-chromeno[4,3-c]pyridin-8-yl)pyrrolidin-2-one

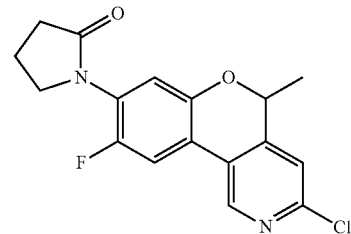 [SMILES: CC1Oc2cc(N3CCCC3=O)c(F)cc2-c2cnc(Cl)cc21]

NaH (752 mg, 18.8 mmol, 60% purity in mineral oil) was added to a solution of 1-(4-(6-chloro-4-(1-hydroxyethyl)pyridin-3-yl)-2,5-difluorophenyl)pyrrolidin-2-one (3.32 g, 9.41 mmol) in THF (100 mL) at 25° C. and the resulting mixture was stirred at 25° C. for 2 hours. The yellow solution turned to red. LCMS showed the purity of the desired product is 65% (Rt=0.799 min; MS Calcd: 332.1. MS Found: 333.1 [M+H]⁺). The mixture was added sat. aq. NH₄Cl (70 mL), extracted with EtOAc (60 mL×3). The combined organic layer was dried over Na₂SO₄, filtered, concentrated. The residue was purified by Combi Flash (50% EA in DCM) to give 1-(3-chloro-9-fluoro-5-methyl-5H-chromeno[4,3-c]pyridin-8-yl)pyrrolidin-2-one (2.75 g, yield: 88%) as a yellow solid.

$^1$H NMR (400 MHz, CDCl₃) δ 1.64 (3H, d, J=6.8 Hz), 2.20-2.24 (2H, m), 2.57-2.60 (2H, m), 3.86-3.91 (2H, m), 5.19 (1H, q, J=6.8 Hz), 7.12-7.15 (2H, m), 7.50 (1H, d, J=11.2 Hz), 8.60 (1H, s).

Step 4: Preparation of 1-(3-amino-9-fluoro-5-methyl-5H-chromeno[4,3-c]pyridin-8-yl)pyrrolidin-2-one

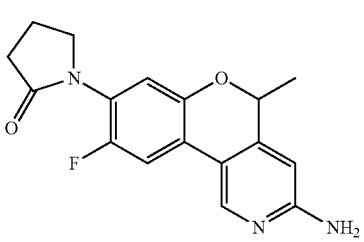 [SMILES: CC1Oc2cc(N3CCCC3=O)c(F)cc2-c2cnc(N)cc21]

A mixture of Pd₂(dba)₃ (68 mg, 0.075 mmol) and Xantphos (86 mg, 0.15 mmol) in 1,4-dioxane (1 mL) was stirred at 50° C. for 10 min. 1-(3-chloro-9-fluoro-5-methyl-5H-chromeno[4,3-c]pyridin-8-yl)pyrrolidin-2-one (500 mg, 1.50 mmol), BocNH₂ (228 mg, 1.95 mmol) in dioxane (20 mL) and Cs₂CO₃ (1.22 g, 3.76 mmol) were added, and the resulting mixture was stirred at 100° C. for 16 hours. A black brown mixture was formed. LCMS showed that the purity of 1-(3-amino-9-fluoro-5-methyl-5H-chromeno[4,3-c]pyridin-8-yl)pyrrolidin-2-one is 22% (Rt=0.615 min; MS Calcd: 313.1. MS Found: 314.2 [M+H]⁺). LCMS showed that the purity of tert-butyl (9-fluoro-5-methyl-8-(2-oxopyrrolidin-1-yl)-5H-chromeno[4,3-c]pyridin-3-yl)carbamate is 22% (Rt=0.833 min; MS Calcd: 413.2. MS Found: 414.3 [M+H]⁺). The reaction mixture was diluted with DCM (30 mL), filtered and concentrated. The residue was purified by Combi Flash (50% EA in PE) to give tert-butyl (9-fluoro-5-methyl-8-(2-oxopyrrolidin-1-yl)-5H-chromeno[4,3-c]pyridin-3-yl)carbamate (220 mg, yield: 35%) as a yellow solid, purified by Combi Flash (EA) to give 1-(3-amino-9-fluoro-5-methyl-5H-chromeno[4,3-c]pyridin-8-yl)pyrrolidin-2-one (110 mg, yield: 23%) as a yellow solid.

Step 5: Preparation of methyl 7-((9-fluoro-5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate

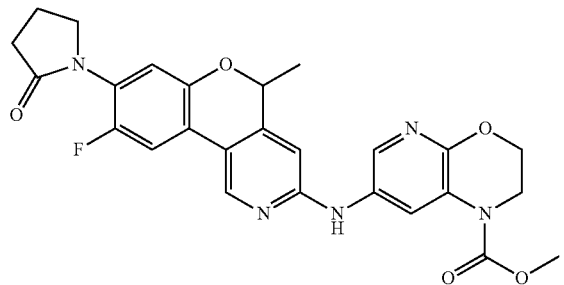 [SMILES: COC(=O)N1CCOc2ncc(Nc3cc4c(cn3)-c3cc(F)c(N5CCCC5=O)cc3OC4C)cc21]

A mixture of Pd₂(dba)₃ (14 mg, 0.015 mmol) and Brettphos (17 mg, 0.031 mmol) in dioxane (1 mL) was stirred at 50° C. for 10 min. 1-(3-amino-9-fluoro-5-methyl-5H-chromeno[4,3-c]pyridin-8-yl)pyrrolidin-2-one (50 mg, 0.16 mmol), methyl 7-bromo-2,3-dihydro-H-pyrido[2,3-b][1,4]oxazine-1-carboxylate (52 mg, 0.19 mmol) in dioxane (6 mL) and Cs₂CO₃ (155 mg, 0.478 mmol) were added and the resulting mixture was stirred at 100° C. for 14 hours. A black brown mixture was formed. LCMS showed that the purity of the desired product is 53% (Rt=0.717 min; MS Calcd: 505.2. MS Found: 506.1 [M+H]⁺). The reaction mixture was diluted with DCM (10 mL), filtered and concentrated. The residue was purified by prep-HPLC (0.05% NH₃.H₂O as an additive) and lyophilized to give methyl 7-((9-fluoro-5-methyl-8-(2-oxopyrrolidin-1-yl)-5H-chromeno[4,3-c]pyridin-3-yl)amino)-2,3-dihydro-H-pyrido[2,3-b][1,4]oxazine-1-carboxylate (37.1 mg, yield: 46%) as a white solid.

¹H NMR (400 MHz, DMSO-d₆) δ 1.52 (3H, d, J=6.4 Hz), 2.06-2.13 (2H, m), 2.42 (2H, t, J=8.0 Hz), 3.73-3.77 (2H, m), 3.78 (3H, s), 3.86 (2H, t, J=4.8 Hz), 4.31 (2H, t, J=4.8 Hz), 5.25 (1H, q, J=6.4 Hz), 6.66 (1H, s), 7.04 (1H, d, J=6.8 Hz), 7.86 (1H, d, J=11.6 Hz), 8.24 (1H, d, J=2.4 Hz), 8.64 (1H, s), 8.67 (1H, brs), 9.32 (1H, brs).

Example 151: 1-(5-((9-fluoro-5-methyl-8-(2-oxopyrrolidin-1-yl)-5H-chromeno[4,3-c]pyridin-3-yl)amino)pyridin-3-yl)imidazolidin-2-one

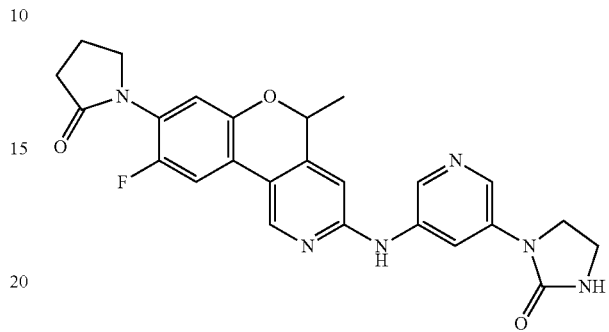

Step 1: Preparation of 1-(5-((9-fluoro-5-methyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one

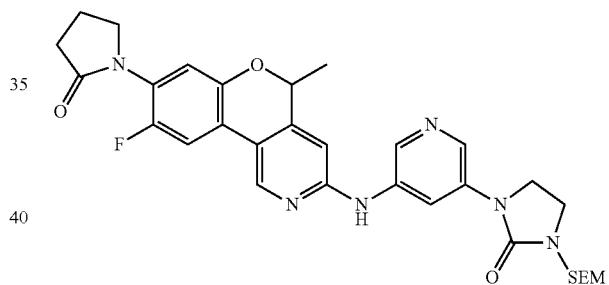

A mixture of Pd₂(dba)₃ (29 mg, 0.032 mmol) and Brettphos (34 mg, 0.064 mmol) in dioxane (1 mL) was stirred at 50° C. for 10 min. 1-(3-amino-9-fluoro-5-methyl-5H-chromeno[4,3-c]pyridin-8-yl)pyrrolidin-2-one (100 mg, 0.319 mmol), 1-(5-bromopyridin-3-yl)-3-((2-(trimethylsilyl)ethoxy)methyl)imidazolidin-2-one (142 mg, 0.383 mmol) in dioxane (7 mL) and Cs₂CO₃ (260 mg, 0.798 mmol) were added and the resulting mixture was stirred at 100° C. for 16 hours. A black brown mixture was formed. LCMS showed the purity of the desired product is 33% (Rt=0.807 min; MS Calcd: 604.3. MS Found: 605.2 [M+H]⁺). The reaction mixture was diluted with dioxane (10 mL), filtered and concentrated. The residue was purified by Combi Flash (EtOAc) to give 1-(5-((9-fluoro-5-methyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (160 mg, yield: 83%) as a yellow solid.

Step 2: Preparation of 1-(5-((9-fluoro-5-methyl-8-(2-oxopyrrolidin-1-yl)-5H-chromeno[4,3-c]pyridin-3-yl)amino)pyridin-3-yl)imidazolidin-2-one

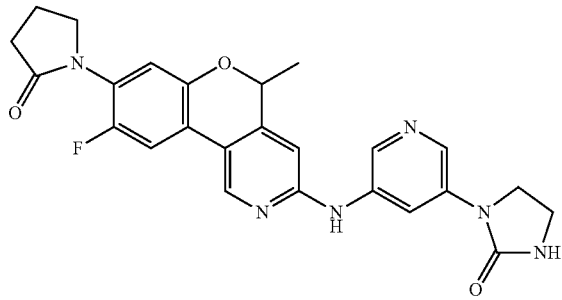 [SMILES: CC1Oc2cc(N3CCCC3=O)c(F)cc2-c2cnc(Nc3cncc(N4CCNC4=O)c3)cc21]

To a solution of 1-(5-((9-fluoro-5-methyl-8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (60 mg, 0.099 mmol) in DCM (5 mL) was added TFA (5 mL) dropwise at 0° C. over a period of 2 minutes under N$_2$ atmosphere. The reaction mixture was stirred at 30° C. for 2 hours, and it turned to a red solution. The reaction mixture was concentrated under reduced pressure to give a residue. The residue was dissolved in dioxane (5 mL) and NH$_3$.H$_2$O (5 mL) at 30° C. The reaction mixture was stirred at 30° C. for another 32 hours. After that, a brown solution was formed. LCMS showed the purity of the desired compound is 85% (Rt=0.672 min; MS Calcd: 474.2. MS Found: 475.1 [M+H]$^+$). The reaction mixture was concentrated and diluted with saturated aqueous Na$_2$CO$_3$ (10 mL), then extracted with EtOAc/THF (20 mL×3, 2/1). The combined organic layer was washed with saturated aqueous Na$_2$CO$_3$ (20 mL×2), brine (20 mL×2) and dried over anhydrous Na$_2$SO$_4$, filtered and concentrated under reduced pressure to give a residue. The residue was purified by prep-HPLC (0.05% NH$_3$.H$_2$O as an additive) and lyophilized to give 1-(5-((9-fluoro-5-methyl-8-(2-oxopyrrolidin-1-yl)-5H-chromeno[4,3-c]pyridin-3-yl)amino)pyridin-3-yl)imidazolidin-2-one (16.1 mg, yield: 34%) as a yellow solid.

$^1$H NMR (400 MHz DMSO-d$_6$) δ 1.54 (3H, d, J=6.4 Hz), 2.08-2.15 (2H, m), 2.43 (2H, t, J=8.0 Hz), 3.44-3.73 (2H, m), 3.75-3.78 (2H, m), 3.80-3.92 (2H, m), 5.28 (1H, q, J=6.5 Hz), 6.77 (1H, s), 7.06 (2H, m), 7.12 (1H, s), 7.88 (1H, d, J=11.6 Hz), 8.28 (1H, d, J=2.0 Hz), 8.42 (1H, t, J=2.4 Hz), 8.66 (1H, d, J=2.0 Hz), 8.71 (1H, s), 9.52 (1H, s).

Example 152: (6aS)-2-((9-fluoro-5-methyl-8-(2-oxopyrrolidin-1-yl)-5H-chromeno[4,3-c]pyridin-3-yl)amino)-8-methyl-6,6a,7,8-tetrahydro-9H-pyrido[2,3-b]pyrrolo[1,2-d][1,4]oxazin-9-one

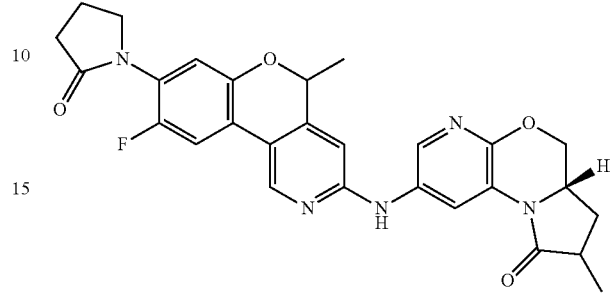

A mixture of 1-(3-chloro-9-fluoro-5-methyl-5H-chromeno[4,3-c]pyridin-8-yl)pyrrolidin-2-one (50 mg, 0.15 mmol), (6aS)-2-amino-8-methyl-6,6a,7,8-tetrahydro-9H-pyrido[2,3-b]pyrrolo[1,2-d][1,4]oxazin-9-one (36 mg, 0.16 mmol), Pd$_2$(dba)$_3$ (14 mg, 0.015 mmol), Brettphos (16 mg, 0.030 mmol), Cs$_2$CO$_3$ (98 mg, 0.30 mmol) in dioxane (3 mL) was degassed and purged with N$_2$ for 3 times. Then the resulting reaction mixture was heated at 90° C. for 15 hours under N$_2$ atmosphere. The reaction mixture turned into brown suspension from red suspension. LCMS showed that the purity of the desired product is 40% (Rt=0.673 min; MS Calcd: 515.2. MS Found: 516.2 [M+H]$^+$). The mixture was diluted with water (10 mL) and extracted with EtOAc (20 mL×3). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give (6aS)-2-((9-fluoro-5-methyl-8-(2-oxopyrrolidin-1-yl)-5H-chromeno[4,3-c]pyridin-3-yl)amino)-8-methyl-6,6a,7,8-tetrahydro-9H-pyrido[2,3-b]pyrrolo[1,2-d][1,4]oxazin-9-one (24.7 mg, yield: 32%, dr=2.5:1) as a light yellow solid.

$^1$H NMR (400 MHz DMSO-d$_6$) δ 1.16 (2.26H, d, J=7.0 Hz), 1.23-1.27 (1.41H, m), 1.30-1.39 (0.87H, m), 1.53 (3H, dd, J=6.4 Hz, 0.8 Hz), 1.91-2.00 (0.72H, m), 2.07-2.16 (2H, m), 2.40-2.48 (2.32H, m), 2.73-2.84 (1H, m), 3.73-3.81 (2H, m), 3.84-3.94 (1H, m), 3.96-4.17 (1H, m), 4.54-4.63 (1H, m), 5.26 (1H, q, J=6.4 Hz), 6.68 (1H, s), 7.05 (1H, d, J=6.8 Hz), 7.87 (1H, d, J=11.8 Hz), 8.30-8.36 (1H, m), 8.64-8.68 (1H, m), 8.96 (0.27H, d, J=4.0 Hz), 9.07 (0.69H, t, J=4.0 Hz), 9.39 (1H, brs).

237

Example 153: (6aS)-2-((9-fluoro-5-methyl-8-(2-oxopyrrolidin-1-yl)-5H-chromeno[4,3-c]pyridin-3-yl)amino)-8,8-dimethyl-6,6a,7,8-tetrahydro-9H-pyrido[2,3-b]pyrrolo[1,2-d][1,4]oxazin-9-one

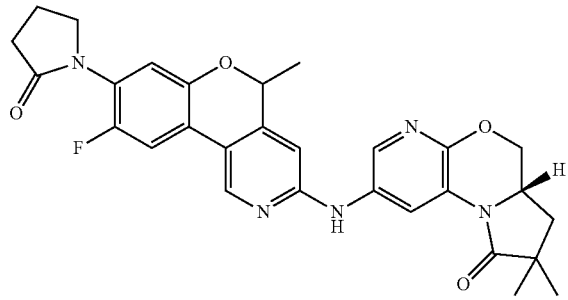 [SMILES: CC1Oc2cc(N3CCCC3=O)c(F)cc2-c2cnc(Nc3cnc4c(c3)N3C(=O)C(C)(C)C[C@H]3CO4)cc21]

A mixture of Pd$_2$(dba)$_3$ (14 mg, 0.015 mmol) and Brettphos (16 mg, 0.030 mmol) in dioxane (1 mL) was stirred at 50° C. for 10 min. 1-(3-chloro-9-fluoro-5-methyl-5H-chromeno[4,3-c]pyridin-8-yl)pyrrolidin-2-one (50 mg, 0.15 mmol), (S)-2-amino-8,8-dimethyl-6,6a,7,8-tetrahydro-9H-pyrido[2,3-b]pyrrolo[,2-d][1,4]oxazin-9-one (39 mg, 0.17 mmol) in dioxane (3 mL) and Cs$_2$CO$_3$ (147 mg, 0.478 mmol) were added and the resulting mixture was stirred at 100° C. for 15 hours. A black brown mixture was formed. LCMS showed that the purity of the desired product is 49% (Rt=0.647 min; MS Calcd: 529.2. MS Found: 530.1 [M+H]$^+$). The reaction mixture was diluted with DCM (10 mL), filtered and concentrated. The residue was purified by prep-HPLC (0.05% NH$_3$.H$_2$O as an additive) and lyophilized to give (6aS)-2-((9-fluoro-5-methyl-8-(2-oxopyrrolidin-1-yl)-5H-chromeno[4,3-c]pyridin-3-yl)amino)-8,8-dimethyl-6,6a,7,8-tetrahydro-9H-pyrido[2,3-b]pyrrolo[1,2-d][1,4]oxazin-9-one (23.6 mg, yield: 30%) as a yellow solid.

$^1$H NMR (400 MHz, DMSO-d$_6$) δ 1.17 (3H, s), 1.21 (3H, s), 1.52 (3H, d, J=6.4 Hz), 1.59 (1H, dd, J=12.4, 10.0 Hz), 2.07-2.14 (3H, m), 2.43 (2H, t, J=7.6 Hz), 3.72-3.79 (2H, m), 3.88 (1H, t, J=10.4 Hz), 4.06-4.14 (1H, m), 4.59 (1H, dd, J=10.8, 3.2 Hz), 5.26 (1H, q, J=6.8 Hz), 6.67 (1H, s), 7.04 (1H, d, J=6.4 Hz), 7.87 (1H, d, J=11.6 Hz), 8.28-8.31 (1H, m), 8.66 (1H, brs), 9.08-9.11 (1H, m), 9.38 (1H, d, J=2.0 Hz).

Example 154: (6a'S)-2'-((9-fluoro-5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one

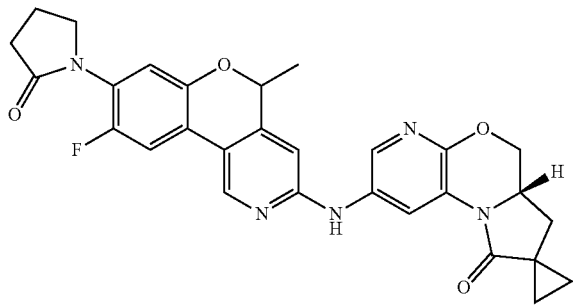 [SMILES: CC1Oc2cc(N3CCCC3=O)c(F)cc2-c2cnc(Nc3cnc4c(c3)N3C(=O)C5(CC5)C[C@H]3CO4)cc21]

238

A mixture of 1-(3-chloro-9-fluoro-5-methyl-5H-chromeno[4,3-c]pyridin-8-yl)pyrrolidin-2-one (50 mg, 0.15 mmol), (S)-2'-amino-6a',7'-dihydro-6'H,9'H-spiro[cyclopropane-1,8'-pyrido[2,3-b]pyrrolo[1,2-d][1,4]oxazin]-9'-one (38 mg, 0.16 mmol), Pd$_2$(dba)$_3$ (14 mg, 0.015 mmol), Brettphos (16 mg, 0.030 mmol), Cs$_2$CO$_3$ (98 mg, 0.30 mmol) in dioxane (3 mL) was degassed and purged with N$_2$ for 3 times. Then the resulting reaction mixture was heated at 90° C. for 15 hours under N$_2$ atmosphere. The reaction mixture turned into brown suspension from red suspension. LCMS showed that the purity of the desired product is 41% (Rt=0.714 min; MS Calcd: 527.2. MS Found: 528.3 [M+H]$^+$). The mixture was diluted with water (10 mL) and extracted with EtOAc (20 mL×3). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give (6a'S)-2'-((9-fluoro-5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one (25.3 mg, yield: 32%) as a light yellow solid.

$^1$H NMR (400 MHz DMSO-d$_6$) δ 0.84-0.88 (1H, m), 0.93-0.98 (1H, m), 1.00-1.06 (1H, m), 1.08-1.13 (1H, m), 1.52 (3H, d, J=6.2 Hz), 1.98-2.05 (1H, m), 2.07-2.14 (2H, m), 2.16-2.23 (1H, m), 2.43 (2H, t, J=7.8 Hz), 3.74-3.80 (2H, m), 3.97-4.04 (1H, m), 4.17-4.24 (1H, m), 4.60-4.65 (1H, m), 5.26 (1H, q, J=6.4 Hz), 6.68 (1H, s), 7.05 (1H, d, J=6.4 Hz), 7.87 (1H, d, J=11.4 Hz), 8.31 (1H, s), 8.64 (1H, s), 8.99 (1H, s), 9.41 (1H, brs)

Example 155: (6aS)-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

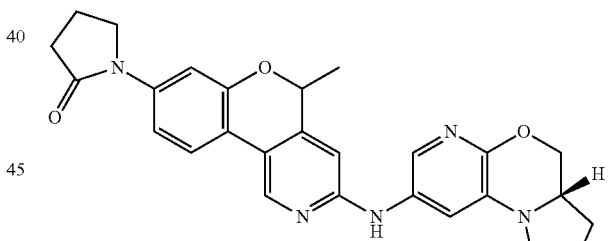

A mixture of 1-(3-chloro-5-methyl-5H-chromeno[4,3-c]pyridin-8-yl)pyrrolidin-2-one (40 mg, 0.13 mmol), (6aS)-2-amino-8-methyl-6,6a,7,8-tetrahydro-9H-pyrido[2,3-b]pyrrolo[1,2-d][1,4]oxazin-9-one (31 mg, 0.14 mmol), Pd$_2$(dba)$_3$ (12 mg, 0.013 mmol), Brettphos (14 mg, 0.026 mmol), Cs$_2$CO$_3$ (83 mg, 0.26 mmol) in dioxane (3 mL) was degassed and purged with N$_2$ for 3 times. Then the resulting reaction mixture was heated at 90° C. for 15 hours under N$_2$ atmosphere. The reaction mixture turned into brown suspension from red suspension. LCMS showed that the purity of the desired product is 50% (Rt=0.664 min; MS Calcd: 497.2. MS Found: 498.2 [M+H]$^+$). The mixture was diluted with water (10 mL) and extracted with EtOAc (20 mL×3). The combined organic layer was washed with water (20 mL×2), brine (20 mL×2), dried over anhydrous Na$_2$SO$_4$, filtered and concentrated. The residue was purified by prep- HPLC (0.225% FA as an additive) and further purified by prep-TLC (DCM/MeOH, 20/1), then lyophilized to give (6aS)-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (16.3 mg, yield: 25%, dr=1.9:1) as a white solid.

¹H NMR (400 Hz DMSO-$d_6$) δ 1.16 (2H, d, J=7.0 Hz), 1.23-1.27 (1H, m), 1.30-1.39 (1H, m), 1.53 (3H, d, J=6.0 Hz), 1.91-2.12 (3H, m), 2.40-2.48 (2H, m), 2.73-2.84 (1H, m), 3.81-3.95 (3H, m), 3.96-4.17 (1H, m), 4.54-4.63 (1H, m), 5.25 (1H, q, J=6.4 Hz), 6.67 (1H, s), 7.31 (1H, d, J=8.8 Hz), 7.39 (1H, d, J=2.0 Hz), 7.87 (1H, d, J=8.4 Hz), 8.30-8.37 (1H, m), 8.59-8.63 (1H, m), 8.96 (0.33H, d, J=2.4 Hz), 9.08 (0.62H, t, J=2.4 Hz), 9.28 (1H, brs).

Example 156: (6aS)-8,8-dimethyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

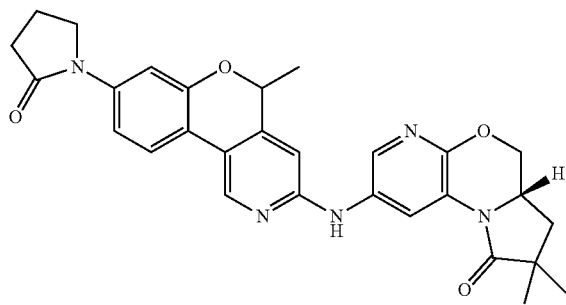 [SMILES: CC1Oc2cc(N3CCCC3=O)ccc2-c2cnc(Nc3cnc4c(c3)N3C(=O)C(C)(C)C[C@H]3CO4)cc21]

A mixture of Pd₂(dba)₃ (14 mg, 0.015 mmol) and Brettphos (17 mg, 0.031 mmol) in dioxane (1 mL) was stirred at 50° C. for 10 min. 1-(3-chloro-5-methyl-5H-chromeno[4,3-c]pyridin-8-yl)pyrrolidin-2-one (50 mg, 0.16 mmol), (S)-2-amino-8,8-dimethyl-6,6a,7,8-tetrahydro-9H-pyrido[2,3-b]pyrrolo[1,2-d][1,4]oxazin-9-one (41 mg, 0.17 mmol) in dioxane (6 mL) and Cs₂CO₃ (155 mg, 0.477 mmol) were added and the resulting mixture was stirred at 100° C. for 15 hours. A black brown mixture was formed. LCMS showed that the purity of the desired product is 48% (Rt=0.633 min; MS Calcd: 511.2. MS Found: 512.1 [M+H]⁺). The reaction mixture was diluted with DCM (10 mL), filtered and concentrated. The residue was purified by prep-HPLC (0.05% NH₃.H₂O as an additive) and lyophilized to give (6aS)-8,8-dimethyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (17.2 mg, yield: 21%) as a yellow solid.

¹H NMR (400 MHz, DMSO-$d_6$) δ 1.15 (3H, s), 1.19 (3H, s), 1.50 (3H, d, J=6.4 Hz), 1.57 (1H, dd, J=12.4, 10.4 Hz), 2.02-2.12 (3H, m), 2.55 (2H, overlapped with DMSO), 3.60-3.89 (3H, m), 4.04-4.11 (1H, m), 4.56 (1H, dd, J=10.8, 2.8 Hz), 5.23 (1H, q, J=6.8 Hz), 6.64 (1H, brs), 7.28 (1H, dd, J=8.4, 2.0 Hz), 7.37 (1H, d, J=2.4 Hz), 7.86 (1H, d, J=8.4 Hz), 8.27 (1H, d, J=2.8 Hz), 8.58 (1H, s), 9.07 (1H, dd, J=2.8, 1.2 Hz), 9.26 (1H, d, J=2.0 Hz).

Example 157: (6a'S)-2'-((5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one

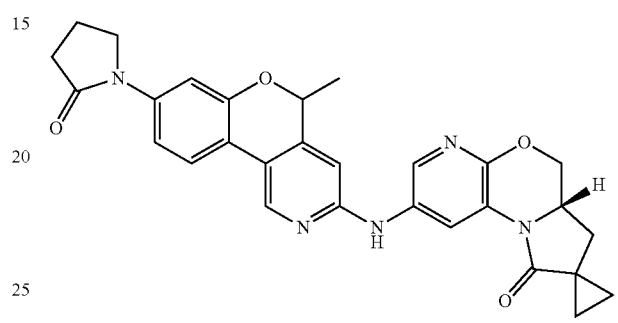

A mixture of 1-(3-chloro-5-methyl-5H-chromeno[4,3-c]pyridin-8-yl)pyrrolidin-2-one (40 mg, 0.13 mmol), (S)-2'-amino-6a',7'-dihydro-6'H,9'H-spiro[cyclopropane-1,8'-pyrido[2,3-b]pyrrolo[1,2-d][1,4]oxazin]-9'-one (32 mg, 0.14 mmol), Pd₂(dba)₃ (12 mg, 0.013 mmol), Brettphos (14 mg, 0.026 mmol), Cs₂CO₃ (83 mg, 0.26 mmol) in dioxane (3 mL) was degassed and purged with N₂ for 3 times. Then the resulting reaction mixture was heated at 90° C. for 15 hours under N₂ atmosphere. The reaction mixture turned into brown suspension from red suspension. LCMS showed that the purity of the desired product is 48% (Rt=0.758 min; MS Calcd: 509.2. MS Found: 510.3 [M+H]⁺). The mixture was diluted with water (10 mL) and extracted with EtOAc (20 mL×3). The combined organic layer was washed with water (20 mL×2), brine (20 mL×2), dried over anhydrous Na₂SO₄, filtered and concentrated. The residue was purified by prep-HPLC (0.225% FA as an additive), further purified by prep-TLC (DCM/MeOH, 10/1) and triturated with MeCN (3 mL), then lyophilized to give (6a'S)-2'-((5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one (24.7 mg, yield: 32%) as an off-white solid.

¹H NMR (400 MHz, DMSO-$d_6$) δ 0.83-0.89 (1H, m), 0.93-0.99 (1H, m), 1.00-1.07 (1H, m), 1.08-1.14 (1H, m), 1.53 (3H, d, J=6.4 Hz), 1.98-2.11 (3H, m), 2.16-2.23 (1H, m), 2.52-2.55 (2H, m, overlapped with DMSO), 3.85 (2H, t, J=8.0 Hz), 4.00 (1H, t, J=8.0 Hz), 4.16-4.25 (1H, m), 4.62 (1H, dd, J=10.8 Hz, 3.0 Hz), 5.28 (1H, q, J=6.4 Hz), 6.66 (1H, s), 7.31 (1H, dd, J=8.4 Hz, 2.2 Hz), 7.39 (1H, d, J=2.2 Hz), 7.87 (1H, d, J=8.5 Hz), 8.31 (1H, d, J=2.0 Hz), 8.60 (1H, s), 9.00 (1H, t, J=4.0 Hz), 9.29 (1H, d, J=2.2 Hz).

Example 158: (3aR)-8-((5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one

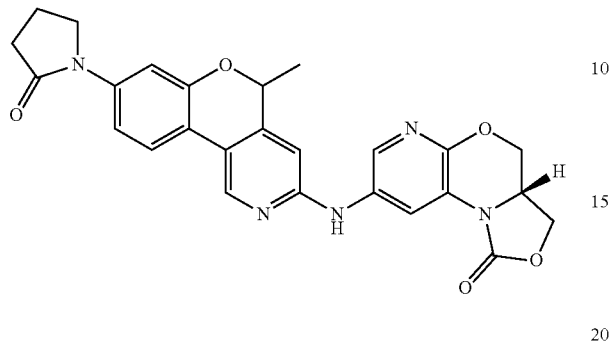

Step 1: Preparation of methyl O-(tert-butyldimethylsilyl)-L-serinate

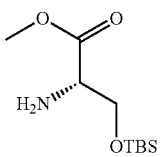

To a mixture of methyl L-serinate (10.0 g, 64.0 mmol) and imidazole (8.75 g, 129 mmol) in MeCN (200 mL) was added TBSCl (12.6 g, 83.6 mmol) drop wise at 10° C. The mixture was stirred at 10° C. for 16 hours. A white suspension was formed. TLC showed that starting material was consumed and a less polar spot was formed. The mixture was concentrated and purified by Flash column (EtOAc in PE from 50 to 100%) to give methyl 0-(tert-butyldimethylsilyl)-L-serinate (14.0 g, yield: 93%) as colorless oil.

$^1$H NMR (400 MHz, DMSO-$d_6$) δ 0.04 (3H, s), 0.05 (3H, s), 0.86 (9H, s), 3.53 (1H, t, J=4.4 Hz), 3.73 (3H, s), 3.81 (1H, dd, J=9.6, 3.6 Hz), 3.92 (1H, dd, J=10.0, 4.0 Hz).

Note: two active protons were not observed.

Step 2: Preparation of methyl N-((benzyloxy)carbonyl)-O-(tert-butyldimethylsilyl)-L-serinate

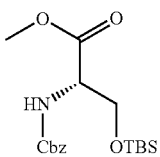

To a mixture of methyl 0-(tert-butyldimethylsilyl)-L-serinate (14.0 g, 60.0 mmol) NaHCO$_3$ (10.1 g, 120 mmol) in THF (200 mL) was added CbzCl (13.3 g, 78.0 mmol) drop wise at 0° C. The mixture was warmed to 10° C. and stirred for 16 hours. A white suspension was formed. TLC showed that starting material was consumed and a less polar spot was formed. The mixture was added sat.NaHCO$_3$ (200 mL), extracted with EtOAc (200 mL×3), the combined layer was washed with brine (200 mL), dried over Na$_2$SO$_4$ and concentrated. The residue was purified by Flash column (EtOAc in PE from 0 to 10%) to give methyl N-((benzyloxy)carbonyl)-O-(tert-butyldimethylsilyl)-L-serinate (18.0 g, yield: 82%) as a colorless oil.

$^1$H NMR (400 MHz, DMSO-$d_6$) δ 0.01 (3H, s), 0.02 (3H, s), 0.85 (9H, s), 3.75 (3H, s), 3.84 (1H, dd, J=10.0, 2.4 Hz), 4.07 (1H, dd, J=10.0, 2.4 Hz), 4.43 (1H, dt, J=8.8, 2.8 Hz), 5.13 (1H, d, J=3.2 Hz), 5.60 (1H, d, J=8.8 Hz), 7.30-7.38 (5H, m).

Step 3: Preparation of benzyl (R)-(1-((tert-butyldimethylsilyl)oxy)-3-hydroxypropan-2-yl)carbamate

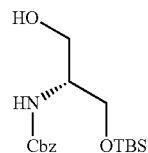

To a mixture of methyl N-((benzyloxy)carbonyl)-O-(tert-butyldimethylsilyl)-L-serinate (18.0 g, 49.0 mmol) in MeOH (200 mL) was added NaBH$_4$ (5.56 g, 147 mmol). The mixture was stirred at 0° C. for 1 hour. The colorless solution was warmed to 20° C. and stirred for another 15 hours. TLC showed that most of starting material was consumed and a more polar spot was formed. The mixture was added sat.NH$_4$Cl (200 mL), extracted with EtOAc (200 mL×3), the combined layer was washed with brine (200 mL), dried over Na$_2$SO$_4$ and concentrated. The residue was purified by Flash column (EtOAc in PE from 0 to 30%) to give benzyl (R)-(1-((tert-butyldimethylsilyl)oxy)-3-hydroxypropan-2-yl)carbamate (15.0 g, yield: 90%) as colorless oil.

$^1$H NMR (400 MHz, DMSO-$d_6$) δ 0.05 (3H, s), 0.06 (3H, s), 0.89 (9H, s), 2.55-2.57 (1H, m), 3.68-3.73 (1H, m), 3.79-3.82 (2H, m), 3.85-3.89 (1H, m), 5.12 (2H, m), 5.39 (1H, m), 7.33-7.38 (5H, m).

Note: one active proton was not observed.

Step 4: Preparation of compound

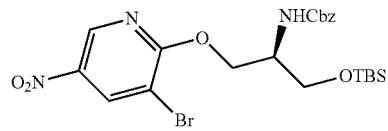 [SMILES: CC(C)(C)[Si](C)(C)OC[C@@H](COc1ncc([N+](=O)[O-])cc1Br)NC(=O)OCc1ccccc1]

To a mixture of benzyl (R)-(1-((tert-butyldimethylsilyl)oxy)-3-hydroxypropan-2-yl)carbamate (15.0 g, 44.0 mmol) in dioxane (200 mL) was added K$_2$CO$_3$ (11.6 g, 84.2 mmol) and 3-bromo-2-chloro-5-nitropyridine (10.0 g, 42.1 mmol). The mixture was stirred at 80° C. for 16 hours. A red suspension was formed. TLC showed that starting material was remained and a more polar spot was formed. The mixture was stirred at 80° C. for another 24 hours. TLC showed that part of starting material was remained. The mixture was stirred at 80° C. for another 72 hours. TLC showed that half starting material was consumed. The mixture was filtered and the solid was washed with EtOAc (100 mL×3). The combined layer was concentrated the residue was purified by flash column (EtOAc in PE from 0 to 10%) to give benzyl (R)-(1-((3-bromo-5-nitropyridin-2-yl)oxy)-3-

((tert-butyldimethylsilyl)oxy)propan-2-yl)carbamate (6.00 g, yield: 26%) as light yellow oil.

¹H NMR (400 MHz, DMSO-d₆) δ 0.04 (6H, s), 0.87 (9H, s), 3.74-3.78-2.34 (1H, m), 3.90-3.92 (1H, m), 4.20-4.22 (1H, m), 4.49-4.53 (1H, m), 4.60-4.63 (1H, m), 5.12 (2H, d, J=4.8 Hz), 5.19-5.21 (1H, m), 7.30-7.37 (5H, m), 8.82 (1H, s), 8.99 (1H, s).

Step 5: Preparation of (R)-2-(((tert-butyldimethylsilyl)oxy)methyl)-7-nitro-2,3-dihydro-1H-pyrido[2,3-b][1,4]oxazine

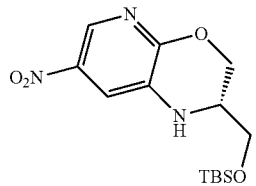 [SMILES: CC(C)(C)[Si](C)(C)OC[C@H]1COc2ncc([N+](=O)[O-])cc2N1]

To a mixture of benzyl (R)-(1-((3-bromo-5-nitropyridin-2-yl)oxy)-3-((tert-butyldimethylsilyl)oxy)propan-2-yl)carbamate (5.00 g, 9.25 mmol) and Cs₂CO₃ (4.52 g, 13.9 mmol) in MeCN (200 mL) was added Pd₂(dba)₃ (424 mg, 0.463 mmol) and Xantphos (535 mg, 0.925 mmol). The mixture was stirred at 100° C. for 16 hours. A black suspension was formed. LCMS showed that starting material was consumed and the desired product was not formed. TLC showed that more polar spots were formed. The mixture was concentrated and purified by flash column (EA in PE form 0 to 20%) to give (R)-2-(((tert-butyldimethylsilyl)oxy)methyl)-7-nitro-2,3-dihydro-1H-pyrido[2,3-b][1,4]oxazine (300 mg, yield: 10%) as a yellow solid.

Step 6: Preparation of (R)-2-(((tert-butyldimethylsilyl)oxy)methyl)-2,3-dihydro-1H-pyrido[2,3-b][1,4]oxazin-7-amine

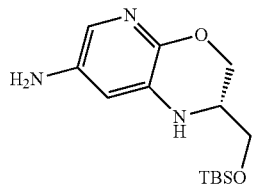

To a solution of (R)-2-(((tert-butyldimethylsilyl)oxy)methyl)-7-nitro-2,3-dihydro-1H-pyrido[2,3-b][1,4]oxazine (300 mg, 0.922 mmol) in THF (5 mL) was added Pd/C (100 mg, 10% purity in activated carbon). The mixture was degassed and purged with H2 for 3 times, stirred at 10° C. for 16 hours under H2 (15 psi). A black suspension was formed. TLC showed that starting material remained and the desired product was formed. The mixture was filtered and concentrated the residue was purified by flash column (EA in PE from 50 to 100%) to give (R)-2-(((tert-butyldimethylsilyl)oxy)methyl)-2,3-dihydro-1H-pyrido[2,3-b][1,4]oxazin-7-amine (200 mg, yield: 73%) as a yellow solid.

¹H NMR (400 MHz, DMSO-d₆) δ 0.05 (3H, s), 0.06 (3H, s), 0.88 (9H, s), 2.33-2.34 (1H, m), 3.48 (1H, dd, J=10.0, 8.4 Hz), 3.56 (1H, dd, J=10.4, 8.4 Hz), 3.99-4.04 (2H, m), 4.56 (2H, s), 5.87 (1H, d, J=2.0 Hz), 6.24 (1H, d, J=2.8 Hz), 6.75 (1H, d, J=2.8 Hz).

Step 7: Preparation of 1-(3-(((R)-2-(((tert-butyldimethylsilyl)oxy)methyl)-2,3-dihydro-1H-pyrido[2,3-b][1,4]oxazin-7-yl)amino)-5-methyl-5H-chromeno[4,3-c]pyridin-8-yl)pyrrolidin-2-one

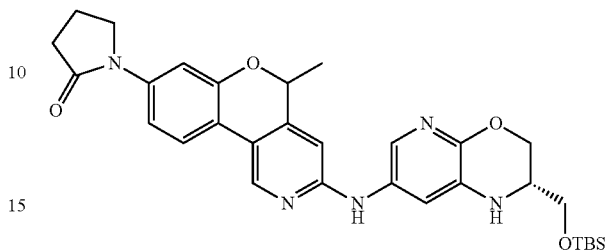

To a mixture of (R)-2-(((tert-butyldimethylsilyl)oxy)methyl)-2,3-dihydro-1H-pyrido[2,3-b][1,4]oxazin-7-amine (100 mg, 0.32 mmol) and 1-(3-chloro-5-methyl-5H-chromeno[4,3-c]pyridin-8-yl)pyrrolidin-2-one (103 mg, 0.349 mmol) in dioxane (2 mL) was added Pd₂(dba)₃ (15 mg, 0.016 mmol), Brettphos (17 mg, 0.032 mmol) and Cs₂CO₃ (155 mg, 0.477 mmol). The mixture was degassed and purged with N₂ and stirred at 100° C. for 16 hours. A brown suspension was formed. LCMS showed the purity of product is 18% (Rt=0.931 min; MS Calcd: 573.8. MS Found: 574.2 [M+H]⁺). The mixture was concentrated and purified by Flash column (EA in PE from 50 to 100%) to give 1-(3-(((R)-2-(((tert-butyldimethylsilyl)oxy)methyl)-2,3-dihydro-1H-pyrido[2,3-b][1,4]oxazin-7-yl)amino)-5-methyl-5H-chromeno[4,3-c]pyridin-8-yl)pyrrolidin-2-one (150 mg, yield: 82%) as a yellow solid.

¹H NMR (400 MHz, DMSO-d₆) δ 0.07 (3H, s), 0.08 (3H, s), 0.89 (9H, s), 1.51 (3H, d, J=6.8 Hz), 2.04-2.08 (2H, m), 2.55-2.57 (2H, m), 3.37-3.43 (2H, m), 3.53-3.60 (2H, m), 3.82-3.87 (2H, m), 4.11-4.14 (1H, m), 4.44-4.46 (1H, m), 5.24 (1H, q, J=6.8 Hz), 6.21 (1H, s), 6.61 (1H, s), 7.30-7.33 (1H, m), 7.38 (1H, d, J=2.4 Hz), 7.60 (1H, d, J=2.0 Hz), 7.84 (1H, d, J=8.8 Hz), 8.56 (1H, s), 8.96 (1H, s).

Step 8: Preparation of 1-(3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one

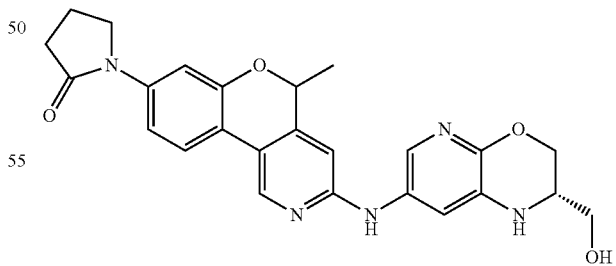

To a solution of 1-(3-(((R)-2-(((tert-butyldimethylsilyl)oxy)methyl)-2,3-dihydro-1H-pyrido[2,3-b][1,4]oxazin-7-yl)amino)-5-methyl-5H-chromeno[4,3-c]pyridin-8-yl)pyrrolidin-2-one (15 mg, 0.26 mmol) in THF (5 mL) was added TBAF (137 mg, 0.523 mmol) at 0° C. The mixture was warmed to 20° C. and stirred for 16 hours to give a red solution. LCMS showed the purity of product is 35%

(Rt=0.747 min; MS Calcd: 485.5. MS Found: 486.6 [M+H]⁺). The mixture was concentrated and the residue was purified by prep.TLC (DCM/MeOH, 10/1) to give 1-(3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one (100 mg, yield: 83%) as a yellow solid.

¹H NMR (400 MHz, DMSO-d₆) δ 1.51 (3H, d, J=6.9 Hz), 2.09-2.15 (2H, m), 2.43 (2H, t, J=7.6 Hz), 3.15-3.19 (2H, m), 3.36-3.44 (2H, m), 3.74-3.79 (2H, m), 4.03-4.08 (1H, m), 4.18-4.21 (1H, m), 4.94 (1H, t, J=5.6 Hz), 5.24 (1H, q, J=6.8 Hz), 6.21 (1H, s), 6.63 (1H, s), 7.04 (1H, d, J=6.8 Hz), 7.36 (1H, d, J=2.4 Hz), 7.60 (1H, d, J=2.4 Hz), 7.84 (1H, d, J=11.6 Hz), 8.60 (1H, s), 9.06 (1H, s).

Step 9: Preparation of (3aR)-8-((5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one

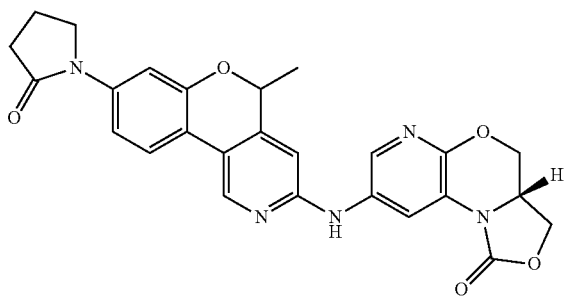 [SMILES: CC1Oc2cc(N3CCCC3=O)ccc2-c2cnc(Nc3cnc4c(c3)N3C(=O)OC[C@H]3CO4)cc21]

To a solution of 1-(3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one in DCM (5 mL) was added TEA (33 mg, 0.33 mmol) and CDI (71 mg, 0.44 mmol). The mixture was stirred at 10° C. for 16 hours. A white suspension was formed. LCMS showed the purity of product is 59% (Rt=0.783 min; MS Calcd: 485.5. MS Found: 486.6 [M+H]⁺). The reaction mixture was purified by prep.TLC (DCM/MeOH, 20/1) to give a yellow solid, the residue was purified by prep-HPLC to give (3aR)-8-((5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one (2.12 mg, yield: 4%) as a white solid.

¹H NMR (400 MHz, DMSO-d₆) δ 1.53 (3H, d, J=6.4 Hz), 2.04-2.08 (2H, m), 2.45-2.47 (2H, overlapped with DMSO), 3.85 (2H, t, J=7.6 Hz), 4.12 (1H, t, J=10.0 Hz), 4.19 (1H, t, J=11.2 Hz), 4.33-4.41 (1H, m), 4.58-4.66 (2H, m), 5.26 (1H, q, J=6.8 Hz), 6.67 (1H, s), 7.31 (1H, dd, J=8.4 Hz, 2.0 Hz), 7.40 (1H, d, J=2.0 Hz), 7.88 (1H, d, J=8.8 Hz), 8.36 (1H, d, J=2.8 Hz), 8.58 (1H, dd, J=6.0 Hz, 2.8 Hz), 8.62 (1H, s), 9.36 (1H, d, J=2.0 Hz).

Example 159: (3aR)-8-((9-fluoro-5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one

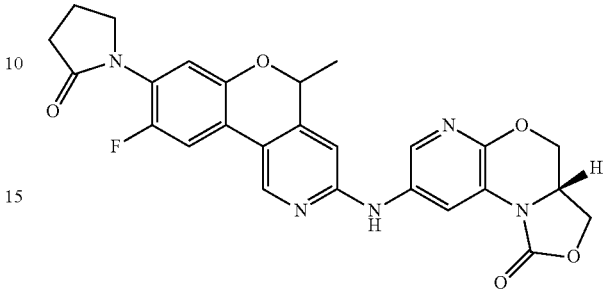

Step 1: Preparation of 1-(3-(((R)-2-(((tert-butyldimethylsilyl)oxy)methyl)-2,3-dihydro-1H-pyrido[2,3-b][1,4]oxazin-7-yl)amino)-9-fluoro-5-methyl-5H-chromeno[4,3-c]pyridin-8-yl)pyrrolidin-2-one

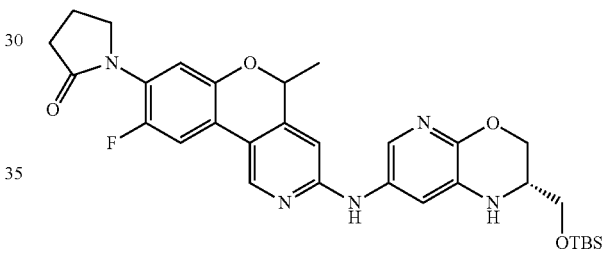

To a mixture of 1-(3-chloro-9-fluoro-5-methyl-5H-chromeno[4,3-c]pyridin-8-yl)pyrrolidin-2-one (158 mg, 0.474 mmol) and (R)-2-(((tert-butyldimethylsilyl)oxy)methyl)-2,3-dihydro-1H-pyrido[2,3-b][1,4]oxazin-7-amine (140 mg, 0.474 mmol) in dioxane (2 mL) was added Pd₂(dba)₃ (21 mg, 0.023 mmol), Brettphos (25 mg, 0.047 mmol) and Cs₂CO₃ (232 mg, 0.711 mmol). The mixture was degassed and purged with N₂. The mixture was stirred at 90° C. for 16 hours. A brown suspension was formed. LCMS showed the purity of product is 55% (Rt=0.944 min; MS Calcd: 591.8. MS Found: 592.2 [M+H]⁺). The mixture was concentrated and the residue was purified by Flash column (MeOH in DCM from 0 to 3%) to give 1-(3-(((R)-2-(((tert-butyldimethylsilyl)oxy)methyl)-2,3-dihydro-1H-pyrido[2,3-b][1,4]oxazin-7-yl)amino)-9-fluoro-5-methyl-5H-chromeno[4,3-c]pyridin-8-yl)pyrrolidin-2-one (200 mg, yield: 71%) as a yellow solid.

¹H NMR (400 MHz, DMSO-d₆) δ 0.07 (3H, s), 0.08 (3H, s), 0.89 (9H, s), 1.51 (3H, d, J=6.4 Hz), 2.08-2.13 (2H, m), 2.41-2.45 (2H, m), 3.52-3.54 (1H, m), 3.57-3.61 (1H, m), 3.76-3.78 (3H, m), 4.11-4.14 (1H, m), 4.44-4.46 (1H, m), 5.24 (1H, q, J=6.8 Hz), 6.23 (1H, s), 6.62 (1H, s), 7.04 (1H, d, J=6.8 Hz), 7.37 (1H, d, J=1.6 Hz), 7.60 (1H, d, J=2.4 Hz), 7.84 (1H, d, J=12.0 Hz), 8.60 (1H, s), 9.06 (1H, s).

Step 2: Preparation of 1-(9-fluoro-3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one

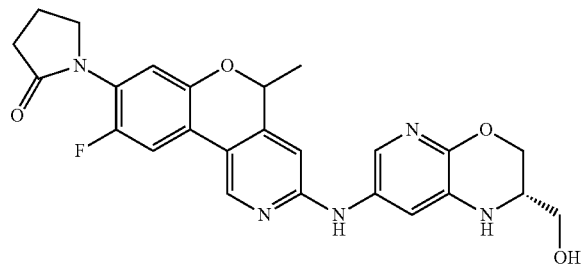 [SMILES: CC1Oc2cc(N3CCCC3=O)c(F)cc2-c2cnc(Nc3cnc4c(c3)N[C@@H](CO)CO4)cc21]

To a solution of 1-(3-(((R)-2-(((tert-butyldimethylsilyl)oxy)methyl)-2,3-dihydro-1H-pyrido[2,3-b][1,4]oxazin-7-yl)amino)-9-fluoro-5-methyl-5H-chromeno[4,3-c]pyridin-8-yl)pyrrolidin-2-one (200 mg, 0.338 mmol) in THF (5 mL) was added TBAF (176 mg, 0.676 mmol) at 0° C. The mixture was warmed to 20° C. and stirred for 1 hour to give a red solution. LCMS showed the purity of product is 67% (Rt=0.698 min; MS Calcd: 477.5. MS Found: 478.1 [M+H]$^+$). The mixture was added H$_2$O (10 mL), extracted with EtOAc (10 mL×2) and DCM (10 mL×2). The combined organic layer was dried over Na$_2$SO$_4$ and concentrated. The residue was purified by Combi Flash (MeOH in DCM from 0 to 5%) to give 1-(9-fluoro-3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one (110 mg, yield: 68%) as a yellow solid.

$^1$H NMR (400 MHz, DMSO-d$_6$) δ 1.51 (3H, d, J=6.8 Hz), 2.07-2.15 (2H, m), 2.43 (2H, t, J=7.6 Hz), 3.15-3.19 (2H, m), 3.37-3.46 (2H, m), 3.74-3.79 (2H, m), 4.02-4.08 (1H, m), 4.18-4.21 (1H, m), 4.94 (1H, t, J=5.6 Hz), 5.24 (1H, q, J=6.0 Hz), 6.21 (1H, s), 6.63 (1H, s), 7.04 (1H, d, J=6.8 Hz), 7.36 (1H, d, J=2.4 Hz), 7.60 (1H, d, J=2.4 Hz), 7.84 (1H, d, J=11.6 Hz), 8.60 (1H, s), 9.06 (1H, s).

Step 3: Preparation of (3aR)-8-((9-fluoro-5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one

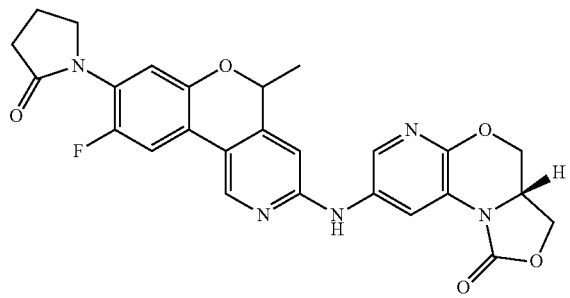 [SMILES: CC1Oc2cc(N3CCCC3=O)c(F)cc2-c2cnc(Nc3cnc4c(c3)N3C(=O)OC[C@H]3CO4)cc21]

To a solution of 1-(9-fluoro-3-(((S)-2-(hydroxymethyl)-2,3-dihydro-1H-pyrido[2,3-b][1,4]oxazin-7-yl)amino)-5-methyl-5H-chromeno[4,3-c]pyridin-8-yl)pyrrolidin-2-one (110 mg, 0.230 mmol) in DCM (5 mL) was added TEA (69 mg, 0.69 mmol) and CDI (149 mg, 0.921 mmol). The mixture was stirred at 20° C. for 16 hours. A white suspension was formed. LCMS showed the purity of product is 72% (Rt=0.698 min; MS Calcd: 503.5; MS Found: 504.2 [M+H]$^+$). The residue was purified by prep-TLC (DCM/MeOH, 20/1) to give a yellow solid, and prep-HPLC to give (3aR)-8-((9-fluoro-5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one (28.6 mg, yield: 24%) as a light yellow solid.

$^1$H NMR (400 MHz, DMSO-d$_6$) δ 1.52 (3H, d, J=6.4 Hz), 2.04-2.08 (2H, m), 2.43 (2H, t, J=8.0 Hz), 3.75-3.79 (2H, m), 4.12 (1H, t, J=10.8 Hz), 4.19 (1H, t, J=10.0 Hz), 4.33-4.41 (1H, m), 4.58-4.68 (2H, m), 5.27 (1H, q, J=6.4 Hz), 6.68 (1H, s), 7.05 (1H, d, J=6.8 Hz), 7.88 (1H, d, J=11.6 Hz), 8.36 (1H, d, J=2.0 Hz), 8.56-8.58 (1H, m), 8.67 (1H, s), 9.45 (1H, d, J=2.0 Hz).

Example 160: 1-(5-((8-(2-oxopyrrolidin-1-yl)-5H-chromeno[4,3-c]pyridin-3-yl)amino)pyridin-3-yl)imidazolidin-2-one

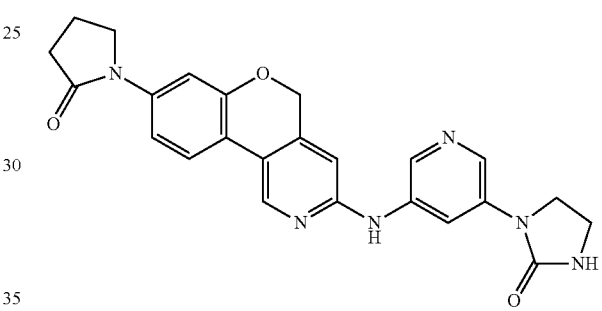

Step 1: Preparation of 1-(5-bromopyridin-3-yl)-3-((2-(trimethylsilyl)ethoxy)methyl)imidazolidin-2-one

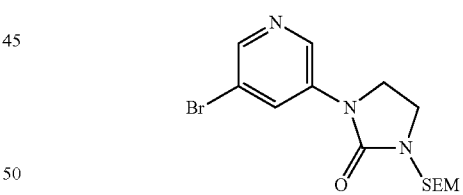

To a solution of 1-(5-bromopyridin-3-yl)imidazolidin-2-one (2.40 g, 9.91 mmol) in anhydrous DMF (25 mL) was added NaH (793 mg, 19.8 mmol, 60% dispersed in mineral oil) portions at 0° C. Then the reaction mixture was stirred at 0° C. for 30 minutes. SEM-C$_1$ (2.53 g, 14.9 mmol) was added dropwise to the reaction mixture at 0° C. After the completion of the addition, the reaction mixture was stirred at 30° C. for 2.5 hours. A yellow suspension was formed. TLC showed the starting material was consumed completely. To the reaction mixture was added saturated aqueous NH$_4$Cl (25 mL) and water (25 mL), then extracted with EtOAc (50 mL×3). The combined organic layer was washed with water (50 mL×2), brine (50 mL), dried over anhydrous Na$_2$SO$_4$ and concentrated. The crude product was purified by Combi Flash (50% to 100% EtOAc in PE) to afford 1-(5-bromopyridin-3-yl)-3-((2-(trimethylsilyl)ethoxy)methyl)imidazolidin-2-one (1.70 g, yield: 46%) as a white solid.

¹H NMR (400 MHz CDCl₃) δ 0.02 (9H, s), 0.90-0.99 (2H, m), 3.55-3.61 (2H, m), 3.66-3.72 (2H, m), 3.85-3.92 (2H, m), 4.78 (2H, s), 8.34-8.37 (1H, m), 8.42 (1H, t, J=2.4 Hz), 8.52-8.55 (1H, m)

Step 2: Preparation of 1-(5-((8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one

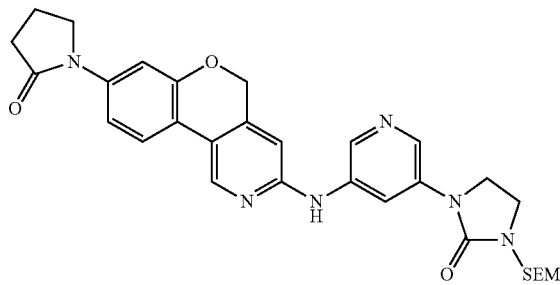 [SMILES: C[Si](C)(C)CCOCN1CCN(c2cncc(Nc3cc4c(cn3)-c3ccc(N5CCCC5=O)cc3OC4)c2)C1=O]

A mixture of 1-(5-bromopyridin-3-yl)-3-((2-(trimethylsilyl)ethoxy)methyl)imidazolidin-2-one (66 mg, 0.18 mmol), 1-(3-amino-5H-chromeno[4,3-c]pyridin-8-yl)pyrrolidin-2-one (50 mg, 0.18 mmol), Pd₂(dba)₃ (16 mg, 0.018 mmol), Brettphos (19 mg, 0.036 mmol) and Cs₂CO₃ (116 mg, 0.116 mmol) in anhydrous dioxane (3 mL) was degassed and purged with N₂ for 3 times. The resulting reaction mixture was stirred at 90° C. for 14 hours under N₂ atmosphere. A yellow suspension was formed. LCMS showed the purity of the desired product is 40% (Rt=0.692 min; MS Calcd: 572.3. MS Found: 573.1 [M+H]⁺). The reaction mixture was diluted with water (20 mL) and extracted with EtOAc (20 mL×2). The combined organic layer was washed with water (20 mL×2), brine (20 mL×2), dried over anhydrous Na₂SO₄, filtered and concentrated to give 1-(5-((8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (90 mg, crude) as a yellow solid, which was used for the next step without further purification.

Step 3: Preparation of 1-(5-((8-(2-oxopyrrolidin-1-yl)-5H-chromeno[4,3-c]pyridin-3-yl)amino)pyridin-3-yl)imidazolidin-2-one

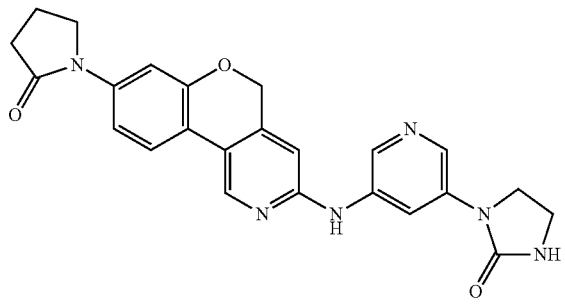 [SMILES: O=C1CCCN1c1ccc2c(c1)OCc1cc(Nc3cncc(N4CCNC4=O)c3)ncc1-2]

To a suspension of 1-(5-((8-(2-oxopyrrolidin-1-yl)-5H-chromeno[4,3-c]pyridin-3-yl)amino)pyridin-3-yl)-3-((2-(trimethylsilyl)ethoxy)methyl)imidazolidin-2-one (90 mg, 0.16 mmol) in DCM (5 mL) was added TFA (5 mL) dropwise at 30° C. The resulting mixture was stirred at 30° C. for 2 hours. A red solution was formed. After that, the reaction mixture was concentrated under reduced pressure to remove TFA. The residue was dissolved in dioxane (5 mL) and NH₃·H₂O (5 mL) and the reaction mixture was stirred at 30° C. for 13 days. A yellow suspension was formed. LCMS showed the purity of the desired product is 60% (Rt=1.526 min; MS Calcd: 442.2. MS Found: 443.2 [M+H]⁺). The reaction mixture was concentrated, then diluted with saturated aqueous Na₂CO₃ (10 mL) and extracted with EtOAc (20 mL×3). The combined organic layer was washed with saturated aqueous Na₂CO₃ (20 mL×2), brine (20 mL×2), dried over anhydrous Na₂SO₄, filtered and concentrated. The residue was purified by prep-HPLC (0.225% FA as an additive) and lyophilized to give 1-(5-((8-(2-oxopyrrolidin-1-yl)-5H-chromeno[4,3-c]pyridin-3-yl)amino)pyridin-3-yl)imidazolidin-2-one (10.6 mg, yield: 10% for two steps) as a yellow solid.

¹H NMR (400 MHz, DMSO-d₆) δ 2.02-2.11 (2H, m), 2.50-2.55 (2H, m, overlapped with DMSO), 3.40-3.52 (2H, m, overlapped with water), 3.84 (2H, t, J=7.0 Hz), 3.87-3.93 (2H, m), 5.11 (2H, s), 6.76 (1H, s), 7.17 (1H, s), 7.34 (1H, dd, J=8.6 Hz, 2.2 Hz), 7.38 (1H, d, J=2.0 Hz), 7.88 (1H, d, J=8.6 Hz), 8.35 (1H, d, J=2.0 Hz), 8.42 (1H, t, J=2.2 Hz), 8.66 (1H, brs), 8.75 (1H, d, J=1.6 Hz), 9.56 (1H, brs).

Example 161: 1-(5-((9-fluoro-8-(2-oxopyrrolidin-1-yl)-5H-chromeno[4,3-c]pyridin-3-yl)amino)pyridin-3-yl)imidazolidin-2-one

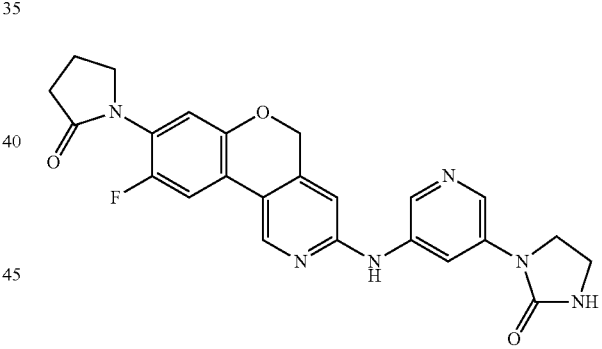

Step 1: Preparation of 1-(5-bromopyridin-3-yl)-3-(4-methoxybenzyl)imidazolidin-2-one

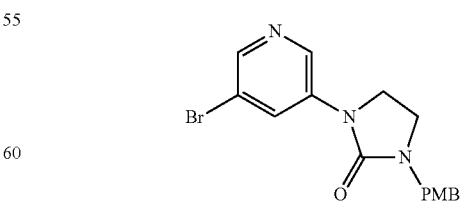

To a solution of 1-(5-bromopyridin-3-yl)imidazolidin-2-one (200 mg, 0.826 mmol) in anhydrous DMF (3 mL) was added NaH (66 mg, 1.6 mmol, 60% dispersed in mineral oil) at 0° C. Then the reaction mixture was stirred at 0° C. for 30 minutes. PMB-Cl (168 mg, 1.07 mmol) was added to the reaction mixture at 0° C. and the reaction mixture was stirred at 25° C. for 2.5 hours. A yellow suspension was formed. TLC showed the starting material was consumed completely. To the reaction mixture was added saturated aqueous NH$_4$Cl (10 mL) and water (10 mL), then extracted with EtOAc (20 mL×3). The combined organic layer was washed with water (20 mL×2), brine (20 mL), dried over anhydrous Na$_2$SO$_4$ and concentrated. The residue was purified by Combi Flash (10% to 50% EtOAc in PE) to afford 1-(5-bromopyridin-3-yl)-3-(4-methoxybenzyl)imidazolidin-2-one (330 mg, quantitative) as a yellow solid.

$^1$H NMR (400 MHz CDCl$_3$) δ 3.37-3.43 (2H, m), 3.75-3.78 (2H, m), 3.79 (3H, s), 4.40 (2H, s), 6.87 (2H, d, J=8.0 Hz), 7.22 (2H, d, J=8.0 Hz), 8.31 (1H, d, J=2.0 Hz), 8.45 (1H, dd, J=2.4 Hz, 2.0 Hz), 8.51 (1H, d, J=2.4 Hz).

Step 2: Preparation of 1-(5-((9-fluoro-8-(2-oxopyrrolidin-1-yl)-5H-chromeno[4,3-c]pyridin-3-yl)amino)pyridin-3-yl)-3-(4-methoxybenzyl)imidazolidin-2-one

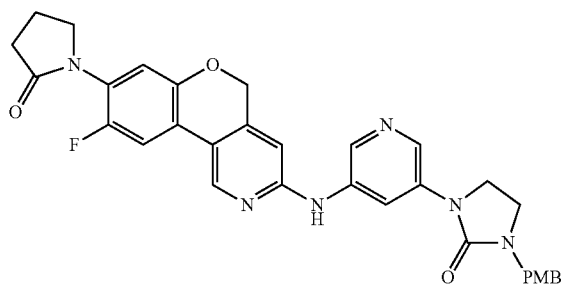

A mixture of 1-(5-bromopyridin-3-yl)-3-(4-methoxybenzyl)imidazolidin-2-one (73 mg, 0.20 mmol), 1-(3-amino-9-fluoro-5H-chromeno[4,3-c]pyridin-8-yl)pyrrolidin-2-one (60 mg, 0.20 mmol), Pd$_2$(dba)$_3$ (18 mg, 0.020 mmol), Brettphos (22 mg, 0.040 mmol) and Cs$_2$CO$_3$ (131 mg, 0.400 mmol) in anhydrous dioxane (3 mL) was degassed and purged with N$_2$ for 3 times. Then the resulting reaction mixture was stirred at 90° C. for 16 hours under N$_2$ atmosphere. A brown suspension was formed. LCMS showed the purity of the desired product is 60% (Rt=0.837 min; MS Calcd: 580.2. MS Found: 581.3 [M+H]$^+$). The reaction mixture was diluted with water (20 mL) and extracted with DCM/MeOH (20 mL×3, 5/1). The combined organic layer was washed with water (20 mL×2), brine (20 mL×2), dried over anhydrous Na$_2$SO$_4$, filtered and concentrated. The residue was purified by Combi Flash (0% to 10% MeOH in DCM) to afford 1-(5-((9-fluoro-8-(2-oxopyrrolidin-1-yl)-5H-chromeno[4,3-c]pyridin-3-yl)amino)pyridin-3-yl)-3-(4-methoxybenzyl)imidazolidin-2-one (130 mg, yield: 95%) as a yellow solid.

Step 3: Preparation of 1-(5-((9-fluoro-8-(2-oxopyrrolidin-1-yl)-5H-chromeno[4,3-c]pyridin-3-yl)amino)pyridin-3-yl)imidazolidin-2-one

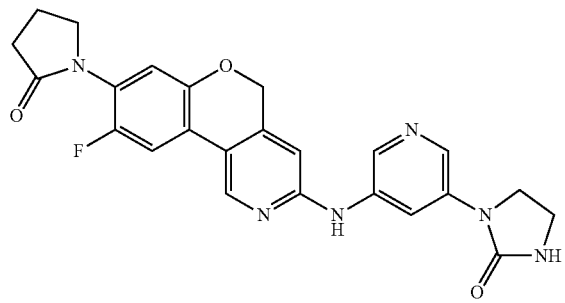 [SMILES: O=C1NCCN1c1cncc(Nc2cc3c(cn2)-c2cc(F)c(N4CCCC4=O)cc2OC3)c1]

A solution of 1-(5-((9-fluoro-8-(2-oxopyrrolidin-1-yl)-5H-chromeno[4,3-c]pyridin-3-yl)amino)pyridin-3-yl)-3-(4-methoxybenzyl)imidazolidin-2-one (90 mg, 0.16 mmol) in TFA (5 mL) was stirred at 50° C. for 16 hours. A red solution was formed. LCMS showed the purity of the desired product is 63% (Rt=0.738 min; MS Calcd: 460.2. MS Found: 461.1 [M+H]$^+$). The reaction mixture was concentrated and the residue was dissolved in DCM/MeOH (20 mL, 1/1), basified with 1 N aqueous NaOH to pH=8. The precipitate was filtrated and washed with water (10 mL) and MeCN (10 mL), then lyophilizated to give 1-(5-((9-fluoro-8-(2-oxopyrrolidin-1-yl)-5H-chromeno[4,3-c]pyridin-3-yl)amino)pyridin-3-yl)imidazolidin-2-one (53.6 mg, yield: 61%) as an off-white solid.

$^1$H NMR (400 MHz, DMSO-d$_6$) δ 2.07-2.18 (2H, m), 2.38-2.46 (2H, m, overlapped with DMSO), 3.40-3.52 (2H, m, overlapped with water), 3.72-3.81 (2H, m), 3.86-3.98 (2H, m), 5.12 (2H, s), 6.75 (1H, s), 7.02-7.15 (2H, m), 7.81-7.92 (1H, m), 8.30 (1H, s), 8.39 (1H, s), 8.62-8.78 (2H, m), 9.50 (1H, brs).

Example 162: 1-(5-((5,5-dimethyl-8-(2-oxopyrrolidin-1-yl)-5H-chromeno[4,3-c]pyridin-3-yl)amino)pyridin-3-yl)imidazolidin-2-one

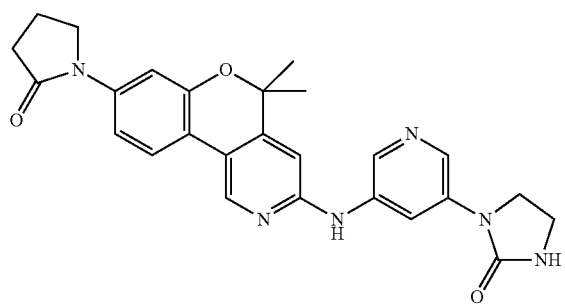 [SMILES: CC1(C)Oc2cc(N3CCCC3=O)ccc2-c2cnc(Nc3cncc(N4CCNC4=O)c3)cc21]

Step 1: Preparation of tert-butyl (5-(3-(4-methoxybenzyl)-2-oxoimidazolidin-1-yl)pyridin-3-yl)carbamate

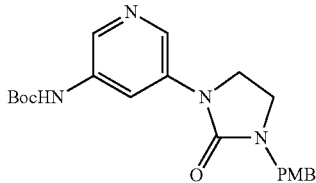

A mixture of 1-(5-bromopyridin-3-yl)-3-(4-methoxybenzyl)imidazolidin-2-one (200 mg, 0.552 mmol), tert-butyl carbamate (97 mg, 0.20 mmol), $Pd_2(dba)_3$ (51 mg, 0.055 mmol), Xantphos (64 mg, 0.110 mmol) and $Cs_2CO_3$ (180 mg, 0.552 mmol) in anhydrous dioxane (5 mL) was degassed and purged with $N_2$ for 3 times. And the resulting mixture was stirred at 90° C. for 15 hours under $N_2$ atmosphere. A yellow suspension was formed. LCMS showed the purity of the desired product is 37% (Rt=0.813 min; MS Calcd: 398.2. MS Found: 399.1 [M+H]$^+$). The reaction mixture was diluted with water (20 mL) and extracted with EtOAc (20 mL×2). The combined organic layer was washed with water (20 mL×2), brine (20 mL×2), and dried over anhydrous $Na_2SO_4$, filtered and concentrated. The residue was purified by Combi Flash (0% to 10% DCM in EtOAc) to afford tert-butyl (5-(3-(4-methoxybenzyl)-2-oxoimidazolidin-1-yl)pyridin-3-yl)carbamate (340 mg, yield: 74%) as a yellow solid.

Step 2: Preparation of 1-(5-aminopyridin-3-yl)-3-(4-methoxybenzyl)imidazolidin-2-one

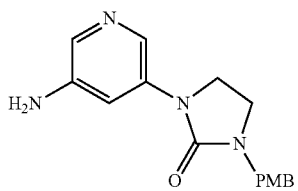

A solution of tert-butyl (5-(3-(4-methoxybenzyl)-2-oxoimidazolidin-1-yl)pyridin-3-yl)carbamate (220 mg, 0.552 mmol) in DCM (3 mL) and TFA (3 mL) was stirred at 25° C. for 1 hour. A red solution was formed. LCMS showed the purity of the desired product is 63% (Rt=0.591 min; MS Calcd: 298.1. MS Found: 298.9 [M+H]$^+$). The reaction mixture was diluted with EtOAc (20 mL) and basified with 1 N aqueous NaOH to pH=8. The aqueous layer was extracted with EtOAc (20 mL×2). The combined organic layer was washed with water (20 mL×2), brine (20 mL×2), and dried over anhydrous $Na_2SO_4$, filtered and concentrated. The residue was purified by Combi Flash (0% to 5% MeOH in DCM) to afford 1-(5-aminopyridin-3-yl)-3-(4-methoxybenzyl)imidazolidin-2-one (150 mg, yield: 87%) as a yellow solid.

Step 3: Preparation of 1-(5-((5,5-dimethyl-8-(2-oxopyrrolidin-1-yl)-5H-chromeno[4,3-c]pyridin-3-yl)amino)pyridin-3-yl)-3-(4-methoxybenzyl)imidazolidin-2-one

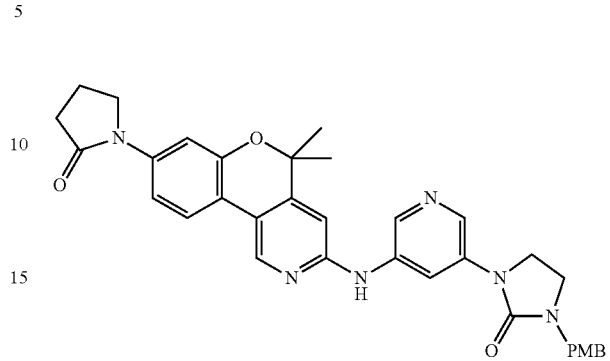

A mixture of 1-(5-aminopyridin-3-yl)-3-(4-methoxybenzyl)imidazolidin-2-one (80 mg, 0.24 mmol), 1-(3-chloro-5,5-dimethyl-5H-chromeno[4,3-c]pyridin-8-yl)pyrrolidin-2-one (73 mg, 0.24 mmol), $Pd_2(dba)_3$ (22 mg, 0.024 mmol), Brettphos (26 mg, 0.048 mmol) and $Cs_2CO_3$ (158 mg, 0.486 mmol) in anhydrous dioxane (3 mL) was degassed and purged with $N_2$ for 3 times. Then the resulting mixture was stirred at 90° C. for 16 hours under $N_2$ atmosphere. A yellow suspension was formed. LCMS showed the purity of the desired product is 26% (Rt=0.840 min; MS Calcd: 590.3. MS Found: 591.2 [M+H]$^+$). The reaction mixture was diluted with water (20 mL) and extracted with DCM/MeOH (20 mL×3, 5/1). The combined organic layer was washed with water (20 mL×2), brine (20 mL×2), dried over anhydrous $Na_2SO_4$, filtered and concentrated. The residue was purified by Combi Flash (0% to 10% MeOH in DCM) to afford 1-(5-((5,5-dimethyl-8-(2-oxopyrrolidin-1-yl)-5H-chromeno[4,3-c]pyridin-3-yl)amino)pyridin-3-yl)-3-(4-methoxybenzyl)imidazolidin-2-one (54 mg, yield: 38%) as a yellow solid.

Step 4: Preparation of 1-(5-((5,5-dimethyl-8-(2-oxopyrrolidin-1-yl)-5H-chromeno[4,3-c]pyridin-3-yl)amino)pyridin-3-yl)imidazolidin-2-one

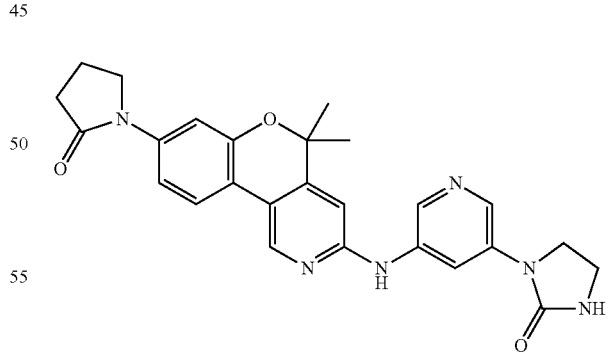

A solution of 1-(5-((5,5-dimethyl-8-(2-oxopyrrolidin-1-yl)-5H-chromeno[4,3-c]pyridin-3-yl)amino)pyridin-3-yl)-3-(4-methoxybenzyl)imidazolidin-2-one (54 mg, 0.091 mmol) in TFA (5 mL) was stirred at 50° C. for 16 hours. A red solution was formed. LCMS showed the purity of the desired product is 42% (Rt=0.754 min; MS Calcd: 471.2. MS Found: 471.1 [M+H]$^+$). The reaction mixture was concentrated and the residue was dissolved in DCM/MeOH (20 mL, 1/1), basified with 1 N aqueous NaOH to pH=8. The aqueous layer was extracted with DCM/MeOH (20 mL×2, 1/1). The combined organic layer was washed with water (20 mL×2), brine (20 mL), dried over anhydrous Na$_2$SO$_4$, filtered and concentrated. The residue was purified by Combi Flash (1% to 10% MeOH in DCM), then further purified by prep-HPLC (0.225% FA as an additive) and lyophilized to give 1-(5-((5,5-dimethyl-8-(2-oxopyrrolidin-1-yl)-5H-chromeno[4,3-c]pyridin-3-yl)amino)pyridin-3-yl)imidazolidin-2-one (11.3 mg, yield: 27%) as a yellow solid.

$^1$H NMR (400 MHz, DMSO-d$_6$) δ 1.57 (6H, s), 2.02-2.11 (2H, m), 2.50-2.55 (2H, m, overlapped with DMSO), 3.40-3.52 (2H, m, overlapped with water), 3.84 (2H, t, J=7.0 Hz), 3.94 (2H, t, J=8.0 Hz), 6.88 (1H, s), 7.31 (1H, dd, J=8.6 Hz, 2.0 Hz), 7.40 (1H, d, J=2.0 Hz), 7.48 (1H, s), 7.92 (1H, d, J=8.6 Hz), 8.45-8.61 (2H, m), 8.74 (1H, s), 9.00 (1H, brs), 10.08 (1H, brs).

Example 163: 1-(3-((2,3-dihydro-[1,4]dioxino[2,3-b]pyridin-7-yl)amino)-5H-chromeno[4,3-c]pyridin-8-yl)pyrrolidin-2-one

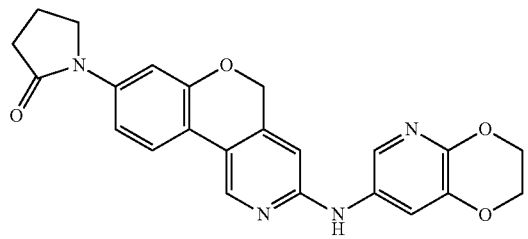 [SMILES: O=C1CCCN1c1ccc2c(c1)OCc1cc(Nc3cnc4c(c3)OCCO4)ncc1-2]

A mixture of 1-(3-chloro-5H-chromeno[4,3-c]pyridin-8-yl)pyrrolidin-2-one (50 mg, 0.17 mmol), 2,3-dihydro-[1,4]dioxino[2,3-b]pyridin-7-amine (34 mg, 0.18 mmol, HCl salt), Pd$_2$(dba)$_3$ (15 mg, 0.017 mmol), Brettphos (18 mg, 0.033 mmol), Cs$_2$CO$_3$ (108 mg, 0.332 mmol) in anhydrous dioxane (3 mL) was degassed and purged with N$_2$ for 3 times. Then the resulting reaction mixture was heated at 90° C. for 14 hours under N$_2$ atmosphere. The reaction mixture turned into yellow suspension from gray suspension. LCMS showed that the purity of the desired product is 35% (Rt=0.658 min; MS Calcd: 416.2. MS Found: 417.1 [M+H]$^+$). The mixture was diluted with water (20 mL) and extracted with EtOAc/THF (20 mL×3, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give 1-(3-((2,3-dihydro-[1,4]dioxino[2,3-b]pyridin-7-yl)amino)-5H-chromeno[4,3-c]pyridin-8-yl)pyrrolidin-2-one (14.1 mg, yield: 20%) as a yellow solid.

$^1$H NMR (400 MHz DMSO-d$_6$) δ 2.01-2.10 (2H, m), 2.55-2.59 (2H, m, overlapped with DMSO), 3.84 (2H, t, J=7.0 Hz), 4.22-4.27 (2H, m), 4.33-4.40 (2H, m), 5.09 (2H, s), 6.65 (1H, s), 7.33 (1H, d, J=8.4 Hz), 7.37 (1H, s), 7.77-7.88 (2H, m), 7.93 (1H, d, J=2.0 Hz), 8.60 (1H, s), 9.24 (1H, brs).

Example 164: 1-(3-((2,3-dihydro-[1,4]dioxino[2,3-b]pyridin-7-yl)amino)-5,5-dimethyl-5H-chromeno[4,3-c]pyridin-8-yl)pyrrolidin-2-one

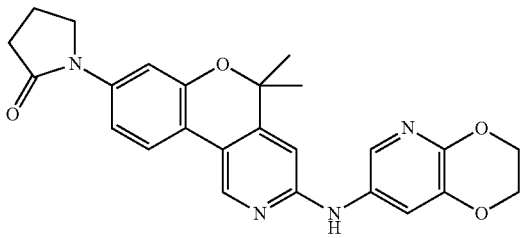 [SMILES: CC1(C)Oc2cc(N3CCCC3=O)ccc2-c2cnc(Nc3cnc4c(c3)OCCO4)cc21]

A mixture of 1-(3-chloro-5,5-dimethyl-5H-chromeno[4,3-c]pyridin-8-yl)pyrrolidin-2-one (25 mg, 0.076 mmol), 2,3-dihydro-[1,4]dioxino[2,3-b]pyridin-7-amine (16 mg, 0.084 mmol, HCl salt), Pd$_2$(dba)$_3$ (7 mg, 0.008 mmol), Brettphos (15 mg, 0.015 mmol), Cs$_2$CO$_3$ (50 mg, 0.152 mmol) in anhydrous dioxane (3 mL) was degassed and purged with N$_2$ for 3 times. Then the resulting reaction mixture was heated at 90° C. for 14 hours under N$_2$ atmosphere. The reaction mixture turned into yellow suspension from gray suspension. LCMS showed that the purity of the desired product is 26% (Rt=0.745 min; MS Calcd: 444.2; MS Found: 445.1 [M+H]$^+$). The mixture was diluted with water (20 mL) and extracted with EtOAc/THF (20 mL×3, 1/1). The combined organic layer was washed with water (20 mL×2), brine (20 mL×2), dried over anhydrous Na$_2$SO$_4$, filtered and concentrated. The residue was purified by prep-HPLC (0.225% FA as an additive) and lyophilized to give 1-(3-((2,3-dihydro-[1,4]dioxino[2,3-b]pyridin-7-yl)amino)-5,5-dimethyl-5H-chromeno[4,3-c]pyridin-8-yl)pyrrolidin-2-one (11.0 mg, yield: 33%) as a yellow solid.

$^1$H NMR (400 MHz DMSO-d$_6$) δ 1.55 (6H, s), 2.01-2.10 (2H, m), 2.52-2.57 (2H, m, overlapped with DMSO), 3.84 (2H, t, J=7.0 Hz), 4.22-4.27 (2H, m), 4.33-4.40 (2H, m), 6.71 (1H, s), 7.29 (1H, dd, J=8.4 Hz, 2.2 Hz), 7.39 (1H, d, J=2.0 Hz), 7.83 (1H, d, J=2.2 Hz), 7.86 (1H, d, J=8.8 Hz), 7.94 (1H, d, J=2.4 Hz), 8.63 (1H, s), 9.25 (1H, brs).

Example 165: 1-(3-((2,3-dihydro-[1,4]dioxino[2,3-b]pyridin-7-yl)amino)-9-fluoro-5H-chromeno[4,3-c]pyridin-8-yl)pyrrolidin-2-one

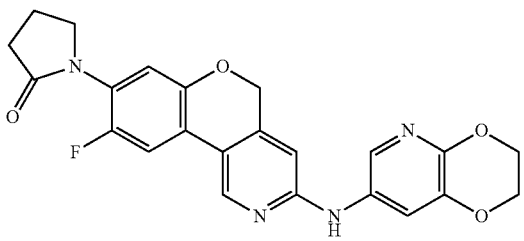 [SMILES: O=C1CCCN1c1cc2c(cc1F)-c1cnc(Nc3cnc4c(c3)OCCO4)cc1CO2]

A mixture of 1-(3-chloro-9-fluoro-5H-chromeno[4,3-c]pyridin-8-yl)pyrrolidin-2-one (50 mg, 0.16 mmol), 2,3-dihydro-[1,4]dioxino[2,3-b]pyridin-7-amine (33 mg, 0.17 mmol, HCl salt), Pd$_2$(dba)$_3$ (14 mg, 0.016 mmol), Brettphos (17 mg, 0.032 mmol), Cs$_2$CO$_3$ (102 mg, 0.314 mmol) in anhydrous dioxane (3 mL) was degassed and purged with N$_2$ for 3 times. Then the resulting reaction mixture was heated at 90° C. for 14 hours under N₂ atmosphere. The reaction mixture turned into yellow suspension from gray suspension. LCMS showed that the purity of the desired product is 27% (Rt=0.670 min; MS Calcd: 434.1. MS Found: 435.1 [M+H]⁺). The mixture was diluted with water (20 mL) and extracted with EtOAc/THF (20 mL×3, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 1-(3-((2,3-dihydro-[1,4]dioxino[2,3-b]pyridin-7-yl)amino)-9-fluoro-5H-chromeno[4,3-c]pyridin-8-yl)pyrrolidin-2-one (16.4 mg, yield: 24%) as a yellow solid.

¹H NMR (400 MHz DMSO-d₆) δ 2.08-2.16 (2H, m), 2.43 (2H, t, J=8.0 Hz), 3.76 (2H, t, J=7.0 Hz), 4.22-4.27 (2H, m), 4.33-4.39 (2H, m), 5.09 (2H, s), 6.65 (1H, s), 7.05 (1H, d, J=6.8 Hz), 7.79-7.86 (2H, m), 7.94 (1H, d, J=2.4 Hz), 8.65 (1H, s), 9.30 (1H, brs).

Example 166: 1-(3-((2,3-dihydro-[1,4]dioxino[2,3-b]pyridin-7-yl)amino)-9-fluoro-5-methyl-5H-chromeno[4,3-c]pyridin-8-yl)pyrrolidin-2-one

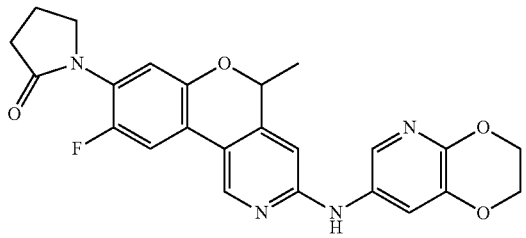 [SMILES: CC1Oc2cc(N3CCCC3=O)c(F)cc2-c2cnc(Nc3cnc4c(c3)OCCO4)cc21]

A mixture of 1-(3-chloro-9-fluoro-5-methyl-5H-chromeno[4,3-c]pyridin-8-yl)pyrrolidin-2-one (50 mg, 0.15 mmol), 2,3-dihydro-[1,4]dioxino[2,3-b]pyridin-7-amine (31 mg, 0.17 mmol, HCl salt), Pd₂(dba)₃ (14 mg, 0.015 mmol), Brettphos (16 mg, 0.030 mmol), Cs₂CO₃ (98 mg, 0.300 mmol) in anhydrous dioxane (3 mL) was degassed and purged with N₂ for 3 times. Then the resulting reaction mixture was heated at 90° C. for 14 hours under N₂ atmosphere. The reaction mixture turned into yellow suspension from gray suspension. LCMS showed that the purity of the desired product is 30% (Rt=0.685 min; MS Calcd: 448.2; MS Found: 449.2 [M+H]⁺). The mixture was diluted with water (20 mL) and extracted with EtOAc/THF (20 mL×3, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 1-(3-((2,3-dihydro-[1,4]dioxino[2,3-b]pyridin-7-yl)amino)-9-fluoro-5-methyl-5H-chromeno[4,3-c]pyridin-8-yl)pyrrolidin-2-one (11.1 mg, yield: 16%) as a yellow solid.

¹H NMR (400 MHz DMSO-d₆) δ 1.52 (3H, d, J=6.4 Hz), 2.06-2.16 (2H, m), 2.43 (2H, t, J=8.0 Hz), 3.73-3.82 (2H, m), 4.22-4.27 (2H, m), 4.33-4.39 (2H, m), 5.26 (1H, q, J=6.4 Hz), 6.65 (1H, s), 7.05 (1H, d, J=6.8 Hz), 7.81-7.88 (2H, m), 7.94 (1H, d, J=2.4 Hz), 8.66 (1H, s), 9.32 (1H, brs).

Example 167: 1-(3-((2,3-dihydro-[1,4]dioxino[2,3-b]pyridin-7-yl)amino)-9-fluoro-5,5-dimethyl-5H-chromeno[4,3-c]pyridin-8-yl)pyrrolidin-2-one

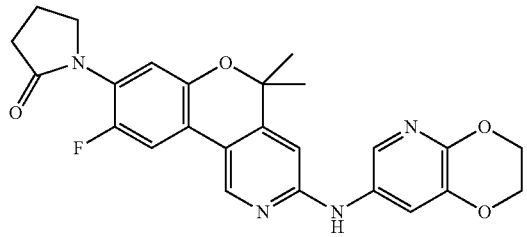 [SMILES: CC1(C)Oc2cc(N3CCCC3=O)c(F)cc2-c2cnc(Nc3cnc4c(c3)OCCO4)cc21]

A mixture of 1-(3-chloro-9-fluoro-5,5-dimethyl-5H-chromeno[4,3-c]pyridin-8-yl)pyrrolidin-2-one (50 mg, 0.14 mmol), 2,3-dihydro-[1,4]dioxino[2,3-b]pyridin-7-amine (30 mg, 0.16 mmol, HCl salt), Pd₂(dba)₃ (13 mg, 0.014 mmol), Brettphos (15 mg, 0.028 mmol), Cs₂CO₃ (94 mg, 0.288 mmol) in anhydrous dioxane (3 mL) was degassed and purged with N₂ for 3 times. Then the resulting reaction mixture was heated at 90° C. for 14 hours under N₂ atmosphere. The reaction mixture turned into black suspension from gray suspension. LCMS showed that the purity of the desired product is 32% (Rt=0.749 min; MS Calcd: 462.2; MS Found: 463.1 [M+H]⁺). The mixture was diluted with water (20 mL) and extracted with EtOAc/THF (20 mL×3, 1/1). The combined organic layer was washed with water (20 mL×2), brine (20 mL×2), dried over anhydrous Na₂SO₄, filtered and concentrated. The residue was purified by prep-HPLC (0.225% FA as an additive) and lyophilized to give 1-(3-((2,3-dihydro-[1,4]dioxino[2,3-b]pyridin-7-yl)amino)-9-fluoro-5,5-dimethyl-5H-chromeno[4,3-c]pyridin-8-yl)pyrrolidin-2-one (24.1 mg, yield: 36%) as a yellow solid.

¹H NMR (400 MHz DMSO-d₆) δ 1.56 (6H, s), 2.06-2.16 (2H, m), 2.43 (2H, t, J=8.0 Hz), 3.78 (2H, t, J=7.0 Hz), 4.22-4.27 (2H, m), 4.33-4.39 (2H, m), 6.71 (1H, s), 7.02 (1H, d, J=6.8 Hz), 7.83 (1H, d, J=2.2 Hz), 7.84-7.89 (1H, m), 7.95 (1H, d, J=2.2 Hz), 8.68 (1H, s), 9.34 (1H, brs).

Example 168: 1-(3-((5-(4-(3-methoxypropanoyl)piperazin-1-yl)pyridin-3-yl)amino)-5H-chromeno[4,3-c]pyridin-8-yl)pyrrolidin-2-one

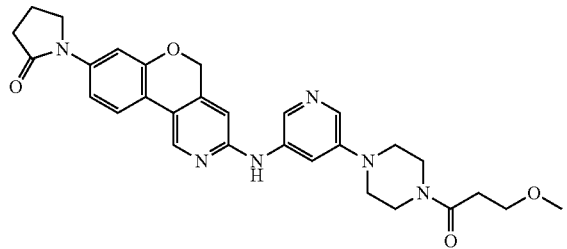 [SMILES: COCCC(=O)N1CCN(c2cncc(Nc3cc4c(cn3)-c3ccc(N5CCCC5=O)cc3OC4)c2)CC1]

Step 1: Preparation of tert-butyl 4-(3-methoxypropanoyl)piperazine-1-carboxylate

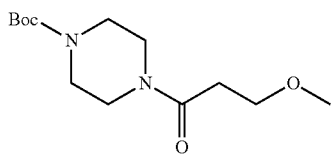 [SMILES: COCCC(=O)N1CCN(C(=O)OC(C)(C)C)CC1]

To a solution of tert-butyl piperazine-1-carboxylate (10.0 g, 53.7 mmol), 3-methoxypropanoic acid (6.71 g, 64.4 mmol), EDCI (15.4 g, 80.5 mmol) and HOBt (14.5 g, 107 mmol) in anhydrous DMF (100 mL) was added $Et_3N$ (16.3 g, 161 mmol) at 20-25° C. Then the reaction mixture was stirred at 20-25° C. for 16 hours. The reaction mixture turned into white suspension from yellow solution. To the reaction mixture was added water (200 mL), then extracted with EtOAc (200 mL×3). The combined organic layer was washed with water (100 mL×3), 1N aqueous HCl (100 mL×2), saturated aqueous $NaHCO_3$ (100 mL), brine (100 mL), dried over anhydrous $Na_2SO_4$ and concentrated to give tert-butyl 4-(3-methoxypropanoyl)piperazine-1-carboxylate (13.0 g, yield: 89%) as a white solid.

$^1$H NMR (400 MHz, $CDCl_3$) δ 1.47 (9H, s), 2.61 (2H, t, J=6.4 Hz), 3.35 (3H, s), 3.35-3.50 (6H, m), 3.55-3.65 (2H, m), 3.70 (2H, t, J=6.8 Hz).

Step 2: Preparation of 3-methoxy-1-(piperazin-1-yl)propan-1-one

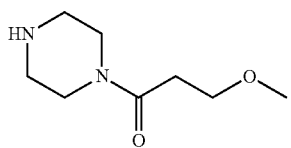

To a solution of tert-butyl 4-(3-methoxypropanoyl)piperazine-1-carboxylate (13.0 g, 47.7 mmol) in EtOAc (50 mL) was added 4N HCl/EtOAc (100 mL) at 20-25° C. Then the reaction mixture was stirred at 20-25° C. for 2 hours. The reaction mixture turned into cloudy from solution. The reaction mixture was concentrated to give 3-methoxy-1-(piperazin-1-yl)propan-1-one (9.80 g, yield: 98%, HCl salt) as a white solid.

$^1$H NMR (400 MHz, DMSO-$d_6$) δ 2.61 (2H, t, J=6.8 Hz), 2.90-3.10 (4H, m), 3.22 (3H, s), 3.54 (2H, t, J=6.4 Hz), 3.65-3.80 (4H, m), 9.66 (2H, s).

The product (9.80 g, 47.0 mmol) was dissolved in water (50 mL), then basified with 2N aqueous NaOH to pH=9 and extracted with DCM/MeOH (25 mL×5, 4/1). The combined organic layer was dried over anhydrous $Na_2SO_4$ and concentrated to give 3-methoxy-1-(piperazin-1-yl)propan-1-one (1.90 g, free form) as yellow oil.

$^1$H NMR (400 MHz, $CDCl_3$) δ 2.23 (1H, brs), 2.59 (2H, t, J=6.4 Hz), 2.80-2.90 (4H, m), 3.35 (3H, s), 3.40-3.45 (2H, m), 3.55-3.60 (2H, m), 3.69 (2H, t, J=6.4 Hz).

The aqueous layer was lyophilized and the solid was suspended in DCM/MeOH (100 mL, 4/1) and stirred for 1 hour. The mixture was filtered and the filtrate was dried over anhydrous $Na_2SO_4$ and concentrated to give 3-methoxy-1-(piperazin-1-yl)propan-1-one (1.50 g, free form) as yellow oil.

$^1$H NMR (400 MHz, $CDCl_3$) δ 2.58 (2H, t, J=6.4 Hz), 2.80-2.90 (4H, m), 3.15 (1H, brs), 3.34 (3H, s), 3.40-3.45 (2H, m), 3.55-3.60 (2H, m), 3.68 (2H, t, J=6.4 Hz).

Step 3: Preparation of tert-butyl (5-(4-(3-methoxypropanoyl)piperazin-1-yl)pyridin-3-yl)carbamate

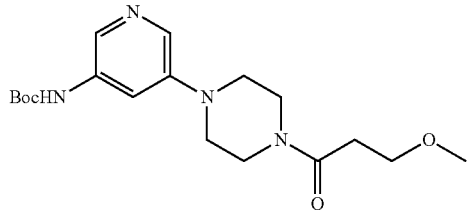 [SMILES: COCCC(=O)N1CCN(c2cncc(NC(=O)OC(C)(C)C)c2)CC1]

A mixture of tert-butyl (5-bromopyridin-3-yl)carbamate (3.50 g, 12.8 mmol), 3-methoxy-1-(piperazin-1-yl)propan-1-one (2.87 g, 16.7 mmol, free form), $Pd_2(dba)_3$ (1.17 g, 1.28 mmol), RuPhos (1.20 g, 2.56 mmol) and $Cs_2CO_3$ (8.35 g, 25.6 mmol) in anhydrous dioxane (50 mL) was degassed and purged with $N_2$ for 3 times. Then the resulting reaction mixture was heated at 90° C. for 16 hour under $N_2$ atmosphere. The reaction mixture turned into yellow suspension from red. LCMS showed the purity of the desired product is 52% (Rt=0.650 min; MS Calcd: 364.2. MS Found: 365.3 [M+H]$^+$). To the reaction mixture was added water (100 mL), then extracted with EtOAc (100 mL×3). The combined organic layer was washed with brine (100 mL), dried over anhydrous $Na_2SO_4$ and concentrated. The residue was purified by Combi Flash (50% to 100% EtOAc in PE) to give tert-butyl (5-(4-(3-methoxypropanoyl)piperazin-1-yl)pyridin-3-yl)carbamate (3.80 g, yield: 81%) as yellow gum.

$^1$H NMR (400 MHz, $CDCl_3$) δ 1.52 (9H, s), 2.65 (2H, t, J=6.4 Hz), 3.15-3.25 (4H, m), 3.37 (3H, s), 3.60-3.65 (2H, m), 3.73 (2H, t, J=6.4 Hz), 3.75-3.80 (2H, m), 6.55 (1H, brs), 7.74 (1H, s), 7.84 (1H, d, J=2.0 Hz), 7.96 (1H, d, J=2.8 Hz).

Step 4: Preparation of 1-(4-(5-aminopyridin-3-yl)piperazin-1-yl)-3-methoxypropan-1-one

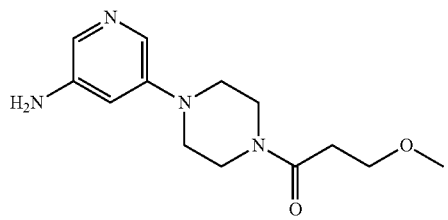 [SMILES: COCCC(=O)N1CCN(c2cncc(N)c2)CC1]

To a solution of tert-butyl (5-(4-(3-methoxypropanoyl)piperazin-1-yl)pyridin-3-yl)carbamate (3.80 g, 10.4 mmol) in EtOAc (20 mL) was added 4N HCl/EtOAc (60 mL) at 20-25° C. Then the resulting reaction mixture was stirred at 20-25° C. for 2 hours. The mixture turned into cloudy from yellow solution. LCMS showed the purity of the desired product is 99% (Rt=0.320 min; MS Calcd: 264.2. MS Found: 265.0 [M+H]$^+$). The reaction mixture was concentrated to give 1-(4-(5-aminopyridin-3-yl)piperazin-1-yl)-3-methoxypropan-1-one (3.40 g, yield: 87%, HCl salt) as a yellow solid.

¹H NMR (400 MHz, DMSO-d₆) δ 2.62 (2H, t, J=6.4 Hz), 3.23 (3H, s), 3.25-3.35 (4H, m), 3.50-3.70 (6H, m), 7.08 (1H, s), 7.46 (1H, d, J=1.6 Hz), 7.72 (1H, d, J=2.0 Hz).
Note: two active protons were not observed.

Step 5: Preparation of 1-(3-((5-(4-(3-methoxypropanoyl)piperazin-1-yl)pyridin-3-yl)amino)-5H-chromeno[4,3-c]pyridin-8-yl)pyrrolidin-2-one

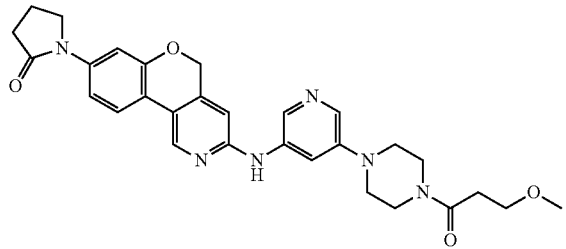 [SMILES: COCCC(=O)N1CCN(c2cncc(Nc3cc4c(cn3)-c3ccc(N5CCCC5=O)cc3OC4)c2)CC1]

A mixture of 1-(3-chloro-5H-chromeno[4,3-c]pyridin-8-yl)pyrrolidin-2-one (60 mg, 0.20 mmol), 1-(4-(5-aminopyridin-3-yl)piperazin-1-yl)-3-methoxypropan-1-one (89 mg, 0.24 mmol, HCl salt), Pd₂(dba)₃ (18 mg, 0.020 mmol), Brettphos (21 mg, 0.040 mmol) and Cs₂CO₃ (325 mg, 0.998 mmol) in anhydrous dioxane (3 mL) was degassed and purged with N₂ for 3 times. Then the resulting reaction mixture was heated at 90° C. for 16 hours under N₂ atmosphere. The reaction mixture turned into brown from red. LCMS showed the purity of the desired product is 21% (Rt=0.708 min; MS Calcd: 528.3. MS Found: 529.2 [M+H]⁺). To the reaction mixture was added water (25 mL), then extracted with EtOAc/THF (25 mL×3, 1/1). The combined organic layer was washed with brine (25 mL), dried over anhydrous Na₂SO₄ and concentrated. The residue was purified by prep-HPLC (0.225% FA as an additive). Most of CH₃CN was removed under reduced pressure and the remaining part was lyophilized to give 1-(3-((5-(4-(3-methoxypropanoyl)piperazin-1-yl)pyridin-3-yl)amino)-5H-chromeno[4,3-c]pyridin-8-yl)pyrrolidin-2-one (18.2 mg, yield: 17%) as a yellow solid.

¹H NMR (400 MHz, DMSO-d₆) δ 2.00-2.11 (2H, m), 2.52-2.54 (2H, m), 2.64 (2H, t, J=6.4 Hz), 3.24 (3H, s), 3.25-3.32 (4H, m), 3.58 (2H, t, J=6.4 Hz), 3.62-3.70 (4H, m), 3.84 (2H, t, J=7.2 Hz), 5.12 (2H, s), 6.76 (1H, s), 7.34 (1H, dd, J=8.4, 2.4 Hz), 7.38 (1H, d, J=2.0 Hz), 7.86-7.91 (2H, m), 7.98 (1H, d, J=2.4 Hz), 8.51 (1H, d, J=1.6 Hz), 8.69 (1H, s), 9.61 (1H, brs).

Example 169: 1-(3-((5-(4-(3-methoxypropanoyl)piperazin-1-yl)pyridin-3-yl)amino)-5-methyl-5H-chromeno[4,3-c]pyridin-8-yl)pyrrolidin-2-one

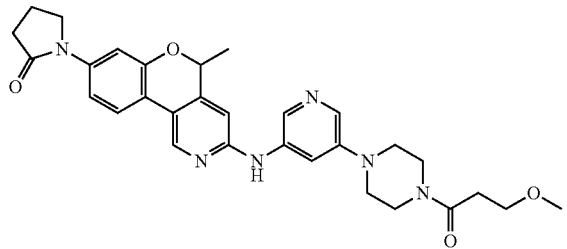 [SMILES: COCCC(=O)N1CCN(c2cncc(Nc3cc4c(cn3)-c3ccc(N5CCCC5=O)cc3OC4C)c2)CC1]

A mixture of 1-(3-chloro-5-methyl-5H-chromeno[4,3-c]pyridin-8-yl)pyrrolidin-2-one (60 mg, 0.19 mmol), 1-(4-(5-aminopyridin-3-yl)piperazin-1-yl)-3-methoxypropan-1-one (85 mg, 0.23 mmol, HCl salt), Pd₂(dba)₃ (17 mg, 0.019 mmol), Brettphos (20 mg, 0.038 mmol) and Cs₂CO₃ (311 mg, 0.953 mmol) in anhydrous dioxane (3 mL) was degassed and purged with N₂ for 3 times. Then the resulting reaction mixture was heated at 90° C. for 16 hours under N₂ atmosphere. The reaction mixture turned into brown from red. LCMS showed the purity of the desired product is 35% (Rt=0.719 min; MS Calcd: 542.3. MS Found: 543.4 [M+H]⁺). To the reaction mixture was added water (25 mL), then extracted with EtOAc/THF (25 mL×3, 1/1). The combined organic layer was washed with brine (25 mL), dried over anhydrous Na₂SO₄ and concentrated. The residue was purified by prep-HPLC (0.225% FA as an additive). Most of CH₃CN was removed under reduced pressure and the remaining part was lyophilized to give 1-(3-((5-(4-(3-methoxypropanoyl)piperazin-1-yl)pyridin-3-yl)amino)-5-methyl-5H-chromeno[4,3-c]pyridin-8-yl)pyrrolidin-2-one (33.7 mg, yield: 33%) as a yellow solid.

¹H NMR (400 MHz, DMSO-d₆) δ 1.54 (3H, d, J=6.4 Hz), 1.90-2.10 (2H, m), 2.52-2.54 (2H, m), 2.64 (2H, t, J=6.4 Hz), 3.24 (3H, s), 3.25-3.32 (4H, m), 3.60 (2H, t, J=6.4 Hz), 3.62-3.70 (4H, m), 3.84 (2H, t, J=7.6 Hz), 5.29 (1H, q, J=6.4 Hz), 6.75 (1H, s), 7.33 (1H, dd, J=8.4, 2.4 Hz), 7.40 (1H, d, J=2.0 Hz), 7.80-7.90 (2H, m), 7.97 (1H, s), 8.48 (1H, s), 8.70 (1H, s), 9.60 (1H, brs).

Example 170: 1-(3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one

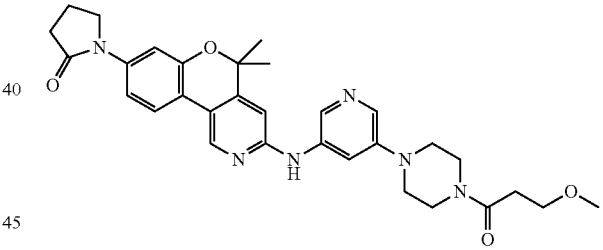

A mixture of 1-(3-chloro-5,5-dimethyl-5H-chromeno[4,3-c]pyridin-8-yl)pyrrolidin-2-one (60 mg, 0.18 mmol), 1-(4-(5-aminopyridin-3-yl)piperazin-1-yl)-3-methoxypropan-1-one (82 mg, 0.22 mmol HCl salt), Pd₂(dba)₃ (17 mg, 0.018 mmol), Brettphos (20 mg, 0.037 mmol) and Cs₂CO₃ (297 mg, 0.912 mmol) in anhydrous dioxane (3 mL) was degassed and purged with N₂ for 3 times. Then the resulting reaction mixture was heated at 90° C. for 16 hours under N₂ atmosphere. The reaction mixture turned into brown from red. LCMS showed the purity of the desired product is 32% (Rt=0.733 min; MS Calcd: 556.3. MS Found: 557.2 [M+H]⁺). To the reaction mixture was added water (25 mL), then extracted with EtOAc (25 mL×3). The combined organic layer was washed with brine (25 mL), dried over anhydrous Na₂SO₄ and concentrated. The residue was purified by prep-HPLC (0.225% FA as an additive). Most of CH₃CN was removed under reduced pressure and the remaining part was lyophilized, then further purified by prep-TLC (DCM/MeOH, 10/1) and lyophilized to give 1-(3-((5-(4-(3-methoxypropanoyl)piperazin-1-yl)pyridin-3- yl)amino)-5,5-dimethyl-5H-chromeno[4,3-c]pyridin-8-yl)pyrrolidin-2-one (15.3 mg, yield: 15%) as an off-white solid.

¹H NMR (400 MHz, DMSO-d₆) δ 1.57 (6H, s), 2.00-2.10 (2H, m), 2.52-2.54 (2H, m), 2.63 (2H, t, J=6.4 Hz), 3.10-3.20 (4H, m), 3.24 (3H, s), 3.58 (2H, t, J=6.4 Hz), 3.60-3.70 (4H, m), 3.85 (2H, t, J=7.2 Hz), 6.79 (1H, s), 7.30 (1H, dd, J=8.4, 2.0 Hz), 7.40 (1H, d, J=2.0 Hz), 7.85-7.92 (3H, m), 8.29 (1H, s), 8.70 (1H, s), 9.32 (1H, brs).

Example 171: 1-(9-fluoro-3-((5-(4-(3-methoxypropanoyl)piperazin-1-yl)pyridin-3-yl)amino)-5H-chromeno[4,3-c]pyridin-8-yl)pyrrolidin-2-one

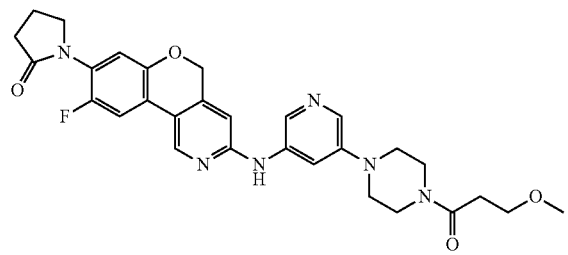 [SMILES: COCCC(=O)N1CCN(c2cncc(Nc3cc4c(cn3)-c3cc(F)c(N5CCCC5=O)cc3OC4)c2)CC1]

A mixture of 1-(3-chloro-9-fluoro-5H-chromeno[4,3-c]pyridin-8-yl)pyrrolidin-2-one (60 mg, 0.19 mmol), 1-(4-(5-aminopyridin-3-yl)piperazin-1-yl)-3-methoxypropan-1-one (84 mg, 0.23 mmol, HCl salt), Pd₂(dba)₃ (17 mg, 0.019 mmol), Brettphos (20 mg, 0.038 mmol) and Cs₂CO₃ (307 mg, 0.941 mmol) in anhydrous dioxane (3 mL) was degassed and purged with N₂ for 3 times. Then the resulting reaction mixture was heated at 90° C. for 16 hours under N₂ atmosphere. The reaction mixture turned into brown from red. LCMS showed the purity of the desired product is 13% (Rt=0.700 min; MS Calcd: 546.2. MS Found: 547.3 [M+H]⁺). To the reaction mixture was added water (25 mL), then extracted with EtOAc/THF (25 mL×3, 1/1). The combined organic layer was washed with brine (25 mL), dried over anhydrous Na₂SO₄ and concentrated. The residue was purified by prep-HPLC (0.225% FA as an additive). Most of CH₃CN was removed under reduced pressure and the remaining part was lyophilized, then further purified by prep-TLC (DCM/MeOH, 10/1) and lyophilized to give 1-(9-fluoro-3-((5-(4-(3-methoxypropanoyl)piperazin-1-yl)pyridin-3-yl)amino)-5H-chromeno[4,3-c]pyridin-8-yl)pyrrolidin-2-one (8.8 mg, yield: 9%) as a yellow solid.

¹H NMR (400 MHz, DMSO-d₆) δ 2.05-2.15 (2H, m), 2.43 (2H, t, J=8.0 Hz), 2.63 (2H, t, J=6.4 Hz), 3.10-3.25 (4+3H, m), 3.58 (2H, t, J=6.4 Hz), 3.60-3.70 (4H, m), 3.77 (2H, t, J=7.2 Hz), 5.11 (2H, s), 6.73 (1H, s), 7.06 (1H, d, J=6.8 Hz), 7.82 (1H, s), 7.86 (1H, d, J=11.6 Hz), 7.93 (1H, d, J=2.4 Hz), 8.34 (1H, d, J=2.0 Hz), 8.71 (1H, s), 9.40 (1H, brs).

Example 172: 1-(9-fluoro-3-((5-(4-(3-methoxypropanoyl)piperazin-1-yl)pyridin-3-yl)amino)-5-methyl-5H-chromeno[4,3-c]pyridin-8-yl)pyrrolidin-2-one

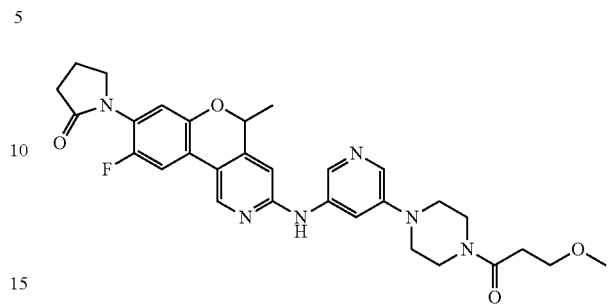

A mixture of 1-(3-chloro-9-fluoro-5-methyl-5H-chromeno[4,3-c]pyridin-8-yl)pyrrolidin-2-one (60 mg, 0.18 mmol), 1-(4-(5-aminopyridin-3-yl)piperazin-1-yl)-3-methoxypropan-1-one (81 mg, 0.22 mmol, HCl salt), Pd₂(dba)₃ (17 mg, 0.018 mmol), Brettphos (19 mg, 0.036 mmol) and Cs₂CO₃ (294 mg, 0.902 mmol) in anhydrous dioxane (3 mL) was degassed and purged with N₂ for 3 times. Then the resulting reaction mixture was heated at 90° C. for 16 hours under N₂ atmosphere. The reaction mixture turned into brown from red. LCMS showed the purity of the desired product is 25% (Rt=0.719 min; MS Calcd: 560.3. MS Found: 561.2 [M+H]⁺). To the reaction mixture was added water (25 mL), then extracted with EtOAc/THF (25 mL×3, 1/1). The combined organic layer was washed with brine (25 mL), dried over anhydrous Na₂SO₄ and concentrated. The residue was purified by prep-HPLC (0.225% FA as an additive). Most of CH₃CN was removed under reduced pressure and the remaining part was lyophilized to give 1-(9-fluoro-3-((5-(4-(3-methoxypropanoyl)piperazin-1-yl)pyridin-3-yl)amino)-5-methyl-5H-chromeno[4,3-c]pyridin-8-yl)pyrrolidin-2-one (21.8 mg, yield: 22%) as a yellow solid.

¹H NMR (400 MHz, DMSO-d₆) δ 1.54 (3H, d, J=6.8 Hz), 2.05-2.15 (2H, m), 2.44 (2H, t, J=8.4 Hz), 2.64 (2H, t, J=6.8 Hz), 3.24 (3H, s), 3.30-3.40 (4H, m), 3.66 (2H, t, J=6.4 Hz), 3.65-3.70 (4H, m), 3.75-3.80 (2H, m), 5.32 (1H, q, J=6.4 Hz), 6.80 (1H, s), 7.08 (1H, d, J=6.8 Hz), 7.90 (1H, d, J=11.6 Hz), 7.95 (1H, s), 8.08 (1H, d, J=2.4 Hz), 8.70 (1H, d, J=1.6 Hz), 8.77 (1H, s), 10.04 (1H, brs).

Example 173: 1-(9-fluoro-3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one

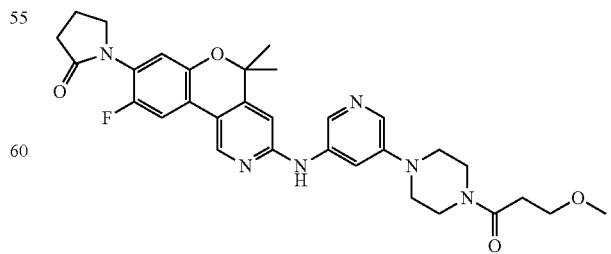

A mixture of 1-(3-chloro-9-fluoro-5,5-dimethyl-5H-chromeno[4,3-c]pyridin-8-yl)pyrrolidin-2-one (60 mg, 0.17 mmol), 1-(4-(5-aminopyridin-3-yl)piperazin-1-yl)-3-methoxypropan-1-one (78 mg, 0.21 mmol, HCl salt), Pd$_2$(dba)$_3$ (16 mg, 0.017 mmol), Brettphos (19 mg, 0.035 mmol) and Cs$_2$CO$_3$ (282 mg, 0.865 mmol) in anhydrous dioxane (3 mL) was degassed and purged with N$_2$ for 3 times. Then the resulting reaction mixture was heated at 90° C. for 16 hours under N$_2$ atmosphere. The reaction mixture turned into brown from red. LCMS showed the purity of the desired product is 20% (Rt=0.742 min; MS Calcd: 574.3. MS Found: 575.3 [M+H]$^+$). To the reaction mixture was added water (25 mL), then extracted with EtOAc (25 mL×3). The combined organic layer was washed with brine (25 mL), dried over anhydrous Na$_2$SO$_4$ and concentrated. The residue was purified by prep-HPLC (0.225% FA as an additive). Most of CH$_3$CN was removed under reduced pressure and the remaining part was lyophilized to give 1-(9-fluoro-3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one (22.3 mg, yield: 22%) as a yellow solid.

$^1$H NMR (400 MHz, DMSO-d$_6$) δ 1.57 (6H, s), 2.05-2.15 (2H, m), 2.43 (2H, t, J=8.0 Hz), 2.64 (2H, t, J=6.8 Hz), 3.24 (3H, s), 3.30-3.40 (4H, m), 3.59 (2H, t, J=6.4 Hz), 3.60-3.70 (4H, m), 3.78 (2H, d, J=6.8 Hz), 6.83 (1H, s), 7.05 (1H, d, J=6.8 Hz), 7.85-7.90 (2H, m), 8.02 (1H, d, J=2.0 Hz), 8.53 (1H, s), 8.78 (1H, s), 9.77 (1H, brs).

Example 174: (E)-4-(4-(dimethylamino)but-2-enamido)-N-(5-((5-methyl-8-(2-oxopyrrolidin-1-yl)-5H-chromeno[4,3-c]pyridin-3-yl)amino)pyridin-3-yl)benzamide 0.944 mmol) and EDC.HCl (271 mg, 1.42 mmol), the reaction mixture was stirred at 50° C. for 2 hours to give a brown solution. LCMS showed the purity of the desired product is 43% (Rt=0.820 min; MS Calcd: 606.3. MS Found: 607.4 [M+H]$^+$). The mixture was concentrated under reduced pressure to give a residue. The residue was purified by washing with DCM/MeOH (10 mL/5 mL) twice to give tert-butyl (4-((5-((5-methyl-8-(2-oxopyrrolidin-1-yl)-5H-chromeno[4,3-c]pyridin-3-yl)amino)pyridin-3-yl)carbamoyl)phenyl)carbamate (300 mg, yield: 38%) as a brown solid.

$^1$H NMR (400 MHz, DMSO-d$_6$) δ 1.51 (9H, s), 1.57 (3H, d, J=6.4 Hz), 2.03-2.11 (2H, m), 2.49-2.51 (2H, m), 3.86 (2H, t, J=8.0 Hz), 5.34 (1H, q, J=6.8 Hz), 6.88 (1H, s), 7.35 (1H, dd, J=8.8, 2.0 Hz), 7.42 (1H, d, J=2.0 Hz), 7.65 (2H, d, J=8.8 Hz), 7.93 (1H, d, J=8.8 Hz), 7.98 (2H, d, J=8.4 Hz), 8.75-8.82 (2H, m), 8.90 (1H, s), 9.10 (1H, s), 9.78 (1H, brs), 10.23 (1H, brs), 10.80 (1H, brs).

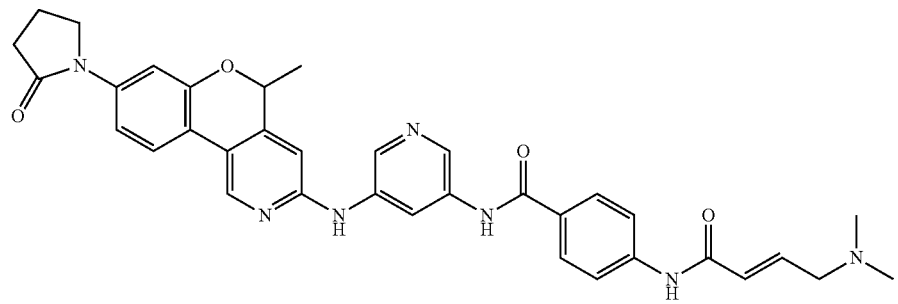 [SMILES: CC1Oc2cc(N3CCCC3=O)ccc2-c2cnc(Nc3cncc(NC(=O)c4ccc(NC(=O)/C=C/CN(C)C)cc4)c3)cc21]

Step 1: Preparation of tert-butyl (4-((5-((5-methyl-8-(2-oxopyrrolidin-1-yl)-5H-chromeno[4,3-c]pyridin-3-yl)amino)pyridin-3-yl)carbamoyl)phenyl)carbamate Step 2: Preparation of 4-amino-N-(5-((5-methyl-8-(2-oxopyrrolidin-1-yl)-5H-chromeno[4,3-c]pyridin-3-yl)amino)pyridin-3-yl)benzamide

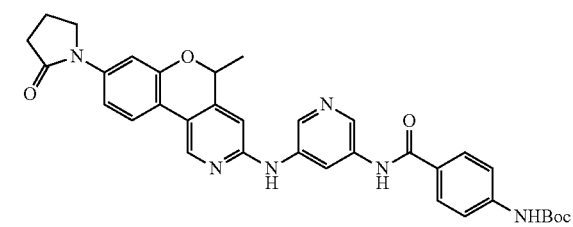 [SMILES: CC1Oc2cc(N3CCCC3=O)ccc2-c2cnc(Nc3cncc(NC(=O)c4ccc(NC(=O)OC(C)(C)C)cc4)c3)cc21]

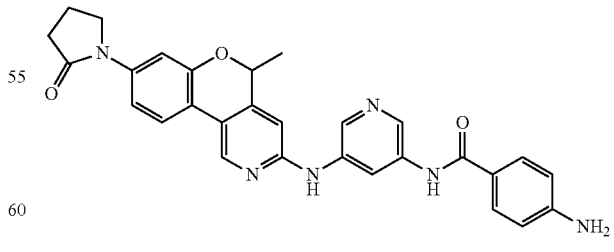

To a mixture of 1-(3-((5-aminopyridin-3-yl)amino)-5-methyl-5H-chromeno[4,3-c]pyridin-8-yl)pyrrolidin-2-one (400 mg, 0.944 mmol, HCl salt) in pyridine (10 mL) was added 4-((tert-butoxycarbonyl)amino)benzoic acid (224 mg, A mixture of tert-butyl (4-((5-((5-methyl-8-(2-oxopyrrolidin-1-yl)-5H-chromeno[4,3-c]pyridin-3-yl)amino)pyridin-3-yl)carbamoyl)phenyl)carbamate (300 mg, 0.494 mmol) in EtOAc (5 mL) was added HCl/EtOAc (10 mL, 4 M in EtOAc), the reaction mixture was stirred at 30° C. for 2 hours to give a yellow suspension. LCMS showed the purity of product is 73% (Rt=0.737 min; MS Calcd: 506.2. MS Found: 507.5 [M+H]⁺). The mixture was concentrated under reduced pressure to give 4-amino-N-(5-((5-methyl-8-(2-oxopyrrolidin-1-yl)-5H-chromeno[4,3-c]pyridin-3-yl)amino)pyridin-3-yl)benzamide (250 mg, crude, HCl salt) as a yellow solid.

Step 3: Preparation of (E)-4-(4-(dimethylamino)but-2-enamido)-N-(5-((5-methyl-8-(2-oxopyrrolidin-1-yl)-5H-chromeno[4,3-c]pyridin-3-yl)amino)pyridin-3-yl)benzamide

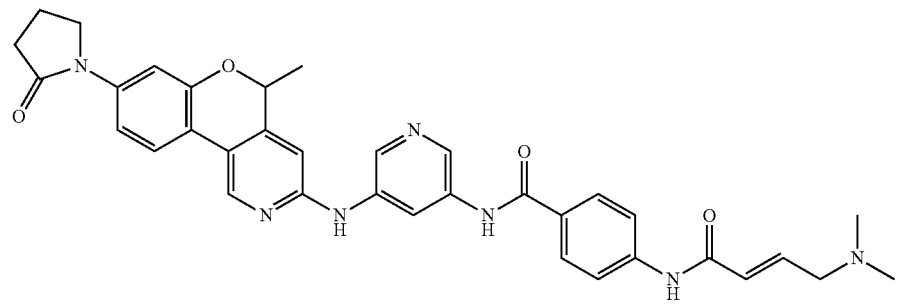 [SMILES: CC1Oc2cc(N3CCCC3=O)ccc2-c2cnc(Nc3cncc(NC(=O)c4ccc(NC(=O)/C=C/CN(C)C)cc4)c3)cc21]

A mixture of 4-amino-N-(5-((5-methyl-8-(2-oxopyrrolidin-1-yl)-5H-chromeno[4,3-c]pyridin-3-yl)amino)pyridin-3-yl)benzamide (100 mg, 0.184 mmol, HCl salt) in pyridine (5 mL) was added (E)-4-(dimethylamino)but-2-enoic acid (61 mg, 0.368 mmol, HCl salt), EDCI (71 mg, 0.368 mmol) and 4 A molecular sieve (100 mg), the reaction mixture was stirred at 25° C. for 4 hours to give a brown suspension. LCMS showed the purity of product is 58% (Rt=0.714 min; MS Calcd: 617.3. MS Found: 618.4 [M+H]⁺). The mixture was concentrated under reduced pressure to give a residue. The residue was purified by prep-HPLC (0.05% NH₃.H₂O as an additive), 20 mg was obtained, but HNMR showed it is impure. The impure product was further purified by prep-HPLC (0.225% FA as an additive) to give (E)-4-(4-(dimethylamino)but-2-enamido)-N-(5-((5-methyl-8-(2-oxopyrrolidin-1-yl)-5H-chromeno[4,3-c]pyridin-3-yl)amino)pyridin-3-yl)benzamide (8.6 mg, yield for two steps: 8%) as a pale yellow solid.

¹H NMR (400 MHz, DMSO-d₆) δ 1.55 (3H, d, J=6.4 Hz), 2.03-2.11 (2H, m), 2.49-2.51 (2H, m), 2.81 (6H, s), 3.85 (2H, t, J=6.8 Hz), 3.98 (2H, d, J=6.8 Hz), 5.28 (1H, q, J=6.8 Hz), 6.52 (1H, d, J=15.6 Hz), 6.71-6.86 (2H, m), 7.32 (1H, d, J=8.8 Hz), 7.39 (1H, s), 7.74-7.89 (3H, m), 8.01 (2H, d, J=8.0 Hz), 8.50 (1H, s), 8.62-8.73 (3H, m), 9.57 (1H, brs), 10.38 (1H, brs), 10.71 (1H, brs).

Example 175: 4-(4-(dimethylamino)butanamido)-N-(5-((5-methyl-8-(2-oxopyrrolidin-1-yl)-5H-chromeno[4,3-c]pyridin-3-yl)amino)pyridin-3-yl)benzamide

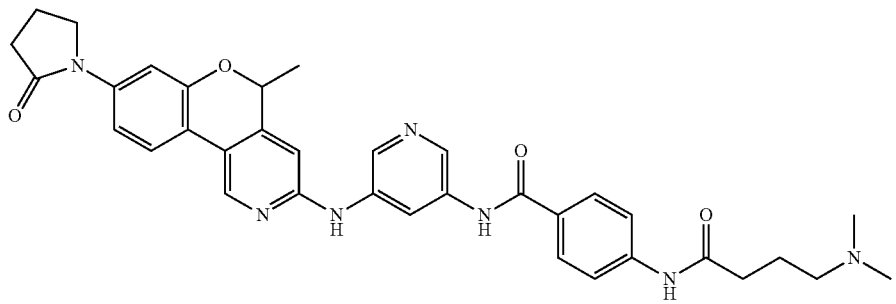 [SMILES: CC1Oc2cc(N3CCCC3=O)ccc2-c2cnc(Nc3cncc(NC(=O)c4ccc(NC(=O)CCCN(C)C)cc4)c3)cc21]

To a mixture of 1-(3-((5-aminopyridin-3-yl)amino)-5-methyl-5H-chromeno[4,3-c]pyridin-8-yl)pyrrolidin-2-one (80 mg, 0.20 mmol, 0.13 HCl) and 4-(4-(dimethylamino)butanamido)benzoic acid (128 mg, 0.510 mmol) in pyridine (3 mL) was added EDCI (78 mg, 0.41 mmol) at 28° C. Then the reaction mixture was stirred at 28° C. for 22 hours. A yellow solution was formed. LCMS showed that the purity of desired product is 95.8% (Rt=0.600 min; MS Calcd: 619.2. MS Found: 620.1 [M+H]$^+$). The reaction mixture was concentrated to dryness. Then the residue was purified by prep-HPLC (0.1% TFA as an additive) and lyophilized to give 4-(4-(dimethylamino)butanamido)-N-(5-((5-methyl-8-(2-oxopyrrolidin-1-yl)-5H-chromeno[4,3-c]pyridin-3-yl)amino)pyridin-3-yl)benzamide (23.6 mg, yield: 18%) as a yellow solid.

$^1$H NMR (400 MHz, DMSO-d$_6$) δ 1.56 (3H, d, J=6.4 Hz), 1.91-2.01 (2H, m), 2.03-2.10 (2H, m), 2.47 (4H, m), 2.81 (6H, d, J=3.6 Hz), 3.11 (2H, d, J=4.8 Hz), 3.85 (2H, d, J=7.2 Hz), 5.32 (1H, q, J=6.4 Hz), 6.84 (1H, s), 7.35 (1H, d, J=8.4 Hz), 7.41 (1H, d, J=2.0 Hz), 7.78 (2H, d, J=8.8 Hz), 7.91 (1H, d, J=3.6 Hz), 8.01 (2H, d, J=8.8 Hz), 8.68 (1H, brs), 8.73 (1H, s), 8.85 (1H, s), 8.97 (1H, brs), 10.00 (1H, brs), 10.39 (1H, brs), 10.68 (1H, brs).

Example 176: (E)-4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)but-2-enamide

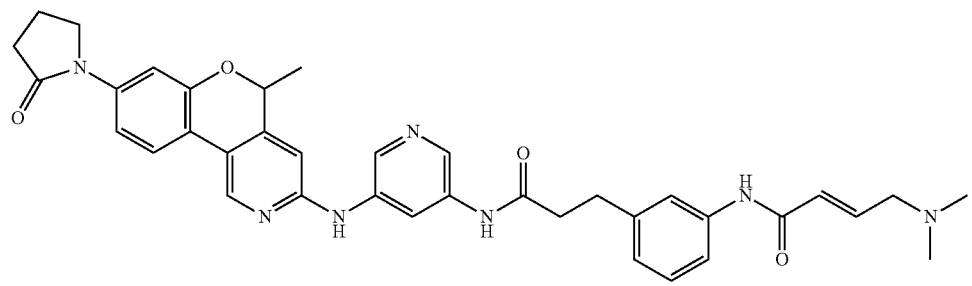 [SMILES: CC1Oc2cc(N3CCCC3=O)ccc2-c2cnc(Nc3cncc(NC(=O)CCc4cccc(NC(=O)/C=C/CN(C)C)c4)c3)cc21]

Step 1: Preparation of tert-butyl (3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)carbamate

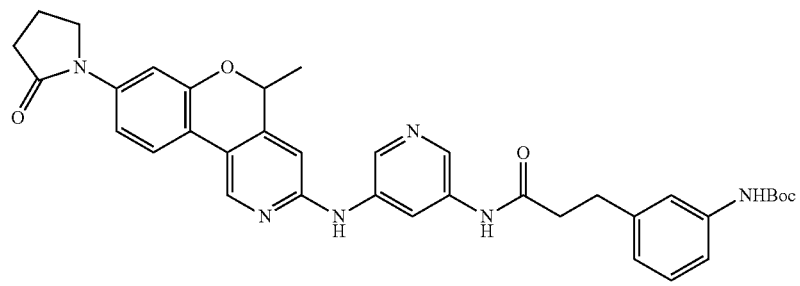 [SMILES: CC1Oc2cc(N3CCCC3=O)ccc2-c2cnc(Nc3cncc(NC(=O)CCc4cccc(NC(=O)OC(C)(C)C)c4)c3)cc21]

To a mixture of 1-(3-((5-aminopyridin-3-yl)amino)-5-methyl-5H-chromeno[4,3-c]pyridin-8-yl)pyrrolidin-2-one (160 mg, 0.377 mmol, HCl salt) in DMF (15 mL) was added 3-(3-((tert-butoxycarbonyl)amino)phenyl)propanoic acid (100 mg, 0.377 mmol), HOBt (102 mg, 0.754 mmol), EDCI (145 mg, 0.754 mmol) and TEA (114 mg, 1.13 mmol), the reaction mixture was stirred at 50° C. for 2 hours to give a brown solution. LCMS showed the purity of the desired product is 48% (Rt=0.769 min; MS Calcd: 634.3. MS Found: 635.2 [M+H]$^+$). The mixture was diluted with water (15 mL), then extracted with EtOAc (20 mL×2), the combined extracts was washed with brine (30 mL×2), dried over Na$_2$SO$_4$, filtered and concentrated under reduced pressure to give a residue. The residue was purified by Combi Flash (EtOAc/MeOH=100/1 to 95/5 to 10/1) to give tert-butyl (3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)carbamate (100 mg, yield: 42%) as a yellow solid.

$^1$H NMR (400 MHz, DMSO-d$_6$) δ 1.47 (9H, s), 1.55 (3H, d, J=6.8 Hz), 2.03-2.11 (2H, m), 2.49-2.51 (2H, m), 2.65-2.71 (2H, m), 2.89-2.93 (2H, m), 3.82-3.89 (2H, m), 5.31 (1H, q, J=6.4 Hz), 6.82 (1H, s), 6.87 (1H, d, J=7.2 Hz), 7.13-7.24 (2H, m), 7.35 (1H, dd, J=8.4, 2.0 Hz), 7.41 (1H, d, J=2.0 Hz), 7.46 (1H, s), 7.92 (1H, d, J=8.8 Hz), 8.52 (1H, s), 8.60 (1H, d, J=2.0 Hz), 8.71 (1H, s), 8.88 (1H, s), 9.30 (1H, brs), 9.95 (1H, brs), 10.54 (1H, brs).

Step 2: Preparation of 3-(3-aminophenyl)-N-(5-((5-methyl-8-(2-oxopyrrolidin-1-yl)-5H-chromeno[4,3-c]pyridin-3-yl)amino)pyridin-3-yl)propanamide

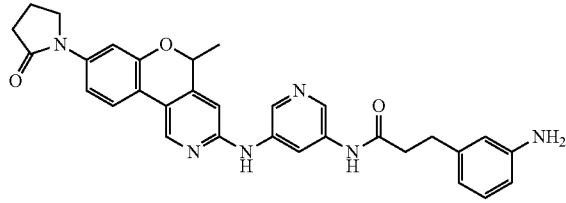 [SMILES: CC1Oc2cc(N3CCCC3=O)ccc2-c2cnc(Nc3cncc(NC(=O)CCc4cccc(N)c4)c3)cc21]

A mixture of tert-butyl (3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)carbamate (100 mg, 0.158 mmol) in EtOAc (5 mL) was added HCl/EtOAc (5 mL, 4 M in EtOAc), the reaction mixture was stirred at 30° C. for 2 hours to give a yellow suspension. LCMS showed the purity of product is 88% (Rt=0.682 min; MS Calcd: 534.2. MS Found: 535.0 [M+H]$^+$). The mixture was concentrated under reduced pressure to give 3-(3-aminophenyl)-N-(5-((5-methyl-8-(2-oxopyrrolidin-1-yl)-5H-chromeno[4,3-c]pyridin-3-yl)amino)pyridin-3-yl)propanamide (90 mg, crude, HCl salt) as a yellow solid.

Step 3: Preparation of (E)-4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)but-2-enamide

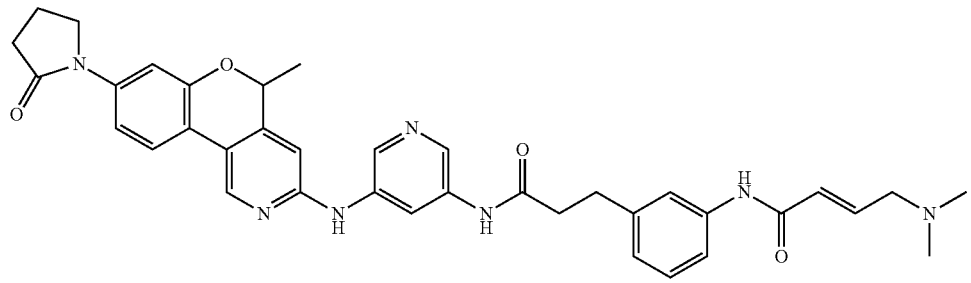 [SMILES: CC1Oc2cc(N3CCCC3=O)ccc2-c2cnc(Nc3cncc(NC(=O)CCc4cccc(NC(=O)/C=C/CN(C)C)c4)c3)cc21]

A mixture of 3-(3-aminophenyl)-N-(5-((5-methyl-8-(2-oxopyrrolidin-1-yl)-5H-chromeno[4,3-c]pyridin-3-yl)amino)pyridin-3-yl)propanamide (50 mg, 0.093 mmol) in pyridine (5 mL) was added (E)-4-(dimethylamino)but-2-enoic acid (31 mg, 0.19 mmol, HCl salt), EDCI (36 mg, 0.19 mmol), the reaction mixture was stirred at 25° C. for 1 hour to give a yellow suspension. LCMS showed the purity of product is 44% (Rt=1.613 min; MS Calcd: 645.3. MS Found: 646.3 [M+H]$^+$). The mixture was concentrated under reduced pressure to give a residue. The residue was purified by prep-HPLC (0.225% FA as an additive) to give (E)-4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)but-2-enamide (11.4 mg, yield for two steps: 18%, FA salt) as a brown solid.

$^1$H NMR (400 MHz, DMSO-d$_6$) δ 1.54 (3H, d, J=6.4 Hz), 2.03-2.11 (2H, m), 2.49-2.51 (2H, m), 2.68 (2H, t, J=8.0 Hz), 2.75 (6H, s), 2.92 (2H, t, J=8.0 Hz), 3.81-3.90 (4H, m), 5.27 (1H, q, J=6.0 Hz), 6.45 (1H, d, J=15.2 Hz), 6.67-6.75 (2H, m), 7.01 (1H, d, J=7.2 Hz), 7.27 (1H, t, J=8.0 Hz), 7.33 (1H, dd, J=8.8, 2.0 Hz), 7.39 (1H, d, J=2.4 Hz), 7.51 (1H, d, J=8.8 Hz), 7.58 (1H, s), 7.89 (1H, d, J=8.8 Hz), 8.33 (1H, s), 8.50 (1H, s), 8.58 (1H, s), 8.65 (1H, s), 9.46 (1H, brs), 10.11 (1H, brs), 10.27 (1H, brs).

Example 177: 4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)butanamide

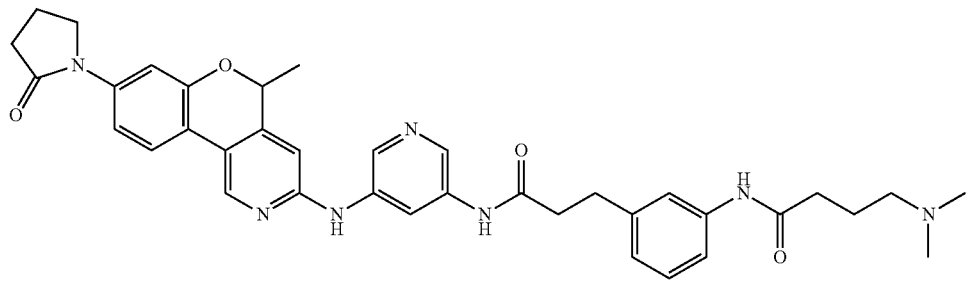 [SMILES: CC1Oc2cc(N3CCCC3=O)ccc2-c2cnc(Nc3cncc(NC(=O)CCc4cccc(NC(=O)CCCN(C)C)c4)c3)cc21]

A mixture of 3-(3-aminophenyl)-N-(5-((5-methyl-8-(2-oxopyrrolidin-1-yl)-5H-chromeno[4,3-c]pyridin-3-yl)amino)pyridin-3-yl)propanamide (130 mg, 0.243 mmol) in pyridine (5 mL) was added 4-(dimethylamino)butanoic acid (82 mg, 0.49 mmol, HCl salt), EDCI (93 mg, 0.49 mmol), the reaction mixture was stirred at 25° C. for 2 hours to give a yellow suspension. LCMS showed the purity of product is 55% (Rt=1.590 min; MS Calcd: 647.3; MS Found: 648.3 [M+H]$^+$). The mixture was concentrated under reduced pressure to give a crude product. MeOH (10 mL) was added. Some red solid was precipitated out and filtered. The filtrate was concentrated under reduced pressure to give a residue. The residue was purified prep-HPLC (0.05% NH$_3$.H$_2$O as an additive) purification to give an impure product. The impure product was further purified by prep-HPLC (0.225% FA as an additive) to give 4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)butanamide (14.0 mg, yield for two steps: 8%, 2 FA salt) as an orange solid.

$^1$H NMR (400 MHz, DMSO-d$_6$) δ 1.54 (3H, d, J=6.4 Hz), 1.65-1.74 (2H, m), 2.02-2.09 (2H, m), 2.14 (6H, s), 2.25 (2H, t, J=7.2 Hz), 2.29-2.34 (2H, m), 2.49-2.51 (2H, m), 2.61-2.69 (2H, m), 2.88 (2H, t, J=8.0 Hz), 3.84 (2H, t, J=8.0 Hz), 5.27 (1H, q, J=6.8 Hz), 6.75 (1H, s), 6.93 (1H, d, J=6.8 Hz), 7.20 (1H, t, J=8.0 Hz), 7.32 (1H, dd, J=8.8, 2.0 Hz), 7.36-7.42 (2H, m), 7.54 (1H, s), 7.88 (1H, d, J=8.8 Hz), 8.31 (1H, d, J=2.4 Hz), 8.48 (1H, t, J=2.0 Hz), 8.59 (1H, d, J=2.0 Hz), 8.65 (1H, s), 9.44 (1H, brs), 9.86 (1H, brs), 10.09 (1H, brs).

Example 178: (E)-4-(dimethylamino)-N-(2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide Step 1: Preparation of 1-(5-((5-methyl-8-(2-oxopyr-rolidin-1-yl)-5H-chromeno[4,3-c]pyridin-3-yl)amino)pyridin-3-yl)-3-(3-nitrobenzyl)imidazolidin-2-one

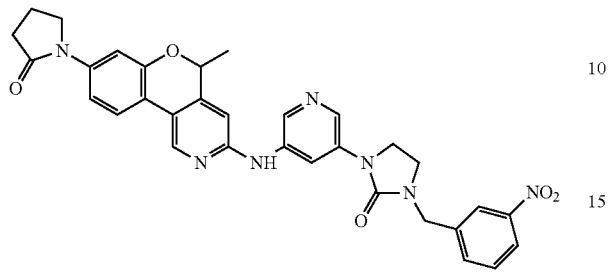

First Batch:
To a mixture of 1-(3-amino-5-methyl-5H-chromeno[4,3-c]pyridin-8-yl)pyrrolidin-2-one (80 mg, 0.24 mmol, HCl salt) in dioxane (4 mL) was added 1-(5-bromopyridin-3-yl)-3-(3-nitrobenzyl)imidazolidin-2-one (109 mg, 0.289 mmol), Pd(dba)$_2$ (14 mg, 0.024 mmol), Brettphos (13 mg, 0.024 mmol) and Cs$_2$CO$_3$ (196 mg, 0.603 mmol), the reaction mixture was purged in N$_2$ atmosphere for 3 times and stirred at 50° C. for 1 hour, then heated to 100° C. under N$_2$ atmosphere and stirred for another 15 hours to give a yellow suspension. LCMS showed the purity of the desired product is 70% (Rt=0.762 min; MS Calcd: 591.2; MS Found: 592.2 [M+H]$^+$). The mixture was combined with next page.

Second Batch:
To a mixture of 1-(3-amino-5-methyl-5H-chromeno[4,3-c]pyridin-8-yl)pyrrolidin-2-one (400 mg, 1.21 mmol, HCl salt) in dioxane (4 mL) was added 1-(5-bromopyridin-3-yl)-3-(3-nitrobenzyl)imidazolidin-2-one (546 mg, 1.45 mmol), Pd(dba)$_2$ (69 mg, 0.12 mmol), Brettphos (65 mg, 0.12 mmol) and Cs$_2$CO$_3$ (786 mg, 2.41 mmol), the reaction mixture was purged in N$_2$ atmosphere for 3 times and stirred at 50° C. for 1 hour, then heated to 100° C. under N$_2$ atmosphere and stirred for another 15 hours to give a yellow suspension. LCMS showed the purity of the desired product is 84% (Rt=0.762 min; MS Calcd: 591.2. MS Found: 592.2 [M+H]$^+$). The mixture and the above batch were combined and filtered. The filter cake was washed with DCM (15 mL×2). The filtrate was concentrated under reduced pressure to give a residue. The residue was washed with MeOH/EtOAc (1/2, 30 mL) to give 1-(5-((5-methyl-8-(2-oxopyr-rolidin-1-yl)-5H-chromeno[4,3-c]pyridin-3-yl)amino)pyridin-3-yl)-3-(3-nitrobenzyl)imidazolidin-2-one (710 mg, average yield: 83%) as a yellow solid.

$^1$H NMR (400 MHz, DMSO-d$_6$) δ 1.54 (3H, d, J=6.4 Hz), 2.03-2.11 (2H, m), 2.49-2.51 (2H, m), 3.48 (2H, t, J=8.0 Hz), 3.79-3.94 (4H, m), 4.58 (2H, s), 5.28 (1H, q, J=6.8 Hz), 6.77 (1H, s), 7.32 (1H, dd, J=8.8, 2.4 Hz), 7.40 (1H, d, J=2.0 Hz), 7.70 (1H, t, J=8.0 Hz), 7.82 (1H, d, J=7.6 Hz), 7.89 (1H, d, J=8.8 Hz), 8.14-8.20 (2H, m), 8.33 (1H, d, J=2.4 Hz), 8.51 (1H, d, J=2.0 Hz), 8.64 (1H, d, J=2.0 Hz), 8.67 (1H, s), 9.47 (1H, brs).

Step 2: Preparation of 1-(3-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one

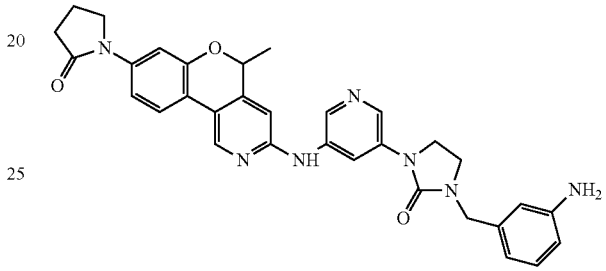

A mixture of 1-(5-((5-methyl-8-(2-oxopyrrolidin-1-yl)-5H-chromeno[4,3-c]pyridin-3-yl)amino)pyridin-3-yl)-3-(3-nitrobenzyl)imidazolidin-2-one (300 mg, 0.507 mmol) in THF (400 mL) was added Pd/C (100 mg, 10% purity, 50% wet), the resulting mixture was purged with H2 atmosphere for 3 times, then stirred at 25° C. under H2 balloon (15 Psi) for 3 hours to give a black suspension. LCMS showed the purity of the desired product is 37% (Rt=0.715 min; MS Calcd: 561.3. MS Found: 562.5 [M+H]$^+$). The mixture was filtered. The filtrate was concentrated under reduced pressure to give 1-(3-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one (220 mg, yield: 55%) as a yellow solid.

Step 3: Preparation of tert-butyl (2-((3-((3-(5-((5-methyl-8-(2-oxopyrrolidin-1-yl)-5H-chromeno[4,3-c]pyridin-3-yl)amino)pyridin-3-yl)-2-oxoimidazoli-din-1-yl)methyl)phenyl)amino)-2-oxoethyl)carbamate

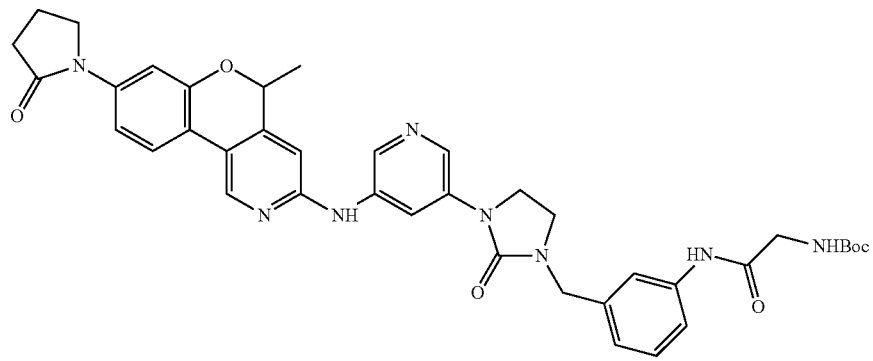 [SMILES: CC1Oc2cc(N3CCCC3=O)ccc2-c2cnc(Nc3cncc(N4CCN(Cc5cccc(NC(=O)CNC(=O)OC(C)(C)C)c5)C4=O)c3)cc21]

To a mixture of 1-(3-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one (220 mg, 0.392 mmol) in DMF (10 mL) was added Boc-gly-OH (343 mg, 1.96 mmol), TEA (159 mg, 1.57 mmol), EDCI (225 mg, 1.18 mmol) and HOBt (159 mg, 1.18 mmol), the reaction mixture was stirred at 25° C. for 2 hours to give a brown solution. LCMS showed the starting material was remained, then heated to 100° C. and stirred for another 46 hours to give a brown solution. LCMS showed the purity of the desired product is 50% (Rt=0.791 min; MS Calcd: 718.3. MS Found: 719.4 [M+H]$^+$). The mixture was extracted with EtOAc (30 mL×2). The combined extracts was washed with brine (40 mL×2), dried over $Na_2SO_4$, filtered and concentrated under reduced pressure to give a residue. The residue and another batch ES6958-291 were combined and purified by Combi Flash (DCM/MeOH=100/1 to 95/5 to 10/1) to give tert-butyl (2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)carbamate (120 mg, average yield: 30%) as an off-white solid.

$^1$H NMR (400 MHz, DMSO-d$_6$) δ 1.38 (9H, s), 1.54 (3H, d, J=6.4 Hz), 2.03-2.11 (2H, m), 2.49-2.51 (2H, m), 3.34-3.48 (2H, m), 3.71 (2H, d, J=6.4 Hz), 3.80-3.94 (4H, m), 4.40 (2H, s), 5.28 (1H, q, J=6.8 Hz), 6.41-6.52 (1H, m), 6.76 (1H, s), 6.95-7.09 (2H, m), 7.25-7.36 (2H, m), 7.40 (1H, d, J=2.4 Hz), 7.51 (1H, s), 7.57 (1H, d, J=8.4 Hz), 7.89 (1H, d, J=8.8 Hz), 8.34 (1H, d, J=2.0 Hz), 8.50 (1H, d, J=2.0 Hz), 8.58-8.70 (1H, m), 9.45 (1H, brs), 9.96 (1H, brs).

Step 4: Preparation of 2-amino-N-(3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide

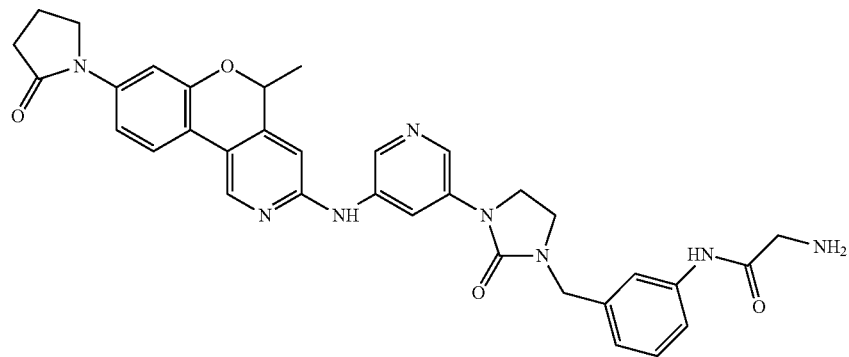 [SMILES: CC1Oc2cc(N3CCCC3=O)ccc2-c2cnc(Nc3cncc(N4CCN(Cc5cccc(NC(=O)CN)c5)C4=O)c3)cc21]

To a mixture of tert-butyl (2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)carbamate (120 mg, 0.167 mmol) in EtOAc (10 mL) was added EtOAc/HCl (10 mL, 4 M in EtOAc), the reaction was stirred at 25° C. for 1 hour to give an off-white suspension. LCMS showed the purity of the desired product is 32% (Rt=1.565 min; MS Calcd: 618.3. MS Found: 619.2 [M+H]$^+$). The mixture was concentrated under reduced pressure to give 2-amino-N-(3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide (100 mg, HCl salt) as an off-white solid.

$^1$H NMR (400 MHz, DMSO-d$_6$) δ 1.55 (3H, d, J=6.4 Hz), 2.03-2.11 (2H, m), 2.49-2.51 (2H, m), 3.52-3.56 (2H, m), 3.74-3.80 (2H, m), 3.86 (2H, t, J=7.6 Hz), 3.91-3.99 (2H, m), 4.46 (2H, s), 5.35 (1H, q, J=6.4 Hz), 6.89 (1H, s), 7.08-7.12 (1H, m), 7.33-7.44 (3H, m), 7.55-7.61 (1H, m), 7.94 (1H, d, J=8.8 Hz), 8.12-8.20 (1H, m), 8.65-8.72 (2H, m), 8.78 (1H, s), 9.14 (1H, s), 10.46 (1H, brs), 10.63 (1H, brs).

Note: Two active protons were not observed.

Step 5: Preparation of (E)-4-(dimethylamino)-N-(2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide

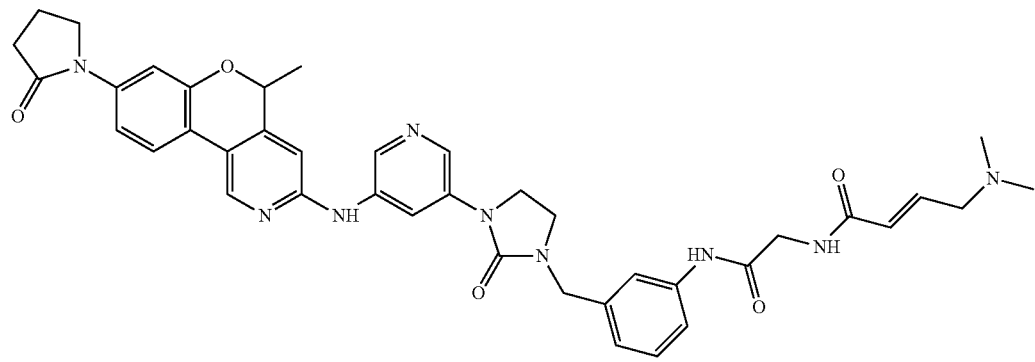 [SMILES: CC1Oc2cc(N3CCCC3=O)ccc2-c2cnc(Nc3cncc(N4CCN(Cc5cccc(NC(=O)CNC(=O)/C=C/CN(C)C)c5)C4=O)c3)cc21]

To a mixture of 2-amino-N-(3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide (50 mg, 0.081 mmol) in pyridine (5 mL) was added (E)-4-(dimethylamino)but-2-enoic acid (54 mg, 0.32 mmol, HCl salt), 4A molecular sieve (100 mg) and EDCI (31 mg, 0.161 mmol), the reaction mixture was stirred at 25° C. for 4 hours to give a red suspension. The reaction was repeated once. LCMS showed the purity of the desired product is 14% (Rt=1.585 min; MS Calcd: 729.3. MS Found: 730.3 [M+H]$^+$). The two batches were combined and filtered. The filter cake was washed with MeOH (10 mL×2). The filtrate was concentrated under reduced pressure to give a residue. The residue was purified by prep-HPLC (0.1% TFA as an additive) to give (E)-4-(dimethylamino)-N-(2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide (32.3 mg, yield for two steps: 21%, TFA salt) as an off-white solid.

$^1$H NMR (400 MHz, DMSO-d$_6$) δ 1.54 (3H, d, J=6.4 Hz), 2.02-2.13 (2H, m), 2.49-2.53 (2H, m), 2.78 (6H, s), 3.41-3.51 (2H, m), 3.84 (2H, t, J=8.0 Hz), 3.90 (2H, t, J=8.4 Hz), 3.97 (2H, d, J=6.0 Hz), 4.31 (2H, s), 4.41 (2H, s), 5.31 (1H, q, J=6.4 Hz), 6.11-6.20 (1H, m), 6.30 (1H, d, J=11.6 Hz), 6.80 (1H, s), 7.03 (1H, d, J=7.6 Hz), 7.30-7.36 (2H, m), 7.40 (1H, d, J=2.0 Hz), 7.51-7.60 (2H, m), 7.91 (1H, d, J=8.8 Hz), 8.54 (1H, d, J=1.6 Hz), 8.58 (1H, d, J=2.0 Hz), 8.70-8.76 (2H, m), 8.89 (1H, brs), 9.92 (1H, brs), 10.15 (1H, brs).

Example 179: (E)-4-(dimethylamino)-N-(2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide

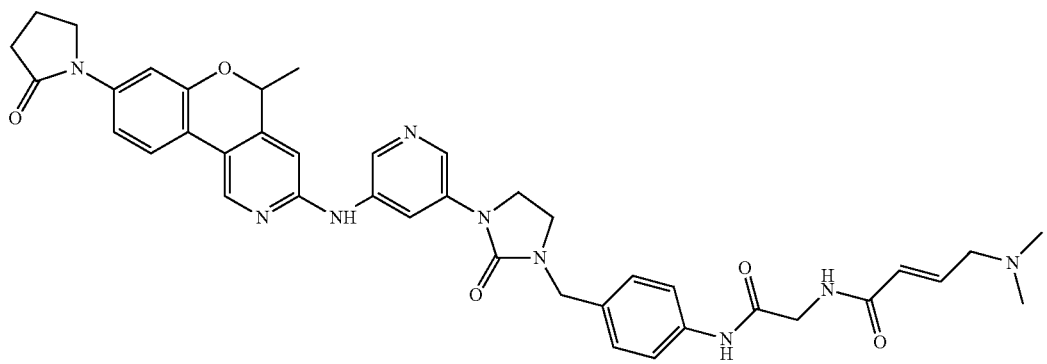 [SMILES: CC1Oc2cc(N3CCCC3=O)ccc2-c2cnc(Nc3cncc(N4CCN(Cc5ccc(NC(=O)CNC(=O)/C=C/CN(C)C)cc5)C4=O)c3)cc21]

Step 1: Preparation of tert-butyl (4-(hydroxymethyl)phenyl)carbamate

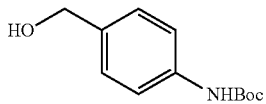

To a mixture of (4-aminophenyl)methanol (2.10 g, 17.1 mmol) in THF (30 mL) was added Boc$_2$O (4.09 g, 18.8 mmol) and Na$_2$CO$_3$ (2.17 g, 20.5 mmol), the reaction mixture was stirred at 25° C. for 12 hours to give a white suspension. TLC (PE/EtOAc=1/1) showed the reaction was completed. The mixture was filtered. The filter cake was washed with EtOAc (10 mL×2). The filtrate was concentrated under reduced pressure to give a residue. The residue was purified by washing with PE (40 mL) to give tert-butyl (4-(hydroxymethyl)phenyl)carbamate (3.8 g, yield: 99%) as a white solid.

$^1$H NMR (400 MHz, DMSO-d$_6$) δ 1.48 (9H, s), 4.41 (2H, d, J=4.8 Hz), 5.05 (1H, brs), 7.18 (2H, d, J=8.4 Hz), 7.39 (2H, d, J=8.4 Hz), 9.27 (1H, brs).

Step 2: Preparation of tert-butyl (4-(chloromethyl)phenyl)carbamate

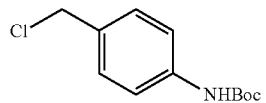 [SMILES: CC(C)(C)OC(=O)Nc1ccc(CCl)cc1]

To a mixture of tert-butyl (4-(hydroxymethyl)phenyl) carbamate (2.00 g, 8.96 mmol), TEA (1.81 g, 17.9 mmol) in THF (30 mL) was added MsCl (1.33 g, 11.6 mmol) dropwise at 0° C. and stirred for 0.5 hour. Then warmed to 25° C. and stirred for another 15.5 hours to give a yellow suspension. TLC (PE/EtOAc=5:1) showed the reaction was completed. The mixture was quenched with ice water (80 mL) slowly, then extracted with EtOAc (60 mL×2), the combined extracts were washed with brine (80 mL×2), dried over Na$_2$SO$_4$, filtered and concentrated under reduced pressure to give tert-butyl (4-(chloromethyl)phenyl)carbamate (2.16 g, crude) as a pale yellow gum.

Note: The product was instability in acid and silica gel. The product should be used directly without purification.

Step 3: Preparation of tert-butyl (4-((3-(5-bromopyridin-3-yl)-2-oxoimidazolidin-1-yl)methyl)phenyl)carbamate

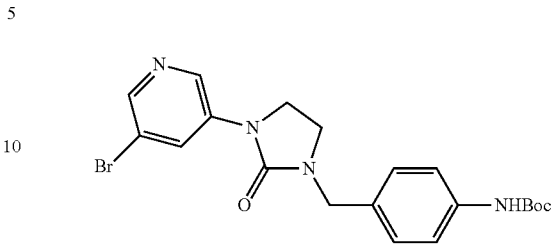

To a mixture of 1-(5-bromopyridin-3-yl)imidazolidin-2-one (800 mg, 3.30 mmol) in anhydrous DMF (15 mL) was added NaH (159 mg, 3.97 mmol, 60% dispersed in mineral oil) at 0° C. in portions, the resulting mixture was stirred at 0° C. for 0.5 hours, then added tert-butyl (4-(chloromethyl) phenyl)carbamate (1.08 g, 4.46 mmol) in anhydrous DMF (5 mL) dropwise at 0° C. and then warmed to 25° C. and stirred for another 5.5 hours to give a pale yellow solution. The reaction was repeated once. LCMS showed the purity of product is 42% (Rt=0.951 min; MS Calcd: 448.1. MS Found: 470.0[M+Na]$^+$). The two batches were combined and poured into water (80 mL) slowly. Some white solid was precipitated out and filtered. The filter cake was dried in high vacuum to give a residue A. The filtrate was extracted with EtOAc (50 mL×2), the combined extracts was washed with brine (80 mL×2), dried over Na$_2$SO$_4$, filtered and concentrated under reduced pressure to give a residue B. The two residues were combined and purified by Combi Flash (PE/EtOAc=6/1 to 3/1 to 1/1) to give tert-butyl (4-((3-(5-bromopyridin-3-yl)-2-oxoimidazolidin-1-yl)methyl)phenyl) carbamate (2.18 g, yield for two steps: 58%) as a pale yellow gum.

Step 4: Preparation of tert-butyl (4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)carbamate

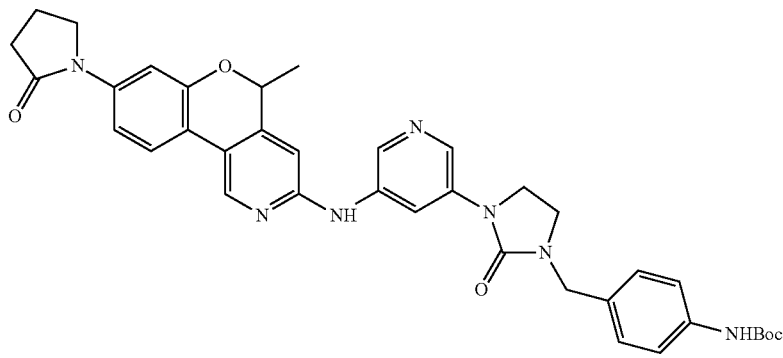 [SMILES: CC1Oc2cc(N3CCCC3=O)ccc2-c2cnc(Nc3cncc(N4CCN(Cc5ccc(NC(=O)OC(C)(C)C)cc5)C4=O)c3)cc21]

To a mixture of 1-(3-amino-5-methyl-5H-chromeno[4,3-c]pyridin-8-yl)pyrrolidin-2-one (99 mg, 0.34 mmol) in dioxane (4 mL) was added tert-butyl (4-((3-(5-bromopyridin-3-yl)-2-oxoimidazolidin-1-yl)methyl)phenyl)carbamate (150 mg, 0.34 mmol), Pd(dba)$_2$ (19 mg, 0.034 mmol), Brettphos (18 mg, 0.034 mmol) and Cs$_2$CO$_3$ (219 mg, 0.671 mmol), the reaction mixture was purged in N₂ atmosphere for 3 times and stirred at 50° C. for 1 hour, then heated to 100° C. under N₂ atmosphere and stirred for another 15 hours to give a brown suspension. LCMS showed the purity of the desired product is 34% (Rt=0.909 min; MS Calcd: 661.3. MS Found: 662.2 [M+H]⁺). The mixture was filtered. The filter cake was washed with DCM (15 mL×2). The filtrate was concentrated under reduced pressure to give a residue. The residue was washed with EtOAc/PE (30 mL, 2/1) twice to give tert-butyl (4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)carbamate (200 mg, yield: 90%) as a red solid.

¹H NMR (400 MHz, DMSO-d₆) δ 1.47 (9H, s), 1.54 (3H, d, J=6.4 Hz), 2.03-2.11 (2H, m), 2.49-2.51 (2H, m), 3.33-3.44 (2H, m), 3.79-3.90 (4H, m), 4.34 (2H, s), 5.27 (1H, q, J=6.4 Hz), 6.76 (1H, s), 7.15-7.24 (2H, m), 7.29-7.34 (1H, m), 7.40 (1H, d, J=2.0 Hz), 7.45 (2H, d, J=8.4 Hz), 7.89 (1H, d, J=8.8 Hz), 8.32 (1H, d, J=2.0 Hz), 8.48 (1H, d, J=2.0 Hz), 8.62 (1H, d, J=2.0 Hz), 8.67 (1H, s), 9.35 (1H, brs), 9.45 (1H, brs).

amino)pyridin-3-yl)-2-oxoimidazolidin-1-yl)methyl)phenyl)carbamate (200 mg, 0.302 mmol) in EtOAc (5 mL) was added HCl/EtOAc (20 mL, 4 M in EtOAc), the reaction mixture was stirred at 25° C. for 4 hours to give a yellow suspension. LCMS showed the purity of the desired product is 47% (Rt=1.658 min; MS Calcd: 561.3. MS Found: 562.2 [M+H]⁺). The mixture was concentrated under reduced pressure to give 1-(4-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one (200 mg, crude, HCl salt) as a yellow solid.

¹H NMR (400 MHz, DMSO-d₆) δ 1.55 (3H, d, J=6.4 Hz), 2.03-2.11 (2H, m), 2.49-2.51 (2H, m), 3.33-3.44 (2H, m), 3.83 (2H, t, J=7.6 Hz), 3.94 (2H, t, J=6.8 Hz), 4.48 (2H, s), 5.35 (1H, q, J=6.4 Hz), 6.90 (1H, s), 7.31-7.41 (3H, m), 7.42-7.50 (4H, m), 7.94 (1H, d, J=8.8 Hz), 8.64-8.71 (2H, m), 8.78 (1H, s), 9.19 (1H, brs).

Note: Two active protons were not observed.

Step 6: Preparation of tert-butyl (2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)carbamate

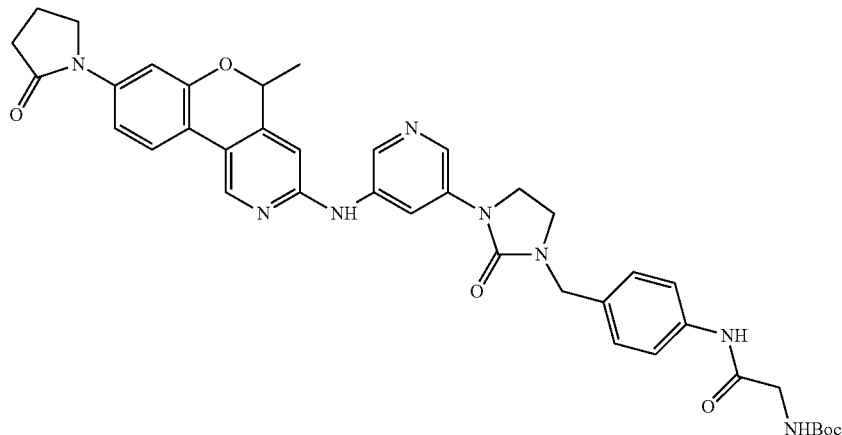

Step 5: Preparation of 1-(4-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one

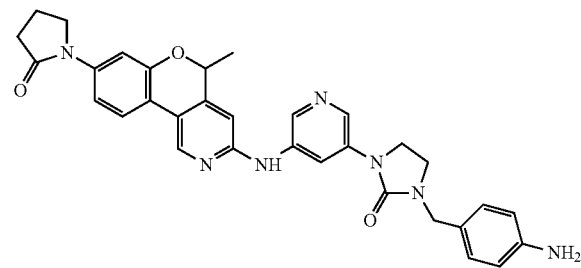 [SMILES: CC1Oc2cc(N3CCCC3=O)ccc2-c2cnc(Nc3cncc(N4CCN(Cc5ccc(N)cc5)C4=O)c3)cc21]

To a mixture of tert-butyl (4-((3-(5-((5-methyl-8-(2-oxopyrrolidin-1-yl)-5H-chromeno[4,3-c]pyridin-3-yl)

To a mixture of 1-(4-aminobenzyl)-3-(5-((5-methyl-8-(2-oxopyrrolidin-1-yl)-5H-chromeno[4,3-c]pyridin-3-yl)amino)pyridin-3-yl)imidazolidin-2-one (200 mg, 0.334 mmol, HCl salt) in DMF (10 mL) was added Boc-gly-OH (293 mg, 1.67 mmol), TEA (135 mg, 1.34 mmol), EDCI (192 mg, 1.00 mmol) and HOBt (136 mg, 1.00 mmol), the reaction mixture was stirred at 25° C. for 1 hour to give a brown suspension. Then heated to 100° C. and stirred for another 15 hours to give a brown suspension. LCMS showed the purity of the desired product is 28% (Rt=0.868 min; MS Calcd: 718.3. MS Found: 719.2 [M+H]⁺). The mixture was quenched with water (20 mL). Some brown solid was precipitated out and filtered. The filter cake was dried in high vacuum to give a residue. The residue was purified by washing with EtOAc (15 mL) twice to give tert-butyl (2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)carbamate (150 mg, yield for two steps: 69%) as a brown solid.

Step 7: Preparation of 2-amino-N-(4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide

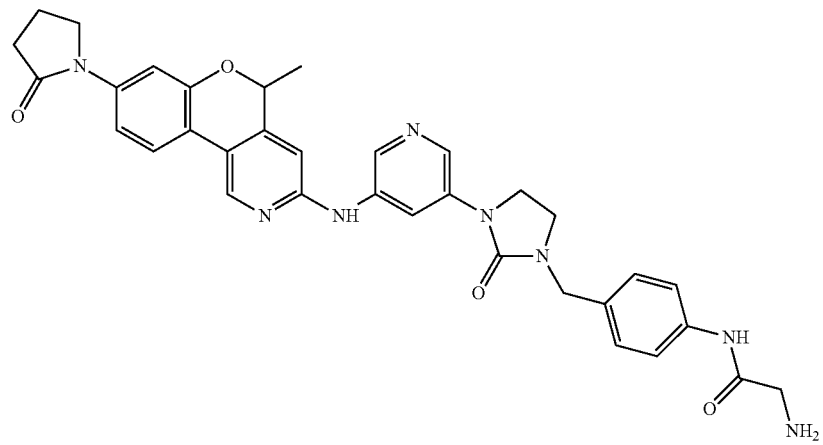 [SMILES: CC1Oc2cc(N3CCCC3=O)ccc2-c2cnc(Nc3cncc(N4CCN(Cc5ccc(NC(=O)CN)cc5)C4=O)c3)cc21]

To a mixture of tert-butyl (2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)carbamate (150 mg, 0.208 mmol) in EtOAc (5 mL) was added HCl/EtOAc (15 mL, 4 M in EtOAc), the reaction mixture was stirred at 25° C. for 4 hours to give a brown suspension. LCMS showed the purity of product is 47% (Rt=0.824 min; MS Calcd: 619.3. MS Found: 620.1 [M+H]$^+$). The mixture was concentrated under reduced pressure to give a residue. The residue was washed with EtOAc (10 mL) to give 2-amino-N-(4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide (120 mg, crude, HCl salt) as a yellow solid.

Step 8: Preparation of (E)-4-(dimethylamino)-N-(2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide

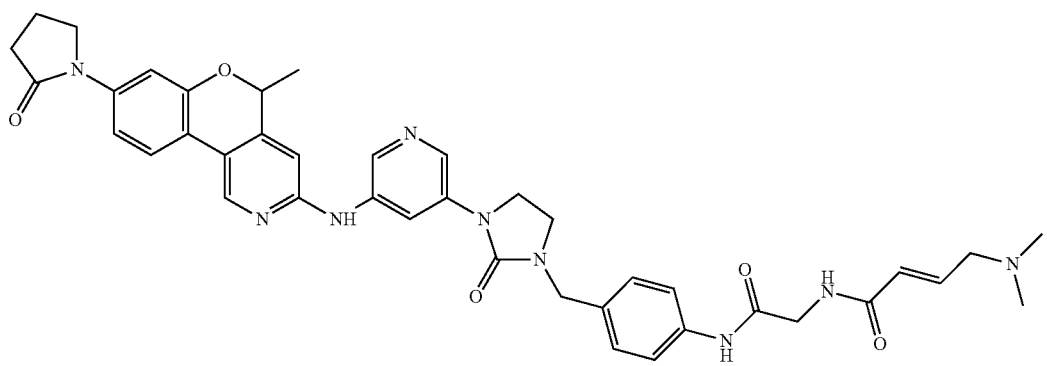 [SMILES: CC1Oc2cc(N3CCCC3=O)ccc2-c2cnc(Nc3cncc(N4CCN(Cc5ccc(NC(=O)CNC(=O)/C=C/CN(C)C)cc5)C4=O)c3)cc21]

To a mixture of 2-amino-N-(4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)acetamide (60 mg, 0.092 mmol, HCl salt) in DMF (5 mL) was added (E)-4-(dimethylamino)but-2-enoic acid (30 mg, 0.18 mmol, HCl salt), HOBt (25 mg, 0.18 mmol), TEA (28 mg, 0.27 mmol) and EDCI (35 mg, 0.18 mmol), the reaction mixture was stirred at 25° C. for 2 hours to give a brown suspension. The reaction was repeated once. LCMS showed the purity of product is 31% (Rt=0.847 min; MS Calcd: 729.3. MS Found: 753.2 [M+Na]$^+$). The two batches were combined and diluted with water (20 mL), then extracted with DCM (25 mL×2), the combined extracts was washed with brine (40 mL×2), dried over Na$_2$SO$_4$, filtered and concentrated under reduced pressure to give a residue. The residue was purified by prep-HPLC (0.225% FA as an additive) to give (E)-4-(dimethylamino)-N-(2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide (14.8 mg, yield for two steps: 10%) as a yellow solid.

$^1$H NMR (400 MHz, DMSO-d$_6$) δ 1.53 (3H, d, J=6.4 Hz), 2.02-2.13 (2H, m), 2.49-2.53 (2H, m), 2.71 (6H, s), 3.46-3.49 (2H, m), 3.81-3.91 (6H, m), 4.00 (2H, d, J=5.6 Hz), 4.36 (2H, s), 5.27 (1H, q, J=6.8 Hz), 6.36 (1H, d, J=15.6 Hz), 6.55-6.64 (1H, m), 6.76 (1H, s), 7.26 (2H, d, J=8.4 Hz), 7.31 (1H, dd, J=8.0, 2.4 Hz), 7.39 (1H, d, J=1.6 Hz), 7.58 (2H, d, J=8.8 Hz), 7.88 (1H, d, J=8.4 Hz), 8.32 (1H, d, J=1.6 Hz), 8.49 (1H, s), 8.59-8.68 (3H, m), 9.46 (1H, brs), 10.11 (1H, brs).

Example 180: (6aR)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

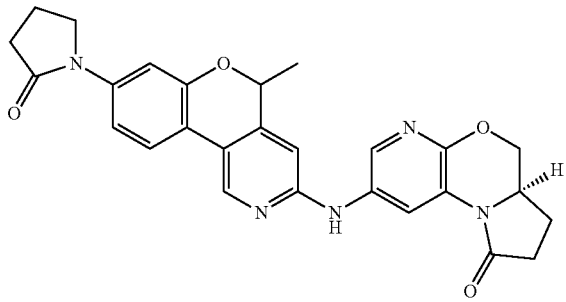 [SMILES: CC1Oc2cc(N3CCCC3=O)ccc2-c2cnc(Nc3cnc4c(c3)N3C(=O)CC[C@@H]3CO4)cc21]

Step 1: Preparation of (R)-5-(((3-bromo-5-nitropyridin-2-yl)oxy)methyl)pyrrolidin-2-one

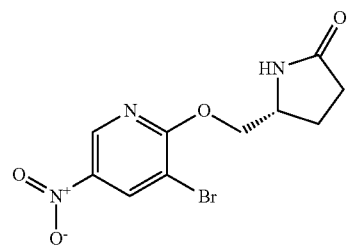 [SMILES: O=C1CC[C@H](COc2ncc([N+](=O)[O-])cc2Br)N1]

To a suspension of (R)-5-(hydroxymethyl)pyrrolidin-2-one (5.00 g, 43.4 mmol), 3-bromo-2-chloro-5-nitropyridine (11.3 g, 47.8 mmol) and K$_2$CO$_3$ (7.80 g, 56.4 mmol) in CH$_3$CN (100 mL) was heated at 100° C. for 16 hours under N$_2$ atmosphere. The reaction mixture turned into brown suspension from yellow. LCMS showed the purity of the desired product is 57% (Rt=0.609 min; MS Calcd: 316.1. MS Found: 316.7 [M+H]$^+$). The reaction mixture was filtered and the solid was washed with CH$_3$CN (50 mL×4). The filtrate was concentrated. The residue was purified by Combi Flash (20% to 100% EtOAc in PE) to give (R)-5-(((3-bromo-5-nitropyridin-2-yl)oxy)methyl)pyrrolidin-2-one (10.8 g, yield: 79%) as a black brown solid.

$^1$H NMR 1 (400 MHz, CDCl$_3$) δ 1.96-2.04 (1H, m), 2.03-2.15 (2H, m), 2.42-2.57 (1H, m), 4.12 (1H, d, J=3.6 Hz), 4.30 (1H, dd, J=10.8, 7.6 Hz), 4.63 (1H, dd, J=10.8, 3.6 Hz), 6.0 (1H, brs), 8.65 (1H, d, J=2.4 Hz). 8.98 (1H, d, J=2.4 Hz).

Step 2: Preparation of (R)-2-nitro-6,6a,7,8-tetrahydro-9H-pyrido[2,3-b]pyrrolo[1,2-d][1,4]oxazin-9-one

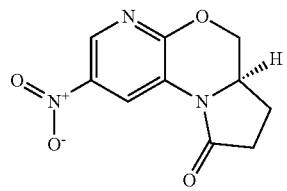 [SMILES: O=C1CC[C@@H]2COc3ncc([N+](=O)[O-])cc3N12]

To a mixture of (R)-5-(((3-bromo-5-nitropyridin-2-yl)oxy)methyl)pyrrolidin-2-one (10.8 g, 34.2 mmol), CuI (1.95 g, 10.2 mmol) and Cs$_2$CO$_3$ (14.5 g, 44.4 mmol) in anhydrous dioxane (200 mL) was added N,N'-dimethylethane-1,2-diamine (2.21 mL, 34.2 mmol). Then the reaction mixture was degassed and purged with N$_2$ for three times and stirred at 100° C. for 20 hours under N$_2$ atmosphere. A brown suspension was formed. LCMS showed the purity of the desired product is 78% (Rt=0.521 min; MS Calcd: 235.2. MS Found: 235.9 [M+H]$^+$). The reaction mixture was filtered through a pad of celite and washed with dioxane (50 mL×3). The filtrate was concentrated under reduced pressure. The residue was purified by Combi Flash (20% to 50% EtOAc in DCM) to give (R)-2-nitro-6,6a,7,8-tetrahydro-9H-pyrido[2,3-b]pyrrolo[1,2-d][1,4]oxazin-9-one (4.30 g, yield: 54%) as a yellow solid.

$^1$H NMR (400 MHz, CDCl$_3$) δ 1.77-1.86 (1H, m), 2.38-2.48 (1H, m), 2.59-2.69 (1H, m), 2.71-2.82 (1H, m), 3.97-4.06 (1H, m) 4.09-4.18 (1H, m), 4.81 (1H, dd, J=3.2, 1.6 Hz), 8.86-8.90 (1H, m), 9.54-9.59 (1H, m).

Step 3: Preparation of (R)-2-amino-6,6a,7,8-tetrahydro-9H-pyrido[2,3-b]pyrrolo[1,2-d][1,4]oxazin-9-one

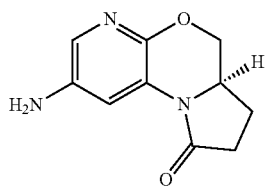 [SMILES: Nc1cnc2c(c1)N1C(=O)CC[C@@H]1CO2]

A mixture of (R)-2-nitro-6,6a,7,8-tetrahydro-9H-pyrido[2,3-b]pyrrolo[1,2-d][1,4]oxazin-9-one (4.30 g, 18.3 mmol) and Pd/C (800 mg, 10% purity in charcoal) in THF (200 mL) was degassed and purged with H2 for 3 times. Then the reaction mixture was hydrogenated with a H2 balloon (15 psi) at 25° C. for 3 hours. A black suspension was formed. LCMS showed the purity of the desired product is 54% (Rt=0.325 min; MS Calcd: 205.2. MS Found: 205.9 [M+H]$^+$). The reaction mixture was filtered and the solid was washed with DCM (25 mL×3). The filtrate was concentrated under reduced pressure. The residue was purified by Combi Flash (20% to 80% EtOAc in DCM), then triturated with PE/EtOAc (20 mL, 1/1), to give (R)-2-amino-6,6a,7,8-tetrahydro-9H-pyrido[2,3-b]pyrrolo[1,2-d][1,4]oxazin-9-one (2.08 g, yield: 55%) as a yellow solid.

$^1$H NMR (400 MHz, DMSO-d$_6$) δ 1.59-1.70 (1H, m), 2.15-2.19 (1H, m), 2.31-2.39 (1H, m), 2.58-2.68 (1H, m), 3.73-3.80 (1H, m), 3.98-4.02 (1H, m), 4.47 (1H, dd, J=9.2, 3.2 Hz), 4.98 (2H, brs), 7.26 (1H, d, J=2.8 Hz), 8.11 (1H, d, J=2.8 Hz) Step 4: Preparation of compound (6aR)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

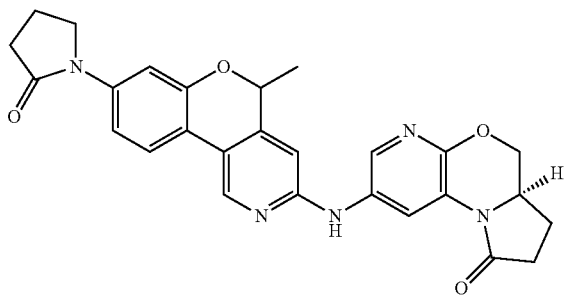 [SMILES: CC1Oc2cc(N3CCCC3=O)ccc2-c2cnc(Nc3cnc4c(c3)N3C(=O)CC[C@@H]3CO4)cc21]

A mixture of 1-(3-chloro-5-methyl-5H-chromeno[4,3-c]pyridin-8-yl)pyrrolidin-2-one (60 mg, 0.19 mmol), (R)-2-amino-6,6a,7,8-tetrahydro-9H-pyrido[2,3-b]pyrrolo[1,2-d][1,4]oxazin-9-one (50 mg, 0.25 mmol), Pd$_2$(dba)$_3$ (17 mg, 0.019 mmol), Cs$_2$CO$_3$ (124 mg, 0.381 mmol), Brettphos (20 mg, 0.038 mmol) in anhydrous dioxane (3 mL) was degassed and purged with N$_2$ for 3 times. Then the resulting reaction mixture was heated at 90° C. for 16 hours under N$_2$ atmosphere. The reaction mixture turned into yellow suspension from red. LCMS showed the purity of the desired product is 36% (Rt=0.586 min; MS Calcd: 483.2; MS Found: 484.2 [M+H]$^+$). The reaction mixture was diluted with H$_2$O (5 mL), EA (5 mL) and extracted with THF (50 mL×4). The combined organic layers were dried over anhydrous Na$_2$SO$_4$, filtered and concentrated under reduced pressure to give a residue. The residue was purified by HPLC (0.225% FA as an additive) and lyophlizated to give (6aR)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (26.5 mg, yield: 29%) as a yellow solid.

$^1$H NMR (400 MHz, DMSO-d$_6$) δ 1.52 (3H, d, J=6.4 Hz), 1.66-1.74 (1H, m), 2.02-2.08 (2H, m), 2.18-2.27 (1H, m), 2.35-2.41 (1H, m), 2.48 (2H, overlapped with DMSO), 2.65-2.70 (1H, m), 3.83 (2H, t, J=7.2 Hz), 3.90 (1H, t, J=10.4 Hz), 4.03-4.11 (1H, m), 4.58 (1H, dd, J=10.8, 2.8 Hz), 5.24 (1H, q, J=6.4 Hz), 6.68 (1H, s), 7.29 (1H, dd, J=7.6, 2.0 Hz), 7.38 (1H, d, J=2.0 Hz), 7.85 (1H, d, J=8.8 Hz), 8.36 (1H, t, J=2.0 Hz), 8.58 (1H, s), 8.97 (1H, t, J=2.8 Hz), 9.31 (1H, brs).

Example 181: (6aR)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

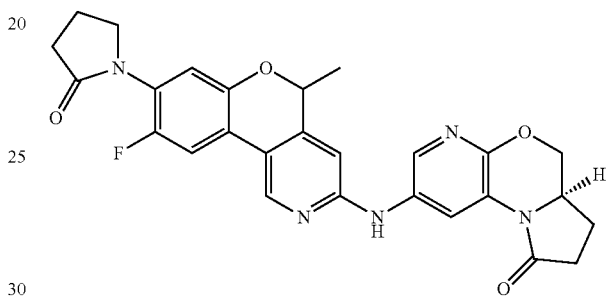

A mixture of 1-(3-chloro-9-fluoro-5-methyl-5H-chromeno[4,3-c]pyridin-8-yl)pyrrolidin-2-one (60 mg, 0.18 mmol), (R)-2-amino-6,6a,7,8-tetrahydro-9H-pyrido[2,3-b]pyrrolo[1,2-d][1,4]oxazin-9-one (48 mg, 0.23 mmol), Pd$_2$(dba)$_3$ (16 mg, 0.018 mmol), Brettphos (19 mg, 0.036 mmol) and Cs$_2$CO$_3$ (117 mg, 0.360 mmol) in anhydrous dioxane (3 mL) was degassed and purged with N$_2$ for 3 times. Then the resulting reaction mixture was heated at 90° C. for 16 hours under N$_2$ atmosphere. The reaction mixture turned into yellow suspension from red. Crude LCMS showed the purity of the desired product is 30% (Rt=0.603 min; MS Calcd: 501.5. MS Found: 502.1 [M+H]$^+$). The reaction mixture was diluted with water (20 mL), EtOAc (20 mL) and separated. The aqueous layer was extracted with EtOAc/THF (20 mL×3, 1/1). The combined organic layer was washed with brine (25 mL), dried over anhydrous Na$_2$SO$_4$ and concentrated. The residue was purified by prep-HPLC (0.225% FA as an additive) and lyophilized to give a impure product further purified by pre-TLC (DCM/MeOH, 30/1) and lyophilized to give (6aR)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (15.1 mg, yield: 17%) as an off-white solid.

$^1$H NMR (400 MHz, DMSO-d$_6$) δ 1.52 (3H, d, J=6.8 Hz), 1.64-1.76 (1H, m), 2.07-2.15 (2H, m), 2.18-2.27 (1H, m), 2.35-2.46 (3H, m), 2.60-2.72 (1H, m), 3.71-3.81 (2H, m), 3.90 (1H, t, J=10.4 Hz), 4.07 (1H, m), 4.58 (1H, dd, J=10.8, 2.8 Hz), 5.25 (1H, q, J=6.8 Hz), 6.67 (1H, s), 7.04 (1H, d, J=6.8 Hz), 7.85 (1H, d, J=11.6 Hz), 8.38 (1H, d, J=2.8 Hz), 8.64 (1H, s), 8.96 (1H, t, J=2.8 Hz), 9.37 (1H, d, J=1.2 Hz),

Example 182: (R)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

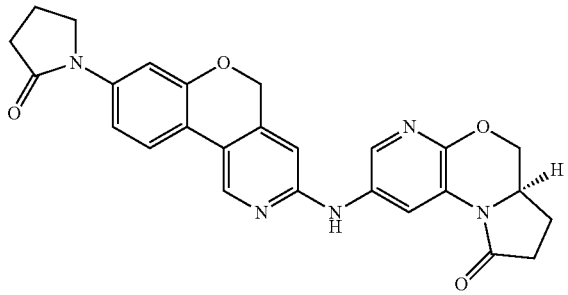 [SMILES: O=C1CCCN1c1ccc2c(c1)OCc1cc(Nc3cnc4c(c3)N3C(=O)CC[C@@H]3CO4)ncc1-2]

A mixture of 1-(3-chloro-5H-chromeno[4,3-c]pyridin-8-yl)pyrrolidin-2-one (60 mg, 0.20 mmol), (R)-2-amino-6,6a,7,8-tetrahydro-9H-pyrido[2,3-b]pyrrolo[1,2-d][1,4]oxazin-9-one (53 mg, 0.26 mmol), Brettphos (21 mg, 0.040 mmol), Pd$_2$(dba)$_3$ (18 mg, 0.020 mmol) and Cs$_2$CO$_3$ (130 mg, 0.399 mmol) in anhydrous dioxane (3 mL) was degassed and purged with N$_2$ for 3 times. Then the resulting reaction mixture was heated at 90° C. for 16 hours under N$_2$ atmosphere. The reaction mixture turned into yellow suspension from red. Crude LCMS showed the purity of the desired product is 15% (Rt=0.583 min; MS Calcd: 469.5; MS Found: 470.1 [M+H]$^+$). The reaction mixture was diluted with water (20 mL) and EtOAc (20 mL). The aqueous layer was extracted with EtOAc/THF (20 mL×3, 1/1). The combined organic layer was washed with brine (25 mL), dried over anhydrous Na$_2$SO$_4$ and concentrated. The residue was purified by prep-HPLC (0.225% FA as an additive) and lyophilized to give (R)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (10.1 mg, yield: 11%) as a yellow solid.

$^1$H NMR (400 MHz, DMSO-d$_6$) δ 1.70 (1H, t, J=10.8 Hz), 2.07 (2H, d, J=7.2 Hz), 2.22 (1H, d, J=10.0 Hz), 2.35 (3H, over lapped with DMSO), 2.68 (1H, s), 3.82-3.86 (3H, m), 4.07 (1H, d, J=8.0 Hz), 4.69 (1H, d, J=10.4 Hz), 5.08 (2H, s), 6.66 (1H, s), 7.33 (1H, d, J=8.4 Hz), 7.37 (1H, s), 7.86 (1H, d, J=8.4 Hz), 8.40 (1H, s), 8.58 (1H, s), 8.96 (1H, s), 9.30 (1H, brs), Example 183: (R)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

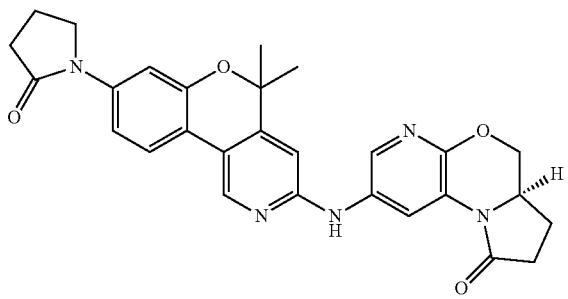 [SMILES: CC1(C)Oc2cc(N3CCCC3=O)ccc2-c2cnc(Nc3cnc4c(c3)N3C(=O)CC[C@@H]3CO4)cc21]

A mixture of 1-(3-chloro-5,5-dimethyl-5H-chromeno[4,3-c]pyridin-8-yl)pyrrolidin-2-one (60 mg, 0.18 mmol), (R)-2-amino-6,6a,7,8-tetrahydro-9H-pyrido[2,3-b]pyrrolo[1,2-d][1,4]oxazin-9-one (48 mg, 0.24 mmol), Pd$_2$(dba)$_3$ (16 mg, 0.018 mmol), Brettphos (19 mg, 0.036 mmol) and Cs$_2$CO$_3$ (118 mg, 0.364 mmol) in anhydrous dioxane (3 mL) was degassed and purged with N$_2$ for 3 times. Then the resulting reaction mixture was heated at 90° C. for 16 hours under N$_2$ atmosphere. The reaction mixture turned into yellow suspension from red. Crude LCMS showed the purity of the desired product is 47% (Rt=0.610 min; MS Calcd: 497.5. MS Found: 498.1 [M+H]$^+$). The reaction mixture was diluted with water (20 mL) and EtOAc (20 mL). The aqueous layer was extracted with EtOAc/THF (20 mL×3, 1/1). The combined organic layer was washed with brine (25 mL), dried over anhydrous Na$_2$SO$_4$ and concentrated. The residue was purified by prep-HPLC (0.225% FA as an additive) and lyophilized to give a impure product. It was further purified by prep-TLC (DCM/MeOH, 30/1) and lyophilized to give (R)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (23.5 mg, yield: 26%) as a yellow solid.

$^1$H NMR (400 MHz, DMSO-d$_6$) δ 1.55 (6H, s), 1.70 (1H, t, J=10.8 Hz), 2.06 (2H, t, J=3.6 Hz), 2.22-2.25 (1H, m), 2.41 (1H, t, J=8.0 Hz), 2.49 (2H, over lapped with DMSO), 2.65-2.74 (1H, m), 3.86 (2H, t, J=10.8 Hz), 3.90 (1H, t, J=10.4 Hz), 4.05-4.10 (1H, m), 4.58 (1H, dd, J=10.8, 2.8 Hz), 6.75 (1H, s), 7.28 (1H, dd, J=8.8, 2.4 Hz), 7.39 (1H, d, J=6.4 Hz), 7.87 (1H, d, J=8.8 Hz), 8.37 (1H, d, J=2.8 Hz), 8.60 (1H, s), 8.97 (1H, d, J=2.8 Hz), 9.28 (1H, brs), Example 184: (R)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one

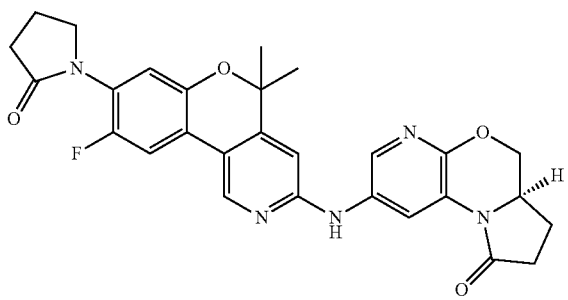 [SMILES: CC1(C)Oc2cc(N3CCCC3=O)c(F)cc2-c2cnc(Nc3cnc4c(c3)N3C(=O)CC[C@@H]3CO4)cc21]

A mixture of 1-(3-chloro-9-fluoro-5,5-dimethyl-5H-chromeno[4,3-c]pyridin-8-yl)pyrrolidin-2-one (60 mg, 0.17 mmol), (R)-2-amino-6,6a,7,8-tetrahydro-9H-pyrido[2,3-b]pyrrolo[1,2-d][1,4]oxazin-9-one (46 mg, 0.22 mmol), Pd$_2$(dba)$_3$ (16 mg, 0.017 mmol), Brettphos (19 mg, 0.034 mmol) and Cs$_2$CO$_3$ (113 mg, 0.0350 mmol) in anhydrous dioxane (3 mL) was degassed and purged with N$_2$ for 3 times. Then the resulting reaction mixture was heated at 90° C. for 15 hours under N$_2$ atmosphere. The reaction mixture turned into yellow suspension from red. Crude LCMS showed the purity of the desired product is 24% (Rt=0.618 min; MS Calcd: 515.5. MS Found: 516.1 [M+H]$^+$). The reaction mixture was diluted with water (20 mL), EtOAc (20 mL) and separated. The aqueous layer was extracted with EtOAc/THF (20 mL×3, 1/1). The combined organic layer was washed with brine (25 mL), dried over anhydrous Na₂SO₄ and concentrated. The residue was purified by prep-HPLC (0.225% FA as an additive) and lyophilized to give a impure product. It was further purified by prep-TLC (DCM/MeOH, 30/1) and lyophilized to give (R)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one (19.8 mg, yield: 22%) as a yellow solid.

¹H NMR (400 MHz, DMSO-d₆) δ 1.55 (6H, s), 1.65-1.74 (1H, m), 2.11 (2H, t, J=7.2 Hz), 2.21-2.25 (1H, m), 2.39-2.48 (3H, m), 2.63-2.69 (1H, m), 3.77 (2H, t, J=6.8 Hz), 3.91 (1H, t, J=10.4 Hz), 4.06-4.09 (1H, m), 4.58 (1H, dd, J=10.8, 3.2 Hz), 6.75 (1H, s), 7.01 (1H, d, J=6.8 Hz), 7.87 (1H, d, J=7.2 Hz), 8.37 (1H, d, J=2.4 Hz), 8.67 (1H, s), 8.96 (1H, d, J=2.4 Hz), 9.38 (1H, brs).

Example 185: 1-(5-methyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one

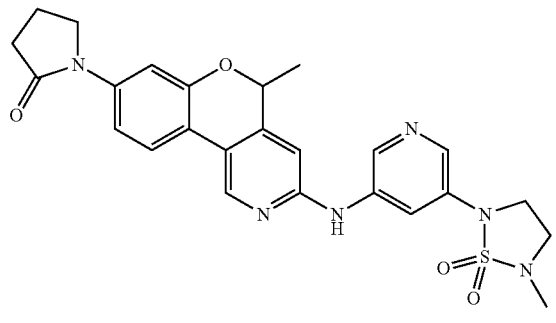 [SMILES: CC1Oc2cc(N3CCCC3=O)ccc2-c2cnc(Nc3cncc(N4CCN(C)S4(=O)=O)c3)cc21]

Step 1: Preparation of tert-butyl (N-(2-chloroethyl)-N-methylsulfamoyl)carbamate

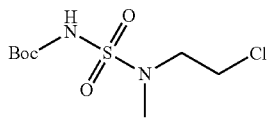 [SMILES: CN(CCCl)S(=O)(=O)NC(=O)OC(C)(C)C]

To a solution of chlorosulfonyl isocyanate (2.50 g, 17.7 mmol) in anhydrous DCM (25 mL) was added t-BuOH (1.69 mL, 17.7 mmol) dropwise at 0° C. After stirring at 0° C. for 0.5 hour, the resulting N-Boc-sulfamoyl chloride and TEA (5.36 g, 53.0 mmol) solution was added dropwise to a solution of 2-chloro-N-methylethan-1-amine-HCl (2.30 g, 17.7 mmol) in DCM (60 mL) at 0-5° C. After the completion of the addition, the reaction mixture was stirred at 0-5° C. for 0.5 hour, then further stirred at 20-25° C. for 2 hours. The reaction mixture turned into yellow suspension from solution. The reaction mixture was diluted with DCM (250 mL), then washed with 1N aqueous HCl (100 mL), brine (100 mL), dried over anhydrous Na₂SO₄ and concentrated. The residue was purified by Combi Flash (10% to 25% EtOAc in PE) to give tert-butyl (N-(2-chloroethyl)-N-methylsulfamoyl)carbamate (4.50 g, yield: 93%) as yellow oil.

¹H NMR (400 MHz, CDCl₃) δ 1.50 (9H, s), 3.05 (3H, s), 3.68 (4H, s), 7.12 (1H, brs).

Step 2: Preparation of tert-butyl 5-methyl-1,2,5-thiadiazolidine-2-carboxylate 1,1-dioxide

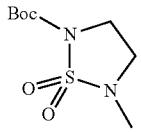

A mixture of tert-butyl (N-(2-chloroethyl)-N-methylsulfamoyl)carbamate (4.00 g, 14.7 mmol) and K₂CO₃ (3.04 g, 22.0 mmol) in DMSO (40 mL) was stirred at 15-20° C. for 16 hours. The reaction mixture turned into white suspension from colorless solution. To the reaction mixture was added water (100 mL), then extracted with EtOAc (100 mL×3). The combined organic layer was washed with water (100 mL×2), brine (100 mL), dried over anhydrous Na₂SO₄ and concentrated. The residue was purified by Combi Flash (10% to 25% EtOAc in PE) to give tert-butyl 5-methyl-1,2,5-thiadiazolidine-2-carboxylate 1,1-dioxide (2.80 g, yield: 81%) as a white solid.

¹H NMR (400 MHz, CDCl₃) δ 1.55 (9H, s), 2.78 (3H, s), 3.31 (2H, t, J=6.4 Hz), 3.81 (2H, t, J=6.4 Hz).

Step 3: Preparation of 2-methyl-1,2,5-thiadiazolidine 1,1-dioxide

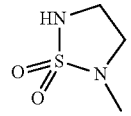

To a solution of tert-butyl 5-methyl-1,2,5-thiadiazolidine-2-carboxylate 1,1-dioxide (2.30 g, 9.73 mmol) in anhydrous DCM (25 mL) was added TFA (25 mL) at 15-20° C. Then the reaction mixture was stirred at 15-20° C. for 1 hour. The reaction turned into pale yellow solution from colorless. The reaction mixture was concentrated and the residue was diluted with DCM (50 mL) and basified with DIPEA to pH=8 and concentrated. The residue was purified by Combi Flash (10% to 50% EtOAc in PE) to give 2-methyl-1,2,5-thiadiazolidine 1,1-dioxide (1.15 g, yield: 87%) as colorless oil.

¹H NMR (400 MHz, CDCl₃) δ 2.75 (3H, s), 3.36-341 (2H, m), 3.48-3.53 (2H, m), 4.47 (1H, brs).

Step 4: Preparation of 2-methyl-5-(5-nitropyridin-3-yl)-1,2,5-thiadiazolidine 1,1-dioxide

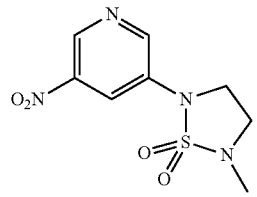 [SMILES: CN1CCN(c2cncc([N+](=O)[O-])c2)S1(=O)=O]

A mixture of 2-methyl-1,2,5-thiadiazolidine 1,1-dioxide (900 mg, 6.61 mmol), 3-bromo-5-nitro-pyridine (1.61 g, 7.93 mmol), CuI (378 mg, 1.98 mmol), Cs$_2$CO$_3$ (3.23 g, 9.91 mmol) and DMEDA (350 mg, 3.97 mmol) in anhydrous dioxane (80 mL) was degassed and purged with N$_2$ for 3 times. Then the resulting reaction mixture was heated at 100° C. for 16 hours under N$_2$ atmosphere. The reaction mixture turned into brown suspension from blue. LCMS showed the purity of the desired product is 91% (Rt=0.693 min; MS Calcd: 258.0; MS Found: 258.8 [M+H]$^+$). The reaction mixture was filtered and the solid was washed with EtOAc (50 mL×3) and the filtrate was concentrated. The residue was purified by Combi Flash (1% to 5% EtOAc in DCM) to give 2-methyl-5-(5-nitropyridin-3-yl)-1,2,5-thiadiazolidine 1,1-dioxide (1.57 g, yield: 92%) as a yellow solid.

$^1$H NMR (400 MHz, CDCl$_3$) 2.91 (3H, s), 3.62 (2H, t, J=6.4 Hz), 3.96 (2H, t, J=6.4 Hz), 8.27 (1H, t, J=2.4 Hz), 8.84 (1H, d, J=2.4 Hz), 9.19 (1H, d, J=2.0 Hz).

Step 5: Preparation of 2-(5-aminopyridin-3-yl)-5-methyl-1,2,5-thiadiazolidine 1,1-dioxide

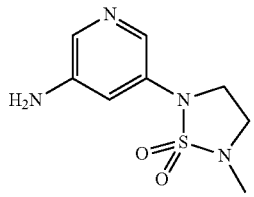

To a solution of 2-methyl-5-(5-nitropyridin-3-yl)-1,2,5-thiadiazolidine 1,1-dioxide (1.57 g, 6.08 mmol) in MeOH (100 mL) was added 10% Pd/C (400 mg) under N$_2$ atmosphere at 15-20° C. Then the reaction mixture was degassed and purged with H2 for 3 times and hydrogenated (30 psi) at 25° C. for 16 hours. The reaction mixture turned into colorless solution from yellow. The reaction mixture was filtered and the solid was washed with MeOH (20 mL×4). The residue was purified by Combi Flash (5% to 10% MeOH in DCM), then triturated with PE/EtOAc (10 mL, 1/1) to give 2-(5-aminopyridin-3-yl)-5-methyl-1,2,5-thiadiazolidine 1,1-dioxide (1.34 g, yield: 97%) as a white solid.

$^1$H NMR (400 MHz, DMSO-d$_6$) δ 2.72 (3H, s), 3.47 (2H, t, J=6.4 Hz), 3.81 (2H, t, J=6.4 Hz), 5.54 (2H, brs), 6.83 (1H, t, J=2.4 Hz), 7.60 (1H, d, J=2.0 Hz), 7.72 (1H, d, J=2.4 Hz).

Step 6: Preparation of 1-(5-methyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one

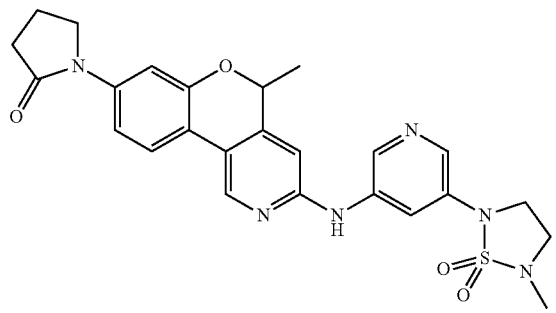 [SMILES: CC1Oc2cc(N3CCCC3=O)ccc2-c2cnc(Nc3cncc(N4CCN(C)S4(=O)=O)c3)cc21]

A mixture of 2-(5-aminopyridin-3-yl)-5-methyl-1,2,5-thiadiazolidine 1,1-dioxide (65 mg, 0.28 mmol), 1-(3-chloro-5-methyl-5H-chromeno[4,3-c]pyridin-8-yl)pyrrolidin-2-one (108 mg, 0.342 mmol), Pd$_2$(dba)$_3$ (26 mg, 0.028 mmol), Brettphos (31 mg, 0.057 mmol) and Cs$_2$CO$_3$ (278 mg, 0.854 mmol) in anhydrous dioxane (4 mL) was degassed and purged with N$_2$ for 3 times. Then the reaction mixture was heated at 90° C. for 16 hours under N$_2$ atmosphere. The reaction mixture turned into brown suspension from red. LCMS showed the purity of the desired product is 52% (Rt=0.744 min; MS Calcd: 506.2. MS Found: 507.1 [M+H]$^+$). To the reaction mixture was added water (20 mL), then extracted with EtOAc/THF (20 mL×3, 1/1). The combined organic layer was washed with brine (20 mL), dried over anhydrous Na$_2$SO$_4$ and concentrated. The residue was purified by Combi Flash (2% to 10% MeOH in DCM), then triturated with EtOAc (5 mL), further purified by prep-HPLC (0.225% FA as an additive). Most of CH$_3$CN was removed under reduced pressure and the remaining part was lyophilized to give 1-(5-methyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one (9.6 mg, yield: 7%) as a yellow solid.

$^1$H NMR (400 MHz, DMSO-d$_6$) δ 1.55 (3H, d, J=6.8 Hz), 2.00-2.10 (2H, m), 2.55-2.60 (2H, m), 2.77 (3H, s), 3.55 (2H, t, J=6.4 Hz), 3.85 (2H, t, J=7.2 Hz), 3.93 (2H, t, J=6.4 Hz), 5.29 (1H, q, J=6.4 Hz), 6.77 (1H, s), 7.33 (1H, dd, J=8.4, 2.0 Hz), 7.41 (1H, d, J=2.4 Hz), 7.90 (1H, d, J=8.4 Hz), 8.03 (1H, s), 8.20 (1H, s), 8.68 (1H, s), 8.75 (1H, s), 9.67 (1H, brs).

Example 186: 1-(5,5-dimethyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one

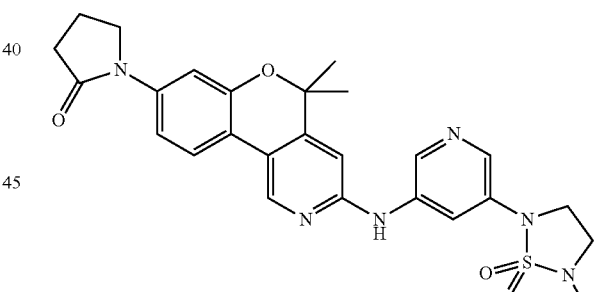

A mixture of 2-(5-aminopyridin-3-yl)-5-methyl-1,2,5-thiadiazolidine 1,1-dioxide (65 mg, 0.28 mmol), 1-(3-chloro-5,5-dimethyl-5H-chromeno[4,3-c]pyridin-8-yl)pyrrolidin-2-one (112 mg, 0.342 mmol), Pd$_2$(dba)$_3$ (26 mg, 0.028 mmol), Brettphos (31 mg, 0.057 mmol) and Cs$_2$CO$_3$ (278 mg, 0.854 mmol) in anhydrous dioxane (4 mL) was degassed and purged with N$_2$ for 3 times. Then the reaction mixture was heated at 90° C. for 16 hours under N$_2$ atmosphere. The reaction mixture turned into brown suspension from red. LCMS showed the purity of the desired product is 77% (Rt=0.772 min; MS Calcd: 520.2. MS Found: 521.1 [M+H]$^+$). To the reaction mixture was added water (20 mL), then extracted with EtOAc/THF (20 mL×3, 1/1). The combined organic layer was washed with brine (20 mL), dried over anhydrous Na$_2$SO$_4$ and concentrated. The residue was triturated with EtOAc (5 mL), then further purified by prep-HPLC (0.225% FA as an additive). Most of CH₃CN was removed under reduced pressure and the remaining part was lyophilized and the product was triturated with CH₃CN (5 mL) and lyophilized to give 1-(5,5-dimethyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one (31.3 mg, yield: 21%) as a white solid.

¹H NMR (400 MHz, DMSO-d₆) δ 1.57 (6H, s), 2.00-2.10 (2H, m), 2.55-2.60 (2H, m), 2.76 (3H, s), 3.54 (2H, t, J=6.0 Hz), 3.84 (2H, t, J=6.8 Hz), 3.92 (2H, t, J=6.4 Hz), 6.83 (1H, s), 7.30 (1H, d, J=8.4 Hz), 7.40 (1H, s), 7.91 (1H, d, J=8.8 Hz), 8.00 (1H, s), 8.17 (1H, s), 8.65-8.70 (2H, m), 9.62 (1H, brs).

Example 187: 1-(5-methyl-3-(((S)-2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one

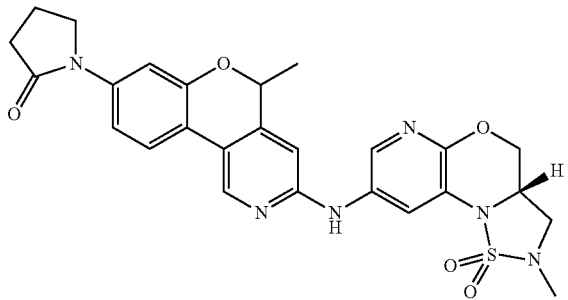 [SMILES: CC1Oc2cc(N3CCCC3=O)ccc2-c2cnc(Nc3cnc4c(c3)N3[C@H](CO4)CN(C)S3(=O)=O)cc21]

Step 1: Preparation of (R)-1-(benzyloxy)-3-(methylamino)propan-2-ol

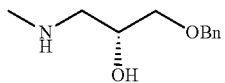

A solution of (S)-2-((benzyloxy)methyl)oxirane (6.00 g, 36.5 mmol) in DCM (25 mL) was added dropwise to MeNH₂ (130 mL, 40% purity in MeOH) at 0° C. After the addition, the reaction mixture was stirred at 10-15° C. for 16 hours. The reaction mixture turned into suspension from solution. The reaction mixture was concentrated and the remaining part was extracted with DCM (100 mL×3). The combined organic layer was washed with brine (50 mL), dried over anhydrous Na₂SO₄ and concentrated to give (R)-1-(benzyloxy)-3-(methylamino)propan-2-ol (6.10 g, yield: 86%) as yellow oil.

¹H NMR (400 MHz, CDCl₃) δ 2.44 (3H, s), 2.65-2.70 (2H, m), 3.45-3.55 (2H, m), 3.90-3.95 (1H, m), 4.55 (2H, s), 7.25-7.40 (5H, m).

Step 2: Preparation of methyl (S)-3-((benzyloxy)methyl)-5-methyl-1,2,5-thiadiazolidine-2-carboxylate 1,1-dioxide

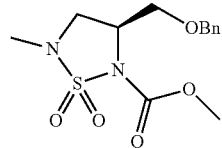

To a solution of (R)-1-(benzyloxy)-3-(methylamino)propan-2-ol (6.10 g, 31.2 mmol) in anhydrous THF (200 mL) was added Burgess reagent (18.6 g, 78.1 mmol) at 10-15° C. Then the reaction mixture was stirred at 75° C. for 16 hours. The reaction mixture turned into yellow solution from colorless. To the reaction mixture was added saturated aqueous NH₄Cl (100 mL), then extracted with EtOAc (200 mL×2). The combined organic layer was washed with brine (100 mL), dried over anhydrous Na₂SO₄ and concentrated. The residue was purified by Combi Flash (10% to 30% EtOAc in PE) to give methyl (S)-3-((benzyloxy)methyl)-5-methyl-1,2,5-thiadiazolidine-2-carboxylate 1,1-dioxide (5.92 g, yield: 60%) as yellow gum.

¹H NMR (400 MHz, CDCl₃) δ 2.77 (3H, s), 3.33-3.39 (1H, m), 3.41-3.45 (1H, m), 3.64-3.69 (1H, m), 3.74-3.79 (1H, m), 3.90 (3H, s), 4.24-4.31 (1H, m), 4.52-4.60 (2H, m), 7.29-7.40 (5H, m).

Step 3: Preparation of methyl (S)-3-(hydroxymethyl)-5-methyl-1,2,5-thiadiazolidine-2-carboxylate 1,1-dioxide

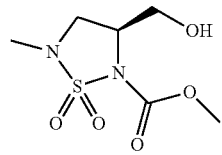

To a solution of methyl (S)-3-((benzyloxy)methyl)-5-methyl-1,2,5-thiadiazolidine-2-carboxylate 1,1-dioxide (5.92 g, 18.8 mmol) in absolute MeOH (200 mL) was added 10% Pd(OH)₂/C (1.00 g) under N₂ atmosphere. The reaction mixture was degassed and purged with H2 for 3 times and the resulting reaction mixture was hydrogenated (50 psi) at 50° C. for 24 hours. The reaction mixture turned into colorless from yellow solution. The reaction mixture was filtered and the solid was washed with MeOH (10 mL×3). The filtrate was concentrated and the residue was dissolved in EtOH (25 mL) and concentrated to give methyl (S)-3-(hydroxymethyl)-5-methyl-1,2,5-thiadiazolidine-2-carboxylate 1,1-dioxide (3.50 g, yield: 83%) as colorless gum.

¹H NMR (400 MHz, CDCl₃) δ 2.80 (3H, s), 3.35-3.45 (2H, m), 3.75-3.85 (2H, m), 3.93 (3H, s), 4.20-4.30 (1H, m).

Step 4: Preparation of methyl (S)-3-(((3-bromo-5-nitropyridin-2-yl)oxy)methyl)-5-methyl-1,2,5-thiadiazolidine-2-carboxylate 1,1-dioxide

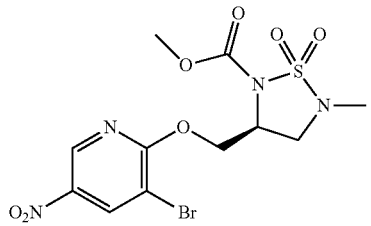 [SMILES: COC(=O)N1[C@H](COc2ncc([N+](=O)[O-])cc2Br)CN(C)S1(=O)=O]

A mixture of methyl (S)-3-(hydroxymethyl)-5-methyl-1,2,5-thiadiazolidine-2-carboxylate 1,1-dioxide (3.30 g, 14.7 mmol), 3-bromo-2-chloro-5-nitro-pyridine (4.19 g, 17.7 mmol) and K$_2$CO$_3$ (4.07 g, 29.4 mmol) in CH$_3$CN (60 mL) was heated at 90° C. for 2 hours under N$_2$ atmosphere. The reaction mixture turned into brown suspension from yellow. The reaction mixture was filtered and the solid was washed with EtOAc (20 mL×3). The filtrate was concentrated and the residue was purified by Combi Flash (20% to 40% EtOAc in PE) to give methyl (S)-3-(((3-bromo-5-nitropyridin-2-yl)oxy)methyl)-5-methyl-1,2,5-thiadiazolidine-2-carboxylate 1,1-dioxide (4.20 g, yield: 67%) as yellow gum.

Step 5: Preparation of methyl (S)-3-(((5-amino-3-bromopyridin-2-yl)oxy)methyl)-5-methyl-1,2,5-thiadiazolidine-2-carboxylate 1,1-dioxide and (S)-3-(((5-amino-3-bromopyridin-2-yl)oxy)methyl)-1,2,512-thiadiazolidine 1,1-dioxide

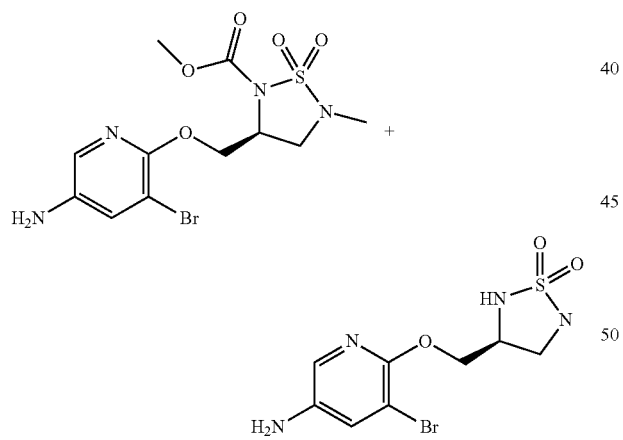

A mixture of methyl (S)-3-(((3-bromo-5-nitropyridin-2-yl)oxy)methyl)-5-methyl-1,2,5-thiadiazolidine-2-carboxylate 1,1-dioxide (4.20 g, 9.88 mmol) and Fe powder (2.21 g, 39.5 mmol), NH$_4$Cl (5.28 g, 98.8 mmol) in EtOH (45 mL) and H$_2$O (15 mL) was heated at 90° C. for 16 hours. The reaction mixture turned into black suspension from gray. The reaction mixture was filtered through a pad of celite and the solid was washed with EtOH (20 mL×3). The filtrate was concentrated and the residue was diluted with water (50 mL) and extracted with EtOAc (50 mL×3). The combined organic layer was washed with brine (50 mL), dried over anhydrous Na$_2$SO$_4$ and concentrated. The residue was purified by Combi Flash (50% to 100% EtOAc in PE) to give methyl (S)-3-(((5-amino-3-bromopyridin-2-yl)oxy)methyl)-5-methyl-1,2,5-thiadiazolidine-2-carboxylate 1,1-dioxide (2.40 g, yield: 61%) as a yellow solid and (S)-3-(((5-amino-3-bromopyridin-2-yl)oxy)methyl)-1,2,512-thiadiazolidine 1,1-dioxide (860 mg, yield: 26%) as a gray solid.

Step 6: Preparation of methyl (S)-3-(((3-bromo-5-((di-tert-butoxycarbonyl)amino)pyridin-2-yl)oxy)methyl)-5-methyl-1,2,5-thiadiazolidine-2-carboxylate-1,1-dioxide

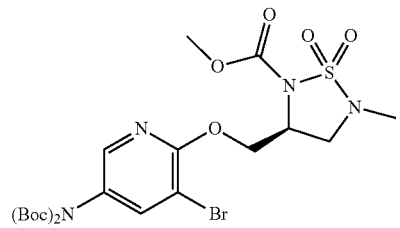

To a solution of methyl (S)-3-(((5-amino-3-bromopyridin-2-yl)oxy)methyl)-5-methyl-1,2,5-thiadiazolidine-2-carboxylate 1,1-dioxide (3.20 g, 8.10 mmol), DIPEA (4.19 g, 32.4 mmol) and DMAP (198 mg, 1.62 mmol) in DCM (80 mL) was added Boc$_2$O (7.07 g, 32.4 mmol) at 15-20° C. Then the reaction mixture was stirred at 15-20° C. for 16 hours under N$_2$ atmosphere. The reaction mixture turned into yellow solution from colorless. The reaction mixture was concentrated and the residue was purified by Combi Flash (30% to 80% EtOAc in PE) to give (S)-3-(((3-bromo-5-((di-tert-butoxycarbonyl)amino)pyridin-2-yl)oxy)methyl)-5-methyl-1,2,5-thiadiazolidine-2-carboxylate-1,1-dioxide (2.20 g, yield: 46%) as yellow gum.

$^1$H NMR (400 MHz, CDCl$_3$) δ 1.45 (18H, s), 2.80 (3H, s), 3.15-3.25 (1H, m), 3.70-3.80 (4H, m), 4.25-4.35 (2H, m), 5.30-5.35 (1H, m), 7.84 (1H, d, J=2.0 Hz), 8.21 (1H, d, J=2.4 Hz).

Step 7: Preparation of tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide

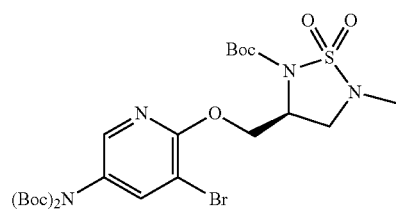

To a solution of (S)-4-(((5-amino-3-bromopyridin-2-yl)oxy)methyl)-2-methyl-1,2,5-thiadiazolidine 1,1-dioxide (860 mg, 2.55 mmol), DIPEA (1.32 g, 10.2 mmol) and DMAP (62 mg, 0.51 mmol) in DCM (25 mL) was added Boc$_2$O (2.23 g, 10.2 mmol) at 15-20° C. Then the reaction mixture was stirred at 15-20° C. for 16 hours under N$_2$ atmosphere. The reaction mixture turned into yellow solution from colorless. The reaction mixture was concentrated and the residue was purified by Combi Flash (20% to 50%

EtOAc in PE) to give tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide (1.50 g, yield: 92%) as colorless gum.

$^1$H NMR (400 MHz, CDCl$_3$) δ 1.45 (27H, s), 2.79 (3H, s), 3.20-3.25 (1H, m), 3.75-3.80 (1H, m), 4.20-4.25 (2H, m), 5.25-5.30 (1H, m), 7.84 (1H, d, J=2.4 Hz), 8.22 (1H, d, J=2.0 Hz).

Step 8: Preparation of tert-butyl (S)-(5-bromo-6-((5-methyl-1,1-dioxido-1,2,5-thiadiazolidin-3-yl)methoxy)pyridin-3-yl)carbamate

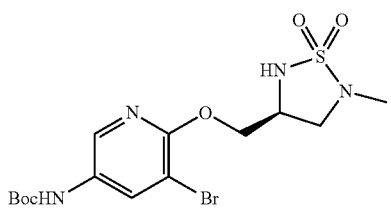 [SMILES: CN1C[C@@H](COc2ncc(NC(=O)OC(C)(C)C)cc2Br)NS1(=O)=O]

To a solution of tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide (2.20 g, 3.69 mmol) in MeOH (40 mL) and H$_2$O (20 mL) was added 10% aqueous NaOH (10 mL) at 15-20° C. Then the reaction mixture was stirred at 15-20° C. for 2 hours. The reaction mixture turned into yellow solution from colorless. The reaction mixture was concentrated. The residue was diluted with water (50 mL), then extracted with EtOAc (50 mL×3). The combined organic layer was washed with brine (50 mL), dried over anhydrous Na$_2$SO$_4$ and concentrated. The residue was purified by Combi Flash (30% to 80% EtOAc in PE) to give tert-butyl (S)-(5-bromo-6-((5-methyl-1,1-dioxido-1,2,5-thiadiazolidin-3-yl)methoxy)pyridin-3-yl)carbamate (2.00 g) as colorless gum. The average yield was 46% for 3 steps.

$^1$H NMR (400 MHz, CDCl$_3$) δ 1.55 (9H, s), 2.27 (1H, dd, J=7.6, 5.6 Hz), 2.84 (3H, s), 3.34-3.40 (1H, m), 3.62-3.70 (3H, m), 4.82-4.90 (1H, m), 6.68 (1H, s), 8.29 (1H, d, J=2.8 Hz), 8.44 (1H, s).

Step 9: Preparation of tert-butyl (S)-(2-methyl-1,1-dioxido-2,3,3a,4-tetrahydropyrido[2,3-b][1,2,5]thiadiazolo[2,3-d][1,4]oxazin-8-yl)carbamate

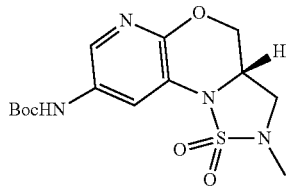 [SMILES: CN1C[C@H]2COc3ncc(NC(=O)OC(C)(C)C)cc3N2S1(=O)=O]

A mixture of tert-butyl (S)-(5-bromo-6-((5-methyl-1,1-dioxido-1,2,5-thiadiazolidin-3-yl)methoxy)pyridin-3-yl)carbamate (2.30 g, 5.26 mmol), CuI (301 mg, 1.58 mmol), Cs$_2$CO$_3$ (3.43 g, 10.5 mmol) and DMEDA (278 mg, 3.16 mmol) in anhydrous dioxane (80 mL) was degassed and purged with N$_2$ for 3 times. Then the resulting reaction mixture was heated at 90° C. for 16 hours under N$_2$ atmosphere. The reaction mixture turned into brown suspension from yellow. LCMS showed the purity of the desired product is 74% (Rt=0.754 min; MS Calcd: 356.1. MS Found: 379.2 [M+Na]$^+$). The reaction mixture was filtered through a pad of celite and the solid was washed with EtOAc (25 mL×4). The filtrate was concentrated and the residue was purified by Combi Flash (35% to 70% EtOAc in PE), then further purified by YMC-Pack CN (0% to 80% EtOH in PE) to give tert-butyl (S)-(2-methyl-1,1-dioxido-2,3,3a,4-tetrahydropyrido[2,3-b][1,2,5]thiadiazolo[2,3-d][1,4]oxazin-8-yl)carbamate (560 mg, yield: 30%) as a yellow solid.

$^1$H NMR (400 MHz, CDCl$_3$) δ 1.51 (9H, s), 2.89 (3H, s), 3.24 (1H, dd, J=10.4, 5.4 Hz), 3.60 (1H, dd, J=10.0, 4.8 Hz), 3.85 (1H, t, J=10.8 Hz), 4.15-4.23 (1H, m), 4.34 (1H, dd, J=10.8, 3.2 Hz), 8.52 (1H, brs), 7.82-7.86 (2H, m).

Step 10: Preparation of (S)-8-amino-2-methyl-2,3,3a,4-tetrahydropyrido[2,3-b][1,2,5]thiadiazolo[2,3-d][1,4]oxazine 1,1-dioxide

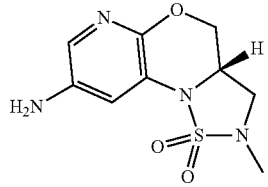 [SMILES: CN1C[C@H]2COc3ncc(N)cc3N2S1(=O)=O]

To a solution of tert-butyl (S)-(2-methyl-1,1-dioxido-2,3,3a,4-tetrahydropyrido[2,3-b][1,2,5]thiadiazolo[2,3-d][1,4]oxazin-8-yl)carbamate (560 mg, 1.57 mmol) in anhydrous DCM (5 mL) was added TFA (5 mL) at 15-20° C. Then the reaction mixture was stirred at 15-20° C. for 2 hours. The reaction mixture turned into yellow solution from colorless. The reaction mixture was concentrated and the residue was basified with saturated aqueous NaHCO$_3$ to pH=8, then extracted with DCM (15 mL×5). The combined organic layer was dried over anhydrous Na$_2$SO$_4$ and concentrated to give (S)-8-amino-2-methyl-2,3,3a,4-tetrahydropyrido[2,3-b][1,2,5]thiadiazolo[2,3-d][1,4]oxazine 1,1-dioxide (339 mg, yield: 84%) as a white solid.

$^1$H NMR (400 MHz, CDCl$_3$) δ 2.80 (3H, s), 3.15 (1H, dd, J=10.4, 4.8 Hz), 3.52 (1H, dd, J=10.4, 7.2 Hz), 3.83 (1H, t, J=10.8 Hz), 4.00-4.10 (1H, m), 4.18 (1H, dd, J=10.8, 3.2 Hz), 6.56 (1H, d, J=2.4 Hz), 7.60 (1H, d, J=2.4 Hz).

Note: Two protons of NH$_2$ were not observed.

Step 11: Preparation of 1-(5-methyl-3-(((S)-2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one

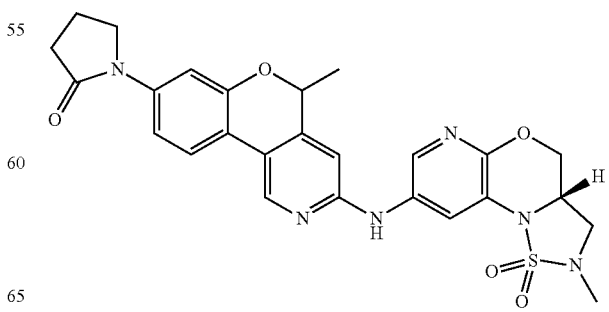

A mixture of (S)-8-amino-2-methyl-2,3,3a,4-tetrahydropyrido[2,3-b][1,2,5]thiadiazolo[2,3-d][1,4]oxazine 1,1-dioxide (60 mg, 0.23 mmol), 1-(3-chloro-5-methyl-5H-chromeno[4,3-c]pyridin-8-yl)pyrrolidin-2-one (88 mg, 0.28 mmol), Pd$_2$(dba)$_3$ (21 mg, 0.023 mmol), Brettphos (25 mg, 0.047 mmol) and Cs$_2$CO$_3$ (229 mg, 0.702 mmol) in anhydrous dioxane (3 mL) was degassed and purged with N$_2$ for 3 times. Then the resulting reaction mixture was heated at 90° C. for 16 hours. The reaction mixture turned into brown suspension from red. LCMS showed the purity of the desired product is 60% (Rt=0.671 min; MS Calcd: 534.2. MS Found: 535.1 [M+H]$^+$). The mixture was filtered through a pad of celite and the solid was washed with DCM/MeOH (10 mL×4, 10/1) and the filtrate was concentrated. The residue was purified by Combi Flash (2% to 10% MeOH in DCM), then triturated with CH$_3$CN (5 mL) and lyophilized to give 1-(5-methyl-3-(((S)-2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one (30.0 mg, yield: 24%) as a yellow solid.

$^1$H NMR (400 MHz, DMSO-d$_6$) δ 1.60 (3H, d, J=6.4 Hz), 2.05-2.16 (2H, m), 2.55-2.60 (2H, m), 2.81 (3H, s), 3.35-3.40 (1H, m), 3.66 (1H, dd, J=10.8, 7.2 Hz), 3.76 (1H, t, J=10.8 Hz), 3.91 (2H, t, J=7.6 Hz), 4.26-4.36 (1H, m), 4.56 (1H, dd, J=11.2, 2.8 Hz), 5.34 (1H, q, J=6.4 Hz), 6.77 (1H, s), 7.38 (1H, dd, J=8.4, 1.6 Hz), 7.46 (1H, d, J=2.0 Hz), 7.93 (1H, d, J=8.4 Hz), 8.15-8.25 (2H, m), 8.72 (1H, s), 9.55 (1H, brs).

Example 188: (S)-1-(5,5-dimethyl-3-((2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one

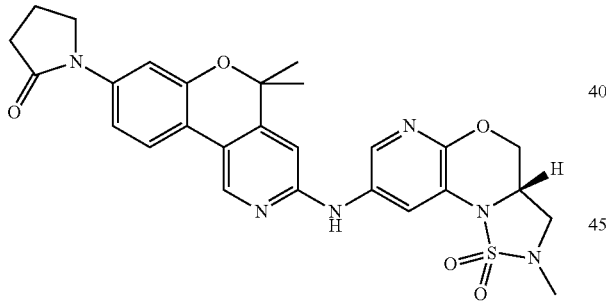

A mixture of (S)-8-amino-2-methyl-2,3,3a,4-tetrahydropyrido[2,3-b][1,2,5]thiadiazolo[2,3-d][1,4]oxazine 1,1-dioxide (60 mg, 0.23 mmol) (see Example 187, steps 1-10), 1-(3-chloro-5,5-dimethyl-5H-chromeno[4,3-c]pyridin-8-yl)pyrrolidin-2-one (92 mg, 0.28 mmol), Pd$_2$(dba)$_3$ (21 mg, 0.023 mmol), Brettphos (25 mg, 0.047 mmol) and Cs$_2$CO$_3$ (229 mg, 0.702 mmol) in anhydrous dioxane (3 mL) was degassed and purged with N$_2$ for 3 times. Then the resulting reaction mixture was heated at 90° C. for 16 hours. The reaction mixture turned into brown suspension from red. LCMS showed the purity of the desired product is 37% (Rt=0.685 min; MS Calcd: 548.2. MS Found: 549.1 [M+H]$^+$). The mixture was filtered through a pad of celite and the solid was washed with DCM/MeOH (10 mL×4, 10/1) and the filtrate was concentrated. The residue was purified by Combi Flash (2% to 10% MeOH in DCM), then triturated with CH$_3$CN (5 mL) twice and lyophilized to give (S)-1-(5,5-dimethyl-3-((2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one (29.8 mg, yield: 23%) as an off-white solid.

$^1$H NMR (400 MHz, DMSO-d$_6$) δ 1.56 (6H, s), 2.00-2.10 (2H, m), 2.55-2.60 (2H, m), 2.75 (3H, s), 3.25-3.30 (1H, m), 3.60 (1H, dd, J=10.8, 6.8 Hz), 3.70 (1H, t, J=10.8 Hz), 3.84 (2H, t, J=6.8 Hz), 4.20-4.30 (1H, m), 4.49 (1H, dd, J=11.2, 3.2 Hz), 6.76 (1H, s), 7.30 (1H, dd, J=8.8, 2.0 Hz), 7.40 (1H, d, J=1.6 Hz), 7.88 (1H, d, J=8.8 Hz), 8.11 (1H, d, J=2.0 Hz), 8.15 (1H, d, J=2.4 Hz), 8.68 (1H, s), 9.47 (1H, brs).

Example 189: (S)-2-((5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one

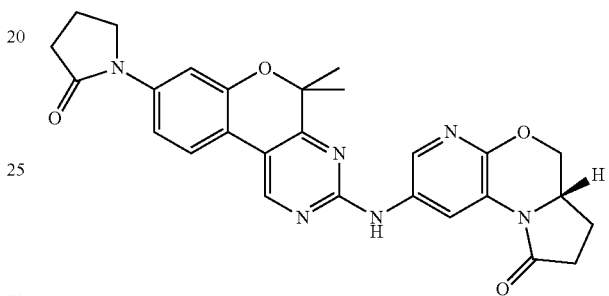

Step 1: Preparation of (S)-2-amino-6,6a,7,8-tetrahydro-9H-pyrido[2,3-b]pyrrolo[1,2-d][1,4]oxazin-9-one

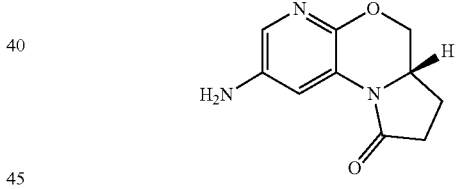

Step 2: Preparation of methyl 5-chloro-2-(methylthio)pyrimidine-4-carboxylate

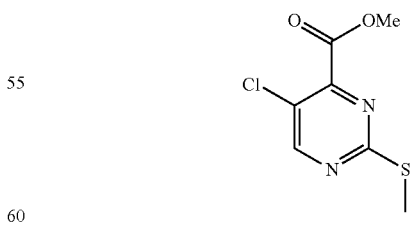

To a stirring mixture of 5-chloro-2-(methylthio)pyrimidine-4-carboxylic acid (2.00 g, 9.77 mmol) and DMF (143 mg, 1.95 mmol) in DCM (40 mL) was added oxalyl chloride (4.3 mL, 48 mmol). The reaction mixture was stirred at 20° C. for 1 hour. A yellow solution was formed. The reaction was concentrated in vacuo. MeOH (20 mL) was slowly added under nitrogen atmosphere at 0° C. The reaction mixture was stirred at 20° C. for 1 hour under N₂ atmosphere. The yellow solution turned to brown gradually. LCMS showed the purity of product is 72% (Rt=0.767 min; MS Calcd: 218.0. MS Found: 218.6 [M+H]⁺). TLC indicated one new major spot was formed. The reaction mixture was concentrated under reduced pressure. The residue was purified by Combi Flash (5% EA in PE) to give methyl 5-chloro-2-(methylthio)pyrimidine-4-carboxylate (1.96 g, yield: 92%) as a light yellow solid.

¹H NMR (400 MHz, CDCl₃) δ 2.57 (3H, s), 4.00 (3H, s), 8.61 (1H, s).

Step 3: Preparation of methyl 5-(2-fluoro-4-(2-oxopyrrolidin-1-yl)phenyl)-2-(methylthio)pyrimidine-4-carboxylate

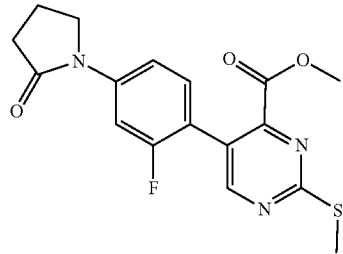 [SMILES: COC(=O)c1nc(SC)ncc1-c1ccc(N2CCCC2=O)cc1F]

A mixture of 1-(3-fluoro-4-(4,4,5,5-tetramethyl-1,3,2-dioxaborolan-2-yl)phenyl)pyrrolidin-2-one (1.26 g, 4.12 mmol), methyl 5-chloro-2-(methylthio)pyrimidine-4-carboxylate (500 mg, 2.29 mmol), Cs₂CO₃ (1.49 g, 4.57 mmol) in H₂O (4 mL) and Pd(t-Bu₃P)₂ (58 mg, 0.11 mmol) in dioxane (20 mL) was stirred at 100° C. for 5 hours under N₂ atmosphere. A black mixture was formed. LCMS showed the purity of the desired product is 49% (Rt=0.690 min; MS Calcd: 361.1. MS Found: 361.9 [M+H]⁺). TLC showed the starting material was consumed completely. The mixture was concentrated under reduced pressure. The residue was purified by Combi Flash (70% EtOAc in PE) to give methyl 5-(2-fluoro-4-(2-oxopyrrolidin-1-yl)phenyl)-2-(methylthio)pyrimidine-4-carboxylate (331 mg, yield: 40%) as a yellow solid.

Step 4: Preparation of 1-(3-fluoro-4-(4-(2-hydroxypropan-2-yl)-2-(methylthio)pyrimidin-5-yl)phenyl)pyrrolidin-2-one

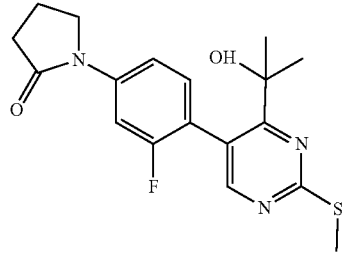 [SMILES: CSc1ncc(-c2ccc(N3CCCC3=O)cc2F)c(C(C)(C)O)n1]

MeMgBr (3 M in Et₂O, 1.1 mL) was added slowly to a solution of methyl 5-(2-fluoro-4-(2-oxopyrrolidin-1-yl)phenyl)-2-(methylthio)pyrimidine-4-carboxylate (330 mg, 0.913 mmol) in THF (12 mL) and DCM (3 mL) at 10° C.

under a nitrogen atmosphere. The resulting mixture was stirred at 10° C. for 2 hours. The yellow solution turned to suspension. LCMS showed the purity of the desired product was 36% (Rt=0.705 min; MS Calcd: 361.1; MS Found: 362.0 [M+H]⁺). Sat. aq. NH₄Cl (15 mL) was added followed by EA (20 mL). The organic layer was separated and the aqueous layer was extracted with EA (15 mL×2). The combined organics were dried over Na₂SO₄, filtered and concentrated to give 1-(3-fluoro-4-(4-(2-hydroxypropan-2-yl)-2-(methylthio)pyrimidin-5-yl)phenyl)pyrrolidin-2-one (330 mg, crude) as a yellow solid. Used for the next step without further purification.

Step 5: Preparation of 1-(5,5-dimethyl-3-(methylthio)-5H-chromeno[3,4-d]pyrimidin-8-yl)pyrrolidin-2-one

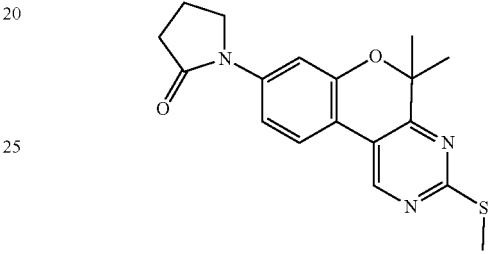

To a solution of 1-(3-fluoro-4-(4-(2-hydroxypropan-2-yl)-2-(methylthio)pyrimidin-5-yl)phenyl)pyrrolidin-2-one (330 mg, 0.913 mmol) in THF (15 mL) was added NaH (109 mg, 2.74 mmol, 60% in mineral oil) at 15° C. and the resulting mixture was stirred at 15° C. for 1 hour. A yellow solution was formed. TLC showed the starting material was consumed completely. Sat. aq. NH₄Cl (10 mL) was added and the mixture was extracted with EtOAc (15 mL×3). The combined organic layer was dried over Na₂SO₄, filtered, concentrated. The residue was purified by Combi Flash (45% EA in PE) to give 1-(5,5-dimethyl-3-(methylthio)-5H-chromeno[3,4-d]pyrimidin-8-yl)pyrrolidin-2-one (280 mg, yield: 90% for two steps) as a yellow solid.

Step 6: Preparation of 1-(5,5-dimethyl-3-(methylsulfonyl)-5H-chromeno[3,4-d]pyrimidin-8-yl)pyrrolidin-2-one

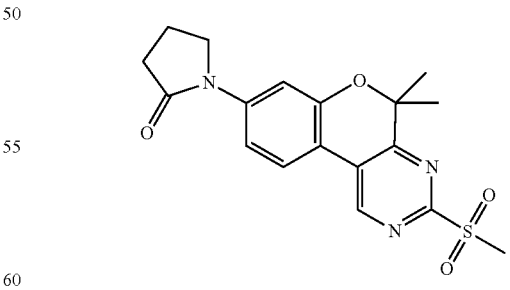

mCPBA (252 mg, 1.46 mmol) was added to a solution of 1-(5,5-dimethyl-3-(methylthio)-5H-chromeno[3,4-d]pyrimidin-8-yl)pyrrolidin-2-one (100 mg, 0.292 mmol) in DCM (5 mL). The resulting mixture was stirred at 50° C. for 20 hours. A yellow solution was formed. LCMS showed the purity of the desired product was 94% (Rt=0.620 min; MS Calcd: 373.1. MS Found: 374.0 [M+H]⁺). Sat. aq. Na₂SO₃ (15 mL) was added followed by DCM (15 mL). The organic layer was separated and the aqueous layer was extracted with DCM (10 mL×2). The combined organic phase was washed with Sat. aq. NaHCO₃ (15 mL) and brine (10 mL), dried over Na₂SO₄, filtered and concentrated to give 1-(5, 5-dimethyl-3-(methylsulfonyl)-5H-chromeno[3,4-d]pyrimidin-8-yl)pyrrolidin-2-one (100 mg, yield: 91%) as a yellow solid. Used for the next step without further purification.

Step 7: Preparation of (S)-2-((5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one

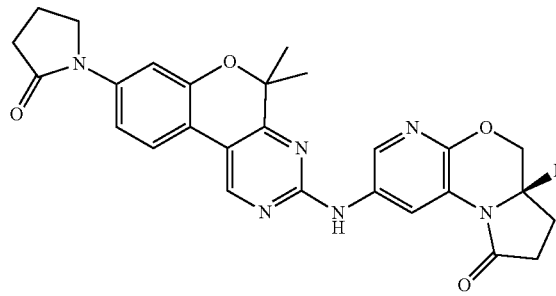

To a solution of 1-(5,5-dimethyl-3-(methylsulfonyl)-5H-chromeno[3,4-d]pyrimidin-8-yl)pyrrolidin-2-one (130 mg, 0.348 mmol) and (S)-2-amino-6,6a,7,8-tetrahydro-9H-pyrido[2,3-b]pyrrolo[1,2-d][1,4]oxazin-9-one (107 mg, 0.522 mmol) in DMF (4 mL) was added NaH (20 mg, 0.52 mmol, 60% in mineral oil) at 20° C. The reaction mixture was stirred at 20° C. for 12 hours under N₂ atmosphere. A black solution was formed gradually. LCMS showed the purity of the desired product is 40% (Rt=0.665 min; MS Calcd: 498.2; MS Found: 499.1 [M+H]⁺). The mixture was filtered. The filtrate was purified by prep-HPLC (0.05% NH₃.H₂O as an additive) and lyophilized to give (S)-2-((5, 5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one (27.1 mg, yield: 16%) as a yellow solid.

¹H NMR (400 MHz, DMSO-d₆) δ 1.60 (3H, s), 1.61 (3H, s), 1.62-1.72 (1H, m), 2.01-2.10 (2H, m), 2.17-2.25 (1H, m), 2.43 (3H, overlapped with DMSO), 2.63-2.71 (1H, m), 3.84 (2H, t, J=6.8 Hz), 3.90 (1H, t, J=10.8 Hz), 4.01-4.09 (1H, m), 4.59 (1H, dd, J=10.8, 2.8 Hz), 7.32 (1H, dd, J=8.4, 1.6 Hz), 7.39 (1H, d, J=2.0 Hz), 7.84 (1H, d, J=8.4 Hz), 8.13 (1H, d, J=2.0 Hz), 8.56 (1H, s), 9.38 (1H, brs), 9.90 (1H, s).

LCMS showed the purity of byproduct 1-(3-hydroxy-5, 5-dimethyl-5H-chromeno[3,4-d]pyrimidin-8-yl)pyrrolidin-2-one is 50% (Rt=0.596 min; MS Calcd: 311.1; MS Found: 311.9 [M+H]⁺). The mixture was filtered. The filtrate was purified by prep-HPLC (0.05% NH₃.H₂O as an additive) and lyophilized to give 1-(3-hydroxy-5,5-dimethyl-5H-chromeno[3,4-d]pyrimidin-8-yl)pyrrolidin-2-one (3.10 mg, yield: 9%) as a white solid.

¹H NMR (400 MHz, DMSO-d₆) δ 1.49 (6H, s), 2.02-2.09 (2H, m), 2.48 (2H, overlapped with DMSO), 3.82 (2H, t, J=6.8 Hz), 7.29 (1H, dd, J=8.8, 2.0 Hz), 7.38 (1H, d, J=2.0 Hz), 7.72 (1H, d, J=8.8 Hz), 8.49 (1H, s), 12.25 (1H, brs).

Example 190: (S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one

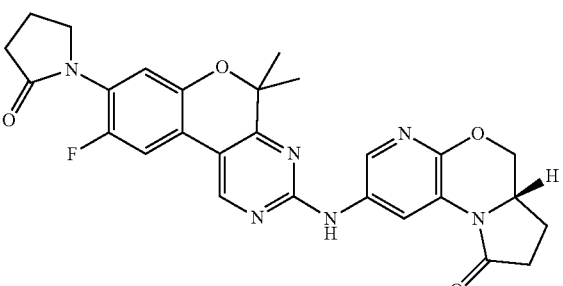

Step 1: Preparation of methyl 5-(2,5-difluoro-4-(2-oxopyrrolidin-1-yl)phenyl)-2-(methylthio)pyrimidine-4-carboxylate

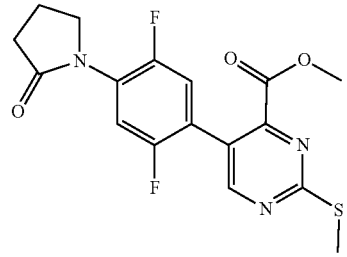 [SMILES: COC(=O)c1nc(SC)ncc1-c1cc(F)c(N2CCCC2=O)cc1F]

A mixture of 1-(2,5-difluoro-4-(4,4,5,5-tetramethyl-1,3,2-dioxaborolan-2-yl)phenyl)pyrrolidin-2-one (962 mg, 2.98 mmol), methyl 5-chloro-2-(methylthio)pyrimidine-4-carboxylate (500 mg, 2.29 mmol), Cs₂CO₃ (1.49 g, 4.58 mmol) in H₂O (4 mL) and Pd(t-Bu₃P)₂ (58 mg, 0.11 mmol) in dioxane (20 mL) was stirred at 100° C. for 5 hours under N₂ atmosphere. A black mixture was formed. LCMS showed the purity of the desired product is 36% (Rt=0.686 min; MS Calcd: 379.1. MS Found: 380.0 [M+H]⁺). Sat. aq. NaHCO₃ (15 mL) was added followed by EA (20 mL). The organic layer was separated and the aqueous layer extracted with EA (20 mL×2). The combined organics were dried over Na₂SO₄, filtered and concentrated. The residue was purified by Combi Flash (60% EtOAc in PE) to give methyl 5-(2, 5-difluoro-4-(2-oxopyrrolidin-1-yl)phenyl)-2-(methylthio)pyrimidine-4-carboxylate (391 mg, yield: 45%) as a yellow gum.

Step 2: Preparation of 1-(2,5-difluoro-4-(4-(2-hydroxypropan-2-yl)-2-(methylthio)pyrimidin-5-yl)phenyl)pyrrolidin-2-one

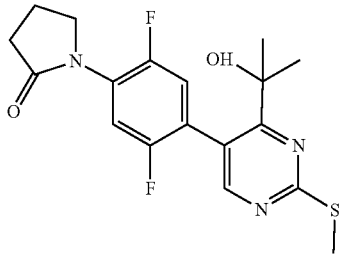 [SMILES: CSc1ncc(-c2cc(F)c(N3CCCC3=O)cc2F)c(C(C)(C)O)n1]

MeMgBr (3 M in Et$_2$O, 1.2 mL) was added slowly to a solution of methyl 5-(2,5-difluoro-4-(2-oxopyrrolidin-1-yl)phenyl)-2-(methylthio)pyrimidine-4-carboxylate (390 mg, 1.03 mmol) in THF (12 mL) and DCM (3 mL) at 15° C. under a nitrogen atmosphere. The resulting mixture was stirred at 15° C. for 2 hours. The yellow solution turned to suspension. LCMS showed the purity of the desired product was 84% (Rt=0.711 min; MS Calcd: 379.1; MS Found: 379.9 [M+H]$^+$). Sat. aq. NH$_4$Cl (15 mL) was added followed by EA (20 mL). The organic layer was separated and the aqueous layer was extracted with EA (15 mL×2). The combined organics were dried over Na$_2$SO$_4$, filtered and concentrated to give 1-(2,5-difluoro-4-(4-(2-hydroxypropan-2-yl)-2-(methylthio)pyrimidin-5-yl)phenyl)pyrrolidin-2-one (390 mg, crude) as a yellow gum. Used for the next step without further purification.

Step 3. Preparation of 1-(9-fluoro-5,5-dimethyl-3-(methylthio)-5H-chromeno[3,4-d]pyrimidin-8-yl)pyrrolidin-2-one

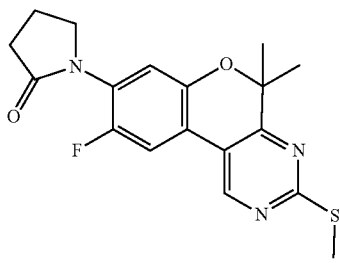 [SMILES: CSc1ncc2c(n1)C(C)(C)Oc1cc(N3CCCC3=O)c(F)cc1-2]

To a solution of 1-(2,5-difluoro-4-(4-(2-hydroxypropan-2-yl)-2-(methylthio)pyrimidin-5-yl)phenyl)pyrrolidin-2-one (390 mg, 1.03 mmol) in THF (15 mL) was added NaH (123 mg, 3.08 mmol, 60% in mineral oil) at 15° C. and the resulting mixture was stirred at 15° C. for 1 hour. A yellow solution was formed. LCMS showed the purity of the desired product was 65% (Rt=0.766 min; MS Calcd: 359.1. MS Found: 360.0 [M+H]$^+$). TLC showed the starting material was consumed completely. Sat. aq. NH$_4$Cl (10 mL) was added and the mixture was extracted with EtOAc (15 mL×3). The combined organic layer was dried over Na$_2$SO$_4$, filtered, concentrated. The residue was purified by Combi Flash (35% EA in PE) to give 1-(9-fluoro-5,5-dimethyl-3-(methylthio)-5H-chromeno[3,4-d]pyrimidin-8-yl)pyrrolidin-2-one (142 mg, yield: 38% for two steps) as a yellow solid.

Step 4: Preparation of 1-(9-fluoro-5,5-dimethyl-3-(methylsulfinyl)-5H-chromeno[3,4-d]pyrimidin-8-yl)pyrrolidin-2-one

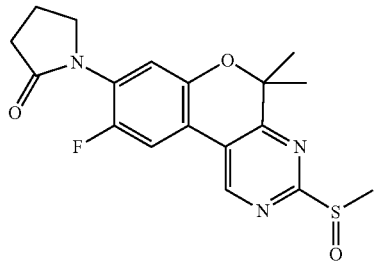 [SMILES: CS(=O)c1ncc2c(n1)C(C)(C)Oc1cc(N3CCCC3=O)c(F)cc1-2]

mCPBA (336 mg, 1.95 mmol) was added to a solution of 1-(9-fluoro-5,5-dimethyl-3-(methylthio)-5H-chromeno[3,4-d]pyrimidin-8-yl)pyrrolidin-2-one (140 mg, 0.389 mmol) in DCM (4 mL) at 25° C. The resulting mixture was stirred at 25° C. for 10 hours. Then the resulting mixture was stirred at 50° C. for 5 hours. The suspension turned to a yellow solution. LCMS showed the purity of the desired product was 96% (Rt=0.642 min; MS Calcd: 391.1; MS Found: 392.0 [M+H]$^+$). Sat. aq. Na$_2$SO$_3$ (15 mL) was added followed by DCM (15 mL). The organic layer was separated and the aqueous layer was extracted with DCM (10 mL×2). The combined organic phase was washed with Sat. aq. NaHCO$_3$ (15 mL) and brine (10 mL), dried over Na$_2$SO$_4$, filtered and concentrated to give 1-(9-fluoro-5,5-dimethyl-3-(methylsulfinyl)-5H-chromeno[3,4-d]pyrimidin-8-yl)pyrrolidin-2-one (150 mg, crude) as a yellow solid. Used for the next step without further purification.

Step 5: Preparation of 1-(9-fluoro-5,5-dimethyl-3-(methylsulfonyl)-5H-chromeno[3,4-d]pyrimidin-8-yl)pyrrolidin-2-one

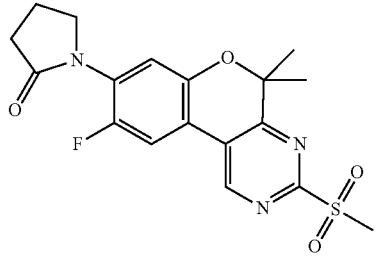 [SMILES: CC1(C)Oc2cc(N3CCCC3=O)c(F)cc2-c2cnc(S(C)(=O)=O)nc21]

mCPBA (345 mg, 2.00 mmol) was added to a solution of 1-(9-fluoro-5,5-dimethyl-3-(methylsulfinyl)-5H-chromeno[3,4-d]pyrimidin-8-yl)pyrrolidin-2-one (150 mg, 0.399 mmol) in DCM (4 mL) at 25° C. The resulting mixture was stirred at 50° C. for 12 hours. The suspension turned to a yellow solution. LCMS showed the purity of the desired product was 93% (Rt=0.657 min; MS Calcd: 391.1. MS Found: 392.0 [M+H]$^+$). Sat. aq. Na$_2$SO$_3$ (15 mL) was added followed by DCM (15 mL). The organic layer was separated and the aqueous layer was extracted with DCM (10 mL×2). The combined organic phase was washed with Sat. aq. NaHCO$_3$ (15 mL) and brine (10 mL), dried over Na$_2$SO$_4$, filtered and concentrated to give 1-(9-fluoro-5,5-dimethyl-3-(methylsulfonyl)-5H-chromeno[3,4-d]pyrimidin-8-yl)

pyrrolidin-2-one (150 mg, yield: 96% for two steps) as a yellow solid. Used for the next step without further purification.

Step 6: Preparation of (S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one

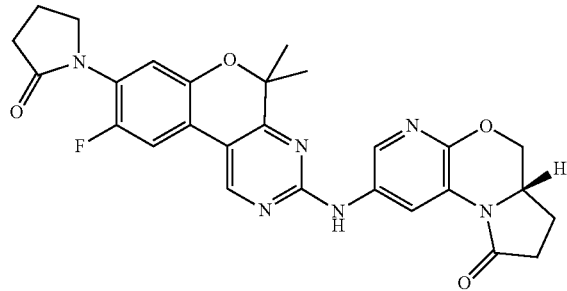 [SMILES: CC1(C)Oc2cc(N3CCCC3=O)c(F)cc2-c2cnc(Nc3cnc4c(c3)N3C(=O)CC[C@H]3CO4)nc21]

To a solution of 1-(9-fluoro-5,5-dimethyl-3-(methylsulfonyl)-5H-chromeno[3,4-d]pyrimidin-8-yl)pyrrolidin-2-one (150 mg, 0.383 mmol) and (S)-2-amino-6,6a,7,8-tetrahydro-9H-pyrido[2,3-b]pyrrolo[1,2-d][1,4]oxazin-9-one (118 mg, 0.574 mmol) in DMF (4 mL) was added NaH (23 mg, 0.58 mmol, 60% in mineral oil) at 20° C. The reaction mixture was stirred at 20° C. for 12 hours under $N_2$ atmosphere. A black solution was formed gradually. LCMS showed the purity of the desired product is 23% (Rt=0.697 min; MS Calcd: 516.2; MS Found: 517.1 [M+H]$^+$). The mixture was filtered. The filtrate was purified by prep-HPLC (0.05% $NH_3.H_2O$ as an additive) and lyophilized to give (S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one (8.9 mg, yield: 5%) as an off-white solid.

$^1$H NMR (400 MHz, DMSO-d$_6$) δ 1.61 (3H, s), 1.62 (3H, s), 1.67-1.73 (1H, m), 2.05-2.11 (2H, m), 2.20-2.25 (1H, m), 2.37-2.45 (3H, m), 2.65-2.72 (1H, m), 3.78 (2H, t, J=7.2 Hz), 3.92 (1H, t, J=10.8 Hz), 4.04-4.11 (1H, m), 4.60 (1H, dd, J=11.2, 2.4 Hz), 7.06 (1H, d, J=7.2 Hz), 7.87 (1H, d, J=11.6 Hz), 7.14 (1H, d, J=2.0 Hz), 9.01 (1H, s), 9.38 (1H, brs), 10.04 (1H, s).

Example 191: N-(5-((5,5-dimethyl-8-(2-oxopyrrolidin-1-yl)-5H-chromeno[4,3-c]pyridin-3-yl)amino)-2-methoxypyridin-3-yl)acetamide

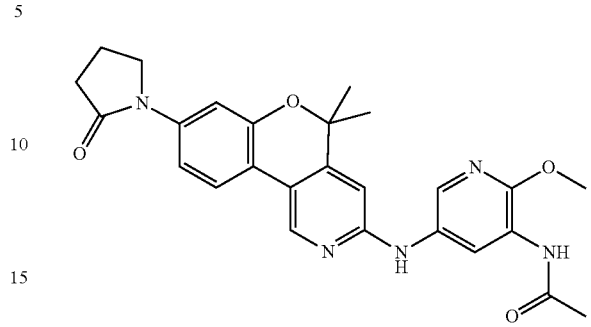

A mixture of Pd$_2$(dba)$_3$ (18 mg, 0.019 mmol) and Brettphos (21 mg, 0.038 mmol) in 1,4-dioxane (1 mL) was stirred at 50° C. for 10 min. 1-(3-amino-5,5-dimethyl-5H-chromeno[4,3-c]pyridin-8-yl)pyrrolidin-2-one (75 mg, 0.24 mmol), N-(5-bromo-2-methoxypyridin-3-yl)acetamide (59 mg, 0.24 mmol) in dioxane (4 mL) and Cs$_2$CO$_3$ (197 mg, 0.606 mmol) were added and the resulting mixture was stirred at 100° C. for 12 hours. A black brown mixture was formed. LCMS showed that the purity of the desired product is 50% (Rt=0.613 min; MS Calcd: 473.2. MS Found: 474.2 [M+H]$^+$). The reaction mixture was diluted with DCM (10 mL), filtered and concentrated. The residue was purified by prep-HPLC (0.225% FA as an additive) and lyophilized to give N-(5-((5,5-dimethyl-8-(2-oxopyrrolidin-1-yl)-5H-chromeno[4,3-c]pyridin-3-yl)amino)-2-methoxypyridin-3-yl)acetamide (19.9 mg, yield: 17%) as a yellow solid.

$^1$H NMR (400 MHz, DMSO-d$_6$) δ 1.54 (6H, s), 2.02-2.11 (2H, m), 2.12 (3H, s), 2.48 (2H, overlapped with DMSO), 3.84 (2H, t, J=6.8 Hz), 3.91 (3H, s), 6.73 (1H, s), 7.28 (1H, dd, J=8.4, 2.0 Hz), 7.38 (1H, d, J=2.4 Hz), 7.86 (1H, d, J=8.8 Hz), 8.30 (1H, d, J=2.4 Hz), 8.58 (1H, d, J=2.4 Hz), 8.61 (1H, s), 9.15 (1H, brs), 9.34 (1H, brs).

The following compounds were prepared according to the general procedure described herein, as well as the individual procedure for any structurally related compounds. The procedure utilized the appropriate reagents, solvents, and starting materials according to the final products. All reactions were carried out under suitable conditions, including but not limited to temperature, pressure, and time.

Table 1 illustrates compounds of the invention that were prepared in accordance with any of the synthetic method described above using suitable starting materials, reagents and appropriate and necessary conditions to these compounds.

| Example | Compound Name | Structure |
|---|---|---|
| 192 | (S)-2-(((R)-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one | 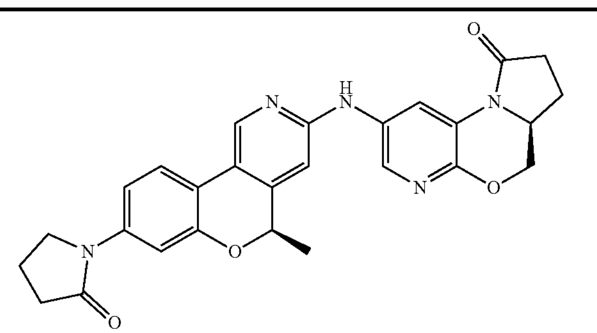 |

| Example | Compound Name | Structure |
|---|---|---|
| 193 | (S)-2-(((S)-5-methyl-8-(2-oxopyrrolidin-1-yl)-5H-chromeno[4,3-c]pyridin-3-yl)amino)-6,6a,7,8-tetrahydro-9H-pyrido[2,3-b]-pyrrolo[1,2-d][1,4]oxazin-9-one | 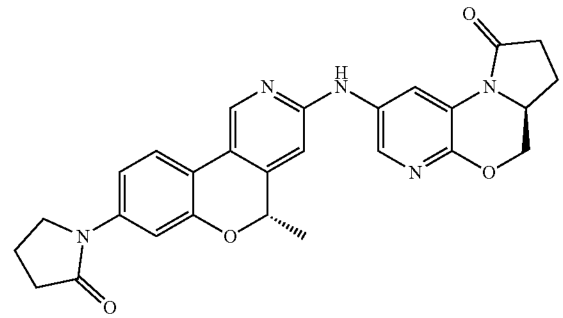 [SMILES: C[C@@H]1Oc2cc(N3CCCC3=O)ccc2-c2cnc(Nc3cnc4c(c3)N3C(=O)CC[C@H]3CO4)cc21] |
| 194 | (S)-2-((8-(2-oxopyrrolidin-1-yl)spiro[chromeno[4,3-c]pyridine-5,3'-oxetan]-3-yl)amino)-6,6a,7,8-tetrahydro-9H-pyrido[2,3-b]-pyrrolo[1,2-d][1,4]oxazin-9-one | 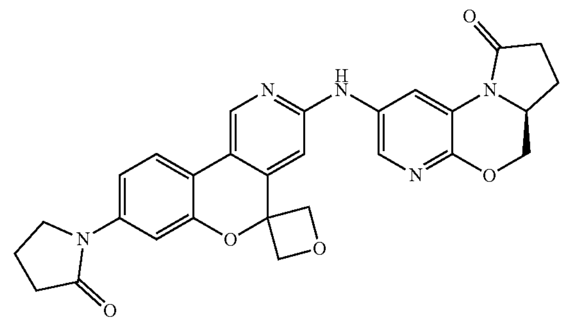 [SMILES: O=C1CCCN1c1ccc2c(c1)OC1(COC1)c1cc(Nc3cnc4c(c3)N3C(=O)CC[C@H]3CO4)ncc1-2] |
| 195 | (S)-2-((8-(2-oxopyrrolidin-1-yl)spiro[chromeno[4,3-c]pyridine-5,1'-cyclobutan]-3-yl)amino)-6,6a,7,8-tetrahydro-9H-pyrido[2,3-b]-pyrrolo[1,2-d][1,4]oxazin-9-one | 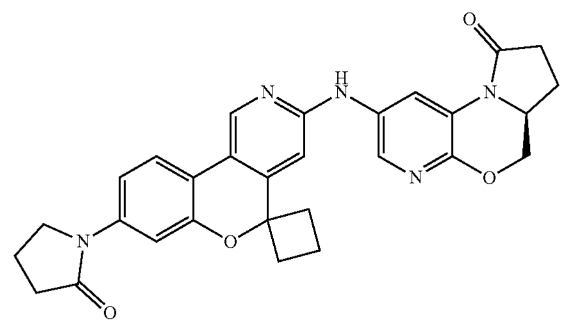 |
| 196 | N-(5-((5-methyl-8-(2-oxopyrrolidin-1-yl)-5H-chromeno[4,3-c]pyridin-3-yl)amino)pyridin-3-yl)-1H-benzo[d]-imidazole-7-carboxamide | 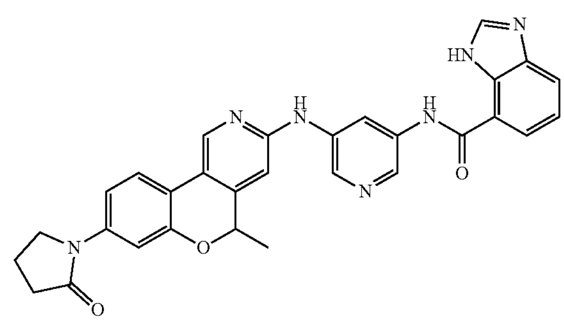 [SMILES: CC1Oc2cc(N3CCCC3=O)ccc2-c2cnc(Nc3cncc(NC(=O)c4cccc5nc[nH]c45)c3)cc21] |
| 197 | (S)-2'-((5-(3-fluoro-4-(2-oxopyrrolidin-1-yl)-phenyl)pyridin-2-yl)-amino)-6a',7'-dihydro-6'H,9'H-spiro[cyclopropane-1,8'-pyrido[2,3-b]-pyrrolo[1,2-d][1,4]-oxazin]-9'-one | 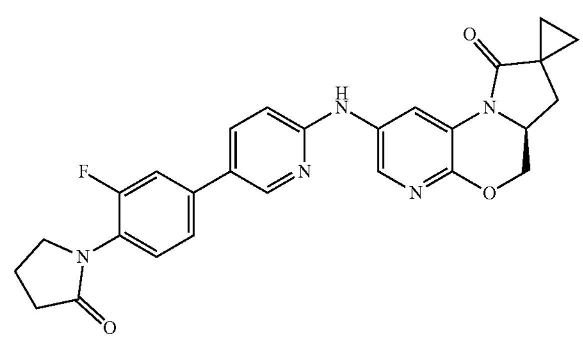 [SMILES: O=C1CCCN1c1ccc(-c2ccc(Nc3cnc4c(c3)N3C(=O)C5(CC5)C[C@H]3CO4)nc2)cc1F] |

-continued

| Example | Compound Name | Structure |
|---|---|---|
| 198 | (E)-N-(5-((5,5-dimethyl-8-(2-oxopyrrolidin-1-yl)-5H-chromeno[4,3-c]pyridin-3-yl)amino)-pyridin-3-yl)-4-(4-(dimethylamino)but-2-enamido)benzamide | 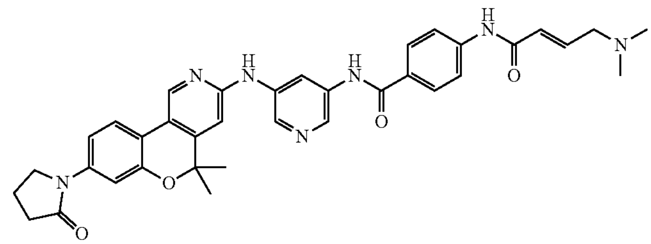 [SMILES: CN(C)C/C=C/C(=O)Nc1ccc(C(=O)Nc2cncc(Nc3cc4c(cn3)-c3ccc(N5CCCC5=O)cc3OC4(C)C)c2)cc1] |
| 199 | (E)-N-(3-(3-((5-((5,5-dimethyl-8-(2-oxo-pyrrolidin-1-yl)-5H-chromeno[4,3-c]pyridin-3-yl)amino)pyridin-3-yl)-amino)-3-oxopropyl)-phenyl)-4-(dimethyl-amino)but-2-enamide | 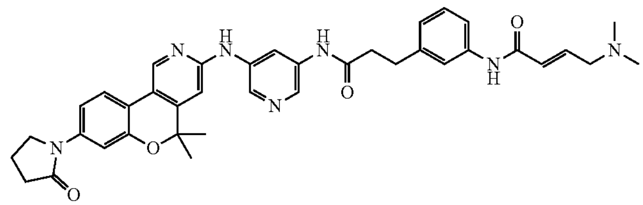 [SMILES: CN(C)C/C=C/C(=O)Nc1cccc(CCC(=O)Nc2cncc(Nc3cc4c(cn3)-c3ccc(N5CCCC5=O)cc3OC4(C)C)c2)c1] |
| 200 | (E)-4-(4-(dimethylamino)-but-2-enamido)-N-(5-((8-(2-oxopyrrolidin-1-yl)-5H-chromeno[4,3-c]pyridin-3-yl)amino)pyridin-3-yl)-benzamide | 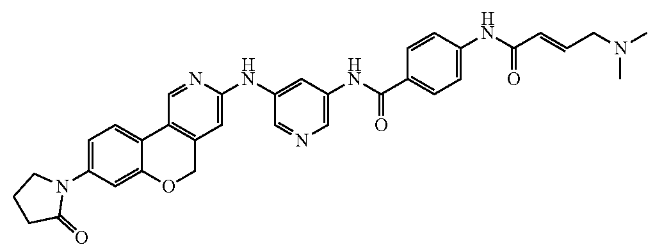 [SMILES: CN(C)C/C=C/C(=O)Nc1ccc(C(=O)Nc2cncc(Nc3cc4c(cn3)-c3ccc(N5CCCC5=O)cc3OC4)c2)cc1] |
| 201 | (6aS)-2-((9-fluoro-5-methyl-8-(2-oxo-pyrrolidin-1-yl)-5H-chromeno[4,3-c]pyridin-3-yl)amino)-8-hydroxy-6,6a,7,8-tetrahydro-9H-pyrido[2,3-b]pyrrolo-[1,2-d][1,4]oxazin-9-one | 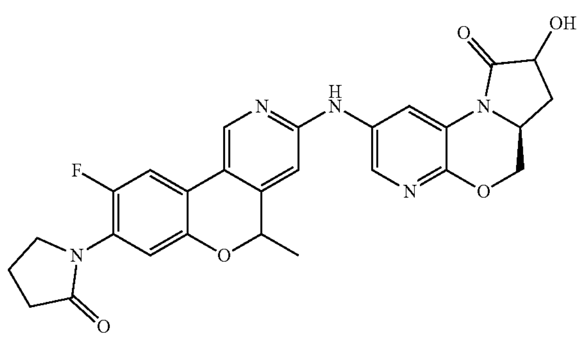 [SMILES: CC1Oc2cc(N3CCCC3=O)c(F)cc2-c2cnc(Nc3cnc4c(c3)N3C(=O)C(O)C[C@H]3CO4)cc21] |
| 202 | 1-(4-(pyridin-4-yl)-5H-chromeno[4,3-c]pyridin-8-yl)pyrrolidin-2-one | 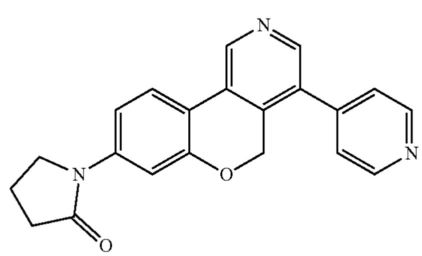 [SMILES: O=C1CCCN1c1ccc2c(c1)OCc1c(-c3ccncc3)cncc1-2] |
| 203 | 1-(5-methyl-4-(pyridin-4-ylamino)-5H-chromeno-[4,3-c]pyridin-8-yl)-pyrrolidin-2-one | 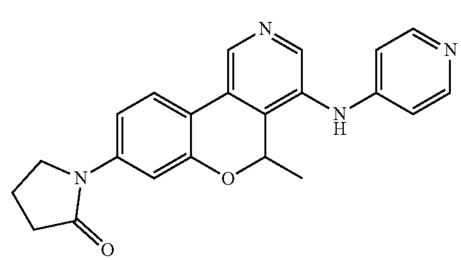 [SMILES: CC1Oc2cc(N3CCCC3=O)ccc2-c2cncc(Nc3ccncc3)c21] |

| Example | Compound Name | Structure |
|---|---|---|
| 204 | (6aS,8R)-2-((9-fluoro-5-methyl-8-(2-oxopyrrolidin-1-yl)-5H-chromeno[4,3-c]-pyridin-3-yl)amino)-8-hydroxy-8-methyl-6,6a,7,8-tetrahydro-9H-pyrido[2,3-b]pyrrolo[1,2-d][1,4]oxazin-9-one | 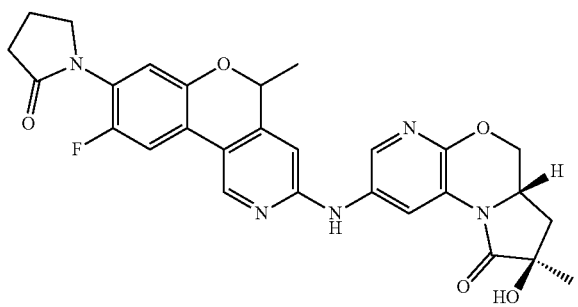 [SMILES: CC1Oc2cc(N3CCCC3=O)c(F)cc2-c2cnc(Nc3cnc4c(c3)N3C(=O)[C@](C)(O)C[C@H]3CO4)cc21] |
| 205 | (6aS,8R)-8-hydroxy-8-methyl-2-((5-methyl-8-(2-oxopyrrolidin-1-yl)-5H-chromeno[4,3-c]-pyridin-3-yl)amino)-6,6a,7,8-tetrahydro-9H-pyrido[2,3-b]pyrrolo[1,2-d][1,4]oxazin-9-one | 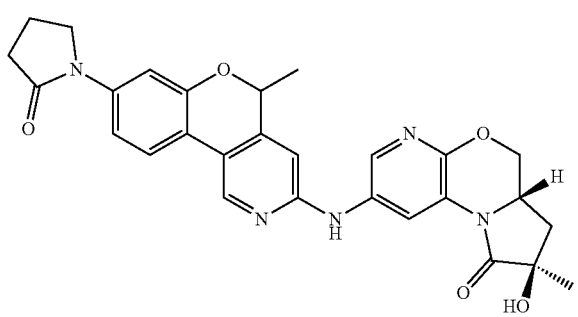 [SMILES: CC1Oc2cc(N3CCCC3=O)ccc2-c2cnc(Nc3cnc4c(c3)N3C(=O)[C@](C)(O)C[C@H]3CO4)cc21] |
| 206 | (6aS)-8-hydroxy-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one | 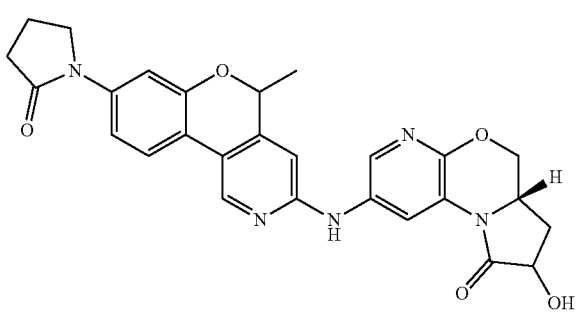 [SMILES: CC1Oc2cc(N3CCCC3=O)ccc2-c2cnc(Nc3cnc4c(c3)N3C(=O)C(O)C[C@H]3CO4)cc21] |
| 207 | 1-(5-methyl-4-(pyridin-4-yl)-5H-chromeno[4,3-c]pyridin-8-yl)pyrrolidin-2-one | 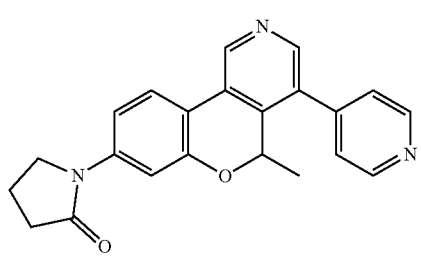 [SMILES: CC1Oc2cc(N3CCCC3=O)ccc2-c2cncc(-c3ccncc3)c21] |
| 208 | 1-(5,5-dimethyl-3-((1-methyl-2,3-dihydro-1H-pyrido[2,3-b][1,4]-oxazin-7-yl)amino)-5H-chromeno[3,4-d]pyrimidin-8-yl)pyrrolidin-2-one | 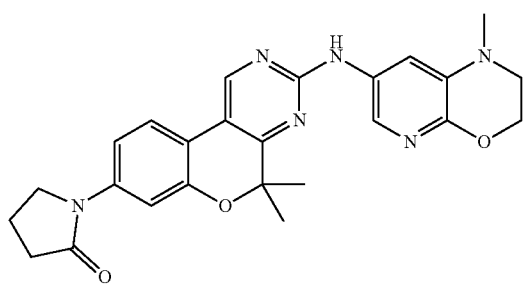 [SMILES: CN1CCOc2ncc(Nc3ncc4c(n3)C(C)(C)Oc3cc(N5CCCC5=O)ccc3-4)cc21] |

| Example | Compound Name | Structure |
|---|---|---|
| 209 | (S)-2-((5,5-dimethyl-8-(4-methylisoxazol-3-yl)-5H-chromeno[4,3-c]-pyridin-3-yl)amino)-6,6a,7,8-tetrahydro-9H-pyrido[2,3-b]pyrrolo-[1,2-d][1,4]oxazin-9-one | 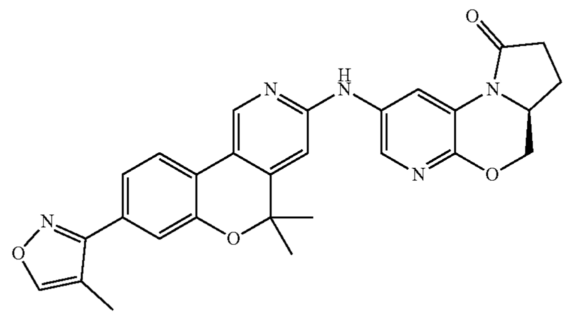 [SMILES: Cc1conc1-c1ccc2c(c1)OC(C)(C)c1cc(Nc3cnc4c(c3)N3C(=O)CC[C@H]3CO4)ncc1-2] |
| 210 | (S)-2-((5,5-dimethyl-8-(4-methyl-4H-1,2,4-triazol-3-yl)-5H-chromeno[3,4-d]-pyrimidin-3-yl)amino)-6,6a,7,8-tetrahydro-9H-pyrido[2,3-b]pyrrolo[1,2-d][1,4]oxazin-9-one | 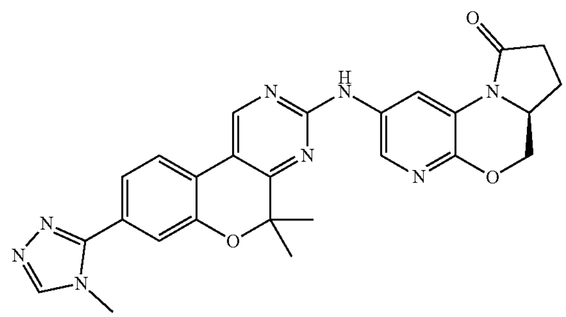 [SMILES: Cn1cnnc1-c1ccc2c(c1)OC(C)(C)c1nc(Nc3cnc4c(c3)N3C(=O)CC[C@H]3CO4)ncc1-2] |
| 211 | (S)-2-((5,5-dimethyl-8-(4-methyl-4H-1,2,4-triazol-3-yl)-5H-chromeno[4,3-c]-pyridin-3-yl)amino)-6,6a,7,8-tetrahydro-9H-pyrido[2,3-b]pyrrolo[1,2-d][1,4]oxazin-9-one | 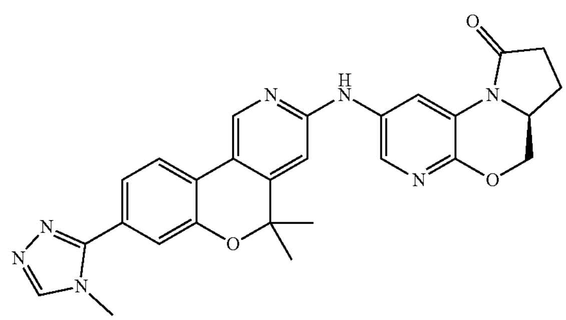 [SMILES: Cn1cnnc1-c1ccc2c(c1)OC(C)(C)c1cc(Nc3cnc4c(c3)N3C(=O)CC[C@H]3CO4)ncc1-2] |
| 212 | N-(5-((5,5-dimethyl-8-(2-oxopyrrolidin-1-yl)-5H-chromeno[4,3-c]-pyridin-3-yl)amino)-pyridin-3-yl)-4-(2-(2-(2-(2-((2-(2,6-dioxo-piperidin-3-yl)-1,3-dioxo-isoindolin-4-yl)amino)-ethoxy)ethoxy)ethoxy)-acetamido)benzamide | 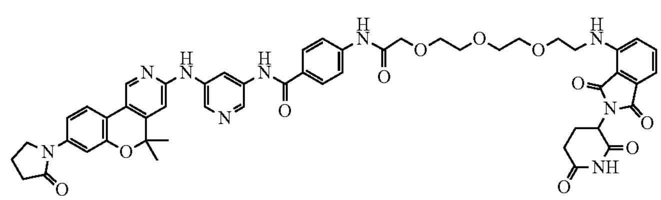 [SMILES: CC1(C)Oc2cc(N3CCCC3=O)ccc2-c2cnc(Nc3cncc(NC(=O)c4ccc(NC(=O)COCCOCCOCCNc5cccc6c5C(=O)N(C5CCC(=O)NC5=O)C6=O)cc4)c3)cc21] |
| 213 | N-(5-((5,5-dimethyl-8-(2-oxopyrrolidin-1-yl)-5H-chromeno[4,3-c]-pyridin-3-yl)amino)-pyridin-3-yl)-4-(4-(2-((2-(2,6-dioxopiperidin-3-yl)-1,3-dioxoisoindolin-4-yl)oxy)acetamido)-butanamido)benzamide | 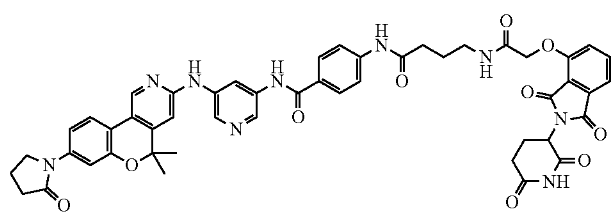 [SMILES: CC1(C)Oc2cc(N3CCCC3=O)ccc2-c2cnc(Nc3cncc(NC(=O)c4ccc(NC(=O)CCCNC(=O)COc5cccc6c5C(=O)N(C5CCC(=O)NC5=O)C6=O)cc4)c3)cc21] |

| Example | Compound Name | Structure |
|---|---|---|
| 109A | 4-formamido-3-hydroxy-N-(5-((5-methyl-8-(2-oxopyrrolidin-1-yl)-5H-chromeno[4,3-c]pyridin-3-yl)amino)pyridin-3-yl)benzamide | 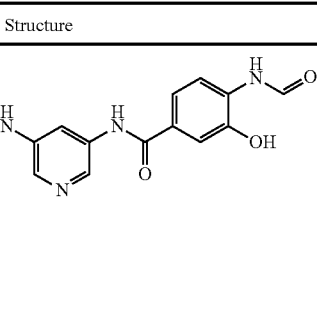 |

Biochemical Assays

Example 214: ADP-Glo Biochemical Assay

Dilution series of the compounds were prepared in DMSO at 100 times the final assay concentration ($n_1=n_0/3$ in 10 points). The compounds were further diluted to three times the assay concentration in assay buffer (20 mM MOPS pH 7.2, 25 mM magnesium chloride, 0.005% Tween 20). 6 μL of the diluted compounds were added to a 384 well assay plate followed by 9 μL of a mix consisting of 4 nM PIP4K$_2$A (full length protein, SignalChem) and 100 μM PI(5)P diC8 (Tebu-Bio). Enzyme and compounds were pre-incubated at room temperature for 15 minutes.

Then 3 μL of a solution containing 60 μM ATP (Promega) in assay buffer was added to the wells containing compound and enzyme and mixing was performed by pipetting several times. The reaction was incubated at room temperature for 1 h. Then 18 μL of ADP-Glo™ Reagent (Promega) was added to stop the kinase reaction and deplete the unconsumed ATP, mixing was performed by pipetting several times. The plate was incubated at room temperature for 40 minutes before addition of 36 μL of Kinase Detection Reagent (Promega) to convert ADP to ATP and introduce luciferase and luciferin to detect ATP. The reaction was incubated at room temperature for 40 minutes before the luminescence was measured in a in a Victor 3V 1420 multilabel counter (Perkin Elmer).

Percent inhibition of the compounds as compared to dimethyl sulfoxide treated control samples was calculated. Compound concentration versus percent inhibition were fitted to generate IC$_{50}$ values. Results obtained with this assay are disclosed in Table 2-4 below.

Example 215: Assay Protocol—PIP4KtypeIIA

GST tagged PIP4KtypeIIA and B enzymes were overexpressed in *E. Coli* and purified to >80% homogeneity. Phosphatidyl inositol-5-phosphate (PI5P, Cat. #850152, Avanti Polar Lipids Inc.) was used as the lipid substrate and phosphatidyl ethanolamine (DOPE 18:1, Cat. #850725, Avanti Polar Lipids Inc.) was used as the carrier lipid for assays. Ultrapure ATP and GTP was purchased from Bellbrooke Labs. ADP Glo reagents were obtained from Promega. Transcreener FI reagent was obtained from Bellbrooke labs.

Buffers:
1. HEPES buffer mix: 200 mM HEPES pH 7.4, 50 mM MgCl2, 0.05% v/v triton X 100
2. HNE buffer: 20 mM HEPES, pH 7.4, 100 mM NaCl, 0.5 mM EGTA
3. H:E buffer: 30 mM HEPES, pH 7.4, 1 mM EGTA Enzyme preparation: GST-tagged PIP4KtypeIIA (5 uL, 1.43 mg/mL) was diluted (1:10) to 50 uL using HNE buffer. From the 1:10 diluted stock, a 6.4 uL aliquot was diluted further to 5 mL using HNE buffer to yield 5× enzyme stock (2.5 nM).
GST-tagged PIP4KtypeIIB (3.4 uL, 2.77 mg/mL) was diluted to 5 mL using HNE buffer to yield 5× enzyme stock (25 nM)

Lipid Preparation: In a 10 mL pyrex glass vial, 1 ug of PI5P and 1 ug of DOPE were suspended in 2.5 mL of HEPES buffer mix and 2.5 mL of H:E buffer. The contents were mixed and sonicated for 3 min to yield a translucent lipid stock.

Compound Preparation: Compounds were stored as 5 mM stocks in neat DMSO as room temperature in glass vials. 5 mM stocks were diluted to 2 mM and then serially diluted (3×) in neat DMSO in 96 well polypropylene plates. From the serially diluted stocks, 3 uL was delivered into 250 uL of 25% DMSO (in water) to generate 5× compound stocks. Typically, the highest compound conc. was 24 uM.

Example 216: PIP4KtypeIIA Inhibition Assay

The assay volume was kept at 25 uL. To each well of the reaction plate, 10 uL of lipid stock (1:1 ratio PI5P:DOPE) was delivered. This was followed by the addition of 5 uL of compound in 25% DMSO. Then, to each well, 5 uL of 2.5 nM (5×) typeIIA enzyme was delivered. The contents were mixed well and incubated for 1 h at 27 C. After 1 h, reaction was initiated by adding 5 uL of 50 uM ATP and the contents were mixed well with a multi-channel pipetteman. The final concentration of the reagents are as follows: 50 mM HEPES, pH 7.3, 10 mM MgCl$_2$, 20 mM NaCl, 0.01% v/v triton-X100, 5% DMSO, 10 uM ATP, 80 uM (2 ug) PI5P, 2 ug DOPE, and 0.5 nM PIP4KIIA. Typically, the highest conc. of compounds was 4.8 uM and the lowest conc. was 0.

After 1 hr, the reaction was quenched by adding 25 uL of ADP Glo reagent. The contents were incubated for 1 hr. Afterwards, 50 uL of kinase detection reagent was delivered. The contents were incubated for another hour. The luminescence was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RLU was converted to uM ADP (product). IC50 was calculated by plotting the residual activity (expressed as % No inhibitor control) vs. log [Inh. conc.]

Example 217: PIP4KtypeIIB Inhibition Assay

The assay volume was kept at 25 uL. To each well of the reaction plate, 10 uL of lipid stock (1:1 ratio PI5P:DOPE) was delivered. This was followed by the addition of 5 uL of compound in 25% DMSO. Then, to each well, 5 uL of 25 nM (5×) typeIIB enzyme was delivered. The contents were mixed well and incubated for 1 h at 27 C. After 1 h, reaction was initiated by adding 5 uL of 500 uM GTP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-X100, 5% DMSO, 100 uM GTP, 80 uM (2 ug) PI5P, 2 ug DOPE, and 5 nM PIP4KIIB Typically, the highest conc. of compounds was 4.8 uM and the lowest conc. was 0.

After 2 h, the reaction was quenched by adding 25 uL of transcreener FI reagent. The contents were incubated at RT for 1 h and the Fluorescence (Ex: 584 Em: 623) was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RFU was converted to uM GDP (product). IC50 was calculated by plotting the residual activity (expressed as % No inhibitor control) vs. log [Inh. conc.]

Table 2 represents PI5P4K activity of compounds (Examples No.:) of the invention arranged in accordance with the inhibition of PIP4K2 A kinase assay.

| Kinase Assay- PIP4K2 A $IC_{50} \leq 1$ nM |
|---|
| 32 |
| 42 |
| 35 |
| 33 |
| 40 |
| 36 |
| 39 |
| 53 |
| 49 |
| 52 |
| 192 |
| 193 |
| 54 |
| 51 |
| 57 |
| 86 |
| 55 |
| 62 |
| 82 |
| 72 |
| 67 |
| 68 |
| 70 |
| 71 |
| 84 |
| 73 |
| 56 |
| 83 |
| 61 |
| 69 |
| 44 |
| 77 |
| 75 |
| 59 |
| 76 |
| 78 |
| 195 |
| 97 |
| 47 |
| 74 |
| 79 |
| 58 |
| 60 |
| 85 |
| 148 |
| 100 |
| 103 |
| 106 |
| 149 |
| 131 |
| 164 |
| 167 |
| 170 |
| 209 |
| 210 |
| 211 |

| Kinase Assay- PIP4K2 A $1 < IC_{50} \leq 10$ nM |
|---|
| 31 |
| 41 |
| 34 |
| 38 |
| 37 |
| 48 |
| 50 |
| 63 |
| 64 |
| 65 |
| 87 |
| 88 |
| 90 |
| 46 |
| 96 |
| 194 |
| 93 |
| 94 |
| 45 |
| 95 |
| 128 |
| 130 |
| 173 |

| Kinase Assay- PIP4K2 A $10 < IC_{50} \leq 100$ nM |
|---|
| 80 |
| 81 |
| 91 |
| 43 |
| 127 |
| 187 |

| Kinase Assay- PIP4K2 A $100 < IC_{50} \leq 1000$ nM |
|---|
| 89 |
| 202 |

Table 3 represents PI5P4K activity of compounds (Examples No.:) of the invention arranged in accordance with the inhibition of ADP-glo kinase assay PIP4K 2A.

| ADP-glo kinase assay PIP4K 2A $IC_{50} \leq 1$ nM |
|---|
| 40 |
| 36 |
| 192 |
| 193 |
| 86 |

| 82 |
| 67 |
| 68 |
| 70 |
| 71 |
| 84 |
| 73 |
| 56 |
| 83 |
| 61 |
| 69 |
| 77 |
| 75 |
| 59 |
| 76 |
| 78 |
| 194 |
| 195 |
| 47 |
| 58 |
| 60 |
| 148 |
| 121 |
| 150 |
| 143 |
| 144 |
| 167 |
| 116 |
| 146 |
| 115 |
| 156 |
| 153 |
| 180 |
| 152 |
| 184 |
| 155 |
| 178 |
| 157 |
| 154 |
| 190 |
| 189 |
| 158 |
| 206 |
| 159 |

| ADP-glo kinase assay |
| PIP4K 2A 1 < IC$_{50}$ ≤ 10 nM |

| 32 |
| 31 |
| 42 |
| 35 |
| 33 |
| 34 |
| 38 |
| 53 |
| 48 |
| 49 |
| 52 |
| 54 |
| 63 |
| 51 |
| 57 |
| 55 |
| 62 |
| 72 |
| 87 |
| 88 |
| 44 |
| 96 |
| 94 |
| 97 |
| 74 |
| 79 |
| 85 |
| 103 |
| 106 |
| 149 |
| 99 |
| 110 |
| 107 |
| 111 |
| 112 |
| 113 |
| 114 |
| 120 |
| 122 |
| 130 |
| 131 |
| 132 |
| 133 |
| 135 |
| 136 |
| 137 |
| 92 |
| 104 |
| 140 |
| 98 |
| 105 |
| 108 |
| 123 |
| 196 |
| 139 |
| 141 |
| 145 |
| 151 |
| 109A |
| 125 |
| 126 |
| 134 |
| 164 |
| 166 |
| 101 |
| 109 |
| 129 |
| 147 |
| 163 |
| 102 |
| 117 |
| 169 |
| 170 |
| 176 |
| 172 |
| 173 |
| 160 |
| 174 |
| 118 |
| 181 |
| 182 |
| 183 |
| 177 |
| 197 |
| 198 |
| 199 |
| 200 |
| 161 |
| 162 |
| 185 |
| 204 |

| ADP-glo kinase assay |
| PIP4K 2A 10 < IC$_{50}$ ≤ 100 nM |

| 41 |
| 37 |
| 50 |
| 64 |
| 80 |
| 65 |
| 90 |
| 91 |
| 43 |
| 46 |
| 93 |
| 45 |
| 95 |
| 100 |
| 128 |

-continued 119
138
142
165
168
171
205
186

ADP-glo kinase assay
PIP4K 2A 100 < IC$_{50}$ ≤ 1000 nM 81
89
127
191

ADP-glo kinase assay
PIP4K 2A IC$_{50}$ > 1000 nM 202
203

Table 4: represents PI5P4K activity of compounds (Examples No.:) of the invention arranged in accordance with the inhibition of PIP4K2 B kinase assay.

Trans-FI P kinase assays:
PIP4K2B 1 < IC$_{50}$ ≤ 10 nM 35
33
40
36
86
82
72
67
68
70
71
84
73
56
83
61
69
77
75
59
76
78
194
195
47
74
58
60
148
121
150
123
143
144
109
146
115
156
153
180
152
181
182
183
184
155
177

-continued 178
157
197
154
198
200
190
189
158
206
209
211
159

Trans-FI P kinase assays:
PIP4K2B 10 < IC$_{50}$ ≤ 100 nM 32
42
39
34
53
192
54
51
57
55
62
87
88
44
94
79
85
100
103
106
149
99
110
107
111
112
113
114
119
122
130
131
132
133
135
136
137
104
138
140
98
105
108
196
139
141
145
151
109A
125
126
134
164
166
167
101
116
129
147
163
102
117

| | |
|---|---|
| 165 | |
| 168 | |
| 169 | |
| 170 | |
| 176 | |
| 171 | |
| 172 | |
| 173 | |
| 160 | |
| 174 | |
| 118 | |
| 199 | |
| 161 | |
| 162 | |
| 204 | |
| 205 | |
| 186 | |

Trans-FI P kinase assays:
PIP4K2B 100 < IC$_{50}$ ≤ 1000 nM

| |
|---|
| 31 |
| 38 |
| 37 |
| 48 |
| 49 |
| 52 |
| 63 |
| 64 |
| 80 |
| 65 |
| 90 |
| 46 |
| 96 |
| 93 |
| 97 |
| 45 |
| 95 |
| 128 |
| 142 |
| 191 |
| 185 |
| 187 |

Trans-FI P kinase assays:
PIP4K2B IC$_{50}$ > 1000 nM

| |
|---|
| 41 |
| 50 |
| 81 |
| 91 |
| 89 |
| 43 |
| 127 |
| 120 |
| 92 |
| 202 |
| 203 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I):

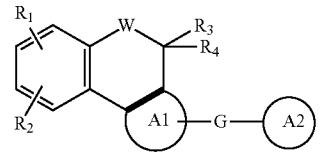

(I)

or a pharmaceutically acceptable salt, stereoisomer, or tautomer thereof,
wherein:
Ring A1 is 6-membered heteroaryl;
Ring A2 is heteroaryl optionally substituted with one or more $R_8$;
W is —O—, —N($C_{1-6}$ alkyl)-, —N($C_{3-8}$ cycloalkyl)-, —N(aryl)-, or —N(heteroaryl)-;
G is a bond, —O—, —NH—, or —N($C_{1-6}$ alkyl)-;
$R_1$ is —N($R_5$)C(O)$R_6$, —C(O)N($R_5$)($R_6$), —S(O)$_2$N($R_5$)($R_6$), —N($R_5$)S(O)$_2$$R_6$, or heteroaryl, wherein the heteroaryl is optionally substituted with one or more $R_7$;
$R_2$ is H, halogen, —OH, —NH$_2$, —NO$_2$, —CN, —COOH, —C(O)NH$_2$, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl;
$R_3$ and $R_4$ are each independently —H, halogen, $C_{1-6}$ alkyl, $C_{1-6}$ alkoxy, or $C_{3-6}$ cycloalkyl, wherein the $C_{1-6}$ alkyl, $C_{1-6}$ alkoxy, or $C_{3-6}$ cycloalkyl is optionally substituted with one or more halogen, —OH, or —NH$_2$; or
$R_3$ and $R_4$ when taken together with the atom to which they are attached form a $C_{3-8}$ cycloalkyl or heterocyclyl;
$R_5$ and $R_6$ are independently, at each occurrence, —H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more $R_7$; or
$R_5$ and $R_6$ when taken together with the atom to which they are each attached form a heterocycle optionally substituted with one or more $R_7$;
each $R_7$ is independently —H, halogen, —OH, —NH$_2$, —NO$_2$, —CN, $C_{1-6}$ alkyl, $C_{1-6}$ alkoxy, $C_{3-8}$ cycloalkyl, heterocyclyl, aryl, or heteroaryl;
each $R_8$ is independently —N($R_9$)C(O)$R_{10}$, —N($R_9$)C(O)O$R_{10}$, —N($R_9$)C(O)N($R_9$)($R_{10}$), —N($R_9$)C(O)N($R_9$)($R_{11}$), —N($R_9$)S(O)$_2$$R_{10}$, —N($R_9$)S(O)$_2$N($R_9$)($R_{10}$), —S(O)$_2$$R_{10}$, —N($R_9$)($R_{10}$), —O$R_{10}$, —CF$_3$, —CHF$_2$, —$R_{10}$, —N($R_9$)C(O)$R_{11}$, —N($R_9$)($R_{11}$), or halogen; or
two $R_8$ with the atoms to which they are attached form a $C_{4-8}$ cycloalkyl or heterocyclyl, wherein the heterocyclyl or $C_{4-8}$ cycloalkyl is optionally substituted with one or more $R_{12}$;
each $R_9$ and $R_{10}$ is independently, at each occurrence, —H, $C_{1-6}$ alkyl, $C_{3-8}$ cycloalkyl, or heterocyclyl, wherein the $C_{1-6}$ alkyl, $C_{3-8}$ cycloalkyl, or heterocyclyl is optionally substituted with one or more $R_{13}$; or
$R_9$ and $R_{10}$ when taken together with the atom to which they are each attached form a heterocycle optionally substituted with one or more $R_{14}$;
each $R_{11}$ is independently aryl, $C_{3-8}$ cycloalkyl, heterocyclyl, or heteroaryl, wherein the aryl or heteroaryl group is optionally substituted with one or more $R_{18}$ and the $C_{3-8}$ cycloalkyl or heterocyclyl is optionally substituted with one or more $R_{19}$;

each $R_{12}$ is independently $C_{1-6}$ alkyl, $C_{3-6}$ cycloalkyl, —$OR_{20}$, —$C(O)R_{20}$, —$C(O)OR_{20}$, —$S(O)_2R_{20}$, or oxo; or two $R_{12}$ taken together can form a $C_{3-8}$ cycloalkyl or heterocyclyl, wherein the $C_{3-8}$ cycloalkyl or heterocyclyl are optionally substituted with one or more $R_{14}$;

each $R_{13}$ is independently —H, halogen, —CN, oxo, $C_{1-6}$ alkyl, —$OR_{20}$, —$C(O)_2R_{20}$, $C_{3-8}$ cycloalkyl, heterocyclyl, heteroaryl, aryl, or —$C(O)N(R_{22})(R_{22})$, wherein the $C_{1-6}$ alkyl, aryl, or heteroaryl, is optionally substituted with one or more $R_{15}$;

each $R_{14}$ is independently —$C(O)OR_{20}$, —$C(O)R_{20}$, —$OR_{20}$, oxo, $C_{1-6}$ alkyl, heterocycle, $C_{3-8}$ cycloalkyl, or aryl, wherein the $C_{1-6}$ alkyl, heterocycle, $C_{3-8}$ cycloalkyl, or aryl is optionally substituted with one or more $R_{16}$; or two $R_{14}$ taken together can form a $C_{3-6}$ cycloalkyl or heterocyclyl;

each $R_{15}$ is independently —H, $C_{1-6}$ alkyl, $C_{1-6}$ alkoxy, heteroaryl, aryl, —$N(R_{22})(R_{22})$, —$N(R_{22})C(O)OR_{22}$, or —$N(R_{22})C(O)$—U—$N(R_{22})$—Z;

U is —$(CH_2)_p$—, —$(CH_2)_p$—Ar—, —CH=CH$(CH_2)_p$—, or heterocyclyl,

Z is —$R_{22}$ or —$C(O)$—U—$N(R_{22})(R_{22})$;

each $R_{16}$ is independently $C_{3-8}$ cycloalkyl, heterocyclyl, heteroaryl, or aryl, wherein the heterocyclyl, $C_{3-8}$ cycloalkyl, heteroaryl, or aryl is optionally substituted with one or more $R_{17}$;

each $R_{17}$ is independently —$OR_{22}$, —$N(R_{22})(R_{22})$, or —$N(R_{22})C(O)$—V—$N(R_{22})$-E;

V is —$(CH_2)_n$—, —$(CH_2)_n$—Ar—, or —CH=CH$(CH_2)_n$—;

E is —$R_{22}$ or —$C(O)$—V—$N(R_{22})(R_{22})$;

Ar is aryl;

each $R_{18}$ is independently halogen, $C_{1-6}$ alkyl, $C_{3-6}$ cycloalkyl, —$OR_{20}$, —$N(R_{20})(R_{21})$, —$C(O)R_{20}$, oxo, —$N(R_{22})C(O)OR_{22}$, —$N(R_{22})C(O)$-Q-$N(R_{22})$—F, or —$N(R_{22})$-Q-$N(R_{22})$—F;

Q is —CH=CH$(CH_2)_m$—, —$(CH_2)_m$—, —$(CH_2O)_m$—, —$(CH_2)_m$—Ar—, or —$(CH_2CH_2O)_o$—$(CH_2)_m$—;

F is —H, $C_{1-6}$ alkyl, aryl, heteroaryl, —C(O)-Q-$R_{22}$, or —C(O)-Q-$N(R_{22})(R_{22})$, wherein the $C_{1-6}$ alkyl, aryl, or heteroaryl is optionally substituted with one or more $R_{22}$; or two $R_{18}$ when on adjacent atoms may be taken together with the atoms to which they are each attached to form a $C_{3-8}$ cycloalkyl or heterocyclic group optionally substituted with —$OR_{21}$ or oxo;

each $R_{19}$ is independently —H, halogen, —OH, —$NH_2$, oxo, —$C(O)R_{20}$, —$OR_{22}$, $C_{3-6}$ cycloalkyl, or $C_{1-6}$ alkyl; or two $R_{19}$ when on adjacent atoms may be taken together with the atoms to which they are each attached to form an aryl or heteroaryl group optionally substituted with one or more $R_{22}$;

each $R_{20}$ is independently —H, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the $C_{1-6}$ alkyl, $C_{2-6}$ alkenyl, $C_{2-6}$ alkynyl, $C_{3-8}$ cycloalkyl, heterocyclyl, heteroaryl, or aryl is optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl;

each $R_{21}$ is independently —H, $C_{1-6}$ alkyl, or —$C(O)R_{22}$;

each $R_{22}$ is independently —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl;

each p is independently 1-4;
each n is independently 1-4;
each m is independently 1-4; and
o is 1-3.

2. The compound of claim 1, represented by formula (Ia), (Ib), (Ic), (Id), or (Ie):

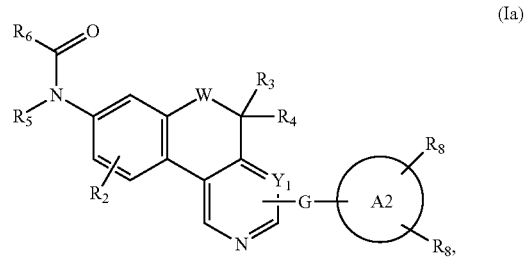

(Ia)

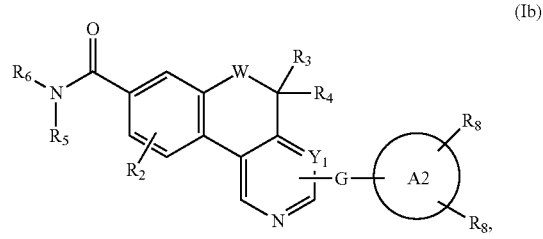

(Ib)

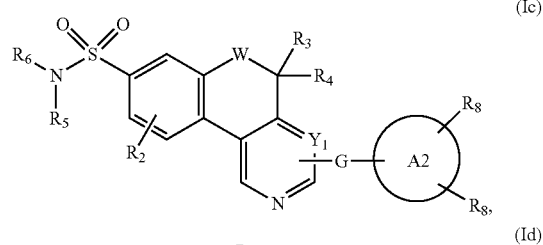

(Ic)

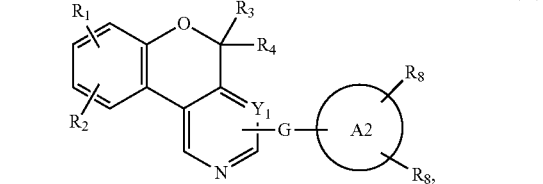

(Id)

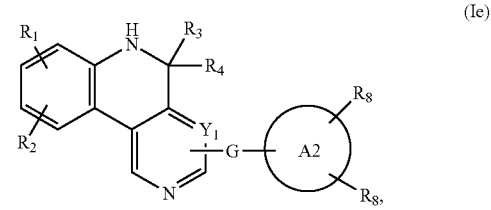

(Ie)

or a pharmaceutically acceptable salt, stereoisomer, or tautomer thereof,
wherein $Y_1$ is CH or N.

3. The compound of claim 1, represented by formula (If):

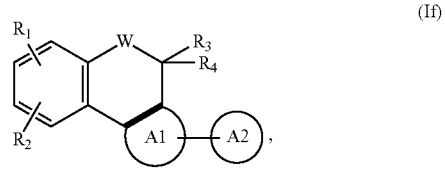

(If)

4. The compound of claim 1, represented by formula (Ih):

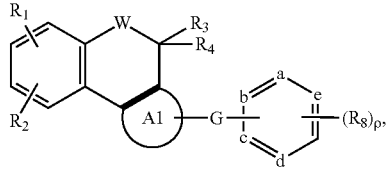

or a pharmaceutically acceptable salt, stereoisomer, or tautomer thereof,
wherein:
a, b, c, d, and e, are each independently C or N, wherein at least one of a, b, c, d, and e is N, and no more than two of a, b, c, d, and e, are N; and
p is 1, 2, or 3.

5. The compound of claim 1, represented by formula (Ij):

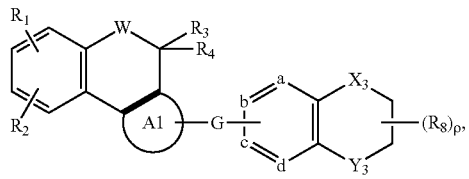

or a pharmaceutically acceptable salt, stereoisomer, or tautomer thereof,
wherein:
a, b, c, and d, are each independently C or N, wherein at least one of a, b, c, and d is N, and no more than two of a, b, c, and d, are N;
$X_3$ and $Y_3$ are each independently —O—, —$CH_2$—, or —N($R_8$)—;
p is 1, 2, or 3.

6. The compound of claim 1, represented by formula (Ii):

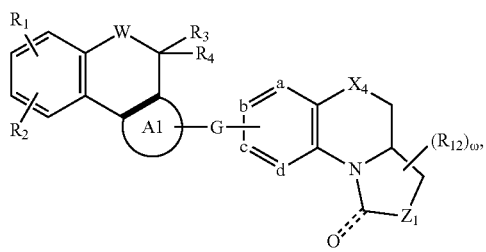

or a pharmaceutically acceptable salt, stereoisomer, or tautomer thereof,
wherein:
a, b, c, and d, are each independently C or N, wherein at least one of a, b, c, and d is N; and no more than two of a, b, c, and d, are N;
$X_4$ and $Z_1$ are each independently —O—, —N($R_{12}$)—, or —C($R_{12}$)($R_{12}$)—; and
ω is 1, 2, or 3.

7. The compound of claim 1, represented by formula (Ij):

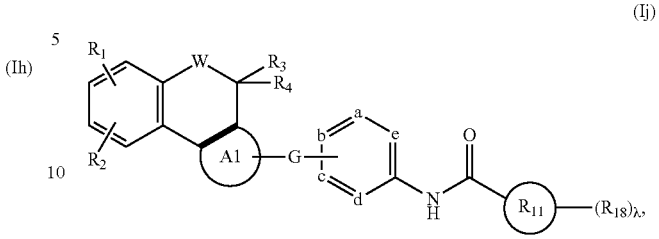

or a pharmaceutically acceptable salt, stereoisomer, or tautomer thereof,
wherein:
$R_{11}$ is aryl or heteroaryl;
a, b, c, d, and e, are each independently C or N, wherein at least one of a, b, c, d, and e is N, and no more than two of a, b, c, d, and e, are N; and
λ is 1, 2, or 3.

8. The compound of claim 1, represented by formula (Ik):

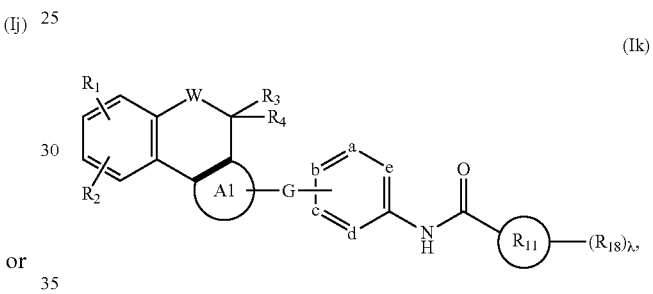

or a pharmaceutically acceptable salt, stereoisomer, or tautomer thereof,
wherein:
$R_{11}$ is $C_{3-8}$ cycloalkyl or heterocyclyl;
a, b, c, d, and e, are each independently C or N, wherein at least one of a, b, c, d, and e is N, and no more than two of a, b, c, d, and e, are N; and
λ is 1, 2, or 3.

9. The compound of claim 1, represented by formula (Il):

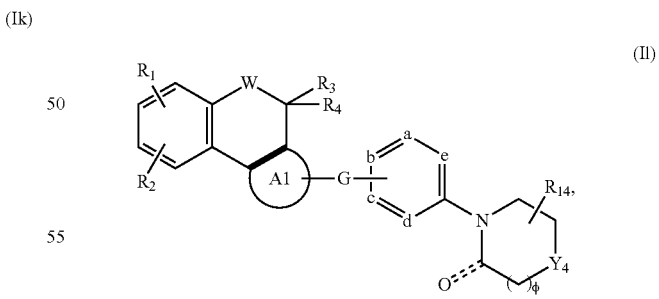

or a pharmaceutically acceptable salt, stereoisomer, or tautomer thereof,
wherein:
a, b, c, d, and e, are each independently C or N, wherein at least one of a, b, c, d, and e is N, and no more than two of a, b, c, d, and e, are N;
$Y_4$ is —O—, —N($R_{14}$)—, or —C($R_{14}$)($R_{14}$)—; and
Φ is 0, 1, or 2.

10. The compound of claim 1, represented by formula (Im):

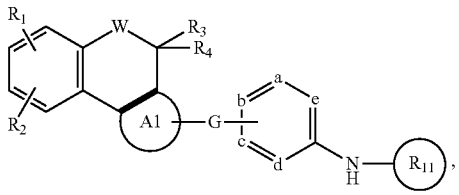

or a pharmaceutically acceptable salt, stereoisomer, or tautomer thereof,
wherein:
a, b, c, d, and e, are each independently C or N, wherein at least one of a, b, c, d, and e is N, and no more than two of a, b, c, d, and e, are N.

11. The compound of claim 1, represented by formula (In):

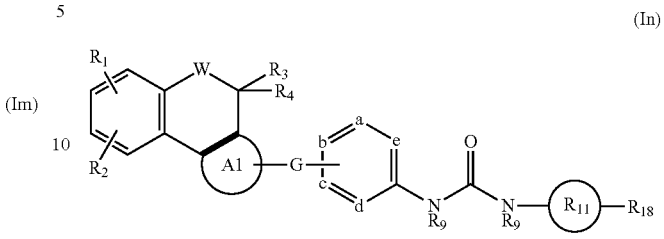

or a pharmaceutically acceptable salt, stereoisomer, or tautomer thereof,
wherein:
$R_{11}$ is aryl or heteroaryl;
a, b, c, d, and e, are each independently C or N, wherein at least one of a, b, c, d, and e is N, and no more than two of a, b, c, d, and e, are N.

12. The compound of claim 1, represented by formula (Io):

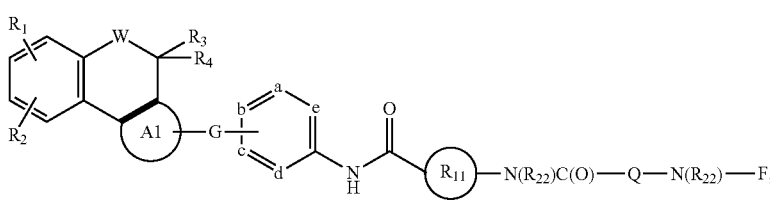

or a pharmaceutically acceptable salt, stereoisomer, or tautomer thereof,
wherein:
$R_{11}$ is aryl or heteroaryl;
a, b, c, d, and e, are each independently C or N, wherein at least one of a, b, c, d, and e is N, and no more than two of a, b, c, d, and e, are N.

13. The compound of claim 1, represented by formula (Ip):

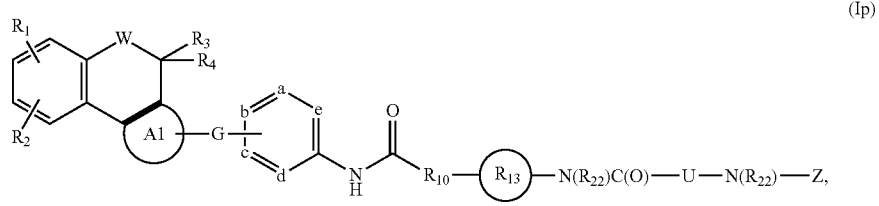

or a pharmaceutically acceptable salt, stereoisomer, or tautomer thereof,
wherein:
$R_{13}$ is aryl or heteroaryl;
a, b, c, d, and e, are each independently C or N, wherein at least one of a, b, c, d, and e is N, and no more than two of a, b, c, d, and e, are N.

14. The compound of claim 1 selected from the groups consisting of:
N,N,5-trimethyl-3-((5-(2-oxopyrrolidin-1-yl)pyridin-3-yl)amino)-5H-chromeno[4,3-c]pyridine-8-carboxamide;
N,N,5-trimethyl-3-(pyridin-3-ylamino)-5H-chromeno[4,3-c]pyridine-8-carboxamide;
1-(3-((1-acetyl-2,3-dihydro-1H-pyrido[2,3-b][1,4]oxazin-7-yl)amino)-5-methyl-5H-chromeno[4,3-c]pyridin-8-yl)pyrrolidin-2-one;
5-cyclopropyl-N,N-dimethyl-3-((5-(2-oxopyrrolidin-1-yl)pyridin-3-yl)amino)-5H-chromeno[4,3-c]pyridine-8-carboxamide;
1-(3-((5-(difluoromethoxy)pyridin-3-yl)amino)-5-methyl-5H-chromeno[4,3-c]pyridin-8-yl)pyrrolidin-2-one;
N,N,5-trimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide;
(6aS)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
5-cyclopropyl-N,N-dimethyl-3-(((S)-9-oxo-6a,7,8,9-tetrahydro-6H-pyrido[2,3-b]pyrrolo[1,2-d][1,4]oxazin-2-yl)amino)-5H-chromeno[4,3-c]pyridine-8-carboxamide;
1-(5-((5-methyl-8-(2-oxopyrrolidin-1-yl)-5H-chromeno[4,3-c]pyridin-3-yl)amino)pyridin-3-yl)cyclopropane-1-carbonitrile;
5-cyclopropyl-N,N-dimethyl-3-(pyridin-3-ylamino)-5H-chromeno[4,3-c]pyridine-8-carboxamide;
1-(5-methyl-3-(pyridin-3-ylamino)-5H-chromeno[4,3-c]pyridin-8-yl)pyrrolidin-2-one;
1-methyl-3-(5-((5-methyl-8-(2-oxopyrrolidin-1-yl)-5H-chromeno[4,3-c]pyridin-3-yl)amino)pyridin-3-yl)imidazolidin-2-one;
N,N,5,6-tetramethyl-3-(pyridin-3-ylamino)-5,6-dihydrobenzo[c][2,6]naphthyridine-8-carboxamide;
N-methyl-N-(5-((5-methyl-8-(2-oxopyrrolidin-1-yl)-5H-chromeno[4,3-c]pyridin-3-yl)amino)pyridin-3-yl)methanesulfonamide;
1-(5-methyl-3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one;
1-(3-((5-fluoropyridin-3-yl)amino)-5-methyl-5H-chromeno[4,3-c]pyridin-8-yl)pyrrolidin-2-one;
1-(3-((1-(cyclopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one;
(S)-2-(((R)-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(S)-2-(((S)-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(5-methyl-3-((5-(2-oxopyrrolidin-1-yl)pyridin-3-yl)amino)-5H-chromeno[4,3-c]pyridin-8-yl)pyrrolidin-2-one;
1-(5-methyl-3-(pyrido[2,3-b]pyrazin-7-ylamino)-5H-chromeno[4,3-c]pyridin-8-yl)pyrrolidin-2-one;
1-(3-((1,5-naphthyridin-3-yl)amino)-5-methyl-5H-chromeno[4,3-c]pyridin-8-yl)pyrrolidin-2-one;
1-(5-methyl-3-(pyrimidin-5-ylamino)-5H-chromeno[4,3-c]pyridin-8-yl)pyrrolidin-2-one;
N-cyclopropyl-N-(5-((5-methyl-8-(2-oxopyrrolidin-1-yl)-5H-chromeno[4,3-c]pyridin-3-yl)amino)pyridin-3-yl)methanesulfonamide;
1-(5-methyl-3-((1-(methylsulfonyl)-1H-pyrrolo[3,2-b]pyridin-6-yl)amino)-5H-chromeno[4,3-c]pyridin-8-yl)pyrrolidin-2-one;
1-(5-methyl-3-((1-pivaloyl-2,3-dihydro-1H-pyrido[2,3-b][1,4]oxazin-7-yl)amino)-5H-chromeno[4,3-c]pyridin-8-yl)pyrrolidin-2-one;
1-(5-((5-methyl-8-(2-oxopyrrolidin-1-yl)-5H-chromeno[4,3-c]pyridin-3-yl)amino)pyridin-3-yl)imidazolidin-2-one;
1-(3-((2,3-dihydro-[1,4]dioxino[2,3-b]pyridin-7-yl)amino)-5-methyl-5H-chromeno[4,3-c]pyridin-8-yl)pyrrolidin-2-one;
1-(5-methyl-3-(thiazolo[5,4-b]pyridin-6-ylamino)-5H-chromeno[4,3-c]pyridin-8-yl)pyrrolidin-2-one;
1-(3-((1-(cyclopropanecarbonyl)-2,3-dihydro-1H-pyrido[2,3-b][1,4]oxazin-7-yl)amino)-5-methyl-5H-chromeno[4,3-c]pyridin-8-yl)pyrrolidin-2-one;
3-((1-(cyclopropylsulfonyl)-2,3-dihydro-1H-pyrido[2,3-b][1,4]oxazin-7-yl)amino)-N,N,5-trimethyl-5H-chromeno[4,3-c]pyridine-8-carboxamide;
N,N,5-trimethyl-3-((1-pivaloyl-2,3-dihydro-1H-pyrido[2,3-b][1,4]oxazin-7-yl)amino)-5H-chromeno[4,3-c]pyridine-8-carboxamide;
3-((1-(cyclopropanecarbonyl)-2,3-dihydro-1H-pyrido[2,3-b][1,4]oxazin-7-yl)amino)-N,N,5-trimethyl-5H-chromeno[4,3-c]pyridine-8-carboxamide;
3-((1-acetyl-2,3-dihydro-1H-pyrido[2,3-b][1,4]oxazin-7-yl)amino)-N,N,5-trimethyl-5H-chromeno[4,3-c]pyridine-8-carboxamide;
N,N,5-trimethyl-3-((1-(methylsulfonyl)-2,3-dihydro-1H-pyrido[2,3-b][1,4]oxazin-7-yl)amino)-5H-chromeno[4,3-c]pyridine-8-carboxamide;
1-(5-methyl-3-((5-(trifluoromethyl)pyridin-3-yl)amino)-5H-chromeno[4,3-c]pyridin-8-yl)pyrrolidin-2-one;
N-(2-methoxy-5-((5-methyl-8-(2-oxopyrrolidin-1-yl)-5H-chromeno[4,3-c]pyridin-3-yl)amino)pyridin-3-yl)acetamide;
N-(2-methoxy-5-((5-methyl-8-(2-oxopyrrolidin-1-yl)-5H-chromeno[4,3-c]pyridin-3-yl)amino)pyridin-3-yl)methanesulfonamide;
1-(3-((1-isobutyryl-2,3-dihydro-1H-pyrido[2,3-b][1,4]oxazin-7-yl)amino)-5-methyl-5H-chromeno[4,3-c]pyridin-8-yl)pyrrolidin-2-one;
(S)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
N-(2-methoxy-5-((5-methyl-8-(2-oxopyrrolidin-1-yl)-5H-chromeno[4,3-c]pyridin-3-yl)amino)pyridin-3-yl)-N-methylmethanesulfonamide;
1-(5-((5-methyl-8-(2-oxopyrrolidin-1-yl)-5H-chromeno[4,3-c]pyridin-3-yl)amino)pyridin-3-yl)-3-(thiazol-4-ylmethyl)imidazolidin-2-one;
methyl 7-((5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate;
1-(5-methyl-3-((5-(methylsulfonyl)pyridin-3-yl)amino)-5H-chromeno[4,3-c]pyridin-8-yl)pyrrolidin-2-one;

1-(3-((1-(2-hydroxyacetyl)-2,3-dihydro-1H-pyrido[2,3-b][1,4]oxazin-7-yl)amino)-5-methyl-5H-chromeno[4,3-c]pyridin-8-yl)pyrrolidin-2-one;

methyl 7-((8-(dimethylcarbamoyl)-5-methyl-5H-chromeno[4,3-c]pyridin-3-yl)amino)-2,3-dihydro-1H-pyrido[2,3-b][1,4]oxazine-1-carboxylate;

N-(2-methoxy-5-((5-methyl-8-(2-oxopyrrolidin-1-yl)-5H-chromeno[4,3-c]pyridin-3-yl)amino)pyridin-3-yl)-N-methylacetamide;

1-(5,6-dimethyl-3-(pyridin-3-ylamino)-5,6-dihydrobenzo[c][2,6]naphthyridin-8-yl)pyrrolidin-2-one;

1-(9-fluoro-5-methyl-3-(pyridin-3-ylamino)-5H-chromeno[4,3-c]pyridin-8-yl)pyrrolidin-2-one;

(6aS)-2-((5,6-dimethyl-8-(2-oxopyrrolidin-1-yl)-5,6-dihydrobenzo[c][2,6]naphthyridin-3-yl)amino)-6,6a,7,8-tetrahydro-9H-pyrido[2,3-b]pyrrolo[1,2-d][1,4]oxazin-9-one;

methyl 7-((8-(2-oxopyrrolidin-1-yl)-5H-chromeno[4,3-c]pyridin-3-yl)amino)-2,3-dihydro-1H-pyrido[2,3-b][1,4]oxazine-1-carboxylate;

(S)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

1-(5-methyl-3-((5-morpholinopyridin-3-yl)amino)-5H-chromeno[4,3-c]pyridin-8-yl)pyrrolidin-2-one;

1-(3-((1-(2-hydroxy-2-methylpropanoyl)-2,3-dihydro-1H-pyrido[2,3-b][1,4]oxazin-7-yl)amino)-5-methyl-5H-chromeno[4,3-c]pyridin-8-yl)pyrrolidin-2-one;

1-(3-((1-(cyclopropanecarbonyl)-2,3-dihydro-1H-pyrido[2,3-b][1,4]oxazin-7-yl)amino)-5H-chromeno[4,3-c]pyridin-8-yl)pyrrolidin-2-one;

1-(3-((1-(methylsulfonyl)-2,3-dihydro-1H-pyrido[2,3-b][1,4]oxazin-7-yl)amino)-5H-chromeno[4,3-c]pyridin-8-yl)pyrrolidin-2-one;

(S)-2-((8-(2-oxopyrrolidin-1-yl)spiro[chromeno[4,3-c]pyridine-5,3'-oxetan]-3-yl)amino)-6,6a,7,8-tetrahydro-9H-pyrido[2,3-b]pyrrolo[1,2-d][1,4]oxazin-9-one;

(S)-2-((8-(2-oxopyrrolidin-1-yl)spiro[chromeno[4,3-c]pyridine-5,1'-cyclobutan]-3-yl)amino)-6,6a,7,8-tetrahydro-9H-pyrido[2,3-b]pyrrolo[1,2-d][1,4]oxazin-9-one;

7-((5-methyl-8-(2-oxopyrrolidin-1-yl)-5H-chromeno[4,3-c]pyridin-3-yl)amino)-1H-pyrido[2,3-b][1,4]oxazin-2(3H)-one;

1-(3-((2,3-dihydro-1H-pyrido[2,3-b][1,4]oxazin-7-yl)amino)-5-methyl-5H-chromeno[4,3-c]pyridin-8-yl)pyrrolidin-2-one;

1-(5-methyl-3-((5-methylpyridin-3-yl)amino)-5H-chromeno[4,3-c]pyridin-8-yl)pyrrolidin-2-one;

(6aS)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

1-(3-((2,3-dihydro-[1,4]dioxino[2,3-b]pyridin-7-yl)amino)-5,6-dimethyl-5,6-dihydrobenzo[c][2,6]naphthyridin-8-yl)pyrrolidin-2-one;

1-(3-((1-(cyclopropylsulfonyl)-2,3-dihydro-1H-pyrido[2,3-b][1,4]oxazin-7-yl)amino)-5H-chromeno[4,3-c]pyridin-8-yl)pyrrolidin-2-one;

1-(3-((1-(isopropylsulfonyl)-2,3-dihydro-1H-pyrido[2,3-b][1,4]oxazin-7-yl)amino)-5H-chromeno[4,3-c]pyridin-8-yl)pyrrolidin-2-one;

4-(5-((5-methyl-8-(2-oxopyrrolidin-1-yl)-5H-chromeno[4,3-c]pyridin-3-yl)amino)pyridin-3-yl)morpholin-3-one;

1-(3-((1-(1-hydroxycyclopropane-1-carbonyl)-2,3-dihydro-1H-pyrido[2,3-b][1,4]oxazin-7-yl)amino)-5-methyl-5H-chromeno[4,3-c]pyridin-8-yl)pyrrolidin-2-one;

1-(3-((1-(2-hydroxypropanoyl)-2,3-dihydro-1H-pyrido[2,3-b][1,4]oxazin-7-yl)amino)-5-methyl-5H-chromeno[4,3-c]pyridin-8-yl)pyrrolidin-2-one;

1-(3-((1-(isopropylsulfonyl)-2,3-dihydro-1H-pyrido[2,3-b][1,4]oxazin-7-yl)amino)-5-methyl-5H-chromeno[4,3-c]pyridin-8-yl)pyrrolidin-2-one;

(S)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

N-(5-((5-methyl-8-(2-oxopyrrolidin-1-yl)-5H-chromeno[4,3-c]pyridin-3-yl)amino)pyridin-3-yl)acetamide;

1-benzyl-3-(5-((5-methyl-8-(2-oxopyrrolidin-1-yl)-5H-chromeno[4,3-c]pyridin-3-yl)amino)pyridin-3-yl)urea;

3-amino-N-(5-((5-methyl-8-(2-oxopyrrolidin-1-yl)-5H-chromeno[4,3-c]pyridin-3-yl)amino)pyridin-3-yl)benzamide;

1-(5-methyl-3-(pyridazin-4-ylamino)-5H-chromeno[4,3-c]pyridin-8-yl)pyrrolidin-2-one;

1-(5-methyl-3-(pyridazin-3-ylamino)-5H-chromeno[4,3-c]pyridin-8-yl)pyrrolidin-2-one;

1-(5-((9-fluoro-5,5-dimethyl-8-(2-oxopyrrolidin-1-yl)-5H-chromeno[4,3-c]pyridin-3-yl)amino)pyridin-3-yl)imidazolidin-2-one;

1-methyl-3-(5-((5-methyl-8-(2-oxopyrrolidin-1-yl)-5H-chromeno[4,3-c]pyridin-3-yl)amino)pyridin-3-yl)urea;

N-(5-((5-methyl-8-(2-oxopyrrolidin-1-yl)-5H-chromeno[4,3-c]pyridin-3-yl)amino)pyridin-3-yl)-3-phenylpropanamide;

N-(5-((5-methyl-8-(2-oxopyrrolidin-1-yl)-5H-chromeno[4,3-c]pyridin-3-yl)amino)pyridin-3-yl)-2-phenylacetamide;

(1S,2S)—N-(5-((5-methyl-8-(2-oxopyrrolidin-1-yl)-5H-chromeno[4,3-c]pyridin-3-yl)amino)pyridin-3-yl)-2-phenylcyclopropane-1-carboxamide;

N-(5-((5-methyl-8-(2-oxopyrrolidin-1-yl)-5H-chromeno[4,3-c]pyridin-3-yl)amino)pyridin-3-yl)picolinamide;

N-(5-((5-methyl-8-(2-oxopyrrolidin-1-yl)-5H-chromeno[4,3-c]pyridin-3-yl)amino)pyridin-3-yl)nicotinamide;

N-(5-((5-methyl-8-(2-oxopyrrolidin-1-yl)-5H-chromeno[4,3-c]pyridin-3-yl)amino)pyridin-3-yl)isonicotinamide;

4-fluoro-N-(5-((5-methyl-8-(2-oxopyrrolidin-1-yl)-5H-chromeno[4,3-c]pyridin-3-yl)amino)pyridin-3-yl)benzamide;

3-fluoro-N-(5-((5-methyl-8-(2-oxopyrrolidin-1-yl)-5H-chromeno[4,3-c]pyridin-3-yl)amino)pyridin-3-yl)benzamide;

3-methoxy-N-(5-((5-methyl-8-(2-oxopyrrolidin-1-yl)-5H-chromeno[4,3-c]pyridin-3-yl)amino)pyridin-3-yl)benzamide;

4-methoxy-N-(5-((5-methyl-8-(2-oxopyrrolidin-1-yl)-5H-chromeno[4,3-c]pyridin-3-yl)amino)pyridin-3-yl)benzamide;

1-(5-methyl-3-((5-(pyridin-2-ylamino)pyridin-3-yl)amino)-5H-chromeno[4,3-c]pyridin-8-yl)pyrrolidin-2-one;

1-(5-methyl-3-((5-(pyridazin-3-ylamino)pyridin-3-yl)amino)-5H-chromeno[4,3-c]pyridin-8-yl)pyrrolidin-2-one;

N-(5-((5-methyl-8-(2-oxopyrrolidin-1-yl)-5H-chromeno[4,3-c]pyridin-3-yl)amino)pyridin-3-yl)-3-phenylbutanamide;

2-methyl-N-(5-((5-methyl-8-(2-oxopyrrolidin-1-yl)-5H-chromeno[4,3-c]pyridin-3-yl)amino)pyridin-3-yl)-3-phenylpropanamide;
N-(5-((5-methyl-8-(2-oxopyrrolidin-1-yl)-5H-chromeno[4,3-c]pyridin-3-yl)amino)pyridin-3-yl)tetrahydrofuran-2-carboxamide;
N-(5-((5-methyl-8-(2-oxopyrrolidin-1-yl)-5H-chromeno[4,3-c]pyridin-3-yl)amino)pyridin-3-yl)benzo[d][1,3]dioxole-5-carboxamide;
N-(5-((5-methyl-8-(2-oxopyrrolidin-1-yl)-5H-chromeno[4,3-c]pyridin-3-yl)amino)pyridin-3-yl)benzo[d][1,3]dioxole-4-carboxamide;
1-(5-methyl-3-((5-(methylsulfonyl)quinolin-3-yl)amino)-5H-chromeno[4,3-c]pyridin-8-yl)pyrrolidin-2-one;
methyl 7-((9-fluoro-5-methyl-8-(2-oxopyrrolidin-1-yl)-5H-chromeno[4,3-c]pyridin-3-yl)amino)-2,3-dihydro-1H-pyrido[2,3-b][1,4]oxazine-1-carboxylate;
N-(5-((5-methyl-8-(2-oxopyrrolidin-1-yl)-5H-chromeno[4,3-c]pyridin-3-yl)amino)pyridin-3-yl)-2-oxopyrrolidine-3-carboxamide;
N-(5-((5-methyl-8-(2-oxopyrrolidin-1-yl)-5H-chromeno[4,3-c]pyridin-3-yl)amino)pyridin-3-yl)-2,3-dihydro-1H-indene-2-carboxamide;
N-(5-((5-methyl-8-(2-oxopyrrolidin-1-yl)-5H-chromeno[4,3-c]pyridin-3-yl)amino)pyridin-3-yl)pyrazolo[1,5-a]pyridine-2-carboxamide;
N-(5-((5-methyl-8-(2-oxopyrrolidin-1-yl)-5H-chromeno[4,3-c]pyridin-3-yl)amino)pyridin-3-yl)-2,3-dihydrobenzofuran-2-carboxamide;
methyl (5-((5-methyl-8-(2-oxopyrrolidin-1-yl)-5H-chromeno[4,3-c]pyridin-3-yl)amino)pyridin-3-yl)carbamate;
4-((5-((5-methyl-8-(2-oxopyrrolidin-1-yl)-5H-chromeno[4,3-c]pyridin-3-yl)amino)pyridin-3-yl)amino)-4-oxobutanoic acid;
N-(5-((5-methyl-8-(2-oxopyrrolidin-1-yl)-5H-chromeno[4,3-c]pyridin-3-yl)amino)pyridin-3-yl)-1H-indole-6-carboxamide;
N-(5-((5-methyl-8-(2-oxopyrrolidin-1-yl)-5H-chromeno[4,3-c]pyridin-3-yl)amino)pyridin-3-yl)-1H-indole-4-carboxamide;
N-(5-((5-methyl-8-(2-oxopyrrolidin-1-yl)-5H-chromeno[4,3-c]pyridin-3-yl)amino)pyridin-3-yl)-1H-benzo[d]imidazole-7-carboxamide;
N-(5-((5-methyl-8-(2-oxopyrrolidin-1-yl)-5H-chromeno[4,3-c]pyridin-3-yl)amino)pyridin-3-yl)imidazo[1,2-a]pyridine-2-carboxamide;
N-(5-((5-methyl-8-(2-oxopyrrolidin-1-yl)-5H-chromeno[4,3-c]pyridin-3-yl)amino)pyridin-3-yl)-1H-indole-2-carboxamide;
2-(imidazo[1,2-a]pyridin-3-yl)-N-(5-((5-methyl-8-(2-oxopyrrolidin-1-yl)-5H-chromeno[4,3-c]pyridin-3-yl)amino)pyridin-3-yl)acetamide;
1-(5-((9-fluoro-5-methyl-8-(2-oxopyrrolidin-1-yl)-5H-chromeno[4,3-c]pyridin-3-yl)amino)pyridin-3-yl)imidazolidin-2-one;
4-formamido-3-hydroxy-N-(5-((5-methyl-8-(2-oxopyrrolidin-1-yl)-5H-chromeno[4,3-c]pyridin-3-yl)amino)pyridin-3-yl)benzamide;
N-(5-((5-methyl-8-(2-oxopyrrolidin-1-yl)-5H-chromeno[4,3-c]pyridin-3-yl)amino)pyridin-3-yl)pyridazine-4-carboxamide;
6-amino-N-(5-((5-methyl-8-(2-oxopyrrolidin-1-yl)-5H-chromeno[4,3-c]pyridin-3-yl)amino)pyridin-3-yl)pyrazine-2-carboxamide;
2-hydroxy-N-(5-((5-methyl-8-(2-oxopyrrolidin-1-yl)-5H-chromeno[4,3-c]pyridin-3-yl)amino)pyridin-3-yl)-3-phenylpropanamide;
N-(5-((5-methyl-8-(2-oxopyrrolidin-1-yl)-5H-chromeno[4,3-c]pyridin-3-yl)amino)pyridin-3-yl)imidazo[1,2-a]pyridine-3-carboxamide;
N-(5-((5-methyl-8-(2-oxopyrrolidin-1-yl)-5H-chromeno[4,3-c]pyridin-3-yl)amino)pyridin-3-yl)pyrazolo[1,5-a]pyridine-3-carboxamide;
1-(3-((2,3-dihydro-[1,4]dioxino[2,3-b]pyridin-7-yl)amino)-5,5-dimethyl-5H-chromeno[4,3-c]pyridin-8-yl)pyrrolidin-2-one;
1-(3-((2,3-dihydro-[1,4]dioxino[2,3-b]pyridin-7-yl)amino)-9-fluoro-5-methyl-5H-chromeno[4,3-c]pyridin-8-yl)pyrrolidin-2-one;
1-(3-((2,3-dihydro-[1,4]dioxino[2,3-b]pyridin-7-yl)amino)-9-fluoro-5,5-dimethyl-5H-chromeno[4,3-c]pyridin-8-yl)pyrrolidin-2-one;
2-hydroxy-N-(5-((5-methyl-8-(2-oxopyrrolidin-1-yl)-5H-chromeno[4,3-c]pyridin-3-yl)amino)pyridin-3-yl)acetamide;
N-(5-((5-methyl-8-(2-oxopyrrolidin-1-yl)-5H-chromeno[4,3-c]pyridin-3-yl)amino)pyridin-3-yl)benzo[d]oxazole-6-carboxamide;
1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-5-carboxamide;
N-(5-((5-methyl-8-(2-oxopyrrolidin-1-yl)-5H-chromeno[4,3-c]pyridin-3-yl)amino)pyridazin-3-yl)acetamide;
N-(5-((5-methyl-8-(2-oxopyrrolidin-1-yl)-5H-chromeno[4,3-c]pyridin-3-yl)amino)pyridin-3-yl)imidazo[1,2-a]pyridine-7-carboxamide;
1-(3-((2,3-dihydro-[1,4]dioxino[2,3-b]pyridin-7-yl)amino)-5H-chromeno[4,3-c]pyridin-8-yl)pyrrolidin-2-one;
1-(5-((5-methyl-8-(2-oxopyrrolidin-1-yl)-5H-chromeno[4,3-c]pyridin-3-yl)amino)pyridin-3-yl)-3-(pyridin-2-yl)urea;
1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-6-carboxamide;
N-(5-((5-methyl-8-(2-oxopyrrolidin-1-yl)-5H-chromeno[4,3-c]pyridin-3-yl)amino)pyridin-3-yl)imidazo[1,2-a]pyridine-5-carboxamide;
1-(3-((2,3-dihydro-[1,4]dioxino[2,3-b]pyridin-7-yl)amino)-9-fluoro-5H-chromeno[4,3-c]pyridin-8-yl)pyrrolidin-2-one;
1-(5-methyl-4-(pyridin-4-yl)-5H-chromeno[4,3-c]pyridin-8-yl)pyrrolidin-2-one;
1-(3-((5-(4-(3-methoxypropanoyl)piperazin-1-yl)pyridin-3-yl)amino)-5H-chromeno[4,3-c]pyridin-8-yl)pyrrolidin-2-one;
1-(3-((5-(4-(3-methoxypropanoyl)piperazin-1-yl)pyridin-3-yl)amino)-5-methyl-5H-chromeno[4,3-c]pyridin-8-yl)pyrrolidin-2-one;
1-(3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one;
(E)-4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)but-2-enamide;
2-amino-N-(5-((5-methyl-8-(2-oxopyrrolidin-1-yl)-5H-chromeno[4,3-c]pyridin-3-yl)amino)pyridin-3-yl)isonicotinamide;

1-(9-fluoro-3-((5-(4-(3-methoxypropanoyl)piperazin-1-yl)pyridin-3-yl)amino)-5H-chromeno[4,3-c]pyridin-8-yl)pyrrolidin-2-one;
1-(9-fluoro-3-((5-(4-(3-methoxypropanoyl)piperazin-1-yl)pyridin-3-yl)amino)-5-methyl-5H-chromeno[4,3-c]pyridin-8-yl)pyrrolidin-2-one;
1-(9-fluoro-3-((5-(4-(3-methoxypropanoyl)piperazin-1-yl)pyridin-3-yl)amino)-5,5-dimethyl-5H-chromeno[4,3-c]pyridin-8-yl)pyrrolidin-2-one;
1-(5-((8-(2-oxopyrrolidin-1-yl)-5H-chromeno[4,3-c]pyridin-3-yl)amino)pyridin-3-yl)imidazolidin-2-one;
(E)-4-(4-(dimethylamino)but-2-enamido)-N-(5-((5-methyl-8-(2-oxopyrrolidin-1-yl)-5H-chromeno[4,3-c]pyridin-3-yl)amino)pyridin-3-yl)benzamide;
(6aS)-8,8-dimethyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(6aS)-2-((9-fluoro-5-methyl-8-(2-oxopyrrolidin-1-yl)-5H-chromeno[4,3-c]pyridin-3-yl)amino)-8,8-dimethyl-6,6a,7,8-tetrahydro-9H-pyrido[2,3-b]pyrrolo[1,2-d][1,4]oxazin-9-one;
1-hydroxy-N-(5-((5-methyl-8-(2-oxopyrrolidin-1-yl)-5H-chromeno[4,3-c]pyridin-3-yl)amino)pyridin-3-yl)-1,3-dihydrobenzo[c][1,2]oxaborole-4-carboxamide;
(6aR)-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(6aS)-2-((9-fluoro-5-methyl-8-(2-oxopyrrolidin-1-yl)-5H-chromeno[4,3-c]pyridin-3-yl)amino)-8-methyl-6,6a,7,8-tetrahydro-9H-pyrido[2,3-b]pyrrolo[1,2-d][1,4]oxazin-9-one;
(6aR)-2-((9-fluoro-5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(R)-2-((8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(R)-2-((5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(R)-2-((9-fluoro-5,5-dimethyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
(6aS)-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
4-(dimethylamino)-N-(3-(3-((5-((5-methyl-8-(2-oxopyrrolidin-1-yl)-5H-chromeno[4,3-c]pyridin-3-yl)amino)pyridin-3-yl)amino)-3-oxopropyl)phenyl)butanamide;
(E)-4-(dimethylamino)-N-(2-((3-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide;
(6a'S)-2'-((5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one;
(S)-2'-((5-fluoro-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one;

(6a'S)-2'-((9-fluoro-5-methyl-8-(2-oxopyrrolidin-1-yl)-5H-chromeno[4,3-c]pyridin-3-yl)amino)-6a',7'-dihydro-6'H,9'H-spiro[cyclopropane-1,8'-pyrido[2,3-b]pyrrolo[1,2-d][1,4]oxazin]-9'-one;
(E)-N-(5-((5,5-dimethyl-8-(2-oxopyrrolidin-1-yl)-5H-chromeno[4,3-c]pyridin-3-yl)amino)pyridin-3-yl)-4-(4-(dimethylamino)but-2-enamido)benzamide;
(E)-N-(3-(3-((5-((5,5-dimethyl-8-(2-oxopyrrolidin-1-yl)-5H-chromeno[4,3-c]pyridin-3-yl)amino)pyridin-3-yl)amino)-3-oxopropyl)phenyl)-4-(dimethylamino)but-2-enamide;
(E)-4-(4-(dimethylamino)but-2-enamido)-N-(5-((8-(2-oxopyrrolidin-1-yl)-5H-chromeno[4,3-c]pyridin-3-yl)amino)pyridin-3-yl)benzamide;
1-(5-((9-fluoro-8-(2-oxopyrrolidin-1-yl)-5H-chromeno[4,3-c]pyridin-3-yl)amino)pyridin-3-yl)imidazolidin-2-one;
1-(5-((5,5-dimethyl-8-(2-oxopyrrolidin-1-yl)-5H-chromeno[4,3-c]pyridin-3-yl)amino)pyridin-3-yl)imidazolidin-2-one;
(6aS)-2-((9-fluoro-5-methyl-8-(2-oxopyrrolidin-1-yl)-5H-chromeno[4,3-c]pyridin-3-yl)amino)-8-hydroxy-6,6a,7,8-tetrahydro-9H-pyrido[2,3-b]pyrrolo[1,2-d][1,4]oxazin-9-one;
(E)-4-(dimethylamino)-N-(2-((4-((3-(5-((5-methyl-8-(2-oxopyrrolidin-1-yl)-5H-chromeno[4,3-c]pyridin-3-yl)amino)pyridin-3-yl)-2-oxoimidazolidin-1-yl)methyl)phenyl)amino)-2-oxoethyl)but-2-enamide;
1-(4-(pyridin-4-yl)-5H-chromeno[4,3-c]pyridin-8-yl)pyrrolidin-2-one;
1-(5-methyl-4-(pyridin-4-ylamino)-5H-chromeno[4,3-c]pyridin-8-yl)pyrrolidin-2-one;
(S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;
(S)-2-((5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;
(3aR)-8-((5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one;
N-(5-((9-fluoro-5,5-dimethyl-8-(2-oxopyrrolidin-1-yl)-5H-chromeno[4,3-c]pyridin-3-yl)amino)-2-methoxypyridin-3-yl)acetamide;
N-(5-((5,5-dimethyl-8-(2-oxopyrrolidin-1-yl)-5H-chromeno[4,3-c]pyridin-3-yl)amino)-2-methoxypyridin-3-yl)acetamide;
1-(5-methyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one;
(6aS,8R)-2-((9-fluoro-5-methyl-8-(2-oxopyrrolidin-1-yl)-5H-chromeno[4,3-c]pyridin-3-yl)amino)-8-hydroxy-8-methyl-6,6a,7,8-tetrahydro-9H-pyrido[2,3-b]pyrrolo[1,2-d][1,4]oxazin-9-one;
(6aS,8R)-8-hydroxy-8-methyl-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;
1-(5,5-dimethyl-3-((5-(5-methyl-1,1-dioxido-1,2,5-thiadiazolidin-2-yl)pyridin-3-yl)amino)-5H-chromeno[4,3-c]pyridin-8-yl)pyrrolidin-2-one;
N-(5-((5-methyl-8-(2-oxopyrrolidin-1-yl)-5H-chromeno[4,3-c]pyridin-3-yl)amino)pyridin-3-yl)-1H-benzo[d]imidazole-4-carboxamide;

(3aR)-8-((9-fluoro-5-methyl-8-(2-oxopyrrolidin-1-yl)-5H-chromeno[4,3-c]pyridin-3-yl)amino)-3a,4-dihydro-1H,3H-oxazolo[3,4-d]pyrido[2,3-b][1,4]oxazin-1-one;

4-(4-(dimethylamino)butanamido)-N-(5-((5-methyl-8-(2-oxopyrrolidin-1-yl)-5H-chromeno[4,3-c]pyridin-3-yl)amino)pyridin-3-yl)benzamide;

1-(5-methyl-3-(((S)-2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one;

(S)-1-(5,5-dimethyl-3-((2-methyl-1,1-dioxido-2,3,3a,4-tetrahydropyrido[2,3-b][1,2,5]thiadiazolo[2,3-d][1,4]oxazin-8-yl)amino)-5H-chromeno[4,3-c]pyridin-8-yl)pyrrolidin-2-one;

(6aS)-8-hydroxy-2-((5-methyl-8-(2-oxopyrrolidin-1-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

1-(5-methyl-3-(oxazolo[4,5-b]pyridin-6-ylamino)-5H-chromeno[4,3-c]pyridin-8-yl)pyrrolidin-2-one;

1-(5,5-dimethyl-3-((1-methyl-2,3-dihydro-1H-pyrido[2,3-b][1,4]oxazin-7-yl)amino)-5H-chromeno[3,4-d]pyrimidin-8-yl)pyrrolidin-2-one;

(S)-2-((5,5-dimethyl-8-(4-methylisoxazol-3-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

(S)-2-((5,5-dimethyl-8-(4-methyl-4H-1,2,4-triazol-3-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one;

(S)-2-((5,5-dimethyl-8-(4-methyl-4H-1,2,4-triazol-3-yl)-5H-chromeno[4,3-c]pyridin-3-yl)amino)-6,6a,7,8-tetrahydro-9H-pyrido[2,3-b]pyrrolo[1,2-d][1,4]oxazin-9-one;

N-(5-((5,5-dimethyl-8-(2-oxopyrrolidin-1-yl)-5H-chromeno[4,3-c]pyridin-3-yl)amino)pyridin-3-yl)-4-(2-(2-(2-(2-((2-(2,6-dioxopiperidin-3-yl)-1,3-dioxoisoindolin-4-yl)amino)ethoxy)ethoxy)ethoxy)acetamido)benzamide;

and

N-(5-((5,5-dimethyl-8-(2-oxopyrrolidin-1-yl)-5H-chromeno[4,3-c]pyridin-3-yl)amino)pyridin-3-yl)-4-(4-(2-((2-(2,6-dioxopiperidin-3-yl)-1,3-dioxoisoindolin-4-yl)oxy)acetamido)butanamido)benzamide, or a pharmaceutically acceptable salt, stereoisomer, or tautomer thereof.

15. A pharmaceutical composition comprising a compound of claim 1, and a pharmaceutically acceptable carrier.

16. A method of inhibiting PI5P4K comprising, administering to a patient in need thereof an effective amount of a compound of claim 1.

\* \* \* \* \*